US010188115B2

(12) United States Patent
Baum et al.

(10) Patent No.: US 10,188,115 B2
(45) Date of Patent: Jan. 29, 2019

(54) PROTEINS TOXIC TO HEMIPTERAN INSECT SPECIES

(71) Applicant: Monsanto Technology LLC, St. Louis, MO (US)

(72) Inventors: James A. Baum, Webster Groves, MO (US); Artem G. Evdokimov, St. Louis, MO (US); Farhad Moshiri, St. Louis, MO (US); Timothy J. Rydel, St. Louis, MO (US); Eric J. Sturman, St. Louis, MO (US); Moritz von Rechenberg, Waltham, MA (US); Halong Vu, St. Louis, MO (US); Andrew M. Wollacott, St. Louis, MO (US); Meiying Zheng, St. Louis, MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 15/651,727

(22) Filed: Jul. 17, 2017

(65) Prior Publication Data

US 2017/0318818 A1 Nov. 9, 2017

Related U.S. Application Data

(60) Division of application No. 15/015,957, filed on Feb. 4, 2016, now Pat. No. 9,713,334, which is a continuation of application No. 13/857,196, filed on Apr. 5, 2013, now Pat. No. 9,322,033.

(60) Provisional application No. 61/621,436, filed on Apr. 6, 2012.

(51) Int. Cl.

| | |
|---|---|
| *C07K 14/325* | (2006.01) |
| *A01N 63/00* | (2006.01) |
| *A01N 63/02* | (2006.01) |
| *C12N 15/82* | (2006.01) |
| *C07K 14/00* | (2006.01) |
| *A01N 37/46* | (2006.01) |
| *C07K 14/435* | (2006.01) |
| *C07K 14/32* | (2006.01) |

(52) U.S. Cl.

CPC ............. *A01N 63/02* (2013.01); *A01N 37/46* (2013.01); *C07K 14/001* (2013.01); *C07K 14/32* (2013.01); *C07K 14/325* (2013.01); *C07K 14/43577* (2013.01); *C12N 15/8286* (2013.01); *Y02A 40/162* (2018.01)

(58) Field of Classification Search

CPC .................................................... C07K 14/325
USPC ......................................................... 536/23.1
See application file for complete search history.

(56) References Cited

U.S. PATENT DOCUMENTS

| | | | |
|---|---|---|---|
| 5,723,440 | A | 3/1998 | Stockhoff et al. |
| 5,885,963 | A | 3/1999 | Stockhoff et al. |
| 5,942,658 | A | 8/1999 | Donovan et al. |
| 7,473,821 | B2 | 1/2009 | Abad et al. |
| 7,524,810 | B1 | 4/2009 | Schnepf |
| 7,615,686 | B2 | 11/2009 | Miles et al. |
| 2006/0021087 | A1 | 1/2006 | Baum et al. |
| 2006/0242732 | A1 | 10/2006 | Carozzi et al. |
| 2008/0295207 | A1 | 11/2008 | Baum et al. |
| 2010/0064394 | A1 | 3/2010 | Baum et al. |
| 2010/0298207 | A1 | 11/2010 | Sampson et al. |
| 2013/0269060 | A1 | 10/2013 | Baum et al. |

FOREIGN PATENT DOCUMENTS

| | | | |
|---|---|---|---|
| WO | WO 93/14205 | A1 | 7/1993 |
| WO | WO 96/39843 | A1 | 12/1996 |
| WO | WO 01/71042 | A2 | 9/2001 |
| WO | WO 02/078437 | A2 | 10/2002 |
| WO | WO 2005/110068 | A2 | 11/2005 |
| WO | WO 2006/107761 | A2 | 10/2006 |
| WO | WO 2007/027776 | A2 | 3/2007 |
| WO | WO 2008/134072 | A2 | 11/2008 |
| WO | WO 2010/025320 | A1 | 3/2010 |
| WO | WO 2010/099365 | A2 | 9/2010 |

OTHER PUBLICATIONS

Baum et al., "Binary Toxins from Bacillus thuringiensis Active against the Western Corn Rootworm," Diabrotica virgifera virgifera LeConte, *Applied and Environmental Microbiology*, 70(8):4889-4898 (2004).

Chan et al., "Unusual Amino Acid Determinants of Host Range in the Mtx2 Family of Mosquitocidal Toxins," *The Journal of Biological Chemistry*, 271(24):14183-14187 (1996).

Chougule et al., "Toxins for Transgenic Resistance to Hemipteran Pests," *Toxins*, 4:405-429 (2012).

Correspondence from NCBI dated Sep. 24, 2010 re Date of First Public Release for DQ836184, 2 pages.

Crickmore et al., "Revision of the Nomenclature for the Bacillus thuringiensis Pesticidal Crystal Proteins," *Microbiology and Molecular Biology Review*, 62(3):807-813 (1998).

Donovan et al., "Characterization of Two Genes Encoding *Bacillus thuringiensis* Insecticial Crystal Proteins Toxic to *Coleoptera* Species," *Applied and Environmental Microbiology*, 58(12):3921-3927 (1992).

EBI Accession No. GSP: ABB68459, "*Drosophila melanogaster* Polypeptide SEQ ID No. 32169. Dyderpskrp Rgkptagtag Rkisprkpgr Veerrsnfned Rplgrrrsek Erttpssald", XP 002600478, Mar. 2002, Database Geneseq.

EMBL Accession No. DQ836184, Bacillus thuringiensis strain F14-1 Cry51Aa1 (cry51Aa1) gene,complete CDs, http://srs.ebi.ac.uk/srsbin/cgi-bin/wgetz?-e+[EMBL:DQ836184]+-newId, created Aug. 1, 2007, 2 pages.

Extended European Search Report dated Oct. 6, 2010, in European Patent Application No. 08754143.9, 6 pages.

(Continued)

*Primary Examiner* — Tekchand Saidha

(74) *Attorney, Agent, or Firm* — Timothy K. Ball; Carine M. Doyle; Arnold & Porter Kaye Scholer LLP

(57) ABSTRACT

The present invention discloses *Hemipteran* insect inhibitory proteins, methods of using such proteins, nucleotide sequences encoding such proteins, methods of detecting and isolating such proteins, and their use in agricultural systems.

22 Claims, 3 Drawing Sheets

Specification includes a Sequence Listing.

(56) References Cited

OTHER PUBLICATIONS

Extended European Search Report dated Sep. 14, 2015, in European Patent Application No. 13772577.6, 7 pages.
GenBank Accession No. DQ836184, Bacillus thuringiensis strain F14-1 Cry51Aa1 (cry51Aa1) gene,complete cds, 1 page, Aug. 1, 2007, Web, Apr. 11, 2009 <http://www.ncbi.nlm.nih.gov/nuccore/112253718>.
Höfte et al., "Insecticidal Crystal Proteins of Bacillus thuringiensis," Microbiological Reviews, *American Society for Microbiology*, 53(2):242-255 (1989).
Huang et al., "Microbial control and biotechnology research on Bacillus thuringiensis in China," *Journal of Invertebrate Pathology*, 95(3):175-180 (2007).
International Search Report and Written Opinion dated Nov. 24, 2008, in International Application No. PCT/US2008/005542.
Lambert et al., "Novel *Bacillus thuringiensis* Insecticidal Crystal Protein with a Silent Activity against Coleopteran Larvae," *Applied and Environmental Microbiology*, 58(8):2536-2542 (1992).
Liu et al., "New Gene from Nine *Bacillus sphaericus* Strains Encoding Highly Conserved 35.8-Kilodalton Mosquitocidal Toxins," *Applied and Environmental Microbiology*, 62(6):2174-2176 (1996).
NCBI Accession No. D0836184, Bacillus thuringiensis strain F14-1 Cry51Aa1 (cry51Aa1) gene, obtained Oct. 1, 2010 from http://www.ncbi.nlm.nih.gov/nuccore/112253718, 1 page.
NCBI Sample GenBank Record obtained Oct. 1, 2010 from http://www.ncbi.nlm.nih.gov/Sitemap/samplerecord.html, 17 pages.
New England Biolabs, Random Primer, Jun. 12, 2004, http://web.archive.org/web/20040619083054/http://www.neb.com/nebecomm/pro- ducts/productS1255.asp, 1 page.
New England Biolabs, Random Primer, Jun. 24, 2004, http://web.archive.org/web/20040618195247/http://www.neb.com/nebecomm/pro- ducts/productS1256.asp, 1 page.
Revision history for NCBI Accession DQ836184, Bacillus thuringiensis strain F14-1 Cry51Aa1(cry51Aa1) gene, obtained on Oct. 1, 2010 from http://www.ncbi.nlm.nih.gov/sviewer/girevhist.cgi?val=DQ836184.1&log$=seq-view, 1 page.
Soberón et al., "Engineering modified Bt toxins to counter insect resistance," *Science*, 318(5856):1640-1642 (2007).
Thanabalu et al., "A *Bacillus sphaericus* Gene Encoding a Novel Type of Mosquitocidal Toxin of 31.8 kDa, Gene," 170(1):85-89 (1996).
UniProt Accession No. A7IZR5_BACTU, 1 page, accessed on Oct. 13, 2015 <http://www.genome.jp/dbget-bin/www_bget?uniprot:A7IZR5_BACTU>.
Vita et al., "Scorpion toxins as natural scaffolds for protein engineering," *Proc. Natl. Acad. Sci. USA*, 92:6404-6408 (1995).
Von Tersch et al., "Membrane-Permeabilizing Activies of *Bacillus thuringiensis* Coleopteran-Active Toxin CryIIIB2 and CryIIIB2 Domain I Peptide," *Applied and Environmental Microbiology*, 60(10):3711-3717 (1994).
Wellman-Desbiens, Elisabeth, et al., Development of a Bacillus thuringiensis-Based Assay on Lygus hesperus, Journal of Economic Entomology, 98(5):1469-1479 (2005).

FIGURE 1
FIG. 1A
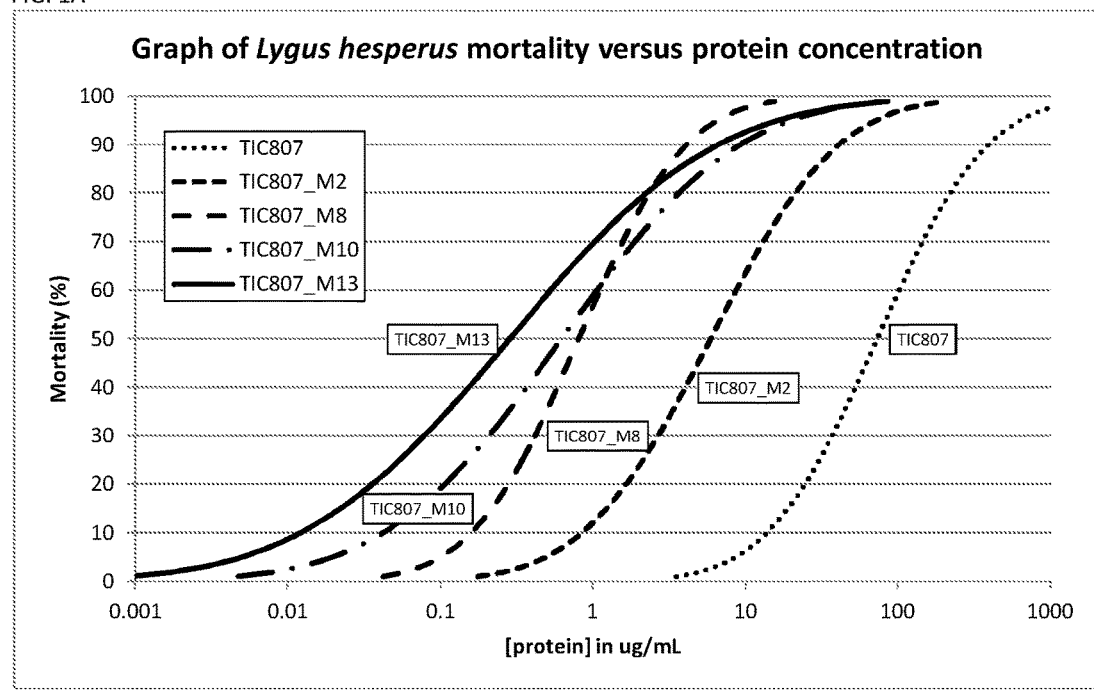
FIG. 1B
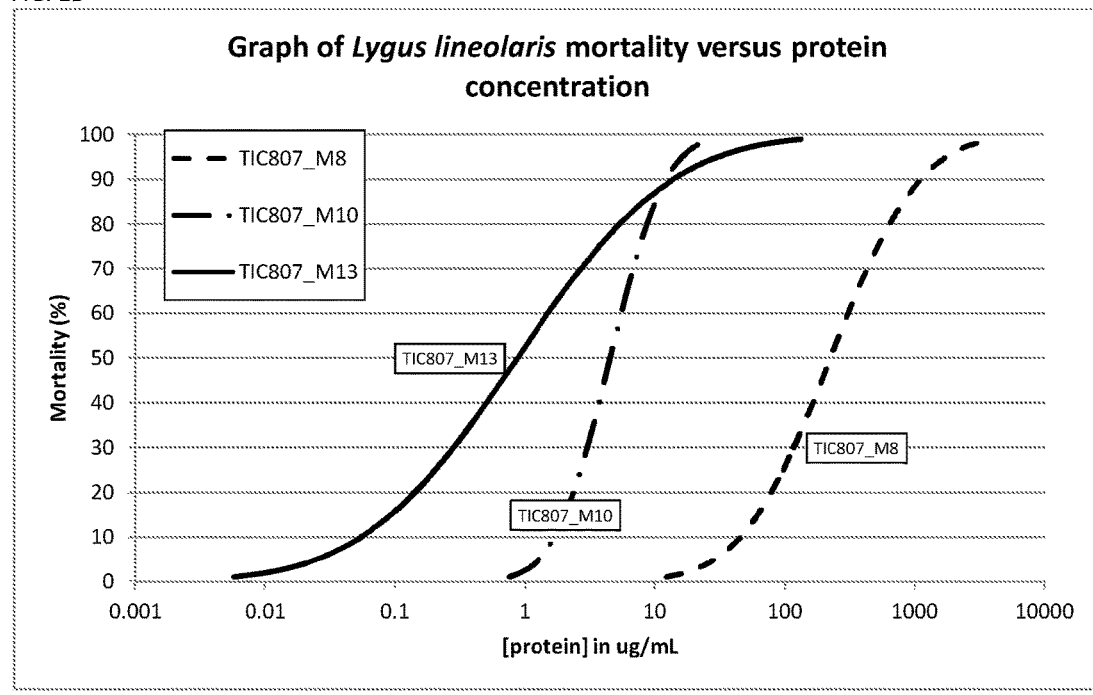

PROTEINS TOXIC TO HEMIPTERAN INSECT SPECIES

CROSS REFERENCE TO RELATED APPLICATIONS

This application is a divisional of U.S. application Ser. No. 15/015,957, filed Feb. 4, 2016, which is a continuation of U.S. application Ser. No. 13/857,196, filed Apr. 5, 2013, which claims priority to U.S. Provisional Application Ser. No. 61/621,436, filed Apr. 6, 2012, all of which are incorporated herein by reference in its entirety their entireties.

INCORPORATION OF SEQUENCE LISTING

The Sequence Listing contained in the file named "P34307US04.txt", which is 529,878 bytes in size (measured in operating system MS-Windows) and was created on Jul. 17, 2017, is contemporaneously filed by electronic submission (using the United States Patent Office EFS-Web filing system) and is incorporated herein by reference in its entirety.

FIELD OF THE INVENTION

The present invention generally relates to the field of insect inhibitory proteins. In particular, the present invention relates to proteins exhibiting insect inhibitory activity against agriculturally relevant pests of crop plants and seeds, particularly Hemipteran species of insect pests.

BACKGROUND OF THE INVENTION

Insect inhibitory proteins derived from *Bacillus thuringiensis* (Bt) are non-toxic to humans, vertebrates, and plants. These proteins are also biodegradable, safe, and effective in controlling pest insects. Some of these proteins have been and are being used to control agriculturally relevant pests of crop plants by spraying plants with formulations containing these proteins or with microorganisms that express them, treating seeds with treatments containing these proteins, or expressing these proteins in crop plants and seeds of crop plants as plant-incorporated protectants.

Certain Hemiptera species, particularly *Amrasca, Empoasca* and *Lygus* bugs, are pests of cotton and alfalfa, and typically are only controlled using broad spectrum chemistries, e.g., endosulfan, acephate, and oxamyl, which can persist in and are harmful to the environment. A few Bt proteins have been developed in formulations or as transgenic traits in crop plants for commercial use by farmers to control *Coleopteran* and *Lepidopteran* pest species, but no Bt proteins have been developed for use in commercial control of *Hemipteran* pest species.

Hemipteran specific toxic proteins have been reported in the art. TIC807 is a *Bacillus thuringiensis* protein disclosed in U.S. Patent Application Publication No. US 2008-0295207 A1 as being toxic to *Hemipteran* pest species. A Cry51Aa1 protein reported as toxic to *Lepidopteran* species that closely resembles the amino acid sequence of TIC807 has also been disclosed (Huang et al., (2007) J. Invertebr. Pathol. 95(3), 175-180), but no *Hemipteran* specific activity was reported. Baum et al. disclosed TIC853, a protein reported to be toxic to *Lygus* pest species (U.S. Patent Application Publication No. US 2010-0064394 A1). A protein referred to as AXMI-171 was reported to exhibit some limited inhibition of *Hemipteran* insects (U.S. Patent Application Publication No. US2010-0298207 A1, example 18), particularly *Lygus hesperus*.

All of these proteins exhibit a narrow range of toxicity only against *Lygus hesperus* and exhibit toxic effects against other *Lygus* pest species only in high doses which are not considered to be achievable by expression in plants. Compared to the *Hemipteran* toxic proteins in the prior art, there is a need for toxin proteins that can be used on and in plants that exhibit a broad host range against *Hemipteran* pest species and at low concentration effective doses.

BRIEF SUMMARY OF THE INVENTION

Recombinantly engineered *Hemipteran* toxic proteins described herein (referred to herein as "engineered toxin proteins", "engineered toxic proteins", "engineered *Hemipteran* toxic proteins", or "engineered *Hemipteran* toxin proteins", are also referred to herein in truncated form as "eHTP's" when referred to in groups of two or more such proteins, and "eHTP" when referred to singularly) are derivatives of naturally occurring *Bacillus thuringiensis* insecticidal toxins, TIC807 (SEQ ID NO:2), TIC807_M2 (SEQ ID NO:8), Cry51Aa1 (SEQ ID NO:182), TIC853 (SEQ ID NO:184), and AXMI-171 (SEQ ID NO:206) have been described previously to exhibit bio-control activity directed to *Hemipteran* pest species, particularly *Lygus hesperus* insect species (references cited elsewhere herein). The recombinant *Hemipteran* insect toxic proteins of the present invention are particularly toxic to insects of the *Amrasca, Empoasca* and *Lygus* species of insect pests and to other insect pest species that are phylogenetically related to each of these species of insect pests, and additionally to insect pests that feed on plants using a piercing and sucking mechanism used by the pest species *Amrasca, Empoasca* and *Lygus* species of the order Hemiptera. Unlike the precursor insecticidal toxins TIC807 (SEQ ID NO:2), TIC807_M2 (SEQ ID NO:8), Cry51Aa1 (SEQ ID NO:182), TIC853 (SEQ ID NO:184), and AXMI-171 (SEQ ID NO:206) from which they are derived, which each require moderately high to high doses of protein to achieve toxic effects upon one *Lygus* species and exhibit very low or virtually undetectable toxic effects upon a second closely related species of *Lygus*, the eHTP proteins of the present invention exhibit surprising and unexpected low dose toxic effects against insect pests of the order Hemiptera, including host range toxic effects that span the spectrum of pests within the order.

The eHTP's of the present invention each contain at least one amino acid substitution, one amino acid addition, or one amino acid deletion compared to the primary amino acid sequence of one or more of the toxin proteins set forth in any of SEQ ID NO:2, SEQ ID NO:8, SEQ ID NO:182, or SEQ ID NO:184. In certain embodiments, an eHTP is provided that contains at least from about 2 to about 260 fold greater inhibitory activity against a *Lygus* pest species than any one or more of the toxins set forth in any of SEQ ID NO:2 (TIC807), SEQ ID NO:8 (TIC807_M2), SEQ ID NO:182 (Cry51Aa1), SEQ ID NO:184 (TIC853), and/or SEQ ID NO:206 (AXMI-171). Optionally the eHTP exhibits at least about 95% amino acid sequence identity to the toxin protein selected from the group consisting of SEQ ID NO:2 (TIC807) and SEQ ID NO:182 (Cry51Aa1). In certain embodiments, an eHTP is provided that contains at least one amino acid substitution, at least one amino acid addition, or at least one amino acid deletion when compared to the amino acid sequence of any of SEQ ID NO:2, SEQ ID NO:8, SEQ ID NO:182, or SEQ ID NO:184. The eHTP exhibits an increased or greater *Lygus* inhibitory activity and target pest species spectrum compared to the activity and target pest species spectrum of the *Bacillus thuringiensis* proteins of set forth in SEQ ID NO:2, SEQ ID NO:8, SEQ ID NO:182, and SEQ ID NO:184. Each of the aforementioned eHTP's contain at least, collectively or in the alternative: (i) the amino acid substitution, addition, or deletion in a solvent accessible amino acid residue of SEQ ID NO:2; (ii) the amino acid substitution, addition, or deletion within 3 consecutive residues of a solvent accessible amino acid residue of SEQ ID NO:2; or, (iii) an amino acid sequence as set forth in SEQ ID NO:180. The aforementioned eHTP's will each contain at least, with reference to the amino acid sequence positions as numbered according to the amino acid positions of TIC807, one substitution or deletion selected from the group consisting of asparagine at position 12 replaced by aspartic acid, phenylalanine at position 46 replaced by serine, isoleucine at position 52 replaced by methionine, tyrosine at position 54 replaced by histidine, threonine at position 68 replaced by alanine, glutamine at position 70 replaced by alanine, alanine at position 87 replaced by serine, threonine at position 93 replaced by alanine, serine at position 95 replaced by alanine, glycines at position 105 replaced by alanine, serine at position 117 replaced by alanine, serine at position 119 replaced by alanine, glutamate at position 125 replaced by cysteine, histidine, arginine, phenylalanine, serine, glutamine, lysine, threonine, asparagine, alanine, leucine, valine, methionine, aspartic acid, or tyrosine, glycines at position 128 replaced by alanine, threonine at position 133 replaced by glutamic acid, tyrosine, or tryptophan, isoleucine at position 134 replaced by alanine, valine, leucine, phenylalanine, lysine, cysteine, or methionine, glutamate at position 135 replaced by serine, alanine, valine, tryptophan, or threonine, asparagine at position 137 replaced by histidine, tyrosine, threonine, glutamic acid, serine, alanine, glutamine, glycine, isoleucine, tryptophan, lysine, cysteine, methionine, aspartic acid, phenylalanine, or arginine, phenylalanine at position 138 replaced by valine, Ala139 replaced by serine, Thr145 replaced by alanine, Phe147 replaced by serine, valine, threonine, cysteine, leucine, aspartic acid, alanine, glycine, glutamic acid, isoleucine, tyrosine, methionine, asparagine, glutamine, hystidine, alanine, arginine, tryptophan, or proline, glutamine at position 148 replaced by alanine, glutamine at position 149 replaced by aspartic acid, glutamic acid, cysteine, alanine, or phenylalanine, alanine at position 150 replaced by serine, leucine, valine, glycine, aspartic acid, tryptophan, glutamic acid, asparagine, tyrosine, phenylalanine, proline, lysine, threonine, glutamine, or arginine, seroine at position 151 replaced by alanine, aspartate at position 153 replaced by alanine, glutamate at position 155 replaced by cysteine, isoleucine, lysine, aspartic acid, histidine, tyrosine, glutamine, lysine, asparagine, threonine, alanine, phenylalanine, arginine, methionine, proline, tryptophan, serine, or valine, asparagine at position 157 replaced by cysteine, aspartic acid, tryptophan, tyrosine, methionine, alanine, phenylalanine, valine, leucine, proline, glutamic acid, threonine, glycine, isoleucine, or arginine, isoleucine at position 158 replaced by alanine, serine at position 159 replaced by alanine or threonine, serine at position 167 replaced by arginine or alanine, valine at position 175 replaced by alanine, methionine at position 177 replaced by alanine, asparagine at position 180 replaced by aspartic acid, threonine at position 182 replaced by alanine, leucine at position 187 replaced by alanine, histidine at position 196 deleted, tyrosine at position 197 deleted, serine at position 198 deleted, histidine at position 199 deleted, tyrosine at position 200 replaced by alanine, tyrosine at position 200 deleted, Ser201 replaced by alanine, serine at position 201 deletion, tryptophan at position 208 replaced by alanine, serine at position 217 replaced by asparagine, proline at position 219 replaced by arginine, tryptophan at position 223 replaced by tyrosine, phenylalanine at position 235 replaced by alanine, asparagine at position 239 replaced by alanine, aspartate at position 241 replaced by alanine, threonine at position 243 replaced by alanine, valine at position 244 replaced by isoleucine, threonine at position 245 replaced by alanine, tyrosine at position 246 replaced by phenylalanine, threonine at position 247 replaced by alanine or lysine, serine at position 249 replaced by alanine or arginine, valine at position 250 replaced by alanine, valine at position 251 replaced by alanine, serine at position 252 replaced by alanine, arginine at position 273 replaced by tryptophan, threonine at position 274 replaced by alanine, isoleucine at position 275 replaced by alanine, arginine at position 282 replaced by alanine, histidine at position 287 replaced by alanine or phenylalanine, serine at position 293 replaced by alanine, asparagine at position 295 replaced by alanine, glutamate at position 299 replaced by alanine, methionine at position 300 replaced by alanine, threonine at position 303 replaced by alanine, proline at position 305 replaced by alanine, isoleucine at position 306 replaced by alanine, and threonine at position 308 replaced by alanine, or wherein the protein comprises any combination of the referenced substitutions and/or deletions. eHTP's contain at least one amino acid substitution, one amino acid addition, or one amino acid deletion at an amino acid residue of SEQ ID NO:2, or the corresponding amino acid position of SEQ ID NO:8, SEQ ID NO:182, or SEQ ID NO:184, selected from the group consisting of (i) an amino acid residue having a relative solvent-accessibility of from at least about 15% to at least about 36%; and (ii) an amino acid residue located within a distance of about 3 consecutive residues from an amino acid having from at least about 15% to at least about 36% relative solvent-accessibility. An eHTP of the present invention contains at least one amino acid substitution, addition, or deletion at an amino acid residue selected from the group consisting of Thr93, Ser95, Ser97, Phe147, Gln149, Ser151, Asn180, Thr182, Val251, Gln253, and Ser255 of SEQ ID NO:2. Any of the aforementioned eHTP's can contain at least one additional amino acid substitution, addition, or deletion at an amino acid residue selected from the group consisting of Val10, Ile14, Asn22, Asn23, Gly24, Ile25, Gln26, Gly27, Phe30, Gln38, Ile39, Asp40, Thr41, Ile43, Ser193, Thr194, Glu195, His196, Tyr197, Ser198, His199, Tyr200, Ser201, Gly202, Tyr203, Pro204, Ile205, Leu206, Thr207, Trp208, Ile209, Ser210, Tyr216, Ser217, Gly218, Pro219, Pro220, Met221, Ser222, Trp223, Tyr224, Phe225, Asn239, and Val244 of SEQ ID NO: 2 or the corresponding amino acid residue position of SEQ ID NO:8, SEQ ID NO:182, or SEQ ID NO:184. Any of the aforementioned eHTP's may contain one or more modifications selected from the group consisting of S95A, F147A, Q149E, V251A, P219R, and a deletion of any three consecutive amino acids from amino acid residues 196-201 as set forth in SEQ ID NO:2. Any of the eHTP's of the present invention can be further modified to exhibit increased solubility compared to the underlying naturally occurring *Bacillus thuringiensis* protein as set forth in any of SEQ ID NO:2, SEQ ID NO:8, SEQ ID NO:182, or SEQ ID NO:184 in which the eHTP contains at least one or more amino acid sequence modifications relative to the amino acid sequence as set forth in SEQ ID NO:2. The modification(s) contain at least a lysine substitution at one or more of the amino acid positions defined as 58, 59, 198, 199, 201, or 202 in SEQ ID NO:2; a glutamic acid residue substitution at one or more of the amino acid positions defined as 198, 248, or 301 in SEQ ID NO:2; or an arginine residue substitution at one or more of the amino acid positions defined as 246, 250, or 253 in SEQ ID NO:2. An eHTP having an amino acid sequence selected from the group consisting of SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:28, SEQ ID NO:30, SEQ ID NO:32, SEQ ID NO:34, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, SEQ ID NO:79, SEQ ID NO:80, SEQ ID NO:81, SEQ ID NO:82, SEQ ID NO:83, SEQ ID NO:84, SEQ ID NO:85, SEQ ID NO:86, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, SEQ ID NO:97, SEQ ID NO:98, SEQ ID NO:99, SEQ ID NO:100, SEQ ID NO:101, SEQ ID NO:102, SEQ ID NO:103, SEQ ID NO:104, SEQ ID NO:105, SEQ ID NO:106, SEQ ID NO:107, SEQ ID NO:108, SEQ ID NO:109, SEQ ID NO:110, SEQ ID NO:111, SEQ ID NO:112, SEQ ID NO:113, SEQ ID NO:114, SEQ ID NO:115, SEQ ID NO:116, SEQ ID NO:117, SEQ ID NO:118, SEQ ID NO:119, SEQ ID NO:120, SEQ ID NO:121, SEQ ID NO:122, SEQ ID NO:13, SEQ ID NO:124, SEQ ID NO:125, SEQ ID NO:126, SEQ ID NO:127, SEQ ID NO:128, SEQ ID NO:129, SEQ ID NO:130, SEQ ID NO:131, SEQ ID NO:132, SEQ ID NO:133, SEQ ID NO:134, SEQ ID NO:135, SEQ ID NO:136, SEQ ID NO:137, SEQ ID NO:138, SEQ ID NO:139, SEQ ID NO:140, SEQ ID NO:141, SEQ ID NO:142, SEQ ID NO:143, SEQ ID NO:144, SEQ ID NO:145, SEQ ID NO:146, SEQ ID NO:147, SEQ ID NO:148, SEQ ID NO:149, SEQ ID NO:150, SEQ ID NO:151, SEQ ID NO:152, SEQ ID NO:153, SEQ ID NO:154, SEQ ID NO:155, SEQ ID NO:156, SEQ ID NO:157, SEQ ID NO:158, SEQ ID NO:159, SEQ ID NO:160, SEQ ID NO:161, SEQ ID NO:162, SEQ ID NO:163, SEQ ID NO:164, SEQ ID NO:165, SEQ ID NO:166, SEQ ID NO:167, SEQ ID NO:168, SEQ ID NO:169, SEQ ID NO:170, SEQ ID NO:171, SEQ ID NO:172, SEQ ID NO:173, SEQ ID NO:174, SEQ ID NO:175, SEQ ID NO:176, SEQ ID NO:177, SEQ ID NO:178, SEQ ID NO:179, SEQ ID NO:202, and SEQ ID NO:204, or an insect inhibitory fragment thereof, is a preferred embodiment of the present invention. The target *Hemipteran* pest species inhibited by the eHTP's of the present invention include at least *Lygus hesperus*, *Lygus lineolaris*, *Empoasca fabae* and *Amrasca devastans*, as well as other pests within the order Hemiptera that are phylogenetically related to each other or which use a piercing and sucking approach for feeding on plants.

Methods of controlling a *Hemipteran* pest by contacting the pest with a *Hemipteran* inhibitory amount of a eHTP of the present invention, as well as an insect inhibitory composition that contains at least a *Hemipteran* controlling amount (or *Hemipteran* inhibitory amount) of one or more of the eHTP's of the present invention, are also provided. In certain embodiments, an insect inhibitory composition comprising any of the eHTP's disclosed herein is provided. In certain embodiments of these methods, the *Hemipteran* pest is in a cotton field, a soybean field or an alfalfa field. *Hemipteran* toxic or *Hemipteran* controlling compositions can contain at least one or more eHTP along with a supplemental agent that is selected from the group consisting of an insect inhibitory protein, an insect inhibitory dsRNA molecule, and an insect inhibitory chemistry. Each of these agents can exhibit *Hemipteran* controlling properties, can exhibit properties for controlling pests unrelated to *Hemipteran* species such as *Lepidopteran* species or *Coleopteran* species, or may exhibit dual mode of action properties in which one or more *Hemipteran* species and one or more *Lepidopteran* or *Coleopteran* species are simultaneously controlled.

Recombinant polynucleotides that encode eHTP's of the present invention are provided. Microbes are also provided that contain the polynucleotides of the present invention, and such polynucleotides within such microbes are functionally positioned within expression cassettes designed to express the eHTP's of the present invention from operably linked functional genetic regulatory elements. Microbes are intended to include bacterial cells, as well as transgenic plant cells. Such transgenic plant cells can be regenerated into whole plants, or plant parts that also contain the recombinant polynucleotide. Methods of controlling a *Hemipteran* pest by exposing the pest to the microbe, whether bacterial cell or transgenic plant cell, plant or plant part, each of which expresses a *Hemipteran* inhibitory amount of an eHTP are also provided. The recombinant polynucleotide may contain a nucleotide sequence selected from the group consisting of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:186, SEQ ID NO:187, SEQ ID NO:188, SEQ ID NO:189, SEQ ID NO:190, SEQ ID NO:191, SEQ ID NO:192, SEQ ID NO:193, SEQ ID NO:194, SEQ ID NO:195, SEQ ID NO:196, SEQ ID NO:197, SEQ ID NO:198, SEQ ID NO:199, SEQ ID NO:200, SEQ ID NO:201, and SEQ ID NO:203, or other sequences that can be assembled to encode one or more of the proteins of the present invention. In certain embodiments, the recombinant polynucleotide can further comprise a nucleotide sequence encoding one or more insect inhibitory agents that are different from the eHTP encoded by the recombinant polynucleotide. The transgenic plant part is a seed, a boll, a leaf, a flower, pollen, a stem, a root, or any portion thereof. The transgenic plant part may be a non-regenerable portion of the seed, boll, leaf, flower, stem, or root. Also provided are methods of controlling a *Hemipteran* pest, comprising exposing the transgenic microbe, bacteria, plant cell, plant or plant part to the target pest, wherein the microbe, bacteria, plant cell, plant or plant part expresses a *Hemipteran* inhibitory amount of a eHTP encoded by the recombinant polynucleotide.

Processed plant products that contain a detectable amount of a recombinant polynucleotide encoding an eHTP or any distinguishing *Hemipteran* controlling portion thereof are also provided. Such processed products include, but are not limited to, plant biomass, oil, meal, animal feed, flour, flakes, bran, lint, hulls, and processed seed. The processed product may be non-regenerable.

Methods of making a transgenic plant by introducing the recombinant polynucleotide into a plant cell and selecting a transgenic plant that expresses an insect inhibitory amount of an eHTP encoded by a recombinant polynucleotide are also provided. The methods include introducing the recombinant polynucleotide encoding any of the eHTP's provided herein into a plant cell and selecting a transgenic plant that expresses an insect inhibitory amount of the eHTP encoded by the recombinant polynucleotide.

Other embodiments, features, and advantages of the invention will be apparent from the following detailed description, the examples, and the claims.

BRIEF DESCRIPTION OF THE DRAWINGS

FIG. 1 illustrates the mortality of *Lygus* species plotted against eHTP protein concentration. FIG. 1A illustrates the mortality of *Lygus hesperus* populations in response to various concentrations of four different eHTP's compared to a control sample containing the naturally occurring TIC807 protein. FIG. 1B illustrates the mortality of *Lygus lineolaris* populations in response to various protein concentrations of three different eHTP's compared to a control sample containing the naturally occurring TIC807 protein.

DETAILED DESCRIPTION

Figure 2:
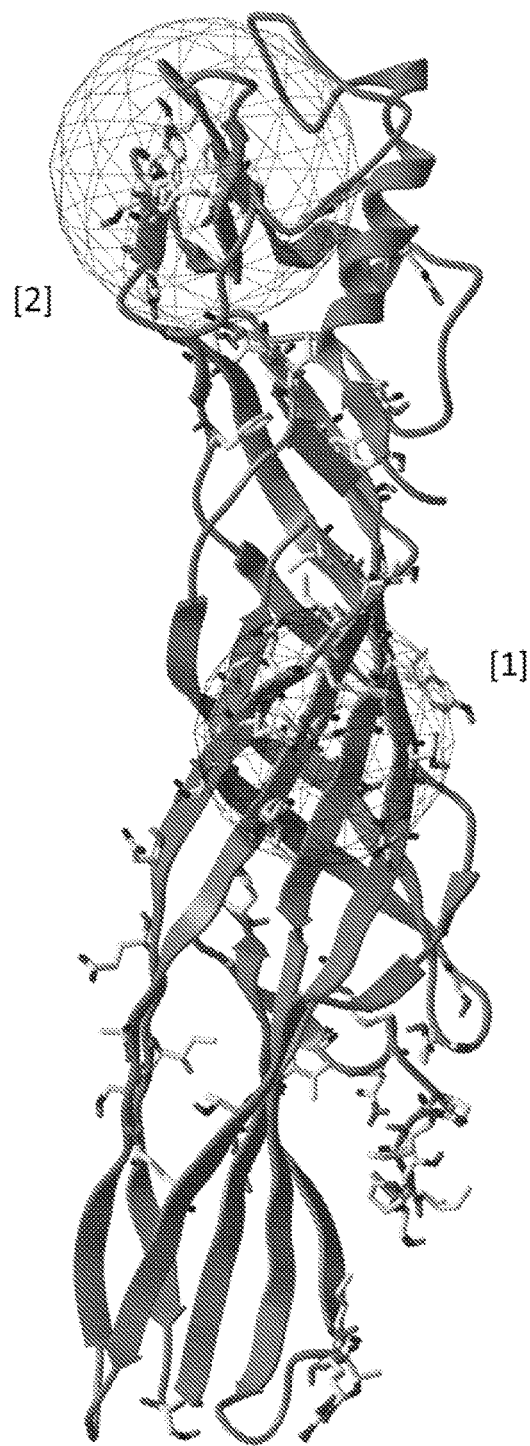
FIG. 2 illustrates a ribbon diagram of the atomic structure of a *Hemipteran* toxic protein of the present invention showing the relative positions of the result effective changes increasing toxic effects and/or broadening host range specificity compared to the relative position of the same amino acid position within a TIC807 or related protein. Two surface patches are illustrated by spheres encircling particular residue positions within the atomic structure in the ribbon diagram: [1] one sphere has an atomic radius of from about 9.2 to about 12.2 Angstroms from the beta carbon atom of S95 (relative to the S95 position as set forth in SEQ ID NO:2); [2] another sphere has an atomic radius of from about 9.2 to about 12.2 Angstroms from the beta carbon atom of P219 (relative to the P219 position as set forth in SEQ ID NO:2). Changes to the amino acids within the ribbon structure that fall within these spheres are result effective in causing increased toxic properties and broader host range toxic effects compared to a protein having a naturally occurring amino acid at that particular position.

This application describes eHTP's (engineered *Hemipteran* species toxic proteins). The eHTP's of the present invention are to be distinguished from proteins such as TIC807, TIC853, Cry51Aa1 and AXMI-171, which are known in the art and are not to be considered to be within the scope or definition of the term eHTP, as the prior art proteins are not engineered to exhibit improved toxic properties directed to one or more *Hemipteran* pest species and do not exhibit broad host range levels of inhibitory activity. eHTP's surprisingly and unexpectedly exhibit high levels of toxic activity against *Hemipteran* and related pest species. An additional feature of these eHTP's that is even more unexpected and surprising is the finding that these proteins exhibit broader host range toxic properties compared to progenitor proteins which provide the foundational basis for the eHTP's of the present invention. The foundational or baseline scaffold toxin proteins, such as TIC807 (SEQ ID NO:2), Cry51Aa1 (SEQ ID NO:8), TIC853 (SEQ ID NO:184), and AXMI-171 (SEQ ID NO:206) do not exhibit the breadth and scope of biological anti-*Hemipteran* activity or host range of the eHTP proteins of the present invention.

More than 2000 different amino acid sequence variants of *Hemipteran* toxic proteins derived from *Bacillus thuringiensis* species were tested to identify the specific amino acid insertions, substitutions, or deletions described herein which confer expanded *Hemipteran* species host range inhibitory spectrum and also provide dramatically increased *Hemipteran* species inhibitory activity when compared to the spectrum and activity of the baseline scaffold protein, TIC807, TIC853, and Cry51Aa1. Amino acid residues are identified in the baseline scaffold proteins that (a) can be modified to yield enhanced *Hemipteran* inhibitory spectrum and/or improved *Lygus* inhibitory activity relative to one or more of the scaffold proteins, (b) accumulate in surface patches of a folded insect inhibitory protein exhibiting the fold structure of one or more of the scaffold proteins, and/or (c) occur in specific positions of one or more of the scaffold protein amino acid sequence that are result effective in decreasing the resulting eHTP proteins' mean effective dose for controlling *Hemipteran* species and broadening the range of *Hemipteran* species that are affected by the eHTP protein.

The *Hemipteran* pest species are intended to mean insects that feed upon plants and plant tissues by slashing or piercing the outer surface of the target plant, and then consume macerated plant exudates pooling in the slash or pierce location by sucking or wicking the pooled exudates. Such insects include adults and nymphs, including but not limited to the following listing of plant bugs: the Family Miridae, cicadas from the Family Cicadidae, leafhoppers (e.g., *Empoasca* spp., *Amrasca* spp.) from the Family Cicadellidae, planthoppers from the families Fulgoroidea and Delphacidae, treehoppers from the Family Membracidae, psyllids from the Family Psyllidae, whiteflies from the Family Aleyrodidae, aphids from the Family Aphididae, phylloxera from the Family Phylloxeridae, mealybugs from the Family Pseudococcidae, scales from the families Coccidae, Diaspididae and Margarodidae, lace bugs from the Family Tingidae, stink bugs from the Family Pentatomidae, cinch bugs (e.g., *Blissus* spp.) and other seed bugs from the Family Lygaeidae, spittlebugs from the Family Cercopidae squash bugs from the Family Coreidae, and red bugs and cotton stainers from the Family Pyrrhocoridae. Other pests from the order Hemiptera include *Acrosternum hilare* (green stink bug), *Anasa tristis* (squash bug), *Blissus leucopterus leucopterus* (chinch bug), *Corythuca gossypii* (cotton lace bug), *Cyrtopeltis modesta* (tomato bug), *Dysdercus suturellus* (cotton stainer), *Euschistus serous* (brown stink bug), *Euschistus variolarius* (one-spotted stink bug), *Graptostethus* spp. (complex of seed bugs), *Leptoglossus corculus* (leaf-footed pine seed bug), *Lygus lineolaris* (tarnished plant bug), *Lygus hesperus* (Western tarnish plant bug), *Nezara viridula* (southern green stink bug), *Oebalus pugnax* (rice stink bug), *Oncopeltus fasciatus* (large milkweed bug), and *Pseudatomoscelis seriatus* (cotton fleahopper). More specifically, the Family Cicadellidae includes, but is not limited to the tribe Empoascini, e.g. *Amrasca biguttula*, *Amrasca devastans*, *Austroasca viridigrisea*, *Asymmetrasca decedens*, *Empoasca decipiens*, *Empoasca distinguenda*, *Empoasca dolichi*, *Empoasca fabae*, *Empoasca kerri*, *Empoasca kraemeri*, *Empoasca onukii*, *Empoasca sakaii*, *Empoasca smithi*, *Empoasca vitis*, *Jacobiasca lybica*, *Sonasasca solana*, tribe Erythroneurini, e.g. *Empoascanara nagpurensis*, *Thaiaassamensis*, *Zygnidia quyumi*, tribe Nirvaniae, e.g. *Sophonia rufofascia*, Family Delphacidae, e.g. *Nilapoarvata lugens, Sogatella furcifera, Unkanodes sapporonus*, and Family Lophopidae, e.g. *Zophiuma lobulata*.

eHTP's of the present invention contain one or more amino acid sequence modifications compared to one or more of the scaffold proteins, including substitutions and deletions, of amino acid residues at seventy-two (72) different amino acid positions. Such modifications provide eHTP's with increased toxicity and/or an enhanced inhibitory spectrum against *Hemipteran* insects when compared to one or more of the scaffold proteins which include but are not limited to TIC807 (SEQ ID NO:2), or related protein such as TIC807_M2 (SEQ ID NO:8), Cry51Aa1 (SEQ ID NO:182), and TIC853 (SEQ ID NO:184). eHTP's include, but are not limited to, modifications of at least one amino acid substitution or one amino acid deletion at any of these seventy-two positions, described as "X" in the amino acid sequence set forth as SEQ ID NO:180 but do not include the amino acid sequences of SEQ ID NO:2, SEQ ID NO:8, SEQ ID NO:182, or SEQ ID NO:184. eHTP's of the present invention also exhibit enhanced *Hemipteran* inhibitory spectrum and/or improved *Hemipteran* inhibitory activity when compared to the spectrum and activity of the baseline or scaffold proteins.

eHTP's include at least one amino acid modification of the relative positions of TIC807 (SEQ ID NO:2). eHTP's can also include at least two, three, four, or more of these aforementioned amino acid substitutions and/or deletions and can also include at least two, three, four, or more of these amino acid substitutions and/or deletions as well as a deletion of any three contiguous amino acids within residues 196-201 of SEQ ID NO:2. Accordingly, eHTP's include proteins set forth as SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:28, SEQ ID NO:30, SEQ ID NO:32, SEQ ID NO:34, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, SEQ ID NO:79, SEQ ID NO:80, SEQ ID NO:81, SEQ ID NO:82, SEQ ID NO:83, SEQ ID NO:84, SEQ ID NO:85, SEQ ID NO:86, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, SEQ ID NO:97, SEQ ID NO:98, SEQ ID NO:99, SEQ ID NO:100, SEQ ID NO:101, SEQ ID NO:102, SEQ ID NO:103, SEQ ID NO:104, SEQ ID NO:105, SEQ ID NO:106, SEQ ID NO:107, SEQ ID NO:108, SEQ ID NO:109, SEQ ID NO:110, SEQ ID NO:111, SEQ ID NO:112, SEQ ID NO:113, SEQ ID NO:114, SEQ ID NO:115, SEQ ID NO:116, SEQ ID NO:117, SEQ ID NO:118, SEQ ID NO:119, SEQ ID NO:120, SEQ ID NO:121, SEQ ID NO:122, SEQ ID NO:123, SEQ ID NO:124, SEQ ID NO:125, SEQ ID NO:126, SEQ ID NO:127, SEQ ID NO:128, SEQ ID NO:129, SEQ ID NO:130, SEQ ID NO:131, SEQ ID NO:132, SEQ ID NO:133, SEQ ID NO:134, SEQ ID NO:135, SEQ ID NO:136, SEQ ID NO:137, SEQ ID NO:138, SEQ ID NO:139, SEQ ID NO:140, SEQ ID NO:141, SEQ ID NO:142, SEQ ID NO:143, SEQ ID NO:144, SEQ ID NO:145, SEQ ID NO:146, SEQ ID NO:147, SEQ ID NO:148, SEQ ID NO:149, SEQ ID NO:150, SEQ ID NO:151, SEQ ID NO:152, SEQ ID NO:153, SEQ ID NO:154, SEQ ID NO:155, SEQ ID NO:156, SEQ ID NO:157, SEQ ID NO:158, SEQ ID NO:159, SEQ ID NO:160, SEQ ID NO:161, SEQ ID NO:162, SEQ ID NO:163, SEQ ID NO:164, SEQ ID NO:165, SEQ ID NO:166, SEQ ID NO:167, SEQ ID NO:168, SEQ ID NO:169, SEQ ID NO:170, SEQ ID NO:171, SEQ ID NO:172, SEQ ID NO:173, SEQ ID NO:174, SEQ ID NO:175, SEQ ID NO:176, SEQ ID NO:177, SEQ ID NO:178, SEQ ID NO:179, SEQ ID NO:202, and SEQ ID NO:204, and insect inhibitory fragments thereof.

eHTP's of the present invention exhibit any amino acid sequence different from any one or more of the scaffold proteins, including SEQ ID NO:2 (TIC807), in at least one amino acid position where the different amino acid residue either (i) has a relative amino acid solvent-accessibility of at least from about 15% to at least about 36% compared to the same residue positions in any one or more of the scaffold proteins; and/or (ii) is located within a distance of about 3 consecutive amino acid residues from an amino acid having at least from about 15% to at least about 36% relative solvent-accessibility compared to the corresponding amino acid residue positions in the primary amino acid sequence of one or more of the scaffold proteins, and exhibits broadened *Hemipteran* inhibitory spectrum and/or increased *Hemipteran* inhibitory activity when compared to the activity correlated with one or more of the scaffold proteins. The words "increased spectrum" are intended to mean, with reference to two different proteins exhibiting toxic effects to a particular single pest, the protein exhibiting increased spectrum exhibits toxic effects to that particular single pest as well as to one or more other pests within the same phylogenetic order or to one or more other pests in one or more different phylogenetic orders other than the order to which the particular single pest belongs. The words "increased *Hemipteran* inhibitory activity" are intended to mean that a particular protein exhibiting such increased activity requires, under standardized conditions, a lower amount of that protein to achieve a particular affect, such as mortality, stunting, morbidity, cessation of feeding, or another measureable phenotypic effect upon a particular single pest, than a control protein.

eHTP's exhibit an amino acid sequence that differs from one or more of the scaffold proteins, including particularly TIC807, in at least one amino acid residue located within at least one of the two different surface patches of a folded insect inhibitory protein (see FIG. 2 and Table 3 data). One surface patch is defined as including the amino acid residues encompassed within a sphere having an atomic radius of from about 9.2 to about 12.2 Angstroms (FIG. 2, sphere [1]) relative to the beta-carbon (Cb) atom of Ser95 as set forth in SEQ ID NO:2 when that protein is folded into a three dimensional structure under physiological conditions; which includes residues Thr93, Ser95, Ser97, Phe147, Gln149, Ser151, Asn180, Thr182, Val251, Gln253, and Ser255. As used herein, the phrase "Cb atom" refers to the beta-carbon atom in the amino acid residue side chain. The Cb atom is thus the first carbon in the protein side chain that is present in all amino acid residues with the exception of Glycyl residues. With reference to FIG. 1, eHTP's can include, but are not limited to, one or more conservative or non-conservative substitutions of surface patch [1] amino acid residues T93, S95, S97, F147, Q149, S151, N180, T182, V251, Q253, and S255 or the equivalent amino acids within one or more of the scaffold proteins, particularly SEQ ID NO:2 (TIC807). eHTP's can include, but are not limited to, one or more substitutions of surface patch [1] amino acid residues such as: T93A; S95A, S95V, S95L, or S95I; F147T, F147C, F147D, F147G, F147E, F147Y, F147M, F147N, F147Q, F147H, F147R, F147W, F147P, F147A, F147V, F147L, or F147I; Q149A, Q149C, Q149F, Q149E or Q149D; S151A; N180D; T182A; V251E or V251A, and/or Q253R. The other or second surface patch that has been identified as amino acid residues that are receptive to modifications which are result effective in conferring improved *Hemipteran* inhibitory bioactivity in the form of eHTP's of the present invention is defined as including the amino acid residues encompassed within a sphere having an atomic radius of from about 9.2 to about 12.2 Angstroms (FIG. 2, sphere [2]) relative to the beta-carbon atom of Pro219 or the equivalent amino acid position in one or more of the scaffold proteins, particularly as set forth in SEQ ID NO:2, when any one of the applicable scaffold proteins is folded into a three dimensional structure under physiological conditions, which includes residues Val10, Ile14, Asn22, Asn23, Gly24, Ile25, Gln26, Gly27, Phe30, Gln38, Ile39, Asp40, Thr41, Ile43, Ser193, Thr194, Glu195, His196, Tyr197, Ser198, His199, Tyr200, Ser201, Gly202, Tyr203, Pro204, Ile205, Leu206, Thr207, Trp208, Ile209, Ser210, Tyr216, Ser217, Gly218, Pro219, Pro220, Met221, Ser222, Trp223, Tyr224, Phe225, Asn239, and Val244. Such eHTP's can include, but are not limited to, one or more conservative or non-conservative amino acid residues substitutions and/or one or more amino acid deletions within surface patch [2] including Val10, Ile14, Asn22, Asn23, Gly24, Ile25, Gln26, Gly27, Phe30, Gln38, Ile39, Asp40, Thr41, Ile43, Ser193, Thr194, Glu195, His196, Tyr197, Ser198, His199, Tyr200, Ser201, Gly202, Tyr203, Pro204, Ile205, Leu206, Thr207, Trp208, Ile209, Ser210, Tyr216, Ser217, Gly218, Pro219, Pro220, Met221, Ser222, Trp223, Tyr224, Phe225, Asn239, and Val244 of SEQ ID NO:2 (TIC807). eHTP's can include, but are not limited to, one or more substitutions and/or deletions within the amino acid residues located within surface patch [2] such as: a deletion of any three contiguous amino acid residues in the sequence His196, Tyr197, Ser198, His199, Tyr200, Ser201; Ser217Asn, Ser217Gln, Ser217Arg; and/or Pro219Arg, Pro219Asn, Pro219Gln. eHTP's can include, but are not limited to, one or more amino acid residue substitutions and/or deletions within surface patch [2] such as: a deletion of any three contiguous HisTyrSer residues in the sequence His196, Tyr197, Ser198, His199, Tyr200, Ser201; Ser217Asn, Ser217Gln, Ser217Arg; and/or Pro219Arg, Pro219Asn, Pro219Gln. An eHTP can have at least one amino acid modification in each of the two aforementioned surface patches of the folded insect inhibitory protein. eHTP can have one, or a combination of more than one modification at residues T93, S95, F147, Q149, S151, N180, T182, H196, Y197, S198, H199, Y200, S201, W208, S217, P219, W223, N239, V244, or V251 relative to SEQ ID NO:2 (TIC807). Conservative amino acid changes can be made by substituting an acidic, basic, neutral polar, or neutral non-polar-type amino acid with another amino acid of the same type. Non-conservative amino acid changes can be made by substituting an acidic, basic, neutral polar, or neutral non-polar amino acid-type with an amino acid of a different type. Furthermore, of the eHTP proteins listed in Table 4B, all 267 are amino acid sequence variants that exhibit increased toxicity to *Lygus* spp. when compared to one or more of the scaffold proteins, including scaffold protein TIC807. Only ten of these amino acid sequence variants exhibit modified amino acid residues compared to one or more of the scaffold proteins that are positioned outside of the two referenced surface patches.

The prior art teaches solubility problems associated with the scaffold proteins. eHTP's exhibit improved solubility compared to the scaffold proteins, and generally exhibit increased solubility at a pH of less than 9.0, in contrast to the observed solubility profile of one or more of the scaffold proteins. This increased solubility at more physiological pH is evident when the eHTP is expressed in *E. coli*, in a plant cell, in a plant cell cytoplasm, a plant cell apoplast, or in or targeted for import into a plastid of a plant cell. Amino acid modifications that improve solubility relative to one or more of the scaffold proteins, including SEQ ID NO:2 (TIC807) include but are not limited to, substitution of a lysine amino acid residue at one or more of the following amino acid positions in TIC807 or the applicable residue in any of the other scaffold proteins: 58, 59, 198, 199, 201, or 202; or, substitution of a glutamic acid amino acid residue at one or more of amino acid positions 198, 248 or 301; or, substitution of a arginine amino acid residue at one or more of amino acid positions 246, 250 or 253.

Insect inhibitory compositions comprising the above described eHTP's are also provided. Such compositions may further comprise at least one additional insect inhibitory agent different from the eHTP included in the composition. The insect inhibitory agent is selected from any number of insect inhibitory agents including an insect inhibitory protein, an insect inhibitory dsRNA molecule, and one or more chemical agents useful in controlling insect pests. Examples of additional inhibitory agents includes, but are not limited to, a TIC1415 protein, a dsRNA directed towards *Hemipteran* orthologs of Nilaparvata lugens V-ATPase-E, 21E01, a dsRNA directed towards *Hemipteran* orthologs of actin ortholog, ADP/ATP translocase, α-tubulin, ribosomal protein L9 (RPL9) or V-ATPase A subunit, AXMI-171 (US20100298207A1), Cry3A, Cry4Aa, Cry11Aa, and Cyt1Aa, DIG11, DIG5, Cry7, eCry3.1Ab, mCry3A, Cry8, Cry34/Cry35, Cry3, DIG2, Cry1, Cry1A.105, Cry2, Cry1F, VIP3, 5307, and Cry9. Chemical agents useful in controlling *Hemipteran* species include but are not limited to pyrethrins and synthetic pyrethroids; oxadizine derivatives; chloronicotinyls; nitroguanidine derivatives; triazoles; organophosphates; pyrrols; pyrazoles; phenyl pyrazoles; diacylhydrazines; biological/fermentation products; and carbamates. Known pesticides within these categories are listed in The Pesticide Manual, 11th Ed., C. D. S. Tomlin, Ed., British Crop Protection Council, Farnham, Surry, UK (1997).

Pyrethroids that are useful in the present composition include pyrethrins and synthetic pyrethroids. The pyrethrins that are preferred for use in the present method include, without limitation, 2-allyl-4-hydroxy-3-methyl-2-cyclopenten-1-one ester of 2,2-dimethyl-3-(2methyl propenyl)-cyclopropane carboxylic acid, and/or (2-methyl-1-propenyl)-2-methoxy-4-oxo-3-(2 propenyl)-2-cyclopenten-1-yl ester and mixtures of cis and trans isomers thereof (Chemical Abstracts Service Registry Number ("CAS RN") 8003-34-7).

Synthetic pyrethroids that are preferred for use in the present invention include (s)-cyano(3-phenoxyphenyl) methyl 4-chloro alpha (1-methylethyl)benzeneacetate (fenvalerate, CAS RN 51630-58-1), (S)-cyano (3-phenoxyphenyl) methyl (S)-4-chloro-alpha-(1-methylethyl) benzeneacetate (esfenvalerate, CAS RN 66230-04-4), (3-phenoxyphenyl)-methyl(+)cis-trans-3-(2,2-dichoroethenyl)-2,2-dimethylcyclopropanecarboxylate (permethrin, CAS RN 52645-53-1), (±) alpha-cyano-(3-phenoxyphenyl)

methyl(+)-cis,trans-3-(2,2-dichloroethenyl)-2,2-dimethyl-cyclopropane carboxylate (cypermethrin, CAS RN 52315-07-8), (beta-cypermethrin, CAS RN 65731-84-2), (theta cypermethrin, CAS RN 71697-59-1), S-cyano (3-phenoxy-phenyl) methyl (±) cis/trans 3-(2,2-dichloroethenyl) 2,2 dimethylcyclopropane carboxylate (zeta-cypermethrin, CAS RN 52315-07-8), (s)-alpha-cyano-3-phenoxybenzyl (IR,3R)-3-(2,2-dibromovinyl)-2,2-dimethyl cyclopropan-ecarboxylate (deltamethrin, CAS RN 52918-63-5), alpha-cyano-3-phenoxybenzyl 2,2,3,3,-tetramethyl cyclopropoan-ecarboxylate (fenpropathrin, CAS RN 64257-84-7), (RS)-alpha-cyano-3-phenoxybenzyl(R)-2-[2-chloro-4-(trifluoromethyl)anilino]-3-methylbutanoate (tau-fluvalinate, CAS RN 102851-06-9), (2,3,5,6-tetrafluoro-4-methylphenyl)-methyl-(1 alpha, 3 alpha)-(Z)-(±)-3-(2-chloro-3,3,3-trifluoro-1-propenyl)-2,2-dimethylcyclopropanecarboxylate (tefluthrin, CAS RN 79538-32-2), (±)-cyano (3-phenoxyphenyl) methyl (±)-4-(difluoromethoxy)-alpha-(1-methyl ethyl) benzeneacetate (flucythrinate, CAS RN 70124-77-5), cyano(4-fluoro-3-phe-noxyphenyl)methyl 3-[2-chloro-2-(4-chlorophenyl)ethe-nyl]-2,2-dimethylcyclopropanecarboxylate (flumethrin, CAS RN 69770-45-2), cyano(4-fluoro-3-phenoxyphenyl) methyl 3-(2,2-dichloroethenyl)-2,2-dimethyl-cyclopropane-darboxylate (cyfluthrin, CAS RN 68359-37-5), (beta cyflu-thrin, CAS RN 68359-37-5), (transfluthrin, CAS RN 118712-89-3), (S)-alpha-cyano-3-phenoxybenzyl(Z)-(IR-cis)-2,2-dimethyl-3-[2-(2,2,2-trifluoro-trifluoromethyl-ethoxycarbonyl)vinyl]cyclopropane carboxylate (acrinath-rin, CAS RN 101007-06-1), (IR cis) S and (IS cis) R enantiomer isomer pair of alpha-cyano-3-phenoxybenzyl-3-(2,2dichlorovinyl)-2,2-dimethylcyclopropane carboxylate (alpha-cypermethrin, CAS RN 67375-30-8), [IR,3S)3(1'RS) (1',2',2',2'-tetrabromoethyl)]-2,2-dimethyl cyclopropanecar-boxylic acid (s)-alpha-cyano-3-phenoxybenzyl ester (tral-omethrin, CAS RN 66841-25-6), cyano-(3-phenoxyphenyl) methyl 2,2-dichloro-1-(4-ethoxyphenyl)cyclopropane car-boxylate (cycloprothrin, CAS RN 63935-38-6), [1α,3α(Z)]-(±)-cyano-(3-phenoxyphenyl)methyl 3-(2-chloro-3,3,3-trif-luoro-1-propenyl)-2,2-cimethylcyclopropanecarboxylate (cyhalothrin, CAS RN 68085-85-8), [1 alpha (s), 3 alpha (z)]-cyano(3-phenoxyphenyl) methyl-3-(2-chloro-3,3,3-trif-luoro-1-propenyl)-2,2-dimethylcyclopropane carboxylate (lambda cyhalothrin, CAS RN 91465-08-6), (2-methyl [1,1'-biphenyl]-3-yl) methyl 3-(2-chloro-3,3,3-trifluoro-1-prope-nyl)-2,2-dimethyl-cyclopropanecarboxylate (bifenthrin, CAS RN 82657-04-3), 5-1-benzyl-3-furylmethyl-d-cis(1R, 3S,E)2,2-dimethyl-3-(2-oxo,-2,2,4,5 tetrahydro thiophe-nylidenemethyl)cyclopropane carboxylate (kadethrin, RU15525, CAS RN 58769-20-3), [5-(phenyl methyl)-3-furanyl]-3-furanyl 2,2-dimethyl-3-(2-methyl-1-propenyl) cyclopropane carboxylate (resmethrin, CAS RN 10453-86-8), (1R-trans)-[5-(phenylmethyl)-3-furanyl]methyl 2,2-dim-ethyl-3-(2-methyl-1-propenyl)cyclopropanecarboxylate (bioresmethrin, CAS RN 28434-01-7), 3,4,5,6-tetra hydro-phthalimidomethyl-(IRS)-cis-trans-chrysanthemate (tetram-ethrin, CAS RN 7696-12-0), 3-phenoxybenzyl-d,l-cis,trans 2,2-dimethyl-3-(2-methylpropenyl) cyclopropane carboxy-late (phenothrin, CAS RN 26002-80-2); (empenthrin, CAS RN 54406-48-3); (cyphenothrin; CAS RN 39515-40-7), (prallethrin, CAS RN 23031-36-9), (imiprothrin, CAS RN 72963-72-5), (RS)-3-allyl-2-methyl-4-oxcyclopent-2-enyl-(1A,3R; 1R,3S)-2,2-dimethyl-3-(2-methylprop-1-enyl) cyclopropane carboxylate (allethrin, CAS RN 584-79-2), (bioallethrin, CAS RN 584-79-2), and (ZXI8901, CAS RN 160791-64-0). It is believed that mixtures of one or more of the aforementioned synthetic pyrethroids can also be used in the present invention. Particularly preferred synthetic pyre-throids are tefluthrin, lambda cyhalothrin, bifenthrin, per-methrin and cyfluthrin. Even more preferred synthetic pyre-throids are tefluthrin and lambda cyhalothrin, and yet more preferred is tefluthrin.

Insecticides that are oxadiazine derivatives are useful in the subject invention. The oxadizine derivatives that are preferred for use in the present invention are those that are identified in U.S. Pat. No. 5,852,012. More preferred oxadi-azine derivatives are 5-(2-chloropyrid-5-ylmethyl)-3-methyl-4-nitro iminoperhydro-1,3,5-oxadiazine, 5-(2-chlo-rothiazo-5-ylmethyl)-3-methyl-4-nitroiminoperhydro-1,3,5-oxadiazine, 3-methyl-4-nitroimino-5-(1-oxido-3-pyridinomethyl) perhydro-1,3,5-oxadiazine, 5-(2-chloro-1-oxido-5-pyridiniomethyl)-3-methyl-4-nitroiminoperhydro-1,3,5-oxidiazine; and 3-methyl-5-(2-methylpyrid-5-ylmethyl)-4-nitroiminoperhydro-1,3,5-oxadiazine. Even more preferred is thiamethoxam (CAS RN 153719-23-4).

Chloronicotinyl insecticides are also useful in the subject invention. Chloronicotinyls that are preferred for use in the subject composition are described in U.S. Pat. No. 5,952,358, and include acetamiprid ((E)-N-[(6-chloro-3-pyridinyl) methyl]-N'-cyano-N-methyleneimidamide, CAS RN 135410-20-7), imidacloprid (1-[(6-chloro-3-pyridinyl) methol]-N-nitro-2-imidazolidinimime, CAS RN 138261-41-3), and nitenpyram (N-[(6-chloro-3-pyridinyl)methyl]-N-ethyl-N'-methyl-2-nitro-1,1-ethenediamine, CAS RN 120738-89-8).

Nitroguanidine insecticides are useful in the present invention. Such nitroguanidines can include those described in U.S. Pat. Nos. 5,633,375, 5,034,404 and 5,245,040.

Pyrrols, pyrazoles and phenyl pyrazoles that are useful in the present invention include those that are described in U.S. Pat. No. 5,952,358. Preferred pyrazoles include chlo-rfenapyr (4-bromo-2-(4-chlorophenyl)-1-ethoxymethyl-5-trifluoromethylpyrrole-3-carbonitrile, CAS RN 122453-73-0), fenpyroximate ((E)-1,1-dimethylethyl-4[[[[(1,3-dimethyl-5-phenoxy-1H-pyrazole-4-yl)methylene]amino] oxy]methyl]benzoate, CAS RN 111812-58-9), and tebufenpyrad (4-chloro-N[[4-1,1-dimethylethyl)phenyl] methyl]-3-ethyl-1-methyl-1H-pyrazole-5-carboxamide, CAS RN 119168-77-3). A preferred phenyl pyrazole is fipronil (5-amino-[2,6-dichloro-4-(trifluoromethyl)phenyl]-4-[(1R,S)-(trifluoromethyl)sulfinyl]-1H-pyrazole-3-carbo-nitrile, CAS RN 120068-37-3).

Diacylhydrazines that are useful in the present invention include halofenozide (4-chlorobenzoate-2-benzoyl-2-(1,1-dimethylethyl)-hydrazide, CAS RN 112226-61-6), methoxyfenozide (RH-2485; N-tert-butyl-N'-(3-methoxy-o-toluoyl)-3,5-xylohydrazide, CAS RN 161050-58-4), and tebufenozide (3,5-dimethylbenzoic acid 1-(1,1-dimethyl-ethyl)-2,(4-ethylbenzoyphydrazide, CAS RN 112410-23-8).

Triazoles, such as amitrole (CAS RN 61-82-5) and tri-azamate are useful in the method of the present invention. A preferred triazole is triazamate (ethyl [[1-[(dimethylamino) carbonyl]-3-(1,1-dimethylethyl)-1H-1,2,4-triazol-5-yl]thio] acetate, CAS RN 112143-82-5).

Biological/fermentation products, such as avermectin (ab-amectin, CAS RN 71751-41-2) and spinosad (XDE-105, CAS RN 131929-60-7) are useful in the present invention.

Organophosphate insecticides are also useful as one of the components of the present invention. Preferred organo-phophate insecticides include acephate (CAS RN 30560-19-1), chlorpyrifos (CAS RN 2921-88-2), chlorpyrifos-methyl (CAS RN 5598-13-0), diazinon (CAS RN 333-41-5), fenamiphos (CAS RN 22224-92-6), and malathion (CAS RN 121-75-5).

In addition, carbamate insecticides are useful in the subject invention. Preferred carbamate insecticides are aldicarb (CAS RN 116-06-3), carbaryl (CAS RN 63-25-2), carbofuran (CAS RN 1563-66-2), oxamyl (CAS RN 23135-22-0) and thiodicarb (CAS RN 59669-26-0).

When a chemical insecticide is described herein, it is to be understood that the description is intended to include salt forms of the insecticide as well as any isomeric and/or tautomeric form of the insecticide that exhibits the same insecticidal activity as the form of the insecticide that is described.

The chemical insecticides that are useful in the present invention can be of any grade or purity that pass in the trade as such insecticide. Other materials that accompany the insecticides in commercial preparations as impurities can be tolerated in the subject invention and compositions, as long as such other materials do not destabilize the composition or significantly reduce or destroy the activity of any of the insecticide components or the transgenic event against the target pest(s). One of ordinary skill in the art of the production of insecticides can readily identify those impurities that can be tolerated and those that cannot.

eHTP's are related by amino acid modifications such that the modified proteins exhibit enhanced *Hemipteran* inhibitory spectrum and/or improved *Hemipteran* inhibitory activity against *Lygus* spp., *Empoasca* spp. and/or *Amrasca* spp. compared to the parent protein, TIC807. The phrases "more active", "improved activity", "enhanced specificity", "increased toxic potency", "increased toxicity", "improved *Hemipteran* inhibitory activity, "enhanced *Hemipteran* inhibitory activity", "improved *Lygus, Empoasca* and/or *Amrasca* inhibitory activity", "greater *Lygus, Empoasca* and/or *Amrasca* inhibitory activity", "greater *Hemipteran* inhibitory activity" and "enhanced *Lygus, Empoasca* and/or *Amrasca* inhibitory spectrum" and "enhanced *Hemipteran* inhibitory spectrum" refer to a comparison of the activity of an eHTP and of the activity of a TIC807 (SEQ ID NO:2), TIC807_M2 (SEQ ID NO:8), Cry51Aa1 (SEQ ID NO:182), TIC853 (SEQ ID NO:184), and/or a AXMI-171 (SEQ ID NO:206) protein against a *Hemipteran* insect, wherein activity attributed by the eHTP of the present invention is greater than the activity attributed to the TIC807 protein (SEQ ID NO:2), TIC807_M2 (SEQ ID NO:8), Cry51Aa1 (SEQ ID NO:182), TIC853 (SEQ ID NO:184), and/or a AXMI-171 (SEQ ID NO:206) protein. eHTP's provided herein exhibit enhanced *Hemipteran* inhibitory spectrum and/or improved or greater *Hemipteran* inhibitory activity when compared to the *Bacillus thuringiensis* proteins of SEQ ID NO:2, SEQ ID NO:8, SEQ ID NO:182, and SEQ ID NO:184, where the *Hemipteran* pest species include *Lygus hesperus, Lygus lineolaris, Empoasca fabae*, and *Amrasca devastans*. *Amrasca devastans* is also called *Amrasca biguttula biguttula*. eHTP's exhibiting enhanced insect inhibitory spectrum and/or improved insect inhibitory activity compared to TIC807 can be identified by many different methods. In general, exemplary and non-limiting methods for identifying eHTP proteins can comprise:

(1) administering identical amounts of a test eHTP and of control TIC807 (SEQ ID NO:2), TIC807_M2 (SEQ ID NO:8), Cry51Aa1 (SEQ ID NO:182), TIC853 (SEQ ID NO:184), and/or an AXMI-171 (SEQ ID NO:206) protein to a test insect under controlled assay conditions; and, measuring and comparing the potency of the test and control proteins; and/or, (2) determining the protein doses (e.g., protein concentration in diet) of a test eHTP and of control TIC807 (SEQ-ID NO:2), TIC807_M2 (SEQ ID NO:8), Cry51Aa1 (SEQ ID NO:182), TIC853 (SEQ ID NO:184), and/or an AXMI-171 (SEQ ID NO:206) protein which elicit equivalent insect population responses under controlled assay conditions (i.e. obtaining a dose response curve).

In the second approach, a statistically robust dose response value used for comparison would be the median lethal concentration (LC50) required to kill 50% of a test population. However, in certain embodiments, other values including but not limited to, a median inhibitory concentration ("IC50") required to result in 50% growth inhibition of a test population can be used. In this context, "growth inhibition" can comprise stunting and/or inhibition of *Hemipteran* development.

As used herein, the phrase "an insect inhibitory amount", refers to an amount of a composition containing an agent that is effective in achieving any measurable inhibition of insect viability, growth, insect development, insect reproduction, insect feeding behavior, insect mating behavior and/or any measurable decrease in the adverse effects caused by insect feeding on a composition containing the agent. Similarly, a "*Hemipteran* inhibitory amount" refers to an amount of a protein of the present invention alone or with other agents targeting the applicable *Hemipteran* species for control, that results in any measurable inhibition of target insects belonging to the order Hemiptera related to viability, growth, development, reproduction, feeding behavior, mating behavior, and or any measurable decrease in the adverse effects caused by *Hemipteran* insects feeding on a plant. Likewise, "*Lygus, Empoasca* and/or *Amrasca* inhibitory amount" refers to an amount of a composition containing one or more proteins of the present invention, i.e., eHTP's, or other agent that results in any measurable inhibition, viability, growth, development, reproduction, feeding behavior, mating behavior and/or any measurable decrease in the adverse effects caused by *Lygus, Empoasca* and/or *Amrasca* feeding on a composition containing that eHTP. As used herein in the context of an eHTP, an "enhanced *Hemipteran* inhibitory activity or "greater enhanced *Hemipteran* inhibitory activity" refers to any measurable increase in the inhibition of *Hemipteran* viability, growth, development, reproduction, feeding behavior, mating behavior and/or any measurable decrease in the adverse effects caused by *Hemipteran* feeding on a composition containing that eHTP relative to the corresponding inhibitory activity observed with any one or more of the scaffold proteins, including TIC807, Cry51Aa1 (SEQ ID NO:182), TIC853 (SEQ ID NO:184), and/or AXMI-171 (SEQ ID NO:206) proteins. Likewise, "enhanced *Lygus, Empoasca* and/or *Amrasca* inhibitory activity" or "greater enhanced *Lygus, Empoasca* and/or *Amrasca* inhibitory activity" refers to any measurable increase in the inhibition, viability, growth, development, reproduction, feeding behavior, mating behavior and/or any measurable decrease in the adverse effects caused by the presence of one or more eHTP of the present invention in a composition or plant provided in the diet of *Lygus, Empoasca* and/or *Amrasca* relative to the corresponding inhibitory activity observed with an equivalent composition or plant containing only an applicable amount of one or more of the scaffold proteins, including but not limited to TIC807 (SEQ ID NO:2), Cry51Aa1 (SEQ ID NO:182), TIC853 (SEQ ID NO:184), and/or AXMI-171 (SEQ ID NO:206) proteins.

As used herein in the context of an eHTP, an "enhanced *Lygus, Empoasca* and/or *Amrasca* inhibitory spectrum" refers to any measurable increase in the inhibition of a specific *Lygus* spp., *Empoasca* spp. and/or *Amrasca* spp.

viability, growth, development, reproduction, feeding behavior, mating behavior and/or any measurable decrease in the adverse effects caused by that Lygus spp., Empoasca spp. and/or Amrasca spp. feeding on a plant relative to the corresponding inhibition of that specific Lygus spp., Empoasca spp. and/or Amrasca spp. observed with the TIC807 protein. In certain embodiments, eHTP provided herein exhibit an enhanced Lygus inhibitory spectrum relative to TIC807 in that those eHTP's can provide increased inhibition of Lygus lineolaris.

An eHTP provided herein can exhibit from about 2 to about 260 fold greater Lygus, Empoasca and/or Amrasca inhibitory activity against a Lygus, Empoasca and/or Amrasca pest species than a protein of SEQ ID NO:2 (TIC807), SEQ ID NO:8 (TIC807_M2), SEQ ID NO:182 (Cry51Aa1), SEQ ID NO:184 (TIC853), and SEQ ID NO:206 (AXMI-171). An eHTP provided herein can exhibit from about 3, 4, 5, 7, 8, 10, 12, 15, 20, 25, 27, 30, 38, 46, 50, 52, 54, 66, 91, 122, 186, 243, or 262 fold greater Lygus, Empoasca and/or Amrasca inhibitory activity against a Lygus, Empoasca and/or Amrasca pest species than a protein of SEQ ID NO:2 (TIC807), SEQ ID NO:8 (TIC807_M2), SEQ ID NO:182 (Cry51Aa1), SEQ ID NO:184 (TIC853), and SEQ ID NO:206 (AXMI-171).

eHTP's can exhibit an enhanced target pest inhibitory spectrum and/or improved target pest inhibitory activity over SEQ ID NO:2 (TIC807), SEQ ID NO:8 (TIC807_M2), SEQ ID NO:182 (Cry51Aa1), SEQ ID NO:184 (TIC853), and/or a SEQ ID NO:206 (AXMI-171) by causing mortality:
 (i) at a dose of about 0.3 µg/mL to about 70 µg/mL against a Lygus hesperus insect species,
 (ii) at a dose of about 0.85 µg/mL to about 100 µg/mL against a Lygus lineolaris insect species,
 (iii) measuring at an LC50 value of about 0.3 to about 70 µg/mL against Lygus hesperus,
 (iv) measuring at an LC50 value of about 0.85 to about 100 µg/mL against Lygus lineolaris, or
 (v) measuring at an LC50 value of more than two-fold lower the LC50 value of TIC807, SEQ ID NO:8, SEQ ID NO:182 (Cry51Aa1), SEQ ID NO:184 (TIC853), and/or a SEQ ID NO:206 (AXMI-171) against Lygus spp, Emrasca spp. and/or Amrasca spp., or
 (vi) at a dose of about 0.69 µg/mL to about 500 µ/mL against a Amrasca devastans or Empoasca fabae insect species, or
 (vii) measuring at an LC50 value of about 3.5 to about 15 µg/mL against Amrasca devastans and/or Empoasca fabae.

Table 4A and 4B tabulate the exemplary eHTP's of the present invention with Amrasca and Lygus spp. mortality data. Mortality data available for Lygus spp. and Amrasca spp. are reported either as (a) a µg/mL LC50 value, or as (b) a % mortality at doses of about 1 to about 3 µg/mL for L. hesperus or about 100 µg/mL protein for L. lineolaris, and about 0.69 to 500 µg/mL for Amrasca devastans. The fold increased toxicity compared to TIC807 (SEQ ID NO:2) and TIC807_M2 (SEQ ID NO:8) is provided for exemplary eHTP's where LC50 values were determined.

The eHTP's of the present invention are particularly useful in controlling insects of the order Hemiptera compared to the scaffold proteins. Lygus lineolaris required high doses of TIC807 protein (e.g., in excess of 100 µg/mL) to elicit mortality. The dose response curve for one eHTP of the present invention TIC807_M8 (SEQ ID NO:16), an eHTP that exhibits remarkably improved toxic effects against both L. lineolaris and L. hesperus, but against L. lineolaris the eHTP exhibits a calculated LC50 value of 223 µg/mL. It has not been possible previously to achieve a protein concentration toxic dose that can elicit greater than 50% mortality against L. lineolaris species because providing significantly large doses of TIC807 and TIC807_M2 protein in excess of 1000 µg/mL in the diet has not been possible. Therefore, LC50 values against L. lineolaris for TIC807 and TIC807_M2 (SEQ ID NO:8) proteins were not determined, but rather estimated as greater than (>) 223 µg/mL (See Tables 1 and 3, Example 4, and FIG. 1B).

Iterative design refers to a semi-random approach for developing and selecting eHTP's including a combination of engineering, testing, and selecting (not necessarily in that order) (see Examples 1 through 4). The word "engineering" is intended to include identifying relevant residues to modify, cloning, and expressing eHTP's described herein. The word "testing" is intended to refer to comparing the Hemipteran activity of an eHTP to the activity of a scaffold protein such as TIC807 (SEQ ID NO:2), TIC807_M2 (SEQ ID NO:8), Cry51Aa1 (SEQ ID NO:182), and/or TIC853 (SEQ ID NO:184); or, comparing an eHTP of the present invention against another protein such as AXMI-171 (SEQ ID NO:206). The word "selecting" is intended to refer to the act of identifying improved variant proteins of the present invention, i.e., eHTP's, and the applicable amino acid residues for "engineering".

Iterative design includes the elucidation of the atomic structure of proteins of the present invention (for example, as set forth in FIG. 2) and the use of the atomic structure to guide and complement semi-random approaches of "selecting" amino acid residues to modify for "engineering", and in this case, has included the identification of amino acid residues at loops and at surface exposed regions of a folded insect inhibitory scaffold protein such as TIC807, TIC853, and Cry51Aa1 that can be modified to confer improvements to insect inhibitory spectrum and activity. Such amino acid residues at loops and at surface exposed regions are selected for "engineering". In this case, iterative design has included the identification of two different regions within the three dimensional structure of the scaffold protein that harbor an accumulation of relevant amino acid residues that, when modified to contain amino acid residues other than those appearing at those positions in the naturally occurring scaffold protein, result in one or more of the eHTP proteins of the present invention.

Figure 3:
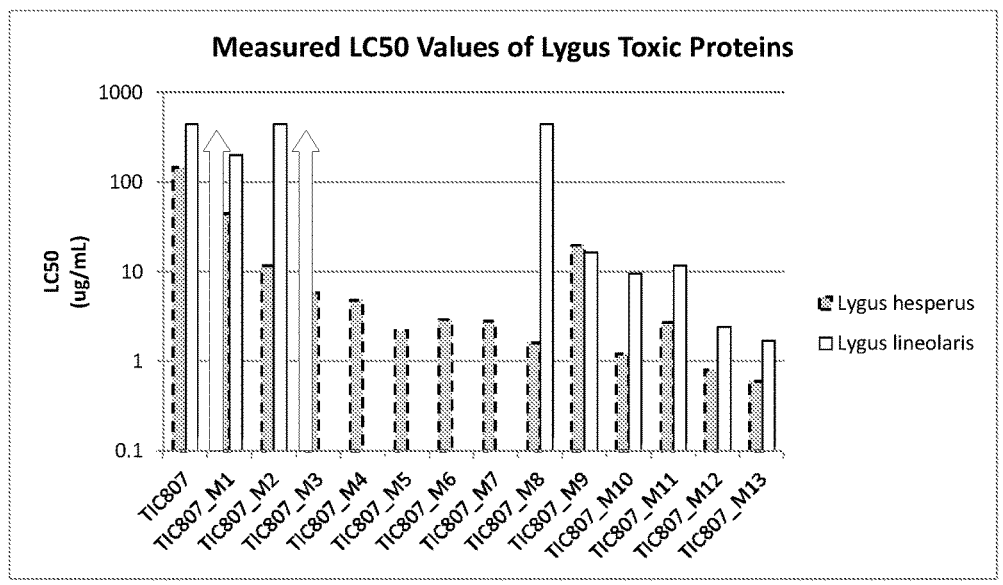
FIG. 3 is a chart view illustrating the population mortality of *Lygus* species for thirteen different eHTP's compared to each other and to the naturally occurring TIC807 protein.

Initially the scaffold protein TIC807 (SEQ ID NO:2) used in this process of iterative design, and 267 different eHTP's were discovered that exhibited increased Lygus spp. inhibitory activity compared to the scaffold protein TIC807. TIC807_M8 (SEQ ID NO:16) was discovered in early rounds of the design process. Subsequent rounds of iterative engineering-testing-selecting led to the discovery of other eHTP proteins that exhibited yet greater levels of toxicity against Lygus species and also exhibited a broader host range of toxic effects when compared to the scaffold protein. Seven variants (eHTP's) exhibited significantly higher levels of increased toxicity against both Lygus species (L. hesperus and L. lineolaris) when compared to TIC807. LC50 values for these seven, and other, eHTP's constructed herein were determined against Lygus hesperus and Lygus lineolaris species and compared to LC50 values for scaffold proteins, particularly TIC807. The results are shown in Table 1, and FIG. 3 is a bar chart showing graphically the results observed as tabulated in Table 1.

TABLE 1

LC50 values of select eHTP's compared to TIC807

| SEQ ID NO: | Toxin | Lygus hesperus | | Lygus lineolaris | |
|---|---|---|---|---|---|
| | | LC50 value (µg/mL) | Toxicity (fold increase) | LC50 value (µg/mL) | Toxicity (fold increase) |
| 2 | TIC807 | 73 | 1 | >223* | 1 |
| 6 | TIC807_M1 | 23 | 3 | 100 | ≥2 |
| 8 | TIC807_M2 | 5.9 | 12 | >223* | ~1 |
| 10 | TIC807_M3 | 2.9 | 25 | ND | — |
| 12 | TIC807_M4 | 2.4 | 30 | ND | — |
| 14 | TIC807_M5 | 1.1 | 66 | ND | — |
| 18 | TIC807_M6 | 1.45 | 50 | ND | — |
| 20 | TIC807_M7 | 1.4 | 52 | ND | — |
| 16 | TIC807_M8 | 0.8 | 91 | 223 | ≥1 |
| 28 | TIC807_M9 | 9.9 | 7 | 8.3 | ≥27 |
| 30 | TIC807_M10 | 0.6 | 122 | 4.8 | ≥46 |
| 32 | TIC807_M11 | 1.35 | 54 | 5.9 | ≥38 |
| 36 | TIC807_M12 | 0.4 | 182 | 1.2 | ≥186 |
| 34 | TIC807_M13 | 0.3 | 243 | 0.85 | ≥262 |

ND = Not Determined. LC50 values are determined by presenting 8-10 different protein concentrations to a population of newly hatched *Lygus* nymphs, allowing nymphs to feed for 5 days, and then scoring for mortality over the dose range provided.
*Toxicity, displayed in terms of a multiple of increased activity compared to the level observed against *Lygus hesperus* using the observed LD50 for TIC807 as the baseline value of 1. Significantly large amounts of protein in excess of 1000 ug/mL have not been possible to provide in *Lygus* diet in order to complete the high range of toxicity dose response to *Lygus lineolaris*. Therefore, an LC50 value was not determined for TIC807 or TIC807_M2. Instead, a 4-dose LC50 estimation in the low range was performed verifying that expected LC50 values for TIC807 and TIC807_M2 are greater than 223 µg/mL.

With reference to Table 1, the iterative design process has provided a means for identifying proteins exhibiting improved toxic properties, not only to *Lygus hesperus*, but also to *Lygus* lineolaris.

Recombinant polynucleotide compositions that encode eHTP's are also provided. In certain embodiments, eHTP's can be expressed with recombinant DNA constructs in which a polynucleotide molecule with the open reading frame encoding the protein is operably linked to elements such as a promoter and any other regulatory element functional for expression in the system for which the construct is intended. For example, plant-functional promoters can be operably linked to an applicable eHTP coding sequence to enable expression of the protein in plants. Promoters functional in bacteria are also contemplated for use in expression cassettes. Promoters functional in an applicable bacterium, for example, in an *E. coli* or in a *Bacillus thuringiensis* species can be operably linked to the eHTP coding sequences for expression of the applicable protein in the applicable bacterial strain. Other useful elements that can be operably linked to the eHTP coding sequences include, but are not limited to, enhancers, introns, leaders, encoded protein immobilization tags (HIS-tag), encoded sub-cellular translocation peptides (i.e. plastid transit peptides, signal peptides), encoded polypeptide sites for post-translational modifying enzymes, ribosomal binding sites, and segments designed for use as RNAi triggers for suppression of one or more genes either in plants or in a particular target pest species.

Exemplary recombinant polynucleotide molecules provided herein include, but are not limited to, SEQ ID NO:186, SEQ ID NO:187, SEQ ID NO:188, SEQ ID NO:189, SEQ ID NO:190, SEQ ID NO:191, SEQ ID NO:192, SEQ ID NO:193, SEQ ID NO:194, SEQ ID NO:195, SEQ ID NO:196, SEQ ID NO:197, SEQ ID NO:198, SEQ ID NO:199, SEQ ID NO:200, SEQ ID NO:35, and SEQ ID NO:201. These sequences encode the respective proteins each having the amino acid sequence as set forth in SEQ ID NO:4 (TIC807_4), SEQ ID NO:6 (TIC807_M1), SEQ ID NO:8 (TIC807_M2), SEQ ID NO:10 (TIC807_M3), SEQ ID NO:12 (TIC807_M4), SEQ ID NO:14 (TIC807_M5), SEQ ID NO:16 (TIC807_M8), SEQ ID NO:18 (TIC807_M6), SEQ ID NO:20 (TIC807_M7), SEQ ID NO:22 (TIC807_22), SEQ ID NO:24 (TIC807_24), SEQ ID NO:26 (TIC807_26), SEQ ID NO:28 (TIC807_M9), SEQ ID NO:30 (TIC807_M10), SEQ ID NO:32 (TIC807_M11), SEQ ID NO:36 (TIC807_M12), and SEQ ID NO:34 (TIC807_M13). Because of the redundancy of the genetic code, the codons of a recombinant polynucleotide molecule encoding for proteins of the present invention may be substituted for synonymous codons (also called a silent substitution); and are within the scope of the present invention. Recombinant polynucleotides encoding any of the eHTP's disclosed herein are thus provided.

A recombinant DNA construct comprising eHTP coding sequences can also further comprise a region of DNA that codes for one or more insect inhibitory agents which can be configured to be co-expressed along with a DNA sequence encoding an applicable eHTP, a protein different from an eHTP, or an insect or plant gene inhibitory dsRNA molecule. A recombinant DNA construct can be assembled so that all agents designed to be expressed from a particular construct are expressed from one promoter or so that separate agents are each under separate promoter control, or some combination thereof. The proteins of this invention can be expressed from a multi-gene expression system in which one or more proteins are expressed from a common nucleotide segment on which is also contained other open reading frames and/or promoters depending on the type of expression system selected.

Recombinant polynucleotide or recombinant DNA construct comprising an eHTP encoding sequence can be delivered to host cells by vectors, e.g., a plasmid, baculovirus, artificial chromosome, virion, cosmid, phagemid, phage, or viral vector. Such vectors can be used to achieve stable or transient expression of an eHTP encoding sequence in a host cell; and, if the case may be, subsequent expression to polypeptide. An exogenous recombinant polynucleotide or recombinant DNA construct that comprises an eHTP encoding sequence and that is introduced into a host cell is also referred to herein as a "transgene".

Also provided herewith are transgenic bacteria, transgenic plant cells, transgenic plants, and transgenic plant parts that contain any a recombinant polynucleotide (i.e. transgene) that expresses any one or more eHTP encoding sequence. It is intended that "bacterial cell" or "bacterium" can include, but are not limited to, an *Agrobacterium*, a *Bacillus*, an *Escherichia*, a *Salmonella*, a *Pseudomonas*, or a *Rhizobium* cell. It is intended that "plant cell" or "plant" include an alfalfa, almont, banana, barley, bean, beet, broccoli, cabbage, brassica, brinjal, carrot, cassava, castor, cauliflower, celery, chickpea, Chinese cabbage, celery, citrus, coconut, coffee, corn, clover, cotton, a cucurbit, cucumber, Douglas fir, eggplant, eucalyptus, flax, garlic, grape, guar, hops, leek, legumes, lettuce, Loblolly pine, millets, melons, nectarine, nut, oat, okra, olive, onion, ornamental, palm, pasture grass, papaya, pea, peach, peanut, pepper, pigeonpea, pine, potato, poplar, pumpkin, Radiata pine, radish, rapeseed, rice, rootstocks, rye, safflower, shrub, sorghum, Southern pine, soybean, spinach, squash, strawberry, sugar beet, sugarcane, sunflower, sweet corn, sweet gum, sweet potato, switchgrass, tea, tobacco, tomato, triticale, turf grass, watermelon, and wheat plant cell or plant. In certain embodiments: transgenic plants and transgenic plant parts regenerated from a transgenic plant cell are provided; transgenic plants can be obtained from a transgenic seed; transgenic plant parts can be obtained by cutting, snapping, grinding or otherwise disassociating the part from the plant; the plant part can be a seed, a boll, a leaf, a flower, a stem, a root, or any portion thereof; and a transgenic plant part provided herein is a non-regenerable portion of a transgenic plant part. As used in this context, a "non-regenerable" portion of a transgenic plant part is a portion that can not be induced to form a whole plant or that can not be induced to form a whole plant that is capable of sexual and/or asexual reproduction. A non-regenerable portion of a plant part is a portion of a transgenic pollen, ovule, seed, boll, leaf, flower, stem, or root.

Also provided herein are methods of making transgenic plants that contain insect or *Lygus* and/or *Amrasca* inhibitory amounts of an eHTP. Such plants can be made by introducing a recombinant polynucleotide that encodes any of the eHTP proteins provided herein into a plant cell, and selecting a plant derived from said plant cell that expresses an insect or *Hemipteran* inhibitory amount of the eHTP's. Plants can be derived from the plant cells by regeneration, seed, pollen, or meristem transformation techniques.

Transgenic plants and host cells are provided that expresse an insect or *Hemipteran* inhibitory amount of the eHTP to control an insect or *Hemipteran* infestation. Any of the aforementioned plant species can be used for protecting a plant from insect or *Hemipteran* infestation provided herein as long as the plant is transformed with a polynucleotide construct designed to express the applicable eHTP.

Additional aspects of the invention include antibodies, kits, methods for detecting polynucleotides that encode eHTP's or distinguishing fragments thereof, or eHTP's or distinguishing fragments thereof, methods for identifying additional insect inhibitory members of the protein genus of the present invention, formulations and methods for controlling insect growth and/or infestation, and methods for providing such control to plants and other recipient hosts. Each composition, construct, cell, plant, formulation, method or kit provides for the industrial application of the proteins of the present invention, for example, by increasing plant productivity through the commercial use of any of these proteins to inhibit insects.

A plant product, other than a seed or a fruit or vegetable, is intended as a commodity or other products which move through commerce and are derived from a transgenic plant or transgenic plant part, in which the commodity or other products can be tracked through commerce by detecting nucleotide segments, RNA or proteins that corresponding to an eHTP of the present invention and are produced in or maintained in the plant or plant tissue or part from which the commodity or other product has been obtained. Such commodity or other products of commerce include, but are not limited to, plant parts, biomass, oil, meal, sugar, animal feed, flour, flakes, bran, lint, processed seed, and seed. Plant parts include but are not limited to a plant seed, boll, leaf, flower, stem, pollen, or root. In certain embodiments, the plant part is a non-regenerable portion of said seed, boll, leaf, flower, stem, pollen, or root. Cotton and flax plant bolls and non-regenerable portions thereof that contain the eHTP's are also provided.

Also provided herewith are processed plant products that contain a detectable amount of an eHTP, an insect inhibitory fragment thereof, or any distinguishing portion thereof. Without seeking to be limited by theory, it is believed that such processed plant products containing a detectable amount of one or more of the eHTP's provided herein can in certain embodiments exhibit reductions in undesirable microorganisms that can be transmitted by Hemiptera and/or reductions in the undesirable side products of such microorganisms. In certain embodiments, a distinguishing portion thereof can comprise any polypeptide of at least from about 20 to about 100 or more contiguous amino acids as set forth in SEQ ID NO:180, in particular in which the polypeptide does not contain a corresponding polypeptide of contiguous amino acids present in SEQ ID NO:2, SEQ ID NO:8, SEQ ID NO:182, or SEQ ID NO:184, and wherein the polypeptide comprises at least one amino acid substitution, addition, or deletion in the corresponding amino acid sequence as set forth in SEQ ID NO:2.

Processed plant products are provided that contain a detectable amount of a recombinant polynucleotide encoding an eHTP, an eHTP or an insect inhibitory fragment thereof, or any distinguishing portion thereof. The processed product is selected from the group consisting of plant biomass, oil, meal, animal feed, flour, flakes, bran, lint, hulls, and processed seed.

Hemiptera infestations of crop plants are controlled by providing in the crop plants a recombinant polynucleotide sequence encoding one or more of the eHTP's of the present invention. Such transgenic crops produce or are treated to contain an insect or Hemiptera inhibitory amounst of an applicable eHTP, and such crops are imbued with sufficient eHTP by (i) applying any composition comprising or encoding an eHTP to the plant or a seed that gives rise to the plant; and/or (ii) transforming the plant or a plant cell that gives rise to the seed and ultimately, the plant, with a polynucleotide encoding an eHTP. The plant may be a transiently or stably transformed transgenic plant comprising a transgene that expresses an insect or Hemiptera inhibitory amount of an eHTP. The plant may be a non-transgenic plant to which a composition comprising an eHTP has been applied. In such methods, the plant is a dicot plant, and more specifically may be a cotton, soybean or alfalfa plant. The *Hemipteran* insects include adults and nymphs.

Preferably, the *Lygus* spp. is *Lygus hesperus* or *Lygus lineolaris*, the *Empoasca* spp. is *Empoasca fabae*, and the *Amrasca* spp. is *Amrasca devastans*.

Other features and advantages of the invention will be apparent from the following detailed description, examples, and claims.

EXAMPLES

In view of the foregoing, those of skill in the art should appreciate that changes can be made in the specific aspects which are disclosed and still obtain a like or similar result without departing from the spirit and scope of the invention. Thus, specific details disclosed herein are not to be interpreted as limiting. The U.S. Provisional Application Ser. No. 61/621,436 to which this application claims the benefit of priority, the Sequence Listing, as well as all references material to the inventions disclosed and claimed, particularly references and published patent applications cited in this application, are incorporated herein by reference in their entirety.

Example 1: Iterative Engineering-Testing-Selecting Approach

This example illustrates the random, combinatorial, and inventive aspects of the iterative (also can be referred to as "recursive") engineering-testing-selecting approach used to identify and describe insect inhibitory proteins exhibiting *Coleopteran* and/or nematicidal activity or increased toxicity to *Hemipteran* insect species compared to TIC807 (SEQ ID NO:2). Several design approaches were employed to engineer for eHTP's with greater inhibitory activity against *Lygus* species; approaches that included but were not limited to semi-random modifications, directed modifications of variances in an alignment of TIC807 with other native Bt proteins, and structure/function assisted design. Numerous rounds of engineering and testing were conducted (both consecutively and concurrently) to select for TIC807 protein variants exhibiting increased toxicity. Design approaches were adjusted as data was collected. This iterative engineering-testing-selection approach also included, but was not limited to steps including cloning, expressing, purifying, and bioassay testing of TIC807 control protein compared to the eHTP's.

About 267 exemplary eHTP's having exhibited increased *Lygus* toxicity compared to TIC807 were obtained from more than 2000 groups of candidate eHTP's (i.e. "test" proteins) that were assayed for improved insect inhibitory activity. The actual total number of candidate eHTP's tested was much greater than 2000 because testing included recombinant nucleotide segments encoding a number of candidate eHTP's derived from library mutagenesis that were not sequenced in the selection process.

Protein stocks of various amounts and purity were prepared depending on the purpose of the test and the testing throughput desired. For example, lower quantity and lower purity protein preparations were prepared for screening higher numbers of variants in bioassay. Larger quantity and higher purity protein stocks were prepared for high-powered bioassays. Testing trended towards the high-powered bioassays as principally relevant residue positions of the improved variants were elucidated. Initially, about 2000 variants were tested on *Lygus hesperus*. Based on data from *L. hesperus* approximately 600 variants were designed and then further tested on *Lygus lineolaris*. Of these, about 267 variants (Table 4B) demonstrated increased toxicity against *Lygus hesperus* and/or *Lygus lineolaris* when compared to TIC807. These 267 variants included twenty-two (22) variants that were confirmed to demonstrate increased toxicity against both *Lygus* species. Further confirmation and dose response testing narrowed the selection to seven (7) variants that were subsequently characterized using an 8-dose replicated bioassay to determine LC50 values against both *Lygus* species.

The selection process included dynamic updates of testing data, constantly adjusting engineering approaches, and performing iterative rounds. Concurrently, labor intensive cloning, protein expression, protein purification, and bioassay experiments were employed test the candidate eHTP's.

Example 2: Engineering Approaches

Alignment Based Approaches

A multiple sequence alignment of protein members of Cry51: Cry51Aa1 (SEQ ID NO:182), TIC853 (SEQ ID NO:184), and TIC807 (SEQ ID NO:2) were used to identify regions of variability, e.g., positions 195 to 201 and positions 211 to 219, relative to SEQ ID NO:2 (TIC807). These regions were targeted for saturation mutagenesis through use of degenerate oligonucleotide primers encoding random amino acid residues in these regions. Construct libraries were prepared for subsequent protein expression in host cells.

A multiple sequence alignment of Cry51Aa1 (SEQ ID NO:182), TIC853 (SEQ ID NO:184), and TIC807 (SEQ ID NO:2) was used in combination with a BLOSUM 80 substitution matrix to calculate average pair-wise distances for each position variant to TIC807. Residue positions with lower average pair-wise distances were substituted with alternative amino acid residues using degenerate oligonucleotide primers encoding for alternative amino acid residues, e.g., G28X, G31X, F46X, E125X, F138X, F147X, S167X, Y216X, P218X, G234X, T247X, D268X, and T308X. Construct libraries were prepared for subsequent protein expression in host cells.

Scanning Approaches

Polynucleotide constructs were engineered to express a single Alanine substitution or a double Alanine substitution (Alanine-<parent residue>-Alanine) at every possible position over the full-length of SEQ ID NO:2 (TIC807). See Table 2 for a hypothetical example.

TABLE 2

A hypothetical example of single and double Alanine scans on a scaffold protein containing the amino acid sequence XXXXAXX.

| | Single Alanine Scan | Double Alanine Scan |
|---|---|---|
| 1 | AXXXaXX | AXAXaXX |
| 2 | XAXXaXX | XAXAaXX |
| 3 | XXAXaXX | XXAXSXX |
| 4 | XXXAaXX | XXXAaAX |
| 5 | XXXXSXX | XXXXSXA |
| 6 | XXXXaAX | — |
| 7 | XXXXaXA | — |

X = parent residue
a = parent residue is an Alanine residue
A = Modified to an Alanine residue
S = Modified to a Serine residue Where an Alanine residue was already present in TIC807, a Serine was substituted instead. Protein variants that exhibited increased toxicity compared to TIC807 were further tested by combination and saturation mutagenesis at those Alanine-substituted residues that conferred increased toxicity. Scanning approaches were also performed on improved combination variants having accumulated modifications from previous iterative rounds of engineering-testing-selecting, e. g., TIC807_M2 (SEQ ID NO:8) having mutations F46S, Y54H, S167R, S217N, and a contiguous triple deletion in residue range 196-201 was further engineered by an additional round of single Alanine substitutions to further improve upon the improved TIC807_M2. Principally relevant residues were identified and further tested by combination and saturation mutagenesis (e. g., A150X, E125X, E155X, F147X, I134X, N157X, Q149X, T133X, E135X, and N137X). Variants engineered by these combined approaches exhibited further improvements to increased toxicity compared to TIC807 and were further combined with other design approaches that took advantage of the atomic structure of TIC807 (SEQ ID NO:2).

Surface Exposed Residues

The atomic structure of proteins of the present invention was determined in the midst of the Iterative Engineering-Testing-Selecting approach; and, the relative solvent-accessibility (% SA) of each residue was determined using Molsoft's ICM-Browser (Molsoft L.L.C., 11199 Sorrento Valley Road, 5209, San Diego, Calif. 92121). Shown in Table 3 in columns (A) and (B), actual % SA was calculated for proteins having the respective amino acid sequences set forth as SEQ ID NO:185 (TIC807_L11M) and SEQ ID NO:8 (TIC807_M2). The predicted % SA for residues of TIC807 and TIC853 are listed in Table 3 in columns (A) and (C), respectively. Altogether, the % SA values reported in Table 3 are calculated as a percentage of the solvent-accessible surface area probed by a water molecule over the maximal solvent accessible area in standard extended conformation (Gly-XXX-Gly) for each residue in each position of the atomic structure. Table 3 aligns the residues of each protein by aligned residues in a Clustal W alignment. % SA greater than 100 can occur when maximal solvent accessible area in standard extended conformation (Gly-XXX-Gly) for each residue is less than the actual solvent accessible area probed by a water molecule. % SA greater than 100 are reported in the table as 100%.

Combined engineering-testing-selecting approaches described herein resulted in a number of principally relevant residues that accumulate in a surface patch ([2] of FIG. 2) of residues having a radius of about 9.2-12.2 Angstroms around the Cb atom of P219 of SEQ ID NO:2 (TIC807): V10, I14, N22, N23, G24, I25, Q26, G27, F30, Q38, I39, D40, T41, I43, S193, T194, E195, H196, Y197, S198, H199, Y200, S201, G202, Y203, P204, I205, L206, T207, W208, I209, S210, Y216, S217, G218, P219, F220, M221, S222, W223, Y224, F225, N239, and V244 of SEQ ID NO:2 (TIC807). At least half of these residues exhibit % SA values of greater or equal to fifteen (15).

TABLE 3

Relative % Solvent Accessibility (SA) of Amino Acids of eHTP's & Scaffold Proteins.

| (A) TIC807_L11M (SEQ ID NO: 185) | | (B) TIC807_M2 (SEQ ID NO: 8) | | (C) TIC853 (SEQ ID NO: 184) | |
|---|---|---|---|---|---|
| Position and amino acid residue | Calculated % SA per residue | Position and amino acid residue | Calculated % SA per residue | Position and amino acid residue | Estimated % SA per residue |
| 2ALA | 82.1# | 2ALA | 64.8# | 2ALA | 60.9# |
| 3ILE | 23.3 | 3ILE | 28.9 | 3ILE | 24.3 |
| 4LEU | 26.4 | 4LEU | 31.9 | 4LEU | 27.9 |
| 5ASP | 26.0 | 5ASP | 22.7 | 5ASP | 29.9 |
| 6LEU | 1.0 | 6LEU | 3.4 | 6LEU | 3.7 |
| 7LYS | 25.1 | 7LYS | 16.2 | 7LYS | 17.1 |
| 8SER | 46.4# | 8SER | 37.6# | 8SER | 44.9# |
| 9LEU | 8.9 | 9LEU | 5.2 | 9LEU | 6.3 |
| 10VAL[p1] | 0.3 | 10VAL | 0.6 | 10VAL | 0.0 |
| 11MET | 25.0 | 11LEU | 17.0 | 11LEU | 16.6 |
| 12ASN* | 49.8# | 12ASN | 43.2# | 12ASP | 39.7# |
| 13ALA | 0.0 | 13ALA | 0.0 | 13ALA | 0.0 |
| 14ILE[p1] | 0.0 | 14ILE | 0.0 | 14ILE | 0.0 |
| 15ASN | 23.7 | 15ASN | 24.9 | 15ASN | 19.2 |
| 16TYR | 29.5 | 16TYR | 47.1# | 16TYR | 52.5# |
| 17TRP | 14.1 | 17TRP | 18.2 | 17TRP | 20.1 |
| 18GLY | 4.3 | 18GLY | 1.4 | 18GLY | 1.0 |
| 19PRO | 63.6# | 19PRO | 57.3# | 19PRO | 59.0# |
| 20LYS | 57.3# | 20LYS | 77.2# | 20LYS | 100# |
| 21ASN | 36.3# | 21ASN | 28.4 | 21ASN | 61.5# |
| 22ASN[p1] | 16.9 | 22ASN | 10.1 | 22ASN | 15.2 |
| 23ASN[p1] | 0.3 | 23ASN | 0.8 | 23ASN | 0.0 |
| 24GLY[p1] | 42.0# | 24GLY | 43.2# | 24GLY | 43.3# |
| 25ILE[p1] | 10.1 | 25ILE | 13.8 | 25ILE | 7.6 |
| 26GLN[p1] | 92.4# | 26GLN | 86.2# | 26GLN | 94.7# |
| 27GLY[p1] | 62.0# | 27GLY | 73.9# | 27GLY | 62.8# |
| 28GLY | 49.0# | 28GLY | 50.6# | 28TYR | 47.7# |
| 29ASP | 66.0# | 29ASP | 68.1# | 29ASN | 80.7# |
| 30PHE[p1] | 4.5 | 30PHE | 4.1 | 30PHE | 1.5 |
| 31GLY | 37.2# | 31GLY | 41.4# | 31ASN | 61.1# |
| 32TYR | 25.2 | 32TYR | 25.3 | 32TYR | 21.5 |
| 33PRO | 70.7# | 33PRO | 76.0# | 33PRO | 78.5# |
| 34ILE | 4.8 | 34ILE | 5.5 | 34ILE | 2.6 |
| 35SER | 42.2# | 35SER | 29.1 | 35SER | 27.0 |
| 36GLU | 54.2# | 36GLU | 47.2# | 36GLU | 50.2# |
| 37LYS | 81.0# | 37LYS | 79.5# | 37ARG | 87.5# |
| 38GLN[p1] | 12.8 | 38GLN | 14.5# | 38GLN | 9.0 |
| 39ILE[p1] | 7.8 | 39ILE | 7.9 | 39ILE | 5.1 |
| 40ASP[p1] | 52.4# | 40ASP | 55.3# | 40ASP | 49.8# |
| 41THR[p1] | 0.3 | 41THR | 0.0 | 41THR | 0.2 |
| 42SER | 53.1# | 42SER | 56.0# | 42SER | 53.0# |
| 43ILE[p1] | 13.1 | 43ILE | 23.5 | 43ILE | 25.1 |
| 44ILE | 8.3 | 44ILE | 12.0 | 44ILE | 8.1 |
| 45THR | 30.7 | 45THR | 37.8# | 45THR | 45.7# |
| 46PHE* | 20.0 | 46SER | 43.7# | 46SER | 40.5# |
| 47THR | 48.1# | 47THR | 45.2# | 47THR | 43.7# |
| 48HIS | 73.5# | 48HIS | 65.3# | 48HIS | 78.3# |
| 49PRO | 9.4 | 49PRO | 12.6 | 49SER | 9.0 |
| 50ARG | 58.7# | 50ARG | 53.7# | 50ARG | 61.5# |
| 51LEU | 13.7 | 51LEU | 8.1 | 51LEU | 3.0 |
| 52ILE* | 32.4 | 52ILE | 31.5 | 52MET | 43.7# |
| 53PRO | 22.2 | 53PRO | 26.5 | 53PRO | 22.8 |
| 54TYR* | 52.7# | 54HIS | 42.2# | 54HIS | 45.5# |
| 55ASP | 57.5# | 55ASP | 59.2# | 55ASP | 55.5# |
| 56LEU | 15.0 | 56LEU | 18.6 | 56LEU | 15.1 |
| 57THR | 62.0# | 57THR | 73.2# | 57THR | 80.0# |
| 58ILE | 67.6# | 58ILE | 60.9# | 58ILE | 68.0# |
| 59PRO | 26.6 | 59PRO | 21.9 | 59PRO | 20.7 |
| 60GLN | 28.8 | 60GLN | 20.7 | 60GLN | 21.3 |
| 61ASN | 71.9# | 61ASN | 73.6# | 61ASN | 74.6# |
| 62LEU | 13.4 | 62LEU | 11.7 | 62LEU | 10.0 |
| 63GLU | 62.2# | 63GLU | 66.0# | 63GLU | 66.4# |
| 64THR | 51.2# | 64THR | 51.1# | 64THR | 49.0# |
| 65ILE | 46.1# | 65ILE | 41.5# | 65ILE | 38.4# |
| 66PHE | 27.0 | 66PHE | 26.3 | 66PHE | 29.6 |
| 67THR | 52.5# | 67THR | 55.5# | 67THR | 62.2# |
| 68THR* | 31.6 | 68THR | 35.8# | 68THR | 35.3 |
| 69THR | 54.3# | 69THR | 51.1# | 69THR | 50.3# |
| 70GLN* | 31.0 | 70GLN | 36.5# | 70GLN | 34.3 |
| 71VAL | 53.4# | 71VAL | 53.2# | 71VAL | 53.1# |
| 72LEU | 7.9 | 72LEU | 11.8 | 72LEU | 8.1 |
| 73THR | 40.5# | 73THR | 44.0# | 73THR | 47.0# |
| 74ASN | 0.6 | 74ASN | 0.0 | 74ASN | 0.0 |
| 75ASN | 69.8# | 75ASN | 63.2# | 75ASN | 65.9# |
| 76THR | 36.7# | 76THR | 40.5# | 76THR | 44.0# |
| 77ASP | 80.2# | 77ASP | 63.0# | 77ASP | 62.1# |
| 78LEU | 62.6# | 78LEU | 62.5# | 78VAL | 63.8# |
| 79GLN | 74.4# | 79GLN | 54.7# | 79GLN | 43.5# |
| 80GLN | 33.3 | 80GLN | 32.1 | 80GLN | 40.1# |
| 81SER | 81.0# | 81SER | 68.6# | 81SER | 75.2# |
| 82GLN | 19.0 | 82GLN | 23.9 | 82GLN | 24.6 |
| 83THR | 62.7# | 83THR | 63.6# | 83THR | 63.7# |
| 84VAL | 1.8 | 84VAL | 0.9 | 84VAL | 0.0 |
| 85SER | 50.8# | 85SER | 55.7# | 85SER | 54.0# |
| 86PHE | 7.2 | 86PHE | 5.8 | 86PHE | 4.0 |
| 87ALA* | 58.5# | 87ALA | 61.9# | 87SER | 68.0# |
| 88LYS | 30.5 | 88LYS | 30.6 | 88LYS | 32.6 |
| 89LYS | 69.8# | 89LYS | 67.8# | 89LYS | 67.9# |
| 90THR | 19.9 | 90THR | 23.1 | 90THR | 16.7 |
| 91THR | 54.1# | 91THR | 55.1# | 91THR | 48.1# |
| 92THR | 1.8 | 92THR | 1.8 | 92THR | 0.0 |
| 93THR[p2*] | 40.3# | 93THR | 36.4# | 93THR | 29.4 |
| 94THR | 0.0 | 94THR | 0.6 | 94THR | 0.2 |
| 95SER[p2*] | 14.4 | 95SER | 15.7 | 95SER | 18.1 |
| 96THR | 5.5 | 96THR | 1.5 | 96THR | 0.0 |
| 97SER[p2] | 16.6 | 97SER | 18.5 | 97SER | 29.9 |
| 98THR | 8.2 | 98THR | 5.9 | 98THR | 1.9 |
| 99THR | 41.8# | 99THR | 46.4# | 99THR | 49.3# |
| 100ASN | 37.7# | 100ASN | 34.1 | 100ASP | 20.1 |
| 101GLY | 1.0 | 101GLY | 1.9 | 101GLY | 0.0 |
| 102TRP | 3.6 | 102TRP | 10.4 | 102TRP | 6.6 |
| 103THR | 8.1 | 103THR | 8.1 | 103THR | 3.9 |
| 104GLU | 9.7 | 104GLU | 21.9 | 104GLU | 14.8 |
| 105GLY* | 35.3 | 105GLY | 46.8# | 105GLY | 31.4 |
| 106GLY | 57.0# | 106GLY | 68.6# | 106GLY | 61.8# |
| 107LYS | 52.4# | 107LYS | 57.2# | 107ARG | 54.6# |
| 108ILE | 61.8# | 108ILE | 63.5# | 108ILE | 67.1# |
| 109SER | 43.5# | 109SER | 47.9# | 109SER | 47.7# |
| 110ASP | 83.1# | 110ASP | 83.5# | 110ASP | 65.7# |
| 111THR | 43.4# | 111THR | 41.3# | 111THR | 39.9# |

TABLE 3-continued

Relative % Solvent Accessibility (SA) of Amino Acids of eHTP's & Scaffold Proteins.

| (A) TIC807_L11M (SEQ ID NO: 185) | | (B) TIC807_M2 (SEQ ID NO: 8) | | (C) TIC853 (SEQ ID NO: 184) | |
|---|---|---|---|---|---|
| Position and amino acid residue | Calculated % SA per residue | Position and amino acid residue | Calculated % SA per residue | Position and amino acid residue | Estimated % SA per residue |
| 112LEU | 26.7 | 112LEU | 29.6 | 112LEU | 31.3 |
| 113GLU | 53.8# | 113GLU | 64.1# | 113GLU | 62.5# |
| 114GLU | 34.8 | 114GLU | 30.9 | 114GLU | 32.6 |
| 115LYS | 62.2# | 115LYS | 55.2# | 115ASN | 54.6# |
| 116VAL | 6.4 | 116VAL | 8.6 | 116VAL | 10.4 |
| 117SER* | 46.6# | 117SER | 48.9# | 117SER | 51.2# |
| 118VAL | 0.9 | 118VAL | 2.5 | 118VAL | 1.3 |
| 119SER* | 20.2 | 119SER | 23.4 | 119SER | 23.7 |
| 120ILE | 0.8 | 120ILE | 0.3 | 120ILE | 0.0 |
| 121PRO | 5.9 | 121PRO | 10.7 | 121PRO | 8.0 |
| 122PHE | 0.2 | 122PHE | 1.4 | 122PHE | 0.3 |
| 123ILE | 19.1 | 123ILE | 20.8 | 123ILE | 18.3 |
| 124GLY | 4.3 | 124GLY | 6.2 | 124GLY | 3.3 |
| 125GLU* | 59.7# | 125GLU | 56.2# | 125ALA | 57.8# |
| 126GLY | 50.0# | 126GLY | 52.5# | 126GLY | 49.6# |
| 127GLY | 47.2# | 127GLY | 56.7# | 127GLY | 38.6# |
| 128GLY* | 34.7 | 128GLY | 30.3 | 128ALA | 23.0 |
| 129LYS | 68.8# | 129LYS | 73.9# | 129LYS | 78.4# |
| 130ASN | 16.2 | 130ASN | 14.6 | 130ASN | 10.1 |
| 131SER | 78.2# | 131SER | 77.9# | 131SER | 80.3# |
| 132THR | 9.8 | 132THR | 10.3 | 132THR | 12.3 |
| 133THR* | 45.7# | 133THR | 42.0# | 133THR | 44.3# |
| 134ILE* | 1.1 | 134ILE | 0.8 | 134ILE | 0.0 |
| 135GLU* | 51.5# | 135GLU | 45.2# | 135GLU | 48.5# |
| 136ALA | 0.0 | 136ALA | 1.3 | 136ALA | 2.4 |
| 137ASN* | 18.1 | 137ASN | 15.5 | 137ASN | 15.6 |
| 138PHE* | 1.9 | 138PHE | 0.9 | 138VAL | 2.5 |
| 139ALA* | 2.8 | 139ALA | 6.3 | 139ALA | 4.1 |
| 140HIS | 2.3 | 140HIS | 2.1 | 140HIS | 0.0 |
| 141ASN | 5.3 | 141ASN | 6.5 | 141ASN | 2.8 |
| 142SER | 5.4 | 142SER | 4.4 | 142SER | 6.6 |
| 143SER | 7.7 | 143SER | 10.6 | 143SER | 7.0 |
| 144THR | 23.5 | 144THR | 17.3 | 144THR | 16.6 |
| 145THR* | 48.3# | 145THR | 52.7# | 145THR | 55.2# |
| 146THR | 50.2# | 146THR | 49.7# | 146THR | 53.6# |
| 147PHE$^{P2}$* | 49.9# | 147PHE | 61.6# | 147SER | 51.7# |
| 148GLN* | 12.9 | 148GLN | 17.8 | 148GLN | 18.4 |
| 149GLN$^{P2}$* | 59.5# | 149GLN | 65.1# | 149GLN | 69.1# |
| 150ALA* | 6.9 | 150ALA | 8.7 | 150ALA | 9.1 |
| 151SER$^{P2}$* | 51.0# | 151SER | 51.7# | 151SER | 57.9# |
| 152THR | 9.9 | 152THR | 8.7 | 152THR | 12.3 |
| 153ASP* | 83.5# | 153ASP | 84.5# | 153GLU | 63.3# |
| 154ILE | 11.2 | 154ILE | 6.1 | 154ILE | 6.3 |
| 155GLU* | 49.5# | 155GLU | 63.9# | 155GLU | 49.7# |
| 156TRP | 1.7 | 156TRP | 3.8 | 156TRP | 1.8 |
| 157ASN* | 59.1# | 157ASN | 59.1# | 157ASN | 53.4# |
| 158ILE* | 13.1 | 158ILE | 5.9 | 158ILE | 0.8 |
| 159SER* | 60.2# | 159SER | 52.9# | 159SER | 52.2# |
| 160GLN | 29.2 | 160GLN | 19.3 | 160GLN | 9.3 |
| 161PRO | 54.0# | 161PRO | 63.6# | 161PRO | 62.6# |
| 162VAL | 0.6 | 162VAL | 4.0 | 162VAL | 2.4 |
| 163LEU | 53.8# | 163LEU | 56.6# | 163LEU | 64.5# |
| 164VAL | 0.0 | 164VAL | 0.0 | 164VAL | 0.0 |
| 165PRO | 22.8 | 165PRO | 22.1 | 165PRO | 26.9 |
| 166PRO | 30.7 | 166PRO | 36.1# | 166PRO | 39.7# |
| 167SER* | 31.0 | 167ARG | 32.8 | 167ARG | 36.7# |
| 168LYS | 18.2 | 168LYS | 18.5 | 168LYS | 19.9 |
| 169GLN | 17.4 | 169GLN | 15.1 | 169GLN | 10.7 |
| 170VAL | 0.0 | 170VAL | 0.0 | 170VAL | 0.0 |
| 171VAL | 13.2 | 171VAL | 13.8 | 171VAL | 12.2 |
| 172ALA | 0.0 | 172ALA | 0.0 | 172ALA | 0.0 |
| 173THR | 9.8 | 173THR | 9.2 | 173THR | 6.5 |
| 174LEU | 1.3 | 174LEU | 2.6 | 174LEU | 0.2 |
| 175VAL* | 17.2 | 175VAL | 17.8 | 175VAL | 13.4 |
| 176ILE | 0.0 | 176ILE | 0.0 | 176ILE | 0.0 |
| 177MET* | 7.0 | 177MET | 7.7 | 177MET | 17.3 |
| 178GLY | 1.6 | 178GLY | 0.5 | 178GLY | 0.0 |
| 179GLY | 15.9 | 179GLY | 22.2 | 179GLY | 16.5 |
| 180ASN$^{P2}$* | 60.0# | 180ASN | 60.1# | 180ASP | 44.9# |
| 181PHE | 0.7 | 181PHE | 2.8 | 181PHE | 1.8 |
| 182THR$^{P2}$* | 50.6# | 182THR | 44.3# | 182THR | 40.8# |
| 183ILE | 0.0 | 183ILE | 1.1 | 183VAL | 0.0 |
| 184PRO | 36.6# | 184PRO | 34.2 | 184PRO | 34.5 |
| 185MET | 4.4 | 185MET | 2.1 | 185MET | 1.8 |
| 186ASP | 52.4# | 186ASP | 23.5 | 186ASP | 20.3 |
| 187LEU* | 0.8 | 187LEU | 0.0 | 187LEU | 0.0 |
| 188MET | 25.9 | 188MET | 12.7 | 188ILE | 24.9 |
| 189THR | 1.4 | 189THR | 2.9 | 189THR | 0.5 |
| 190THR | 26.1 | 190THR | 26.2 | 190THR | 24.1 |
| 191ILE | 4.0 | 191ILE | 6.2 | 191ILE | 1.8 |
| 192ASP | 25.9 | 192ASP | 29.2 | 192ASP | 21.4 |
| 193SER$^{P1}$ | 7.4 | 193SER | 7.7 | 193SER | 2.7 |
| 194THR$^{P1}$ | 66.2# | 194THR | 60.2# | 194THR | 59.9# |
| 195GLU$^{P1}$ | 38.5# | 195GLU | 35.0 | 195GLN | 35.5# |
| 196HIS* | 37.7# | — | 100 | — | 100# |
| 197TYR* | 32.2 | — | 100# | — | 100# |
| 198SER* | 35.5# | — | 100# | — | 100# |
| 199HIS$^{P1}$* | 64.3# | 196HIS | 55.5# | 196HIS | 51.7# |
| 200TYR$^{P1}$ | 85.3# | 197TYR | 56.2# | 197PHE | 45.8# |
| 201SER$^{P1}$* | 50.3# | 198SER | 68.3# | 198THR | 64.5# |
| 202GLY$^{P1}$ | 32.8 | 199GLY | 50.0# | 199GLY | 51.1# |
| 203TYR$^{P1}$ | 21.5 | 200TYR | 22.6 | 200TYR | 26.0 |
| 204PRO$^{P1}$ | 1.4 | 201PRO | 1.0 | 201PRO | 1.0 |
| 205ILE$^{P1}$ | 1.1 | 202ILE | 0.3 | 202ILE | 0.0 |
| 206LEU$^{P1}$ | 1.8 | 203LEU | 2.6 | 203LEU | 0.0 |
| 207THR$^{P1}$ | 0.0 | 204THR | 0.0 | 204THR | 0.0 |
| 208TRP$^{P1}$* | 38.8# | 205TRP | 35.6# | 205TRP | 22.5 |
| 209ILE$^{P1}$ | 0.0 | 206ILE | 0.0 | 206ILE | 0.0 |
| 210SER$^{P1}$ | 22.5 | 207SER | 20.1 | 207GLU | 17.0 |
| 211SER | 3.1 | 208SER | 3.4 | 208ASN | 4.6 |
| 212PRO | 56.5# | 209PRO | 58.4# | 209PRO | 56.2# |
| 213ASP | 68.0# | 210ASP | 55.2# | 210GLU | 60.5# |
| 214ASN | 65.5# | 211ASN | 66.4# | 211HIS | 64.4# |
| 215SER | 67.2# | 212SER | 74.1# | 212ASN | 74.2# |
| 216TYR$^{P1}$ | 42.5# | 213TYR | 39.8# | 213VAL | 29.4 |
| 217SER$^{P1}$* | 43.2# | 214ARG | 46.3# | 214ARG | 57.1# |
| 218GLY$^{P1}$ | 1.2 | 215GLY | 4.1 | 215GLY | 6.1 |
| 219PRO$^{P1}$* | 14.4 | 216PRO | 14.7 | 216ARG | 33.7 |
| 220PHE$^{P1}$ | 0.0 | 217PHE | 0.0 | 217PHE | 0.0 |
| 221MET$^{P1}$ | 15.2 | 218MET | 16.1 | 218LEU | 8.4 |
| 222SER$^{P1}$ | 3.3 | 219SER | 3.3 | 219SER | 0.0 |
| 223TRP$^{P1}$* | 35.6# | 220TRP | 34.3 | 220TRP | 42.5# |
| 224TYR$^{P1}$ | 13.5 | 221TYR | 15.9 | 221PHE | 11.3 |
| 225PHE$^{P1}$ | 0.9 | 222PHE | 1.4 | 222PHE | 0.0 |
| 226ALA | 15.9 | 223ALA | 13.1 | 223ALA | 7.8 |
| 227ASN | 40.7# | 224ASN | 41.9# | 224ASN | 43.2# |
| 228TRP | 9.0 | 225TRP | 8.9 | 225TRP | 7.3 |
| 229PRO | 56.3# | 226PRO | 61.5# | 226PRO | 65.5# |
| 230ASN | 67.6# | 227ASN | 67.3# | 227ASN | 67.3# |
| 231LEU | 21.1 | 228LEU | 16.1 | 228LEU | 16.1 |
| 232PRO | 23.7 | 229PRO | 23.0 | 229PRO | 23.6 |
| 233SER | 97.0# | 230SER | 95.8# | 230SER | 88.1# |
| 234GLY | 23.0 | 231GLY | 19.5 | 231GLU | 13.0 |
| 235PHE* | 8.3 | 232PHE | 9.0 | 232PHE | 6.1 |
| 236GLY | 26.1 | 233GLY | 18.3 | 233GLY | 28.5 |
| 237PRO | 72.6# | 234PRO | 70.8# | 234SER | 81.9# |
| 238LEU | 27.7 | 235LEU | 28.1 | 235LEU | 25.9 |
| 239ASN* | 33.2 | 236ASN | 26.5 | 236ASN | 42.2# |
| 240SER | 100# | 237SER | 100 | 237SER | 100# |
| 241ASP* | 62.2# | 238ASP | 61.7# | 238ASP | 55.2# |
| 242ASN | 15.1 | 239ASN | 20.8 | 239ASN | 21.7 |
| 243THR* | 3.3 | 240THR | 2.4 | 240THR | 2.6 |
| 244VAL* | 1.8 | 241VAL | 3.1 | 241ILE | 0.0 |
| 245THR* | 19.0 | 242THR | 23.8 | 242THR | 30.1 |
| 246TYR* | 8.6 | 243TYR | 4.8 | 243TYR | 0.4 |
| 247THR* | 36.8# | 244THR | 40.8# | 244LYS | 58.8# |

TABLE 3-continued

Relative % Solvent Accessability (SA) of
Amino Acids of eHTP's & Scaffold Proteins.

| (A) TIC807_L11M (SEQ ID NO: 185) | | (B) TIC807_M2 (SEQ ID NO: 8) | | (C) TIC853 (SEQ ID NO: 184) | |
|---|---|---|---|---|---|
| Position and amino acid residue | Calculated % SA per residue | Position and amino acid residue | Calculated % SA per residue | Position and amino acid residue | Estimated % SA per residue |
| 248GLY | 2.5 | 245GLY | 1.4 | 245GLY | 0.0 |
| 249SER* | 20.7 | 246SER | 23.9 | 246SER | 27.0 |
| 250VAL* | 6.0 | 247VAL | 1.4 | 247VAL | 0.0 |
| 251VAL$^{P2}$* | 32.6 | 248VAL | 30.0 | 248VAL | 29.7 |
| 252SER* | 0.0 | 249SER | 0.0 | 249SER | 0.0 |
| 253GLN$^{P2}$ | 40.2# | 250GLN | 37.6# | 250ARG | 51.3# |
| 254VAL | 1.2 | 251VAL | 1.5 | 251ILE | 2.7 |
| 255SER$^{P2}$ | 35.3 | 252SER | 37.3# | 252SER | 43.7# |
| 256ALA | 6.1 | 253ALA | 2.4 | 253ALA | 2.1 |
| 257GLY | 4.1 | 254GLY | 6.1 | 254GLY | 1.2 |
| 258VAL | 0.3 | 255VAL | 0.0 | 255VAL | 0.0 |
| 259TYR | 2.2 | 256TYR | 1.1 | 256TYR | 1.0 |
| 260ALA | 0.7 | 257ALA | 0.7 | 257ALA | 0.0 |
| 261THR | 9.2 | 258THR | 9.3 | 258THR | 5.0 |
| 262VAL | 3.6 | 259VAL | 1.5 | 259VAL | 0.2 |
| 263ARG | 26.6 | 260ARG | 29.8 | 260ARG | 26.9 |
| 264PHE | 0.5 | 261PHE | 3.8 | 261PHE | 1.5 |
| 265ASP | 6.9 | 262ASP | 7.2 | 262ASP | 10.8 |
| 266GLN | 5.6 | 263GLN | 5.8 | 263GLN | 2.6 |
| 267TYR | 16.1 | 264TYR | 14.5 | 264TYR | 12.4 |
| 268ASP | 29.8 | 265ASP | 31.4 | 265ALA | 19.3 |
| 269ILE | 25.4 | 266ILE | 18.2 | 266ILE | 14.5 |
| 270HIS | 85.5# | 267HIS | 72.2# | 267ASN | 92.0# |
| 271ASN | 43.4# | 268ASN | 46.9# | 268ASN | 64.0# |
| 272LEU | 40.3# | 269LEU | 43.1# | 269LEU | 39.8# |
| 273ARG* | 86.3# | 270ARG | 63.1# | 270ARG | 84.4# |
| 274THR* | 52.0# | 271THR | 66.1# | 271THR | 76.8# |
| 275ILE* | 41.0# | 272ILE | 37.9# | 272ILE | 32.4 |
| 276GLU | 47.9# | 273GLU | 50.1# | 273GLU | 53.0# |
| 277LYS | 49.8# | 274LYS | 47.2# | 274LYS | 70.2# |
| 278THR | 46.3# | 275THR | 51.2# | 275THR | 53.7# |
| 279TRP | 25.2 | 276TRP | 25.0 | 276TRP | 33.4 |
| 280TYR | 35.5 | 277TYR | 30.7 | 277TYR | 21.3 |
| 281ALA | 6.6 | 278ALA | 7.9 | 278ALA | 4.4 |
| 282ARG* | 77.6# | 279ARG | 80.6# | 279ARG | 86.1# |
| 283HIS | 45.2# | 280HIS | 36.6# | 280HIS | 35.8# |
| 284ALA | 0.8 | 281ALA | 0.8 | 281GLY | 0.6 |
| 285THR | 14.7 | 282THR | 8.6 | 282THR | 2.0 |
| 286LEU | 3.6 | 283LEU | 5.9 | 283LEU | 2.3 |
| 287HIS* | 8.4 | 284HIS | 16.5 | 284HIS | 11.9 |
| 288ASN | 40.4# | 285ASN | 43.9# | 285ASN | 38.7# |
| 289GLY | 61.0# | 286GLY | 53.5# | 286GLY | 61.1# |
| 290LYS | 61.7# | 287LYS | 61.6# | 287LYS | 73.8# |
| 291LYS | 68.4# | 288LYS | 66.2# | 288LYS | 51.9# |
| 292ILE | 19.2 | 289ILE | 19.5 | 289ILE | 21.0 |
| 293SER* | 40.3# | 290SER | 47.9# | 290SER | 45.7# |
| 294ILE | 3.4 | 291ILE | 4.8 | 291ILE | 5.1 |
| 295ASN* | 29.3 | 292ASN | 21.9 | 292ASN | 18.0 |
| 296ASN | 38.2# | 293ASN | 40.4# | 293ASN | 37.4# |
| 297VAL | 1.3 | 294VAL | 1.4 | 294VAL | 0.7 |
| 298THR | 10.1 | 295THR | 9.5# | 295THR | 4.3 |
| 299GLU* | 77.1# | 296GLU | 72.7# | 296GLU | 68.8# |
| 300MET* | 48.6# | 297MET | 46.4# | 297MET | 42.8# |
| 301ALA | 65.3# | 298ALA | 54.1# | 298ALA | 60.4# |
| 302PRO | 66.0# | 299PRO | 73.0# | 299PRO | 77.8# |
| 303THR* | 83.7# | 300THR | 85.8# | 300THR | 94.1# |
| 304SER | 77.4# | 301SER | 76.1# | 301SER | 84.9# |
| 305PRO* | 81.1# | 302PRO | 65.7# | 302PRO | 83.4# |
| 306ILE* | 78.1# | 303ILE | 81.6# | 303ILE | 91.3# |
| 307LYS | 81.9# | 304LYS | 99.3# | 304GLU | 100# |
| 308THR* | 89.4# | 305THR | 100# | 305ARG | 100# |
| 309ASN | 100# | 306ASN | 100# | 306ASN | 100# |

P1 designates an amino acid in surface patch [1] of FIG. 2.
P2 designates an amino acid in surface patch [1] of FIG. 2.
*designates one of the 72 principally relevant amino acids described herein (see FIG. 2).
Shown are residues of TIC807_L11M, TIC807_M2, and TIC853 aligned by Clustal W.
Numbers marked with # represent % SA of at least about 36%.

Receptor Binding

A surface patch ([1] of FIG. 2) of residues having % SA values greater than 36% or within about 3 residues of a residue having % SA greater than 36% in a radius of about 9.2-12.2 Angstroms from the Cb atom of S95 of SEQ ID NO:2 (TIC807) was identified as a region comprising residues of a TIC807 protein that can be substituted to provide for eHTP's that exhibit enhanced Lygus inhibitory spectrum and/or improved Lygus inhibitory activity, This surface patch region may be associated with target insect receptor binding activity; and, includes residues T93, S95, S97, F147, Q149, S151, N180, T182, V251, Q253, and S255 of SEQ ID NO:2 (TIC807). eHTP's can include, but are not limited to, one or more substitutions of surface patch 1 amino acid residues such as S95A, F147A, Q149E, and/or, V251A.

The combined engineering-testing-selecting approaches described herein identified residues located in surface patch 1 that can provide for eHTP's when substituted or otherwise modified. These residues may be important for productive binding of eHTP's to receptors in Lygus insect gut to provide for enhanced Lygus inhibitory spectrum and/or improved Lygus inhibitory activity when compared to TIC807. Modifications of the surface patch 1 amino acid residues that can provide for eHTP's include substitutions that provide aromatic groups and/or hydrogen-bonding groups which favoring binding to sugar groups found on glycosylated receptors of insects.

Membrane Binding

Certain amino acid residues located in beta-sheet regions of the protein were identified from the atomic structure of TIC807 and were substituted with aromatic residues. More specifically, amino acids L78, I123, H270, R273, I275 of the folded TIC807 beta sheet regions were substituted with Phenylalanine, Tyrosine, or Tryptophan. Aromatic amino acid substitutions of R273 and I275 were amongst those residues that provided for an enhanced Lygus inhibitory spectrum and/or improved Lygus inhibitory activity (See Table 4, data for SEQ ID NOs:32, 34, 68, 92, and 122). Amino acid side chains of residues in these positions may be likely to interact with the membrane of target insects.

Proteolytic Activation Sites

Glycine residues generally thought to be involved in proteolysis were substituted with Serines to alter proteolytic cleavage dynamics. The presence of a glycine residue in a loop region can impart more flexibility and therefore susceptibility to proteolysis, which can either increase insect inhibitory activity or decrease insect inhibitory activity. Residues in structurally identified loop regions were substituted with a glycine residue, and no improvements were observed. Positions in loops that were already glycines, (e.g. G18, G24, G27) were substituted with a serine, a small residue in an attempt to reduce proteolytic susceptibility, and no improvements were observed.

Combined Structure Design Approaches

The atomic structure of TIC807 (SEQ ID NO:2) was used to identify loop regions for library mutagenesis followed by testing of the engineered variants. A loop at amino acid positions 211-216 of SEQ ID NO:2 (TIC807) was library-mutagenized and tested. Consecutive loops in close proximity at amino acid positions 75-83, 161-167, and 267-276 of SEQ ID NO:2 (TIC807) was library-mutagenized and tested.

Analysis of the atomic structure of TIC807 suggests that a structural loop resides at residues 113-138 of SEQ ID NO:2, and variants were engineered to stabilize and destabilize the loop.

In another region spanning two beta-strands connected by a short loop, the two beta-strands exhibited an alternating pattern of hydrophobic and hydrophilic amino acid residues at positions 116 to 121 and at positions 133 to 138 relative to SEQ ID NO:2, characteristic of pore-forming loops. An expression library was engineered to modify both beta-strand segments replacing residues V116, V118, and I120 with respective combinations 116V/Y/L/H/F/D, 118V/Y/L/H/F/D, and 120I/D/F/H/L/N/V/Y for a total of 288 possible variants in the library. This procedure was repeated for: residues S117, S119, and P121 with respective combinations 117S/A/D/E/G/K/N/R/T, 119S/A/D/E/G/K/N/R/T, and 121P/S/T for 243 potential variants; residues I133, A135, and F137 with respective combinations 133I/D/F/N/V/Y, 135A/D/F/H/L/V/Y, and 137F/D/H/L/V/Y for 252 possible variants; and residues T134, E136, and N138 with respective combinations 134T/A/D/E/G/K/N/R/S, 136E/A/D/G/K/N/R/S/T, and 138N/A/D/G/S/T for 486 possible variants. An enhanced *Lygus* inhibitory spectrum and/or improved *Lygus* inhibitory activity was associated with certain of these substitutions as shown in Table 4.

Structure-Function Relationship

Altogether, more than 2000 clones (including mixed library clones) expressing variants of TIC807 were tested for enhanced *Lygus* inhibitory spectrum and/or improved *Lygus* inhibitory activity against *Lygus* spp. compared to TIC807. Semi-random modifications, directed modifications, and predictive structure-function modifications, including structure modeling, receptor binding potential, metal binding potential, oligomerization potential, uniformity of surface charge distribution, pore formation potential, ion channel function, and identification of surface exposed patches to with an objective of identifying eHTP's with an enhanced *Lygus* inhibitory spectrum and/or improved *Lygus* inhibitory activity compared to TIC807. These clones were expressed for bioassay testing.

Example 3: Protein Expression and Purification of TIC807, Including Variants and Fragments Control protein TIC807 is a protein of 309 amino acids in length that can be expressed in crystalline form in *Bacillus thuringiensis* (Bt) or aggregate form in *E. coli*. Test variants thereof were recombinantly expressed in Bt. An expression characteristic of TIC807 and variants of TIC807 is the predominant crystalline and aggregate forms extracted from Bt and *E. coli* cells, respectively. To test for *Lygus* bioactivity, test and control samples were made suitable for *Lygus* bioassay by solubilizing samples in 25 mM Sodium Carbonate buffer and removing unsolubilized materials by centrifugation. The amount of protein in test and control samples were measured using total protein methods, e.g.s, a Bradford assay, an ELISA method, or similar. Gel electrophoresis was used to determine the purity and stock concentration of the solubilized recombinant protein. C-terminal HIS-tagged TIC807 protein was engineered to facilitate detection, purification, and quantification of large amounts of TIC807 control protein. C-terminal HIS-tagged TIC807 and un-tagged TIC807 test samples were separately assayed and confirmed to have equivalent activity against *Lygus* (see Examples 4, 5, and 6).

Site-directed amino acid substitutions were made to TIC807_M13 (SEQ ID NO:34) to elevate expression of a soluble form. Inventors postulate that more readily soluble variants of the proteins of the present invention can facilitate expression and purification, e.g., expressed in *E. coli* host cells; and can increase insect inhibitory efficacy when expressed in plant host cells. Recombinant DNA constructs encoding TIC807_M13 (SEQ ID NO:34) were engineered three different ways to reflect three different variants: Relative to TIC807_M13, the modifications were for Variant #1: I58K and P59K, for Variant #2: S198K and G199K, and for Variant #3: S246R, V248E, and Q250R. Relative to TIC807 (SEQ ID NO:2), the modifications can be alternatively described as follows for Variant #1: I58K and P59K, for Variant #2: S201K and G202K, and for Variant #3: S249R, V251E, and Q253R; this positional difference is congruent due to a contiguous triple deletion of SEQ ID NO:2 (TIC807) in residue range 196-201 that is reflected in TIC807_M13 (SEQ ID NO:34). The four engineered recombinant DNA constructs were each cloned and expressed in *E. coli*. The soluble fraction from the four *E. coli* preparations were evaluated by coomassie-stained SDS-PAGE, which showed that TIC807_M13 (SEQ ID NO:34) was not detectable in the soluble fraction; but, in contrast, Variant #s 1, 2, and 3 were soluble. Similar amino acid substitutions either singly or in combination are made to proteins of the present invention to elevate their solubility in non-Bt or plant host cells. Recombinant DNA constructs were engineered to encode for and express TIC807_M13 variant #3 (renamed TIC807_M14; nucleotide SEQ ID NO:203 and amino acid SEQ ID NO:204). Prepared *E. coli* lysate was clarified, and the recombinant protein purified and enriched-for on a series of columns, including ion-exchange and gel filtration methods. Pooled protein fractions were quantified and determined to be active against *Lygus* insects (See Example 4, Table 4B).

Proteins of the present invention, including but not limited to proteins having the amino acid sequence as set forth as SEQ ID NO:28, SEQ ID NO:30, SEQ ID NO:32, or SEQ ID NO:36, are engineered to elevate expression of a soluble form when expressed in a host cell, e.g., expressed in Bt, *E. coli*, or in a plant cell or in a compartment of a plant cell. Engineering includes substituting a lysine amino acid residue at one or more of the following positions 58, 59, 198, 199, 201, or 202; or, a Glutamic acid at one or more of the following positions 198, 248, or 301; or, an Arginine at one or more of the following positions 246, 250, or 253.

The C-terminal region protrudes away from the monomeric core of the protein (See FIG. 2). A recombinant DNA construct was engineered to encode for and express a protein having the amino acid sequence of SEQ ID NO:202, which is a protein fragment (amino acids 1 to 301) of TIC807_M8 (SEQ ID NO:16); and, the expressed protein was purified, quantified, and determined active against *Lygus* insects (See Example 4, Table 4B). Recombinant DNA constructs were designed to encode for and express TIC807 fragments exhibiting varying truncations off of the C-terminus end of the proteins of the present invention at the respective TIC807 positions A281, G289, S293, A301, and S304. Protein fragments are engineered to encode for and express proteins having the amino acid sequences set forth as SEQ ID NO:28, SEQ ID NO:30, SEQ ID NO:32, SEQ ID NO:34, and SEQ ID NO:36; and, the expressed protein fragments are used as test samples against *Lygus* insects.

Example 4: Hemipteran Activity of Engineered Proteins

This example illustrates eHTP's to have improved insecticidal activity or enhanced insecticidal specificity against *Hemipteran* insects when provided in the diet of *Hemipteran* insects, including but not limited to members of the Heteroptera miridae, including the genus *Lygus*, e.g., *Lygus* hesperus and Lygus lineolaris, and the family Cicadellidae, including the genus Amrasca, e.g. Amrasca devastans, and Empoasca, e.g. Empoasca fabae. This example with Table 4B illustrates the feeding assay used to determine the enhanced Lygus inhibitory spectrum and/or improved Lygus inhibitory activity of a Bt expressed recombinant proteins of the present invention against both Lygus hesperus and Lygus lineolaris. Proteins expressed in recombinant bacterium host cells were solubilized in carbonate buffer and analyzed by SDS polyacrylamide gel electrophoresis (SDS-PAGE); and, protein concentrations determined by densitometry using bovine serum albumin (BSA) as a standard. Protein stock (2×) prepared this way were mixed with diet for feeding assays.

Feeding assays with the Hemipteran species Lygus hesperus and Lygus lineolaris were based on a 96 well microtiter plate format with Lygus diet encapsulated between stretched Parafilm® and Mylar sheets. Artificial diet was obtained from Bio-Serv® (Bio-Serv® Diet F9644B, Frenchtown, N.J.). Autoclaved, boiling water (518 mL) was combined with 156.3 grams of Bio-Serv® diet F9644B in a surface-sterilized blender. The contents of four surface-sterilized chicken eggs were added and the mixture blended until smooth, then adjusted to one liter total volume and allowed to cool to room temperature, this being the 2× diet. Test samples were prepared by mixing in a 1:1 ratio of 2× diet and 2× sample. A sheet of Parafilm® (Pechiney Plastic Packing, Chicago, Ill.) was placed over a vacuum manifold designed for 96-well format (Analytical Research Systems, Gainesville, Fla.) and a vacuum of approximately −20 millimeters mercury was applied, sufficient to cause extrusion of the Parafilm® into the wells. Twenty to forty microliters of test sample were added to the Parafilm® extrusions. A sheet of Mylar film (Clear Lam Packaging, Inc., Elk Grove Village, Ill.) was placed over the sample filled Parafilm® extrusions and sealed with a tacking iron (Bienfang Sealector II, Hunt Corporation, Philadelphia, Pa.), thus forming diet filled Parafilm® sachets. These Parafilm® sachets were positioned over a flat-bottom 96-well plate containing Lygus eggs suspended in a dilute agarose solution. Upon hatching, Lygus nymphs feed on the diet by piercing the diet filled Parafilm® sachets. Alternatively, newly hatched Lygus nymphs instead of eggs were manually infested into each well. Stunting and mortality scores were determined on day 5 and compared to controls. Data were analyzed using JMP4 statistical software. For each protein at a test concentration, three populations of eight nymphs were subjected to this bioassay, and mortality scores reported in Table 4B.

For LC50 determinations listed in Table 1 and Table 4B, proteins were presented to newly hatched Lygus nymphs at 8-10 concentrations and the nymphs allowed to feed for 5 days before scoring for mortality over the dose range. For each concentration, three populations of eight nymphs were subjected to this bioassay, and all LC50 determinations in Table 1 and Table 4B were repeated at least once.

For LC50 estimations, proteins were presented to newly hatched Lygus lineolaris nymphs at 4 concentrations and the nymphs allowed to feed for 5 days before scoring for mortality over the dose range. Lygus lineolaris LC50 estimations were performed on TIC807 and TIC807_M2 because significantly large amounts of these proteins in excess of 1000 µg/mL have not been possible to provide in Lygus diet in order to complete the high range of toxicity dose response to Lygus lineolaris; and therefore, an LC50 value was not determined for TIC807 or TIC807_M2. Instead, a 4-dose LC50 estimation in the low range was performed, and reported in Table 1 and Table 4B. The estimated Lygus lineolaris LC50 for TIC807_M14 is 4.4 µg/mL. For each concentration, three populations of eight nymphs were subjected to this bioassay.

This example with Tables 4A and 4B illustrate the feeding assay used to determine the enhanced inhibitory spectrum and/or improved inhibitory activity of a Bt expressed recombinant protein disclosed herein against Amrasca devastans. TIC807 variants with improved insecticidal activity or enhanced insecticidal specificity against Lygus hesperus and Lygus lineolaris exhibit improved insecticidal activity against Amrasca devastans.

TIC807, and TIC807-M13 were dissolved in 25 mM sodium carbonate buffer, pH 10. Amrasca devastans eggs were collected on Okra leaf and incubated in a petriplate containing 2% agar. Upon hatching the neonates were used for bioassays using the diluted (1:5) Lygus diet. The proteins and diet were mixed at equal proportion (bringing final concentration of protein to 500 µg/mL) and dispensed into test arena. Untreated control was prepared by mixing the buffer with the diet. Individual neonates were infested into the test arena, the assays were incubated at 25° C., 60% RH. Twenty neonate nymphs were tested for each concentration, protein and in 2 replicates. A control was maintained with 25 mM Sodium Carbonate buffer, pH 10, in 1:5 diluted Lygus diet. Mortality of the insects was determined on the fifth day. Mortality values were calculated by the following formula: (% mortality in treatment−% mortality in control)/(100−% mortality in control)×100. Table 4A tabulates Amrasca activity for TIC807 and TIC807_M13 at 5 different concentrations.

TABLE 4A

TIC807 and TIC807_M13 Percent Mortality Directed to Amrasca species

| SEQ ID NO: | Protein Name | Mortality (%) | | | | |
|---|---|---|---|---|---|---|
| | | 500 µg/mL | 166.66 µg/mL | 55.55 µg/mL | 18.51 µg/mL | 6.17 µg/mL |
| 2 | TIC807 | 100% | 55.88% | 17.64% | 0 | 0 |
| 34 | TIC807_M13 | 100% | 88.23% | 73.52% | 44.11% | 26.47% |

LC50 values were determined for TIC807 and TIC807_M13 in a separate test. SEQ ID NO:2 (TIC807) exhibited a LC50 value of 116.79 µg/mL and LC90 of 437.27 µg/mL. SEQ ID NO:34 (TIC807_M13) exhibited a LC50 value of 7.59 µg/mL and LC90 value of 239.8 µg/mL.

A feeding assay as described for Amrasca devastans is used to test eHTP's for improved insecticidal activity and/or enhanced insecticidal specificity against Empoasca fabae. TIC807 variants with improved insecticidal activity or enhanced insecticidal specificity against Lygus hesperus and Lygus lineolaris exhibit improved insecticidal activity against Empoasca fabae.

The LC50 values of Cry51Aa1 (SEQ ID NO:182), for TIC807 (SEQ ID NO:2), TIC807_M2 (SEQ ID NO:8), TIC807_M10 (SEQ ID NO:30) and TIC807-M13 (SEQ ID NO:34) against Lygus hesperus and Lygus lineolaris were determined in one testset. TIC807_M2, TIC807_M10 and TIC807_M12 exhibit improved LC50 values compared to Cry51Aa1.

It should be apparent to those skilled in the art that variations to this procedure can exist that should not affect results.

TABLE 4B

Iterative engineering-testing-selecting of eHTP's against *Lygus* spp. resulted in 267 proteins with enhanced *Lygus* inhibitory spectrum and/or improved *Lygus* inhibitory activity against *Lygus* spp. compared to TIC807.

| | | Amino acid differences compared to TIC807 parent protein | | | *Lygus hesperus* | | | *Lygus lineolaris* | | |
|---|---|---|---|---|---|---|---|---|---|---|
| SEQ ID NO: | Protein Name | Amino acid difference(s) relative to SEQ ID NO: 2 (TIC807) | Amino acid difference(s) in the first patch | Amino acid difference(s) in the second patch | LC50 value (μg/mL) | fold increased toxicity (LC50) | % Mortality at about 1-3 μg/mL protein* | LC50 value (μg/mL) | fold increased toxicity (LC50) | % Mortality at about 100 μg/mL protein* |
| 2 | TIC807 | Parent | Parent | Parent | 73 | 1 | 0 | >223 | 1 | 0 |
| 6 | TIC807_M1 | F147A | F147A | None | 23 | 3 | ND | 100 | at least 2 | ND |
| 8 | TIC807_M2 | F46S, Y54H, S167R, S217N, then a contiguous triple deletion in residue range 196-201 | none | S217N, then a contiguous triple deletion in residue range 196-201 | 6.0 | 12 | 39 | >223 | — | 14 |
| 10 | TIC807_M3 | F46S, Y54H, T93A, S167R, S217N, then a contiguous triple deletion in residue range 196-201 | T93A | S217N, then a contiguous triple deletion in residue range 196-201 | 2.9 | 25 | 43 | ND | — | ND |
| 12 | TIC807_M4 | F46S, Y54H, S95A, S167R, S217N, then a contiguous triple deletion in residue range 196-201 | S95A | S217N, then a contiguous triple deletion in residue range 196-201 | 2.4 | 30 | 20 | ND | — | ND |
| 14 | TIC807_M5 | F46S, Y54H, F147A, S167R, S217N, then a contiguous triple deletion in residue range 196-201 | F147A | S217N, then a contiguous triple deletion in residue range 196-201 | 1.1 | 66 | 34 | ND | — | ND |
| 16 | TIC807_M8 | F46S, Y54H, S95A, F147A, S167R, S217N, then a contiguous triple deletion in residue range 196-201 | S95A, F147A | S217N, then a contiguous triple deletion in residue range 196-201 | 0.8 | 91 | ND | 223 | at least 1 | ND |
| 18 | TIC807_M6 | F46S, Y54H, T93A, F147A, S167R, S217N, then a contiguous triple deletion in residue range 196-201 | T93A, F147A | S217N, then a contiguous triple deletion in residue range 196-201 | 1.5 | 50 | ND | ND | — | ND |
| 20 | TIC807_M7 | F46S, Y54H, Q149E, S167R, S217N, then a contiguous triple deletion in residue range 196-201 | Q149E | S217N, then a contiguous triple deletion in residue range 196-201 | 1.4 | 52 | 62 | ND | — | 49 |
| 28 | TIC807_M9 | F46S, Y54H, S95A, F147A, S167R, P219R, then a contiguous triple deletion in residue range 196-201 | S95A, F147A | P219R, then a contiguous triple deletion in residue range 196-201 | 9.9 | 7 | ND | 8.3 | at least 27 | ND |
| 30 | TIC807_M10 | F46S, Y54H, S95A, F147A, S167R, P219R, V251A, then a contiguous triple deletion in residue range 196-201 | S95A, F147A, V251A | P219R, then a contiguous triple deletion in residue range 196-201 | 0.6 | 122 | ND | 4.8 | at least 46 | ND |
| 32 | TIC807_M11 | F46S, Y54H, S95A, F147A, S167R, P219R, R273W, then a contiguous triple deletion in residue range 196-201 | S95A, F147A | P219R, then a contiguous triple deletion in residue range 196-201 | 1.4 | 54 | ND | 5.9 | at least 38 | ND |
| 34 | TIC807_M13 | F46S, Y54H, S95A, F147S, Q149E, S167R, P219R, R273W, then a contiguous triple deletion in residue range 196-201 | S95A, F147A, Q149E | P219R, then a contiguous triple deletion in residue range 196-201 | 0.3 | 243 | ND | 0.85 | at least 262 | ND |
| 36 | TIC807_M12 | F46S, Y54H, S95A, F147A, S167R, P219R, N239A, V251A, then a contiguous triple deletion in residue range 196-201 | S95A, F147A, V251A | P219R, then a contiguous triple deletion in residue range 196-201 | 0.4 | 182 | ND | 1.2 | at least 186 | ND |

TABLE 4B-continued

Iterative engineering-testing-selecting of eHTP's against *Lygus* spp. resulted in 267 proteins with enhanced *Lygus* inhibitory spectrum and/or improved *Lygus* inhibitory activity against *Lygus* spp. compared to TIC807.

| | | Amino acid differences compared to TIC807 parent protein | | | *Lygus hesperus* | | | *Lygus lineolaris* | | |
|---|---|---|---|---|---|---|---|---|---|---|
| SEQ ID NO: | Protein Name | Amino acid difference(s) relative to SEQ ID NO: 2 (TIC807) | Amino acid difference(s) in the first patch | Amino acid difference(s) in the second patch | LC50 value (μg/mL) | fold increased toxicity (LC50) | % Mortality at about 1-3 μg/mL protein* | LC50 value (μg/mL) | fold increased toxicity (LC50) | % Mortality at about 100 μg/mL protein* |
| 37 | TIC807_37 | TIC807_HYS_deletion | none | a contiguous triple deletion in HYSHYS residues (positions 196-201) | 22.4 | 3 | ND | ND | — | ND |
| 38 | TIC807_38 | F46S, Y54H, F138V, S167R, S217N, then a contiguous triple deletion in residue range 196-201 | none | S217N, then a contiguous triple deletion in residue range 196-201 | ND | — | 41 | ND | — | 44 |
| 39 | TIC807_39 | F46S, Y54H, S167R, S217N, H287F, then a contiguous triple deletion in residue range 196-201 | none | S217N, then a contiguous triple deletion in residue range 196-201 | ND | — | 57 | ND | — | 31 |
| 40 | TIC807_40 | F46S, I52M, Y54H, S167R, S217N, then a contiguous triple deletion in residue range 196-201 | none | S217N, then a contiguous triple deletion in residue range 196-201 | ND | — | 52 | ND | — | 36 |
| 41 | TIC807_41 | N12D, F46S, Y54H, S167R, S217N, then a contiguous triple deletion in residue range 196-201 | none | S217N, then a contiguous triple deletion in residue range 196-201 | ND | — | 52 | ND | — | 31 |
| 42 | TIC807_42 | F46S, Y54H, S167R, N180D, S217N, then a contiguous triple deletion in residue range 196-201 | N180D | S217N, then a contiguous triple deletion in residue range 196-201 | ND | — | 63 | ND | — | 50 |
| 43 | TIC807_43 | F46S, Y54H, S167R, then a contiguous triple deletion in residue range 196-201 | none | a contiguous triple deletion in HYSHYS residues (positions 196-201) | ND | — | 46 | ND | — | 87 |
| 44 | TIC807_44 | F46S, Y54H, S167R, S217N, P219R, then a contiguous triple deletion in residue range 196-201 | none | S217N, P219R, then a contiguous triple deletion in residue range 196-201 | ND | — | 30 | ND | — | 94 |
| 45 | TIC807_45 | F46S, Y54H, S159T, S167R, S217N, then a contiguous triple deletion in residue range 196-201 | none | S217N, then a contiguous triple deletion in residue range 196-201 | ND | — | 67 | ND | — | 21 |
| 46 | TIC807_46 | F46S, Y54H, S167R, S217N, I247K, then a contiguous triple deletion in residue range 196-201 | none | S217N, then a contiguous triple deletion in residue range 196-201 | ND | — | 52 | ND | — | 31 |
| 47 | TIC807_47 | F46S, Y54H, S167R, S217N, V244I, then a contiguous triple deletion in residue range 196-201 | none | S217N, then a contiguous triple deletion in residue range 196-201 | ND | — | 59 | ND | — | 31 |
| 48 | TIC807_48 | F46S, Y54H, S167R, S217N, V244I, T247K, then a contiguous triple deletion in residue range 196-201 | none | S217N, then a contiguous triple deletion in residue range 196-201 | ND | — | 58 | ND | — | 34 |
| 49 | TIC807_49 | F46S, Y54H, S167R, S217N, W223Y, then a contiguous triple deletion in residue range 196-201 | none | S217N, W223Y, then a contiguous triple deletion in residue range 196-201 | ND | — | 17 | ND | — | 13 |

TABLE 4B-continued

Iterative engineering-testing-selecting of eHTP's against *Lygus* spp. resulted in 267 proteins with enhanced *Lygus* inhibitory spectrum and/or improved *Lygus* inhibitory activity against *Lygus* spp. compared to TIC807.

| | | Amino acid differences compared to TIC807 parent protein | | | *Lygus hesperus* | | | *Lygus lineolaris* | | |
|---|---|---|---|---|---|---|---|---|---|---|
| SEQ ID NO: | Protein Name | Amino acid difference(s) relative to SEQ ID NO: 2 (TIC807) | Amino acid difference(s) in the first patch | Amino acid difference(s) in the second patch | LC50 value (μg/mL) | fold increased toxicity (LC50) | % Mortality at about 1-3 μg/mL protein* | LC50 value (μg/mL) | fold increased toxicity (LC50) | % Mortality at about 100 μg/mL protein* |
| 50 | TIC807_50 | F46S, Y54H, S167R, S217N, Y246F, then contiguous triple deletion in residue range 196-201 | none | S217N, then a contiguous triple deletion in residue range 196-201 | ND | — | 48 | ND | — | 19 |
| 51 | TIC807_51 | F46S, Y54H, F147A, G128A, S167R, S217N, then a contiguous triple deletion in residue range 196-201 | F147A | S217N, then a contiguous triple deletion in residue range 196-201 | ND | — | 77 | ND | — | ND |
| 52 | TIC807_52 | F46S, Y54H, F147A, S167R, S217N, M300A, then a contiguous triple deletion in residue range 196-201 | F147A | S217N, then a contiguous triple deletion in residue range 196-201 | ND | — | 73 | ND | — | ND |
| 53 | TIC807_53 | F46S, Y54H, F147A, S167R, S217N, S293A, then a contiguous triple deletion in residue range 196-201 | F147A | S217N, then a contiguous triple deletion in residue range 196-201 | ND | — | 73 | ND | — | ND |
| 54 | TIC807_54 | F46S, Y54H, F147A, S167R, S217N, H287A, then a contiguous triple deletion in residue range 196-201 | F147A | S217N, then a contiguous triple deletion in residue range 196-201 | ND | — | 67 | ND | — | ND |
| 55 | TIC807_55 | F46S, Y54H, F147A, S167R, S217N, T274A, then a contiguous triple deletion in residue range 196-201 | F147A | S217N, then a contiguous triple deletion in residue range 196-201 | ND | — | 65 | ND | — | ND |
| 56 | TIC807_56 | F46S, Y54H, F147A, S167R, S217N, R282A, then a contiguous triple deletion in residue range 196-201 | F147A | S217N, then a contiguous triple deletion in residue range 196-201 | ND | — | 64 | ND | — | ND |
| 57 | TIC807_57 | F46S, Y54H, T93A, S167R, S217N, T308A, then a contiguous triple deletion in residue range 196-201 | T93A | S217N, then a contiguous triple deletion in residue range 196-201 | ND | — | 63 | ND | — | ND |
| 58 | TIC807_58 | F46S, Y54H, Q70A, T93A, S167R, S217N, then a contiguous triple deletion in residue range 196-201 | T93A | S217N, then a contiguous triple deletion in residue range 196-201 | ND | — | 61 | ND | — | ND |
| 59 | TIC807_59 | F46S, Y54H, E125A, F147A, S167R, S217N, then a contiguous triple deletion in residue range 196-201 | F147A | then a S217N, contiguous triple deletion in residue range 196-201 | ND | — | 61 | ND | — | ND |
| 60 | TIC807_60 | F46S, Y54H, F147A, S167R, S217N, I247A, then a contiguous triple deletion in residue range 196-201 | F147A | S217N, then a contiguous triple deletion in residue range 196-201 | ND | — | 61 | ND | — | ND |
| 61 | TIC807_61 | F46S, Y54H, T93A, S167R, S217N, P305A, then a contiguous triple deletion in residue range 196-201 | T93A | S217N, then a contiguous triple deletion in residue range 196-201 | ND | — | 59 | ND | — | ND |
| 62 | TIC807_62 | F46S, Y54H, F147A, S167R, S217N, I306A, then a contiguous triple deletion in residue range 196-201 | F147A | S217N, then a contiguous triple deletion in residue range 196-201 | ND | — | 57 | ND | — | ND |

TABLE 4B-continued

Iterative engineering-testing-selecting of eHTP's against *Lygus* spp. resulted in 267 proteins with enhanced *Lygus* inhibitory spectrum and/or improved *Lygus* inhibitory activity against *Lygus* spp. compared to TIC807.

| | | Amino acid differences compared to TIC807 parent protein | | | *Lygus hesperus* | | | *Lygus lineolaris* | | |
|---|---|---|---|---|---|---|---|---|---|---|
| | | | | | | | % Mortality | | | % Mortality |
| SEQ ID NO: | Protein Name | Amino acid difference(s) relative to SEQ ID NO: 2 (TIC807) | Amino acid difference(s) in the first patch | Amino acid difference(s) in the second patch | LC50 value (μg/mL) | fold increased toxicity (LC50) | at about 1-3 μg/mL protein* | LC50 value (μg/mL) | fold increased toxicity (LC50) | at about 100 μg/mL protein* |
| 63 | TIC807_63 | F46S, Y54H, T93A, S167R, S217N, R282A, then a contiguous triple deletion in residue range 196-201 | T93A | S217N, then a contiguous triple deletion in residue range 196-201 | ND | — | 56 | ND | — | ND |
| 64 | TIC807_64 | F46S, Y54H, T93A, S167R, S217N, T308A, then a contiguous triple deletion in residue range 196-201 | T93A | S217N, then a contiguous triple deletion in residue range 196-201 | ND | — | 55 | ND | — | ND |
| 65 | TIC807_65 | F46S, Y54H, T93A, S167R, S217N, M300A, then a contiguous triple deletion in residue range 196-201 | T93A | S217N, then a contiguous triple deletion in residue range 196-201 | ND | — | 55 | ND | — | ND |
| 66 | TIC807_66 | F46S, Y54H, T93A, S167R, S217N, H287A, then a contiguous triple deletion in residue range 196-201 | T93A | S217N, then a contiguous triple deletion in residue range 196-201 | ND | — | 53 | ND | — | ND |
| 67 | TIC807_67 | F46S, Y54H, S95A, S167R, S217N, M300A, then a contiguous triple deletion in residue range 196-201 | S95A | S217N, then a contiguous triple deletion in residue range 196-201 | ND | — | 52 | ND | — | ND |
| 68 | TIC807_68 | F46S, Y54H, F147A, S167R, S217N, I275A, then a contiguous triple deletion in residue range 196-201 | F147A | S217N, then a contiguous triple deletion in residue range 196-201 | ND | — | 52 | ND | — | ND |
| 69 | TIC807_69 | F46S, Y54H, S95A, S167R, S217N, T247A, then a contiguous triple deletion in residue range 196-201 | S95A | S217N, then a contiguous triple deletion in residue range 196-201 | ND | — | 51 | ND | — | ND |
| 70 | TIC807_70 | F46S, Y54H, F147A, S167R, V175A, S217N, then a contiguous triple deletion in residue range 196-201 | F147A | S217N, then a contiguous triple deletion in residue range 196-201 | ND | — | 50 | ND | — | ND |
| 71 | TIC807_71 | F46S, Y54H, F147A, S159A, S167R, S217N, then a contiguous triple deletion in residue range 196-201 | F147A | S217N, then a contiguous triple deletion in residue range 196-201 | ND | — | 50 | ND | — | ND |
| 72 | TIC807_72 | F46S, Y54H, S95A, F147A, S167R, S217N, then a contiguous triple deletion in residue range 196-201 | S95A, F147A | S217N, then a contiguous triple deletion in residue range 196-201 | ND | — | 48 | ND | — | ND |
| 73 | TIC807_73 | F46S, Y54H, F147A, S167R, L187A, S217N, then a contiguous triple deletion in residue range 196-201 | F147A | S217N, then a contiguous triple deletion in residue range 196-201 | ND | — | 47 | ND | — | ND |
| 74 | TIC807_74 | F46S, Y54H, T93A, S167R, T182A, S217N, then a contiguous triple deletion in residue range 196-201 | T93A | S217N, then a contiguous triple deletion in residue range 196-201 | ND | — | 47 | ND | — | ND |
| 75 | TIC807_75 | F46S, Y54H, F147A, S167R, S217N, T245A, then a contiguous triple deletion in residue range 196-201 | F147A | S217N, then a contiguous triple deletion in residue range 196-201 | ND | — | 46 | ND | — | ND |
| 76 | TIC807_76 | F46S, Y54H, T93A, S167R, S217N, S249A, | T93A | S217N, then a contiguous triple | ND | — | 46 | ND | — | ND |

TABLE 4B-continued

Iterative engineering-testing-selecting of eHTP's against *Lygus* spp. resulted in 267 proteins with enhanced *Lygus* inhibitory spectrum and/or improved *Lygus* inhibitory activity against *Lygus* spp. compared to TIC807.

| | | Amino acid differences compared to TIC807 parent protein | | | *Lygus hesperus* | | | *Lygus lineolaris* | | |
|---|---|---|---|---|---|---|---|---|---|---|
| SEQ ID NO: | Protein Name | Amino acid difference(s) relative to SEQ ID NO: 2 (TIC807) | Amino acid difference(s) in the first patch | Amino acid difference(s) in the second patch | LC50 value (μg/mL) | fold increased toxicity (LC50) | % Mortality at about 1-3 μg/mL protein* | LC50 value (μg/mL) | fold increased toxicity (LC50) | % Mortality at about 100 μg/mL protein* |
| 77 | TIC807_77 | F46S, Y54H, T93A, Q149A, S167R, S217N, then a contiguous triple deletion in residue range 196-201 | T93A, Q149A | S217N, then a contiguous triple deletion in residue range 196-201 | ND | — | 45 | ND | — | ND |
| 78 | TIC807_78 | F46S, Y54H, T93A, S151A, S167R, S217N, then a contiguous triple deletion in residue range 196-201 | T93A, S151A | S217N, then a contiguous triple deletion in residue range 196-201 | ND | — | 45 | ND | — | ND |
| 79 | TIC807_79 | F46S, Y54H, Q70A, F147A, S167R, S217N, then a contiguous triple deletion in residue range 196-201 | F147A | S217N, then a contiguous triple deletion in residue range 196-201 | ND | — | 45 | ND | — | ND |
| 80 | TIC807_80 | F46S, Y54H, S95A, Q148A, S167R, S217N, then a contiguous triple deletion in residue range 196-201 | S95A | S217N, then a contiguous triple deletion in residue range 196-201 | ND | — | 44 | ND | — | ND |
| 81 | TIC807_81 | F46S, Y54H, T93A, S167R, S217N, T274A, then a contiguous triple deletion in residue range 196-201 | T93A | S217N, then a contiguous triple deletion in residue range 196-201 | ND | — | 44 | ND | — | ND |
| 82 | TIC807_82 | F46S, Y54H, T93A, S167R, S217N, then a contiguous triple deletion in residue range 196-201 | T93A | S217N, then a contiguous triple deletion in residue range 196-201 | ND | — | 43 | ND | — | ND |
| 83 | TIC807_83 | F46S, Y54H, T93A, S167R, M177A, S217N, then a contiguous triple deletion in residue range 196-201 | T93A | S217N, then a contiguous triple deletion in residue range 196-201 | ND | — | 42 | ND | — | ND |
| 84 | TIC807_84 | F46S, Y54H, S95A, S167R, S217N, V250A, then a contiguous triple deletion in residue range 196-201 | S95A | S217N, then a contiguous triple deletion in residue range 196-201 | ND | — | 42 | ND | — | ND |
| 85 | TIC807_85 | F46S, Y54H, T93A, E155A, S167R, S217N, then a contiguous triple deletion in residue range 196-201 | T93A | S217N, then a contiguous triple deletion in residue range 196-201 | ND | — | 42 | ND | — | ND |
| 86 | TIC807_86 | F46S, Y54H, I134A, F147A, S167R, S217N, then a contiguous triple deletion in residue range 196-201 | F147A | S217N, then a contiguous triple deletion in residue range 196-201 | ND | — | 41 | ND | — | ND |
| 87 | TIC807_87 | F46S, Y54H, T93A, S167R, S217N, T245A, then a contiguous triple deletion in residue range 196-201 | T93A | S217N, then a contiguous triple deletion in residue range 196-201 | ND | — | 41 | ND | — | ND |
| 88 | TIC807_88 | F46S, Y54H, T93A, S167R, S217N, then a contiguous triple deletion in residue range 196-201 followed by a S198A | T93A | S217N, then a contiguous triple deletion in residue range 196-201 followed by S198A | ND | — | 40 | ND | — | ND |
| 89 | TIC807_89 | F46S, Y54H, F147A, S167R, S217N, N295A, then a contiguous triple | F147A | S217N, then a contiguous triple deletion in residue | ND | — | 40 | ND | — | ND |

TABLE 4B-continued

Iterative engineering-testing-selecting of eHTP's against *Lygus* spp. resulted in 267 proteins with enhanced *Lygus* inhibitory spectrum and/or improved *Lygus* inhibitory activity against *Lygus* spp. compared to TIC807.

| | | Amino acid differences compared to TIC807 parent protein | | | *Lygus hesperus* | | | *Lygus lineolaris* | | |
|---|---|---|---|---|---|---|---|---|---|---|
| SEQ ID NO: | Protein Name | Amino acid difference(s) relative to SEQ ID NO: 2 (TIC807) | Amino acid difference(s) in the first patch | Amino acid difference(s) in the second patch | LC50 value (μg/mL) | fold increased toxicity (LC50) | % Mortality at about 1-3 μg/mL protein* | LC50 value (μg/mL) | fold increased toxicity (LC50) | % Mortality at about 100 μg/mL protein* |
| 90 | TIC807_90 | F46S, Y54H, A87S, F147A, S167R, S217N, then a contiguous triple deletion in residue range 196-201 | F147A | S217N, then a contiguous triple deletion in residue range 196-201 | ND | — | 38 | ND | — | ND |
| 91 | TIC807_91 | F46S, Y54H, F147A, S167R, S217N, S249A, then a contiguous triple deletion in residue range 196-201 | F147A | S217N, then a contiguous triple deletion in residue range 196-201 | ND | — | 38 | ND | — | ND |
| 92 | TIC807_92 | F46S, Y54H, S95A, S167R, S217N, I275A, then a contiguous triple deletion in residue range 196-201 | S95A | S217N, then a contiguous triple deletion in residue range 196-201 | ND | — | 37 | ND | — | ND |
| 93 | TIC807_93 | F46S, Y54H, T93A, A139S, S167R, S217N, then a contiguous triple deletion in residue range 196-201 | T93A | S217N, then a contiguous triple deletion in residue range 196-201 | ND | — | 37 | ND | — | ND |
| 94 | TIC807_94 | F46S, Y54H, F147A, S167R, S217N, P305A, then a contiguous triple deletion in residue range 196-201 | F147A | S217N, then a contiguous triple deletion in residue range 196-201 | ND | — | 36 | ND | — | ND |
| 95 | TIC807_95 | F46S, Y54H, F147A, S167R, S217N, then a contiguous triple deletion in residue range 196-201 followed by a S198A | F147A | S217N, then a contiguous triple deletion in residue range 196-201 followed by S198A | ND | — | 36 | ND | — | ND |
| 96 | TIC807_96 | F46S, Y54H, F147A, S167R, S217N, S252A, then a contiguous triple deletion in residue range 196-201 | F147A | S217N, then a contiguous triple deletion in residue range 196-201 | ND | — | 36 | ND | — | ND |
| 97 | TIC807_97 | F46S, Y54H, T93A, F147A, S167R, S217N, then a contiguous triple deletion in residue range 196-201 | T93A, F147A | S217N, then a contiguous triple deletion in residue range 196-201 | ND | — | 36 | ND | — | ND |
| 98 | TIC807_98 | F46S, Y54H, F147A, S167R, S217N, V250A, then a contiguous triple deletion in residue range 196-201 | F147A | S217N, then a contiguous triple deletion in residue range 196-201 | ND | — | 36 | ND | — | ND |
| 99 | TIC807_99 | F46S, Y54H, F147A, S167R, S217N, T243A, then a contiguous triple deletion in residue range 196-201 | F147A | S217N, then a contiguous triple deletion in residue range 196-201 | ND | — | 35 | ND | — | ND |
| 100 | TIC807_100 | F46S, Y54H, F147A, S167R, S217N, then a contiguous triple deletion in residue range 196-201 followed by a Y197A | F147A | S217N, then a contiguous triple deletion in residue range 196-201 followed by Y197A | ND | — | 35 | ND | — | ND |
| 101 | TIC807_101 | F46S, Y54H, S95A, S167R, S217N, N295A, then a contiguous triple deletion in residue range 196-201 | S95A | S217N, then a contiguous triple deletion in residue range 196-201 | ND | — | 35 | ND | — | ND |
| 102 | TIC807_102 | F46S, Y54H, F147A, S167R, S217N, then a contiguous triple | F147A | S217N, then a contiguous triple deletion in residue | ND | — | 34 | ND | — | ND |

TABLE 4B-continued

Iterative engineering-testing-selecting of eHTP's against *Lygus* spp. resulted in 267 proteins with enhanced *Lygus* inhibitory spectrum and/or improved *Lygus* inhibitory activity against *Lygus* spp. compared to TIC807.

| | | Amino acid differences compared to TIC807 parent protein | | | *Lygus hesperus* | | | *Lygus lineolaris* | | |
|---|---|---|---|---|---|---|---|---|---|---|
| SEQ ID NO: | Protein Name | Amino acid difference(s) relative to SEQ ID NO: 2 (TIC807) | Amino acid difference(s) in the first patch | Amino acid difference(s) in the second patch | LC50 value (μg/mL) | fold increased toxicity (LC50) | % Mortality at about 1-3 μg/mL protein* | LC50 value (μg/mL) | fold increased toxicity (LC50) | % Mortality at about 100 μg/mL protein* |
| | | deletion in residue range 196-201 | | range 196-201 | ND | — | 32 | ND | — | ND |
| 103 | TIC807_103 | F46S, Y54H, F147A, S167R, S217N, E299A, then a contiguous triple deletion in residue range 196-201 | F147A | S217N, then a contiguous triple deletion in residue range 196-201 | ND | — | 32 | ND | — | ND |
| 104 | TIC807_104 | F46S, Y54H, S95A, S167R, S217N, R282A, then a contiguous triple deletion in residue range 196-201 | S95A | S217N, then a contiguous triple deletion in residue range 196-201 | ND | — | 32 | ND | — | ND |
| 105 | TIC807_105 | F46S, Y54H, T93A, S167R, S217N, I306A, then a contiguous triple deletion in residue range 196-201 | T93A | S217N, then a contiguous triple deletion in residue range 196-201 | ND | — | 32 | ND | — | ND |
| 106 | TIC807_106 | F46S, Y54H, S95A, S167R, S217N, S249A, then a contiguous triple deletion in residue range 196-201 | S95A | S217N, then a contiguous triple deletion in residue range 196-201 | ND | — | 30 | ND | — | ND |
| 107 | TIC807_107 | F46S, Y54H, A87S, T93A, S167R, S217N, then a contiguous triple deletion in residue range 196-201 | T93A | S217N, then a contiguous triple deletion in residue range 196-201 | ND | — | 30 | ND | — | ND |
| 108 | TIC807_108 | F46S, Y54H, T93A, S159A, S167R, S217N, then a contiguous triple deletion in residue range 196-201 | T93A | S217N, then a contiguous triple deletion in residue range 196-201 | ND | — | 29 | ND | — | ND |
| 109 | TIC807_109 | F46S, Y54H, F147A, S167R, S217N, T303A, then a contiguous triple deletion in residue range 196-201 | F147A | S217N, then a contiguous triple deletion in residue range 196-201 | ND | — | 28 | ND | — | ND |
| 110 | TIC807_110 | F46S, Y54H, T93A, Q148A, S167R, S217N, then a contiguous triple deletion in residue range 196-201 | T93A | S217N, then a contiguous triple deletion in residue range 196-201 | ND | — | 27 | ND | — | ND |
| 111 | TIC807_111 | F46S, Y54H, S95A, S167R, V175A, S217N, then a contiguous triple deletion in residue range 196-201 | S95A | S217N, then a contiguous triple deletion in residue range 196-201 | ND | — | 27 | ND | — | ND |
| 112 | TIC807_112 | F46S, Y54H, F147A, S167R, S217N, D241A, then a contiguous triple deletion in residue range 196-201 | F147A | S217N, then a contiguous triple deletion in residue range 196-201 | ND | — | 27 | ND | — | ND |
| 113 | TIC807_113 | F46S, Y54H, S95A, F147A, S167R, S217N, then a contiguous triple deletion in residue range 196-201 | S95A, F147A | S217N, then a contiguous triple deletion in residue range 196-201 | ND | — | 26 | ND | — | ND |
| 114 | TIC807_114 | F46S, Y54H, F147A, S167R, M177A, S217N, then a contiguous triple deletion in residue range 196-201 | F147A | S217N, then a contiguous triple deletion in residue range 196-201 | ND | — | 26 | ND | — | ND |
| 115 | TIC807_115 | F46S, Y54H, F147A, S167R, S217N, M300A, then a contiguous triple deletion in residue range 196-201 | F147A | S217N, then a contiguous triple deletion in residue range 196-201 | ND | — | 26 | ND | — | ND |

TABLE 4B-continued

Iterative engineering-testing-selecting of eHTP's against *Lygus* spp. resulted in 267 proteins with enhanced *Lygus* inhibitory spectrum and/or improved *Lygus* inhibitory activity against *Lygus* spp. compared to TIC807.

| | | Amino acid differences compared to TIC807 parent protein | | | *Lygus hesperus* | | | *Lygus lineolaris* | | |
|---|---|---|---|---|---|---|---|---|---|---|
| | | | | | | | % Mortality | | | % Mortality |
| SEQ ID NO: | Protein Name | Amino acid difference(s) relative to SEQ ID NO: 2 (TIC807) | Amino acid difference(s) in the first patch | Amino acid difference(s) in the second patch | LC50 value (μg/mL) | fold increased toxicity (LC50) | at about 1-3 μg/mL protein* | LC50 value (μg/mL) | fold increased toxicity (LC50) | at about 100 μg/mL protein* |
| 116 | TIC807_116 | F46S, Y54H, S95A, S167R, S217N, P305A, then a contiguous triple deletion in residue range 196-201 | S95A | S217N, then a contiguous triple deletion in residue range 196-201 | ND | — | 26 | ND | — | ND |
| 117 | TIC807_117 | F46S, Y54H, F147A, S167R, S217N, then a contiguous triple deletion in residue range 196-201 followed by H196A | F147A | S217N, then a contiguous triple deletion in residue range 196-201 followed by H196A | ND | — | 25 | ND | — | ND |
| 118 | TIC807_118 | F46S, Y54H, A139S, F147A, S167R, S217N, then a contiguous triple deletion in residue range 196-201 | F147A | S217N, then a contiguous triple deletion in residue range 196-201 | ND | — | 25 | ND | — | ND |
| 119 | TIC807_119 | F46S, Y54H, T93A, S167R, S217N, N295A, then a contiguous triple deletion in residue range 196-201 | T93A | S217N, then a contiguous triple deletion in residue range 196-201 | ND | — | 25 | ND | — | ND |
| 120 | TIC807_120 | F46S, Y54H, T93A, T145A, S167R, S217N, then a contiguous triple deletion in residue range 196-201 | T93A | S217N, then a contiguous triple deletion in residue range 196-201 | ND | — | 24 | ND | — | ND |
| 121 | TIC807_121 | F46S, Y54H, S117A, F147A, S167R, S217N, then a contiguous triple deletion in residue range 196-201 | F147A | S217N, then a contiguous triple deletion in residue range 196-201 | ND | — | 24 | ND | — | ND |
| 122 | TIC807_122 | F46S, Y54H, T93A, S167R, S217N, I275A, then a contiguous triple deletion in residue range 196-201 | T93A | S217N, then a contiguous triple deletion in residue range 196-201 | ND | — | 23 | ND | — | ND |
| 123 | TIC807_123 | F46S, Y54H, S95A, S167R, S217N, H287A, then a contiguous triple deletion in residue range 196-201 | S95A | S217N, then a contiguous triple deletion in residue range 196-201 | ND | — | 23 | ND | — | ND |
| 124 | TIC807_124 | F46S, Y54H, S95A, G105A, S167R, S217N, then a contiguous triple deletion in residue range 196-201 | S95A | S217N, then a contiguous triple deletion in residue range 196-201 | ND | — | 21 | ND | — | ND |
| 125 | TIC807_125 | F46S, Y54H, S95A, S167R, S217N, then a contiguous triple deletion in residue range 196-201 | S95A | S217N, then a contiguous triple deletion in residue range 196-201 | ND | — | 20 | ND | — | ND |
| 126 | TIC807_126 | F46S, Y54H, S95A, I134A, S167R, S217N, then a contiguous triple deletion in residue range 196-201 | S95A | S217N, then a contiguous triple deletion in residue range 196-201 | ND | — | 20 | ND | — | ND |
| 127 | TIC807_127 | F46S, Y54H, T93A, S167R, S217N, M300A, then a contiguous triple deletion in residue range 196-201 | T93A | S217N, then a contiguous triple deletion in residue range 196-201 | ND | — | 20 | ND | — | ND |
| 128 | TIC807_128 | F46S, Y54H, T93A, S167R, S217N, T303A, then a contiguous triple deletion in residue range 196-201 | T93A | S217N, then a contiguous triple deletion in residue range 196-201 | ND | — | 18 | ND | — | ND |

TABLE 4B-continued

Iterative engineering-testing-selecting of eHTP's against *Lygus* spp. resulted in 267 proteins with enhanced *Lygus* inhibitory spectrum and/or improved *Lygus* inhibitory activity against *Lygus* spp. compared to TIC807.

| | | Amino acid differences compared to TIC807 parent protein | | | *Lygus hesperus* | | | *Lygus lineolaris* | | |
|---|---|---|---|---|---|---|---|---|---|---|
| SEQ ID NO: | Protein Name | Amino acid difference(s) relative to SEQ ID NO: 2 (TIC807) | Amino acid difference(s) in the first patch | Amino acid difference(s) in the second patch | LC50 value (μg/mL) | fold increased toxicity (LC50) | % Mortality at about 1-3 μg/mL protein* | LC50 value (μg/mL) | fold increased toxicity (LC50) | % Mortality at about 100 μg/mL protein* |
| 129 | TIC807_129 | F46S, Y54H, T93A, A150S, S167R, S217N, then a contiguous triple deletion in residue range 196-201 | T93A | S217N, then a contiguous triple deletion in residue range 196-201 | ND | — | 18 | ND | — | ND |
| 130 | TIC807_130 | F46S, Y54H, S95A, E155A, S167R, S217N, then a contiguous triple deletion in residue range 196-201 | S95A | S217N, then a contiguous triple deletion in residue range 196-201 | ND | — | 18 | ND | — | ND |
| 131 | TIC807_131 | F46S, Y54H, T93A, T145A, S167R, S217N, then a contiguous triple deletion in residue range 196-201 | T93A | S217N, then a contiguous triple deletion in residue range 196-201 | ND | — | 17 | ND | — | ND |
| 132 | TIC807_132 | F46S, Y54H, S95A, S167R, W208A, S217N, then a contiguous triple deletion in residue range 196-201 | S95A | W208A, S217N, then a contiguous triple deletion in residue range 196-201 | ND | — | 17 | ND | — | ND |
| 133 | TIC807_133 | F46S, Y54H, S95A, S167R, T182A, S217N, then a contiguous triple deletion in residue range 196-201 | S95A, T182A | S217N, then a contiguous triple deletion in residue range 196-201 | ND | — | 17 | ND | — | ND |
| 134 | TIC807_134 | F46S, Y54H, T93A, S167R, S217N, T243A, then a contiguous triple deletion in residue range 196-201 | T93A | S217N, then a contiguous triple deletion in residue range 196-201 | ND | — | 17 | ND | — | ND |
| 135 | TIC807_135 | F46S, Y54H, S95A, S167R, S217N, I306A, then a contiguous triple deletion in residue range 196-201 | S95A | S217N, then a contiguous triple deletion in residue range 196-201 | ND | — | 16 | ND | — | ND |
| 136 | TIC807_136 | F46S, Y54H, S95A, S117A, S167R, S217N, then a contiguous triple deletion in residue range 196-201 | S95A | S217N, then a contiguous triple deletion in residue range 196-201 | ND | — | 16 | ND | — | ND |
| 137 | TIC807_137 | F46S, Y54H, T93A, S119A, S167R, S217N, then a contiguous triple deletion in residue range 196-201 | T93A | S217N, then a contiguous triple deletion in residue range 196-201 | ND | — | 15 | ND | — | ND |
| 138 | TIC807_138 | F46S, Y54H, T68A, F147A, S167R, S217N, then a contiguous triple deletion in residue range 196-201 | F147A | S217N, then a contiguous triple deletion in residue range 196-201 | ND | — | 15 | ND | — | ND |
| 139 | TIC807_139 | F46S, Y54H, G105A, F147A, S167R, S217N, then a contiguous triple deletion in residue range 196-201 | F147A | S217N, then a contiguous triple deletion in residue range 196-201 | ND | — | 15 | ND | — | ND |
| 140 | TIC807_140 | F46S, Y54H, S95A, E125A, S167R, S217N, then a contiguous triple deletion in residue range 196-201 | S95A | S217N, then a contiguous triple deletion in residue range 196-201 | ND | — | 15 | ND | — | ND |
| 141 | TIC807_141 | F46S, Y54H, T93A, E155A, S167R, S217N, then a contiguous triple deletion in residue range 196-201 | T93A | S217N, then a contiguous triple deletion in residue range 196-201 | ND | — | 14 | ND | — | ND |
| 142 | TIC807_142 | F46S, Y54H, T93A, S167R, S217N, P305A, | T93A | S217N, then a contiguous triple | ND | — | 14 | ND | — | ND |

TABLE 4B-continued

Iterative engineering-testing-selecting of eHTP's against *Lygus* spp. resulted in 267 proteins with enhanced *Lygus* inhibitory spectrum and/or improved *Lygus* inhibitory activity against *Lygus* spp. compared to TIC807.

| | | Amino acid differences compared to TIC807 parent protein | | | *Lygus hesperus* | | | *Lygus lineolaris* | | |
|---|---|---|---|---|---|---|---|---|---|---|
| SEQ ID NO: | Protein Name | Amino acid difference(s) relative to SEQ ID NO: 2 (TIC807) | Amino acid difference(s) in the first patch | Amino acid difference(s) in the second patch | LC50 value (μg/mL) | fold increased toxicity (LC50) | % Mortality at about 1-3 μg/mL protein* | LC50 value (μg/mL) | fold increased toxicity (LC50) | % Mortality at about 100 μg/mL protein* |
| 143 | TIC807_143 | F46S, Y54H, S95A, S167R, M177A, S217N, then a contiguous triple deletion in residue range 196-201 | S95A | S217N, then a contiguous triple deletion in residue range 196-201 | ND | — | 13 | ND | — | ND |
| 144 | TIC807_144 | F46S, Y54H, T93A, S167R, S217N, then a contiguous triple deletion in residue range 196-201 followed by H196A | T93A | S217N, then a contiguous triple deletion in residue range 196-201 followed by H196A | ND | — | 13 | ND | — | ND |
| 145 | TIC807_145 | F46S, Y54H, T93A, D153A, S167R, S217N, then a contiguous triple deletion in residue range 196-201-T93A-D153A | T93A | S217N, then a contiguous triple deletion in residue range 196-201 | ND | — | 11 | ND | — | ND |
| 146 | TIC807_146 | F46S, Y54H, F147A, S167R, S217N, W208A, then a contiguous triple deletion in residue range 196-201 | F147A | W208A, S217N, then a contiguous triple deletion in residue range 196-201 | ND | — | 10 | ND | — | ND |
| 147 | TIC807_147 | F46S, Y54H, T93A, S167R, S217N, I306A, then a contiguous triple deletion in residue range 196-201 | T93A | S217N, then a contiguous triple deletion in residue range 196-201 | ND | — | 9 | ND | — | ND |
| 148 | TIC807_148 | F46S, Y54H, S95A, S167R, S217N, then a contiguous triple deletion in residue range 196-201 followed by H196A | S95A | S217N, then a contiguous triple deletion in residue range 196-201 followed by H196A | ND | — | 9 | ND | — | ND |
| 149 | TIC807_149 | F46S, Y54H, S95A, Q149A, S167R, S217N, then a contiguous triple deletion in residue range 196-201 | S95A, Q149A | S217N, then a contiguous triple deletion in residue range 196-201 | ND | — | 9 | ND | — | ND |
| 150 | TIC807_150 | F46S, Y54H, S95A, S167R, S217N, S293A, then a contiguous triple deletion in residue range 196-201 | S95A | S217N, then a contiguous triple deletion in residue range 196-201 | ND | — | 8 | ND | — | ND |
| 151 | TIC807_151 | F46S, Y54H, S95A, A150S, S167R, S217N, then a contiguous triple deletion in residue range 196-201 | S95A | S217N, then a contiguous triple deletion in residue range 196-201 | ND | — | 8 | ND | — | ND |
| 152 | TIC807_152 | F46S, Y54H, S119A, F147A, S167R, S217N, then a contiguous triple deletion in residue range 196-201 | F147A | S217N, then a contiguous triple deletion in residue range 196-201 | ND | — | 7 | ND | — | ND |
| 153 | TIC807_153 | F46S, Y54H, S95A, S167A, S217N, then a contiguous triple deletion in residue range 196-201 | S95A | S217N, then a contiguous triple deletion in residue range 196-201 | ND | — | 7 | ND | — | ND |
| 154 | TIC807_154 | F46S, Y54H, F147A, I158A, S167R, S217N, then a contiguous triple deletion in residue range 196-201 | F147A | S217N, then a contiguous triple deletion in residue range 196-201 | ND | — | 7 | ND | — | ND |
| 155 | TIC807_155 | F46S, Y54H, S95A, S167R, S217N, M300A, | S95A | S217N, then a contiguous triple | ND | — | 7 | ND | — | ND |

TABLE 4B-continued

Iterative engineering-testing-selecting of eHTP's against *Lygus* spp. resulted in 267 proteins with enhanced *Lygus* inhibitory spectrum and/or improved *Lygus* inhibitory activity against *Lygus* spp. compared to TIC807.

| | | Amino acid differences compared to TIC807 parent protein | | | *Lygus hesperus* | | | *Lygus lineolaris* | | |
|---|---|---|---|---|---|---|---|---|---|---|
| | | | | | | | % Mortality | | | % Mortality |
| SEQ ID NO: | Protein Name | Amino acid difference(s) relative to SEQ ID NO: 2 (TIC807) | Amino acid difference(s) in the first patch | Amino acid difference(s) in the second patch | LC50 value (μg/mL) | fold increased toxicity (LC50) | at about 1-3 μg/mL protein* | LC50 value (μg/mL) | fold increased toxicity (LC50) | at about 100 μg/mL protein* |
| 156 | TIC807_156 | F46S, Y54H, F147A, T182A, S167R, S217N, then a contiguous triple deletion in residue range 196-201 | F147A, T182A | S217N, then a contiguous triple deletion in residue range 196-201 | ND | — | 6 | ND | — | ND |
| 157 | TIC807_157 | F46S, Y54H, F147A, S167R, S217N, F235A, then a contiguous triple deletion in residue range 196-201 | F147A | S217N, then a contiguous triple deletion in residue range 196-201 | ND | — | 5 | ND | — | ND |
| 158 | TIC807_158 | F46S, Y54H, F147A, S167A, S217N, then a contiguous triple deletion in residue range 196-201 | F147A | S217N, then a contiguous triple deletion in residue range 196-201 | ND | — | 5 | ND | — | ND |
| 159 | TIC807_159 | F46S, Y54H, T93A, S167R, S217N, D241A, then a contiguous triple deletion in residue range 196-201 | T93A | S217N, then a contiguous triple deletion in residue range 196-201 | ND | — | 5 | ND | — | ND |
| 160 | TIC807_160 | F46S, Y54H, S95A, S167R, S217N, T274A, then a contiguous triple deletion in residue range 196-201 | S95A | S217N, then a contiguous triple deletion in residue range 196-201 | ND | — | 4 | ND | — | ND |
| 161 | TIC807_161 | F46S, Y54H, T93A, Q148A, S167R, S217N, then a contiguous triple deletion in residue range 196-201 | T93A | S217N, then a contiguous triple deletion in residue range 196-201 | ND | — | 4 | ND | — | ND |
| 162 | TIC807_162 | F46S, Y54H, S95A, S167R, S217N, D241A, then a contiguous triple deletion in residue range 196-201 | S95A | S217N, then a contiguous triple deletion in residue range 196-201 | ND | — | 4 | ND | — | ND |
| 163 | TIC807_163 | F46S, Y54H, S95A, E155A, S167R, S217N, then a contiguous triple deletion in residue range 196-201 | S95A | S217N, then a contiguous triple deletion in residue range 196-201 | ND | — | 4 | ND | — | ND |
| 164 | TIC807_164 | F46S, Y54H, T93A, S167R, L187A, S217N, then a contiguous triple deletion in residue range 196-201 | T93A | S217N, then a contiguous triple deletion in residue range 196-201 | ND | — | 4 | ND | — | ND |
| 165 | TIC807_165 | F46S, Y54H, T93A, S167R, S217N, T303A, then a contiguous triple deletion in residue range 196-201 | T93A | S217N, then a contiguous triple deletion in residue range 196-201 | ND | — | 4 | ND | — | ND |
| 166 | TIC807_166 | F46S, Y54H, T93A, E155A, S167R, S217N, then a contiguous triple deletion in residue range 196-201 | T93A | S217N, then a contiguous triple deletion in residue range 196-201 | ND | — | 3 | ND | — | ND |
| 167 | TIC807_167 | F46S, Y54H, T93A, D153A, S167R, S217N, then a contiguous triple deletion in residue range 196-201 | T93A | S217N, then a contiguous triple deletion in residue range 196-201 | ND | — | 3 | ND | — | ND |

TABLE 4B-continued

Iterative engineering-testing-selecting of eHTP's against *Lygus* spp. resulted in 267 proteins with enhanced *Lygus* inhibitory spectrum and/or improved *Lygus* inhibitory activity against *Lygus* spp. compared to TIC807.

| | | | | | *Lygus hesperus* | | | *Lygus lineolaris* | | |
|---|---|---|---|---|---|---|---|---|---|---|
| | | Amino acid differences compared to TIC807 parent protein | | | | | % Mortality | | | % Mortality |
| SEQ ID NO: | Protein Name | Amino acid difference(s) relative to SEQ ID NO: 2 (TIC807) | Amino acid difference(s) in the first patch | Amino acid difference(s) in the second patch | LC50 value (µg/mL) | fold increased toxicity (LC50) | at about 1-3 µg/mL protein* | LC50 value (µg/mL) | fold increased toxicity (LC50) | at about 100 µg/mL protein* |
| 168 | TIC807_168 | F46S, Y54H, T93A, I134A, S167R, S217N, then a contiguous triple deletion in residue range 196-201 | T93A | S217N, then a contiguous triple deletion in residue range 196-201 | ND | — | 3 | ND | — | ND |
| 169 | TIC807_169 | N137T | none | None | ND | — | 44* | ND | — | ND |
| 169 | TIC807_169 | E135S | none | None | ND | — | 20* | ND | — | ND |
| 169 | TIC807_169 | N137T, E135S | none | None | ND | — | 34* | ND | — | ND |
| 169 | TIC807_169 | E135T, N137D | none | None | ND | — | 16* | ND | — | ND |
| 169 | TIC807_169 | E133E | none | None | ND | — | 60* | ND | — | ND |
| 169 | TIC807_169 | E135A, N137G | none | None | ND | — | 50* | ND | — | ND |
| 170 | TIC807_170 | E125C | none | None | ND | — | 12 | ND | — | ND |
| 170 | TIC807_170 | E125H | none | None | ND | — | 38 | ND | — | ND |
| 170 | TIC807_170 | E125R | none | None | ND | — | 14 | ND | — | ND |
| 170 | TIC807_170 | E125F | none | None | ND | — | 33 | ND | — | ND |
| 170 | TIC807_170 | E125S | none | None | ND | — | 24 | ND | — | ND |
| 170 | TIC807_170 | E125Q | none | None | ND | — | 21 | ND | — | ND |
| 170 | TIC807_170 | E125K | none | None | ND | — | 20 | ND | — | ND |
| 170 | TIC807_170 | E125T | none | None | ND | — | 33 | ND | — | ND |
| 170 | TIC807_170 | E125N | none | None | ND | — | 19 | ND | — | ND |
| 170 | TIC807_170 | E125A | none | None | ND | — | 41 | ND | — | ND |
| 170 | TIC807_170 | E125L | none | None | ND | — | 13 | ND | — | ND |
| 170 | TIC807_170 | E125V | none | None | ND | — | 14 | ND | — | ND |
| 170 | TIC807_170 | E125M | none | None | ND | — | 13 | ND | — | ND |
| 170 | TIC807_170 | E125D | none | None | ND | — | 15 | ND | — | ND |
| 170 | TIC807_170 | E125Y | none | None | ND | — | 38 | ND | — | ND |
| 171 | TIC807_171 | T133E | none | None | ND | — | 23 | ND | — | ND |
| 171 | TIC807_171 | T133Y | none | None | ND | — | 17 | ND | — | ND |
| 171 | TIC807_171 | T133W | none | None | ND | — | 13 | ND | — | ND |
| 172 | TIC807_172 | I134V | none | None | ND | — | 18 | ND | — | ND |
| 172 | TIC807_172 | I134L | none | None | ND | — | 10 | ND | — | ND |
| 172 | TIC807_172 | I134F | none | None | ND | — | 18 | ND | — | ND |
| 172 | TIC807_172 | I134K | none | None | ND | — | 13 | ND | — | ND |
| 172 | TIC807_172 | I134C | none | None | ND | — | 30 | ND | — | ND |
| 172 | TIC807_172 | I134M | none | None | ND | — | 33 | ND | — | ND |
| 173 | TIC807_173 | E135V | none | None | ND | — | 13 | ND | — | ND |
| 173 | TIC807_173 | E135W | none | None | ND | — | 13 | ND | — | ND |
| 173 | TIC807_173 | E135T | none | None | ND | — | 39 | ND | — | ND |
| 174 | TIC807_174 | N137H | none | None | ND | — | 42 | ND | — | ND |
| 174 | TIC807_174 | N137Y | none | None | ND | — | 17 | ND | — | ND |
| 174 | TIC807_174 | N137T | none | None | ND | — | 31 | ND | — | ND |
| 174 | TIC807_174 | N137E | none | None | ND | — | 32 | ND | — | ND |
| 174 | TIC807_174 | N137S | none | None | ND | — | 24 | ND | — | ND |
| 174 | TIC807_174 | N137A | none | None | ND | — | 24 | ND | — | ND |
| 174 | TIC807_174 | N137Q | none | None | ND | — | 21 | ND | — | ND |
| 174 | TIC807_174 | N137G | none | None | ND | — | 18 | ND | — | ND |
| 174 | TIC807_174 | N137I | none | None | ND | — | 10 | ND | — | ND |
| 174 | TIC807_174 | N137W | none | None | ND | — | 17 | ND | — | ND |
| 174 | TIC807_174 | N137K | none | None | ND | — | 66 | ND | — | ND |
| 174 | TIC807_174 | N137C | none | None | ND | — | 19 | ND | — | ND |
| 174 | TIC807_174 | N137M | none | None | ND | — | 41 | ND | — | ND |
| 174 | TIC807_174 | N137D | none | None | ND | — | 69 | ND | — | ND |
| 174 | TIC807_174 | N137F | none | None | ND | — | 13 | ND | — | ND |
| 174 | TIC807_174 | N137R | none | None | ND | — | 37 | ND | — | ND |
| 175 | TIC807_175 | F147V | F147V | None | ND | — | 87 | ND | — | ND |
| 175 | TIC807_175 | F147T | F147T | None | ND | — | 68 | ND | — | ND |
| 175 | TIC807_175 | F147C | F147C | None | ND | — | 74 | ND | — | ND |
| 175 | TIC807_175 | F147L | F147L | None | ND | — | 62 | ND | — | ND |
| 175 | TIC807_175 | F147D | F147D | None | ND | — | 51 | ND | — | ND |
| 175 | TIC807_175 | F147A | F147A | None | ND | — | 57 | ND | — | ND |
| 175 | TIC807_175 | F147G | F147G | None | ND | — | 56 | ND | — | ND |
| 175 | TIC807_175 | F147E | F147E | None | ND | — | 50 | ND | — | ND |
| 175 | TIC807_175 | F147I | F147I | None | ND | — | 69 | ND | — | ND |
| 175 | TIC807_175 | F147Y | F147Y | None | ND | — | 67 | ND | — | ND |
| 175 | TIC807_175 | F147M | F147M | None | ND | — | 64 | ND | — | ND |
| 175 | TIC807_175 | F147N | F147N | None | ND | — | 64 | ND | — | ND |
| 175 | TIC807_175 | F147Q | F147Q | None | ND | — | 50 | ND | — | ND |

TABLE 4B-continued

Iterative engineering-testing-selecting of eHTP's against *Lygus* spp. resulted in 267 proteins with enhanced *Lygus* inhibitory spectrum and/or improved *Lygus* inhibitory activity against *Lygus* spp. compared to TIC807.

| | | Amino acid differences compared to TIC807 parent protein | | | *Lygus hesperus* | | | *Lygus lineolaris* | | |
|---|---|---|---|---|---|---|---|---|---|---|
| SEQ ID NO: | Protein Name | Amino acid difference(s) relative to SEQ ID NO: 2 (TIC807) | Amino acid difference(s) in the first patch | Amino acid difference(s) in the second patch | LC50 value (µg/mL) | fold increased toxicity (LC50) | % Mortality at about 1-3 µg/mL protein* | LC50 value (µg/mL) | fold increased toxicity (LC50) | % Mortality at about 100 µg/mL protein* |
| 175 | TIC807_175 | F147H | F147H | None | ND | — | 60 | ND | — | ND |
| 175 | TIC807_175 | F147R | F147R | None | ND | — | 20 | ND | — | ND |
| 175 | TIC807_175 | F147W | F147W | None | ND | — | 82 | ND | — | ND |
| 175 | TIC807_175 | F147P | F147P | None | ND | — | 7 | ND | — | ND |
| 176 | TIC807_176 | Q149D | Q149D | None | ND | — | 92 | ND | — | ND |
| 176 | TIC807_176 | Q149E | Q149E | None | ND | — | 89 | ND | — | ND |
| 176 | TIC807_176 | Q149C | Q149C | None | ND | — | 87 | ND | — | ND |
| 176 | TIC807_176 | Q149A | Q149A | None | ND | — | 76 | ND | — | ND |
| 176 | TIC807_176 | Q149F | Q149F | None | ND | — | 54 | ND | — | ND |
| 177 | TIC807_177 | A150S | none | None | ND | — | 34 | ND | — | ND |
| 177 | TIC807_177 | A150L | none | None | ND | — | 24 | ND | — | ND |
| 177 | TIC807_177 | A150V | none | None | ND | — | 25 | ND | — | ND |
| 177 | TIC807_177 | A150G | none | None | ND | — | 28 | ND | — | ND |
| 177 | TIC807_177 | A150D | none | None | ND | — | 19 | ND | — | ND |
| 177 | TIC807_177 | A150W | none | None | ND | — | 13 | ND | — | ND |
| 177 | TIC807_177 | A150E | none | None | ND | — | 24 | ND | — | ND |
| 177 | TIC807_177 | A150N | none | None | ND | — | 18 | ND | — | ND |
| 177 | TIC807_177 | A150Y | none | None | ND | — | 11 | ND | — | ND |
| 177 | TIC807_177 | A150F | none | None | ND | — | 11 | ND | — | ND |
| 177 | TIC807_177 | A150P | none | None | ND | — | 11 | ND | — | ND |
| 177 | TIC807_177 | A150K | none | None | ND | — | 17 | ND | — | ND |
| 177 | TIC807_177 | A150T | none | None | ND | — | 17 | ND | — | ND |
| 177 | TIC807_177 | A150Q | none | None | ND | — | 11 | ND | — | ND |
| 177 | TIC807_177 | A150R | none | None | ND | — | 11 | ND | — | ND |
| 178 | TIC807_178 | E155C | none | None | ND | — | 82 | ND | — | ND |
| 178 | TIC807_178 | E155I | none | None | ND | — | 36 | ND | — | ND |
| 178 | TIC807_178 | E155K | none | None | ND | — | 28 | ND | — | ND |
| 178 | TIC807_178 | E155D | none | None | ND | — | 22 | ND | — | ND |
| 178 | TIC807_178 | E155H | none | None | ND | — | 22 | ND | — | ND |
| 178 | TIC807_178 | E155Y | none | None | ND | — | 16 | ND | — | ND |
| 178 | TIC807_178 | E155Q | none | None | ND | — | 16 | ND | — | ND |
| 178 | TIC807_178 | E155L | none | None | ND | — | 15 | ND | — | ND |
| 178 | TIC807_178 | E155N | none | None | ND | — | 14 | ND | — | ND |
| 178 | TIC807_178 | E155T | none | None | ND | — | 13 | ND | — | ND |
| 178 | TIC807_178 | E155A | none | None | ND | — | 11 | ND | — | ND |
| 178 | TIC807_178 | E155F | none | None | ND | — | 7 | ND | — | ND |
| 178 | TIC807_178 | E155R | none | None | ND | — | 6 | ND | — | ND |
| 178 | TIC807_178 | E155M | none | None | ND | — | 6 | ND | — | ND |
| 178 | TIC807_178 | E155P | none | None | ND | — | 5 | ND | — | ND |
| 178 | TIC807_178 | E155W | none | None | ND | — | 5 | ND | — | ND |
| 178 | TIC807_178 | E155S | none | None | ND | — | 4 | ND | — | ND |
| 178 | TIC807_178 | E155V | none | None | ND | — | 4 | ND | — | ND |
| 179 | TIC807_179 | N157C | none | None | ND | — | 86 | ND | — | ND |
| 179 | TIC807_179 | N157D | none | None | ND | — | 64 | ND | — | ND |
| 179 | TIC807_179 | N157W | none | None | ND | — | 52 | ND | — | ND |
| 179 | TIC807_179 | N157Y | none | None | ND | — | 39 | ND | — | ND |
| 179 | TIC807_179 | N157M | none | None | ND | — | 22 | ND | — | ND |
| 179 | TIC807_179 | N157A | none | None | ND | — | 22 | ND | — | ND |
| 179 | TIC807_179 | N157F | none | None | ND | — | 20 | ND | — | ND |
| 179 | TIC807_179 | N157V | none | None | ND | — | 18 | ND | — | ND |
| 179 | TIC807_179 | N157L | none | None | ND | — | 18 | ND | — | ND |
| 179 | TIC807_179 | N157P | none | None | ND | — | 18 | ND | — | ND |
| 179 | TIC807_179 | N157E | none | None | ND | — | 17 | ND | — | ND |
| 179 | TIC807_179 | N157T | none | None | ND | — | 8 | ND | — | ND |
| 179 | TIC807_179 | N157G | none | None | ND | — | 7 | ND | — | ND |
| 179 | TIC807_179 | N157I | none | None | ND | — | 7 | ND | — | ND |
| 179 | TIC807_179 | N157R | none | None | ND | — | 6 | ND | — | ND |
| 202 | TIC807_M8_d5C | F46S, Y54H, S95A, F147A, S167R, S217N, then a five amino acid deletion at 305-309, then a contiguous triple deletion in residue range 196-201 | S95A, F147A | S217N, then a contiguous triple deletion in residue range 196-201 | ND | — | 92* | ND | — | ND |

TABLE 4B-continued

Iterative engineering-testing-selecting of eHTP's against *Lygus* spp. resulted in 267 proteins with enhanced *Lygus* inhibitory spectrum and/or improved *Lygus* inhibitory activity against *Lygus* spp. compared to TIC807.

| | | Amino acid differences compared to TIC807 parent protein | | | *Lygus hesperus* | | | *Lygus lineolaris* | | |
|---|---|---|---|---|---|---|---|---|---|---|
| | | | | | | % Mortality | | | % Mortality | |
| SEQ ID NO: | Protein Name | Amino acid difference(s) relative to SEQ ID NO: 2 (TIC807) | Amino acid difference(s) in the first patch | Amino acid difference(s) in the second patch | LC50 value (µg/mL) | fold increased toxicity (LC50) | at about 1-3 µg/mL protein* | LC50 value (µg/mL) | fold increased toxicity (LC50) | at about 100 µg/mL protein* |
| 204 | TIC807_M14 | F46S, Y54H, S95A, F147S, Q149E, S167R, P219R, S249R, V251E, Q253R, R273W, then a contiguous triple deletion in residue range 196-201 | S95A, F147A, Q149E, V251E, Q253R | P219R, then a contiguous triple deletion in residue range 196-201 | ND | — | — | ND | — | 60* |

ND = Not Determined;
*tested at about 5 µg/mL.

Example 5: Insect Inhibitory Activities of Protein Members of the Present Invention Proteins of the present invention, such as but not limited to TIC807 M1 (SEQ ID NO:6), TIC807_M2 (SEQ ID NO:8), TIC807_M3 (SEQ ID NO:10), TIC807_M4 (SEQ ID NO:12), TIC807_M5 (SEQ ID NO:14), TIC807_M6 (SEQ ID NO:16), TIC807_M7 (SEQ ID NO:18), TIC807_M8 (SEQ ID NO:20), TIC807_M9 (SEQ ID NO:22), TIC807_M14 (SEQ ID NO:32), TIC807_M15 (SEQ ID NO:34), and TIC807_M16 (SEQ ID NO:36), are prepared and tested for bioactivity against pests of plants other than from *Lygus*.

Proteins TIC807_M10 (SEQ ID NO:24), TIC807_M11 (SEQ ID NO:26), TIC807_M12 (SEQ ID NO:28), and TIC807_M13 (SEQ ID NO:30) were prepared and tested for bioactivity against pests from the order Lepidoptera, Coleoptera, Heteroptera, and Homoptera. Protein TIC807_M5 (SEQ ID NO:14) was prepared and tested for bioactivity against *Coleopteran* pests. Bioassays were conducted to evaluate the effects of these proteins on insects as shown in Table 5. Feeding assays were conducted on an artificial diet containing the insecticidal protein. The insecticidal protein was prepared as described in example 3 and topically applied using an insect-specific artificial diet, depending on the insect being tested. The toxin was suspended in a buffer and applied at a rate of 500 µg/mL of sample per well, and in the case of TIC807_M5 of 1000 µg/mL, and then allowed to dry. Mean stunting scores and population mortalities were determined on three populations of 8 insects per insect species tested. Results were expressed as positive (+) for insect reactions such as stunting and mortality that were statistically significant compared to the untreated control. Results were expressed as negative (−) if the insects were similar to the UTC, that is, feeding diet to which the above buffer only has been applied.

TABLE 5 eHTP's demonstrate additional insect inhibitory activities against pests other than *Lygus* spp.

| Protein | µg/mL | CPB | WCR | ECB | SWCB | CEW | FAW | SGSB | NBSB | GPA |
|---|---|---|---|---|---|---|---|---|---|---|
| UTC | 0 | − | − | − | − | − | − | − | − | − |
| TIC807_M5 | 1000 | + | − | ND | ND | ND | ND | ND | ND | ND |
| TIC807_M10 | 500 | − | − | − | − | − | − | − | − | − |
| TIC807_M11 | 500 | + | − | − | − | − | − | − | − | − |
| TIC807_M12 | 500 | − | − | − | − | − | − | − | − | − |
| TIC807_M13 | 500 | + | − | − | − | − | − | − | − | − |

UTC = UnTreated Control;
ND = Not Determined
CPB = Colorado potato beetle (*Leptinotarsa decemlineata*);
WCR = western corn rootworm (*Diabrotica virgifera*);
ECB = European corn borer (*Ostrinia nubilalis*);
southwestern corn borer (*Diatraea grandiosella*);
CEW = corn earworm (*Helicoverpa zea*);
FAW = Fall armyworm (*Spodoptera frugiperda*);
SGSB = southern green stink bug (*Nezara viridula*);
NBSB = neotropical brown stink bug (*Euschistus heros*);
GPA = Green peach aphid (*Myzus persicae*).

The proteins of the present invention are also tested for bioactivity against a pest from the phylum Nematoda.

Example 6: Plants Expressing Proteins of the Present Invention Exhibit Insect Inhibitory Activity This example illustrates expression of proteins of the present invention in plants, and demonstrates that cotton plants expressing proteins of the present invention exhibit insect inhibitory activity.

Polynucleotide segments for use in expression of the proteins of the present invention in plants are made according to the methods set forth in U.S. Pat. No. 7,741,118. For example, toxin proteins having the amino acid sequence as set forth in SEQ ID NO:4 (TIC807_4), SEQ ID NO:6 (TIC807_M1), SEQ ID NO:8 (TIC807_M2), SEQ ID NO:10 (TIC807_M3), SEQ ID NO:12 (TIC807_M4), SEQ ID NO:14 (TIC807_M5), SEQ ID NO:16 (TIC807_M8), SEQ ID NO:18 (TIC807_M6), SEQ ID NO:20 (TIC807_M7), SEQ ID NO:22 (TIC807 22), SEQ ID NO:24 (TIC807_24), SEQ ID NO:26 (TIC807_26), SEQ ID NO:28 (TIC807_M9), SEQ ID NO:30 (TIC807_M10), SEQ ID NO:32 (TIC807_M11), and SEQ ID NO:34 (TIC807_M13), are expressed from polynucleotide segments designed for use in plants and encoding the proteins of the present invention, including the polynucleotide sequences as set forth in SEQ ID NO:186, SEQ ID NO:187, SEQ ID NO:188, SEQ ID NO:189, SEQ ID NO:190, SEQ ID NO:191, SEQ ID NO:192, SEQ ID NO:193, SEQ ID NO:194, SEQ ID NO:195, SEQ ID NO:196, SEQ ID NO:197, SEQ ID NO:198, SEQ ID NO:199, SEQ ID NO:200, and SEQ ID NO:201, respectively.

It is intended that polynucleotide segments (or polynucleotide molecules) encoding each of the variant proteins or insect inhibitory fragments thereof, be used alone or in combination with each other, or in combination with other insect inhibitory proteins or insect inhibitory agents such as dsRNA mediated gene suppression molecules. Such combinations designed to work in synergistic or compatible mechanism with the proteins of the present invention. The intention of these combinations is to achieve plants and plant cells protected from pest, particularly insect pest, infestation. The specific variant proteins within the scope of the invention include the proteins corresponding to SEQ ID NOs listed in Table 4B and described throughout the application as filed.

Polynucleotide segments from SEQ ID NO:188 (encodes for TIC807_M2, SEQ ID NO:8) and from SEQ ID NO:192 (encodes for TIC807_M8, SEQ ID NO:16) were each recombinantly engineered into expression constructs for cotton transformation.

Transgenic cotton plants (recombinant cotton plants) were produced and tested for efficacy. Regenerated (R0) transgenic plants were selected that were low in copy number and high in expression of the respective variant protein, as determined by various quantitative and semi-quantitative methods, e.g. PCR, ELISAs and Westerns. Expression levels in R0 cotton leaf tissue typically ranged from 0.5 to 500 ppm fresh weight. R0 plants expressing high levels of protein were transferred to soil and selfed. Thirty seed from each of the selfed R0 plants were planted and progeny homozygous for the transgene were grown to flowering. Eleven to 18 plants per 4 to 5 events per each construct of this example were tested for efficacy against *Lygus* (Tables 6A, 6B, and 6C). The untransformed cotton cultivar, plants from the pooled negative segregate population (progeny not containing the transgene), and plants expressing TIC807 parent protein served as negative controls. A branch of a flowering stage cotton plant was enclosed in a mesh bag made from breathable plastic 'pollination' sleeves (Vilutis and Co. Inc., Frankfort, Ill.), and multiple branches set up in similar fashion. Each mesh bag was secured at the stem using a twist tie. About 4-6 *Lygus hesperus* nymphs (<24 hours post-hatch) were placed into a 1.4 ml conical tube (Matrix Technologies Corp., NH). The branch inside a mesh bag was infested with nymphs by sliding the uncapped conical tube into the mesh bag. Insects were allowed to feed for a period of 10-11 days before all surviving insects in the mesh bag were collected on dry ice. Survivors were weighed to obtain a gross mass. Percent mortality and mean survivor mass were calculated. Missing insects were included in the mortality percent mortality calculation. As shown in Tables 6A, 6B, and 6C, cotton plants expressing the variant proteins TIC807_M2 and TIC807_M8 significantly impacted the growth and development of *Lygus hesperus* nymphs. Based on these results, these plants, seed, expression constructs were advanced for further development.

TABLE 6A

Mean % mortality determined from flowering stage Lygus feeding assays with cotton plants expressing the variant TIC807 proteins TIC807_M2 and TIC807_M8.

| Plant Event ID | Protein | N | Mean % Mortality | Std Dev | SEM | Lo 95% | Up 95% | Mortality t group |
|---|---|---|---|---|---|---|---|---|
| 64 | TIC807_M8 | 18 | 78.889 | 19.967 | 4.706 | 68.959 | 88.818 | A |
| 49 | TIC807_M8 | 18 | 75.556 | 22.288 | 5.253 | 64.472 | 86.639 | A |
| 91 | TIC807_M2 | 18 | 74.444 | 20.356 | 4.798 | 64.321 | 84.567 | A |
| 20 | TIC807_M8 | 18 | 73.333 | 19.403 | 4.573 | 63.685 | 82.982 | A |
| 15 | TIC807_M8 | 18 | 66.667 | 25.668 | 6.050 | 53.902 | 79.431 | AB |
| 58 | TIC807_M2 | 18 | 65.556 | 19.166 | 4.517 | 56.025 | 75.086 | AB |
| 48 | TIC807_M2 | 18 | 64.444 | 21.206 | 4.998 | 53.899 | 74.990 | AB |
| 19 | TIC807_M2 | 18 | 53.333 | 25.668 | 6.050 | 40.569 | 66.098 | BC |
| 68 | TIC807_M2 | 18 | 47.778 | 25.795 | 6.080 | 34.950 | 60.605 | C |
| Negative | | 24 | 41.667 | 22.001 | 4.491 | 32.376 | 50.957 | C |

TABLE 6B

Mean Instar determined from flowering stage Lygus feeding assays with cotton plants expressing the variant TIC807 proteins TIC807_M2 and TIC807_M8.

| Plant Event ID | Construct | N | Mean Instar | Std Dev | SEM | Lo 95% | Up 95% | Instar t group |
|---|---|---|---|---|---|---|---|---|
| 64 | TIC807_M8 | 11 | 3.636 | 0.552 | 0.166 | 3.266 | 4.007 | C |
| 68 | TIC807_M2 | 16 | 3.949 | 0.803 | 0.201 | 3.521 | 4.377 | BC |
| 48 | TIC807_M2 | 16 | 4.042 | 0.604 | 0.151 | 3.720 | 4.364 | BC |
| 58 | TIC807_M2 | 17 | 4.069 | 0.802 | 0.194 | 3.657 | 4.481 | BC |
| 15 | TIC807_M8 | 15 | 4.094 | 0.747 | 0.193 | 3.681 | 4.508 | BC |
| 19 | TIC807_M2 | 17 | 4.100 | 0.698 | 0.169 | 3.741 | 4.459 | BC |
| 91 | TIC807_M2 | 12 | 4.125 | 0.829 | 0.239 | 3.598 | 4.652 | ABC |
| 49 | TIC807_M8 | 12 | 4.139 | 0.762 | 0.220 | 3.655 | 4.623 | ABC |
| 20 | TIC807_M8 | 14 | 4.298 | 0.918 | 0.245 | 3.768 | 4.828 | AB |
| Negative | | 24 | 4.599 | 0.774 | 0.158 | 4.273 | 4.926 | A |

TABLE 6C

Mean Survival Mass determined from flowering stage Lygus feeding assays with cotton plants expressing the variant TIC807 proteins TIC807_M2 and TIC807_M8.

| Plant Event ID | Construct | N | Mean Survival Mass | Std Dev | SEM | Lo 95% | Up 95% | Survivor Mass t group |
|---|---|---|---|---|---|---|---|---|
| 64 | TIC807_M8 | 11 | 2.315 | 1.489 | 0.449 | 1.314 | 3.315 | C |
| 68 | TIC807_M2 | 16 | 3.548 | 1.325 | 0.331 | 2.843 | 4.254 | B |
| 58 | TIC807_M2 | 17 | 3.561 | 1.348 | 0.327 | 2.868 | 4.255 | B |
| 48 | TIC807_M2 | 16 | 3.596 | 1.436 | 0.359 | 2.831 | 4.362 | B |
| 91 | TIC807_M2 | 12 | 3.775 | 1.775 | 0.512 | 2.647 | 4.902 | AB |
| 49 | TIC807_M8 | 12 | 3.837 | 2.135 | 0.616 | 2.481 | 5.193 | AB |
| 19 | TIC807_M2 | 17 | 3.908 | 1.467 | 0.356 | 3.154 | 4.662 | AB |
| 20 | TIC807_M8 | 14 | 3.918 | 1.950 | 0.521 | 2.792 | 5.044 | AB |
| 15 | TIC807_M8 | 15 | 3.937 | 1.906 | 0.492 | 2.881 | 4.993 | AB |
| Negative | | 24 | 4.735 | 1.179 | 0.241 | 4.237 | 5.233 | A |

Std Dev—standard deviation
SEM—Standard error on the mean
Lo 95% = Lower limit at 95% confidence interval
Up 95% = Upper limit at 95% confidence interval
T grouping = Using a least significant difference test, F value = 101.1756, df = 15, 44, Pr < 0.0001

In another example, cotton plants from five transgenic events expressing TIC807_M11 were tested in a field trial having natural *Lygus* infestation pressures. These plants demonstrated field efficacy compared to the non-transgenic recipient line (DP393 germplasm used for transformation). The average number of *Lygus lineolaris* insects on five plants per event was significantly lower than the average number of *Lygus lineolaris* insects on plants from the non-transgenic control. Seed cotton yield from plants from the five events was statistically comparable to seed cotton yield of the non-transgenic control, e.g. season-long square retention.

In another similar field trial, cotton plants from seven transgenic events expressing TIC807_M10 demonstrated field efficacy compared to the non-transgenic control. The average number of *Lygus lineolaris* insects on five plants per event was significantly lower than the average number of *Lygus lineolaris* insects on plants from the non-transgenic control. Seed cotton yield from plants from three of the seven events was statistically higher than to seed cotton yield of the non-transgenic control.

In another example, cotton plants from thirty-four transgenic events expressing TIC807_M13 demonstrated growth chamber efficacy compared to the non-transgenic control. Mesh bags were placed around the whole cotton plants at flowering stage (instead of just around single branches described earlier in this example). Five plants per event were evaluated and the average number of *Lygus lineolaris* insects recovered (nymphs to adults to $2^{nd}$ generation *Lygus*) per plant was significantly lower than the average number of *Lygus lineolaris* insects per non-transgenic plant.

Similar experiments are performed with plants expressing proteins listed in Table 1 and in Tables 4A and 4B.

Example 7: Tissue from Alfalfa Plants Expressing Proteins of the Present Invention Exhibit Insect Inhibitory Activity This example illustrates expression of proteins of the present invention in alfalfa plants, and demonstrates that tissue from alfalfa plants expressing proteins of the present invention exhibit insect inhibitory activity.

Polynucleotide segment from SEQ ID NO:192 (encodes for TIC807_M8, SEQ ID NO:16) was recombinantly engineered into three differently configured expression constructs for alfalfa transformation. For purposes of data reporting, the three recombinant constructs are coded [ER], [ES], and [ET].

Transgenic alfalfa plants (recombinant alfalfa plants) were recovered from transformants that were outcrossed and then selfed. Recombinant alfalfa plants were selected that were low in copy number and high in TIC807 expression as determined by RT-PCR and semi-quantitative Western methods, respectively. Alfalfa plant tissue from ten separate events were pooled, lyophilized, ground, and resuspended in stock buffer, 25 mM NaCarb, pH 10.5. Plant tissue from Alfalfa having no TIC807_M8 expressing transgene was prepared for use as control. Stock preparations were serially diluted 100, 300, and 900 fold for incorporation into *Lygus* diet. Using the feeding assay method of Example 4, mortality and stunting scores were determined on day 5 and compared to controls (See Tables 7A and 7B; data were analyzed using JMP4 statistical software). For each test sample and each dilution, three populations of eight nymphs were subjected to this bioassay. Stunting scores correspond to visual mass ratings where 0=no difference to negative control, 1=about 25% less mass, 2=about 50% less mass, and 3=about 75% less mass. The average of the stunting scores for each population of eight nymphs is reported.

Example 8: Plants Co-Expressing an eHTP and a Second Insect Inhibitory Protein Exhibiting *Lygus* Species Inhibitory Activity Protein samples were prepared containing various mixtures of TIC1415 and TIC807_M13 and tested in bioassay. The TIC1415 protein and other *Lygus* inhibitory proteins are described in PCT Patent Application Publication No. WO 2012/139004. Sample mixtures were fed to *Lygus lineolaris* using bioactivity assay. TIC1415 protein alone and TIC807_M13 alone were also prepared as positive controls. Buffer was used as negative control. Samples from all three types of preparations exhibited mortality against *Lygus lineolaris* and survivors were stunted. Mortality and stunting scores were significant compared to bioactivity scores of insects fed with buffer (see Table 8A). The data suggests that there are no antagonistic effects. Additional bioassay tests are performed on mixtures to demonstrate synergistic and/or additive effects.

TABLE 7A

Mean % mortality determined from *Lygus* feeding assays with diet incorporated with tissue from alfalfa plants expressing the variant TIC807 protein TIC807_M8.

| Construct | Sample Source | Dilution fold | Mean Stunting Score | Std Dev | SEM | Lower 95% | Upper 95% | t Grouping |
|---|---|---|---|---|---|---|---|---|
| [ER] | Pooled Alfalfa | 100 | 2.00 | 0.00 | 0.00 | 2.00 | 2.00 | CD |
| TIC807_M8 | tissue from 10 | 300 | 0.00 | 0.00 | 0.00 | 0.00 | 0.00 | E |
|  | events per construct | 900 | 0.00 | 0.00 | 0.00 | 0.00 | 0.00 | E |
| [ES] |  | 100 | 3.00 | 0.00 | 0.00 | 3.00 | 3.00 | A |
| TIC807_M8 |  | 300 | 2.33 | 0.58 | 0.33 | 0.90 | 3.77 | BC |
|  |  | 900 | 0.00 | 0.00 | 0.00 | 0.00 | 0.00 | E |
| [ET] |  | 100 | 2.67 | 0.58 | 0.33 | 1.23 | 4.10 | AB |
| TIC807_M8 |  | 300 | 1.67 | 0.58 | 0.33 | 0.23 | 3.10 | D |
|  |  | 900 | 0.00 | 0.00 | 0.00 | 0.00 | 0.00 | E |
| None | Control Alfalfa | 100 | 2.00 | 0.00 | 0.00 | 2.00 | 2.00 | CD |
|  |  | 300 | 0.00 | 0.00 | 0.00 | 0.00 | 0.00 | E |
|  |  | 900 | 0.00 | 0.00 | 0.00 | 0.00 | 0.00 | E |
| No Alfalfa incorporated in the diet |  | 0 | 0.00 | 0.00 | 0.00 | 0.00 | 0.00 | E |

TABLE 7B

Mean stunting determined from *Lygus* feeding assays with diet incorporated with tissue from alfalfa plants expressing the variant TIC807 protein TIC807_M8.

| Construct | Sample Source | Dilution fold | Mean Percent mortality | Std Dev | SEM | Lower 95% | Upper 95% | t Grouping |
|---|---|---|---|---|---|---|---|---|
| [ER] | Pooled Alfalfa | 100 | 4.17 | 7.22 | 4.17 | −13.76 | 22.09 | CD |
| TIC807_M8 | tissue from 10 | 300 | 0.00 | 0.00 | 0.00 | 0.00 | 0.00 | CD |
|  | events per construct | 900 | 13.10 | 12.54 | 7.24 | −18.06 | 44.25 | CD |
| [ES] |  | 100 | 56.55 | 6.27 | 3.62 | 40.97 | 72.12 | AB |
| TI807_M8 |  | 300 | 41.67 | 19.09 | 11.02 | −5.77 | 89.10 | B |
|  |  | 900 | 0.00 | 0.00 | 0.00 | 0.00 | 0.00 | CD |
| [ET] |  | 100 | 64.88 | 19.91 | 11.50 | 15.42 | 114.34 | A |
| TIC807_M8 |  | 300 | 16.67 | 19.09 | 11.02 | −30.77 | 64.10 | C |
|  |  | 900 | 12.50 | 12.50 | 7.22 | −18.55 | 43.55 | CD |
| None | Control Alfalfa | 100 | 12.50 | 12.50 | 7.22 | −18.55 | 43.55 | CD |
|  |  | 300 | 0.00 | 0.00 | 0.00 | 0.00 | 0.00 | CD |
|  |  | 900 | 8.33 | 14.43 | 8.33 | −27.52 | 44.19 | CD |
| No Alfalfa incorporated in the diet |  | 0 | 2.50 | 7.01 | 1.81 | −1.38 | 6.38 | D |

TABLE 8A

Bioassay data for protein mix: TIC1415 combined with TIC807_M13

| SAMPLE | TIC1415 (μg/mL) | TIC807_M13 (μg/mL) | Mean† Population mortality | T Grouping on mort | Mean† stunting‡ score | T Grouping on stunting |
|---|---|---|---|---|---|---|
| TIC1415 + TIC807_M13 | 4.35 | 1 | 21.79 | AB* | 0.60 | AB* |
| TIC1415 + TIC807_M13 | 2.175 | 1 | 20.36 | B* | 0.60 | AB* |
| TIC1415 + TIC807_M13 | 1.0875 | 1 | 12.50 | BC | 0.60 | AB* |
| TIC1415 + TIC807_M13 | 4.35 | 0.5 | 32.50 | A* | 0.80 | A* |
| TIC1415 + TIC807_M13 | 1.75 | 0.265 | 7.86 | CD | 0.40 | ABC |
| TIC1415 + TIC807_M13 | 0.875 | 0.265 | 0.00 | D | 0.00 | C |
| TIC1415 + TIC807_M13 | 0.4375 | 0.265 | 5.36 | CD | 0.00 | C |
| TIC1415 + TIC807_M13 | 4.35 | 0.25 | 13.21 | BC | 0.40 | ABC |
| TIC1415 + TIC807_M13 | 1.75 | 0.1325 | 0.00 | D | 0.00 | C |
| TIC1415 + TIC807_M13 | 1.75 | 0.06625 | 0.00 | D | 0.00 | C |
| TIC1415 | 4.35 | 0 | 12.50 | BC | 0.40 | ABC |
| TIC1415 | 1.75 | 0 | 7.86 | CD | 0.00 | C |
| TIC807_M13 | 0 | 1 | 0.00 | D | 0.20 | BC |
| TIC807_M13 | 0 | 0.265 | 2.50 | CD | 0.00 | C |
| Buffer (negative) control | 0 | 0 | 0.00 | D | 0.00 | C |

†Average (mean) of 5 populations of 8 nymphs per population.
‡Stunting scores correspond to visual mass ratings where 0 = no difference to negative control, 1 = about 25% less mass, 2 = about 50% less mass, and 3 = about 75% less mass. The average of the stunting scores for each population of eight nymphs is reported.
*At 95% confidence interval.

Cotton plants comprising events with transgenic DNA were designed to co-express respective proteins TIC1415 and TIC807_M13. Such plants were evaluated in a caged whole plant assay infested with *Lygus lineolaris*. Five plants each from ten events were caged and infested with 2 pairs of male and female *L. lineolaris* per plant. The assay was incubated in a growth chamber under normal environmental conditions for cotton plant development for 21 days. DP393 negative control plants were grown in similar manner. At the end of the 3 week period, *Lygus* of various stages of development were counted. The mean number per plant of *Lygus hesperus* insects at each stage in development were calculated (see Table 8B).

TABLE 8B

In-planta data for for protein mix: TIC1415 combined with TIC807_M13

| Construct | Event | N | Mean 3rd Instar or < | Mean 4th Instar Nymphs | Mean 5th Instar Nymphs | Mean Live 2nd Gen. Adults | Mean Total 2nd Gen. *Lygus* | SEM | Tukey Grouping |
|---|---|---|---|---|---|---|---|---|---|
| 12 | 021 | 5 | 0.00 | 0.00 | 0.00 | 0.00 | 0.00 | 0.00 | B |
|  | 625 | 5 | 0.20 | 0.20 | 0.20 | 0.00 | 0.60 | 0.24 | B |
|  | 830 | 5 | 2.20 | 0.20 | 0.00 | 0.00 | 2.40 | 1.12 | AB |
|  | 890 | 5 | 4.40 | 0.00 | 0.20 | 0.00 | 4.60 | 2.62 | AB |
|  | 521 | 5 | 4.60 | 0.60 | 0.00 | 0.00 | 5.20 | 4.27 | AB |
|  | 980 | 5 | 3.40 | 1.20 | 1.20 | 0.00 | 5.80 | 4.86 | AB |
| 13 | 426 | 5 | 0.00 | 0.00 | 0.00 | 0.00 | 0.00 | 0.00 | B |
|  | 611 | 5 | 0.60 | 0.00 | 0.00 | 0.00 | 0.60 | 0.60 | B |
|  | 999 | 5 | 0.40 | 0.00 | 0.40 | 0.00 | 0.80 | 0.37 | B |
|  | 356 | 5 | 6.20 | 0.00 | 0.40 | 0.00 | 6.60 | 4.73 | AB |
| Inbred | DP393 (Negative) | 10 | 7.00 | 2.50 | 0.80 | 0.00 | 10.30 | 3.75 | A |

What is claimed is:

1. An insect inhibitory recombinant polypeptide comprising the amino acid sequence as set forth in SEQ ID NO: 36.

2. The insect inhibitory recombinant polypeptide of claim 1, wherein the polypeptide exhibits inhibitory activity against an insect species of the order Hemiptera.

3. The insect inhibitory recombinant polypeptide of claim 2, wherein the *Hemipteran* species is selected from the group consisting of a *Lygus* sp., an *Emrasca* sp., and an *Amrasca* sp.

4. The insect inhibitory recombinant polypeptide of claim 2, wherein the *Hemipteran* species is selected from the group consisting of *Lygus Hesperus, Lygus lineolaris*, and *Amrasca devastans*.

5. A polynucleotide encoding a pesticidal polypeptide or pesticidal fragment thereof, wherein the pesticidal polypeptide comprises the amino acid sequence as set forth in SEQ ID NO: 36.

6. The polynucleotide of claim 5, wherein the polynucleotide comprises the nucleotide sequence as set forth in SEQ ID NO: 35.

7. A host cell comprising the polynucleotide of claim 5, wherein the host cell is selected from the group consisting of a bacterial host cell and a plant host cell.

8. The host cell of claim 7, wherein the bacterial host cell is selected from the group consisting of *Agrobacterium, Rhizobium, Bacillus, Escherichia, Pseudomonas*, and *Salmonella*; and wherein the *Bacillus* species is a *Bacillus thuringiensis*, and the *Escherichia* is an *Escherichia coli*.

9. The host cell of claim 7, wherein the plant host cell is selected from the group consisting of a monocot cell and a dicot cell.

10. An insect inhibitory composition comprising the insect inhibitory recombinant polypeptide of claim 1.

11. The composition of claim 10, wherein the composition is prepared by lyophilization, extraction, filtration, or centrifugation.

12. The insect inhibitory composition of claim 10, further comprising at least one insect inhibitory agent different from the insect inhibitory recombinant polypeptide.

13. The insect inhibitory composition of claim 12, wherein the at least one insect inhibitory agent is selected from the group consisting of an insect inhibitory protein, an insect inhibitory dsRNA molecule, and an insect inhibitory chemistry.

14. The insect inhibitory composition of claim 12, wherein the at least one pesticidal agent exhibits activity against one or more pest species of the order Lepidoptera, Coleoptera, Hemiptera, or Homoptera.

15. A seed comprising the polynucleotide of claim 5.

16. The seed of claim 15, wherein the polynucleotide comprises the sequence as set forth in SEQ ID NO: 35.

17. A method of controlling a *Hemipteran* pest, the method comprising presenting the *Hemipteran* pest with an inhibitory amount of the insect inhibitory recombinant polypeptide of claim 1.

18. The method of claim 17, wherein said presenting is via expressing the insect inhibitory recombinant polypeptide in a cotton plant.

19. A transgenic plant cell, plant, or plant part comprising the insect inhibitory recombinant polypeptide of claim 1.

20. A method of controlling a *Hemipteran* pest, comprising exposing the *Hemipteran* pest to the transgenic plant cell, plant or plant part of claim 19, wherein the plant cell, plant or plant part expresses a *Hemipteran* inhibitory amount of the insect inhibitory recombinant polypeptide.

21. A commodity product obtained from the plant cell, plant, or plant part of claim 19, wherein the commodity product comprises a detectable amount of the insect inhibitory recombinant polypeptide, wherein the commodity product is selected from the group consisting of plant biomass, oil, meal, animal feed, flour, flakes, bran, lint, hulls, and processed seed.

22. A method of producing a seed, the method comprising:

planting at least one seed comprising a polynucleotide encoding the insect inhibitory recombinant polypeptide of claim 1;

growing at least one plant from the at least one seed; and harvesting a seed from the at least one plant, wherein the harvested seed comprises the polynucleotide encoding the insect inhibitory recombinant polypeptide.

* * * *

UNITED STATES PATENT AND TRADEMARK OFFICE
CERTIFICATE OF CORRECTION

PATENT NO. : 10,188,115 B2
APPLICATION NO. : 15/651727
DATED : January 29, 2019
INVENTOR(S) : Baum et al.

Page 1 of 1

It is certified that error appears in the above-identified patent and that said Letters Patent is hereby corrected as shown below:

At Claim 5, Column 425, Lines 42 and 43 please delete: "or pesticidal fragment thereof"

Signed and Sealed this
Seventh Day of May, 2019

Andrei Iancu
*Director of the United States Patent and Trademark Office*

SEQUENCE LISTING

<160> NUMBER OF SEQ ID NOS: 206

<210> SEQ ID NO 1

<211> LENGTH: 927
<212> TYPE: DNA
<213> ORGANISM: Bacillus thuringiensis
<220> FEATURE:
<221> NAME/KEY: misc_feature
<223> OTHER INFORMATION: A sequence representing a recombinant polynucleotide derived from a native gene from a Bacillus thuringiensis (Bt) species encoding a TIC807 protein.

<400> SEQUENCE: 1

```
atggctatcc tagaccttaa gtccctcgtg ctgaacgcca ttaactactg gggccctaag      60
aacaacaacg gcatccaggg cggtgacttc ggctacccca tctctgagaa gcagatcgac     120
actagcatca ttaccttcac ccaccctcgc ttgatcccct acgatcttac tatcccgcag     180
aaccttgaga ccatcttcac cacaacgcag gtgctcacca ataacactga cctccagcaa     240
tcccagaccg tgagctttgc gaagaagacc actaccacga cctcaactag cacgaccaac     300
ggttggacag aaggaggcaa gatcagcgac acgctggagg agaaagtttc ggttagcatt     360
ccgttcatcg gtgagggtgg cgggaagaac tcgactacca tagaggccaa cttcgcacac     420
aactctagca ccactacctt ccagcaagca agcactgaca ttgagtggaa cattagccaa     480
ccggtgctgg ttcctccctc taaacaagtt gtcgcgaccc ttgtgatcat gggaggcaac     540
tttaccatcc ctatggactt gatgaccacg attgatagta cagagcacta ctcccactac     600
tccggttacc ctatcctcac ctggatctcg tccccagata actcttactc cggtcccttt     660
atgtcatggt actttgcaaa ctggcctaac cttccgagtg gattcggccc actgaatagt     720
gataacacgg tcacatacac tggctctgtc gtgtcccaag tttcggccgg tgtctacgct     780
accgtccggt tcgatcagta tgacattcac aatctccgta ctatcgagaa gacttggtat     840
gctcgccatg cgacgctgca taatggcaag aagatttcta tcaacaatgt cacggaaatg     900
gctccaacat ccctatcaa gacaaat                                           927
```

<210> SEQ ID NO 2
<211> LENGTH: 309
<212> TYPE: PRT
<213> ORGANISM: Artificial Sequence
<220> FEATURE:
<223> OTHER INFORMATION: engineered
<220> FEATURE:
<221> NAME/KEY: MISC_FEATURE
<223> OTHER INFORMATION: TIC807
<220> FEATURE:
<221> NAME/KEY: misc_feature
<223> OTHER INFORMATION: The amino acid sequence translation of of the open reading frame of SEQ ID NO: 1 from nucleotides 1 through 927.

<400> SEQUENCE: 2

```
Met Ala Ile Leu Asp Leu Lys Ser Leu Val Leu Asn Ala Ile Asn Tyr
1               5                   10                  15

Trp Gly Pro Lys Asn Asn Asn Gly Ile Gln Gly Gly Asp Phe Gly Tyr
            20                  25                  30

Pro Ile Ser Glu Lys Gln Ile Asp Thr Ser Ile Ile Thr Phe Thr His
        35                  40                  45

Pro Arg Leu Ile Pro Tyr Asp Leu Thr Ile Pro Gln Asn Leu Glu Thr
    50                  55                  60

Ile Phe Thr Thr Thr Gln Val Leu Thr Asn Asn Thr Asp Leu Gln Gln
65                  70                  75                  80

Ser Gln Thr Val Ser Phe Ala Lys Lys Thr Thr Thr Thr Ser Thr
                85                  90                  95

Ser Thr Thr Asn Gly Trp Thr Glu Gly Gly Lys Ile Ser Asp Thr Leu
```

```
            100                 105                 110
Glu Glu Lys Val Ser Val Ser Ile Pro Phe Ile Gly Glu Gly Gly Gly
        115                 120                 125

Lys Asn Ser Thr Thr Ile Glu Ala Asn Phe Ala His Asn Ser Ser Thr
130                 135                 140

Thr Thr Phe Gln Gln Ala Ser Thr Asp Ile Glu Trp Asn Ile Ser Gln
145                 150                 155                 160

Pro Val Leu Val Pro Ser Lys Gln Val Val Ala Thr Leu Val Ile
                165                 170                 175

Met Gly Gly Asn Phe Thr Ile Pro Met Asp Leu Met Thr Thr Ile Asp
                180                 185                 190

Ser Thr Glu His Tyr Ser His Tyr Ser Gly Tyr Pro Ile Leu Thr Trp
                195                 200                 205

Ile Ser Ser Pro Asp Asn Ser Tyr Ser Gly Pro Phe Met Ser Trp Tyr
210                 215                 220

Phe Ala Asn Trp Pro Asn Leu Pro Ser Gly Phe Gly Pro Leu Asn Ser
225                 230                 235                 240

Asp Asn Thr Val Thr Tyr Thr Gly Ser Val Val Ser Gln Val Ser Ala
                245                 250                 255

Gly Val Tyr Ala Thr Val Arg Phe Asp Gln Tyr Asp Ile His Asn Leu
                260                 265                 270

Arg Thr Ile Glu Lys Thr Trp Tyr Ala Arg His Ala Thr Leu His Asn
                275                 280                 285

Gly Lys Lys Ile Ser Ile Asn Asn Val Thr Glu Met Ala Pro Thr Ser
                290                 295                 300

Pro Ile Lys Thr Asn
305

<210> SEQ ID NO 3
<211> LENGTH: 927
<212> TYPE: DNA
<213> ORGANISM: Artificial Sequence
<220> FEATURE:
<223> OTHER INFORMATION: engineered
<220> FEATURE:
<221> NAME/KEY: misc_feature
<223> OTHER INFORMATION: A nucleotide sequence encoding SEQ ID NO: 4
      with an open reading frame from 1 to 927.

<400> SEQUENCE: 3
atggctatcc tagaccttaa gtccctcgtg ctgaacgcca ttaactactg gggccctaag      60
aacaacaacg gcatccaggg cggtgacttc ggctaccccc tctctgagaa gcagatcgac     120
actagcatca ttaccttcac ccaccctcgc ttgatcccct acgatcttac tatcccgcag     180
aaccttgaga ccatcttcac cacaacgcag gtgctcacca taacactga cctccagcaa     240 tcccagaccg tgagctttgc gaagaagacc actaccacga cctcaactag cacgaccaac     300
ggttggacag aaggaggcaa gatcagcgac acgctggagg agaaagtttc ggttagcatt     360
ccgttcatcg gtgcgggtgg cgggaagaac tcgactacca tagaggccaa cttcgcacac     420
aactctagca ccactacctt ccagcaagca agcactgaca ttgagtggaa cattagccaa     480
ccggtgctgg ttcctccctc taaacaagtt gtcgcgaccc ttgtgatcat gggaggcaac     540
tttaccatcc ctatggactt gatgaccacg attgatagta cagagcacta ctcccactac     600
tccggttacc ctatcctcac ctggatctcg tccccagata actcttactc cggtcccttt     660
atgtcatggt actttgcaaa ctggcctaac cttccgagtg gattcggccc actgaatagt     720
```

```
gataacacgg tcacatacac tggctctgtc gtgtcccaag tttcggccgg tgtctacgct    780
accgtccggt tcgatcagta tgacattcac aatctccgta ctatcgagaa gacttggtat    840
gctcgccatg cgacgctgca taatggcaag aagatttcta tcaacaatgt cacggaaatg    900
gctccaacat cccctatcaa gacaaat                                        927
```

<210> SEQ ID NO 4
<211> LENGTH: 309
<212> TYPE: PRT
<213> ORGANISM: Artificial Sequence
<220> FEATURE:
<223> OTHER INFORMATION: engineered
<220> FEATURE:
<221> NAME/KEY: misc_feature
<223> OTHER INFORMATION: The amino acid sequence translation of of the
    open reading frame set forth as SEQ ID NO: 3.

<400> SEQUENCE: 4

```
Met Ala Ile Leu Asp Leu Lys Ser Leu Val Leu Asn Ala Ile Asn Tyr
1               5                   10                  15

Trp Gly Pro Lys Asn Asn Gly Ile Gln Gly Gly Asp Phe Gly Tyr
                20                  25                  30

Pro Ile Ser Glu Lys Gln Ile Asp Thr Ser Ile Thr Phe Thr His
            35                  40                  45

Pro Arg Leu Ile Pro Tyr Asp Leu Thr Ile Pro Gln Asn Leu Glu Thr
50                  55                  60

Ile Phe Thr Thr Thr Gln Val Leu Thr Asn Asn Thr Asp Leu Gln Gln
65                  70                  75                  80

Ser Gln Thr Val Ser Phe Ala Lys Lys Thr Thr Thr Thr Ser Thr
                85                  90                  95

Ser Thr Thr Asn Gly Trp Thr Glu Gly Gly Lys Ile Ser Asp Thr Leu
                100                 105                 110

Glu Glu Lys Val Ser Val Ser Ile Pro Phe Ile Gly Ala Gly Gly Gly
            115                 120                 125

Lys Asn Ser Thr Thr Ile Glu Ala Asn Phe Ala His Asn Ser Ser Thr
130                 135                 140

Thr Thr Phe Gln Gln Ala Ser Thr Asp Ile Glu Trp Asn Ile Ser Gln
145                 150                 155                 160

Pro Val Leu Val Pro Pro Ser Lys Gln Val Val Ala Thr Leu Val Ile
                165                 170                 175

Met Gly Gly Asn Phe Thr Ile Pro Met Asp Leu Met Thr Thr Ile Asp
                180                 185                 190

Ser Thr Glu His Tyr Ser His Tyr Ser Gly Tyr Pro Ile Leu Thr Trp
            195                 200                 205

Ile Ser Ser Pro Asp Asn Ser Tyr Ser Gly Pro Phe Met Ser Trp Tyr
210                 215                 220

Phe Ala Asn Trp Pro Asn Leu Pro Ser Gly Phe Gly Pro Leu Asn Ser
225                 230                 235                 240

Asp Asn Thr Val Thr Tyr Thr Gly Ser Val Val Ser Gln Val Ser Ala
                245                 250                 255

Gly Val Tyr Ala Thr Val Arg Phe Asp Gln Tyr Asp Ile His Asn Leu
                260                 265                 270

Arg Thr Ile Glu Lys Thr Trp Tyr Ala Arg His Ala Thr Leu His Asn
            275                 280                 285

Gly Lys Lys Ile Ser Ile Asn Asn Val Thr Glu Met Ala Pro Thr Ser
290                 295                 300
```

Pro Ile Lys Thr Asn
305

<210> SEQ ID NO 5
<211> LENGTH: 927
<212> TYPE: DNA
<213> ORGANISM: Artificial Sequence
<220> FEATURE:
<223> OTHER INFORMATION: engineered
<220> FEATURE:
<221> NAME/KEY: misc_feature
<223> OTHER INFORMATION: A nucleotide sequence encoding SEQ ID NO: 6
      with an open reading frame from 1 to 927.

<400> SEQUENCE: 5

```
atggctatcc tagaccttaa gtccctcgtg ctgaacgcca ttaactactg gggccctaag      60
aacaacaacg gcatccaggg cggtgacttc ggctacccca tctctgagaa gcagatcgac     120
actagcatca ttaccttcac ccaccctcgc ttgatcccct acgatcttac tatcccgcag     180
aaccttgaga ccatcttcac cacaacgcag gtgctcacca taacactga cctccagcaa     240
tcccagaccg tgagctttgc gaagaagacc actaccacga cctcaactag cacgaccaac     300
ggttggacag aaggaggcaa gatcagcgac acgctggagg agaaagtttc ggttagcatt     360
ccgttcatcg gtgagggtgg cgggaagaac tcgactacca tagaggccaa cttcgcacac     420
aactctagca ccactaccgc ccagcaagca agcactgaca ttgagtggaa cattagccaa     480
ccggtgctgg ttcctccctc taaacaagtt gtcgcgaccc ttgtgatcat gggaggcaac     540
tttaccatcc ctatggactt gatgaccacg attgatagta cagagcacta ctcccactac     600
tccggttacc ctatcctcac ctggatctcg tccccagata actcttactc cggtcccttt     660
atgtcatggt actttgcaaa ctggcctaac cttccgagtg gattcggccc actgaatagt     720
gataacacgg tcacatacac tggctctgtc gtgtcccaag tttcggccgg tgtctacgct     780
accgtccggt tcgatcagta tgacattcac aatctccgta ctatcgagaa gacttggtat     840
gctcgccatg cgacgctgca taatggcaag aagatttcta tcaacaatgt cacggaaatg     900
gctccaacat ccctatcaa gacaaat                                          927
```

<210> SEQ ID NO 6
<211> LENGTH: 309
<212> TYPE: PRT
<213> ORGANISM: Artificial Sequence
<220> FEATURE:
<223> OTHER INFORMATION: engineered
<220> FEATURE:
<221> NAME/KEY: misc_feature
<223> OTHER INFORMATION: The amino acid sequence translation of the
      open reading frame set forth as SEQ ID NO: 5.

<400> SEQUENCE: 6

Met Ala Ile Leu Asp Leu Lys Ser Leu Val Leu Asn Ala Ile Asn Tyr
1               5                   10                  15

Trp Gly Pro Lys Asn Asn Asn Gly Ile Gln Gly Gly Asp Phe Gly Tyr
            20                  25                  30

Pro Ile Ser Glu Lys Gln Ile Asp Thr Ser Ile Ile Thr Phe Thr His
        35                  40                  45

Pro Arg Leu Ile Pro Tyr Asp Leu Thr Ile Pro Gln Asn Leu Glu Thr
    50                  55                  60

Ile Phe Thr Thr Thr Gln Val Leu Thr Asn Asn Thr Asp Leu Gln Gln
65                  70                  75                  80

Ser Gln Thr Val Ser Phe Ala Lys Lys Thr Thr Thr Thr Thr Ser Thr

```
            85                  90                  95
Ser Thr Thr Asn Gly Trp Thr Glu Gly Gly Lys Ile Ser Asp Thr Leu
            100                 105                 110

Glu Glu Lys Val Ser Val Ser Ile Pro Phe Ile Gly Glu Gly Gly Gly
            115                 120                 125

Lys Asn Ser Thr Thr Ile Glu Ala Asn Phe Ala His Asn Ser Ser Thr
130                 135                 140

Thr Thr Ala Gln Gln Ala Ser Thr Asp Ile Glu Trp Asn Ile Ser Gln
145                 150                 155                 160

Pro Val Leu Val Pro Pro Ser Lys Gln Val Val Ala Thr Leu Val Ile
                165                 170                 175

Met Gly Gly Asn Phe Thr Ile Pro Met Asp Leu Met Thr Thr Ile Asp
                180                 185                 190

Ser Thr Glu His Tyr Ser His Tyr Ser Gly Tyr Pro Ile Leu Thr Trp
                195                 200                 205

Ile Ser Ser Pro Asp Asn Ser Tyr Ser Gly Pro Phe Met Ser Trp Tyr
210                 215                 220

Phe Ala Asn Trp Pro Asn Leu Pro Ser Gly Phe Gly Pro Leu Asn Ser
225                 230                 235                 240

Asp Asn Thr Val Thr Tyr Thr Gly Ser Val Val Ser Gln Val Ser Ala
                245                 250                 255

Gly Val Tyr Ala Thr Val Arg Phe Asp Gln Tyr Asp Ile His Asn Leu
                260                 265                 270

Arg Thr Ile Glu Lys Thr Trp Tyr Ala Arg His Ala Thr Leu His Asn
                275                 280                 285

Gly Lys Lys Ile Ser Ile Asn Asn Val Thr Glu Met Ala Pro Thr Ser
                290                 295                 300

Pro Ile Lys Thr Asn
305
```

<210> SEQ ID NO 7
<211> LENGTH: 918
<212> TYPE: DNA
<213> ORGANISM: Artificial Sequence
<220> FEATURE:
<223> OTHER INFORMATION: engineered
<220> FEATURE:
<221> NAME/KEY: misc_feature
<223> OTHER INFORMATION: A nucleotide sequence encoding SEQ ID NO: 8
      with an open reading frame from 1 to 918.

<400> SEQUENCE: 7

```
atggctatcc tagaccttaa gtccctcgtg ctgaacgcca ttaactactg gggccctaag      60
aacaacaacg gcatccaggg cggtgacttc ggctacccca tctctgagaa gcagatcgac     120
actagcatca ttacctccac ccaccctcgc ttgatccccc acgatcttac tatcccgcag     180
aaccttgaga ccatcttcac cacaacgcag gtgctcacca taacactga cctccagcaa     240 tcccagaccg tgagctttgc gaagaagacc actaccacga cctcaactag cacgaccaac     300
ggttggacag aaggaggcaa gatcagcgac acgctggagg agaaagtttc ggttagcatt     360
ccgttcatcg gtgagggtgg cgggaagaac tcgactacca tagaggccaa cttcgcacac     420
aactctagca ccactacctt ccagcaagca agcactgaca ttgagtggaa cattagccaa     480
ccggtccttg tgcctccccg caaacaggtt gttgccactc tcgttatcat gggtggcaac     540
ttcactattc ctatggatct tatgactacc attgactcta ctgagcacta ctctggctac     600
cccattctca cttggatctc ttctcctgac aatagctaca acggtccatt catgtcatgg     660
```

```
tacttcgcta actggccgaa tctcccttct ggctttggtc ctcttaactc tgataacact      720
gtgacctaca ctggctctgt cgtcagtcag gtctctgccg gtgtgtacgc aactgttcgc      780
ttcgatcagt atgacatcca taatctcagg actattgaga agacctggta cgctcgtcat      840
gcgacgcttc acaacggcaa gaagatcagc atcaataacg tgacagaaat ggcccctacc      900
agcccgatca agactaac                                                   918
```

<210> SEQ ID NO 8
<211> LENGTH: 306
<212> TYPE: PRT
<213> ORGANISM: Artificial Sequence
<220> FEATURE:
<223> OTHER INFORMATION: engineered
<220> FEATURE:
<221> NAME/KEY: MISC_FEATURE
<223> OTHER INFORMATION: TIC807M2
<220> FEATURE:
<221> NAME/KEY: misc_feature
<223> OTHER INFORMATION: The amino acid sequence translation of the open
      reading frame set forth as SEQ ID NO: 7.

<400> SEQUENCE: 8

```
Met Ala Ile Leu Asp Leu Lys Ser Leu Val Leu Asn Ala Ile Asn Tyr
1               5                   10                  15

Trp Gly Pro Lys Asn Asn Asn Gly Ile Gln Gly Gly Asp Phe Gly Tyr
            20                  25                  30

Pro Ile Ser Glu Lys Gln Ile Asp Thr Ser Ile Ile Thr Ser Thr His
        35                  40                  45

Pro Arg Leu Ile Pro His Asp Leu Thr Ile Pro Gln Asn Leu Glu Thr
    50                  55                  60

Ile Phe Thr Thr Thr Gln Val Leu Thr Asn Asn Thr Asp Leu Gln Gln
65                  70                  75                  80

Ser Gln Thr Val Ser Phe Ala Lys Lys Thr Thr Thr Thr Ser Thr
                85                  90                  95

Ser Thr Thr Asn Gly Trp Thr Glu Gly Gly Lys Ile Ser Asp Thr Leu
            100                 105                 110

Glu Glu Lys Val Ser Val Ser Ile Pro Phe Ile Gly Glu Gly Gly Gly
        115                 120                 125

Lys Asn Ser Thr Thr Ile Glu Ala Asn Phe Ala His Asn Ser Ser Thr
    130                 135                 140

Thr Thr Phe Gln Gln Ala Ser Thr Asp Ile Glu Trp Asn Ile Ser Gln
145                 150                 155                 160

Pro Val Leu Val Pro Pro Arg Lys Gln Val Ala Thr Leu Val Ile
                165                 170                 175

Met Gly Gly Asn Phe Thr Ile Pro Met Asp Leu Met Thr Thr Ile Asp
            180                 185                 190

Ser Thr Glu His Tyr Ser Gly Tyr Pro Ile Leu Thr Trp Ile Ser Ser
        195                 200                 205

Pro Asp Asn Ser Tyr Asn Gly Pro Phe Met Ser Trp Tyr Phe Ala Asn
    210                 215                 220

Trp Pro Asn Leu Pro Ser Gly Phe Gly Pro Leu Asn Ser Asp Asn Thr
225                 230                 235                 240

Val Thr Tyr Thr Gly Ser Val Val Ser Gln Val Ser Ala Gly Val Tyr
                245                 250                 255

Ala Thr Val Arg Phe Asp Gln Tyr Asp Ile His Asn Leu Arg Thr Ile
            260                 265                 270
```

Glu Lys Thr Trp Tyr Ala Arg His Ala Thr Leu His Asn Gly Lys Lys
        275                 280                 285

Ile Ser Ile Asn Asn Val Thr Glu Met Ala Pro Thr Ser Pro Ile Lys
        290                 295                 300

Thr Asn
305

<210> SEQ ID NO 9
<211> LENGTH: 918
<212> TYPE: DNA
<213> ORGANISM: Artificial Sequence
<220> FEATURE:
<223> OTHER INFORMATION: engineered
<220> FEATURE:
<221> NAME/KEY: misc_feature
<223> OTHER INFORMATION: A nucleotide sequence encoding SEQ ID NO: 10
      with an open reading frame from 1 to 918.

<400> SEQUENCE: 9
atggctatcc tagaccttaa gtccctcgtg ctgaacgcca ttaactactg gggccctaag      60
aacaacaacg gcatccaggg cggtgacttc ggctacccca tctctgagaa gcagatcgac     120
actagcatca ttacctccac ccaccctcgc ttgatccccc acgatcttac tatcccgcag     180
aaccttgaga ccatcttcac cacaacgcag gtgctcacca taacactga cctccagcaa     240 tcccagaccg tgagctttgc gaagaagacc actaccgcga cctcaactag cacgaccaac     300
ggttggacag aaggaggcaa gatcagcgac acgctggagg agaaagtttc ggttagcatt     360
ccgttcatcg gtgagggtgg cgggaagaac tcgactacca tagaggccaa cttcgcacac     420
aactctagca ccactacctt ccagcaagca agcactgaca ttgagtggaa cattagccaa     480
ccggtccttg tgcctccccg caaacaggtt gttgccactc tcgttatcat gggtggcaac     540
ttcactattc ctatggatct tatgactacc attgactcta ctgagcacta ctctggctac     600
cccattctca cttggatctc ttctcctgac aatagctaca acggtccatt catgtcatgg     660
tacttcgcta actggccgaa tctcccttct ggctttggtc ctcttaactc tgataacact     720
gtgacctaca ctggctctgt cgtcagtcag gtctctgccg gtgtgtacgc aactgttcgc     780
ttcgatcagt atgacatcca taatctcagg actattgaga agacctggta cgctcgtcat     840
gcgacgcttc acaacggcaa gaagatcagc atcaataacg tgacagaaat ggcccctacc     900
agcccgatca agactaac                                                  918

<210> SEQ ID NO 10
<211> LENGTH: 306
<212> TYPE: PRT
<213> ORGANISM: Artificial Sequence
<220> FEATURE:
<223> OTHER INFORMATION: engineered
<220> FEATURE:
<221> NAME/KEY: misc_feature
<223> OTHER INFORMATION: The amino acid sequence translation of the open
      reading frame set forth as SEQ ID NO: 9.

<400> SEQUENCE: 10

Met Ala Ile Leu Asp Leu Lys Ser Leu Val Leu Asn Ala Ile Asn Tyr
1               5                   10                  15

Trp Gly Pro Lys Asn Asn Gly Ile Gln Gly Gly Asp Phe Gly Tyr
            20                  25                  30

Pro Ile Ser Glu Lys Gln Ile Asp Thr Ser Ile Ile Thr Ser Thr His
        35                  40                  45

Pro Arg Leu Ile Pro His Asp Leu Thr Ile Pro Gln Asn Leu Glu Thr

```
            50                  55                  60
Ile Phe Thr Thr Thr Gln Val Leu Thr Asn Asn Thr Asp Leu Gln Gln
 65                      70                  75                  80

Ser Gln Thr Val Ser Phe Ala Lys Lys Thr Thr Ala Thr Ser Thr
                 85                  90                  95

Ser Thr Thr Asn Gly Trp Thr Glu Gly Gly Lys Ile Ser Asp Thr Leu
             100                 105                 110

Glu Glu Lys Val Ser Val Ser Ile Pro Phe Ile Gly Glu Gly Gly Gly
         115                 120                 125

Lys Asn Ser Thr Thr Ile Glu Ala Asn Phe Ala His Asn Ser Ser Thr
    130                 135                 140

Thr Thr Phe Gln Gln Ala Ser Thr Asp Ile Glu Trp Asn Ile Ser Gln
145                 150                 155                 160

Pro Val Leu Val Pro Pro Arg Lys Gln Val Val Ala Thr Leu Val Ile
                165                 170                 175

Met Gly Gly Asn Phe Thr Ile Pro Met Asp Leu Met Thr Thr Ile Asp
            180                 185                 190

Ser Thr Glu His Tyr Ser Gly Tyr Pro Ile Leu Thr Trp Ile Ser Ser
        195                 200                 205

Pro Asp Asn Ser Tyr Asn Gly Pro Phe Met Ser Trp Tyr Phe Ala Asn
    210                 215                 220

Trp Pro Asn Leu Pro Ser Gly Phe Gly Pro Leu Asn Ser Asp Asn Thr
225                 230                 235                 240

Val Thr Tyr Thr Gly Ser Val Val Ser Gln Val Ser Ala Gly Val Tyr
                245                 250                 255

Ala Thr Val Arg Phe Asp Gln Tyr Asp Ile His Asn Leu Arg Thr Ile
            260                 265                 270

Glu Lys Thr Trp Tyr Ala Arg His Ala Thr Leu His Asn Gly Lys Lys
        275                 280                 285

Ile Ser Ile Asn Asn Val Thr Glu Met Ala Pro Thr Ser Pro Ile Lys
    290                 295                 300

Thr Asn
305

<210> SEQ ID NO 11
<211> LENGTH: 918
<212> TYPE: DNA
<213> ORGANISM: Artificial Sequence
<220> FEATURE:
<223> OTHER INFORMATION: engineered
<220> FEATURE:
<221> NAME/KEY: misc_feature
<223> OTHER INFORMATION: A nucleotide sequence encoding SEQ ID NO: 12
      with an open reading frame from 1 to 918.

<400> SEQUENCE: 11
atggctatcc tagaccttaa gtccctcgtg ctgaacgcca ttaactactg gggccctaag      60
aacaacaacg gcatccaggg cggtgacttc ggctacccca tctctgagaa gcagatcgac     120
actagcatca ttacctccac ccaccctcgc ttgatccccc acgatcttac tatcccgcag     180
aaccttgaga ccatcttcac cacaacgcag gtgctcacca taacactga cctccagcaa     240 tcccagaccg tgagctttgc gaagaagacc actaccacga ccgcaactag cacgaccaac     300
ggttggacag aaggaggcaa gatcagcgac acgctggagg agaaagtttc ggttagcatt     360
ccgttcatcg gtgagggtgg cgggaagaac tcgactacca tagaggccaa cttcgcacac     420
aactctagca ccactaccct tcagcaagca agcactgaca ttgagtggaa cattagccaa     480
```

```
ccggtccttg tgcctccccg caaacaggtt gttgccactc tcgttatcat gggtggcaac       540
ttcactattc ctatggatct tatgactacc attgactcta ctgagcacta ctctggctac       600
cccattctca cttggatctc ttctcctgac aatagctaca acggtccatt catgtcatgg       660
tacttcgcta actggccgaa tctcccttct ggctttggtc ctcttaactc tgataacact       720
gtgacctaca ctggctctgt cgtcagtcag gtctctgccg gtgtgtacgc aactgttcgc       780
ttcgatcagt atgacatcca taatctcagg actattgaga agacctggta cgctcgtcat       840
gcgacgcttc acaacggcaa gaagatcagc atcaataacg tgacagaaat ggcccctacc       900
agcccgatca agactaac                                                     918
```

<210> SEQ ID NO 12
<211> LENGTH: 306
<212> TYPE: PRT
<213> ORGANISM: Artificial Sequence
<220> FEATURE:
<223> OTHER INFORMATION: engineered
<220> FEATURE:
<221> NAME/KEY: misc_feature
<223> OTHER INFORMATION: The amino acid sequence translation of the open
      reading frame set forth as SEQ ID NO: 11.

<400> SEQUENCE: 12

```
Met Ala Ile Leu Asp Leu Lys Ser Leu Val Leu Asn Ala Ile Asn Tyr
1               5                   10                  15

Trp Gly Pro Lys Asn Asn Gly Ile Gln Gly Gly Asp Phe Gly Tyr
                20                  25                  30

Pro Ile Ser Glu Lys Gln Ile Asp Thr Ser Ile Ile Thr Ser Thr His
            35                  40                  45

Pro Arg Leu Ile Pro His Asp Leu Thr Ile Pro Gln Asn Leu Glu Thr
        50                  55                  60

Ile Phe Thr Thr Thr Gln Val Leu Thr Asn Asn Thr Asp Leu Gln Gln
65                  70                  75                  80

Ser Gln Thr Val Ser Phe Ala Lys Lys Thr Thr Thr Thr Ala Thr
                85                  90                  95

Ser Thr Thr Asn Gly Trp Thr Glu Gly Gly Lys Ile Ser Asp Thr Leu
            100                 105                 110

Glu Glu Lys Val Ser Val Ser Ile Pro Phe Ile Gly Glu Gly Gly Gly
        115                 120                 125

Lys Asn Ser Thr Thr Ile Glu Ala Asn Phe Ala His Asn Ser Ser Thr
    130                 135                 140

Thr Thr Phe Gln Gln Ala Ser Thr Asp Ile Glu Trp Asn Ile Ser Gln
145                 150                 155                 160

Pro Val Leu Val Pro Arg Lys Gln Val Ala Thr Leu Val Ile
                165                 170                 175

Met Gly Gly Asn Phe Thr Ile Pro Met Asp Leu Met Thr Thr Ile Asp
            180                 185                 190

Ser Thr Glu His Tyr Ser Gly Tyr Pro Ile Leu Thr Trp Ile Ser Ser
        195                 200                 205

Pro Asp Asn Ser Tyr Asn Gly Pro Phe Met Ser Trp Tyr Phe Ala Asn
    210                 215                 220

Trp Pro Asn Leu Pro Ser Gly Phe Gly Pro Leu Asn Ser Asp Asn Thr
225                 230                 235                 240

Val Thr Tyr Thr Gly Ser Val Val Ser Gln Val Ser Ala Gly Val Tyr
                245                 250                 255
```

```
Ala Thr Val Arg Phe Asp Gln Tyr Asp Ile His Asn Leu Arg Thr Ile
            260                 265                 270

Glu Lys Thr Trp Tyr Ala Arg His Ala Thr Leu His Asn Gly Lys Lys
        275                 280                 285

Ile Ser Ile Asn Asn Val Thr Glu Met Ala Pro Thr Ser Pro Ile Lys
    290                 295                 300

Thr Asn
305

<210> SEQ ID NO 13
<211> LENGTH: 918
<212> TYPE: DNA
<213> ORGANISM: Artificial Sequence
<220> FEATURE:
<223> OTHER INFORMATION: engineered
<220> FEATURE:
<221> NAME/KEY: misc_feature
<223> OTHER INFORMATION: A nucleotide sequence encoding SEQ ID NO: 14
      with an open reading frame from 1 to 918.

<400> SEQUENCE: 13
atggctatcc tagaccttaa gtccctcgtg ctgaacgcca ttaactactg gggccctaag      60
aacaacaacg gcatccaggg cggtgacttc ggctacccca tctctgagaa gcagatcgac     120
actagcatca ttacctccac ccaccctcgc ttgatccccc acgatcttac tatcccgcag     180
aaccttgaga ccatcttcac cacaacgcag gtgctcacca taacactga cctccagcaa     240 tcccagaccg tgagctttgc gaagaagacc actaccacga cctcaactag cacgaccaac     300
ggttggacag aaggaggcaa gatcagcgac acgctggagg agaaagtttc ggttagcatt     360
ccgttcatcg gtgagggtgg cgggaagaac tcgactacca tagaggccaa cttcgcacac     420
aactctagca ccactaccgc ccagcaagca agcactgaca ttgagtggaa cattagccaa     480
ccggtccttg tgcctccccg caaacaggtt gttgccactc tcgttatcat gggtggcaac     540
ttcactattc ctatggatct tatgactacc attgactcta ctgagcacta ctctggctac     600
cccattctca cttggatctc ttctcctgac aatagctaca acggtccatt catgtcatgg     660
tacttcgcta actggccgaa tctcccttct ggctttggtc ctcttaactc tgataacact     720
gtgacctaca ctggctctgt cgtcagtcag gtctctgccg gtgtgtacgc aactgttcgc     780
ttcgatcagt atgacatcca taatctcagg actattgaga agacctggta cgctcgtcat     840
gcgacgcttc acaacggcaa gaagatcagc atcaataacg tgacagaaat ggcccctacc     900
agcccgatca agactaac                                                   918

<210> SEQ ID NO 14
<211> LENGTH: 306
<212> TYPE: PRT
<213> ORGANISM: Artificial Sequence
<220> FEATURE:
<223> OTHER INFORMATION: engineered
<220> FEATURE:
<221> NAME/KEY: misc_feature
<223> OTHER INFORMATION: The amino acid sequence translation of the open
      reading frame set forth as SEQ ID NO: 13.

<400> SEQUENCE: 14

Met Ala Ile Leu Asp Leu Lys Ser Leu Val Leu Asn Ala Ile Asn Tyr
1               5                   10                  15

Trp Gly Pro Lys Asn Asn Asn Gly Ile Gln Gly Gly Asp Phe Gly Tyr
            20                  25                  30

Pro Ile Ser Glu Lys Gln Ile Asp Thr Ser Ile Ile Thr Ser Thr His
```

```
                  35                  40                  45
Pro Arg Leu Ile Pro His Asp Leu Thr Ile Pro Gln Asn Leu Glu Thr
 50                  55                  60
Ile Phe Thr Thr Thr Gln Val Leu Thr Asn Asn Thr Asp Leu Gln Gln
 65                  70                  75                  80
Ser Gln Thr Val Ser Phe Ala Lys Lys Thr Thr Thr Thr Ser Thr
                 85                  90                  95
Ser Thr Thr Asn Gly Trp Thr Glu Gly Gly Lys Ile Ser Asp Thr Leu
                100                 105                 110
Glu Glu Lys Val Ser Val Ser Ile Pro Phe Ile Gly Glu Gly Gly
             115                 120                 125
Lys Asn Ser Thr Thr Ile Glu Ala Asn Phe Ala His Asn Ser Ser Thr
         130                 135                 140
Thr Thr Ala Gln Gln Ala Ser Thr Asp Ile Glu Trp Asn Ile Ser Gln
145                 150                 155                 160
Pro Val Leu Val Pro Pro Arg Lys Gln Val Val Ala Thr Leu Val Ile
                 165                 170                 175
Met Gly Gly Asn Phe Thr Ile Pro Met Asp Leu Met Thr Thr Ile Asp
             180                 185                 190
Ser Thr Glu His Tyr Ser Gly Tyr Pro Ile Leu Thr Trp Ile Ser Ser
         195                 200                 205
Pro Asp Asn Ser Tyr Asn Gly Pro Phe Met Ser Trp Tyr Phe Ala Asn
210                 215                 220
Trp Pro Asn Leu Pro Ser Gly Phe Gly Pro Leu Asn Ser Asp Asn Thr
225                 230                 235                 240
Val Thr Tyr Thr Gly Ser Val Val Ser Gln Val Ser Ala Gly Val Tyr
                 245                 250                 255
Ala Thr Val Arg Phe Asp Gln Tyr Asp Ile His Asn Leu Arg Thr Ile
             260                 265                 270
Glu Lys Thr Trp Tyr Ala Arg His Ala Thr Leu His Asn Gly Lys Lys
         275                 280                 285
Ile Ser Ile Asn Asn Val Thr Glu Met Ala Pro Thr Ser Pro Ile Lys
290                 295                 300
Thr Asn
305

<210> SEQ ID NO 15
<211> LENGTH: 918
<212> TYPE: DNA
<213> ORGANISM: Artificial Sequence
<220> FEATURE:
<223> OTHER INFORMATION: engineered
<220> FEATURE:
<221> NAME/KEY: misc_feature
<223> OTHER INFORMATION: A nucleotide sequence encoding SEQ ID NO: 16
      with an open reading frame from 1 to 918.

<400> SEQUENCE: 15
atggctatcc tagaccttaa gtccctcgtg ctgaacgcca ttaactactg gggccctaag      60
aacaacaacg gcatccaggg cggtgacttc ggctacccca tctctgagaa gcagatcgac     120
actagcatca ttcctccac ccaccctcgc ttgatccccc acgatcttac tatcccgcag     180
aaccttgaga ccatcttcac cacaacgcag gtgctcacca ataacactga cctccagcaa     240
tcccagaccg tgagctttgc gaagaagacc actaccacga ccgcaactag cacgaccaac     300
ggttggacag aaggaggcaa gatcagcgac acgctggagg agaaagtttc ggttagcatt     360
```

```
ccgttcatcg gtgagggtgg cgggaagaac tcgactacca tagaggccaa cttcgcacac    420
aactctagca ccactaccgc ccagcaagca agcactgaca ttgagtggaa cattagccaa    480
ccggtccttg tgcctccccg caaacaggtt gttgccactc tcgttatcat gggtggcaac    540
ttcactattc ctatggatct tatgactacc attgactcta ctgagcacta ctctggctac    600
cccattctca cttggatctc ttctcctgac aatagctaca acggtccatt catgtcatgg    660
tacttcgcta actggccgaa tctcccttct ggctttggtc ctcttaactc tgataacact    720
gtgacctaca ctggctctgt cgtcagtcag gtctctgccg gtgtgtacgc aactgttcgc    780
ttcgatcagt atgacatcca taatctcagg actattgaga agacctggta cgctcgtcat    840
gcgacgcttc acaacggcaa gaagatcagc atcaataacg tgacagaaat ggcccctacc    900
agcccgatca agactaac                                                  918
```

```
<210> SEQ ID NO 16
<211> LENGTH: 306
<212> TYPE: PRT
<213> ORGANISM: Artificial Sequence
<220> FEATURE:
<223> OTHER INFORMATION: engineered
<220> FEATURE:
<221> NAME/KEY: MISC_FEATURE
<223> OTHER INFORMATION: TIC807M8
<220> FEATURE:
<221> NAME/KEY: misc_feature
<223> OTHER INFORMATION: The amino acid sequence translation of the open
      reading frame set forth as SEQ ID NO: 15.
```

<400> SEQUENCE: 16

```
Met Ala Ile Leu Asp Leu Lys Ser Leu Val Leu Asn Ala Ile Asn Tyr
1               5                   10                  15

Trp Gly Pro Lys Asn Asn Asn Gly Ile Gln Gly Gly Asp Phe Gly Tyr
            20                  25                  30

Pro Ile Ser Glu Lys Gln Ile Asp Thr Ser Ile Ile Thr Ser Thr His
        35                  40                  45

Pro Arg Leu Ile Pro His Asp Leu Thr Ile Pro Gln Asn Leu Glu Thr
    50                  55                  60

Ile Phe Thr Thr Thr Gln Val Leu Thr Asn Asn Thr Asp Leu Gln Gln
65                  70                  75                  80

Ser Gln Thr Val Ser Phe Ala Lys Lys Thr Thr Thr Thr Ala Thr
                85                  90                  95

Ser Thr Thr Asn Gly Trp Thr Glu Gly Gly Lys Ile Ser Asp Thr Leu
            100                 105                 110

Glu Glu Lys Val Ser Val Ser Ile Pro Phe Ile Gly Glu Gly Gly Gly
        115                 120                 125

Lys Asn Ser Thr Thr Ile Glu Ala Asn Phe Ala His Asn Ser Ser Thr
    130                 135                 140

Thr Thr Ala Gln Gln Ala Ser Thr Asp Ile Glu Trp Asn Ile Ser Gln
145                 150                 155                 160

Pro Val Leu Val Pro Pro Arg Lys Gln Val Ala Thr Leu Val Ile
                165                 170                 175

Met Gly Gly Asn Phe Thr Ile Pro Met Asp Leu Met Thr Thr Ile Asp
            180                 185                 190

Ser Thr Glu His Tyr Ser Gly Tyr Pro Ile Leu Thr Trp Ile Ser Ser
        195                 200                 205

Pro Asp Asn Ser Tyr Asn Gly Pro Phe Met Ser Trp Tyr Phe Ala Asn
    210                 215                 220
```

```
Trp Pro Asn Leu Pro Ser Gly Phe Gly Pro Leu Asn Ser Asp Asn Thr
225                 230                 235                 240

Val Thr Tyr Thr Gly Ser Val Val Ser Gln Val Ser Ala Gly Val Tyr
            245                 250                 255

Ala Thr Val Arg Phe Asp Gln Tyr Asp Ile His Asn Leu Arg Thr Ile
        260                 265                 270

Glu Lys Thr Trp Tyr Ala Arg His Ala Thr Leu His Asn Gly Lys Lys
    275                 280                 285

Ile Ser Ile Asn Asn Val Thr Glu Met Ala Pro Thr Ser Pro Ile Lys
    290                 295                 300

Thr Asn
305
```

<210> SEQ ID NO 17
<211> LENGTH: 918
<212> TYPE: DNA
<213> ORGANISM: Artificial Sequence
<220> FEATURE:
<223> OTHER INFORMATION: engineered
<220> FEATURE:
<221> NAME/KEY: misc_feature
<223> OTHER INFORMATION: A nucleotide sequence encoding SEQ ID NO: 18 with an open reading frame from 1 to 918.

<400> SEQUENCE: 17

```
atggctatcc tagaccttaa gtccctcgtg ctgaacgcca ttaactactg gggccctaag      60
aacaacaacg gcatccaggg cggtgacttc ggctacccca tctctgagaa gcagatcgac     120
actagcatca ttcctccac ccaccctcgc ttgatccccc acgatcttac tatcccgcag     180
aaccttgaga ccatcttcac cacaacgcag gtgctcacca ataacactga cctccagcaa     240
tcccagaccg tgagctttgc gaagaagacc actaccgcga cctcaactag cacgaccaac     300
ggttggacag aaggaggcaa gatcagcgac acgctggagg agaaagtttc ggttagcatt     360
ccgttcatcg gtgagggtgg cgggaagaac tcgactacca tagaggccaa cttcgcacac     420
aactctagca ccactaccgc ccagcaagca agcactgaca ttgagtggaa cattagccaa     480
ccggtccttg tgcctccccg caaacaggtt gttgccactc tcgttatcat gggtggcaac     540
ttcactattc ctatggatct tatgactacc attgactcta ctgagcacta ctctggctac     600
cccattctca cttggatctc ttctcctgac aatagctaca acggtccatt catgtcatgg     660
tacttcgcta actggccgaa tctccccttct ggctttggtc ctcttaactc tgataacact     720
gtgacctaca ctggctctgt cgtcagtcag gtctctgccg gtgtgtacgc aactgttcgc     780
ttcgatcagt atgacatcca taatctcagg actattgaga gacctggta cgctcgtcat     840
gcgacgcttc acaacggcaa gaagatcagc atcaataacg tgacagaaat ggcccctacc     900
agcccgatca agactaac                                                   918
```

<210> SEQ ID NO 18
<211> LENGTH: 306
<212> TYPE: PRT
<213> ORGANISM: Artificial Sequence
<220> FEATURE:
<223> OTHER INFORMATION: engineered
<220> FEATURE:
<221> NAME/KEY: misc_feature
<223> OTHER INFORMATION: The amino acid sequence translation of the open reading frame set forth as SEQ ID NO: 17.

<400> SEQUENCE: 18

```
Met Ala Ile Leu Asp Leu Lys Ser Leu Val Leu Asn Ala Ile Asn Tyr
```

```
            1               5                  10                 15
         Trp Gly Pro Lys Asn Asn Gly Ile Gln Gly Gly Asp Phe Gly Tyr
                         20                  25                  30

Pro Ile Ser Glu Lys Gln Ile Asp Thr Ser Ile Ile Thr Ser Thr His
                         35                  40                  45

Pro Arg Leu Ile Pro His Asp Leu Thr Ile Pro Gln Asn Leu Glu Thr
                50                  55                  60

Ile Phe Thr Thr Thr Gln Val Leu Thr Asn Asn Thr Asp Leu Gln Gln
         65                  70                  75                  80

Ser Gln Thr Val Ser Phe Ala Lys Lys Thr Thr Thr Ala Thr Ser Thr
                         85                  90                  95

Ser Thr Thr Asn Gly Trp Thr Glu Gly Gly Lys Ile Ser Asp Thr Leu
                         100                 105                 110

Glu Glu Lys Val Ser Val Ser Ile Pro Phe Ile Gly Glu Gly Gly Gly
                         115                 120                 125

Lys Asn Ser Thr Thr Ile Glu Ala Asn Phe Ala His Asn Ser Ser Thr
                 130                 135                 140

Thr Thr Ala Gln Gln Ala Ser Thr Asp Ile Glu Trp Asn Ile Ser Gln
         145                 150                 155                 160

Pro Val Leu Val Pro Pro Arg Lys Gln Val Val Ala Thr Leu Val Ile
                         165                 170                 175

Met Gly Gly Asn Phe Thr Ile Pro Met Asp Leu Met Thr Thr Ile Asp
                         180                 185                 190

Ser Thr Glu His Tyr Ser Gly Tyr Pro Ile Leu Thr Trp Ile Ser Ser
                         195                 200                 205

Pro Asp Asn Ser Tyr Asn Gly Pro Phe Met Ser Trp Tyr Phe Ala Asn
                 210                 215                 220

Trp Pro Asn Leu Pro Ser Gly Phe Gly Pro Leu Asn Ser Asp Asn Thr
         225                 230                 235                 240

Val Thr Tyr Thr Gly Ser Val Val Ser Gln Val Ser Ala Gly Val Tyr
                         245                 250                 255

Ala Thr Val Arg Phe Asp Gln Tyr Asp Ile His Asn Leu Arg Thr Ile
                         260                 265                 270

Glu Lys Thr Trp Tyr Ala Arg His Ala Thr Leu His Asn Gly Lys Lys
                         275                 280                 285

Ile Ser Ile Asn Asn Val Thr Glu Met Ala Pro Thr Ser Pro Ile Lys
                 290                 295                 300

Thr Asn
         305

<210> SEQ ID NO 19
<211> LENGTH: 918
<212> TYPE: DNA
<213> ORGANISM: Artificial Sequence
<220> FEATURE:
<223> OTHER INFORMATION: engineered
<220> FEATURE:
<221> NAME/KEY: misc_feature
<223> OTHER INFORMATION: A nucleotide sequence encoding SEQ ID NO: 20
      with an open reading frame from 1 to 918.

<400> SEQUENCE: 19
atggctatcc tagaccttaa gtccctcgtg ctgaacgcca ttaactactg gggccctaag      60
aacaacaacg gcatccaggg cggtgacttc ggctacccca tctctgagaa gcagatcgac     120
actagcatca ttacctccac ccaccctcgc ttgatccccc acgatcttac tatcccgcag     180
```

```
aaccttgaga ccatcttcac cacaacgcag gtgctcacca ataacactga cctccagcaa    240
tcccagaccg tgagctttgc gaagaagacc actaccacga cctcaactag cacgaccaac    300
ggttggacag aaggaggcaa gatcagcgac acgctggagg agaaagtttc ggttagcatt    360
ccgttcatcg gtgagggtgg cgggaagaac tcgactacca tagaggccaa cttcgcacac    420
aactctagca ccactacctt ccaggaggca agcactgaca ttgagtggaa cattagccaa    480
ccggtccttg tgcctccccg caaacaggtt gttgccactc tcgttatcat gggtggcaac    540
ttcactattc ctatggatct tatgactacc attgactcta ctgagcacta ctctggctac    600
cccattctca cttggatctc ttctcctgac aatagctaca acggtccatt catgtcatgg    660
tacttcgcta actggccgaa tctcccttct ggctttggtc ctcttaactc tgataacact    720
gtgacctaca ctggctctgt cgtcagtcag gtctctgccg gtgtgtacgc aactgttcgc    780
ttcgatcagt atgacatcca taatctcagg actattgaga gacctggta cgctcgtcat    840 gcgacgcttc acaacggcaa gaagatcagc atcaataacg tgacagaaat ggcccctacc    900
agcccgatca agactaac                                                  918
```

<210> SEQ ID NO 20
<211> LENGTH: 306
<212> TYPE: PRT
<213> ORGANISM: Artificial Sequence
<220> FEATURE:
<223> OTHER INFORMATION: engineered
<220> FEATURE:
<221> NAME/KEY: misc_feature
<223> OTHER INFORMATION: The amino acid sequence translation of the open reading frame set forth as SEQ ID NO: 19.

<400> SEQUENCE: 20

```
Met Ala Ile Leu Asp Leu Lys Ser Leu Val Leu Asn Ala Ile Asn Tyr
1               5                   10                  15

Trp Gly Pro Lys Asn Asn Gly Ile Gln Gly Gly Asp Phe Gly Tyr
            20                  25                  30

Pro Ile Ser Glu Lys Gln Ile Asp Thr Ser Ile Ile Thr Ser Thr His
        35                  40                  45

Pro Arg Leu Ile Pro His Asp Leu Thr Ile Pro Gln Asn Leu Glu Thr
    50                  55                  60

Ile Phe Thr Thr Thr Gln Val Leu Thr Asn Asn Thr Asp Leu Gln Gln
65                  70                  75                  80

Ser Gln Thr Val Ser Phe Ala Lys Lys Thr Thr Thr Thr Ser Thr
                85                  90                  95

Ser Thr Thr Asn Gly Trp Thr Glu Gly Gly Lys Ile Ser Asp Thr Leu
            100                 105                 110

Glu Glu Lys Val Ser Val Ser Ile Pro Phe Ile Gly Glu Gly Gly Gly
        115                 120                 125

Lys Asn Ser Thr Thr Ile Glu Ala Asn Phe Ala His Asn Ser Ser Thr
    130                 135                 140

Thr Thr Phe Gln Glu Ala Ser Thr Asp Ile Glu Trp Asn Ile Ser Gln
145                 150                 155                 160

Pro Val Leu Val Pro Pro Arg Lys Gln Val Val Ala Thr Leu Val Ile
                165                 170                 175

Met Gly Gly Asn Phe Thr Ile Pro Met Asp Leu Met Thr Thr Ile Asp
            180                 185                 190

Ser Thr Glu His Tyr Ser Gly Tyr Pro Ile Leu Thr Trp Ile Ser Ser
        195                 200                 205
```

```
Pro Asp Asn Ser Tyr Asn Gly Pro Phe Met Ser Trp Tyr Phe Ala Asn
    210                 215                 220

Trp Pro Asn Leu Pro Ser Gly Phe Gly Pro Leu Asn Ser Asp Asn Thr
225                 230                 235                 240

Val Thr Tyr Thr Gly Ser Val Val Ser Gln Val Ser Ala Gly Val Tyr
                245                 250                 255

Ala Thr Val Arg Phe Asp Gln Tyr Asp Ile His Asn Leu Arg Thr Ile
            260                 265                 270

Glu Lys Thr Trp Tyr Ala Arg His Ala Thr Leu His Asn Gly Lys Lys
        275                 280                 285

Ile Ser Ile Asn Asn Val Thr Glu Met Ala Pro Thr Ser Pro Ile Lys
    290                 295                 300

Thr Asn
305

<210> SEQ ID NO 21
<211> LENGTH: 918
<212> TYPE: DNA
<213> ORGANISM: Artificial Sequence
<220> FEATURE:
<223> OTHER INFORMATION: engineered
<220> FEATURE:
<221> NAME/KEY: misc_feature
<223> OTHER INFORMATION: A nucleotide sequence encoding SEQ ID NO: 22
      with an open reading frame from 1 to 918.

<400> SEQUENCE: 21
atggctatcc tagaccttaa gtccctcgtg ctgaacgcca ttaactactg gggccctaag      60
aacaacaacg gcatccaggg cggtgacttc ggctacccca tctctgagaa gcagatcgac     120
actagcatca ttacctccac ccaccctcgc ttgatccccc acgatcttac tatcccgcag     180
aaccttgaga ccatcttcac cacaacgcag gtgctcacca ataacactga cctccagcaa     240
tcccagaccg tgagctttgc gaagaagacc actaccgcga cctcaactag cacgaccaac     300
ggttggacag aaggaggcaa gatcagcgac acgctggagg agaaagtttc ggttagcatt     360
ccgttcatcg gtgagggtgg cgggaagaac tcgactacca tagaggccaa cttcgcacac     420
aactctagca ccactacctt ccaggcagca agcactgaca ttgagtggaa cattagccaa     480
ccggtccttg tgcctccccg caaacaggtt gttgccactc tcgttatcat gggtggcaac     540
ttcactattc ctatggatct tatgactacc attgactcta ctgagcacta ctctggctac     600
cccattctca cttggatctc ttctcctgac aatagctaca acggtccatt catgtcatgg     660
tacttcgcta actggccgaa tctcccttct ggctttggtc ctcttaactc tgataacact     720
gtgacctaca ctggctctgt cgtcagtcag gtctctgccg gtgtgtacgc aactgttcgc     780
ttcgatcagt atgacatcca taatctcagg actattgaga gacctggta cgctcgtcat     840 gcgacgcttc acaacggcaa gaagatcagc atcaataacg tgacagaaat ggcccctacc     900
agcccgatca agactaac                                                   918

<210> SEQ ID NO 22
<211> LENGTH: 306
<212> TYPE: PRT
<213> ORGANISM: Artificial Sequence
<220> FEATURE:
<223> OTHER INFORMATION: engineered
<220> FEATURE:
<221> NAME/KEY: misc_feature
<223> OTHER INFORMATION: The amino acid sequence translation of the open
      reading frame set forth as SEQ ID NO: 21.
```

```
<400> SEQUENCE: 22

Met Ala Ile Leu Asp Leu Lys Ser Leu Val Leu Asn Ala Ile Asn Tyr
 1               5                  10                  15

Trp Gly Pro Lys Asn Asn Asn Gly Ile Gln Gly Gly Asp Phe Gly Tyr
            20                  25                  30

Pro Ile Ser Glu Lys Gln Ile Asp Thr Ser Ile Ile Thr Ser Thr His
        35                  40                  45

Pro Arg Leu Ile Pro His Asp Leu Thr Ile Pro Gln Asn Leu Glu Thr
    50                  55                  60

Ile Phe Thr Thr Thr Gln Val Leu Thr Asn Asn Thr Asp Leu Gln Gln
65                  70                  75                  80

Ser Gln Thr Val Ser Phe Ala Lys Lys Thr Thr Ala Thr Ser Thr
                85                  90                  95

Ser Thr Thr Asn Gly Trp Thr Glu Gly Gly Lys Ile Ser Asp Thr Leu
                100                 105                 110

Glu Glu Lys Val Ser Val Ser Ile Pro Phe Ile Gly Glu Gly Gly Gly
            115                 120                 125

Lys Asn Ser Thr Thr Ile Glu Ala Asn Phe Ala His Asn Ser Ser Thr
        130                 135                 140

Thr Thr Phe Gln Ala Ala Ser Thr Asp Ile Glu Trp Asn Ile Ser Gln
145                 150                 155                 160

Pro Val Leu Val Pro Arg Lys Gln Val Val Ala Thr Leu Val Ile
                165                 170                 175

Met Gly Gly Asn Phe Thr Ile Pro Met Asp Leu Met Thr Thr Ile Asp
                180                 185                 190

Ser Thr Glu His Tyr Ser Gly Tyr Pro Ile Leu Thr Trp Ile Ser Ser
            195                 200                 205

Pro Asp Asn Ser Tyr Asn Gly Pro Phe Met Ser Trp Tyr Phe Ala Asn
        210                 215                 220

Trp Pro Asn Leu Pro Ser Gly Phe Gly Pro Leu Asn Ser Asp Asn Thr
225                 230                 235                 240

Val Thr Tyr Thr Gly Ser Val Val Ser Gln Val Ser Ala Gly Val Tyr
                245                 250                 255

Ala Thr Val Arg Phe Asp Gln Tyr Asp Ile His Asn Leu Arg Thr Ile
                260                 265                 270

Glu Lys Thr Trp Tyr Ala Arg His Ala Thr Leu His Asn Gly Lys Lys
            275                 280                 285

Ile Ser Ile Asn Asn Val Thr Glu Met Ala Pro Thr Ser Pro Ile Lys
        290                 295                 300

Thr Asn
305

<210> SEQ ID NO 23
<211> LENGTH: 918
<212> TYPE: DNA
<213> ORGANISM: Artificial Sequence
<220> FEATURE:
<223> OTHER INFORMATION: engineered
<220> FEATURE:
<221> NAME/KEY: misc_feature
<223> OTHER INFORMATION: A nucleotide sequence encoding SEQ ID NO: 24
      with an open reading frame from 1 to 918.

<400> SEQUENCE: 23
atggctatcc tagaccttaa gtccctcgtg ctgaacgcca ttaactactg gggccctaag      60
aacaacaacg gcatccaggg cggtgacttc ggctacccca tctctgagaa gcagatcgac     120
```

```
actagcatca ttacctccac ccaccctcgc ttgatccccc acgatcttac tatcccgcag    180
aaccttgaga ccatcttcac cacaacgcag gtgctcacca ataacactga cctccagcaa    240
tcccagaccg tgagctttgc gaagaagacc actaccgcga cctcaactag cacgaccaac    300
ggttggacag aaggaggcaa gatcagcgac acgctggagg agaaagtttc ggttagcatt    360
ccgttcatcg gtgagggtgg cggaagaac tcgactacca tagaggccaa cttcgcacac    420
aactctagca ccactacctt ccaggaggca agcactgaca ttgagtggaa cattagccaa    480
ccggtccttg tgcctccccg caaacaggtt gttgccactc tcgttatcat gggtggcaac    540
ttcactattc ctatggatct tatgactacc attgactcta ctgagcacta ctctggctac    600
cccattctca cttggatctc ttctcctgac aatagctaca acggtccatt catgtcatgg    660
tacttcgcta actggccgaa tctcccttct ggctttggtc ctcttaactc tgataacact    720
gtgacctaca ctggctctgt cgtcagtcag gtctctgccg gtgtgtacgc aactgttcgc    780
ttcgatcagt atgacatcca taatctcagg actattgaga agacctggta cgctcgtcat    840
gcgacgcttc acaacggcaa gaagatcagc atcaataacg tgacagaaat ggcccctacc    900
agcccgatca agactaac                                                  918
```

<210> SEQ ID NO 24
<211> LENGTH: 306
<212> TYPE: PRT
<213> ORGANISM: Artificial Sequence
<220> FEATURE:
<223> OTHER INFORMATION: engineered
<220> FEATURE:
<221> NAME/KEY: misc_feature
<223> OTHER INFORMATION: The amino acid sequence translation of the open
      reading frame set forth as SEQ ID NO: 23.

<400> SEQUENCE: 24

```
Met Ala Ile Leu Asp Leu Lys Ser Leu Val Leu Asn Ala Ile Asn Tyr
1               5                   10                  15

Trp Gly Pro Lys Asn Asn Gly Ile Gln Gly Gly Asp Phe Gly Tyr
            20                  25                  30

Pro Ile Ser Glu Lys Gln Ile Asp Thr Ser Ile Thr Ser Thr His
        35                  40                  45

Pro Arg Leu Ile Pro His Asp Leu Thr Ile Pro Gln Asn Leu Glu Thr
    50                  55                  60

Ile Phe Thr Thr Thr Gln Val Leu Thr Asn Asn Thr Asp Leu Gln Gln
65                  70                  75                  80

Ser Gln Thr Val Ser Phe Ala Lys Lys Thr Thr Thr Ala Thr Ser Thr
                85                  90                  95

Ser Thr Asn Gly Trp Thr Glu Gly Gly Lys Ile Ser Asp Thr Leu
            100                 105                 110

Glu Glu Lys Val Ser Val Ser Ile Pro Phe Ile Gly Glu Gly Gly Gly
        115                 120                 125

Lys Asn Ser Thr Thr Ile Glu Ala Asn Phe Ala His Asn Ser Ser Thr
    130                 135                 140

Thr Thr Phe Gln Glu Ala Ser Thr Asp Ile Glu Trp Asn Ile Ser Gln
145                 150                 155                 160

Pro Val Leu Val Pro Pro Arg Lys Gln Val Val Ala Thr Leu Val Ile
                165                 170                 175

Met Gly Gly Asn Phe Thr Ile Pro Met Asp Leu Met Thr Thr Ile Asp
            180                 185                 190
```

```
Ser Thr Glu His Tyr Ser Gly Tyr Pro Ile Leu Thr Trp Ile Ser Ser
        195                 200                 205

Pro Asp Asn Ser Tyr Asn Gly Pro Phe Met Ser Trp Tyr Phe Ala Asn
    210                 215                 220

Trp Pro Asn Leu Pro Ser Gly Phe Gly Pro Leu Asn Ser Asp Asn Thr
225                 230                 235                 240

Val Thr Tyr Thr Gly Ser Val Val Ser Gln Val Ser Ala Gly Val Tyr
                245                 250                 255

Ala Thr Val Arg Phe Asp Gln Tyr Asp Ile His Asn Leu Arg Thr Ile
            260                 265                 270

Glu Lys Thr Trp Tyr Ala Arg His Ala Thr Leu His Asn Gly Lys Lys
        275                 280                 285

Ile Ser Ile Asn Asn Val Thr Glu Met Ala Pro Thr Ser Pro Ile Lys
    290                 295                 300

Thr Asn
305

<210> SEQ ID NO 25
<211> LENGTH: 918
<212> TYPE: DNA
<213> ORGANISM: Artificial Sequence
<220> FEATURE:
<223> OTHER INFORMATION: engineered
<220> FEATURE:
<221> NAME/KEY: misc_feature
<223> OTHER INFORMATION: A nucleotide sequence encoding SEQ ID NO: 26
      with an open reading frame from 1 to 918.

<400> SEQUENCE: 25
atggctatcc tagaccttaa gtccctcgtg ctgaacgcca ttaactactg gggccctaag      60
aacaacaacg gcatccaggg cggtgacttc ggctacccca tctctgagaa gcagatcgac     120
actagcatca ttacctccac ccaccctcgc ttgatccccc acgatcttac tatcccgcag     180
aaccttgaga ccatcttcac cacaacgcag gtgctcacca taacactga cctccagcaa     240 tcccagaccg tgagctttgc gaagaagacc actaccacga ccgcaactag cacgaccaac     300
ggttggacag aaggaggcaa gatcagcgac acgctggagg agaaagtttc ggttagcatt     360
ccgttcatcg gtgagggtgg cgggaagaac tcgactacca tagaggccaa cttcgcacac     420
aactctagca ccactaccgc ccagcaagca agcactgaca ttgagtggaa cattagccaa     480
ccggtccttg tgcctccccg caaacaggtt gttgccactc tcgttatcat gggtggcaac     540
ttcactattc ctatggatct tatgactacc attgactcta ctgagcacta ctctggctac     600
cccattctca cttggatctc ttctcctgac aatagctaca gcggtccatt catgtcatgg     660
tacttcgcta actggccgaa tctcccttct ggctttggtc ctcttaactc tgataacact     720
gtgacctaca ctggctctgt cgtcagtcag gtctctgccg gtgtgtacgc aactgttcgc     780
ttcgatcagt atgacatcca taatctcagg actattgaga gacctggta cgctcgtcat     840 gcgacgcttc acaacggcaa gaagatcagc atcaataacg tgacagaaat ggcccctacc     900
agcccgatca agactaac                                                   918

<210> SEQ ID NO 26
<211> LENGTH: 306
<212> TYPE: PRT
<213> ORGANISM: Artificial Sequence
<220> FEATURE:
<223> OTHER INFORMATION: engineered
<220> FEATURE:
<221> NAME/KEY: misc_feature
```

<223> OTHER INFORMATION: The amino acid sequence translation of the open
      reading frame set forth as SEQ ID NO: 25.

<400> SEQUENCE: 26

```
Met Ala Ile Leu Asp Leu Lys Ser Leu Val Leu Asn Ala Ile Asn Tyr
1               5                   10                  15

Trp Gly Pro Lys Asn Asn Asn Gly Ile Gln Gly Gly Asp Phe Gly Tyr
            20                  25                  30

Pro Ile Ser Glu Lys Gln Ile Asp Thr Ser Ile Ile Thr Ser Thr His
        35                  40                  45

Pro Arg Leu Ile Pro His Asp Leu Thr Ile Pro Gln Asn Leu Glu Thr
    50                  55                  60

Ile Phe Thr Thr Thr Gln Val Leu Thr Asn Asn Thr Asp Leu Gln Gln
65                  70                  75                  80

Ser Gln Thr Val Ser Phe Ala Lys Lys Thr Thr Thr Thr Thr Ala Thr
                85                  90                  95

Ser Thr Thr Asn Gly Trp Thr Glu Gly Gly Lys Ile Ser Asp Thr Leu
            100                 105                 110

Glu Glu Lys Val Ser Val Ser Ile Pro Phe Ile Gly Glu Gly Gly Gly
        115                 120                 125

Lys Asn Ser Thr Thr Ile Glu Ala Asn Phe Ala His Asn Ser Ser Thr
    130                 135                 140

Thr Thr Ala Gln Gln Ala Ser Thr Asp Ile Glu Trp Asn Ile Ser Gln
145                 150                 155                 160

Pro Val Leu Val Pro Pro Arg Lys Gln Val Val Ala Thr Leu Val Ile
                165                 170                 175

Met Gly Gly Asn Phe Thr Ile Pro Met Asp Leu Met Thr Thr Ile Asp
            180                 185                 190

Ser Thr Glu His Tyr Ser Gly Tyr Pro Ile Leu Thr Trp Ile Ser Ser
        195                 200                 205

Pro Asp Asn Ser Tyr Ser Gly Pro Phe Met Ser Trp Tyr Phe Ala Asn
    210                 215                 220

Trp Pro Asn Leu Pro Ser Gly Phe Gly Pro Leu Asn Ser Asp Asn Thr
225                 230                 235                 240

Val Thr Tyr Thr Gly Ser Val Val Ser Gln Val Ser Ala Gly Val Tyr
                245                 250                 255

Ala Thr Val Arg Phe Asp Gln Tyr Asp Ile His Asn Leu Arg Thr Ile
            260                 265                 270

Glu Lys Thr Trp Tyr Ala Arg His Ala Thr Leu His Asn Gly Lys Lys
        275                 280                 285

Ile Ser Ile Asn Asn Val Thr Glu Met Ala Pro Thr Ser Pro Ile Lys
    290                 295                 300

Thr Asn
305
```

<210> SEQ ID NO 27
<211> LENGTH: 918
<212> TYPE: DNA
<213> ORGANISM: Artificial Sequence
<220> FEATURE:
<223> OTHER INFORMATION: engineered
<220> FEATURE:
<221> NAME/KEY: misc_feature
<223> OTHER INFORMATION: A nucleotide sequence encoding SEQ ID NO: 28
      with an open reading frame from 1 to 918.

<400> SEQUENCE: 27

```
atggctatcc tagaccttaa gtccctcgtg ctgaacgcca ttaactactg gggccctaag    60
aacaacaacg gcatccaggg cggtgacttc ggctacccca tctctgagaa gcagatcgac   120
actagcatca ttacctccac ccaccctcgc ttgatccccc acgatcttac tatcccgcag   180
aaccttgaga ccatcttcac cacaacgcag gtgctcacca ataacactga cctccagcaa   240
tcccagaccg tgagctttgc gaagaagacc actaccacga ccgcaactag cacgaccaac   300
ggttggacag aaggaggcaa gatcagcgac acgctggagg agaaagtttc ggttagcatt   360
ccgttcatcg gtgagggtgg cgggaagaac tcgactacca tagaggccaa cttcgcacac   420
aactctagca ccactaccgc ccagcaagca agcactgaca ttgagtggaa cattagccaa   480
ccggtccttg tgcctccccg caaacaggtt gttgccactc tcgttatcat gggtggcaac   540
ttcactattc ctatggatct tatgactacc attgactcta ctgagcacta ctctggctac   600
cccattctca cttggatctc ttctcctgac aatagctaca gcggtcgatt catgtcatgg   660
tacttcgcta actggccgaa tctcccttct ggctttggtc ctcttaactc tgataacact   720
gtgacctaca ctggctctgt cgtcagtcag gtctctgccg gtgtgtacgc aactgttcgc   780
ttcgatcagt atgacatcca taatctcagg actattgaga agacctggta cgctcgtcat   840
gcgacgcttc acaacggcaa gaagatcagc atcaataacg tgacagaaat ggcccctacc   900
agcccgatca agactaac                                                 918
```

<210> SEQ ID NO 28
<211> LENGTH: 306
<212> TYPE: PRT
<213> ORGANISM: Artificial Sequence
<220> FEATURE:
<223> OTHER INFORMATION: engineered
<220> FEATURE:
<221> NAME/KEY: misc_feature
<223> OTHER INFORMATION: The amino acid sequence translation of the open
      reading frame set forth as SEQ ID NO: 27.

<400> SEQUENCE: 28

```
Met Ala Ile Leu Asp Leu Lys Ser Leu Val Leu Asn Ala Ile Asn Tyr
1               5                   10                  15

Trp Gly Pro Lys Asn Asn Asn Gly Ile Gln Gly Gly Asp Phe Gly Tyr
            20                  25                  30

Pro Ile Ser Glu Lys Gln Ile Asp Thr Ser Ile Ile Thr Ser Thr His
        35                  40                  45

Pro Arg Leu Ile Pro His Asp Leu Thr Ile Pro Gln Asn Leu Glu Thr
    50                  55                  60

Ile Phe Thr Thr Thr Gln Val Leu Thr Asn Asn Thr Asp Leu Gln Gln
65                  70                  75                  80

Ser Gln Thr Val Ser Phe Ala Lys Lys Thr Thr Thr Thr Thr Ala Thr
                85                  90                  95

Ser Thr Thr Asn Gly Trp Thr Glu Gly Gly Lys Ile Ser Asp Thr Leu
            100                 105                 110

Glu Glu Lys Val Ser Val Ser Ile Pro Phe Ile Gly Glu Gly Gly Gly
        115                 120                 125

Lys Asn Ser Thr Thr Ile Glu Ala Asn Phe Ala His Asn Ser Ser Thr
    130                 135                 140

Thr Thr Ala Gln Gln Ala Ser Thr Asp Ile Glu Trp Asn Ile Ser Gln
145                 150                 155                 160

Pro Val Leu Val Pro Pro Arg Lys Gln Val Val Ala Thr Leu Val Ile
                165                 170                 175
```

```
Met Gly Gly Asn Phe Thr Ile Pro Met Asp Leu Met Thr Ile Asp
            180                 185                 190
Ser Thr Glu His Tyr Ser Gly Tyr Pro Ile Leu Thr Trp Ile Ser Ser
        195                 200                 205
Pro Asp Asn Ser Tyr Ser Gly Arg Phe Met Ser Trp Tyr Phe Ala Asn
        210                 215                 220
Trp Pro Asn Leu Pro Ser Gly Phe Gly Pro Leu Asn Ser Asp Asn Thr
225                 230                 235                 240
Val Thr Tyr Thr Gly Ser Val Val Ser Gln Val Ser Ala Gly Val Tyr
                245                 250                 255
Ala Thr Val Arg Phe Asp Gln Tyr Asp Ile His Asn Leu Arg Thr Ile
            260                 265                 270
Glu Lys Thr Trp Tyr Ala Arg His Ala Thr Leu His Asn Gly Lys Lys
        275                 280                 285
Ile Ser Ile Asn Asn Val Thr Glu Met Ala Pro Thr Ser Pro Ile Lys
        290                 295                 300
Thr Asn
305
```

<210> SEQ ID NO 29
<211> LENGTH: 918
<212> TYPE: DNA
<213> ORGANISM: Artificial Sequence
<220> FEATURE:
<223> OTHER INFORMATION: engineered
<220> FEATURE:
<221> NAME/KEY: misc_feature
<223> OTHER INFORMATION: A nucleotide sequence encoding SEQ ID NO: 30
      with an open reading frame from 1 to 918.

<400> SEQUENCE: 29

```
atggctatcc tagaccttaa gtccctcgtg ctgaacgcca ttaactactg gggccctaag      60
aacaacaacg gcatccaggg cggtgacttc ggctacccca tctctgagaa gcagatcgac     120
actagcatca ttacctccac ccaccctcgc ttgatccccc acgatcttac tatcccgcag     180
aaccttgaga ccatcttcac cacaacgcag gtgctcacca taacactga cctccagcaa     240
tcccagaccg tgagctttgc gaagaagacc actaccacga ccgcaactag cacgaccaac     300
ggttggacag aaggaggcaa gatcagcgac acgctggagg agaaagtttc ggttagcatt     360
ccgttcatcg gtgagggtgg cgggaagaac tcgactacca tagaggccaa cttcgcacac     420
aactctagca ccactaccgc ccagcaagca agcactgaca ttgagtggaa cattagccaa     480
ccggtccttg tgcctccccg caaacaggtt gttgccactc tcgttatcat gggtggcaac     540
ttcactattc ctatggatct tatgactacc attgactcta ctgagcacta ctctggctac     600
cccattctca cttggatctc ttctcctgac aatagctaca gcggtcgatt catgtcatgg     660
tacttcgcta actggccgaa tctccccttct ggctttggtc ctcttaactc tgataacact     720
gtgacctaca ctggctctgt cgccagtcag gtctctgccg gtgtgtacgc aactgttcgc     780
ttcgatcagt atgacatcca taatctcagg actattgaga gacctggta cgctcgtcat     840
gcgacgcttc acaacggcaa gaagatcagc atcaataacg tgacagaaat ggcccctacc     900
agcccgatca gactaac                                                   918
```

<210> SEQ ID NO 30
<211> LENGTH: 306
<212> TYPE: PRT
<213> ORGANISM: Artificial Sequence
<220> FEATURE:

<223> OTHER INFORMATION: engineered
<220> FEATURE:
<221> NAME/KEY: MISC_FEATURE
<223> OTHER INFORMATION: TIC807M10
<220> FEATURE:
<221> NAME/KEY: misc_feature
<223> OTHER INFORMATION: The amino acid sequence translation of the open
      reading frame set forth as SEQ ID NO: 29.

<400> SEQUENCE: 30

Met Ala Ile Leu Asp Leu Lys Ser Leu Val Leu Asn Ala Ile Asn Tyr
1               5                   10                  15

Trp Gly Pro Lys Asn Asn Asn Gly Ile Gln Gly Gly Asp Phe Gly Tyr
            20                  25                  30

Pro Ile Ser Glu Lys Gln Ile Asp Thr Ser Ile Ile Thr Ser Thr His
        35                  40                  45

Pro Arg Leu Ile Pro His Asp Leu Thr Ile Pro Gln Asn Leu Glu Thr
    50                  55                  60

Ile Phe Thr Thr Thr Gln Val Leu Thr Asn Asn Thr Asp Leu Gln Gln
65                  70                  75                  80

Ser Gln Thr Val Ser Phe Ala Lys Lys Thr Thr Thr Thr Ala Thr
                85                  90                  95

Ser Thr Thr Asn Gly Trp Thr Glu Gly Gly Lys Ile Ser Asp Thr Leu
            100                 105                 110

Glu Glu Lys Val Ser Val Ser Ile Pro Phe Ile Gly Glu Gly Gly Gly
        115                 120                 125

Lys Asn Ser Thr Thr Ile Glu Ala Asn Phe Ala His Asn Ser Ser Thr
    130                 135                 140

Thr Thr Ala Gln Gln Ala Ser Thr Asp Ile Glu Trp Asn Ile Ser Gln
145                 150                 155                 160

Pro Val Leu Val Pro Arg Lys Gln Val Ala Thr Leu Val Ile
                165                 170                 175

Met Gly Gly Asn Phe Thr Ile Pro Met Asp Leu Met Thr Thr Ile Asp
            180                 185                 190

Ser Thr Glu His Tyr Ser Gly Tyr Pro Ile Leu Thr Trp Ile Ser Ser
        195                 200                 205

Pro Asp Asn Ser Tyr Ser Gly Arg Phe Met Ser Trp Tyr Phe Ala Asn
    210                 215                 220

Trp Pro Asn Leu Pro Ser Gly Phe Gly Pro Leu Asn Ser Asp Asn Thr
225                 230                 235                 240

Val Thr Tyr Thr Gly Ser Val Ala Ser Gln Val Ser Ala Gly Val Tyr
                245                 250                 255

Ala Thr Val Arg Phe Asp Gln Tyr Asp Ile His Asn Leu Arg Thr Ile
            260                 265                 270

Glu Lys Thr Trp Tyr Ala Arg His Ala Thr Leu His Asn Gly Lys Lys
        275                 280                 285

Ile Ser Ile Asn Asn Val Thr Glu Met Ala Pro Thr Ser Pro Ile Lys
    290                 295                 300

Thr Asn
305

<210> SEQ ID NO 31
<211> LENGTH: 918
<212> TYPE: DNA
<213> ORGANISM: Artificial Sequence
<220> FEATURE:
<223> OTHER INFORMATION: engineered
<220> FEATURE:

```
<221> NAME/KEY: misc_feature
<223> OTHER INFORMATION: A nucleotide sequence encoding SEQ ID NO: 32
      with an open reading frame from 1 to 918.

<400> SEQUENCE: 31
atggctatcc tagaccttaa gtccctcgtg ctgaacgcca ttaactactg gggccctaag      60
aacaacaacg gcatccaggg cggtgacttc ggctacccca tctctgagaa gcagatcgac     120
actagcatca ttacctccac ccaccctcgc ttgatccccc acgatcttac tatcccgcag     180
aaccttgaga ccatcttcac cacaacgcag gtgctcacca ataacactga cctccagcaa     240
tcccagaccg tgagctttgc gaagaagacc actaccacga ccgcaactag cacgaccaac     300
ggttggacag aaggaggcaa gatcagcgac acgctggagg agaaagtttc ggttagcatt     360
ccgttcatcg gtgagggtgg cgggaagaac tcgactacca tagaggccaa cttcgcacac     420
aactctagca ccactaccgc ccagcaagca agcactgaca ttgagtggaa cattagccaa     480
ccggtccttg tgcctccccg caaacaggtt gttgccactc tcgttatcat gggtggcaac     540
ttcactattc ctatggatct tatgactacc attgactcta ctgagcacta ctctggctac     600
cccattctca cttggatctc ttctcctgac aatagctaca gcggtcgatt catgtcatgg     660
tacttcgcta actggccgaa tctcccttct ggctttggtc ctcttaactc tgataacact     720
gtgacctaca ctggctctgt cgtcagtcag gtctctgccg gtgtgtacgc aactgttcgc     780
ttcgatcagt atgacatcca taatctctgg actattgaga gacctggta cgctcgtcat     840 gcgacgcttc acaacggcaa gaagatcagc atcaataacg tgacagaaat ggcccctacc     900
agcccgatca agactaac                                                   918

<210> SEQ ID NO 32
<211> LENGTH: 306
<212> TYPE: PRT
<213> ORGANISM: Artificial Sequence
<220> FEATURE:
<223> OTHER INFORMATION: engineered
<220> FEATURE:
<221> NAME/KEY: misc_feature
<223> OTHER INFORMATION: The amino acid sequence translation of the open
      reading frame set forth as SEQ ID NO: 31.

<400> SEQUENCE: 32

Met Ala Ile Leu Asp Leu Lys Ser Leu Val Leu Asn Ala Ile Asn Tyr
 1               5                  10                  15

Trp Gly Pro Lys Asn Asn Asn Gly Ile Gln Gly Gly Asp Phe Gly Tyr
            20                  25                  30

Pro Ile Ser Glu Lys Gln Ile Asp Thr Ser Ile Ile Thr Ser Thr His
        35                  40                  45

Pro Arg Leu Ile Pro His Asp Leu Thr Ile Pro Gln Asn Leu Glu Thr
    50                  55                  60

Ile Phe Thr Thr Thr Gln Val Leu Thr Asn Asn Thr Asp Leu Gln Gln
65                  70                  75                  80

Ser Gln Thr Val Ser Phe Ala Lys Lys Thr Thr Thr Thr Ala Thr
            85                  90                  95

Ser Thr Thr Asn Gly Trp Thr Glu Gly Gly Lys Ile Ser Asp Thr Leu
        100                 105                 110

Glu Glu Lys Val Ser Val Ser Ile Pro Phe Ile Gly Glu Gly Gly Gly
    115                 120                 125

Lys Asn Ser Thr Thr Ile Glu Ala Asn Phe Ala His Asn Ser Ser Thr
130                 135                 140
```

```
Thr Thr Ala Gln Gln Ala Ser Thr Asp Ile Glu Trp Asn Ile Ser Gln
145                 150                 155                 160

Pro Val Leu Val Pro Pro Arg Lys Gln Val Val Ala Thr Leu Val Ile
                165                 170                 175

Met Gly Gly Asn Phe Thr Ile Pro Met Asp Leu Met Thr Thr Ile Asp
            180                 185                 190

Ser Thr Glu His Tyr Ser Gly Tyr Pro Ile Leu Thr Trp Ile Ser Ser
        195                 200                 205

Pro Asp Asn Ser Tyr Ser Gly Arg Phe Met Ser Trp Tyr Phe Ala Asn
    210                 215                 220

Trp Pro Asn Leu Pro Ser Gly Phe Gly Pro Leu Asn Ser Asp Asn Thr
225                 230                 235                 240

Val Thr Tyr Thr Gly Ser Val Val Ser Gln Val Ser Ala Gly Val Tyr
                245                 250                 255

Ala Thr Val Arg Phe Asp Gln Tyr Asp Ile His Asn Leu Trp Thr Ile
                260                 265                 270

Glu Lys Thr Trp Tyr Ala Arg His Ala Thr Leu His Asn Gly Lys Lys
            275                 280                 285

Ile Ser Ile Asn Asn Val Thr Glu Met Ala Pro Thr Ser Pro Ile Lys
    290                 295                 300

Thr Asn
305

<210> SEQ ID NO 33
<211> LENGTH: 918
<212> TYPE: DNA
<213> ORGANISM: Artificial Sequence
<220> FEATURE:
<223> OTHER INFORMATION: engineered
<220> FEATURE:
<221> NAME/KEY: misc_feature
<223> OTHER INFORMATION: A nucleotide sequence encoding SEQ ID NO: 34
      with an open reading frame from 1 to 918.

<400> SEQUENCE: 33
atggctatcc tagaccttaa gtccctcgtg ctgaacgcca ttaactactg gggccctaag      60
aacaacaacg gcatccaggg cggtgacttc ggctacccca tctctgagaa gcagatcgac     120
actagcatca ttacctccac ccaccctcgc ttgatccccc acgatcttac tatcccgcag     180
aaccttgaga ccatcttcac cacaacgcag gtgctcacca ataacactga cctccagcaa     240
tcccagaccg tgagctttgc gaagaagacc actaccacga ccgcaactag cacgaccaac     300
ggttggacag aaggaggcaa gatcagcgac acgctgaggg agaaagtttc ggttagcatt     360
ccgttcatcg gtgagggtgg cgggaagaac tcgactacca tagaggccaa cttcgcacac     420
aactctagca ccactaccct ccaggaagca agcactgaca ttgagtggaa cattagccaa     480
ccggtccttg tgcctccccg caaacaggtt gttgccactc tcgttatcat gggtggcaac     540
ttcactattc ctatggatct tatgactacc attgactcta ctgagcacta ctctggctac     600
cccattctca cttggatctc ttctcctgac aatagctaca gcggtcgatt catgtcatgg     660
tacttcgcta actggccgaa tctcccttct ggctttggtc ctcttaactc tgataacact     720
gtgacctaca ctggctctgt cgtcagtcag gtctctgccg gtgtgtacgc aactgttcgc     780
ttcgatcagt atgacatcca taatctctgg actattgaga gacctggta cgctcgtcat     840 gcgacgcttc acaacggcaa gaagatcagc atcaataacg tgacagaaat ggcccctacc     900
agcccgatca agactaac                                                  918
```

```
<210> SEQ ID NO 34
<211> LENGTH: 306
<212> TYPE: PRT
<213> ORGANISM: Artificial Sequence
<220> FEATURE:
<223> OTHER INFORMATION: engineered
<220> FEATURE:
<221> NAME/KEY: misc_feature
<223> OTHER INFORMATION: TIC807M13
<220> FEATURE:
<221> NAME/KEY: misc_feature
<223> OTHER INFORMATION: The amino acid sequence translation of the open
      reading frame set forth as SEQ ID NO: 33.

<400> SEQUENCE: 34

Met Ala Ile Leu Asp Leu Lys Ser Leu Val Leu Asn Ala Ile Asn Tyr
1               5                   10                  15

Trp Gly Pro Lys Asn Asn Asn Gly Ile Gln Gly Gly Asp Phe Gly Tyr
            20                  25                  30

Pro Ile Ser Glu Lys Gln Ile Asp Thr Ser Ile Ile Thr Ser Thr His
        35                  40                  45

Pro Arg Leu Ile Pro His Asp Leu Thr Ile Pro Gln Asn Leu Glu Thr
    50                  55                  60

Ile Phe Thr Thr Thr Gln Val Leu Thr Asn Asn Thr Asp Leu Gln Gln
65                  70                  75                  80

Ser Gln Thr Val Ser Phe Ala Lys Lys Thr Thr Thr Thr Thr Ala Thr
                85                  90                  95

Ser Thr Thr Asn Gly Trp Thr Glu Gly Gly Lys Ile Ser Asp Thr Leu
            100                 105                 110

Glu Glu Lys Val Ser Val Ser Ile Pro Phe Ile Gly Glu Gly Gly Gly
        115                 120                 125

Lys Asn Ser Thr Thr Ile Glu Ala Asn Phe Ala His Asn Ser Ser Thr
    130                 135                 140

Thr Thr Ser Gln Glu Ala Ser Thr Asp Ile Glu Trp Asn Ile Ser Gln
145                 150                 155                 160

Pro Val Leu Val Pro Pro Arg Lys Gln Val Val Ala Thr Leu Val Ile
                165                 170                 175

Met Gly Gly Asn Phe Thr Ile Pro Met Asp Leu Met Thr Thr Ile Asp
            180                 185                 190

Ser Thr Glu His Tyr Ser Gly Tyr Pro Ile Leu Thr Trp Ile Ser Ser
        195                 200                 205

Pro Asp Asn Ser Tyr Ser Gly Arg Phe Met Ser Trp Tyr Phe Ala Asn
    210                 215                 220

Trp Pro Asn Leu Pro Ser Gly Phe Gly Pro Leu Asn Ser Asp Asn Thr
225                 230                 235                 240

Val Thr Tyr Thr Gly Ser Val Val Ser Gln Val Ser Ala Gly Val Tyr
                245                 250                 255

Ala Thr Val Arg Phe Asp Gln Tyr Asp Ile His Asn Leu Trp Thr Ile
            260                 265                 270

Glu Lys Thr Trp Tyr Ala Arg His Ala Thr Leu His Asn Gly Lys Lys
        275                 280                 285

Ile Ser Ile Asn Asn Val Thr Glu Met Ala Pro Thr Ser Pro Ile Lys
    290                 295                 300

Thr Asn
305

<210> SEQ ID NO 35
```

<211> LENGTH: 918
<212> TYPE: DNA
<213> ORGANISM: Artificial Sequence
<220> FEATURE:
<223> OTHER INFORMATION: engineered
<220> FEATURE:
<221> NAME/KEY: misc_feature
<223> OTHER INFORMATION: A nucleotide sequence encoding SEQ ID NO: 36 with an open reading frame from 1 to 918.

<400> SEQUENCE: 35

```
atggctatcc tagaccttaa gtccctcgtg ctgaacgcca ttaactactg gggccctaag      60
aacaacaacg gcatccaggg cggtgacttc ggctacccca tctctgagaa gcagatcgac     120
actagcatca ttacctccac ccaccctcgc ttgatccccc acgatcttac tatcccgcag     180
aaccttgaga ccatcttcac cacaacgcag gtgctcacca ataacactga cctccagcaa     240
tcccagaccg tgagctttgc gaagaagacc actaccacga ccgcaactag cacgaccaac     300
ggttggacag aaggaggcaa gatcagcgac acgctggagg agaaagtttc ggttagcatt     360
ccgttcatcg gtgagggtgg cgggaagaac tcgactacca tagaggccaa cttcgcacac     420
aactctagca ccactaccgc ccagcaagca agcactgaca ttgagtggaa cattagccaa     480
ccggtccttg tgcctccccg caaacaggtt gttgccactc tcgttatcat gggtggcaac     540
ttcactattc ctatggatct tatgactacc attgactcta ctgagcacta ctctggctac     600
cccattctca cttggatctc ttctcctgac aatagctaca gcggtcgatt catgtcatgg     660
tacttcgcta actggccgaa tctcccttct ggctttggtc ctcttgcctc tgataacact     720
gtgacctaca ctggctctgt cgccagtcag gtctctgccg gtgtgtacgc aactgttcgc     780
ttcgatcagt atgacatcca taatctcagg actattgaga agacctggta cgctcgtcat     840
gcgacgcttc acaacggcaa gaagatcagc atcaataacg tgacagaaat ggcccctacc     900
agcccgatca agactaac                                                   918
```

<210> SEQ ID NO 36
<211> LENGTH: 306
<212> TYPE: PRT
<213> ORGANISM: Artificial Sequence
<220> FEATURE:
<223> OTHER INFORMATION: engineered
<220> FEATURE:
<221> NAME/KEY: misc_feature
<223> OTHER INFORMATION: The amino acid sequence translation of the open reading frame set forth as SEQ ID NO: 35.

<400> SEQUENCE: 36

```
Met Ala Ile Leu Asp Leu Lys Ser Leu Val Leu Asn Ala Ile Asn Tyr
1               5                   10                  15

Trp Gly Pro Lys Asn Asn Asn Gly Ile Gln Gly Gly Asp Phe Gly Tyr
            20                  25                  30

Pro Ile Ser Glu Lys Gln Ile Asp Thr Ser Ile Ile Thr Ser Thr His
        35                  40                  45

Pro Arg Leu Ile Pro His Asp Leu Thr Ile Pro Gln Asn Leu Glu Thr
    50                  55                  60

Ile Phe Thr Thr Thr Gln Val Leu Thr Asn Asn Thr Asp Leu Gln Gln
65                  70                  75                  80

Ser Gln Thr Val Ser Phe Ala Lys Lys Thr Thr Thr Thr Ala Thr
            85                  90                  95

Ser Thr Thr Asn Gly Trp Thr Glu Gly Gly Lys Ile Ser Asp Thr Leu
            100                 105                 110
```

Glu Glu Lys Val Ser Val Ser Ile Pro Phe Ile Gly Glu Gly Gly
            115                 120                 125

Lys Asn Ser Thr Thr Ile Glu Ala Asn Phe Ala His Asn Ser Ser Thr
    130                 135                 140

Thr Thr Ala Gln Gln Ala Ser Thr Asp Ile Glu Trp Asn Ile Ser Gln
145                 150                 155                 160

Pro Val Leu Val Pro Pro Arg Lys Gln Val Val Ala Thr Leu Val Ile
                165                 170                 175

Met Gly Gly Asn Phe Thr Ile Pro Met Asp Leu Met Thr Thr Ile Asp
            180                 185                 190

Ser Thr Glu His Tyr Ser Gly Tyr Pro Ile Leu Thr Trp Ile Ser Ser
    195                 200                 205

Pro Asp Asn Ser Tyr Ser Gly Arg Phe Met Ser Trp Tyr Phe Ala Asn
    210                 215                 220

Trp Pro Asn Leu Pro Ser Gly Phe Gly Pro Leu Ala Ser Asp Asn Thr
225                 230                 235                 240

Val Thr Tyr Thr Gly Ser Val Ala Ser Gln Val Ser Ala Gly Val Tyr
                245                 250                 255

Ala Thr Val Arg Phe Asp Gln Tyr Asp Ile His Asn Leu Arg Thr Ile
            260                 265                 270

Glu Lys Thr Trp Tyr Ala Arg His Ala Thr Leu His Asn Gly Lys Lys
    275                 280                 285

Ile Ser Ile Asn Asn Val Thr Glu Met Ala Pro Thr Ser Pro Ile Lys
    290                 295                 300

Thr Asn
305

<210> SEQ ID NO 37
<211> LENGTH: 306
<212> TYPE: PRT
<213> ORGANISM: Artificial Sequence
<220> FEATURE:
<223> OTHER INFORMATION: engineered

<400> SEQUENCE: 37

Met Ala Ile Leu Asp Leu Lys Ser Leu Val Leu Asn Ala Ile Asn Tyr
1               5                   10                  15

Trp Gly Pro Lys Asn Asn Gly Ile Gln Gly Gly Asp Phe Gly Tyr
            20                  25                  30

Pro Ile Ser Glu Lys Gln Ile Asp Thr Ser Ile Ile Thr Phe Thr His
            35                  40                  45

Pro Arg Leu Ile Pro Tyr Asp Leu Thr Ile Pro Gln Asn Leu Glu Thr
    50                  55                  60

Ile Phe Thr Thr Thr Gln Val Leu Thr Asn Asn Thr Asp Leu Gln Gln
65                  70                  75                  80

Ser Gln Thr Val Ser Phe Ala Lys Lys Thr Thr Thr Thr Ser Thr
                85                  90                  95

Ser Thr Thr Asn Gly Trp Thr Glu Gly Gly Lys Ile Ser Asp Thr Leu
            100                 105                 110

Glu Glu Lys Val Ser Val Ser Ile Pro Phe Ile Gly Glu Gly Gly
            115                 120                 125

Lys Asn Ser Thr Thr Ile Glu Ala Asn Phe Ala His Asn Ser Ser Thr
    130                 135                 140

Thr Thr Phe Gln Gln Ala Ser Thr Asp Ile Glu Trp Asn Ile Ser Gln
145                 150                 155                 160

```
Pro Val Leu Val Pro Pro Ser Lys Gln Val Ala Thr Leu Val Ile
            165                 170                 175

Met Gly Gly Asn Phe Thr Ile Pro Met Asp Leu Met Thr Ile Asp
            180                 185                 190

Ser Thr Glu His Tyr Ser Gly Tyr Pro Ile Leu Thr Trp Ile Ser Ser
            195                 200                 205

Pro Asp Asn Ser Tyr Ser Gly Pro Phe Met Ser Trp Tyr Phe Ala Asn
            210                 215                 220

Trp Pro Asn Leu Pro Ser Gly Phe Gly Pro Leu Asn Ser Asp Asn Thr
225                 230                 235                 240

Val Thr Tyr Thr Gly Ser Val Val Ser Gln Val Ser Ala Gly Val Tyr
            245                 250                 255

Ala Thr Val Arg Phe Asp Gln Tyr Asp Ile His Asn Leu Arg Thr Ile
            260                 265                 270

Glu Lys Thr Trp Tyr Ala Arg His Ala Thr Leu His Asn Gly Lys Lys
            275                 280                 285

Ile Ser Ile Asn Asn Val Thr Glu Met Ala Pro Thr Ser Pro Ile Lys
            290                 295                 300

Thr Asn
305

<210> SEQ ID NO 38
<211> LENGTH: 306
<212> TYPE: PRT
<213> ORGANISM: Artificial Sequence
<220> FEATURE:
<223> OTHER INFORMATION: engineered

<400> SEQUENCE: 38

Met Ala Ile Leu Asp Leu Lys Ser Leu Val Leu Asn Ala Ile Asn Tyr
1               5                   10                  15

Trp Gly Pro Lys Asn Asn Gly Ile Gln Gly Gly Asp Phe Gly Tyr
            20                  25                  30

Pro Ile Ser Glu Lys Gln Ile Asp Thr Ser Ile Ile Thr Ser Thr His
            35                  40                  45

Pro Arg Leu Ile Pro His Asp Leu Thr Ile Pro Gln Asn Leu Glu Thr
        50                  55                  60

Ile Phe Thr Thr Thr Gln Val Leu Thr Asn Asn Thr Asp Leu Gln Gln
65                  70                  75                  80

Ser Gln Thr Val Ser Phe Ala Lys Lys Thr Thr Thr Thr Ser Thr
                85                  90                  95

Ser Thr Thr Asn Gly Trp Thr Glu Gly Gly Lys Ile Ser Asp Thr Leu
            100                 105                 110

Glu Glu Lys Val Ser Val Ser Ile Pro Phe Ile Gly Glu Gly Gly Gly
            115                 120                 125

Lys Asn Ser Thr Thr Ile Glu Ala Asn Val Ala His Asn Ser Ser Thr
130                 135                 140

Thr Thr Phe Gln Gln Ala Ser Thr Asp Ile Glu Trp Asn Ile Ser Gln
145                 150                 155                 160

Pro Val Leu Val Pro Arg Lys Gln Val Ala Thr Leu Val Ile
            165                 170                 175

Met Gly Gly Asn Phe Thr Ile Pro Met Asp Leu Met Thr Ile Asp
            180                 185                 190

Ser Thr Glu His Tyr Ser Gly Tyr Pro Ile Leu Thr Trp Ile Ser Ser
            195                 200                 205
```

```
Pro Asp Asn Ser Tyr Asn Gly Pro Phe Met Ser Trp Tyr Phe Ala Asn
    210                 215                 220

Trp Pro Asn Leu Pro Ser Gly Phe Gly Pro Leu Asn Ser Asp Asn Thr
225                 230                 235                 240

Val Thr Tyr Thr Gly Ser Val Val Ser Gln Val Ser Ala Gly Val Tyr
                245                 250                 255

Ala Thr Val Arg Phe Asp Gln Tyr Asp Ile His Asn Leu Arg Thr Ile
            260                 265                 270

Glu Lys Thr Trp Tyr Ala Arg His Ala Thr Leu His Asn Gly Lys Lys
        275                 280                 285

Ile Ser Ile Asn Asn Val Thr Glu Met Ala Pro Thr Ser Pro Ile Lys
    290                 295                 300

Thr Asn
305

<210> SEQ ID NO 39
<211> LENGTH: 306
<212> TYPE: PRT
<213> ORGANISM: Artificial Sequence
<220> FEATURE:
<223> OTHER INFORMATION: engineered

<400> SEQUENCE: 39

Met Ala Ile Leu Asp Leu Lys Ser Leu Val Leu Asn Ala Ile Asn Tyr
1               5                   10                  15

Trp Gly Pro Lys Asn Asn Gly Ile Gln Gly Gly Asp Phe Gly Tyr
                20                  25                  30

Pro Ile Ser Glu Lys Gln Ile Asp Thr Ser Ile Ile Thr Ser Thr His
            35                  40                  45

Pro Arg Leu Ile Pro His Asp Leu Thr Ile Pro Gln Asn Leu Glu Thr
        50                  55                  60

Ile Phe Thr Thr Thr Gln Val Leu Thr Asn Asn Thr Asp Leu Gln Gln
65                  70                  75                  80

Ser Gln Thr Val Ser Phe Ala Lys Lys Thr Thr Thr Thr Ser Thr
                85                  90                  95

Ser Thr Thr Asn Gly Trp Thr Glu Gly Gly Lys Ile Ser Asp Thr Leu
                100                 105                 110

Glu Glu Lys Val Ser Val Ser Ile Pro Phe Ile Gly Glu Gly Gly Gly
            115                 120                 125

Lys Asn Ser Thr Thr Ile Glu Ala Asn Phe Ala His Asn Ser Ser Thr
        130                 135                 140

Thr Thr Phe Gln Gln Ala Ser Thr Asp Ile Glu Trp Asn Ile Ser Gln
145                 150                 155                 160

Pro Val Leu Val Pro Pro Arg Lys Gln Val Val Ala Thr Leu Val Ile
                165                 170                 175

Met Gly Gly Asn Phe Thr Ile Pro Met Asp Leu Met Thr Thr Ile Asp
            180                 185                 190

Ser Thr Glu His Tyr Ser Gly Tyr Pro Ile Leu Thr Trp Ile Ser Ser
        195                 200                 205

Pro Asp Asn Ser Tyr Asn Gly Pro Phe Met Ser Trp Tyr Phe Ala Asn
    210                 215                 220

Trp Pro Asn Leu Pro Ser Gly Phe Gly Pro Leu Asn Ser Asp Asn Thr
225                 230                 235                 240

Val Thr Tyr Thr Gly Ser Val Val Ser Gln Val Ser Ala Gly Val Tyr
                245                 250                 255
```

-continued

```
Ala Thr Val Arg Phe Asp Gln Tyr Asp Ile His Asn Leu Arg Thr Ile
            260                 265                 270

Glu Lys Thr Trp Tyr Ala Arg His Ala Thr Leu Phe Asn Gly Lys Lys
        275                 280                 285

Ile Ser Ile Asn Asn Val Thr Glu Met Ala Pro Thr Ser Pro Ile Lys
    290                 295                 300

Thr Asn
305

<210> SEQ ID NO 40
<211> LENGTH: 306
<212> TYPE: PRT
<213> ORGANISM: Artificial Sequence
<220> FEATURE:
<223> OTHER INFORMATION: engineered

<400> SEQUENCE: 40

Met Ala Ile Leu Asp Leu Lys Ser Leu Val Leu Asn Ala Ile Asn Tyr
1               5                   10                  15

Trp Gly Pro Lys Asn Asn Gly Ile Gln Gly Gly Asp Phe Gly Tyr
            20                  25                  30

Pro Ile Ser Glu Lys Gln Ile Asp Thr Ser Ile Thr Ser Thr His
        35                  40                  45

Pro Arg Leu Met Pro His Asp Leu Thr Ile Pro Gln Asn Leu Glu Thr
    50                  55                  60

Ile Phe Thr Thr Thr Gln Val Leu Thr Asn Asn Thr Asp Leu Gln Gln
65                  70                  75                  80

Ser Gln Thr Val Ser Phe Ala Lys Lys Thr Thr Thr Thr Ser Thr
                85                  90                  95

Ser Thr Thr Asn Gly Trp Thr Glu Gly Gly Lys Ile Ser Asp Thr Leu
            100                 105                 110

Glu Glu Lys Val Ser Val Ser Ile Pro Phe Ile Gly Glu Gly Gly Gly
        115                 120                 125

Lys Asn Ser Thr Thr Ile Glu Ala Asn Phe Ala His Asn Ser Ser Thr
130                 135                 140

Thr Thr Phe Gln Gln Ala Ser Thr Asp Ile Glu Trp Asn Ile Ser Gln
145                 150                 155                 160

Pro Val Leu Val Pro Pro Arg Lys Gln Val Val Ala Thr Leu Val Ile
                165                 170                 175

Met Gly Gly Asn Phe Thr Ile Pro Met Asp Leu Met Thr Thr Ile Asp
            180                 185                 190

Ser Thr Glu His Tyr Ser Gly Tyr Pro Ile Leu Thr Trp Ile Ser Ser
        195                 200                 205

Pro Asp Asn Ser Tyr Asn Gly Pro Phe Met Ser Trp Tyr Phe Ala Asn
    210                 215                 220

Trp Pro Asn Leu Pro Ser Gly Phe Gly Pro Leu Asn Ser Asp Asn Thr
225                 230                 235                 240

Val Thr Tyr Thr Gly Ser Val Val Ser Gln Val Ser Ala Gly Val Tyr
                245                 250                 255

Ala Thr Val Arg Phe Asp Gln Tyr Asp Ile His Asn Leu Arg Thr Ile
            260                 265                 270

Glu Lys Thr Trp Tyr Ala Arg His Ala Thr Leu His Asn Gly Lys Lys
        275                 280                 285

Ile Ser Ile Asn Asn Val Thr Glu Met Ala Pro Thr Ser Pro Ile Lys
    290                 295                 300
```

Thr Asn
305

<210> SEQ ID NO 41
<211> LENGTH: 306
<212> TYPE: PRT
<213> ORGANISM: Artificial Sequence
<220> FEATURE:
<223> OTHER INFORMATION: engineered

<400> SEQUENCE: 41

Met Ala Ile Leu Asp Leu Lys Ser Leu Val Leu Asp Ala Ile Asn Tyr
1               5                   10                  15

Trp Gly Pro Lys Asn Asn Asn Gly Ile Gln Gly Gly Asp Phe Gly Tyr
            20                  25                  30

Pro Ile Ser Glu Lys Gln Ile Asp Thr Ser Ile Ile Thr Ser Thr His
        35                  40                  45

Pro Arg Leu Ile Pro His Asp Leu Thr Ile Pro Gln Asn Leu Glu Thr
    50                  55                  60

Ile Phe Thr Thr Thr Gln Val Leu Thr Asn Asn Thr Asp Leu Gln Gln
65                  70                  75                  80

Ser Gln Thr Val Ser Phe Ala Lys Lys Thr Thr Thr Thr Thr Ser Thr
                85                  90                  95

Ser Thr Thr Asn Gly Trp Thr Glu Gly Gly Lys Ile Ser Asp Thr Leu
            100                 105                 110

Glu Glu Lys Val Ser Val Ser Ile Pro Phe Ile Gly Glu Gly Gly Gly
        115                 120                 125

Lys Asn Ser Thr Thr Ile Glu Ala Asn Phe Ala His Asn Ser Ser Thr
    130                 135                 140

Thr Thr Phe Gln Gln Ala Ser Thr Asp Ile Glu Trp Asn Ile Ser Gln
145                 150                 155                 160

Pro Val Leu Val Pro Pro Arg Lys Gln Val Val Ala Thr Leu Val Ile
                165                 170                 175

Met Gly Gly Asn Phe Thr Ile Pro Met Asp Leu Met Thr Thr Ile Asp
            180                 185                 190

Ser Thr Glu His Tyr Ser Gly Tyr Pro Ile Leu Thr Trp Ile Ser Ser
        195                 200                 205

Pro Asp Asn Ser Tyr Asn Gly Pro Phe Met Ser Trp Tyr Phe Ala Asn
    210                 215                 220

Trp Pro Asn Leu Pro Ser Gly Phe Gly Pro Leu Asn Ser Asp Asn Thr
225                 230                 235                 240

Val Thr Tyr Thr Gly Ser Val Val Ser Gln Val Ser Ala Gly Val Tyr
                245                 250                 255

Ala Thr Val Arg Phe Asp Gln Tyr Asp Ile His Asn Leu Arg Thr Ile
            260                 265                 270

Glu Lys Thr Trp Tyr Ala Arg His Ala Thr Leu His Asn Gly Lys Lys
        275                 280                 285

Ile Ser Ile Asn Asn Val Thr Glu Met Ala Pro Thr Ser Pro Ile Lys
    290                 295                 300

Thr Asn
305

<210> SEQ ID NO 42
<211> LENGTH: 306
<212> TYPE: PRT
<213> ORGANISM: Artificial Sequence
<220> FEATURE:

<223> OTHER INFORMATION: engineered

<400> SEQUENCE: 42

Met Ala Ile Leu Asp Leu Lys Ser Leu Val Leu Asn Ala Ile Asn Tyr
1               5                   10                  15

Trp Gly Pro Lys Asn Asn Asn Gly Ile Gln Gly Gly Asp Phe Gly Tyr
            20                  25                  30

Pro Ile Ser Glu Lys Gln Ile Asp Thr Ser Ile Ile Thr Ser Thr His
        35                  40                  45

Pro Arg Leu Ile Pro His Asp Leu Thr Ile Pro Gln Asn Leu Glu Thr
    50                  55                  60

Ile Phe Thr Thr Thr Gln Val Leu Thr Asn Asn Thr Asp Leu Gln Gln
65                  70                  75                  80

Ser Gln Thr Val Ser Phe Ala Lys Lys Thr Thr Thr Thr Thr Ser Thr
                85                  90                  95

Ser Thr Thr Asn Gly Trp Thr Glu Gly Gly Lys Ile Ser Asp Thr Leu
            100                 105                 110

Glu Glu Lys Val Ser Val Ser Ile Pro Phe Ile Gly Glu Gly Gly Gly
        115                 120                 125

Lys Asn Ser Thr Thr Ile Glu Ala Asn Phe Ala His Asn Ser Ser Thr
    130                 135                 140

Thr Thr Phe Gln Gln Ala Ser Thr Asp Ile Glu Trp Asn Ile Ser Gln
145                 150                 155                 160

Pro Val Leu Val Pro Pro Arg Lys Gln Val Val Ala Thr Leu Val Ile
                165                 170                 175

Met Gly Gly Asp Phe Thr Ile Pro Met Asp Leu Met Thr Thr Ile Asp
            180                 185                 190

Ser Thr Glu His Tyr Ser Gly Tyr Pro Ile Leu Thr Trp Ile Ser Ser
        195                 200                 205

Pro Asp Asn Ser Tyr Asn Gly Pro Phe Met Ser Trp Tyr Phe Ala Asn
    210                 215                 220

Trp Pro Asn Leu Pro Ser Gly Phe Gly Pro Leu Asn Ser Asp Asn Thr
225                 230                 235                 240

Val Thr Tyr Thr Gly Ser Val Val Ser Gln Val Ser Ala Gly Val Tyr
                245                 250                 255

Ala Thr Val Arg Phe Asp Gln Tyr Asp Ile His Asn Leu Arg Thr Ile
            260                 265                 270

Glu Lys Thr Trp Tyr Ala Arg His Ala Thr Leu His Asn Gly Lys Lys
        275                 280                 285

Ile Ser Ile Asn Asn Val Thr Glu Met Ala Pro Thr Ser Pro Ile Lys
    290                 295                 300

Thr Asn
305

<210> SEQ ID NO 43
<211> LENGTH: 306
<212> TYPE: PRT
<213> ORGANISM: Artificial Sequence
<220> FEATURE:
<223> OTHER INFORMATION: engineered

<400> SEQUENCE: 43

Met Ala Ile Leu Asp Leu Lys Ser Leu Val Leu Asn Ala Ile Asn Tyr
1               5                   10                  15

Trp Gly Pro Lys Asn Asn Asn Gly Ile Gln Gly Gly Asp Phe Gly Tyr
            20                  25                  30

Pro Ile Ser Glu Lys Gln Ile Asp Thr Ser Ile Ile Thr Ser Thr His
        35                  40                  45

Pro Arg Leu Ile Pro His Asp Leu Thr Ile Pro Gln Asn Leu Glu Thr
 50                  55                  60

Ile Phe Thr Thr Thr Gln Val Leu Thr Asn Asn Thr Asp Leu Gln Gln
 65                  70                  75                  80

Ser Gln Thr Val Ser Phe Ala Lys Lys Thr Thr Thr Thr Ser Thr
                85                  90                  95

Ser Thr Thr Asn Gly Trp Thr Glu Gly Gly Lys Ile Ser Asp Thr Leu
            100                 105                 110

Glu Glu Lys Val Ser Val Ser Ile Pro Phe Ile Gly Gly Gly Gly
        115                 120                 125

Lys Asn Ser Thr Thr Ile Glu Ala Asn Phe Ala His Asn Ser Ser Thr
        130                 135                 140

Thr Thr Phe Gln Gln Ala Ser Thr Asp Ile Glu Trp Asn Ile Ser Gln
145                 150                 155                 160

Pro Val Leu Val Pro Pro Arg Lys Gln Val Val Ala Thr Leu Val Ile
                165                 170                 175

Met Gly Gly Asn Phe Thr Ile Pro Met Asp Leu Met Thr Thr Ile Asp
            180                 185                 190

Ser Thr Glu His Tyr Ser Gly Tyr Pro Ile Leu Thr Trp Ile Ser Ser
        195                 200                 205

Pro Asp Asn Ser Tyr Ser Gly Pro Phe Met Ser Trp Tyr Phe Ala Asn
    210                 215                 220

Trp Pro Asn Leu Pro Ser Gly Phe Gly Pro Leu Asn Ser Asp Asn Thr
225                 230                 235                 240

Val Thr Tyr Thr Gly Ser Val Val Ser Gln Val Ser Ala Gly Val Tyr
                245                 250                 255

Ala Thr Val Arg Phe Asp Gln Tyr Asp Ile His Asn Leu Arg Thr Ile
            260                 265                 270

Glu Lys Thr Trp Tyr Ala Arg His Ala Thr Leu His Asn Gly Lys Lys
        275                 280                 285

Ile Ser Ile Asn Asn Val Thr Glu Met Ala Pro Thr Ser Pro Ile Lys
    290                 295                 300

Thr Asn
305

<210> SEQ ID NO 44
<211> LENGTH: 306
<212> TYPE: PRT
<213> ORGANISM: Artificial Sequence
<220> FEATURE:
<223> OTHER INFORMATION: engineered

<400> SEQUENCE: 44

Met Ala Ile Leu Asp Leu Lys Ser Leu Val Leu Asn Ala Ile Asn Tyr
 1               5                  10                  15

Trp Gly Pro Lys Asn Asn Asn Gly Ile Gln Gly Gly Asp Phe Gly Tyr
                20                  25                  30

Pro Ile Ser Glu Lys Gln Ile Asp Thr Ser Ile Ile Thr Ser Thr His
        35                  40                  45

Pro Arg Leu Ile Pro His Asp Leu Thr Ile Pro Gln Asn Leu Glu Thr
 50                  55                  60

Ile Phe Thr Thr Thr Gln Val Leu Thr Asn Asn Thr Asp Leu Gln Gln
 65                  70                  75                  80

```
Ser Gln Thr Val Ser Phe Ala Lys Lys Thr Thr Thr Thr Ser Thr
            85                  90                  95

Ser Thr Thr Asn Gly Trp Thr Glu Gly Gly Lys Ile Ser Asp Thr Leu
            100                 105                 110

Glu Glu Lys Val Ser Val Ser Ile Pro Phe Ile Gly Glu Gly Gly Gly
            115                 120                 125

Lys Asn Ser Thr Thr Ile Glu Ala Asn Phe Ala His Asn Ser Ser Thr
130                 135                 140

Thr Thr Phe Gln Gln Ala Ser Thr Asp Ile Glu Trp Asn Ile Ser Gln
145                 150                 155                 160

Pro Val Leu Val Pro Pro Arg Lys Gln Val Val Ala Thr Leu Val Ile
            165                 170                 175

Met Gly Gly Asn Phe Thr Ile Pro Met Asp Leu Met Thr Thr Ile Asp
            180                 185                 190

Ser Thr Glu His Tyr Ser Gly Tyr Pro Ile Leu Thr Trp Ile Ser Ser
            195                 200                 205

Pro Asp Asn Ser Tyr Asn Gly Arg Phe Met Ser Trp Tyr Phe Ala Asn
210                 215                 220

Trp Pro Asn Leu Pro Ser Gly Phe Gly Pro Leu Asn Ser Asp Asn Thr
225                 230                 235                 240

Val Thr Tyr Thr Gly Ser Val Val Ser Gln Val Ser Ala Gly Val Tyr
            245                 250                 255

Ala Thr Val Arg Phe Asp Gln Tyr Asp Ile His Asn Leu Arg Thr Ile
            260                 265                 270

Glu Lys Thr Trp Tyr Ala Arg His Ala Thr Leu His Asn Gly Lys Lys
            275                 280                 285

Ile Ser Ile Asn Asn Val Thr Glu Met Ala Pro Thr Ser Pro Ile Lys
            290                 295                 300

Thr Asn
305

<210> SEQ ID NO 45
<211> LENGTH: 306
<212> TYPE: PRT
<213> ORGANISM: Artificial Sequence
<220> FEATURE:
<223> OTHER INFORMATION: engineered

<400> SEQUENCE: 45

Met Ala Ile Leu Asp Leu Lys Ser Leu Val Leu Asn Ala Ile Asn Tyr
1               5                   10                  15

Trp Gly Pro Lys Asn Asn Gly Ile Gln Gly Gly Asp Phe Gly Tyr
            20                  25                  30

Pro Ile Ser Glu Lys Gln Ile Asp Thr Ser Ile Ile Thr Ser Thr His
            35                  40                  45

Pro Arg Leu Ile Pro His Asp Leu Thr Ile Pro Gln Asn Leu Glu Thr
            50                  55                  60

Ile Phe Thr Thr Thr Gln Val Leu Thr Asn Asn Thr Asp Leu Gln Gln
65                  70                  75                  80

Ser Gln Thr Val Ser Phe Ala Lys Lys Thr Thr Thr Thr Ser Thr
            85                  90                  95

Ser Thr Thr Asn Gly Trp Thr Glu Gly Gly Lys Ile Ser Asp Thr Leu
            100                 105                 110

Glu Glu Lys Val Ser Val Ser Ile Pro Phe Ile Gly Glu Gly Gly Gly
            115                 120                 125
```

```
Lys Asn Ser Thr Thr Ile Glu Ala Asn Phe Ala His Asn Ser Ser Thr
            130                 135                 140

Thr Thr Phe Gln Gln Ala Ser Thr Asp Ile Glu Trp Asn Ile Thr Gln
145                 150                 155                 160

Pro Val Leu Val Pro Pro Arg Lys Gln Val Val Ala Thr Leu Val Ile
                165                 170                 175

Met Gly Gly Asn Phe Thr Ile Pro Met Asp Leu Met Thr Thr Ile Asp
            180                 185                 190

Ser Thr Glu His Tyr Ser Gly Tyr Pro Ile Leu Thr Trp Ile Ser Ser
            195                 200                 205

Pro Asp Asn Ser Tyr Asn Gly Pro Phe Met Ser Trp Tyr Phe Ala Asn
            210                 215                 220

Trp Pro Asn Leu Pro Ser Gly Phe Gly Pro Leu Asn Ser Asp Asn Thr
225                 230                 235                 240

Val Thr Tyr Thr Gly Ser Val Val Ser Gln Val Ser Ala Gly Val Tyr
                245                 250                 255

Ala Thr Val Arg Phe Asp Gln Tyr Asp Ile His Asn Leu Arg Thr Ile
            260                 265                 270

Glu Lys Thr Trp Tyr Ala Arg His Ala Thr Leu His Asn Gly Lys Lys
            275                 280                 285

Ile Ser Ile Asn Asn Val Thr Glu Met Ala Pro Thr Ser Pro Ile Lys
290                 295                 300

Thr Asn
305

<210> SEQ ID NO 46
<211> LENGTH: 306
<212> TYPE: PRT
<213> ORGANISM: Artificial Sequence
<220> FEATURE:
<223> OTHER INFORMATION: engineered

<400> SEQUENCE: 46

Met Ala Ile Leu Asp Leu Lys Ser Leu Val Leu Asn Ala Ile Asn Tyr
1               5                   10                  15

Trp Gly Pro Lys Asn Asn Gly Ile Gln Gly Gly Asp Phe Gly Tyr
                20                  25                  30

Pro Ile Ser Glu Lys Gln Ile Asp Thr Ser Ile Ile Thr Ser Thr His
            35                  40                  45

Pro Arg Leu Ile Pro His Asp Leu Thr Ile Pro Gln Asn Leu Glu Thr
50                  55                  60

Ile Phe Thr Thr Thr Gln Val Leu Thr Asn Asn Thr Asp Leu Gln Gln
65                  70                  75                  80

Ser Gln Thr Val Ser Phe Ala Lys Lys Thr Thr Thr Thr Ser Thr
                85                  90                  95

Ser Thr Thr Asn Gly Trp Thr Glu Gly Gly Lys Ile Ser Asp Thr Leu
            100                 105                 110

Glu Glu Lys Val Ser Val Ser Ile Pro Phe Ile Gly Glu Gly Gly Gly
            115                 120                 125

Lys Asn Ser Thr Thr Ile Glu Ala Asn Phe Ala His Asn Ser Ser Thr
            130                 135                 140

Thr Thr Phe Gln Gln Ala Ser Thr Asp Ile Glu Trp Asn Ile Ser Gln
145                 150                 155                 160

Pro Val Leu Val Pro Pro Arg Lys Gln Val Val Ala Thr Leu Val Ile
                165                 170                 175
```

```
Met Gly Gly Asn Phe Thr Ile Pro Met Asp Leu Met Thr Ile Asp
            180                 185                 190

Ser Thr Glu His Tyr Ser Gly Tyr Pro Ile Leu Thr Trp Ile Ser Ser
            195                 200                 205

Pro Asp Asn Ser Tyr Asn Gly Pro Phe Met Ser Trp Tyr Phe Ala Asn
210                 215                 220

Trp Pro Asn Leu Pro Ser Gly Phe Gly Pro Leu Asn Ser Asp Asn Thr
225                 230                 235                 240

Val Thr Tyr Lys Gly Ser Val Val Ser Gln Val Ser Ala Gly Val Tyr
                245                 250                 255

Ala Thr Val Arg Phe Asp Gln Tyr Asp Ile His Asn Leu Arg Thr Ile
            260                 265                 270

Glu Lys Thr Trp Tyr Ala Arg His Ala Thr Leu His Asn Gly Lys Lys
            275                 280                 285

Ile Ser Ile Asn Asn Val Thr Glu Met Ala Pro Thr Ser Pro Ile Lys
            290                 295                 300

Thr Asn
305

<210> SEQ ID NO 47
<211> LENGTH: 306
<212> TYPE: PRT
<213> ORGANISM: Artificial Sequence
<220> FEATURE:
<223> OTHER INFORMATION: engineered

<400> SEQUENCE: 47

Met Ala Ile Leu Asp Leu Lys Ser Leu Val Leu Asn Ala Ile Asn Tyr
1               5                   10                  15

Trp Gly Pro Lys Asn Asn Asn Gly Ile Gln Gly Gly Asp Phe Gly Tyr
            20                  25                  30

Pro Ile Ser Glu Lys Gln Ile Asp Thr Ser Ile Ile Thr Ser Thr His
        35                  40                  45

Pro Arg Leu Ile Pro His Asp Leu Thr Ile Pro Gln Asn Leu Glu Thr
50                  55                  60

Ile Phe Thr Thr Thr Gln Val Leu Thr Asn Asn Thr Asp Leu Gln Gln
65                  70                  75                  80

Ser Gln Thr Val Ser Phe Ala Lys Lys Thr Thr Thr Thr Ser Thr
                85                  90                  95

Ser Thr Thr Asn Gly Trp Thr Glu Gly Gly Lys Ile Ser Asp Thr Leu
            100                 105                 110

Glu Glu Lys Val Ser Val Ser Ile Pro Phe Ile Gly Glu Gly Gly Gly
            115                 120                 125

Lys Asn Ser Thr Thr Ile Glu Ala Asn Phe Ala His Asn Ser Ser Thr
            130                 135                 140

Thr Thr Phe Gln Gln Ala Ser Thr Asp Ile Glu Trp Asn Ile Ser Gln
145                 150                 155                 160

Pro Val Leu Val Pro Pro Arg Lys Gln Val Val Ala Thr Leu Val Ile
                165                 170                 175

Met Gly Gly Asn Phe Thr Ile Pro Met Asp Leu Met Thr Ile Asp
            180                 185                 190

Ser Thr Glu His Tyr Ser Gly Tyr Pro Ile Leu Thr Trp Ile Ser Ser
            195                 200                 205

Pro Asp Asn Ser Tyr Asn Gly Pro Phe Met Ser Trp Tyr Phe Ala Asn
210                 215                 220
```

```
Trp Pro Asn Leu Pro Ser Gly Phe Gly Pro Leu Asn Ser Asp Asn Thr
225                 230                 235                 240

Ile Thr Tyr Thr Gly Ser Val Val Ser Gln Val Ser Ala Gly Val Tyr
            245                 250                 255

Ala Thr Val Arg Phe Asp Gln Tyr Asp Ile His Asn Leu Arg Thr Ile
        260                 265                 270

Glu Lys Thr Trp Tyr Ala Arg His Ala Thr Leu His Asn Gly Lys Lys
    275                 280                 285

Ile Ser Ile Asn Asn Val Thr Glu Met Ala Pro Thr Ser Pro Ile Lys
290                 295                 300

Thr Asn
305

<210> SEQ ID NO 48
<211> LENGTH: 306
<212> TYPE: PRT
<213> ORGANISM: Artificial Sequence
<220> FEATURE:
<223> OTHER INFORMATION: engineered

<400> SEQUENCE: 48

Met Ala Ile Leu Asp Leu Lys Ser Leu Val Leu Asn Ala Ile Asn Tyr
1               5                   10                  15

Trp Gly Pro Lys Asn Asn Asn Gly Ile Gln Gly Gly Asp Phe Gly Tyr
            20                  25                  30

Pro Ile Ser Glu Lys Gln Ile Asp Thr Ser Ile Ile Thr Ser Thr His
        35                  40                  45

Pro Arg Leu Ile Pro His Asp Leu Thr Ile Pro Gln Asn Leu Glu Thr
    50                  55                  60

Ile Phe Thr Thr Thr Gln Val Leu Thr Asn Asn Thr Asp Leu Gln Gln
65                  70                  75                  80

Ser Gln Thr Val Ser Phe Ala Lys Lys Thr Thr Thr Thr Ser Thr
                85                  90                  95

Ser Thr Thr Asn Gly Trp Thr Glu Gly Gly Lys Ile Ser Asp Thr Leu
            100                 105                 110

Glu Glu Lys Val Ser Val Ser Ile Pro Phe Ile Gly Glu Gly Gly Gly
        115                 120                 125

Lys Asn Ser Thr Thr Ile Glu Ala Asn Phe Ala His Asn Ser Ser Thr
    130                 135                 140

Thr Thr Phe Gln Gln Ala Ser Thr Asp Ile Glu Trp Asn Ile Ser Gln
145                 150                 155                 160

Pro Val Leu Val Pro Pro Arg Lys Gln Val Val Ala Thr Leu Val Ile
                165                 170                 175

Met Gly Gly Asn Phe Thr Ile Pro Met Asp Leu Met Thr Thr Ile Asp
            180                 185                 190

Ser Thr Glu His Tyr Ser Gly Tyr Pro Ile Leu Thr Trp Ile Ser Ser
        195                 200                 205

Pro Asp Asn Ser Tyr Asn Gly Pro Phe Met Ser Trp Tyr Phe Ala Asn
    210                 215                 220

Trp Pro Asn Leu Pro Ser Gly Phe Gly Pro Leu Asn Ser Asp Asn Thr
225                 230                 235                 240

Ile Thr Tyr Lys Gly Ser Val Val Ser Gln Val Ser Ala Gly Val Tyr
                245                 250                 255

Ala Thr Val Arg Phe Asp Gln Tyr Asp Ile His Asn Leu Arg Thr Ile
            260                 265                 270
```

```
Glu Lys Thr Trp Tyr Ala Arg His Ala Thr Leu His Asn Gly Lys Lys
        275                 280                 285

Ile Ser Ile Asn Asn Val Thr Glu Met Ala Pro Thr Ser Pro Ile Lys
        290                 295                 300

Thr Asn
305

<210> SEQ ID NO 49
<211> LENGTH: 306
<212> TYPE: PRT
<213> ORGANISM: Artificial Sequence
<220> FEATURE:
<223> OTHER INFORMATION: engineered

<400> SEQUENCE: 49

Met Ala Ile Leu Asp Leu Lys Ser Leu Val Leu Asn Ala Ile Asn Tyr
1               5                   10                  15

Trp Gly Pro Lys Asn Asn Gly Ile Gln Gly Gly Asp Phe Gly Tyr
            20                  25                  30

Pro Ile Ser Glu Lys Gln Ile Asp Thr Ser Ile Ile Thr Ser Thr His
        35                  40                  45

Pro Arg Leu Ile Pro His Asp Leu Thr Ile Pro Gln Asn Leu Glu Thr
    50                  55                  60

Ile Phe Thr Thr Thr Gln Val Leu Thr Asn Asn Thr Asp Leu Gln Gln
65                  70                  75                  80

Ser Gln Thr Val Ser Phe Ala Lys Lys Thr Thr Thr Thr Ser Thr
                85                  90                  95

Ser Thr Thr Asn Gly Trp Thr Glu Gly Gly Lys Ile Ser Asp Thr Leu
            100                 105                 110

Glu Glu Lys Val Ser Val Ser Ile Pro Phe Ile Gly Glu Gly Gly Gly
        115                 120                 125

Lys Asn Ser Thr Thr Ile Glu Ala Asn Phe Ala His Asn Ser Ser Thr
    130                 135                 140

Thr Thr Phe Gln Gln Ala Ser Thr Asp Ile Glu Trp Asn Ile Ser Gln
145                 150                 155                 160

Pro Val Leu Val Pro Pro Arg Lys Gln Val Val Ala Thr Leu Val Ile
                165                 170                 175

Met Gly Gly Asn Phe Thr Ile Pro Met Asp Leu Met Thr Thr Ile Asp
            180                 185                 190

Ser Thr Glu His Tyr Ser Gly Tyr Pro Ile Leu Thr Trp Ile Ser Ser
        195                 200                 205

Pro Asp Asn Ser Tyr Asn Gly Pro Phe Met Ser Tyr Tyr Phe Ala Asn
    210                 215                 220

Trp Pro Asn Leu Pro Ser Gly Phe Gly Pro Leu Asn Ser Asp Asn Thr
225                 230                 235                 240

Val Thr Tyr Thr Gly Ser Val Val Ser Gln Val Ser Ala Gly Val Tyr
                245                 250                 255

Ala Thr Val Arg Phe Asp Gln Tyr Asp Ile His Asn Leu Arg Thr Ile
            260                 265                 270

Glu Lys Thr Trp Tyr Ala Arg His Ala Thr Leu His Asn Gly Lys Lys
        275                 280                 285

Ile Ser Ile Asn Asn Val Thr Glu Met Ala Pro Thr Ser Pro Ile Lys
    290                 295                 300

Thr Asn
305
```

<210> SEQ ID NO 50
<211> LENGTH: 306
<212> TYPE: PRT
<213> ORGANISM: Artificial Sequence
<220> FEATURE:
<223> OTHER INFORMATION: engineered

<400> SEQUENCE: 50

```
Met Ala Ile Leu Asp Leu Lys Ser Leu Val Leu Asn Ala Ile Asn Tyr
1               5                   10                  15

Trp Gly Pro Lys Asn Asn Gly Ile Gln Gly Gly Asp Phe Gly Tyr
            20                  25                  30

Pro Ile Ser Glu Lys Gln Ile Asp Thr Ser Ile Ile Thr Ser Thr His
                35                  40                  45

Pro Arg Leu Ile Pro His Asp Leu Thr Ile Pro Gln Asn Leu Glu Thr
        50                  55                  60

Ile Phe Thr Thr Thr Gln Val Leu Thr Asn Asn Thr Asp Leu Gln Gln
65                  70                  75                  80

Ser Gln Thr Val Ser Phe Ala Lys Lys Thr Thr Thr Thr Ser Thr
                85                  90                  95

Ser Thr Thr Asn Gly Trp Thr Glu Gly Gly Lys Ile Ser Asp Thr Leu
            100                 105                 110

Glu Glu Lys Val Ser Val Ser Ile Pro Phe Ile Gly Glu Gly Gly Gly
            115                 120                 125

Lys Asn Ser Thr Thr Ile Glu Ala Asn Phe Ala His Asn Ser Ser Thr
130                 135                 140

Thr Thr Phe Gln Gln Ala Ser Thr Asp Ile Glu Trp Asn Ile Ser Gln
145                 150                 155                 160

Pro Val Leu Val Pro Arg Lys Gln Val Val Ala Thr Leu Val Ile
                165                 170                 175

Met Gly Gly Asn Phe Thr Ile Pro Met Asp Leu Met Thr Thr Ile Asp
            180                 185                 190

Ser Thr Glu His Tyr Ser Gly Tyr Pro Ile Leu Thr Trp Ile Ser Ser
            195                 200                 205

Pro Asp Asn Ser Tyr Asn Gly Pro Phe Met Ser Trp Tyr Phe Ala Asn
        210                 215                 220

Trp Pro Asn Leu Pro Ser Gly Phe Gly Pro Leu Asn Ser Asp Asn Thr
225                 230                 235                 240

Val Thr Phe Thr Gly Ser Val Val Ser Gln Val Ser Ala Gly Val Tyr
                245                 250                 255

Ala Thr Val Arg Phe Asp Gln Tyr Asp Ile His Asn Leu Arg Thr Ile
            260                 265                 270

Glu Lys Thr Trp Tyr Ala Arg His Ala Thr Leu His Asn Gly Lys Lys
            275                 280                 285

Ile Ser Ile Asn Asn Val Thr Glu Met Ala Pro Thr Ser Pro Ile Lys
        290                 295                 300

Thr Asn
305
```

<210> SEQ ID NO 51
<211> LENGTH: 306
<212> TYPE: PRT
<213> ORGANISM: Artificial Sequence
<220> FEATURE:
<223> OTHER INFORMATION: engineered

<400> SEQUENCE: 51

```
Met Ala Ile Leu Asp Leu Lys Ser Leu Val Leu Asn Ala Ile Asn Tyr
1               5                   10                  15

Trp Gly Pro Lys Asn Asn Asn Gly Ile Gln Gly Gly Asp Phe Gly Tyr
            20                  25                  30

Pro Ile Ser Glu Lys Gln Ile Asp Thr Ser Ile Ile Thr Ser Thr His
        35                  40                  45

Pro Arg Leu Ile Pro His Asp Leu Thr Ile Pro Gln Asn Leu Glu Thr
    50                  55                  60

Ile Phe Thr Thr Thr Gln Val Leu Thr Asn Asn Thr Asp Leu Gln Gln
65                  70                  75                  80

Ser Gln Thr Val Ser Phe Ala Lys Lys Thr Thr Thr Thr Ser Thr
                85                  90                  95

Ser Thr Thr Asn Gly Trp Thr Glu Gly Gly Lys Ile Ser Asp Thr Leu
                100                 105                 110

Glu Glu Lys Val Ser Val Ser Ile Pro Phe Ile Gly Glu Gly Gly Ala
            115                 120                 125

Lys Asn Ser Thr Thr Ile Glu Ala Asn Phe Ala His Asn Ser Ser Thr
    130                 135                 140

Thr Thr Ala Gln Gln Ala Ser Thr Asp Ile Glu Trp Asn Ile Ser Gln
145                 150                 155                 160

Pro Val Leu Val Pro Arg Lys Gln Val Val Ala Thr Leu Val Ile
                165                 170                 175

Met Gly Gly Asn Phe Thr Ile Pro Met Asp Leu Met Thr Thr Ile Asp
                180                 185                 190

Ser Thr Glu His Tyr Ser Gly Tyr Pro Ile Leu Thr Trp Ile Ser Ser
            195                 200                 205

Pro Asp Asn Ser Tyr Asn Gly Pro Phe Met Ser Trp Tyr Phe Ala Asn
    210                 215                 220

Trp Pro Asn Leu Pro Ser Gly Phe Gly Pro Leu Asn Ser Asp Asn Thr
225                 230                 235                 240

Val Thr Tyr Thr Gly Ser Val Val Ser Gln Val Ser Ala Gly Val Tyr
                245                 250                 255

Ala Thr Val Arg Phe Asp Gln Tyr Asp Ile His Asn Leu Arg Thr Ile
                260                 265                 270

Glu Lys Thr Trp Tyr Ala Arg His Ala Thr Leu His Asn Gly Lys Lys
            275                 280                 285

Ile Ser Ile Asn Asn Val Thr Glu Met Ala Pro Thr Ser Pro Ile Lys
    290                 295                 300

Thr Asn
305
```

<210> SEQ ID NO 52
<211> LENGTH: 306
<212> TYPE: PRT
<213> ORGANISM: Artificial Sequence
<220> FEATURE:
<223> OTHER INFORMATION: engineered

<400> SEQUENCE: 52

```
Met Ala Ile Leu Asp Leu Lys Ser Leu Val Leu Asn Ala Ile Asn Tyr
1               5                   10                  15

Trp Gly Pro Lys Asn Asn Asn Gly Ile Gln Gly Gly Asp Phe Gly Tyr
            20                  25                  30

Pro Ile Ser Glu Lys Gln Ile Asp Thr Ser Ile Ile Thr Ser Thr His
```

```
                35                  40                  45
Pro Arg Leu Ile Pro His Asp Leu Thr Ile Pro Gln Asn Leu Glu Thr
 50                  55                  60
Ile Phe Thr Thr Thr Gln Val Leu Thr Asn Asn Thr Asp Leu Gln Gln
 65                  70                  75                  80
Ser Gln Thr Val Ser Phe Ala Lys Lys Thr Thr Thr Thr Thr Ser Thr
                85                  90                  95
Ser Thr Thr Asn Gly Trp Thr Glu Gly Gly Lys Ile Ser Asp Thr Leu
            100                 105                 110
Glu Glu Lys Val Ser Val Ser Ile Pro Phe Ile Gly Glu Gly Gly Gly
        115                 120                 125
Lys Asn Ser Thr Thr Ile Glu Ala Asn Phe Ala His Asn Ser Ser Thr
    130                 135                 140
Thr Thr Ala Gln Gln Ala Ser Thr Asp Ile Glu Trp Asn Ile Ser Gln
145                 150                 155                 160
Pro Val Leu Val Pro Pro Arg Lys Gln Val Val Ala Thr Leu Val Ile
                165                 170                 175
Met Gly Gly Asn Phe Thr Ile Pro Met Asp Leu Met Thr Thr Ile Asp
            180                 185                 190
Ser Thr Glu His Tyr Ser Gly Tyr Pro Ile Leu Thr Trp Ile Ser Ser
        195                 200                 205
Pro Asp Asn Ser Tyr Asn Gly Pro Phe Met Ser Trp Tyr Phe Ala Asn
    210                 215                 220
Trp Pro Asn Leu Pro Ser Gly Phe Gly Pro Leu Asn Ser Asp Asn Thr
225                 230                 235                 240
Val Thr Tyr Thr Gly Ser Val Val Ser Gln Val Ser Ala Gly Val Tyr
                245                 250                 255
Ala Thr Val Arg Phe Asp Gln Tyr Asp Ile His Asn Leu Arg Thr Ile
            260                 265                 270
Glu Lys Thr Trp Tyr Ala Arg His Ala Thr Leu His Asn Gly Lys Lys
        275                 280                 285
Ile Ser Ile Asn Asn Val Thr Glu Ala Ala Pro Thr Ser Pro Ile Lys
    290                 295                 300
Thr Asn
305

<210> SEQ ID NO 53
<211> LENGTH: 306
<212> TYPE: PRT
<213> ORGANISM: Artificial Sequence
<220> FEATURE:
<223> OTHER INFORMATION: engineered

<400> SEQUENCE: 53

Met Ala Ile Leu Asp Leu Lys Ser Leu Val Leu Asn Ala Ile Asn Tyr
  1               5                  10                  15
Trp Gly Pro Lys Asn Asn Asn Gly Ile Gln Gly Gly Asp Phe Gly Tyr
                 20                  25                  30
Pro Ile Ser Glu Lys Gln Ile Asp Thr Ser Ile Ile Thr Ser Thr His
                 35                  40                  45
Pro Arg Leu Ile Pro His Asp Leu Thr Ile Pro Gln Asn Leu Glu Thr
 50                  55                  60
Ile Phe Thr Thr Thr Gln Val Leu Thr Asn Asn Thr Asp Leu Gln Gln
 65                  70                  75                  80
Ser Gln Thr Val Ser Phe Ala Lys Lys Thr Thr Thr Thr Thr Ser Thr
```

```
                 85                  90                  95
Ser Thr Thr Asn Gly Trp Thr Glu Gly Gly Lys Ile Ser Asp Thr Leu
                100                 105                 110

Glu Glu Lys Val Ser Val Ser Ile Pro Phe Ile Gly Glu Gly Gly Gly
            115                 120                 125

Lys Asn Ser Thr Thr Ile Glu Ala Asn Phe Ala His Asn Ser Ser Thr
        130                 135                 140

Thr Thr Ala Gln Gln Ala Ser Thr Asp Ile Glu Trp Asn Ile Ser Gln
145                 150                 155                 160

Pro Val Leu Val Pro Pro Arg Lys Gln Val Val Ala Thr Leu Val Ile
                165                 170                 175

Met Gly Gly Asn Phe Thr Ile Pro Met Asp Leu Met Thr Thr Ile Asp
                180                 185                 190

Ser Thr Glu His Tyr Ser Gly Tyr Pro Ile Leu Thr Trp Ile Ser Ser
            195                 200                 205

Pro Asp Asn Ser Tyr Asn Gly Pro Phe Met Ser Trp Tyr Phe Ala Asn
        210                 215                 220

Trp Pro Asn Leu Pro Ser Gly Phe Gly Pro Leu Asn Ser Asp Asn Thr
225                 230                 235                 240

Val Thr Tyr Thr Gly Ser Val Val Ser Gln Val Ser Ala Gly Val Tyr
                245                 250                 255

Ala Thr Val Arg Phe Asp Gln Tyr Asp Ile His Asn Leu Arg Thr Ile
                260                 265                 270

Glu Lys Thr Trp Tyr Ala Arg His Ala Thr Leu His Asn Gly Lys Lys
            275                 280                 285

Ile Ala Ile Asn Asn Val Thr Glu Met Ala Pro Thr Ser Pro Ile Lys
        290                 295                 300

Thr Asn
305

<210> SEQ ID NO 54
<211> LENGTH: 306
<212> TYPE: PRT
<213> ORGANISM: Artificial Sequence
<220> FEATURE:
<223> OTHER INFORMATION: engineered

<400> SEQUENCE: 54

Met Ala Ile Leu Asp Leu Lys Ser Leu Val Leu Asn Ala Ile Asn Tyr
1               5                   10                  15

Trp Gly Pro Lys Asn Asn Asn Gly Ile Gln Gly Gly Asp Phe Gly Tyr
            20                  25                  30

Pro Ile Ser Glu Lys Gln Ile Asp Thr Ser Ile Ile Thr Ser Thr His
        35                  40                  45

Pro Arg Leu Ile Pro His Asp Leu Thr Ile Pro Gln Asn Leu Glu Thr
50                  55                  60

Ile Phe Thr Thr Thr Gln Val Leu Thr Asn Thr Asp Leu Gln Gln
65                  70                  75                  80

Ser Gln Thr Val Ser Phe Ala Lys Lys Thr Thr Thr Thr Ser Thr
                85                  90                  95

Ser Thr Thr Asn Gly Trp Thr Glu Gly Gly Lys Ile Ser Asp Thr Leu
                100                 105                 110

Glu Glu Lys Val Ser Val Ser Ile Pro Phe Ile Gly Glu Gly Gly Gly
            115                 120                 125

Lys Asn Ser Thr Thr Ile Glu Ala Asn Phe Ala His Asn Ser Ser Thr
```

```
                130                 135                 140
Thr Thr Ala Gln Gln Ala Ser Thr Asp Ile Glu Trp Asn Ile Ser Gln
145                 150                 155                 160

Pro Val Leu Val Pro Pro Arg Lys Gln Val Val Ala Thr Leu Val Ile
                165                 170                 175

Met Gly Gly Asn Phe Thr Ile Pro Met Asp Leu Met Thr Thr Ile Asp
                180                 185                 190

Ser Thr Glu His Tyr Ser Gly Tyr Pro Ile Leu Thr Trp Ile Ser Ser
                195                 200                 205

Pro Asp Asn Ser Tyr Asn Gly Pro Phe Met Ser Trp Tyr Phe Ala Asn
                210                 215                 220

Trp Pro Asn Leu Pro Ser Gly Phe Gly Pro Leu Asn Ser Asp Asn Thr
225                 230                 235                 240

Val Thr Tyr Thr Gly Ser Val Val Ser Gln Val Ser Ala Gly Val Tyr
                245                 250                 255

Ala Thr Val Arg Phe Asp Gln Tyr Asp Ile His Asn Leu Arg Thr Ile
                260                 265                 270

Glu Lys Thr Trp Tyr Ala Arg His Ala Thr Leu Ala Asn Gly Lys Lys
                275                 280                 285

Ile Ser Ile Asn Asn Val Thr Glu Met Ala Pro Thr Ser Pro Ile Lys
                290                 295                 300

Thr Asn
305

<210> SEQ ID NO 55
<211> LENGTH: 306
<212> TYPE: PRT
<213> ORGANISM: Artificial Sequence
<220> FEATURE:
<223> OTHER INFORMATION: engineered

<400> SEQUENCE: 55

Met Ala Ile Leu Asp Leu Lys Ser Leu Val Leu Asn Ala Ile Asn Tyr
1               5                   10                  15

Trp Gly Pro Lys Asn Asn Asn Gly Ile Gln Gly Gly Asp Phe Gly Tyr
                20                  25                  30

Pro Ile Ser Glu Lys Gln Ile Asp Thr Ser Ile Ile Thr Ser Thr His
                35                  40                  45

Pro Arg Leu Ile Pro His Asp Leu Thr Ile Pro Gln Asn Leu Glu Thr
                50                  55                  60

Ile Phe Thr Thr Thr Gln Val Leu Thr Asn Asn Thr Asp Leu Gln Gln
65                  70                  75                  80

Ser Gln Thr Val Ser Phe Ala Lys Lys Thr Thr Thr Thr Thr Ser Thr
                85                  90                  95

Ser Thr Thr Asn Gly Trp Thr Glu Gly Gly Lys Ile Ser Asp Thr Leu
                100                 105                 110

Glu Glu Lys Val Ser Val Ser Ile Pro Phe Ile Gly Glu Gly Gly Gly
                115                 120                 125

Lys Asn Ser Thr Thr Ile Glu Ala Asn Phe Ala His Asn Ser Ser Thr
                130                 135                 140

Thr Thr Ala Gln Gln Ala Ser Thr Asp Ile Glu Trp Asn Ile Ser Gln
145                 150                 155                 160

Pro Val Leu Val Pro Pro Arg Lys Gln Val Val Ala Thr Leu Val Ile
                165                 170                 175

Met Gly Gly Asn Phe Thr Ile Pro Met Asp Leu Met Thr Thr Ile Asp
```

```
            180                 185                 190
Ser Thr Glu His Tyr Ser Gly Tyr Pro Ile Leu Thr Trp Ile Ser Ser
                195                 200                 205

Pro Asp Asn Ser Tyr Asn Gly Pro Phe Met Ser Trp Tyr Phe Ala Asn
    210                 215                 220

Trp Pro Asn Leu Pro Ser Gly Phe Gly Pro Leu Asn Ser Asp Asn Thr
225                 230                 235                 240

Val Thr Tyr Thr Gly Ser Val Val Ser Gln Val Ser Ala Gly Val Tyr
                245                 250                 255

Ala Thr Val Arg Phe Asp Gln Tyr Asp Ile His Asn Leu Arg Ala Ile
            260                 265                 270

Glu Lys Thr Trp Tyr Ala Arg His Ala Thr Leu His Asn Gly Lys Lys
        275                 280                 285

Ile Ser Ile Asn Asn Val Thr Glu Met Ala Pro Thr Ser Pro Ile Lys
    290                 295                 300

Thr Asn
305

<210> SEQ ID NO 56
<211> LENGTH: 306
<212> TYPE: PRT
<213> ORGANISM: Artificial Sequence
<220> FEATURE:
<223> OTHER INFORMATION: engineered

<400> SEQUENCE: 56

Met Ala Ile Leu Asp Leu Lys Ser Leu Val Leu Asn Ala Ile Asn Tyr
1               5                   10                  15

Trp Gly Pro Lys Asn Asn Gly Ile Gln Gly Gly Asp Phe Gly Tyr
            20                  25                  30

Pro Ile Ser Glu Lys Gln Ile Asp Thr Ser Ile Ile Thr Ser Thr His
        35                  40                  45

Pro Arg Leu Ile Pro His Asp Leu Thr Ile Pro Gln Asn Leu Glu Thr
    50                  55                  60

Ile Phe Thr Thr Thr Gln Val Leu Thr Asn Asn Thr Asp Leu Gln Gln
65                  70                  75                  80

Ser Gln Thr Val Ser Phe Ala Lys Lys Thr Thr Thr Thr Ser Thr
                85                  90                  95

Ser Thr Thr Asn Gly Trp Thr Glu Gly Gly Lys Ile Ser Asp Thr Leu
            100                 105                 110

Glu Glu Lys Val Ser Val Ser Ile Pro Phe Ile Gly Glu Gly Gly Gly
        115                 120                 125

Lys Asn Ser Thr Thr Ile Glu Ala Asn Phe Ala His Asn Ser Ser Thr
    130                 135                 140

Thr Thr Ala Gln Gln Ala Ser Thr Asp Ile Glu Trp Asn Ile Ser Gln
145                 150                 155                 160

Pro Val Leu Val Pro Arg Lys Gln Val Val Ala Thr Leu Val Ile
                165                 170                 175

Met Gly Gly Asn Phe Thr Ile Pro Met Asp Leu Met Thr Thr Ile Asp
            180                 185                 190

Ser Thr Glu His Tyr Ser Gly Tyr Pro Ile Leu Thr Trp Ile Ser Ser
        195                 200                 205

Pro Asp Asn Ser Tyr Asn Gly Pro Phe Met Ser Trp Tyr Phe Ala Asn
    210                 215                 220

Trp Pro Asn Leu Pro Ser Gly Phe Gly Pro Leu Asn Ser Asp Asn Thr
```

```
                225                 230                 235                 240
Val Thr Tyr Thr Gly Ser Val Val Ser Gln Val Ser Ala Gly Val Tyr
                245                 250                 255

Ala Thr Val Arg Phe Asp Gln Tyr Asp Ile His Asn Leu Arg Thr Ile
                260                 265                 270

Glu Lys Thr Trp Tyr Ala Ala His Ala Thr Leu His Asn Gly Lys Lys
                275                 280                 285

Ile Ser Ile Asn Asn Val Thr Glu Met Ala Pro Thr Ser Pro Ile Lys
                290                 295                 300

Thr Asn
305

<210> SEQ ID NO 57
<211> LENGTH: 306
<212> TYPE: PRT
<213> ORGANISM: Artificial Sequence
<220> FEATURE:
<223> OTHER INFORMATION: engineered

<400> SEQUENCE: 57

Met Ala Ile Leu Asp Leu Lys Ser Leu Val Leu Asn Ala Ile Asn Tyr
1               5                   10                  15

Trp Gly Pro Lys Asn Asn Gly Ile Gln Gly Gly Asp Phe Gly Tyr
                20                  25                  30

Pro Ile Ser Glu Lys Gln Ile Asp Thr Ser Ile Ile Thr Ser Thr His
                35                  40                  45

Pro Arg Leu Ile Pro His Asp Leu Thr Ile Pro Gln Asn Leu Glu Thr
50                  55                  60

Ile Phe Thr Thr Thr Gln Val Leu Thr Asn Asn Thr Asp Leu Gln Gln
65                  70                  75                  80

Ser Gln Thr Val Ser Phe Ala Lys Lys Thr Thr Ala Thr Ser Thr
                85                  90                  95

Ser Thr Thr Asn Gly Trp Thr Glu Gly Gly Lys Ile Ser Asp Thr Leu
                100                 105                 110

Glu Glu Lys Val Ser Val Ser Ile Pro Phe Ile Gly Glu Gly Gly Gly
                115                 120                 125

Lys Asn Ser Thr Thr Ile Glu Ala Asn Phe Ala His Asn Ser Ser Thr
                130                 135                 140

Thr Thr Phe Gln Gln Ala Ser Thr Asp Ile Glu Trp Asn Ile Ser Gln
145                 150                 155                 160

Pro Val Leu Val Pro Pro Arg Lys Gln Val Val Ala Thr Leu Val Ile
                165                 170                 175

Met Gly Gly Asn Phe Thr Ile Pro Met Asp Leu Met Thr Thr Ile Asp
                180                 185                 190

Ser Thr Glu His Tyr Ser Gly Tyr Pro Ile Leu Thr Trp Ile Ser Ser
                195                 200                 205

Pro Asp Asn Ser Tyr Asn Gly Pro Phe Met Ser Trp Tyr Phe Ala Asn
                210                 215                 220

Trp Pro Asn Leu Pro Ser Gly Phe Gly Pro Leu Asn Ser Asp Asn Thr
225                 230                 235                 240

Val Thr Tyr Thr Gly Ser Val Val Ser Gln Val Ser Ala Gly Val Tyr
                245                 250                 255

Ala Thr Val Arg Phe Asp Gln Tyr Asp Ile His Asn Leu Arg Thr Ile
                260                 265                 270

Glu Lys Thr Trp Tyr Ala Arg His Ala Thr Leu His Asn Gly Lys Lys
```

```
            275                 280                 285
Ile Ser Ile Asn Asn Val Thr Glu Met Ala Pro Thr Ser Pro Ile Lys
    290                 295                 300

Ala Asn
305

<210> SEQ ID NO 58
<211> LENGTH: 306
<212> TYPE: PRT
<213> ORGANISM: Artificial Sequence
<220> FEATURE:
<223> OTHER INFORMATION: engineered

<400> SEQUENCE: 58

Met Ala Ile Leu Asp Leu Lys Ser Leu Val Leu Asn Ala Ile Asn Tyr
1               5                   10                  15

Trp Gly Pro Lys Asn Asn Gly Ile Gln Gly Gly Asp Phe Gly Tyr
            20                  25                  30

Pro Ile Ser Glu Lys Gln Ile Asp Thr Ser Ile Ile Thr Ser Thr His
        35                  40                  45

Pro Arg Leu Ile Pro His Asp Leu Thr Ile Pro Gln Asn Leu Glu Thr
    50                  55                  60

Ile Phe Thr Thr Thr Ala Val Leu Thr Asn Asn Thr Asp Leu Gln Gln
65                  70                  75                  80

Ser Gln Thr Val Ser Phe Ala Lys Lys Thr Thr Ala Thr Ser Thr
                85                  90                  95

Ser Thr Thr Asn Gly Trp Thr Glu Gly Gly Lys Ile Ser Asp Thr Leu
            100                 105                 110

Glu Glu Lys Val Ser Val Ser Ile Pro Phe Ile Gly Glu Gly Gly Gly
        115                 120                 125

Lys Asn Ser Thr Thr Ile Glu Ala Asn Phe Ala His Asn Ser Ser Thr
    130                 135                 140

Thr Thr Phe Gln Gln Ala Ser Thr Asp Ile Glu Trp Asn Ile Ser Gln
145                 150                 155                 160

Pro Val Leu Val Pro Pro Arg Lys Gln Val Val Ala Thr Leu Val Ile
                165                 170                 175

Met Gly Gly Asn Phe Thr Ile Pro Met Asp Leu Met Thr Thr Ile Asp
            180                 185                 190

Ser Thr Glu His Tyr Ser Gly Tyr Pro Ile Leu Thr Trp Ile Ser Ser
        195                 200                 205

Pro Asp Asn Ser Tyr Asn Gly Pro Phe Met Ser Trp Tyr Phe Ala Asn
    210                 215                 220

Trp Pro Asn Leu Pro Ser Gly Phe Gly Pro Leu Asn Ser Asp Asn Thr
225                 230                 235                 240

Val Thr Tyr Thr Gly Ser Val Val Ser Gln Val Ser Ala Gly Val Tyr
                245                 250                 255

Ala Thr Val Arg Phe Asp Gln Tyr Asp Ile His Asn Leu Arg Thr Ile
            260                 265                 270

Glu Lys Thr Trp Tyr Ala Arg His Ala Thr Leu His Asn Gly Lys Lys
        275                 280                 285

Ile Ser Ile Asn Asn Val Thr Glu Met Ala Pro Thr Ser Pro Ile Lys
    290                 295                 300

Thr Asn
305
```

<210> SEQ ID NO 59
<211> LENGTH: 306
<212> TYPE: PRT
<213> ORGANISM: Artificial Sequence
<220> FEATURE:
<223> OTHER INFORMATION: engineered

<400> SEQUENCE: 59

```
Met Ala Ile Leu Asp Leu Lys Ser Leu Val Leu Asn Ala Ile Asn Tyr
1               5                   10                  15

Trp Gly Pro Lys Asn Asn Asn Gly Ile Gln Gly Gly Asp Phe Gly Tyr
            20                  25                  30

Pro Ile Ser Glu Lys Gln Ile Asp Thr Ser Ile Ile Thr Ser Thr His
        35                  40                  45

Pro Arg Leu Ile Pro His Asp Leu Thr Ile Pro Gln Asn Leu Glu Thr
    50                  55                  60

Ile Phe Thr Thr Thr Gln Val Leu Thr Asn Asn Thr Asp Leu Gln Gln
65                  70                  75                  80

Ser Gln Thr Val Ser Phe Ala Lys Lys Thr Thr Thr Thr Ser Thr
                85                  90                  95

Ser Thr Thr Asn Gly Trp Thr Glu Gly Gly Lys Ile Ser Asp Thr Leu
            100                 105                 110

Glu Glu Lys Val Ser Val Ser Ile Pro Phe Ile Gly Ala Gly Gly Gly
        115                 120                 125

Lys Asn Ser Thr Thr Ile Glu Ala Asn Phe Ala His Asn Ser Ser Thr
    130                 135                 140

Thr Thr Ala Gln Gln Ala Ser Thr Asp Ile Glu Trp Asn Ile Ser Gln
145                 150                 155                 160

Pro Val Leu Val Pro Pro Arg Lys Gln Val Val Ala Thr Leu Val Ile
                165                 170                 175

Met Gly Gly Asn Phe Thr Ile Pro Met Asp Leu Met Thr Thr Ile Asp
            180                 185                 190

Ser Thr Glu His Tyr Ser Gly Tyr Pro Ile Leu Thr Trp Ile Ser Ser
        195                 200                 205

Pro Asp Asn Ser Tyr Asn Gly Pro Phe Met Ser Trp Tyr Phe Ala Asn
    210                 215                 220

Trp Pro Asn Leu Pro Ser Gly Phe Gly Pro Leu Asn Ser Asp Asn Thr
225                 230                 235                 240

Val Thr Tyr Thr Gly Ser Val Val Ser Gln Val Ser Ala Gly Val Tyr
                245                 250                 255

Ala Thr Val Arg Phe Asp Gln Tyr Asp Ile His Asn Leu Arg Thr Ile
            260                 265                 270

Glu Lys Thr Trp Tyr Ala Arg His Ala Thr Leu His Asn Gly Lys Lys
        275                 280                 285

Ile Ser Ile Asn Asn Val Thr Glu Met Ala Pro Thr Ser Pro Ile Lys
    290                 295                 300

Thr Asn
305
```

<210> SEQ ID NO 60
<211> LENGTH: 306
<212> TYPE: PRT
<213> ORGANISM: Artificial Sequence
<220> FEATURE:
<223> OTHER INFORMATION: engineered

<400> SEQUENCE: 60

Met Ala Ile Leu Asp Leu Lys Ser Leu Val Leu Asn Ala Ile Asn Tyr
1               5                   10                  15

Trp Gly Pro Lys Asn Asn Asn Gly Ile Gln Gly Gly Asp Phe Gly Tyr
            20                  25                  30

Pro Ile Ser Glu Lys Gln Ile Asp Thr Ser Ile Ile Thr Ser Thr His
            35                  40                  45

Pro Arg Leu Ile Pro His Asp Leu Thr Ile Pro Gln Asn Leu Glu Thr
        50                  55                  60

Ile Phe Thr Thr Thr Gln Val Leu Thr Asn Asn Thr Asp Leu Gln Gln
65                  70                  75                  80

Ser Gln Thr Val Ser Phe Ala Lys Lys Thr Thr Thr Thr Thr Ser Thr
                85                  90                  95

Ser Thr Thr Asn Gly Trp Thr Glu Gly Gly Lys Ile Ser Asp Thr Leu
            100                 105                 110

Glu Glu Lys Val Ser Val Ser Ile Pro Phe Ile Gly Glu Gly Gly Gly
            115                 120                 125

Lys Asn Ser Thr Thr Ile Glu Ala Asn Phe Ala His Asn Ser Ser Thr
        130                 135                 140

Thr Thr Ala Gln Gln Ala Ser Thr Asp Ile Glu Trp Asn Ile Ser Gln
145                 150                 155                 160

Pro Val Leu Val Pro Pro Arg Lys Gln Val Val Ala Thr Leu Val Ile
                165                 170                 175

Met Gly Gly Asn Phe Thr Ile Pro Met Asp Leu Met Thr Thr Ile Asp
            180                 185                 190

Ser Thr Glu His Tyr Ser Gly Tyr Pro Ile Leu Thr Trp Ile Ser Ser
        195                 200                 205

Pro Asp Asn Ser Tyr Asn Gly Pro Phe Met Ser Trp Tyr Phe Ala Asn
210                 215                 220

Trp Pro Asn Leu Pro Ser Gly Phe Gly Pro Leu Asn Ser Asp Asn Thr
225                 230                 235                 240

Val Thr Tyr Ala Gly Ser Val Val Ser Gln Val Ser Ala Gly Val Tyr
                245                 250                 255

Ala Thr Val Arg Phe Asp Gln Tyr Asp Ile His Asn Leu Arg Thr Ile
            260                 265                 270

Glu Lys Thr Trp Tyr Ala Arg His Ala Thr Leu His Asn Gly Lys Lys
        275                 280                 285

Ile Ser Ile Asn Asn Val Thr Glu Met Ala Pro Thr Ser Pro Ile Lys
            290                 295                 300

Thr Asn
305

<210> SEQ ID NO 61
<211> LENGTH: 306
<212> TYPE: PRT
<213> ORGANISM: Artificial Sequence
<220> FEATURE:
<223> OTHER INFORMATION: engineered

<400> SEQUENCE: 61

Met Ala Ile Leu Asp Leu Lys Ser Leu Val Leu Asn Ala Ile Asn Tyr
1               5                   10                  15

Trp Gly Pro Lys Asn Asn Asn Gly Ile Gln Gly Gly Asp Phe Gly Tyr
            20                  25                  30

Pro Ile Ser Glu Lys Gln Ile Asp Thr Ser Ile Ile Thr Ser Thr His
            35                  40                  45

```
Pro Arg Leu Ile Pro His Asp Leu Thr Ile Pro Gln Asn Leu Glu Thr
    50                  55                  60

Ile Phe Thr Thr Thr Gln Val Leu Thr Asn Asn Thr Asp Leu Gln Gln
65                  70                  75                  80

Ser Gln Thr Val Ser Phe Ala Lys Lys Thr Thr Thr Ala Thr Ser Thr
                85                  90                  95

Ser Thr Thr Asn Gly Trp Thr Glu Gly Gly Lys Ile Ser Asp Thr Leu
            100                 105                 110

Glu Glu Lys Val Ser Val Ser Ile Pro Phe Ile Gly Glu Gly Gly Gly
        115                 120                 125

Lys Asn Ser Thr Thr Ile Glu Ala Asn Phe Ala His Asn Ser Ser Thr
130                 135                 140

Thr Thr Phe Gln Gln Ala Ser Thr Asp Ile Glu Trp Asn Ile Ser Gln
145                 150                 155                 160

Pro Val Leu Val Pro Pro Arg Lys Gln Val Val Ala Thr Leu Val Ile
                165                 170                 175

Met Gly Gly Asn Phe Thr Ile Pro Met Asp Leu Met Thr Thr Ile Asp
            180                 185                 190

Ser Thr Glu His Tyr Ser Gly Tyr Pro Ile Leu Thr Trp Ile Ser Ser
        195                 200                 205

Pro Asp Asn Ser Tyr Asn Gly Pro Phe Met Ser Trp Tyr Phe Ala Asn
210                 215                 220

Trp Pro Asn Leu Pro Ser Gly Phe Gly Pro Leu Asn Ser Asp Asn Thr
225                 230                 235                 240

Val Thr Tyr Thr Gly Ser Val Val Ser Gln Val Ser Ala Gly Val Tyr
                245                 250                 255

Ala Thr Val Arg Phe Asp Gln Tyr Asp Ile His Asn Leu Arg Thr Ile
            260                 265                 270

Glu Lys Thr Trp Tyr Ala Arg His Ala Thr Leu His Asn Gly Lys Lys
        275                 280                 285

Ile Ser Ile Asn Asn Val Thr Glu Met Ala Pro Thr Ser Ala Ile Lys
    290                 295                 300

Thr Asn
305

<210> SEQ ID NO 62
<211> LENGTH: 306
<212> TYPE: PRT
<213> ORGANISM: Artificial Sequence
<220> FEATURE:
<223> OTHER INFORMATION: engineered

<400> SEQUENCE: 62

Met Ala Ile Leu Asp Leu Lys Ser Leu Val Leu Asn Ala Ile Asn Tyr
1               5                   10                  15

Trp Gly Pro Lys Asn Asn Gly Ile Gln Gly Gly Asp Phe Gly Tyr
            20                  25                  30

Pro Ile Ser Glu Lys Gln Ile Asp Thr Ser Ile Ile Thr Ser Thr His
        35                  40                  45

Pro Arg Leu Ile Pro His Asp Leu Thr Ile Pro Gln Asn Leu Glu Thr
    50                  55                  60

Ile Phe Thr Thr Thr Gln Val Leu Thr Asn Asn Thr Asp Leu Gln Gln
65                  70                  75                  80

Ser Gln Thr Val Ser Phe Ala Lys Lys Thr Thr Thr Thr Ser Thr
                85                  90                  95
```

Ser Thr Thr Asn Gly Trp Thr Glu Gly Gly Lys Ile Ser Asp Thr Leu
            100                 105                 110

Glu Glu Lys Val Ser Val Ser Ile Pro Phe Ile Gly Glu Gly Gly Gly
        115                 120                 125

Lys Asn Ser Thr Thr Ile Glu Ala Asn Phe Ala His Asn Ser Ser Thr
    130                 135                 140

Thr Thr Ala Gln Gln Ala Ser Thr Asp Ile Glu Trp Asn Ile Ser Gln
145                 150                 155                 160

Pro Val Leu Val Pro Pro Arg Lys Gln Val Val Ala Thr Leu Val Ile
                165                 170                 175

Met Gly Gly Asn Phe Thr Ile Pro Met Asp Leu Met Thr Thr Ile Asp
            180                 185                 190

Ser Thr Glu His Tyr Ser Gly Tyr Pro Ile Leu Thr Trp Ile Ser Ser
            195                 200                 205

Pro Asp Asn Ser Tyr Asn Gly Pro Phe Met Ser Trp Tyr Phe Ala Asn
            210                 215                 220

Trp Pro Asn Leu Pro Ser Gly Phe Gly Pro Leu Asn Ser Asp Asn Thr
225                 230                 235                 240

Val Thr Tyr Thr Gly Ser Val Val Ser Gln Val Ser Ala Gly Val Tyr
                245                 250                 255

Ala Thr Val Arg Phe Asp Gln Tyr Asp Ile His Asn Leu Arg Thr Ile
            260                 265                 270

Glu Lys Thr Trp Tyr Ala Arg His Ala Thr Leu His Asn Gly Lys Lys
            275                 280                 285

Ile Ser Ile Asn Asn Val Thr Glu Met Ala Pro Thr Ser Pro Ala Lys
            290                 295                 300

Thr Asn
305

<210> SEQ ID NO 63
<211> LENGTH: 306
<212> TYPE: PRT
<213> ORGANISM: Artificial Sequence
<220> FEATURE:
<223> OTHER INFORMATION: engineered

<400> SEQUENCE: 63

Met Ala Ile Leu Asp Leu Lys Ser Leu Val Leu Asn Ala Ile Asn Tyr
1               5                   10                  15

Trp Gly Pro Lys Asn Asn Gly Ile Gln Gly Gly Asp Phe Gly Tyr
            20                  25                  30

Pro Ile Ser Glu Lys Gln Ile Asp Thr Ser Ile Ile Thr Ser Thr His
            35                  40                  45

Pro Arg Leu Ile Pro His Asp Leu Thr Ile Pro Gln Asn Leu Glu Thr
    50                  55                  60

Ile Phe Thr Thr Thr Gln Val Leu Thr Asn Asn Thr Asp Leu Gln Gln
65                  70                  75                  80

Ser Gln Thr Val Ser Phe Ala Lys Lys Thr Thr Thr Ala Thr Ser Thr
                85                  90                  95

Ser Thr Thr Asn Gly Trp Thr Glu Gly Gly Lys Ile Ser Asp Thr Leu
            100                 105                 110

Glu Glu Lys Val Ser Val Ser Ile Pro Phe Ile Gly Glu Gly Gly Gly
        115                 120                 125

Lys Asn Ser Thr Thr Ile Glu Ala Asn Phe Ala His Asn Ser Ser Thr
    130                 135                 140

```
Thr Thr Phe Gln Gln Ala Ser Thr Asp Ile Glu Trp Asn Ile Ser Gln
145                 150                 155                 160

Pro Val Leu Val Pro Arg Lys Gln Val Val Ala Thr Leu Val Ile
                165                 170                 175

Met Gly Gly Asn Phe Thr Ile Pro Met Asp Leu Met Thr Thr Ile Asp
            180                 185                 190

Ser Thr Glu His Tyr Ser Gly Tyr Pro Ile Leu Thr Trp Ile Ser Ser
        195                 200                 205

Pro Asp Asn Ser Tyr Asn Gly Pro Phe Met Ser Trp Tyr Phe Ala Asn
    210                 215                 220

Trp Pro Asn Leu Pro Ser Gly Phe Gly Pro Leu Asn Ser Asp Asn Thr
225                 230                 235                 240

Val Thr Tyr Thr Gly Ser Val Val Ser Gln Val Ser Ala Gly Val Tyr
                245                 250                 255

Ala Thr Val Arg Phe Asp Gln Tyr Asp Ile His Asn Leu Arg Thr Ile
            260                 265                 270

Glu Lys Thr Trp Tyr Ala Ala His Ala Thr Leu His Asn Gly Lys Lys
        275                 280                 285

Ile Ser Ile Asn Asn Val Thr Glu Met Ala Pro Thr Ser Pro Ile Lys
    290                 295                 300

Thr Asn
305

<210> SEQ ID NO 64
<211> LENGTH: 306
<212> TYPE: PRT
<213> ORGANISM: Artificial Sequence
<220> FEATURE:
<223> OTHER INFORMATION: engineered

<400> SEQUENCE: 64

Met Ala Ile Leu Asp Leu Lys Ser Leu Val Leu Asn Ala Ile Asn Tyr
1               5                   10                  15

Trp Gly Pro Lys Asn Asn Gly Ile Gln Gly Gly Asp Phe Gly Tyr
            20                  25                  30

Pro Ile Ser Glu Lys Gln Ile Asp Thr Ser Ile Ile Thr Ser Thr His
        35                  40                  45

Pro Arg Leu Ile Pro His Asp Leu Thr Ile Pro Gln Asn Leu Glu Thr
    50                  55                  60

Ile Phe Thr Thr Thr Gln Val Leu Thr Asn Asn Thr Asp Leu Gln Gln
65                  70                  75                  80

Ser Gln Thr Val Ser Phe Ala Lys Lys Thr Thr Ala Thr Ser Thr
                85                  90                  95

Ser Thr Asn Gly Trp Thr Glu Gly Gly Lys Ile Ser Asp Thr Leu
            100                 105                 110

Glu Glu Lys Val Ser Val Ser Ile Pro Phe Ile Gly Glu Gly Gly Gly
        115                 120                 125

Lys Asn Ser Thr Thr Ile Glu Ala Asn Phe Ala His Asn Ser Ser Thr
    130                 135                 140

Thr Thr Phe Gln Gln Ala Ser Thr Asp Ile Glu Trp Asn Ile Ser Gln
145                 150                 155                 160

Pro Val Leu Val Pro Arg Lys Gln Val Val Ala Thr Leu Val Ile
                165                 170                 175

Met Gly Gly Asn Phe Thr Ile Pro Met Asp Leu Met Thr Thr Ile Asp
            180                 185                 190
```

```
Ser Thr Glu His Tyr Ser Gly Tyr Pro Ile Leu Thr Trp Ile Ser Ser
        195                 200                 205

Pro Asp Asn Ser Tyr Asn Gly Pro Phe Met Ser Trp Tyr Phe Ala Asn
    210                 215                 220

Trp Pro Asn Leu Pro Ser Gly Phe Gly Pro Leu Asn Ser Asp Asn Thr
225                 230                 235                 240

Val Thr Tyr Thr Gly Ser Val Val Ser Gln Val Ser Ala Gly Val Tyr
                245                 250                 255

Ala Thr Val Arg Phe Asp Gln Tyr Asp Ile His Asn Leu Arg Thr Ile
                260                 265                 270

Glu Lys Thr Trp Tyr Ala Arg His Ala Thr Leu His Asn Gly Lys Lys
            275                 280                 285

Ile Ser Ile Asn Asn Val Thr Glu Met Ala Pro Thr Ser Pro Ile Lys
        290                 295                 300

Ala Asn
305

<210> SEQ ID NO 65
<211> LENGTH: 306
<212> TYPE: PRT
<213> ORGANISM: Artificial Sequence
<220> FEATURE:
<223> OTHER INFORMATION: engineered

<400> SEQUENCE: 65

Met Ala Ile Leu Asp Leu Lys Ser Leu Val Leu Asn Ala Ile Asn Tyr
1               5                   10                  15

Trp Gly Pro Lys Asn Asn Asn Gly Ile Gln Gly Gly Asp Phe Gly Tyr
                20                  25                  30

Pro Ile Ser Glu Lys Gln Ile Asp Thr Ser Ile Ile Thr Ser Thr His
                35                  40                  45

Pro Arg Leu Ile Pro His Asp Leu Thr Ile Pro Gln Asn Leu Glu Thr
    50                  55                  60

Ile Phe Thr Thr Thr Gln Val Leu Thr Asn Asn Thr Asp Leu Gln Gln
65                  70                  75                  80

Ser Gln Thr Val Ser Phe Ala Lys Lys Thr Thr Thr Ala Thr Ser Thr
                85                  90                  95

Ser Thr Thr Asn Gly Trp Thr Glu Gly Gly Lys Ile Ser Asp Thr Leu
                100                 105                 110

Glu Glu Lys Val Ser Val Ser Ile Pro Phe Ile Gly Glu Gly Gly Gly
            115                 120                 125

Lys Asn Ser Thr Thr Ile Glu Ala Asn Phe Ala His Asn Ser Ser Thr
        130                 135                 140

Thr Thr Phe Gln Gln Ala Ser Thr Asp Ile Glu Trp Asn Ile Ser Gln
145                 150                 155                 160

Pro Val Leu Val Pro Arg Lys Gln Val Val Ala Thr Leu Val Ile
                165                 170                 175

Met Gly Gly Asn Phe Thr Ile Pro Met Asp Leu Met Thr Thr Ile Asp
                180                 185                 190

Ser Thr Glu His Tyr Ser Gly Tyr Pro Ile Leu Thr Trp Ile Ser Ser
        195                 200                 205

Pro Asp Asn Ser Tyr Asn Gly Pro Phe Met Ser Trp Tyr Phe Ala Asn
    210                 215                 220

Trp Pro Asn Leu Pro Ser Gly Phe Gly Pro Leu Asn Ser Asp Asn Thr
225                 230                 235                 240
```

```
Val Thr Tyr Thr Gly Ser Val Val Ser Gln Val Ser Ala Gly Val Tyr
                245                 250                 255

Ala Thr Val Arg Phe Asp Gln Tyr Asp Ile His Asn Leu Arg Thr Ile
            260                 265                 270

Glu Lys Thr Trp Tyr Ala Arg His Ala Thr Leu His Asn Gly Lys Lys
        275                 280                 285

Ile Ser Ile Asn Asn Val Thr Glu Ala Ala Pro Thr Ser Pro Ile Lys
    290                 295                 300

Thr Asn
305

<210> SEQ ID NO 66
<211> LENGTH: 306
<212> TYPE: PRT
<213> ORGANISM: Artificial Sequence
<220> FEATURE:
<223> OTHER INFORMATION: engineered

<400> SEQUENCE: 66

Met Ala Ile Leu Asp Leu Lys Ser Leu Val Leu Asn Ala Ile Asn Tyr
1               5                   10                  15

Trp Gly Pro Lys Asn Asn Asn Gly Ile Gln Gly Gly Asp Phe Gly Tyr
            20                  25                  30

Pro Ile Ser Glu Lys Gln Ile Asp Thr Ser Ile Ile Thr Ser Thr His
        35                  40                  45

Pro Arg Leu Ile Pro His Asp Leu Thr Ile Pro Gln Asn Leu Glu Thr
    50                  55                  60

Ile Phe Thr Thr Thr Gln Val Leu Thr Asn Asn Thr Asp Leu Gln Gln
65                  70                  75                  80

Ser Gln Thr Val Ser Phe Ala Lys Lys Thr Thr Thr Ala Thr Ser Thr
                85                  90                  95

Ser Thr Thr Asn Gly Trp Thr Glu Gly Gly Lys Ile Ser Asp Thr Leu
            100                 105                 110

Glu Glu Lys Val Ser Val Ser Ile Pro Phe Ile Gly Glu Gly Gly Gly
        115                 120                 125

Lys Asn Ser Thr Thr Ile Glu Ala Asn Phe Ala His Asn Ser Ser Thr
    130                 135                 140

Thr Thr Phe Gln Gln Ala Ser Thr Asp Ile Glu Trp Asn Ile Ser Gln
145                 150                 155                 160

Pro Val Leu Val Pro Arg Lys Gln Val Val Ala Thr Leu Val Ile
                165                 170                 175

Met Gly Gly Asn Phe Thr Ile Pro Met Asp Leu Met Thr Thr Ile Asp
            180                 185                 190

Ser Thr Glu His Tyr Ser Gly Tyr Pro Ile Leu Thr Trp Ile Ser Ser
        195                 200                 205

Pro Asp Asn Ser Tyr Asn Gly Pro Phe Met Ser Trp Tyr Phe Ala Asn
    210                 215                 220

Trp Pro Asn Leu Pro Ser Gly Phe Gly Pro Leu Asn Ser Asp Asn Thr
225                 230                 235                 240

Val Thr Tyr Thr Gly Ser Val Val Ser Gln Val Ser Ala Gly Val Tyr
                245                 250                 255

Ala Thr Val Arg Phe Asp Gln Tyr Asp Ile His Asn Leu Arg Thr Ile
            260                 265                 270

Glu Lys Thr Trp Tyr Ala Arg His Ala Thr Leu Ala Asn Gly Lys Lys
        275                 280                 285
```

Ile Ser Ile Asn Asn Val Thr Glu Met Ala Pro Thr Ser Pro Ile Lys
            290                 295                 300

Thr Asn
305

<210> SEQ ID NO 67
<211> LENGTH: 306
<212> TYPE: PRT
<213> ORGANISM: Artificial Sequence
<220> FEATURE:
<223> OTHER INFORMATION: engineered

<400> SEQUENCE: 67

Met Ala Ile Leu Asp Leu Lys Ser Leu Val Leu Asn Ala Ile Asn Tyr
 1               5                  10                  15

Trp Gly Pro Lys Asn Asn Gly Ile Gln Gly Gly Asp Phe Gly Tyr
                20                  25                  30

Pro Ile Ser Glu Lys Gln Ile Asp Thr Ser Ile Ile Thr Ser Thr His
            35                  40                  45

Pro Arg Leu Ile Pro His Asp Leu Thr Ile Pro Gln Asn Leu Glu Thr
    50                  55                  60

Ile Phe Thr Thr Thr Gln Val Leu Thr Asn Asn Thr Asp Leu Gln Gln
65                  70                  75                  80

Ser Gln Thr Val Ser Phe Ala Lys Lys Thr Thr Thr Thr Thr Ala Thr
                85                  90                  95

Ser Thr Thr Asn Gly Trp Thr Glu Gly Gly Lys Ile Ser Asp Thr Leu
            100                 105                 110

Glu Glu Lys Val Ser Val Ser Ile Pro Phe Ile Gly Glu Gly Gly Gly
        115                 120                 125

Lys Asn Ser Thr Thr Ile Glu Ala Asn Phe Ala His Asn Ser Ser Thr
130                 135                 140

Thr Thr Phe Gln Gln Ala Ser Thr Asp Ile Glu Trp Asn Ile Ser Gln
145                 150                 155                 160

Pro Val Leu Val Pro Pro Arg Lys Gln Val Val Ala Thr Leu Val Ile
                165                 170                 175

Met Gly Gly Asn Phe Thr Ile Pro Met Asp Leu Met Thr Thr Ile Asp
            180                 185                 190

Ser Thr Glu His Tyr Ser Gly Tyr Pro Ile Leu Thr Trp Ile Ser Ser
        195                 200                 205

Pro Asp Asn Ser Tyr Asn Gly Pro Phe Met Ser Trp Tyr Phe Ala Asn
    210                 215                 220

Trp Pro Asn Leu Pro Ser Gly Phe Gly Pro Leu Asn Ser Asp Asn Thr
225                 230                 235                 240

Val Thr Tyr Thr Gly Ser Val Val Ser Gln Val Ser Ala Gly Val Tyr
                245                 250                 255

Ala Thr Val Arg Phe Asp Gln Tyr Asp Ile His Asn Leu Arg Thr Ile
            260                 265                 270

Glu Lys Thr Trp Tyr Ala Arg His Ala Thr Leu His Asn Gly Lys Lys
        275                 280                 285

Ile Ser Ile Asn Asn Val Thr Glu Ala Ala Pro Thr Ser Pro Ile Lys
    290                 295                 300

Thr Asn
305

<210> SEQ ID NO 68
<211> LENGTH: 306

-continued

```
<212> TYPE: PRT
<213> ORGANISM: Artificial Sequence
<220> FEATURE:
<223> OTHER INFORMATION: engineered

<400> SEQUENCE: 68
```

| Met | Ala | Ile | Leu | Asp | Leu | Lys | Ser | Leu | Val | Leu | Asn | Ala | Ile | Asn | Tyr |
|---|---|---|---|---|---|---|---|---|---|---|---|---|---|---|---|
| 1 | | | | 5 | | | | | 10 | | | | | 15 | |

| Trp | Gly | Pro | Lys | Asn | Asn | Asn | Gly | Ile | Gln | Gly | Gly | Asp | Phe | Gly | Tyr |
| | | | 20 | | | | | 25 | | | | | 30 | | |

| Pro | Ile | Ser | Glu | Lys | Gln | Ile | Asp | Thr | Ser | Ile | Ile | Thr | Ser | Thr | His |
| | | | 35 | | | | | 40 | | | | | 45 | | |

| Pro | Arg | Leu | Ile | Pro | His | Asp | Leu | Thr | Ile | Pro | Gln | Asn | Leu | Glu | Thr |
| | 50 | | | | | 55 | | | | | 60 | | | | |

| Ile | Phe | Thr | Thr | Thr | Gln | Val | Leu | Thr | Asn | Asn | Thr | Asp | Leu | Gln | Gln |
| 65 | | | | | 70 | | | | | 75 | | | | | 80 |

| Ser | Gln | Thr | Val | Ser | Phe | Ala | Lys | Lys | Thr | Thr | Thr | Thr | Ser | Thr |
| | | | | 85 | | | | | 90 | | | | | 95 |

| Ser | Thr | Thr | Asn | Gly | Trp | Thr | Glu | Gly | Lys | Ile | Ser | Asp | Thr | Leu |
| | | | 100 | | | | | 105 | | | | | 110 | |

| Glu | Glu | Lys | Val | Ser | Val | Ser | Ile | Pro | Phe | Ile | Gly | Glu | Gly | Gly |
| | | 115 | | | | | 120 | | | | | 125 | | |

| Lys | Asn | Ser | Thr | Thr | Ile | Glu | Ala | Asn | Phe | Ala | His | Asn | Ser | Ser | Thr |
| | 130 | | | | | 135 | | | | | 140 | | | | |

| Thr | Thr | Ala | Gln | Gln | Ala | Ser | Thr | Asp | Ile | Glu | Trp | Asn | Ile | Ser | Gln |
| 145 | | | | | 150 | | | | | 155 | | | | | 160 |

| Pro | Val | Leu | Val | Pro | Pro | Arg | Lys | Gln | Val | Val | Ala | Thr | Leu | Val | Ile |
| | | | | 165 | | | | | 170 | | | | | 175 | |

| Met | Gly | Gly | Asn | Phe | Thr | Ile | Pro | Met | Asp | Leu | Met | Thr | Thr | Ile | Asp |
| | | | 180 | | | | | 185 | | | | | 190 | | |

| Ser | Thr | Glu | His | Tyr | Ser | Gly | Tyr | Pro | Ile | Leu | Thr | Trp | Ile | Ser | Ser |
| | | | 195 | | | | | 200 | | | | | 205 | | |

| Pro | Asp | Asn | Ser | Tyr | Asn | Gly | Pro | Phe | Met | Ser | Trp | Tyr | Phe | Ala | Asn |
| | 210 | | | | | 215 | | | | | 220 | | | | |

| Trp | Pro | Asn | Leu | Pro | Ser | Gly | Phe | Gly | Pro | Leu | Asn | Ser | Asp | Asn | Thr |
| 225 | | | | | 230 | | | | | 235 | | | | | 240 |

| Val | Thr | Tyr | Thr | Gly | Ser | Val | Val | Ser | Gln | Val | Ser | Ala | Gly | Val | Tyr |
| | | | | 245 | | | | | 250 | | | | | 255 | |

| Ala | Thr | Val | Arg | Phe | Asp | Gln | Tyr | Asp | Ile | His | Asn | Leu | Arg | Thr | Ala |
| | | | 260 | | | | | 265 | | | | | 270 | | |

| Glu | Lys | Thr | Trp | Tyr | Ala | Arg | His | Ala | Thr | Leu | His | Asn | Gly | Lys | Lys |
| | | | 275 | | | | | 280 | | | | | 285 | | |

| Ile | Ser | Ile | Asn | Asn | Val | Thr | Glu | Met | Ala | Pro | Thr | Ser | Pro | Ile | Lys |
| | 290 | | | | | 295 | | | | | 300 | | | | |

| Thr | Asn |
| 305 | |

```
<210> SEQ ID NO 69
<211> LENGTH: 306
<212> TYPE: PRT
<213> ORGANISM: Artificial Sequence
<220> FEATURE:
<223> OTHER INFORMATION: engineered

<400> SEQUENCE: 69
```

| Met | Ala | Ile | Leu | Asp | Leu | Lys | Ser | Leu | Val | Leu | Asn | Ala | Ile | Asn | Tyr |
|---|---|---|---|---|---|---|---|---|---|---|---|---|---|---|---|
| 1 | | | | 5 | | | | | 10 | | | | | 15 | |

Trp Gly Pro Lys Asn Asn Asn Gly Ile Gln Gly Gly Asp Phe Gly Tyr
            20                  25                  30

Pro Ile Ser Glu Lys Gln Ile Asp Thr Ser Ile Ile Thr Ser Thr His
            35                  40                  45

Pro Arg Leu Ile Pro His Asp Leu Thr Ile Pro Gln Asn Leu Glu Thr
        50                  55                  60

Ile Phe Thr Thr Thr Gln Val Leu Thr Asn Asn Thr Asp Leu Gln Gln
65                  70                  75                  80

Ser Gln Thr Val Ser Phe Ala Lys Lys Thr Thr Thr Thr Ala Thr
                85                  90                  95

Ser Thr Thr Asn Gly Trp Thr Glu Gly Gly Lys Ile Ser Asp Thr Leu
            100                 105                 110

Glu Glu Lys Val Ser Val Ser Ile Pro Phe Ile Gly Glu Gly Gly Gly
            115                 120                 125

Lys Asn Ser Thr Thr Ile Glu Ala Asn Phe Ala His Asn Ser Ser Thr
130                 135                 140

Thr Thr Phe Gln Gln Ala Ser Thr Asp Ile Glu Trp Asn Ile Ser Gln
145                 150                 155                 160

Pro Val Leu Val Pro Pro Arg Lys Gln Val Val Ala Thr Leu Val Ile
                165                 170                 175

Met Gly Gly Asn Phe Thr Ile Pro Met Asp Leu Met Thr Thr Ile Asp
            180                 185                 190

Ser Thr Glu His Tyr Ser Gly Tyr Pro Ile Leu Thr Trp Ile Ser Ser
            195                 200                 205

Pro Asp Asn Ser Tyr Asn Gly Pro Phe Met Ser Trp Tyr Phe Ala Asn
        210                 215                 220

Trp Pro Asn Leu Pro Ser Gly Phe Gly Pro Leu Asn Ser Asp Asn Thr
225                 230                 235                 240

Val Thr Tyr Ala Gly Ser Val Val Ser Gln Val Ser Ala Gly Val Tyr
                245                 250                 255

Ala Thr Val Arg Phe Asp Gln Tyr Asp Ile His Asn Leu Arg Thr Ile
            260                 265                 270

Glu Lys Thr Trp Tyr Ala Arg His Ala Thr Leu His Asn Gly Lys Lys
            275                 280                 285

Ile Ser Ile Asn Asn Val Thr Glu Met Ala Pro Thr Ser Pro Ile Lys
        290                 295                 300

Thr Asn
305

<210> SEQ ID NO 70
<211> LENGTH: 306
<212> TYPE: PRT
<213> ORGANISM: Artificial Sequence
<220> FEATURE:
<223> OTHER INFORMATION: engineered

<400> SEQUENCE: 70

Met Ala Ile Leu Asp Leu Lys Ser Leu Val Leu Asn Ala Ile Asn Tyr
1               5                   10                  15

Trp Gly Pro Lys Asn Asn Asn Gly Ile Gln Gly Gly Asp Phe Gly Tyr
            20                  25                  30

Pro Ile Ser Glu Lys Gln Ile Asp Thr Ser Ile Ile Thr Ser Thr His
            35                  40                  45

Pro Arg Leu Ile Pro His Asp Leu Thr Ile Pro Gln Asn Leu Glu Thr
        50                  55                  60

Ile Phe Thr Thr Thr Gln Val Leu Thr Asn Asn Thr Asp Leu Gln Gln
65                  70                  75                  80

Ser Gln Thr Val Ser Phe Ala Lys Lys Thr Thr Thr Thr Ser Thr
            85                  90                  95

Ser Thr Thr Asn Gly Trp Thr Glu Gly Gly Lys Ile Ser Asp Thr Leu
            100                 105                 110

Glu Glu Lys Val Ser Val Ser Ile Pro Phe Ile Gly Glu Gly Gly Gly
            115                 120                 125

Lys Asn Ser Thr Thr Ile Glu Ala Asn Phe Ala His Asn Ser Ser Thr
            130                 135                 140

Thr Thr Ala Gln Gln Ala Ser Thr Asp Ile Glu Trp Asn Ile Ser Gln
145                 150                 155                 160

Pro Val Leu Val Pro Pro Arg Lys Gln Val Val Ala Thr Leu Ala Ile
                165                 170                 175

Met Gly Gly Asn Phe Thr Ile Pro Met Asp Leu Met Thr Thr Ile Asp
                180                 185                 190

Ser Thr Glu His Tyr Ser Gly Tyr Pro Ile Leu Thr Trp Ile Ser Ser
            195                 200                 205

Pro Asp Asn Ser Tyr Asn Gly Pro Phe Met Ser Trp Tyr Phe Ala Asn
            210                 215                 220

Trp Pro Asn Leu Pro Ser Gly Phe Gly Pro Leu Asn Ser Asp Asn Thr
225                 230                 235                 240

Val Thr Tyr Thr Gly Ser Val Val Ser Gln Val Ser Ala Gly Val Tyr
                245                 250                 255

Ala Thr Val Arg Phe Asp Gln Tyr Asp Ile His Asn Leu Arg Thr Ile
            260                 265                 270

Glu Lys Thr Trp Tyr Ala Arg His Ala Thr Leu His Asn Gly Lys Lys
            275                 280                 285

Ile Ser Ile Asn Asn Val Thr Glu Met Ala Pro Thr Ser Pro Ile Lys
            290                 295                 300

Thr Asn
305

<210> SEQ ID NO 71
<211> LENGTH: 306
<212> TYPE: PRT
<213> ORGANISM: Artificial Sequence
<220> FEATURE:
<223> OTHER INFORMATION: engineered

<400> SEQUENCE: 71

Met Ala Ile Leu Asp Leu Lys Ser Leu Val Leu Asn Ala Ile Asn Tyr
1               5                   10                  15

Trp Gly Pro Lys Asn Asn Asn Gly Ile Gln Gly Gly Asp Phe Gly Tyr
            20                  25                  30

Pro Ile Ser Glu Lys Gln Ile Asp Thr Ser Ile Thr Ser Thr His
            35                  40                  45

Pro Arg Leu Ile Pro His Asp Leu Thr Ile Pro Gln Asn Leu Glu Thr
        50                  55                  60

Ile Phe Thr Thr Thr Gln Val Leu Thr Asn Asn Thr Asp Leu Gln Gln
65                  70                  75                  80

Ser Gln Thr Val Ser Phe Ala Lys Lys Thr Thr Thr Thr Ser Thr
            85                  90                  95

Ser Thr Thr Asn Gly Trp Thr Glu Gly Gly Lys Ile Ser Asp Thr Leu
            100                 105                 110

```
Glu Glu Lys Val Ser Val Ser Ile Pro Phe Ile Gly Glu Gly Gly Gly
            115                 120                 125

Lys Asn Ser Thr Thr Ile Glu Ala Asn Phe Ala His Asn Ser Ser Thr
    130                 135                 140

Thr Thr Ala Gln Gln Ala Ser Thr Asp Ile Glu Trp Asn Ile Ala Gln
145                 150                 155                 160

Pro Val Leu Val Pro Arg Lys Gln Val Val Ala Thr Leu Val Ile
                165                 170                 175

Met Gly Gly Asn Phe Thr Ile Pro Met Asp Leu Met Thr Thr Ile Asp
                180                 185                 190

Ser Thr Glu His Tyr Ser Gly Tyr Pro Ile Leu Thr Trp Ile Ser Ser
            195                 200                 205

Pro Asp Asn Ser Tyr Asn Gly Pro Phe Met Ser Trp Tyr Phe Ala Asn
            210                 215                 220

Trp Pro Asn Leu Pro Ser Gly Phe Gly Pro Leu Asn Ser Asp Asn Thr
225                 230                 235                 240

Val Thr Tyr Thr Gly Ser Val Val Ser Gln Val Ser Ala Gly Val Tyr
                245                 250                 255

Ala Thr Val Arg Phe Asp Gln Tyr Asp Ile His Asn Leu Arg Thr Ile
                260                 265                 270

Glu Lys Thr Trp Tyr Ala Arg His Ala Thr Leu His Asn Gly Lys Lys
            275                 280                 285

Ile Ser Ile Asn Asn Val Thr Glu Met Ala Pro Thr Ser Pro Ile Lys
            290                 295                 300

Thr Asn
305

<210> SEQ ID NO 72
<211> LENGTH: 306
<212> TYPE: PRT
<213> ORGANISM: Artificial Sequence
<220> FEATURE:
<223> OTHER INFORMATION: engineered

<400> SEQUENCE: 72

Met Ala Ile Leu Asp Leu Lys Ser Leu Val Leu Asn Ala Ile Asn Tyr
1               5                   10                  15

Trp Gly Pro Lys Asn Asn Asn Gly Ile Gln Gly Gly Asp Phe Gly Tyr
            20                  25                  30

Pro Ile Ser Glu Lys Gln Ile Asp Thr Ser Ile Thr Ser Thr His
            35                  40                  45

Pro Arg Leu Ile Pro His Asp Leu Thr Ile Pro Gln Asn Leu Glu Thr
50                  55                  60

Ile Phe Thr Thr Thr Gln Val Leu Thr Asn Asn Thr Asp Leu Gln Gln
65                  70                  75                  80

Ser Gln Thr Val Ser Phe Ala Lys Lys Thr Thr Thr Thr Ala Thr
                85                  90                  95

Ser Thr Thr Asn Gly Trp Thr Glu Gly Gly Lys Ile Ser Asp Thr Leu
            100                 105                 110

Glu Glu Lys Val Ser Val Ser Ile Pro Phe Ile Gly Glu Gly Gly Gly
            115                 120                 125

Lys Asn Ser Thr Thr Ile Glu Ala Asn Phe Ala His Asn Ser Ser Thr
    130                 135                 140

Thr Thr Ala Gln Gln Ala Ser Thr Asp Ile Glu Trp Asn Ile Ser Gln
145                 150                 155                 160
```

-continued

```
Pro Val Leu Val Pro Pro Arg Lys Gln Val Val Ala Thr Leu Val Ile
            165                 170                 175

Met Gly Gly Asn Phe Thr Ile Pro Met Asp Leu Met Thr Thr Ile Asp
        180                 185                 190

Ser Thr Glu His Tyr Ser Gly Tyr Pro Ile Leu Thr Trp Ile Ser Ser
    195                 200                 205

Pro Asp Asn Ser Tyr Asn Gly Pro Phe Met Ser Trp Tyr Phe Ala Asn
210                 215                 220

Trp Pro Asn Leu Pro Ser Gly Phe Gly Pro Leu Asn Ser Asp Asn Thr
225                 230                 235                 240

Val Thr Tyr Thr Gly Ser Val Val Ser Gln Val Ser Ala Gly Val Tyr
                245                 250                 255

Ala Thr Val Arg Phe Asp Gln Tyr Asp Ile His Asn Leu Arg Thr Ile
            260                 265                 270

Glu Lys Thr Trp Tyr Ala Arg His Ala Thr Leu His Asn Gly Lys Lys
        275                 280                 285

Ile Ser Ile Asn Asn Val Thr Glu Met Ala Pro Thr Ser Pro Ile Lys
    290                 295                 300

Thr Asn
305

<210> SEQ ID NO 73
<211> LENGTH: 306
<212> TYPE: PRT
<213> ORGANISM: Artificial Sequence
<220> FEATURE:
<223> OTHER INFORMATION: engineered

<400> SEQUENCE: 73

Met Ala Ile Leu Asp Leu Lys Ser Leu Val Leu Asn Ala Ile Asn Tyr
1               5                   10                  15

Trp Gly Pro Lys Asn Asn Asn Gly Ile Gln Gly Gly Asp Phe Gly Tyr
            20                  25                  30

Pro Ile Ser Glu Lys Gln Ile Asp Thr Ser Ile Ile Thr Ser Thr His
        35                  40                  45

Pro Arg Leu Ile Pro His Asp Leu Thr Ile Pro Gln Asn Leu Glu Thr
    50                  55                  60

Ile Phe Thr Thr Thr Gln Val Leu Thr Asn Asn Thr Asp Leu Gln Gln
65                  70                  75                  80

Ser Gln Thr Val Ser Phe Ala Lys Lys Thr Thr Thr Thr Ser Thr
                85                  90                  95

Ser Thr Thr Asn Gly Trp Thr Glu Gly Gly Lys Ile Ser Asp Thr Leu
            100                 105                 110

Glu Glu Lys Val Ser Val Ser Ile Pro Phe Ile Gly Glu Gly Gly Gly
        115                 120                 125

Lys Asn Ser Thr Thr Ile Glu Ala Asn Phe Ala His Asn Ser Ser Thr
    130                 135                 140

Thr Thr Ala Gln Gln Ala Ser Thr Asp Ile Glu Trp Asn Ile Ser Gln
145                 150                 155                 160

Pro Val Leu Val Pro Pro Arg Lys Gln Val Val Ala Thr Leu Val Ile
                165                 170                 175

Met Gly Gly Asn Phe Thr Ile Pro Met Asp Ala Met Thr Thr Ile Asp
            180                 185                 190

Ser Thr Glu His Tyr Ser Gly Tyr Pro Ile Leu Thr Trp Ile Ser Ser
        195                 200                 205
```

```
Pro Asp Asn Ser Tyr Asn Gly Pro Phe Met Ser Trp Tyr Phe Ala Asn
    210                 215                 220

Trp Pro Asn Leu Pro Ser Gly Phe Gly Pro Leu Asn Ser Asp Asn Thr
225                 230                 235                 240

Val Thr Tyr Thr Gly Ser Val Val Ser Gln Val Ser Ala Gly Val Tyr
                245                 250                 255

Ala Thr Val Arg Phe Asp Gln Tyr Asp Ile His Asn Leu Arg Thr Ile
            260                 265                 270

Glu Lys Thr Trp Tyr Ala Arg His Ala Thr Leu His Asn Gly Lys Lys
            275                 280                 285

Ile Ser Ile Asn Asn Val Thr Glu Met Ala Pro Thr Ser Pro Ile Lys
    290                 295                 300

Thr Asn
305

<210> SEQ ID NO 74
<211> LENGTH: 306
<212> TYPE: PRT
<213> ORGANISM: Artificial Sequence
<220> FEATURE:
<223> OTHER INFORMATION: engineered

<400> SEQUENCE: 74

Met Ala Ile Leu Asp Leu Lys Ser Leu Val Leu Asn Ala Ile Asn Tyr
1               5                   10                  15

Trp Gly Pro Lys Asn Asn Gly Ile Gln Gly Gly Asp Phe Gly Tyr
                20                  25                  30

Pro Ile Ser Glu Lys Gln Ile Asp Thr Ser Ile Ile Thr Ser Thr His
            35                  40                  45

Pro Arg Leu Ile Pro His Asp Leu Thr Ile Pro Gln Asn Leu Glu Thr
        50                  55                  60

Ile Phe Thr Thr Thr Gln Val Leu Thr Asn Asn Thr Asp Leu Gln Gln
65                  70                  75                  80

Ser Gln Thr Val Ser Phe Ala Lys Lys Thr Thr Thr Ala Thr Ser Thr
                85                  90                  95

Ser Thr Thr Asn Gly Trp Thr Glu Gly Gly Lys Ile Ser Asp Thr Leu
                100                 105                 110

Glu Glu Lys Val Ser Val Ser Ile Pro Phe Ile Gly Glu Gly Gly Gly
            115                 120                 125

Lys Asn Ser Thr Thr Ile Glu Ala Asn Phe Ala His Asn Ser Ser Thr
        130                 135                 140

Thr Thr Phe Gln Gln Ala Ser Thr Asp Ile Glu Trp Asn Ile Ser Gln
145                 150                 155                 160

Pro Val Leu Val Pro Pro Arg Lys Gln Val Val Ala Thr Leu Val Ile
                165                 170                 175

Met Gly Gly Asn Phe Ala Ile Pro Met Asp Leu Met Thr Thr Ile Asp
                180                 185                 190

Ser Thr Glu His Tyr Ser Gly Tyr Pro Ile Leu Thr Trp Ile Ser Ser
            195                 200                 205

Pro Asp Asn Ser Tyr Asn Gly Pro Phe Met Ser Trp Tyr Phe Ala Asn
        210                 215                 220

Trp Pro Asn Leu Pro Ser Gly Phe Gly Pro Leu Asn Ser Asp Asn Thr
225                 230                 235                 240

Val Thr Tyr Thr Gly Ser Val Val Ser Gln Val Ser Ala Gly Val Tyr
                245                 250                 255
```

```
Ala Thr Val Arg Phe Asp Gln Tyr Asp Ile His Asn Leu Arg Thr Ile
            260                 265                 270

Glu Lys Thr Trp Tyr Ala Arg His Ala Thr Leu His Asn Gly Lys Lys
        275                 280                 285

Ile Ser Ile Asn Asn Val Thr Glu Met Ala Pro Thr Ser Pro Ile Lys
    290                 295                 300

Thr Asn
305

<210> SEQ ID NO 75
<211> LENGTH: 306
<212> TYPE: PRT
<213> ORGANISM: Artificial Sequence
<220> FEATURE:
<223> OTHER INFORMATION: engineered

<400> SEQUENCE: 75

Met Ala Ile Leu Asp Leu Lys Ser Leu Val Leu Asn Ala Ile Asn Tyr
1               5                   10                  15

Trp Gly Pro Lys Asn Asn Asn Gly Ile Gln Gly Gly Asp Phe Gly Tyr
            20                  25                  30

Pro Ile Ser Glu Lys Gln Ile Asp Thr Ser Ile Ile Thr Ser Thr His
        35                  40                  45

Pro Arg Leu Ile Pro His Asp Leu Thr Ile Pro Gln Asn Leu Glu Thr
    50                  55                  60

Ile Phe Thr Thr Thr Gln Val Leu Thr Asn Thr Asp Leu Gln Gln
65                  70                  75                  80

Ser Gln Thr Val Ser Phe Ala Lys Lys Thr Thr Thr Thr Ser Thr
            85                  90                  95

Ser Thr Thr Asn Gly Trp Thr Glu Gly Gly Lys Ile Ser Asp Thr Leu
            100                 105                 110

Glu Glu Lys Val Ser Val Ser Ile Pro Phe Ile Gly Glu Gly Gly Gly
        115                 120                 125

Lys Asn Ser Thr Thr Ile Glu Ala Asn Phe Ala His Asn Ser Ser Thr
    130                 135                 140

Thr Thr Ala Gln Gln Ala Ser Thr Asp Ile Glu Trp Asn Ile Ser Gln
145                 150                 155                 160

Pro Val Leu Val Pro Arg Lys Gln Val Val Ala Thr Leu Val Ile
            165                 170                 175

Met Gly Gly Asn Phe Thr Ile Pro Met Asp Leu Met Thr Thr Ile Asp
            180                 185                 190

Ser Thr Glu His Tyr Ser Gly Tyr Pro Ile Leu Thr Trp Ile Ser Ser
        195                 200                 205

Pro Asp Asn Ser Tyr Asn Gly Pro Phe Met Ser Trp Tyr Phe Ala Asn
    210                 215                 220

Trp Pro Asn Leu Pro Ser Gly Phe Gly Pro Leu Asn Ser Asp Asn Thr
225                 230                 235                 240

Val Ala Tyr Thr Gly Ser Val Val Ser Gln Val Ser Ala Gly Val Tyr
            245                 250                 255

Ala Thr Val Arg Phe Asp Gln Tyr Asp Ile His Asn Leu Arg Thr Ile
            260                 265                 270

Glu Lys Thr Trp Tyr Ala Arg His Ala Thr Leu His Asn Gly Lys Lys
        275                 280                 285

Ile Ser Ile Asn Asn Val Thr Glu Met Ala Pro Thr Ser Pro Ile Lys
    290                 295                 300
```

Thr Asn
305

<210> SEQ ID NO 76
<211> LENGTH: 306
<212> TYPE: PRT
<213> ORGANISM: Artificial Sequence
<220> FEATURE:
<223> OTHER INFORMATION: engineered

<400> SEQUENCE: 76

Met Ala Ile Leu Asp Leu Lys Ser Leu Val Leu Asn Ala Ile Asn Tyr
1               5                   10                  15

Trp Gly Pro Lys Asn Asn Asn Gly Ile Gln Gly Gly Asp Phe Gly Tyr
            20                  25                  30

Pro Ile Ser Glu Lys Gln Ile Asp Thr Ser Ile Ile Thr Ser Thr His
        35                  40                  45

Pro Arg Leu Ile Pro His Asp Leu Thr Ile Pro Gln Asn Leu Glu Thr
50                  55                  60

Ile Phe Thr Thr Thr Gln Val Leu Thr Asn Asn Thr Asp Leu Gln Gln
65                  70                  75                  80

Ser Gln Thr Val Ser Phe Ala Lys Lys Thr Thr Thr Ala Thr Ser Thr
                85                  90                  95

Ser Thr Thr Asn Gly Trp Thr Glu Gly Gly Lys Ile Ser Asp Thr Leu
            100                 105                 110

Glu Glu Lys Val Ser Val Ser Ile Pro Phe Ile Gly Glu Gly Gly Gly
        115                 120                 125

Lys Asn Ser Thr Thr Ile Glu Ala Asn Phe Ala His Asn Ser Ser Thr
130                 135                 140

Thr Thr Phe Gln Gln Ala Ser Thr Asp Ile Glu Trp Asn Ile Ser Gln
145                 150                 155                 160

Pro Val Leu Val Pro Pro Arg Lys Gln Val Val Ala Thr Leu Val Ile
                165                 170                 175

Met Gly Gly Asn Phe Thr Ile Pro Met Asp Leu Met Thr Thr Ile Asp
            180                 185                 190

Ser Thr Glu His Tyr Ser Gly Tyr Pro Ile Leu Thr Trp Ile Ser Ser
        195                 200                 205

Pro Asp Asn Ser Tyr Asn Gly Pro Phe Met Ser Trp Tyr Phe Ala Asn
210                 215                 220

Trp Pro Asn Leu Pro Ser Gly Phe Gly Pro Leu Asn Ser Asp Asn Thr
225                 230                 235                 240

Val Thr Tyr Thr Gly Ala Val Val Ser Gln Val Ser Ala Gly Val Tyr
                245                 250                 255

Ala Thr Val Arg Phe Asp Gln Tyr Asp Ile His Asn Leu Arg Thr Ile
            260                 265                 270

Glu Lys Thr Trp Tyr Ala Arg His Ala Thr Leu His Asn Gly Lys Lys
        275                 280                 285

Ile Ser Ile Asn Asn Val Thr Glu Met Ala Pro Thr Ser Pro Ile Lys
290                 295                 300

Thr Asn
305

<210> SEQ ID NO 77
<211> LENGTH: 306
<212> TYPE: PRT
<213> ORGANISM: Artificial Sequence
<220> FEATURE:
<223> OTHER INFORMATION: engineered

<400> SEQUENCE: 77

Met Ala Ile Leu Asp Leu Lys Ser Leu Val Leu Asn Ala Ile Asn Tyr
1               5                   10                  15

Trp Gly Pro Lys Asn Asn Asn Gly Ile Gln Gly Gly Asp Phe Gly Tyr
            20                  25                  30

Pro Ile Ser Glu Lys Gln Ile Asp Thr Ser Ile Ile Thr Ser Thr His
        35                  40                  45

Pro Arg Leu Ile Pro His Asp Leu Thr Ile Pro Gln Asn Leu Glu Thr
    50                  55                  60

Ile Phe Thr Thr Thr Gln Val Leu Thr Asn Asn Thr Asp Leu Gln Gln
65                  70                  75                  80

Ser Gln Thr Val Ser Phe Ala Lys Lys Thr Thr Thr Ala Thr Ser Thr
                85                  90                  95

Ser Thr Thr Asn Gly Trp Thr Glu Gly Gly Lys Ile Ser Asp Thr Leu
            100                 105                 110

Glu Glu Lys Val Ser Val Ser Ile Pro Phe Ile Gly Glu Gly Gly Gly
        115                 120                 125

Lys Asn Ser Thr Thr Ile Glu Ala Asn Phe Ala His Asn Ser Ser Thr
    130                 135                 140

Thr Thr Phe Gln Ala Ala Ser Thr Asp Ile Glu Trp Asn Ile Ser Gln
145                 150                 155                 160

Pro Val Leu Val Pro Pro Arg Lys Gln Val Ala Thr Leu Val Ile
                165                 170                 175

Met Gly Gly Asn Phe Thr Ile Pro Met Asp Leu Met Thr Thr Ile Asp
            180                 185                 190

Ser Thr Glu His Tyr Ser Gly Tyr Pro Ile Leu Thr Trp Ile Ser Ser
        195                 200                 205

Pro Asp Asn Ser Tyr Asn Gly Pro Phe Met Ser Trp Tyr Phe Ala Asn
    210                 215                 220

Trp Pro Asn Leu Pro Ser Gly Phe Gly Pro Leu Asn Ser Asp Asn Thr
225                 230                 235                 240

Val Thr Tyr Thr Gly Ser Val Val Ser Gln Val Ser Ala Gly Val Tyr
                245                 250                 255

Ala Thr Val Arg Phe Asp Gln Tyr Asp Ile His Asn Leu Arg Thr Ile
            260                 265                 270

Glu Lys Thr Trp Tyr Ala Arg His Ala Thr Leu His Asn Gly Lys Lys
        275                 280                 285

Ile Ser Ile Asn Asn Val Thr Glu Met Ala Pro Thr Ser Pro Ile Lys
    290                 295                 300

Thr Asn
305

<210> SEQ ID NO 78
<211> LENGTH: 306
<212> TYPE: PRT
<213> ORGANISM: Artificial Sequence
<220> FEATURE:
<223> OTHER INFORMATION: engineered

<400> SEQUENCE: 78

Met Ala Ile Leu Asp Leu Lys Ser Leu Val Leu Asn Ala Ile Asn Tyr
1               5                   10                  15

Trp Gly Pro Lys Asn Asn Asn Gly Ile Gln Gly Gly Asp Phe Gly Tyr

```
                20                  25                  30
Pro Ile Ser Glu Lys Gln Ile Asp Thr Ser Ile Ile Thr Ser Thr His
            35                  40                  45

Pro Arg Leu Ile Pro His Asp Leu Thr Ile Pro Gln Asn Leu Glu Thr
        50                  55                  60

Ile Phe Thr Thr Thr Gln Val Leu Thr Asn Asn Thr Asp Leu Gln Gln
65                  70                  75                  80

Ser Gln Thr Val Ser Phe Ala Lys Lys Thr Thr Thr Ala Thr Ser Thr
                85                  90                  95

Ser Thr Thr Asn Gly Trp Thr Glu Gly Gly Lys Ile Ser Asp Thr Leu
            100                 105                 110

Glu Glu Lys Val Ser Val Ser Ile Pro Phe Ile Gly Glu Gly Gly Gly
        115                 120                 125

Lys Asn Ser Thr Thr Ile Glu Ala Asn Phe Ala His Asn Ser Ser Thr
130                 135                 140

Thr Thr Phe Gln Gln Ala Ala Thr Asp Ile Glu Trp Asn Ile Ser Gln
145                 150                 155                 160

Pro Val Leu Val Pro Pro Arg Lys Gln Val Val Ala Thr Leu Val Ile
                165                 170                 175

Met Gly Gly Asn Phe Thr Ile Pro Met Asp Leu Met Thr Thr Ile Asp
            180                 185                 190

Ser Thr Glu His Tyr Ser Gly Tyr Pro Ile Leu Thr Trp Ile Ser Ser
        195                 200                 205

Pro Asp Asn Ser Tyr Asn Gly Pro Phe Met Ser Trp Tyr Phe Ala Asn
210                 215                 220

Trp Pro Asn Leu Pro Ser Gly Phe Gly Pro Leu Asn Ser Asp Asn Thr
225                 230                 235                 240

Val Thr Tyr Thr Gly Ser Val Val Ser Gln Val Ser Ala Gly Val Tyr
                245                 250                 255

Ala Thr Val Arg Phe Asp Gln Tyr Asp Ile His Asn Leu Arg Thr Ile
            260                 265                 270

Glu Lys Thr Trp Tyr Ala Arg His Ala Thr Leu His Asn Gly Lys Lys
        275                 280                 285

Ile Ser Ile Asn Asn Val Thr Glu Met Ala Pro Thr Ser Pro Ile Lys
290                 295                 300

Thr Asn
305

<210> SEQ ID NO 79
<211> LENGTH: 306
<212> TYPE: PRT
<213> ORGANISM: Artificial Sequence
<220> FEATURE:
<223> OTHER INFORMATION: engineered

<400> SEQUENCE: 79

Met Ala Ile Leu Asp Leu Lys Ser Leu Val Leu Asn Ala Ile Asn Tyr
1               5                   10                  15

Trp Gly Pro Lys Asn Asn Gly Ile Gln Gly Gly Asp Phe Gly Tyr
            20                  25                  30

Pro Ile Ser Glu Lys Gln Ile Asp Thr Ser Ile Ile Thr Ser Thr His
        35                  40                  45

Pro Arg Leu Ile Pro His Asp Leu Thr Ile Pro Gln Asn Leu Glu Thr
    50                  55                  60

Ile Phe Thr Thr Thr Ala Val Leu Thr Asn Asn Thr Asp Leu Gln Gln
```

```
                65                  70                  75                  80
Ser Gln Thr Val Ser Phe Ala Lys Lys Thr Thr Thr Thr Ser Thr
                    85                  90                  95
Ser Thr Thr Asn Gly Trp Thr Glu Gly Gly Lys Ile Ser Asp Thr Leu
                    100                 105                 110
Glu Glu Lys Val Ser Val Ser Ile Pro Phe Ile Gly Glu Gly Gly Gly
                    115                 120                 125
Lys Asn Ser Thr Thr Ile Glu Ala Asn Phe Ala His Asn Ser Ser Thr
    130                 135                 140
Thr Thr Ala Gln Gln Ala Ser Thr Asp Ile Glu Trp Asn Ile Ser Gln
145                 150                 155                 160
Pro Val Leu Val Pro Pro Arg Lys Gln Val Val Ala Thr Leu Val Ile
                    165                 170                 175
Met Gly Gly Asn Phe Thr Ile Pro Met Asp Leu Met Thr Thr Ile Asp
                180                 185                 190
Ser Thr Glu His Tyr Ser Gly Tyr Pro Ile Leu Thr Trp Ile Ser Ser
                195                 200                 205
Pro Asp Asn Ser Tyr Asn Gly Pro Phe Met Ser Trp Tyr Phe Ala Asn
    210                 215                 220
Trp Pro Asn Leu Pro Ser Gly Phe Gly Pro Leu Asn Ser Asp Asn Thr
225                 230                 235                 240
Val Thr Tyr Thr Gly Ser Val Val Ser Gln Val Ser Ala Gly Val Tyr
                245                 250                 255
Ala Thr Val Arg Phe Asp Gln Tyr Asp Ile His Asn Leu Arg Thr Ile
                260                 265                 270
Glu Lys Thr Trp Tyr Ala Arg His Ala Thr Leu His Asn Gly Lys Lys
            275                 280                 285
Ile Ser Ile Asn Asn Val Thr Glu Met Ala Pro Thr Ser Pro Ile Lys
            290                 295                 300
Thr Asn
305

<210> SEQ ID NO 80
<211> LENGTH: 306
<212> TYPE: PRT
<213> ORGANISM: Artificial Sequence
<220> FEATURE:
<223> OTHER INFORMATION: engineered

<400> SEQUENCE: 80

Met Ala Ile Leu Asp Leu Lys Ser Leu Val Leu Asn Ala Ile Asn Tyr
1               5                   10                  15
Trp Gly Pro Lys Asn Asn Gly Ile Gln Gly Gly Asp Phe Gly Tyr
            20                  25                  30
Pro Ile Ser Glu Lys Gln Ile Asp Thr Ser Ile Ile Thr Ser Thr His
        35                  40                  45
Pro Arg Leu Ile Pro His Asp Leu Thr Ile Pro Gln Asn Leu Glu Thr
    50                  55                  60
Ile Phe Thr Thr Thr Gln Val Leu Thr Asn Asn Thr Asp Leu Gln Gln
65                  70                  75                  80
Ser Gln Thr Val Ser Phe Ala Lys Lys Thr Thr Thr Thr Ala Thr
                85                  90                  95
Ser Thr Thr Asn Gly Trp Thr Glu Gly Gly Lys Ile Ser Asp Thr Leu
                100                 105                 110
Glu Glu Lys Val Ser Val Ser Ile Pro Phe Ile Gly Glu Gly Gly Gly
```

```
            115                 120                 125
Lys Asn Ser Thr Thr Ile Glu Ala Asn Phe Ala His Asn Ser Ser Thr
    130                 135                 140

Thr Thr Phe Ala Gln Ala Ser Thr Asp Ile Glu Trp Asn Ile Ser Gln
145                 150                 155                 160

Pro Val Leu Val Pro Pro Arg Lys Gln Val Val Ala Thr Leu Val Ile
                165                 170                 175

Met Gly Gly Asn Phe Thr Ile Pro Met Asp Leu Met Thr Thr Ile Asp
            180                 185                 190

Ser Thr Glu His Tyr Ser Gly Tyr Pro Ile Leu Thr Trp Ile Ser Ser
        195                 200                 205

Pro Asp Asn Ser Tyr Asn Gly Pro Phe Met Ser Trp Tyr Phe Ala Asn
    210                 215                 220

Trp Pro Asn Leu Pro Ser Gly Phe Gly Pro Leu Asn Ser Asp Asn Thr
225                 230                 235                 240

Val Thr Tyr Thr Gly Ser Val Val Ser Gln Val Ser Ala Gly Val Tyr
                245                 250                 255

Ala Thr Val Arg Phe Asp Gln Tyr Asp Ile His Asn Leu Arg Thr Ile
            260                 265                 270

Glu Lys Thr Trp Tyr Ala Arg His Ala Thr Leu His Asn Gly Lys Lys
        275                 280                 285

Ile Ser Ile Asn Asn Val Thr Glu Met Ala Pro Thr Ser Pro Ile Lys
    290                 295                 300

Thr Asn
305

<210> SEQ ID NO 81
<211> LENGTH: 306
<212> TYPE: PRT
<213> ORGANISM: Artificial Sequence
<220> FEATURE:
<223> OTHER INFORMATION: engineered

<400> SEQUENCE: 81

Met Ala Ile Leu Asp Leu Lys Ser Leu Val Leu Asn Ala Ile Asn Tyr
1               5                   10                  15

Trp Gly Pro Lys Asn Asn Gly Ile Gln Gly Gly Asp Phe Gly Tyr
                20                  25                  30

Pro Ile Ser Glu Lys Gln Ile Asp Thr Ser Ile Ile Thr Ser Thr His
            35                  40                  45

Pro Arg Leu Ile Pro His Asp Leu Thr Ile Pro Gln Asn Leu Glu Thr
        50                  55                  60

Ile Phe Thr Thr Thr Gln Val Leu Thr Asn Asn Thr Asp Leu Gln Gln
65                  70                  75                  80

Ser Gln Thr Val Ser Phe Ala Lys Lys Thr Thr Thr Ala Thr Ser Thr
                85                  90                  95

Ser Thr Thr Asn Gly Trp Thr Glu Gly Gly Lys Ile Ser Asp Thr Leu
            100                 105                 110

Glu Glu Lys Val Ser Val Ser Ile Pro Phe Ile Gly Glu Gly Gly Gly
        115                 120                 125

Lys Asn Ser Thr Thr Ile Glu Ala Asn Phe Ala His Asn Ser Ser Thr
    130                 135                 140

Thr Thr Phe Gln Gln Ala Ser Thr Asp Ile Glu Trp Asn Ile Ser Gln
145                 150                 155                 160

Pro Val Leu Val Pro Pro Arg Lys Gln Val Val Ala Thr Leu Val Ile
```

165                 170                 175

Met Gly Gly Asn Phe Thr Ile Pro Met Asp Leu Met Thr Thr Ile Asp
                180                 185                 190

Ser Thr Glu His Tyr Ser Gly Tyr Pro Ile Leu Thr Trp Ile Ser Ser
                195                 200                 205

Pro Asp Asn Ser Tyr Asn Gly Pro Phe Met Ser Trp Tyr Phe Ala Asn
            210                 215                 220

Trp Pro Asn Leu Pro Ser Gly Phe Gly Pro Leu Asn Ser Asp Asn Thr
225                 230                 235                 240

Val Thr Tyr Thr Gly Ser Val Val Ser Gln Val Ser Ala Gly Val Tyr
                245                 250                 255

Ala Thr Val Arg Phe Asp Gln Tyr Asp Ile His Asn Leu Arg Ala Ile
                260                 265                 270

Glu Lys Thr Trp Tyr Ala Arg His Ala Thr Leu His Asn Gly Lys Lys
            275                 280                 285

Ile Ser Ile Asn Asn Val Thr Glu Met Ala Pro Thr Ser Pro Ile Lys
            290                 295                 300

Thr Asn
305

<210> SEQ ID NO 82
<211> LENGTH: 306
<212> TYPE: PRT
<213> ORGANISM: Artificial Sequence
<220> FEATURE:
<223> OTHER INFORMATION: engineered

<400> SEQUENCE: 82

Met Ala Ile Leu Asp Leu Lys Ser Leu Val Leu Asn Ala Ile Asn Tyr
1               5                   10                  15

Trp Gly Pro Lys Asn Asn Gly Ile Gln Gly Gly Asp Phe Gly Tyr
            20                  25                  30

Pro Ile Ser Glu Lys Gln Ile Asp Thr Ser Ile Ile Thr Ser Thr His
            35                  40                  45

Pro Arg Leu Ile Pro His Asp Leu Thr Ile Pro Gln Asn Leu Glu Thr
50                  55                  60

Ile Phe Thr Thr Thr Gln Val Leu Thr Asn Asn Thr Asp Leu Gln Gln
65                  70                  75                  80

Ser Gln Thr Val Ser Phe Ala Lys Lys Thr Thr Ala Thr Ser Thr
                85                  90                  95

Ser Thr Thr Asn Gly Trp Thr Glu Gly Gly Lys Ile Ser Asp Thr Leu
            100                 105                 110

Glu Glu Lys Val Ser Val Ser Ile Pro Phe Ile Gly Glu Gly Gly Gly
            115                 120                 125

Lys Asn Ser Thr Thr Ile Glu Ala Asn Phe Ala His Asn Ser Ser Thr
            130                 135                 140

Thr Thr Phe Gln Gln Ala Ser Asp Ile Glu Trp Asn Ile Ser Gln
145                 150                 155                 160

Pro Val Leu Val Pro Pro Arg Lys Gln Val Val Ala Thr Leu Val Ile
                165                 170                 175

Met Gly Gly Asn Phe Thr Ile Pro Met Asp Leu Met Thr Thr Ile Asp
                180                 185                 190

Ser Thr Glu His Tyr Ser Gly Tyr Pro Ile Leu Thr Trp Ile Ser Ser
                195                 200                 205

Pro Asp Asn Ser Tyr Asn Gly Pro Phe Met Ser Trp Tyr Phe Ala Asn

```
                210                 215                 220
Trp Pro Asn Leu Pro Ser Gly Phe Gly Pro Leu Asn Ser Asp Asn Thr
225                 230                 235                 240

Val Thr Tyr Thr Gly Ser Val Val Ser Gln Val Ser Ala Gly Val Tyr
                245                 250                 255

Ala Thr Val Arg Phe Asp Gln Tyr Asp Ile His Asn Leu Arg Thr Ile
                260                 265                 270

Glu Lys Thr Trp Tyr Ala Arg His Ala Thr Leu His Asn Gly Lys Lys
            275                 280                 285

Ile Ser Ile Asn Asn Val Thr Glu Met Ala Pro Thr Ser Pro Ile Lys
            290                 295                 300

Thr Asn
305

<210> SEQ ID NO 83
<211> LENGTH: 306
<212> TYPE: PRT
<213> ORGANISM: Artificial Sequence
<220> FEATURE:
<223> OTHER INFORMATION: engineered

<400> SEQUENCE: 83

Met Ala Ile Leu Asp Leu Lys Ser Leu Val Leu Asn Ala Ile Asn Tyr
1               5                   10                  15

Trp Gly Pro Lys Asn Asn Gly Ile Gln Gly Gly Asp Phe Gly Tyr
            20                  25                  30

Pro Ile Ser Glu Lys Gln Ile Asp Thr Ser Ile Ile Thr Ser Thr His
            35                  40                  45

Pro Arg Leu Ile Pro His Asp Leu Thr Ile Pro Gln Asn Leu Glu Thr
        50                  55                  60

Ile Phe Thr Thr Thr Gln Val Leu Thr Asn Asn Thr Asp Leu Gln Gln
65                  70                  75                  80

Ser Gln Thr Val Ser Phe Ala Lys Lys Thr Thr Thr Ala Thr Ser Thr
                85                  90                  95

Ser Thr Thr Asn Gly Trp Thr Glu Gly Gly Lys Ile Ser Asp Thr Leu
            100                 105                 110

Glu Glu Lys Val Ser Val Ser Ile Pro Phe Ile Gly Glu Gly Gly Gly
        115                 120                 125

Lys Asn Ser Thr Thr Ile Glu Ala Asn Phe Ala His Asn Ser Ser Thr
130                 135                 140

Thr Thr Phe Gln Gln Ala Ser Thr Asp Ile Glu Trp Asn Ile Ser Gln
145                 150                 155                 160

Pro Val Leu Val Pro Pro Arg Lys Gln Val Val Ala Thr Leu Val Ile
                165                 170                 175

Ala Gly Gly Asn Phe Thr Ile Pro Met Asp Leu Met Thr Thr Ile Asp
            180                 185                 190

Ser Thr Glu His Tyr Ser Gly Tyr Pro Ile Leu Thr Trp Ile Ser Ser
        195                 200                 205

Pro Asp Asn Ser Tyr Asn Gly Pro Phe Met Ser Trp Tyr Phe Ala Asn
    210                 215                 220

Trp Pro Asn Leu Pro Ser Gly Phe Gly Pro Leu Asn Ser Asp Asn Thr
225                 230                 235                 240

Val Thr Tyr Thr Gly Ser Val Val Ser Gln Val Ser Ala Gly Val Tyr
                245                 250                 255

Ala Thr Val Arg Phe Asp Gln Tyr Asp Ile His Asn Leu Arg Thr Ile
```

```
                    260               265                 270
Glu Lys Thr Trp Tyr Ala Arg His Ala Thr Leu His Asn Gly Lys Lys
            275                 280             285
Ile Ser Ile Asn Asn Val Thr Glu Met Ala Pro Thr Ser Pro Ile Lys
        290                 295             300
Thr Asn
305

<210> SEQ ID NO 84
<211> LENGTH: 306
<212> TYPE: PRT
<213> ORGANISM: Artificial Sequence
<220> FEATURE:
<223> OTHER INFORMATION: engineered

<400> SEQUENCE: 84

Met Ala Ile Leu Asp Leu Lys Ser Leu Val Leu Asn Ala Ile Asn Tyr
1               5                   10                  15
Trp Gly Pro Lys Asn Asn Gly Ile Gln Gly Gly Asp Phe Gly Tyr
            20                  25                  30
Pro Ile Ser Glu Lys Gln Ile Asp Thr Ser Ile Ile Thr Ser Thr His
        35                  40                  45
Pro Arg Leu Ile Pro His Asp Leu Thr Ile Pro Gln Asn Leu Glu Thr
    50                  55                  60
Ile Phe Thr Thr Thr Gln Val Leu Thr Asn Asn Thr Asp Leu Gln Gln
65                  70                  75                  80
Ser Gln Thr Val Ser Phe Ala Lys Lys Thr Thr Thr Thr Thr Ala Thr
                85                  90                  95
Ser Thr Thr Asn Gly Trp Thr Glu Gly Gly Lys Ile Ser Asp Thr Leu
            100                 105                 110
Glu Glu Lys Val Ser Val Ser Ile Pro Phe Ile Gly Glu Gly Gly Gly
        115                 120                 125
Lys Asn Ser Thr Thr Ile Glu Ala Asn Phe Ala His Asn Ser Ser Thr
    130                 135                 140
Thr Thr Phe Gln Gln Ala Ser Thr Asp Ile Glu Trp Asn Ile Ser Gln
145                 150                 155                 160
Pro Val Leu Val Pro Arg Lys Gln Val Val Ala Thr Leu Val Ile
                165                 170                 175
Met Gly Gly Asn Phe Thr Ile Pro Met Asp Leu Met Thr Thr Ile Asp
            180                 185                 190
Ser Thr Glu His Tyr Ser Gly Tyr Pro Ile Leu Thr Trp Ile Ser Ser
        195                 200                 205
Pro Asp Asn Ser Tyr Asn Gly Pro Phe Met Ser Trp Tyr Phe Ala Asn
    210                 215                 220
Trp Pro Asn Leu Pro Ser Gly Phe Gly Pro Leu Asn Ser Asp Asn Thr
225                 230                 235                 240
Val Thr Tyr Thr Gly Ser Ala Val Ser Gln Val Ser Ala Gly Val Tyr
                245                 250                 255
Ala Thr Val Arg Phe Asp Gln Tyr Asp Ile His Asn Leu Arg Thr Ile
            260                 265                 270
Glu Lys Thr Trp Tyr Ala Arg His Ala Thr Leu His Asn Gly Lys Lys
        275                 280                 285
Ile Ser Ile Asn Asn Val Thr Glu Met Ala Pro Thr Ser Pro Ile Lys
    290                 295                 300
Thr Asn
```

-continued

```
<210> SEQ ID NO 85
<211> LENGTH: 306
<212> TYPE: PRT
<213> ORGANISM: Artificial Sequence
<220> FEATURE:
<223> OTHER INFORMATION: engineered

<400> SEQUENCE: 85

Met Ala Ile Leu Asp Leu Lys Ser Leu Val Leu Asn Ala Ile Asn Tyr
1               5                   10                  15

Trp Gly Pro Lys Asn Asn Asn Gly Ile Gln Gly Gly Asp Phe Gly Tyr
            20                  25                  30

Pro Ile Ser Glu Lys Gln Ile Asp Thr Ser Ile Ile Thr Ser Thr His
        35                  40                  45

Pro Arg Leu Ile Pro His Asp Leu Thr Ile Pro Gln Asn Leu Glu Thr
    50                  55                  60

Ile Phe Thr Thr Thr Gln Val Leu Thr Asn Asn Thr Asp Leu Gln Gln
65                  70                  75                  80

Ser Gln Thr Val Ser Phe Ala Lys Lys Thr Thr Thr Ala Thr Ser Thr
                85                  90                  95

Ser Thr Thr Asn Gly Trp Thr Glu Gly Gly Lys Ile Ser Asp Thr Leu
            100                 105                 110

Glu Glu Lys Val Ser Val Ser Ile Pro Phe Ile Gly Glu Gly Gly Gly
        115                 120                 125

Lys Asn Ser Thr Thr Ile Glu Ala Asn Phe Ala His Asn Ser Ser Thr
    130                 135                 140

Thr Thr Phe Gln Gln Ala Ser Thr Asp Ile Ala Trp Asn Ile Ser Gln
145                 150                 155                 160

Pro Val Leu Val Pro Pro Arg Lys Gln Val Val Ala Thr Leu Val Ile
                165                 170                 175

Met Gly Gly Asn Phe Thr Ile Pro Met Asp Leu Met Thr Thr Ile Asp
            180                 185                 190

Ser Thr Glu His Tyr Ser Gly Tyr Pro Ile Leu Thr Trp Ile Ser Ser
        195                 200                 205

Pro Asp Asn Ser Tyr Asn Gly Pro Phe Met Ser Trp Tyr Phe Ala Asn
    210                 215                 220

Trp Pro Asn Leu Pro Ser Gly Phe Gly Pro Leu Asn Ser Asp Asn Thr
225                 230                 235                 240

Val Thr Tyr Thr Gly Ser Val Val Ser Gln Val Ser Ala Gly Val Tyr
                245                 250                 255

Ala Thr Val Arg Phe Asp Gln Tyr Asp Ile His Asn Leu Arg Thr Ile
            260                 265                 270

Glu Lys Thr Trp Tyr Ala Arg His Ala Thr Leu His Asn Gly Lys Lys
        275                 280                 285

Ile Ser Ile Asn Asn Val Thr Glu Met Ala Pro Thr Ser Pro Ile Lys
    290                 295                 300

Thr Asn
305

<210> SEQ ID NO 86
<211> LENGTH: 306
<212> TYPE: PRT
<213> ORGANISM: Artificial Sequence
<220> FEATURE:
<223> OTHER INFORMATION: engineered
```

<400> SEQUENCE: 86

```
Met Ala Ile Leu Asp Leu Lys Ser Leu Val Leu Asn Ala Ile Asn Tyr
1               5                   10                  15

Trp Gly Pro Lys Asn Asn Asn Gly Ile Gln Gly Gly Asp Phe Gly Tyr
            20                  25                  30

Pro Ile Ser Glu Lys Gln Ile Asp Thr Ser Ile Ile Thr Ser Thr His
        35                  40                  45

Pro Arg Leu Ile Pro His Asp Leu Thr Ile Pro Gln Asn Leu Glu Thr
    50                  55                  60

Ile Phe Thr Thr Thr Gln Val Leu Thr Asn Asn Thr Asp Leu Gln Gln
65                  70                  75                  80

Ser Gln Thr Val Ser Phe Ala Lys Lys Thr Thr Thr Thr Thr Ser Thr
                85                  90                  95

Ser Thr Thr Asn Gly Trp Thr Glu Gly Gly Lys Ile Ser Asp Thr Leu
            100                 105                 110

Glu Glu Lys Val Ser Val Ser Ile Pro Phe Ile Gly Glu Gly Gly Gly
        115                 120                 125

Lys Asn Ser Thr Thr Ala Glu Ala Asn Phe Ala His Asn Ser Ser Thr
    130                 135                 140

Thr Thr Ala Gln Gln Ala Ser Thr Asp Ile Glu Trp Asn Ile Ser Gln
145                 150                 155                 160

Pro Val Leu Val Pro Pro Arg Lys Gln Val Val Ala Thr Leu Val Ile
                165                 170                 175

Met Gly Gly Asn Phe Thr Ile Pro Met Asp Leu Met Thr Thr Ile Asp
            180                 185                 190

Ser Thr Glu His Tyr Ser Gly Tyr Pro Ile Leu Thr Trp Ile Ser Ser
        195                 200                 205

Pro Asp Asn Ser Tyr Asn Gly Pro Phe Met Ser Trp Tyr Phe Ala Asn
    210                 215                 220

Trp Pro Asn Leu Pro Ser Gly Phe Gly Pro Leu Asn Ser Asp Asn Thr
225                 230                 235                 240

Val Thr Tyr Thr Gly Ser Val Val Ser Gln Val Ser Ala Gly Val Tyr
                245                 250                 255

Ala Thr Val Arg Phe Asp Gln Tyr Asp Ile His Asn Leu Arg Thr Ile
            260                 265                 270

Glu Lys Thr Trp Tyr Ala Arg His Ala Thr Leu His Asn Gly Lys Lys
        275                 280                 285

Ile Ser Ile Asn Asn Val Thr Glu Met Ala Pro Thr Ser Pro Ile Lys
    290                 295                 300

Thr Asn
305
```

<210> SEQ ID NO 87
<211> LENGTH: 306
<212> TYPE: PRT
<213> ORGANISM: Artificial Sequence
<220> FEATURE:
<223> OTHER INFORMATION: engineered

<400> SEQUENCE: 87

```
Met Ala Ile Leu Asp Leu Lys Ser Leu Val Leu Asn Ala Ile Asn Tyr
1               5                   10                  15

Trp Gly Pro Lys Asn Asn Asn Gly Ile Gln Gly Gly Asp Phe Gly Tyr
            20                  25                  30
```

Pro Ile Ser Glu Lys Gln Ile Asp Thr Ser Ile Ile Thr Ser Thr His
            35                  40                  45

Pro Arg Leu Ile Pro His Asp Leu Thr Ile Pro Gln Asn Leu Glu Thr
     50                  55                  60

Ile Phe Thr Thr Thr Gln Val Leu Thr Asn Asn Thr Asp Leu Gln Gln
 65                  70                  75                  80

Ser Gln Thr Val Ser Phe Ala Lys Lys Thr Thr Ala Thr Ser Thr
                85                  90                  95

Ser Thr Thr Asn Gly Trp Thr Glu Gly Gly Lys Ile Ser Asp Thr Leu
            100                 105                 110

Glu Glu Lys Val Ser Val Ser Ile Pro Phe Ile Gly Glu Gly Gly Gly
            115                 120                 125

Lys Asn Ser Thr Thr Ile Glu Ala Asn Phe Ala His Asn Ser Ser Thr
130                 135                 140

Thr Thr Phe Gln Gln Ala Ser Thr Asp Ile Glu Trp Asn Ile Ser Gln
145                 150                 155                 160

Pro Val Leu Val Pro Arg Lys Gln Val Val Ala Thr Leu Val Ile
            165                 170                 175

Met Gly Gly Asn Phe Thr Ile Pro Met Asp Leu Met Thr Thr Ile Asp
            180                 185                 190

Ser Thr Glu His Tyr Ser Gly Tyr Pro Ile Leu Thr Trp Ile Ser Ser
            195                 200                 205

Pro Asp Asn Ser Tyr Asn Gly Pro Phe Met Ser Trp Tyr Phe Ala Asn
            210                 215                 220

Trp Pro Asn Leu Pro Ser Gly Phe Gly Pro Leu Asn Ser Asp Asn Thr
225                 230                 235                 240

Val Ala Tyr Thr Gly Ser Val Val Ser Gln Val Ser Ala Gly Val Tyr
            245                 250                 255

Ala Thr Val Arg Phe Asp Gln Tyr Asp Ile His Asn Leu Arg Thr Ile
            260                 265                 270

Glu Lys Thr Trp Tyr Ala Arg His Ala Thr Leu His Asn Gly Lys Lys
            275                 280                 285

Ile Ser Ile Asn Asn Val Thr Glu Met Ala Pro Thr Ser Pro Ile Lys
            290                 295                 300

Thr Asn
305

<210> SEQ ID NO 88
<211> LENGTH: 306
<212> TYPE: PRT
<213> ORGANISM: Artificial Sequence
<220> FEATURE:
<223> OTHER INFORMATION: engineered

<400> SEQUENCE: 88

Met Ala Ile Leu Asp Leu Lys Ser Leu Val Leu Asn Ala Ile Asn Tyr
 1               5                  10                  15

Trp Gly Pro Lys Asn Asn Gly Ile Gln Gly Gly Asp Phe Gly Tyr
            20                  25                  30

Pro Ile Ser Glu Lys Gln Ile Asp Thr Ser Ile Ile Thr Ser Thr His
            35                  40                  45

Pro Arg Leu Ile Pro His Asp Leu Thr Ile Pro Gln Asn Leu Glu Thr
     50                  55                  60

Ile Phe Thr Thr Thr Gln Val Leu Thr Asn Asn Thr Asp Leu Gln Gln
 65                  70                  75                  80

Ser Gln Thr Val Ser Phe Ala Lys Lys Thr Thr Thr Thr Ser Thr
                85                  90                  95

Ser Thr Thr Asn Gly Trp Thr Glu Gly Gly Lys Ile Ser Asp Thr Leu
            100                 105                 110

Glu Glu Lys Val Ser Val Ser Ile Pro Phe Ile Gly Glu Gly Gly Gly
        115                 120                 125

Lys Asn Ser Thr Thr Ile Glu Ala Asn Phe Ala His Asn Ser Ser Thr
    130                 135                 140

Thr Thr Phe Gln Gln Ala Ser Thr Asp Ile Glu Trp Asn Ile Ser Gln
145                 150                 155                 160

Pro Val Leu Val Pro Arg Lys Gln Val Val Ala Thr Leu Val Ile
                165                 170                 175

Met Gly Gly Asn Phe Thr Ile Pro Met Asp Leu Met Thr Thr Ile Asp
            180                 185                 190

Ser Thr Glu His Tyr Ala Gly Tyr Pro Ile Leu Thr Trp Ile Ser Ser
        195                 200                 205

Pro Asp Asn Ser Tyr Asn Gly Pro Phe Met Ser Trp Tyr Phe Ala Asn
    210                 215                 220

Trp Pro Asn Leu Pro Ser Gly Phe Gly Pro Leu Asn Ser Asp Asn Thr
225                 230                 235                 240

Val Thr Tyr Thr Gly Ser Val Val Ser Gln Val Ser Ala Gly Val Tyr
                245                 250                 255

Ala Thr Val Arg Phe Asp Gln Tyr Asp Ile His Asn Leu Arg Thr Ile
            260                 265                 270

Glu Lys Thr Trp Tyr Ala Arg His Ala Thr Leu His Asn Gly Lys Lys
        275                 280                 285

Ile Ser Ile Asn Asn Val Thr Glu Met Ala Pro Thr Ser Pro Ile Lys
    290                 295                 300

Thr Asn
305

<210> SEQ ID NO 89
<211> LENGTH: 306
<212> TYPE: PRT
<213> ORGANISM: Artificial Sequence
<220> FEATURE:
<223> OTHER INFORMATION: engineered

<400> SEQUENCE: 89

Met Ala Ile Leu Asp Leu Lys Ser Leu Val Leu Asn Ala Ile Asn Tyr
1               5                   10                  15

Trp Gly Pro Lys Asn Asn Asn Gly Ile Gln Gly Gly Asp Phe Gly Tyr
            20                  25                  30

Pro Ile Ser Glu Lys Gln Ile Asp Thr Ser Ile Thr Ser Thr His
        35                  40                  45

Pro Arg Leu Ile Pro His Asp Leu Thr Ile Pro Gln Asn Leu Glu Thr
    50                  55                  60

Ile Phe Thr Thr Thr Gln Val Leu Thr Asn Asn Thr Asp Leu Gln Gln
65                  70                  75                  80

Ser Gln Thr Val Ser Phe Ala Lys Lys Thr Thr Thr Thr Ser Thr
                85                  90                  95

Ser Thr Thr Asn Gly Trp Thr Glu Gly Gly Lys Ile Ser Asp Thr Leu
            100                 105                 110

Glu Glu Lys Val Ser Val Ser Ile Pro Phe Ile Gly Glu Gly Gly Gly
        115                 120                 125

```
Lys Asn Ser Thr Thr Ile Glu Ala Asn Phe Ala His Asn Ser Ser Thr
130                 135                 140

Thr Thr Ala Gln Gln Ala Ser Thr Asp Ile Glu Trp Asn Ile Ser Gln
145                 150                 155                 160

Pro Val Leu Val Pro Pro Arg Lys Gln Val Val Ala Thr Leu Val Ile
                165                 170                 175

Met Gly Gly Asn Phe Thr Ile Pro Met Asp Leu Met Thr Thr Ile Asp
                180                 185                 190

Ser Thr Glu His Tyr Ser Gly Tyr Pro Ile Leu Thr Trp Ile Ser Ser
                195                 200                 205

Pro Asp Asn Ser Tyr Asn Gly Pro Phe Met Ser Trp Tyr Phe Ala Asn
210                 215                 220

Trp Pro Asn Leu Pro Ser Gly Phe Gly Pro Leu Asn Ser Asp Asn Thr
225                 230                 235                 240

Val Thr Tyr Thr Gly Ser Val Val Ser Gln Val Ser Ala Gly Val Tyr
                245                 250                 255

Ala Thr Val Arg Phe Asp Gln Tyr Asp Ile His Asn Leu Arg Thr Ile
                260                 265                 270

Glu Lys Thr Trp Tyr Ala Arg His Ala Thr Leu His Asn Gly Lys Lys
                275                 280                 285

Ile Ser Ile Ala Asn Val Thr Glu Met Ala Pro Thr Ser Pro Ile Lys
290                 295                 300

Thr Asn
305

<210> SEQ ID NO 90
<211> LENGTH: 306
<212> TYPE: PRT
<213> ORGANISM: Artificial Sequence
<220> FEATURE:
<223> OTHER INFORMATION: engineered

<400> SEQUENCE: 90

Met Ala Ile Leu Asp Leu Lys Ser Leu Val Leu Asn Ala Ile Asn Tyr
1               5                   10                  15

Trp Gly Pro Lys Asn Asn Gly Ile Gln Gly Gly Asp Phe Gly Tyr
                20                  25                  30

Pro Ile Ser Glu Lys Gln Ile Asp Thr Ser Ile Ile Thr Ser Thr His
                35                  40                  45

Pro Arg Leu Ile Pro His Asp Leu Thr Ile Pro Gln Asn Leu Glu Thr
50                  55                  60

Ile Phe Thr Thr Thr Gln Val Leu Thr Asn Asn Thr Asp Leu Gln Gln
65                  70                  75                  80

Ser Gln Thr Val Ser Phe Ser Lys Lys Thr Thr Thr Thr Thr Ser Thr
                85                  90                  95

Ser Thr Thr Asn Gly Trp Thr Glu Gly Gly Lys Ile Ser Asp Thr Leu
                100                 105                 110

Glu Glu Lys Val Ser Val Ser Ile Pro Phe Ile Gly Glu Gly Gly Gly
                115                 120                 125

Lys Asn Ser Thr Thr Ile Glu Ala Asn Phe Ala His Asn Ser Ser Thr
130                 135                 140

Thr Thr Ala Gln Gln Ala Ser Thr Asp Ile Glu Trp Asn Ile Ser Gln
145                 150                 155                 160

Pro Val Leu Val Pro Pro Arg Lys Gln Val Val Ala Thr Leu Val Ile
                165                 170                 175
```

```
Met Gly Gly Asn Phe Thr Ile Pro Met Asp Leu Met Thr Thr Ile Asp
            180                 185                 190

Ser Thr Glu His Tyr Ser Gly Tyr Pro Ile Leu Thr Trp Ile Ser Ser
            195                 200                 205

Pro Asp Asn Ser Tyr Asn Gly Pro Phe Met Ser Trp Tyr Phe Ala Asn
            210                 215                 220

Trp Pro Asn Leu Pro Ser Gly Phe Gly Pro Leu Asn Ser Asp Asn Thr
225                 230                 235                 240

Val Thr Tyr Thr Gly Ser Val Val Ser Gln Val Ser Ala Gly Val Tyr
            245                 250                 255

Ala Thr Val Arg Phe Asp Gln Tyr Asp Ile His Asn Leu Arg Thr Ile
            260                 265                 270

Glu Lys Thr Trp Tyr Ala Arg His Ala Thr Leu His Asn Gly Lys Lys
            275                 280                 285

Ile Ser Ile Asn Asn Val Thr Glu Met Ala Pro Thr Ser Pro Ile Lys
            290                 295                 300

Thr Asn
305

<210> SEQ ID NO 91
<211> LENGTH: 306
<212> TYPE: PRT
<213> ORGANISM: Artificial Sequence
<220> FEATURE:
<223> OTHER INFORMATION: engineered

<400> SEQUENCE: 91

Met Ala Ile Leu Asp Leu Lys Ser Leu Val Leu Asn Ala Ile Asn Tyr
1               5                   10                  15

Trp Gly Pro Lys Asn Asn Asn Gly Ile Gln Gly Gly Asp Phe Gly Tyr
            20                  25                  30

Pro Ile Ser Glu Lys Gln Ile Asp Thr Ser Ile Ile Thr Ser Thr His
            35                  40                  45

Pro Arg Leu Ile Pro His Asp Leu Thr Ile Pro Gln Asn Leu Glu Thr
        50                  55                  60

Ile Phe Thr Thr Thr Gln Val Leu Thr Asn Asn Thr Asp Leu Gln Gln
65                  70                  75                  80

Ser Gln Thr Val Ser Phe Ala Lys Lys Thr Thr Thr Thr Ser Thr
            85                  90                  95

Ser Thr Thr Asn Gly Trp Thr Glu Gly Gly Lys Ile Ser Asp Thr Leu
            100                 105                 110

Glu Glu Lys Val Ser Val Ser Ile Pro Phe Ile Gly Glu Gly Gly Gly
            115                 120                 125

Lys Asn Ser Thr Thr Ile Glu Ala Asn Phe Ala His Asn Ser Ser Thr
            130                 135                 140

Thr Thr Ala Gln Gln Ala Ser Thr Asp Ile Glu Trp Asn Ile Ser Gln
145                 150                 155                 160

Pro Val Leu Val Pro Pro Arg Lys Gln Val Val Ala Thr Leu Val Ile
            165                 170                 175

Met Gly Gly Asn Phe Thr Ile Pro Met Asp Leu Met Thr Thr Ile Asp
            180                 185                 190

Ser Thr Glu His Tyr Ser Gly Tyr Pro Ile Leu Thr Trp Ile Ser Ser
            195                 200                 205

Pro Asp Asn Ser Tyr Asn Gly Pro Phe Met Ser Trp Tyr Phe Ala Asn
            210                 215                 220
```

```
Trp Pro Asn Leu Pro Ser Gly Phe Gly Pro Leu Asn Ser Asp Asn Thr
225                 230                 235                 240

Val Thr Tyr Thr Gly Ala Val Val Ser Gln Val Ser Ala Gly Val Tyr
                245                 250                 255

Ala Thr Val Arg Phe Asp Gln Tyr Asp Ile His Asn Leu Arg Thr Ile
            260                 265                 270

Glu Lys Thr Trp Tyr Ala Arg His Ala Thr Leu His Asn Gly Lys Lys
        275                 280                 285

Ile Ser Ile Asn Asn Val Thr Glu Met Ala Pro Thr Ser Pro Ile Lys
        290                 295                 300

Thr Asn
305

<210> SEQ ID NO 92
<211> LENGTH: 306
<212> TYPE: PRT
<213> ORGANISM: Artificial Sequence
<220> FEATURE:
<223> OTHER INFORMATION: engineered

<400> SEQUENCE: 92

Met Ala Ile Leu Asp Leu Lys Ser Leu Val Leu Asn Ala Ile Asn Tyr
1               5                   10                  15

Trp Gly Pro Lys Asn Asn Gly Ile Gln Gly Gly Asp Phe Gly Tyr
            20                  25                  30

Pro Ile Ser Glu Lys Gln Ile Asp Thr Ser Ile Ile Thr Ser Thr His
            35                  40                  45

Pro Arg Leu Ile Pro His Asp Leu Thr Ile Pro Gln Asn Leu Glu Thr
        50                  55                  60

Ile Phe Thr Thr Thr Gln Val Leu Thr Asn Asn Thr Asp Leu Gln Gln
65                  70                  75                  80

Ser Gln Thr Val Ser Phe Ala Lys Lys Thr Thr Thr Thr Ala Thr
                85                  90                  95

Ser Thr Thr Asn Gly Trp Thr Glu Gly Gly Lys Ile Ser Asp Thr Leu
            100                 105                 110

Glu Glu Lys Val Ser Val Ser Ile Pro Phe Ile Gly Glu Gly Gly Gly
        115                 120                 125

Lys Asn Ser Thr Thr Ile Glu Ala Asn Phe Ala His Asn Ser Ser Thr
        130                 135                 140

Thr Thr Phe Gln Gln Ala Ser Thr Asp Ile Glu Trp Asn Ile Ser Gln
145                 150                 155                 160

Pro Val Leu Val Pro Pro Arg Lys Gln Val Val Ala Thr Leu Val Ile
                165                 170                 175

Met Gly Gly Asn Phe Thr Ile Pro Met Asp Leu Met Thr Thr Ile Asp
            180                 185                 190

Ser Thr Glu His Tyr Ser Gly Tyr Pro Ile Leu Thr Trp Ile Ser Ser
        195                 200                 205

Pro Asp Asn Ser Tyr Asn Gly Pro Phe Met Ser Trp Tyr Phe Ala Asn
        210                 215                 220

Trp Pro Asn Leu Pro Ser Gly Phe Gly Pro Leu Asn Ser Asp Asn Thr
225                 230                 235                 240

Val Thr Tyr Thr Gly Ser Val Val Ser Gln Val Ser Ala Gly Val Tyr
                245                 250                 255

Ala Thr Val Arg Phe Asp Gln Tyr Asp Ile His Asn Leu Arg Thr Ala
            260                 265                 270
```

Glu Lys Thr Trp Tyr Ala Arg His Ala Thr Leu His Asn Gly Lys Lys
275                 280                 285

Ile Ser Ile Asn Asn Val Thr Glu Met Ala Pro Thr Ser Pro Ile Lys
290                 295                 300

Thr Asn
305

<210> SEQ ID NO 93
<211> LENGTH: 306
<212> TYPE: PRT
<213> ORGANISM: Artificial Sequence
<220> FEATURE:
<223> OTHER INFORMATION: engineered

<400> SEQUENCE: 93

Met Ala Ile Leu Asp Leu Lys Ser Leu Val Leu Asn Ala Ile Asn Tyr
1               5                   10                  15

Trp Gly Pro Lys Asn Asn Gly Ile Gln Gly Gly Asp Phe Gly Tyr
            20                  25                  30

Pro Ile Ser Glu Lys Gln Ile Asp Thr Ser Ile Ile Thr Ser Thr His
        35                  40                  45

Pro Arg Leu Ile Pro His Asp Leu Thr Ile Pro Gln Asn Leu Glu Thr
    50                  55                  60

Ile Phe Thr Thr Thr Gln Val Leu Thr Asn Asn Thr Asp Leu Gln Gln
65                  70                  75                  80

Ser Gln Thr Val Ser Phe Ala Lys Lys Thr Thr Ala Thr Ser Thr
                85                  90                  95

Ser Thr Thr Asn Gly Trp Thr Glu Gly Gly Lys Ile Ser Asp Thr Leu
            100                 105                 110

Glu Glu Lys Val Ser Val Ser Ile Pro Phe Ile Gly Glu Gly Gly Gly
        115                 120                 125

Lys Asn Ser Thr Thr Ile Glu Ala Asn Phe Ser His Asn Ser Ser Thr
130                 135                 140

Thr Thr Phe Gln Gln Ala Ser Thr Asp Ile Glu Trp Asn Ile Ser Gln
145                 150                 155                 160

Pro Val Leu Val Pro Pro Arg Lys Gln Val Ala Thr Leu Val Ile
                165                 170                 175

Met Gly Gly Asn Phe Thr Ile Pro Met Asp Leu Met Thr Thr Ile Asp
            180                 185                 190

Ser Thr Glu His Tyr Ser Gly Tyr Pro Ile Leu Thr Trp Ile Ser Ser
        195                 200                 205

Pro Asp Asn Ser Tyr Asn Gly Pro Phe Met Ser Trp Tyr Phe Ala Asn
    210                 215                 220

Trp Pro Asn Leu Pro Ser Gly Phe Gly Pro Leu Asn Ser Asp Asn Thr
225                 230                 235                 240

Val Thr Tyr Thr Gly Ser Val Val Ser Gln Val Ser Ala Gly Val Tyr
                245                 250                 255

Ala Thr Val Arg Phe Asp Gln Tyr Asp Ile His Asn Leu Arg Thr Ile
            260                 265                 270

Glu Lys Thr Trp Tyr Ala Arg His Ala Thr Leu His Asn Gly Lys Lys
        275                 280                 285

Ile Ser Ile Asn Asn Val Thr Glu Met Ala Pro Thr Ser Pro Ile Lys
    290                 295                 300

Thr Asn
305

```
<210> SEQ ID NO 94
<211> LENGTH: 306
<212> TYPE: PRT
<213> ORGANISM: Artificial Sequence
<220> FEATURE:
<223> OTHER INFORMATION: engineered

<400> SEQUENCE: 94

Met Ala Ile Leu Asp Leu Lys Ser Leu Val Leu Asn Ala Ile Asn Tyr
1               5                   10                  15

Trp Gly Pro Lys Asn Asn Gly Ile Gln Gly Asp Phe Gly Tyr
            20                  25                  30

Pro Ile Ser Glu Lys Gln Ile Asp Thr Ser Ile Ile Thr Ser Thr His
        35                  40                  45

Pro Arg Leu Ile Pro His Asp Leu Thr Ile Pro Gln Asn Leu Glu Thr
    50                  55                  60

Ile Phe Thr Thr Thr Gln Val Leu Thr Asn Asn Thr Asp Leu Gln Gln
65                  70                  75                  80

Ser Gln Thr Val Ser Phe Ala Lys Lys Thr Thr Thr Thr Ser Thr
                85                  90                  95

Ser Thr Thr Asn Gly Trp Thr Glu Gly Gly Lys Ile Ser Asp Thr Leu
            100                 105                 110

Glu Glu Lys Val Ser Val Ser Ile Pro Phe Ile Gly Glu Gly Gly Gly
            115                 120                 125

Lys Asn Ser Thr Thr Ile Glu Ala Asn Phe Ala His Asn Ser Ser Thr
            130                 135                 140

Thr Thr Ala Gln Gln Ala Ser Thr Asp Ile Glu Trp Asn Ile Ser Gln
145                 150                 155                 160

Pro Val Leu Val Pro Pro Arg Lys Gln Val Val Ala Thr Leu Val Ile
                165                 170                 175

Met Gly Gly Asn Phe Thr Ile Pro Met Asp Leu Met Thr Thr Ile Asp
            180                 185                 190

Ser Thr Glu His Tyr Ser Gly Tyr Pro Ile Leu Thr Trp Ile Ser Ser
            195                 200                 205

Pro Asp Asn Ser Tyr Asn Gly Pro Phe Met Ser Trp Tyr Phe Ala Asn
        210                 215                 220

Trp Pro Asn Leu Pro Ser Gly Phe Gly Pro Leu Asn Ser Asp Asn Thr
225                 230                 235                 240

Val Thr Tyr Thr Gly Ser Val Ser Gln Val Ser Ala Gly Val Tyr
                245                 250                 255

Ala Thr Val Arg Phe Asp Gln Tyr Asp Ile His Asn Leu Arg Thr Ile
            260                 265                 270

Glu Lys Thr Trp Tyr Ala Arg His Ala Thr Leu His Asn Gly Lys Lys
            275                 280                 285

Ile Ser Ile Asn Asn Val Thr Glu Met Ala Pro Thr Ser Ala Ile Lys
            290                 295                 300

Thr Asn
305

<210> SEQ ID NO 95
<211> LENGTH: 306
<212> TYPE: PRT
<213> ORGANISM: Artificial Sequence
<220> FEATURE:
<223> OTHER INFORMATION: engineered

<400> SEQUENCE: 95
```

```
Met Ala Ile Leu Asp Leu Lys Ser Leu Val Leu Asn Ala Ile Asn Tyr
1               5                   10                  15

Trp Gly Pro Lys Asn Asn Gly Ile Gln Gly Gly Asp Phe Gly Tyr
            20                  25                  30

Pro Ile Ser Glu Lys Gln Ile Asp Thr Ser Ile Ile Thr Ser Thr His
                35                  40                  45

Pro Arg Leu Ile Pro His Asp Leu Thr Ile Pro Gln Asn Leu Glu Thr
        50                  55                  60

Ile Phe Thr Thr Thr Gln Val Leu Thr Asn Asn Thr Asp Leu Gln Gln
65                  70                  75                  80

Ser Gln Thr Val Ser Phe Ala Lys Lys Thr Thr Thr Thr Thr Ser Thr
                85                  90                  95

Ser Thr Thr Asn Gly Trp Thr Glu Gly Gly Lys Ile Ser Asp Thr Leu
                100                 105                 110

Glu Glu Lys Val Ser Val Ser Ile Pro Phe Ile Gly Glu Gly Gly Gly
            115                 120                 125

Lys Asn Ser Thr Thr Ile Glu Ala Asn Phe Ala His Asn Ser Ser Thr
        130                 135                 140

Thr Thr Ala Gln Gln Ala Ser Thr Asp Ile Glu Trp Asn Ile Ser Gln
145                 150                 155                 160

Pro Val Leu Val Pro Pro Arg Lys Gln Val Val Ala Thr Leu Val Ile
                165                 170                 175

Met Gly Gly Asn Phe Thr Ile Pro Met Asp Leu Met Thr Thr Ile Asp
                180                 185                 190

Ser Thr Glu His Tyr Ala Gly Tyr Pro Ile Leu Thr Trp Ile Ser Ser
                195                 200                 205

Pro Asp Asn Ser Tyr Asn Gly Pro Phe Met Ser Trp Tyr Phe Ala Asn
        210                 215                 220

Trp Pro Asn Leu Pro Ser Gly Phe Gly Pro Leu Asn Ser Asp Asn Thr
225                 230                 235                 240

Val Thr Tyr Thr Gly Ser Val Val Ser Gln Val Ser Ala Gly Val Tyr
                245                 250                 255

Ala Thr Val Arg Phe Asp Gln Tyr Asp Ile His Asn Leu Arg Thr Ile
            260                 265                 270

Glu Lys Thr Trp Tyr Ala Arg His Ala Thr Leu His Asn Gly Lys Lys
        275                 280                 285

Ile Ser Ile Asn Asn Val Thr Glu Met Ala Pro Thr Ser Pro Ile Lys
        290                 295                 300

Thr Asn
305

<210> SEQ ID NO 96
<211> LENGTH: 306
<212> TYPE: PRT
<213> ORGANISM: Artificial Sequence
<220> FEATURE:
<223> OTHER INFORMATION: engineered

<400> SEQUENCE: 96

Met Ala Ile Leu Asp Leu Lys Ser Leu Val Leu Asn Ala Ile Asn Tyr
1               5                   10                  15

Trp Gly Pro Lys Asn Asn Gly Ile Gln Gly Gly Asp Phe Gly Tyr
            20                  25                  30

Pro Ile Ser Glu Lys Gln Ile Asp Thr Ser Ile Ile Thr Ser Thr His
                35                  40                  45
```

Pro Arg Leu Ile Pro His Asp Leu Thr Ile Pro Gln Asn Leu Glu Thr
         50                  55                  60

Ile Phe Thr Thr Thr Gln Val Leu Thr Asn Asn Thr Asp Leu Gln Gln
 65                  70                  75                  80

Ser Gln Thr Val Ser Phe Ala Lys Lys Thr Thr Thr Thr Ser Thr Thr
                 85                  90                  95

Ser Thr Thr Asn Gly Trp Thr Glu Gly Gly Lys Ile Ser Asp Thr Leu
            100                 105                 110

Glu Glu Lys Val Ser Val Ser Ile Pro Phe Ile Gly Glu Gly Gly Gly
        115                 120                 125

Lys Asn Ser Thr Thr Ile Glu Ala Asn Phe Ala His Asn Ser Ser Thr
    130                 135                 140

Thr Thr Ala Gln Gln Ala Ser Thr Asp Ile Glu Trp Asn Ile Ser Gln
145                 150                 155                 160

Pro Val Leu Val Pro Pro Arg Lys Gln Val Val Ala Thr Leu Val Ile
                165                 170                 175

Met Gly Gly Asn Phe Thr Ile Pro Met Asp Leu Met Thr Thr Ile Asp
            180                 185                 190

Ser Thr Glu His Tyr Ser Gly Tyr Pro Ile Leu Thr Trp Ile Ser Ser
        195                 200                 205

Pro Asp Asn Ser Tyr Asn Gly Pro Phe Met Ser Trp Tyr Phe Ala Asn
    210                 215                 220

Trp Pro Asn Leu Pro Ser Gly Phe Gly Pro Leu Asn Ser Asp Asn Thr
225                 230                 235                 240

Val Thr Tyr Thr Gly Ser Val Val Ala Gln Val Ser Ala Gly Val Tyr
                245                 250                 255

Ala Thr Val Arg Phe Asp Gln Tyr Asp Ile His Asn Leu Arg Thr Ile
            260                 265                 270

Glu Lys Thr Trp Tyr Ala Arg His Ala Thr Leu His Asn Gly Lys Lys
        275                 280                 285

Ile Ser Ile Asn Asn Val Thr Glu Met Ala Pro Thr Ser Pro Ile Lys
    290                 295                 300

Thr Asn
305

<210> SEQ ID NO 97
<211> LENGTH: 306
<212> TYPE: PRT
<213> ORGANISM: Artificial Sequence
<220> FEATURE:
<223> OTHER INFORMATION: engineered

<400> SEQUENCE: 97

Met Ala Ile Leu Asp Leu Lys Ser Leu Val Leu Asn Ala Ile Asn Tyr
  1               5                  10                  15

Trp Gly Pro Lys Asn Asn Asn Gly Ile Gln Gly Gly Asp Phe Gly Tyr
             20                  25                  30

Pro Ile Ser Glu Lys Gln Ile Asp Thr Ser Ile Ile Thr Ser Thr His
         35                  40                  45

Pro Arg Leu Ile Pro His Asp Leu Thr Ile Pro Gln Asn Leu Glu Thr
     50                  55                  60

Ile Phe Thr Thr Thr Gln Val Leu Thr Asn Asn Thr Asp Leu Gln Gln
 65                  70                  75                  80

Ser Gln Thr Val Ser Phe Ala Lys Lys Thr Thr Thr Ala Thr Ser Thr
                 85                  90                  95

```
Ser Thr Thr Asn Gly Trp Thr Glu Gly Gly Lys Ile Ser Asp Thr Leu
            100                 105                 110

Glu Glu Lys Val Ser Val Ser Ile Pro Phe Ile Gly Glu Gly Gly Gly
            115                 120                 125

Lys Asn Ser Thr Thr Ile Glu Ala Asn Phe Ala His Asn Ser Ser Thr
130                 135                 140

Thr Thr Ala Gln Gln Ala Ser Thr Asp Ile Glu Trp Asn Ile Ser Gln
145                 150                 155                 160

Pro Val Leu Val Pro Pro Arg Lys Gln Val Val Ala Thr Leu Val Ile
                165                 170                 175

Met Gly Gly Asn Phe Thr Ile Pro Met Asp Leu Met Thr Thr Ile Asp
            180                 185                 190

Ser Thr Glu His Tyr Ser Gly Tyr Pro Ile Leu Thr Trp Ile Ser Ser
            195                 200                 205

Pro Asp Asn Ser Tyr Asn Gly Pro Phe Met Ser Trp Tyr Phe Ala Asn
210                 215                 220

Trp Pro Asn Leu Pro Ser Gly Phe Gly Pro Leu Asn Ser Asp Asn Thr
225                 230                 235                 240

Val Thr Tyr Thr Gly Ser Val Val Ser Gln Val Ser Ala Gly Val Tyr
                245                 250                 255

Ala Thr Val Arg Phe Asp Gln Tyr Asp Ile His Asn Leu Arg Thr Ile
            260                 265                 270

Glu Lys Thr Trp Tyr Ala Arg His Ala Thr Leu His Asn Gly Lys Lys
            275                 280                 285

Ile Ser Ile Asn Asn Val Thr Glu Met Ala Pro Thr Ser Pro Ile Lys
            290                 295                 300

Thr Asn
305

<210> SEQ ID NO 98
<211> LENGTH: 306
<212> TYPE: PRT
<213> ORGANISM: Artificial Sequence
<220> FEATURE:
<223> OTHER INFORMATION: engineered

<400> SEQUENCE: 98

Met Ala Ile Leu Asp Leu Lys Ser Leu Val Leu Asn Ala Ile Asn Tyr
1               5                   10                  15

Trp Gly Pro Lys Asn Asn Gly Ile Gln Gly Gly Asp Phe Gly Tyr
            20                  25                  30

Pro Ile Ser Glu Lys Gln Ile Asp Thr Ser Ile Thr Ser Thr His
            35                  40                  45

Pro Arg Leu Ile Pro His Asp Leu Thr Ile Pro Gln Asn Leu Glu Thr
    50                  55                  60

Ile Phe Thr Thr Thr Gln Val Leu Thr Asn Asn Thr Asp Leu Gln Gln
65                  70                  75                  80

Ser Gln Thr Val Ser Phe Ala Lys Lys Thr Thr Thr Thr Ser Thr
                85                  90                  95

Ser Thr Thr Asn Gly Trp Thr Glu Gly Gly Lys Ile Ser Asp Thr Leu
            100                 105                 110

Glu Glu Lys Val Ser Val Ser Ile Pro Phe Ile Gly Glu Gly Gly Gly
            115                 120                 125

Lys Asn Ser Thr Thr Ile Glu Ala Asn Phe Ala His Asn Ser Ser Thr
130                 135                 140
```

```
Thr Thr Ala Gln Gln Ala Ser Thr Asp Ile Glu Trp Asn Ile Ser Gln
145                 150                 155                 160

Pro Val Leu Val Pro Pro Arg Lys Gln Val Val Ala Thr Leu Val Ile
                165                 170                 175

Met Gly Gly Asn Phe Thr Ile Pro Met Asp Leu Met Thr Thr Ile Asp
            180                 185                 190

Ser Thr Glu His Tyr Ser Gly Tyr Pro Ile Leu Thr Trp Ile Ser Ser
            195                 200                 205

Pro Asp Asn Ser Tyr Asn Gly Pro Phe Met Ser Trp Tyr Phe Ala Asn
            210                 215                 220

Trp Pro Asn Leu Pro Ser Gly Phe Gly Pro Leu Asn Ser Asp Asn Thr
225                 230                 235                 240

Val Thr Tyr Thr Gly Ser Ala Val Ser Gln Val Ser Ala Gly Val Tyr
                245                 250                 255

Ala Thr Val Arg Phe Asp Gln Tyr Asp Ile His Asn Leu Arg Thr Ile
                260                 265                 270

Glu Lys Thr Trp Tyr Ala Arg His Ala Thr Leu His Asn Gly Lys Lys
            275                 280                 285

Ile Ser Ile Asn Asn Val Thr Glu Met Ala Pro Thr Ser Pro Ile Lys
            290                 295                 300

Thr Asn
305

<210> SEQ ID NO 99
<211> LENGTH: 306
<212> TYPE: PRT
<213> ORGANISM: Artificial Sequence
<220> FEATURE:
<223> OTHER INFORMATION: engineered

<400> SEQUENCE: 99

Met Ala Ile Leu Asp Leu Lys Ser Leu Val Leu Asn Ala Ile Asn Tyr
1               5                   10                  15

Trp Gly Pro Lys Asn Asn Asn Gly Ile Gln Gly Gly Asp Phe Gly Tyr
                20                  25                  30

Pro Ile Ser Glu Lys Gln Ile Asp Thr Ser Ile Ile Thr Ser Thr His
            35                  40                  45

Pro Arg Leu Ile Pro His Asp Leu Thr Ile Pro Gln Asn Leu Glu Thr
        50                  55                  60

Ile Phe Thr Thr Thr Gln Val Leu Thr Asn Asn Thr Asp Leu Gln Gln
65                  70                  75                  80

Ser Gln Thr Val Ser Phe Ala Lys Lys Thr Thr Thr Thr Ser Thr
                85                  90                  95

Ser Thr Thr Asn Gly Trp Thr Glu Gly Gly Lys Ile Ser Asp Thr Leu
            100                 105                 110

Glu Glu Lys Val Ser Val Ser Ile Pro Phe Ile Gly Glu Gly Gly Gly
            115                 120                 125

Lys Asn Ser Thr Thr Ile Glu Ala Asn Phe Ala His Asn Ser Ser Thr
            130                 135                 140

Thr Thr Ala Gln Gln Ala Ser Thr Asp Ile Glu Trp Asn Ile Ser Gln
145                 150                 155                 160

Pro Val Leu Val Pro Pro Arg Lys Gln Val Val Ala Thr Leu Val Ile
                165                 170                 175

Met Gly Gly Asn Phe Thr Ile Pro Met Asp Leu Met Thr Thr Ile Asp
            180                 185                 190
```

```
Ser Thr Glu His Tyr Ser Gly Tyr Pro Ile Leu Thr Trp Ile Ser Ser
        195                 200                 205

Pro Asp Asn Ser Tyr Asn Gly Pro Phe Met Ser Trp Tyr Phe Ala Asn
    210                 215                 220

Trp Pro Asn Leu Pro Ser Gly Phe Gly Pro Leu Asn Ser Asp Asn Ala
225                 230                 235                 240

Val Thr Tyr Thr Gly Ser Val Val Ser Gln Val Ser Ala Gly Val Tyr
                245                 250                 255

Ala Thr Val Arg Phe Asp Gln Tyr Asp Ile His Asn Leu Arg Thr Ile
            260                 265                 270

Glu Lys Thr Trp Tyr Ala Arg His Ala Thr Leu His Asn Gly Lys Lys
        275                 280                 285

Ile Ser Ile Asn Asn Val Thr Glu Met Ala Pro Thr Ser Pro Ile Lys
    290                 295                 300

Thr Asn
305

<210> SEQ ID NO 100
<211> LENGTH: 306
<212> TYPE: PRT
<213> ORGANISM: Artificial Sequence
<220> FEATURE:
<223> OTHER INFORMATION: engineered

<400> SEQUENCE: 100

Met Ala Ile Leu Asp Leu Lys Ser Leu Val Leu Asn Ala Ile Asn Tyr
1               5                   10                  15

Trp Gly Pro Lys Asn Asn Asn Gly Ile Gln Gly Gly Asp Phe Gly Tyr
                20                  25                  30

Pro Ile Ser Glu Lys Gln Ile Asp Thr Ser Ile Ile Thr Ser Thr His
            35                  40                  45

Pro Arg Leu Ile Pro His Asp Leu Thr Ile Pro Gln Asn Leu Glu Thr
        50                  55                  60

Ile Phe Thr Thr Thr Gln Val Leu Thr Asn Asn Thr Asp Leu Gln Gln
65                  70                  75                  80

Ser Gln Thr Val Ser Phe Ala Lys Lys Thr Thr Thr Thr Thr Ser Thr
                85                  90                  95

Ser Thr Thr Asn Gly Trp Thr Glu Gly Gly Lys Ile Ser Asp Thr Leu
                100                 105                 110

Glu Glu Lys Val Ser Val Ser Ile Pro Phe Ile Gly Glu Gly Gly Gly
            115                 120                 125

Lys Asn Ser Thr Thr Ile Glu Ala Asn Phe Ala His Asn Ser Ser Thr
        130                 135                 140

Thr Thr Ala Gln Gln Ala Ser Thr Asp Ile Glu Trp Asn Ile Ser Gln
145                 150                 155                 160

Pro Val Leu Val Pro Pro Arg Lys Gln Val Val Ala Thr Leu Val Ile
                165                 170                 175

Met Gly Gly Asn Phe Thr Ile Pro Met Asp Leu Met Thr Thr Ile Asp
                180                 185                 190

Ser Thr Glu His Ala Ser Gly Tyr Pro Ile Leu Thr Trp Ile Ser Ser
            195                 200                 205

Pro Asp Asn Ser Tyr Asn Gly Pro Phe Met Ser Trp Tyr Phe Ala Asn
        210                 215                 220

Trp Pro Asn Leu Pro Ser Gly Phe Gly Pro Leu Asn Ser Asp Asn Thr
225                 230                 235                 240
```

Val Thr Tyr Thr Gly Ser Val Val Ser Gln Val Ser Ala Gly Val Tyr
            245                 250                 255

Ala Thr Val Arg Phe Asp Gln Tyr Asp Ile His Asn Leu Arg Thr Ile
            260                 265                 270

Glu Lys Thr Trp Tyr Ala Arg His Ala Thr Leu His Asn Gly Lys Lys
            275                 280                 285

Ile Ser Ile Asn Asn Val Thr Glu Met Ala Pro Thr Ser Pro Ile Lys
290                 295                 300

Thr Asn
305

<210> SEQ ID NO 101
<211> LENGTH: 306
<212> TYPE: PRT
<213> ORGANISM: Artificial Sequence
<220> FEATURE:
<223> OTHER INFORMATION: engineered

<400> SEQUENCE: 101

Met Ala Ile Leu Asp Leu Lys Ser Leu Val Leu Asn Ala Ile Asn Tyr
1               5                   10                  15

Trp Gly Pro Lys Asn Asn Gly Ile Gln Gly Gly Asp Phe Gly Tyr
            20                  25                  30

Pro Ile Ser Glu Lys Gln Ile Asp Thr Ser Ile Ile Thr Ser Thr His
            35                  40                  45

Pro Arg Leu Ile Pro His Asp Leu Thr Ile Pro Gln Asn Leu Glu Thr
        50                  55                  60

Ile Phe Thr Thr Thr Gln Val Leu Thr Asn Asn Thr Asp Leu Gln Gln
65                  70                  75                  80

Ser Gln Thr Val Ser Phe Ala Lys Lys Thr Thr Thr Thr Ala Thr
            85                  90                  95

Ser Thr Thr Asn Gly Trp Thr Glu Gly Gly Lys Ile Ser Asp Thr Leu
            100                 105                 110

Glu Glu Lys Val Ser Val Ser Ile Pro Phe Ile Gly Glu Gly Gly Gly
            115                 120                 125

Lys Asn Ser Thr Thr Ile Glu Ala Asn Phe Ala His Asn Ser Ser Thr
        130                 135                 140

Thr Thr Phe Gln Gln Ala Ser Thr Asp Ile Glu Trp Asn Ile Ser Gln
145                 150                 155                 160

Pro Val Leu Val Pro Pro Arg Lys Gln Val Val Ala Thr Leu Val Ile
            165                 170                 175

Met Gly Gly Asn Phe Thr Ile Pro Met Asp Leu Met Thr Thr Ile Asp
            180                 185                 190

Ser Thr Glu His Tyr Ser Gly Tyr Pro Ile Leu Thr Trp Ile Ser Ser
            195                 200                 205

Pro Asp Asn Ser Tyr Asn Gly Pro Phe Met Ser Trp Tyr Phe Ala Asn
        210                 215                 220

Trp Pro Asn Leu Pro Ser Gly Phe Gly Pro Leu Asn Ser Asp Asn Thr
225                 230                 235                 240

Val Thr Tyr Thr Gly Ser Val Val Ser Gln Val Ser Ala Gly Val Tyr
            245                 250                 255

Ala Thr Val Arg Phe Asp Gln Tyr Asp Ile His Asn Leu Arg Thr Ile
            260                 265                 270

Glu Lys Thr Trp Tyr Ala Arg His Ala Thr Leu His Asn Gly Lys Lys
            275                 280                 285

Ile Ser Ile Ala Asn Val Thr Glu Met Ala Pro Thr Ser Pro Ile Lys
    290                 295                 300

Thr Asn
305

<210> SEQ ID NO 102
<211> LENGTH: 306
<212> TYPE: PRT
<213> ORGANISM: Artificial Sequence
<220> FEATURE:
<223> OTHER INFORMATION: engineered

<400> SEQUENCE: 102

Met Ala Ile Leu Asp Leu Lys Ser Leu Val Leu Asn Ala Ile Asn Tyr
1               5                   10                  15

Trp Gly Pro Lys Asn Asn Asn Gly Ile Gln Gly Gly Asp Phe Gly Tyr
            20                  25                  30

Pro Ile Ser Glu Lys Gln Ile Asp Thr Ser Ile Ile Thr Ser Thr His
        35                  40                  45

Pro Arg Leu Ile Pro His Asp Leu Thr Ile Pro Gln Asn Leu Glu Thr
    50                  55                  60

Ile Phe Thr Thr Thr Gln Val Leu Thr Asn Asn Thr Asp Leu Gln Gln
65                  70                  75                  80

Ser Gln Thr Val Ser Phe Ala Lys Lys Thr Thr Thr Thr Thr Ser Thr
                85                  90                  95

Ser Thr Thr Asn Gly Trp Thr Glu Gly Gly Lys Ile Ser Asp Thr Leu
            100                 105                 110

Glu Glu Lys Val Ser Val Ser Ile Pro Phe Ile Gly Glu Gly Gly Gly
        115                 120                 125

Lys Asn Ser Thr Thr Ile Glu Ala Asn Phe Ala His Asn Ser Ser Thr
    130                 135                 140

Thr Thr Ala Gln Gln Ala Ser Thr Asp Ile Glu Trp Asn Ile Ser Gln
145                 150                 155                 160

Pro Val Leu Val Pro Pro Arg Lys Gln Val Val Ala Thr Leu Val Ile
                165                 170                 175

Met Gly Gly Asn Phe Thr Ile Pro Met Asp Leu Met Thr Thr Ile Asp
            180                 185                 190

Ser Thr Glu His Tyr Ser Gly Tyr Pro Ile Leu Thr Trp Ile Ser Ser
        195                 200                 205

Pro Asp Asn Ser Tyr Asn Gly Pro Phe Met Ser Trp Tyr Phe Ala Asn
    210                 215                 220

Trp Pro Asn Leu Pro Ser Gly Phe Gly Pro Leu Asn Ser Asp Asn Thr
225                 230                 235                 240

Val Thr Tyr Thr Gly Ser Val Val Ser Gln Val Ser Ala Gly Val Tyr
                245                 250                 255

Ala Thr Val Arg Phe Asp Gln Tyr Asp Ile His Asn Leu Arg Thr Ile
            260                 265                 270

Glu Lys Thr Trp Tyr Ala Arg His Ala Thr Leu His Asn Gly Lys Lys
        275                 280                 285

Ile Ser Ile Asn Asn Val Thr Glu Met Ala Pro Thr Ser Pro Ile Lys
    290                 295                 300

Thr Asn
305

<210> SEQ ID NO 103

```
<211> LENGTH: 306
<212> TYPE: PRT
<213> ORGANISM: Artificial Sequence
<220> FEATURE:
<223> OTHER INFORMATION: engineered

<400> SEQUENCE: 103
```

Met Ala Ile Leu Asp Leu Lys Ser Leu Val Leu Asn Ala Ile Asn Tyr
1               5                   10                  15

Trp Gly Pro Lys Asn Asn Gly Ile Gln Gly Gly Asp Phe Gly Tyr
            20                  25                  30

Pro Ile Ser Glu Lys Gln Ile Asp Thr Ser Ile Ile Thr Ser Thr His
            35                  40                  45

Pro Arg Leu Ile Pro His Asp Leu Thr Ile Pro Gln Asn Leu Glu Thr
        50                  55                  60

Ile Phe Thr Thr Thr Gln Val Leu Thr Asn Asn Thr Asp Leu Gln Gln
65                  70                  75                  80

Ser Gln Thr Val Ser Phe Ala Lys Lys Thr Thr Thr Thr Ser Thr
                85                  90                  95

Ser Thr Thr Asn Gly Trp Thr Glu Gly Gly Lys Ile Ser Asp Thr Leu
                100                 105                 110

Glu Glu Lys Val Ser Val Ser Ile Pro Phe Ile Gly Glu Gly Gly Gly
            115                 120                 125

Lys Asn Ser Thr Thr Ile Glu Ala Asn Phe Ala His Asn Ser Ser Thr
    130                 135                 140

Thr Thr Ala Gln Gln Ala Ser Thr Asp Ile Glu Trp Asn Ile Ser Gln
145                 150                 155                 160

Pro Val Leu Val Pro Pro Arg Lys Gln Val Val Ala Thr Leu Val Ile
                165                 170                 175

Met Gly Gly Asn Phe Thr Ile Pro Met Asp Leu Met Thr Thr Ile Asp
                180                 185                 190

Ser Thr Glu His Tyr Ser Gly Tyr Pro Ile Leu Thr Trp Ile Ser Ser
            195                 200                 205

Pro Asp Asn Ser Tyr Asn Gly Pro Phe Met Ser Trp Tyr Phe Ala Asn
    210                 215                 220

Trp Pro Asn Leu Pro Ser Gly Phe Gly Pro Leu Asn Ser Asp Asn Thr
225                 230                 235                 240

Val Thr Tyr Thr Gly Ser Val Val Ser Gln Val Ser Ala Gly Val Tyr
                245                 250                 255

Ala Thr Val Arg Phe Asp Gln Tyr Asp Ile His Asn Leu Arg Thr Ile
            260                 265                 270

Glu Lys Thr Trp Tyr Ala Arg His Ala Thr Leu His Asn Gly Lys Lys
        275                 280                 285

Ile Ser Ile Asn Asn Val Thr Ala Met Ala Pro Thr Ser Pro Ile Lys
    290                 295                 300

Thr Asn
305

```
<210> SEQ ID NO 104
<211> LENGTH: 306
<212> TYPE: PRT
<213> ORGANISM: Artificial Sequence
<220> FEATURE:
<223> OTHER INFORMATION: engineered

<400> SEQUENCE: 104
```

Met Ala Ile Leu Asp Leu Lys Ser Leu Val Leu Asn Ala Ile Asn Tyr

```
                1               5                  10                 15
        Trp Gly Pro Lys Asn Asn Gly Ile Gln Gly Gly Asp Phe Gly Tyr
                        20                  25                 30

Pro Ile Ser Glu Lys Gln Ile Asp Thr Ser Ile Ile Thr Ser Thr His
                        35                  40                 45

Pro Arg Leu Ile Pro His Asp Leu Thr Ile Pro Gln Asn Leu Glu Thr
                        50                  55                 60

Ile Phe Thr Thr Thr Gln Val Leu Thr Asn Asn Thr Asp Leu Gln Gln
        65                      70                  75                 80

Ser Gln Thr Val Ser Phe Ala Lys Lys Thr Thr Thr Thr Ala Thr
                            85                  90                 95

Ser Thr Thr Asn Gly Trp Thr Glu Gly Gly Lys Ile Ser Asp Thr Leu
                        100                 105                110

Glu Glu Lys Val Ser Val Ser Ile Pro Phe Ile Gly Glu Gly Gly Gly
                        115                 120                125

Lys Asn Ser Thr Thr Ile Glu Ala Asn Phe Ala His Asn Ser Ser Thr
                        130                 135                140

Thr Thr Phe Gln Gln Ala Ser Thr Asp Ile Glu Trp Asn Ile Ser Gln
        145                     150                 155                160

Pro Val Leu Val Pro Pro Arg Lys Gln Val Val Ala Thr Leu Val Ile
                        165                 170                175

Met Gly Gly Asn Phe Thr Ile Pro Met Asp Leu Met Thr Thr Ile Asp
                        180                 185                190

Ser Thr Glu His Tyr Ser Gly Tyr Pro Ile Leu Thr Trp Ile Ser Ser
                        195                 200                205

Pro Asp Asn Ser Tyr Asn Gly Pro Phe Met Ser Trp Tyr Phe Ala Asn
                        210                 215                220

Trp Pro Asn Leu Pro Ser Gly Phe Gly Pro Leu Asn Ser Asp Asn Thr
        225                     230                 235                240

Val Thr Tyr Thr Gly Ser Val Val Ser Gln Val Ser Ala Gly Val Tyr
                        245                 250                255

Ala Thr Val Arg Phe Asp Gln Tyr Asp Ile His Asn Leu Arg Thr Ile
                        260                 265                270

Glu Lys Thr Trp Tyr Ala Ala His Ala Thr Leu His Asn Gly Lys Lys
                        275                 280                285

Ile Ser Ile Asn Asn Val Thr Glu Met Ala Pro Thr Ser Pro Ile Lys
                        290                 295                300

Thr Asn
        305

<210> SEQ ID NO 105
        <211> LENGTH: 306
        <212> TYPE: PRT
        <213> ORGANISM: Artificial Sequence
        <220> FEATURE:
        <223> OTHER INFORMATION: engineered

<400> SEQUENCE: 105

Met Ala Ile Leu Asp Leu Lys Ser Leu Val Leu Asn Ala Ile Asn Tyr
        1               5                   10                 15

Trp Gly Pro Lys Asn Asn Gly Ile Gln Gly Gly Asp Phe Gly Tyr
                        20                  25                 30

Pro Ile Ser Glu Lys Gln Ile Asp Thr Ser Ile Ile Thr Ser Thr His
                        35                  40                 45

Pro Arg Leu Ile Pro His Asp Leu Thr Ile Pro Gln Asn Leu Glu Thr
```

```
            50                  55                  60
Ile Phe Thr Thr Thr Gln Val Leu Thr Asn Asn Thr Asp Leu Gln Gln
 65                  70                  75                  80

Ser Gln Thr Val Ser Phe Ala Lys Lys Thr Thr Thr Ala Thr Ser Thr
                 85                  90                  95

Ser Thr Thr Asn Gly Trp Thr Glu Gly Gly Lys Ile Ser Asp Thr Leu
                100                 105                 110

Glu Glu Lys Val Ser Val Ser Ile Pro Phe Ile Gly Glu Gly Gly Gly
                115                 120                 125

Lys Asn Ser Thr Thr Ile Glu Ala Asn Phe Ala His Asn Ser Ser Thr
                130                 135                 140

Thr Thr Phe Gln Gln Ala Ser Thr Asp Ile Glu Trp Asn Ile Ser Gln
145                 150                 155                 160

Pro Val Leu Val Pro Arg Lys Gln Val Ala Thr Leu Val Ile
                165                 170                 175

Met Gly Gly Asn Phe Thr Ile Pro Met Asp Leu Met Thr Thr Ile Asp
                180                 185                 190

Ser Thr Glu His Tyr Ser Gly Tyr Pro Ile Leu Thr Trp Ile Ser Ser
                195                 200                 205

Pro Asp Asn Ser Tyr Asn Gly Pro Phe Met Ser Trp Tyr Phe Ala Asn
                210                 215                 220

Trp Pro Asn Leu Pro Ser Gly Phe Gly Pro Leu Asn Ser Asp Asn Thr
225                 230                 235                 240

Val Thr Tyr Thr Gly Ser Val Val Ser Gln Val Ser Ala Gly Val Tyr
                245                 250                 255

Ala Thr Val Arg Phe Asp Gln Tyr Asp Ile His Asn Leu Arg Thr Ile
                260                 265                 270

Glu Lys Thr Trp Tyr Ala Arg His Ala Thr Leu His Asn Gly Lys Lys
                275                 280                 285

Ile Ser Ile Asn Asn Val Thr Glu Met Ala Pro Thr Ser Pro Ala Lys
                290                 295                 300

Thr Asn
305

<210> SEQ ID NO 106
<211> LENGTH: 306
<212> TYPE: PRT
<213> ORGANISM: Artificial Sequence
<220> FEATURE:
<223> OTHER INFORMATION: engineered

<400> SEQUENCE: 106

Met Ala Ile Leu Asp Leu Lys Ser Leu Val Leu Asn Ala Ile Asn Tyr
 1               5                  10                  15

Trp Gly Pro Lys Asn Asn Gly Ile Gln Gly Gly Asp Phe Gly Tyr
                 20                  25                  30

Pro Ile Ser Glu Lys Gln Ile Asp Thr Ser Ile Ile Thr Ser Thr His
                 35                  40                  45

Pro Arg Leu Ile Pro His Asp Leu Thr Ile Pro Gln Asn Leu Glu Thr
                 50                  55                  60

Ile Phe Thr Thr Thr Gln Val Leu Thr Asn Asn Thr Asp Leu Gln Gln
 65                  70                  75                  80

Ser Gln Thr Val Ser Phe Ala Lys Lys Thr Thr Thr Thr Ala Thr
                 85                  90                  95

Ser Thr Thr Asn Gly Trp Thr Glu Gly Gly Lys Ile Ser Asp Thr Leu
```

```
              100                 105                 110
Glu Glu Lys Val Ser Val Ser Ile Pro Phe Ile Gly Glu Gly Gly Gly
            115                 120                 125

Lys Asn Ser Thr Thr Ile Glu Ala Asn Phe Ala His Asn Ser Ser Thr
        130                 135                 140

Thr Thr Phe Gln Gln Ala Ser Thr Asp Ile Glu Trp Asn Ile Ser Gln
145                 150                 155                 160

Pro Val Leu Val Pro Arg Lys Gln Val Val Ala Thr Leu Val Ile
                165                 170                 175

Met Gly Gly Asn Phe Thr Ile Pro Met Asp Leu Met Thr Thr Ile Asp
            180                 185                 190

Ser Thr Glu His Tyr Ser Gly Tyr Pro Ile Leu Thr Trp Ile Ser Ser
        195                 200                 205

Pro Asp Asn Ser Tyr Asn Gly Pro Phe Met Ser Trp Tyr Phe Ala Asn
        210                 215                 220

Trp Pro Asn Leu Pro Ser Gly Phe Gly Pro Leu Asn Ser Asp Asn Thr
225                 230                 235                 240

Val Thr Tyr Thr Gly Ala Val Val Ser Gln Val Ser Ala Gly Val Tyr
                245                 250                 255

Ala Thr Val Arg Phe Asp Gln Tyr Asp Ile His Asn Leu Arg Thr Ile
                260                 265                 270

Glu Lys Thr Trp Tyr Ala Arg His Ala Thr Leu His Asn Gly Lys Lys
            275                 280                 285

Ile Ser Ile Asn Asn Val Thr Glu Met Ala Pro Thr Ser Pro Ile Lys
        290                 295                 300

Thr Asn
305

<210> SEQ ID NO 107
<211> LENGTH: 306
<212> TYPE: PRT
<213> ORGANISM: Artificial Sequence
<220> FEATURE:
<223> OTHER INFORMATION: engineered

<400> SEQUENCE: 107

Met Ala Ile Leu Asp Leu Lys Ser Leu Val Leu Asn Ala Ile Asn Tyr
1               5                   10                  15

Trp Gly Pro Lys Asn Asn Gly Ile Gln Gly Gly Asp Phe Gly Tyr
            20                  25                  30

Pro Ile Ser Glu Lys Gln Ile Asp Thr Ser Ile Thr Ser Thr His
        35                  40                  45

Pro Arg Leu Ile Pro His Asp Leu Thr Ile Pro Gln Asn Leu Glu Thr
    50                  55                  60

Ile Phe Thr Thr Thr Gln Val Leu Thr Asn Asn Thr Asp Leu Gln Gln
65                  70                  75                  80

Ser Gln Thr Val Ser Phe Ser Lys Lys Thr Thr Thr Ala Thr Ser Thr
                85                  90                  95

Ser Thr Thr Asn Gly Trp Thr Glu Gly Gly Lys Ile Ser Asp Thr Leu
            100                 105                 110

Glu Glu Lys Val Ser Val Ser Ile Pro Phe Ile Gly Glu Gly Gly Gly
            115                 120                 125

Lys Asn Ser Thr Thr Ile Glu Ala Asn Phe Ala His Asn Ser Ser Thr
        130                 135                 140

Thr Thr Phe Gln Gln Ala Ser Thr Asp Ile Glu Trp Asn Ile Ser Gln
```

```
                145                 150                 155                 160
Pro Val Leu Val Pro Pro Arg Lys Gln Val Val Ala Thr Leu Val Ile
                165                 170                 175

Met Gly Gly Asn Phe Thr Ile Pro Met Asp Leu Met Thr Thr Ile Asp
                180                 185                 190

Ser Thr Glu His Tyr Ser Gly Tyr Pro Ile Leu Thr Trp Ile Ser Ser
                195                 200                 205

Pro Asp Asn Ser Tyr Asn Gly Pro Phe Met Ser Trp Tyr Phe Ala Asn
                210                 215                 220

Trp Pro Asn Leu Pro Ser Gly Phe Gly Pro Leu Asn Ser Asp Asn Thr
225                 230                 235                 240

Val Thr Tyr Thr Gly Ser Val Val Ser Gln Val Ser Ala Gly Val Tyr
                245                 250                 255

Ala Thr Val Arg Phe Asp Gln Tyr Asp Ile His Asn Leu Arg Thr Ile
                260                 265                 270

Glu Lys Thr Trp Tyr Ala Arg His Ala Thr Leu His Asn Gly Lys Lys
                275                 280                 285

Ile Ser Ile Asn Asn Val Thr Glu Met Ala Pro Thr Ser Pro Ile Lys
                290                 295                 300

Thr Asn
305

<210> SEQ ID NO 108
<211> LENGTH: 306
<212> TYPE: PRT
<213> ORGANISM: Artificial Sequence
<220> FEATURE:
<223> OTHER INFORMATION: engineered

<400> SEQUENCE: 108

Met Ala Ile Leu Asp Leu Lys Ser Leu Val Leu Asn Ala Ile Asn Tyr
1               5                   10                  15

Trp Gly Pro Lys Asn Asn Asn Gly Ile Gln Gly Gly Asp Phe Gly Tyr
                20                  25                  30

Pro Ile Ser Glu Lys Gln Ile Asp Thr Ser Ile Ile Thr Ser Thr His
                35                  40                  45

Pro Arg Leu Ile Pro His Asp Leu Thr Ile Pro Gln Asn Leu Glu Thr
                50                  55                  60

Ile Phe Thr Thr Thr Gln Val Leu Thr Asn Asn Thr Asp Leu Gln Gln
65                  70                  75                  80

Ser Gln Thr Val Ser Phe Ala Lys Lys Thr Thr Thr Ala Thr Ser Thr
                85                  90                  95

Ser Thr Thr Asn Gly Trp Thr Glu Gly Gly Lys Ile Ser Asp Thr Leu
                100                 105                 110

Glu Glu Lys Val Ser Val Ser Ile Pro Phe Ile Gly Glu Gly Gly Gly
                115                 120                 125

Lys Asn Ser Thr Thr Ile Glu Ala Asn Phe Ala His Asn Ser Ser Thr
                130                 135                 140

Thr Thr Phe Gln Gln Ala Ser Thr Asp Ile Glu Trp Asn Ile Ala Gln
145                 150                 155                 160

Pro Val Leu Val Pro Pro Arg Lys Gln Val Val Ala Thr Leu Val Ile
                165                 170                 175

Met Gly Gly Asn Phe Thr Ile Pro Met Asp Leu Met Thr Thr Ile Asp
                180                 185                 190

Ser Thr Glu His Tyr Ser Gly Tyr Pro Ile Leu Thr Trp Ile Ser Ser
```

```
                195                 200                 205
Pro Asp Asn Ser Tyr Asn Gly Pro Phe Met Ser Trp Tyr Phe Ala Asn
210                 215                 220

Trp Pro Asn Leu Pro Ser Gly Phe Gly Pro Leu Asn Ser Asp Asn Thr
225                 230                 235                 240

Val Thr Tyr Thr Gly Ser Val Val Ser Gln Val Ser Ala Gly Val Tyr
                245                 250                 255

Ala Thr Val Arg Phe Asp Gln Tyr Asp Ile His Asn Leu Arg Thr Ile
            260                 265                 270

Glu Lys Thr Trp Tyr Ala Arg His Ala Thr Leu His Asn Gly Lys Lys
        275                 280                 285

Ile Ser Ile Asn Asn Val Thr Glu Met Ala Pro Thr Ser Pro Ile Lys
290                 295                 300

Thr Asn
305

<210> SEQ ID NO 109
<211> LENGTH: 306
<212> TYPE: PRT
<213> ORGANISM: Artificial Sequence
<220> FEATURE:
<223> OTHER INFORMATION: engineered

<400> SEQUENCE: 109

Met Ala Ile Leu Asp Leu Lys Ser Leu Val Leu Asn Ala Ile Asn Tyr
1               5                   10                  15

Trp Gly Pro Lys Asn Asn Asn Gly Ile Gln Gly Gly Asp Phe Gly Tyr
            20                  25                  30

Pro Ile Ser Glu Lys Gln Ile Asp Thr Ser Ile Ile Thr Ser Thr His
        35                  40                  45

Pro Arg Leu Ile Pro His Asp Leu Thr Ile Pro Gln Asn Leu Glu Thr
    50                  55                  60

Ile Phe Thr Thr Thr Gln Val Leu Thr Asn Asn Thr Asp Leu Gln Gln
65                  70                  75                  80

Ser Gln Thr Val Ser Phe Ala Lys Lys Thr Thr Thr Thr Thr Ser Thr
                85                  90                  95

Ser Thr Thr Asn Gly Trp Thr Glu Gly Gly Lys Ile Ser Asp Thr Leu
            100                 105                 110

Glu Glu Lys Val Ser Val Ser Ile Pro Phe Ile Gly Glu Gly Gly Gly
        115                 120                 125

Lys Asn Ser Thr Thr Ile Glu Ala Asn Phe Ala His Asn Ser Ser Thr
    130                 135                 140

Thr Thr Ala Gln Gln Ala Ser Thr Asp Ile Glu Trp Asn Ile Ser Gln
145                 150                 155                 160

Pro Val Leu Val Pro Pro Arg Lys Gln Val Val Ala Thr Leu Val Ile
                165                 170                 175

Met Gly Gly Asn Phe Thr Ile Pro Met Asp Leu Met Thr Thr Ile Asp
            180                 185                 190

Ser Thr Glu His Tyr Ser Gly Tyr Pro Ile Leu Thr Trp Ile Ser Ser
        195                 200                 205

Pro Asp Asn Ser Tyr Asn Gly Pro Phe Met Ser Trp Tyr Phe Ala Asn
    210                 215                 220

Trp Pro Asn Leu Pro Ser Gly Phe Gly Pro Leu Asn Ser Asp Asn Thr
225                 230                 235                 240

Val Thr Tyr Thr Gly Ser Val Val Ser Gln Val Ser Ala Gly Val Tyr
```

```
                        245                 250                 255
Ala Thr Val Arg Phe Asp Gln Tyr Asp Ile His Asn Leu Arg Thr Ile
                    260                 265                 270

Glu Lys Thr Trp Tyr Ala Arg His Ala Thr Leu His Asn Gly Lys Lys
                275                 280                 285

Ile Ser Ile Asn Asn Val Thr Glu Met Ala Pro Ala Ser Pro Ile Lys
            290                 295                 300

Thr Asn
305

<210> SEQ ID NO 110
<211> LENGTH: 306
<212> TYPE: PRT
<213> ORGANISM: Artificial Sequence
<220> FEATURE:
<223> OTHER INFORMATION: engineered

<400> SEQUENCE: 110

Met Ala Ile Leu Asp Leu Lys Ser Leu Val Leu Asn Ala Ile Asn Tyr
1               5                   10                  15

Trp Gly Pro Lys Asn Asn Gly Ile Gln Gly Gly Asp Phe Gly Tyr
            20                  25                  30

Pro Ile Ser Glu Lys Gln Ile Asp Thr Ser Ile Ile Thr Ser Thr His
        35                  40                  45

Pro Arg Leu Ile Pro His Asp Leu Thr Ile Pro Gln Asn Leu Glu Thr
    50                  55                  60

Ile Phe Thr Thr Thr Gln Val Leu Thr Asn Asn Thr Asp Leu Gln Gln
65                  70                  75                  80

Ser Gln Thr Val Ser Phe Ala Lys Lys Thr Thr Thr Ala Thr Ser Thr
                85                  90                  95

Ser Thr Thr Asn Gly Trp Thr Glu Gly Gly Lys Ile Ser Asp Thr Leu
            100                 105                 110

Glu Glu Lys Val Ser Val Ser Ile Pro Phe Ile Gly Glu Gly Gly Gly
        115                 120                 125

Lys Asn Ser Thr Thr Ile Glu Ala Asn Phe Ala His Asn Ser Ser Thr
    130                 135                 140

Thr Thr Phe Ala Gln Ala Ser Thr Asp Ile Glu Trp Asn Ile Ser Gln
145                 150                 155                 160

Pro Val Leu Val Pro Pro Arg Lys Gln Val Ala Thr Leu Val Ile
                165                 170                 175

Met Gly Gly Asn Phe Thr Ile Pro Met Asp Leu Met Thr Thr Ile Asp
            180                 185                 190

Ser Thr Glu His Tyr Ser Gly Tyr Pro Ile Leu Thr Trp Ile Ser Ser
        195                 200                 205

Pro Asp Asn Ser Tyr Asn Gly Pro Phe Met Ser Trp Tyr Phe Ala Asn
    210                 215                 220

Trp Pro Asn Leu Pro Ser Gly Phe Gly Pro Leu Asn Ser Asp Asn Thr
225                 230                 235                 240

Val Thr Tyr Thr Gly Ser Val Val Ser Gln Val Ser Ala Gly Val Tyr
                245                 250                 255

Ala Thr Val Arg Phe Asp Gln Tyr Asp Ile His Asn Leu Arg Thr Ile
            260                 265                 270

Glu Lys Thr Trp Tyr Ala Arg His Ala Thr Leu His Asn Gly Lys Lys
        275                 280                 285

Ile Ser Ile Asn Asn Val Thr Glu Met Ala Pro Thr Ser Pro Ile Lys
```

290                 295                 300

Thr Asn
305

<210> SEQ ID NO 111
<211> LENGTH: 306
<212> TYPE: PRT
<213> ORGANISM: Artificial Sequence
<220> FEATURE:
<223> OTHER INFORMATION: engineered

<400> SEQUENCE: 111

Met Ala Ile Leu Asp Leu Lys Ser Leu Val Leu Asn Ala Ile Asn Tyr
1               5                   10                  15

Trp Gly Pro Lys Asn Asn Gly Ile Gln Gly Gly Asp Phe Gly Tyr
            20                  25                  30

Pro Ile Ser Glu Lys Gln Ile Asp Thr Ser Ile Ile Thr Ser Thr His
        35                  40                  45

Pro Arg Leu Ile Pro His Asp Leu Thr Ile Pro Gln Asn Leu Glu Thr
    50                  55                  60

Ile Phe Thr Thr Thr Gln Val Leu Thr Asn Asn Thr Asp Leu Gln Gln
65                  70                  75                  80

Ser Gln Thr Val Ser Phe Ala Lys Lys Thr Thr Thr Thr Ala Thr
                85                  90                  95

Ser Thr Thr Asn Gly Trp Thr Glu Gly Gly Lys Ile Ser Asp Thr Leu
            100                 105                 110

Glu Glu Lys Val Ser Val Ser Ile Pro Phe Ile Gly Glu Gly Gly Gly
        115                 120                 125

Lys Asn Ser Thr Thr Ile Glu Ala Asn Phe Ala His Asn Ser Ser Thr
130                 135                 140

Thr Phe Gln Gln Ala Ser Thr Asp Ile Glu Trp Asn Ile Ser Gln
145                 150                 155                 160

Pro Val Leu Val Pro Pro Arg Lys Gln Val Val Ala Thr Leu Ala Ile
                165                 170                 175

Met Gly Gly Asn Phe Thr Ile Pro Met Asp Leu Met Thr Thr Ile Asp
            180                 185                 190

Ser Thr Glu His Tyr Ser Gly Tyr Pro Ile Leu Thr Trp Ile Ser Ser
        195                 200                 205

Pro Asp Asn Ser Tyr Asn Gly Pro Phe Met Ser Trp Tyr Phe Ala Asn
    210                 215                 220

Trp Pro Asn Leu Pro Ser Gly Phe Gly Pro Leu Asn Ser Asp Asn Thr
225                 230                 235                 240

Val Thr Tyr Thr Gly Ser Val Val Ser Gln Val Ser Ala Gly Val Tyr
                245                 250                 255

Ala Thr Val Arg Phe Asp Gln Tyr Asp Ile His Asn Leu Arg Thr Ile
            260                 265                 270

Glu Lys Thr Trp Tyr Ala Arg His Ala Thr Leu His Asn Gly Lys Lys
        275                 280                 285

Ile Ser Ile Asn Asn Val Thr Glu Met Ala Pro Thr Ser Pro Ile Lys
    290                 295                 300

Thr Asn
305

<210> SEQ ID NO 112
<211> LENGTH: 306
<212> TYPE: PRT

<213> ORGANISM: Artificial Sequence
<220> FEATURE:
<223> OTHER INFORMATION: engineered

<400> SEQUENCE: 112

| | | | | | | | | | | | | | | | |
|---|---|---|---|---|---|---|---|---|---|---|---|---|---|---|---|
| Met | Ala | Ile | Leu | Asp | Leu | Lys | Ser | Leu | Val | Leu | Asn | Ala | Ile | Asn | Tyr |
| 1 | | | | 5 | | | | | 10 | | | | | 15 | |
| Trp | Gly | Pro | Lys | Asn | Asn | Gly | Ile | Gln | Gly | Gly | Asp | Phe | Gly | Tyr | |
| | | | 20 | | | | | 25 | | | | | 30 | | |
| Pro | Ile | Ser | Glu | Lys | Gln | Ile | Asp | Thr | Ser | Ile | Ile | Thr | Ser | Thr | His |
| | | 35 | | | | | 40 | | | | | 45 | | | |
| Pro | Arg | Leu | Ile | Pro | His | Asp | Leu | Thr | Ile | Pro | Gln | Asn | Leu | Glu | Thr |
| | 50 | | | | | 55 | | | | | 60 | | | | |
| Ile | Phe | Thr | Thr | Thr | Gln | Val | Leu | Thr | Asn | Asn | Thr | Asp | Leu | Gln | Gln |
| 65 | | | | | 70 | | | | | 75 | | | | | 80 |
| Ser | Gln | Thr | Val | Ser | Phe | Ala | Lys | Lys | Thr | Thr | Thr | Thr | Ser | Thr | |
| | | | | 85 | | | | | 90 | | | | | 95 | |
| Ser | Thr | Thr | Asn | Gly | Trp | Thr | Glu | Gly | Gly | Lys | Ile | Ser | Asp | Thr | Leu |
| | | | 100 | | | | | 105 | | | | | 110 | | |
| Glu | Glu | Lys | Val | Ser | Val | Ser | Ile | Pro | Phe | Ile | Gly | Glu | Gly | Gly | Gly |
| | | 115 | | | | | 120 | | | | | 125 | | | |
| Lys | Asn | Ser | Thr | Thr | Ile | Glu | Ala | Asn | Phe | Ala | His | Asn | Ser | Ser | Thr |
| | 130 | | | | | 135 | | | | | 140 | | | | |
| Thr | Thr | Ala | Gln | Gln | Ala | Ser | Thr | Asp | Ile | Glu | Trp | Asn | Ile | Ser | Gln |
| 145 | | | | | 150 | | | | | 155 | | | | | 160 |
| Pro | Val | Leu | Val | Pro | Pro | Arg | Lys | Gln | Val | Val | Ala | Thr | Leu | Val | Ile |
| | | | | 165 | | | | | 170 | | | | | 175 | |
| Met | Gly | Gly | Asn | Phe | Thr | Ile | Pro | Met | Asp | Leu | Met | Thr | Thr | Ile | Asp |
| | | | 180 | | | | | 185 | | | | | 190 | | |
| Ser | Thr | Glu | His | Tyr | Ser | Gly | Tyr | Pro | Ile | Leu | Thr | Trp | Ile | Ser | Ser |
| | | 195 | | | | | 200 | | | | | 205 | | | |
| Pro | Asp | Asn | Ser | Tyr | Asn | Gly | Pro | Phe | Met | Ser | Trp | Tyr | Phe | Ala | Asn |
| | 210 | | | | | 215 | | | | | 220 | | | | |
| Trp | Pro | Asn | Leu | Pro | Ser | Gly | Phe | Gly | Pro | Leu | Asn | Ser | Ala | Asn | Thr |
| 225 | | | | | 230 | | | | | 235 | | | | | 240 |
| Val | Thr | Tyr | Thr | Gly | Ser | Val | Val | Ser | Gln | Val | Ser | Ala | Gly | Val | Tyr |
| | | | | 245 | | | | | 250 | | | | | 255 | |
| Ala | Thr | Val | Arg | Phe | Asp | Gln | Tyr | Asp | Ile | His | Asn | Leu | Arg | Thr | Ile |
| | | | 260 | | | | | 265 | | | | | 270 | | |
| Glu | Lys | Thr | Trp | Tyr | Ala | Arg | His | Ala | Thr | Leu | His | Asn | Gly | Lys | Lys |
| | | 275 | | | | | 280 | | | | | 285 | | | |
| Ile | Ser | Ile | Asn | Asn | Val | Thr | Glu | Met | Ala | Pro | Thr | Ser | Pro | Ile | Lys |
| | 290 | | | | | 295 | | | | | 300 | | | | |
| Thr | Asn | | | | | | | | | | | | | | |
| 305 | | | | | | | | | | | | | | | |

<210> SEQ ID NO 113
<211> LENGTH: 306
<212> TYPE: PRT
<213> ORGANISM: Artificial Sequence
<220> FEATURE:
<223> OTHER INFORMATION: engineered

<400> SEQUENCE: 113

| | | | | | | | | | | | | | | | |
|---|---|---|---|---|---|---|---|---|---|---|---|---|---|---|---|
| Met | Ala | Ile | Leu | Asp | Leu | Lys | Ser | Leu | Val | Leu | Asn | Ala | Ile | Asn | Tyr |
| 1 | | | | 5 | | | | | 10 | | | | | 15 | |

Trp Gly Pro Lys Asn Asn Asn Gly Ile Gln Gly Gly Asp Phe Gly Tyr
            20                  25                  30

Pro Ile Ser Glu Lys Gln Ile Asp Thr Ser Ile Ile Thr Ser Thr His
            35                  40                  45

Pro Arg Leu Ile Pro His Asp Leu Thr Ile Pro Gln Asn Leu Glu Thr
50                      55                  60

Ile Phe Thr Thr Thr Gln Val Leu Thr Asn Asn Thr Asp Leu Gln Gln
65                  70                  75                  80

Ser Gln Thr Val Ser Phe Ala Lys Lys Thr Thr Thr Thr Thr Ala Thr
                85                  90                  95

Ser Thr Thr Asn Gly Trp Thr Glu Gly Gly Lys Ile Ser Asp Thr Leu
            100                 105                 110

Glu Glu Lys Val Ser Val Ser Ile Pro Phe Ile Gly Glu Gly Gly Gly
            115                 120                 125

Lys Asn Ser Thr Thr Ile Glu Ala Asn Phe Ala His Asn Ser Ser Thr
            130                 135                 140

Thr Thr Ala Gln Gln Ala Ser Thr Asp Ile Glu Trp Asn Ile Ser Gln
145                 150                 155                 160

Pro Val Leu Val Pro Pro Arg Lys Gln Val Val Ala Thr Leu Val Ile
                165                 170                 175

Met Gly Gly Asn Phe Thr Ile Pro Met Asp Leu Met Thr Thr Ile Asp
            180                 185                 190

Ser Thr Glu His Tyr Ser Gly Tyr Pro Ile Leu Thr Trp Ile Ser Ser
            195                 200                 205

Pro Asp Asn Ser Tyr Asn Gly Pro Phe Met Ser Trp Tyr Phe Ala Asn
            210                 215                 220

Trp Pro Asn Leu Pro Ser Gly Phe Gly Pro Leu Asn Ser Asp Asn Thr
225                 230                 235                 240

Val Thr Tyr Thr Gly Ser Val Val Ser Gln Val Ser Ala Gly Val Tyr
                245                 250                 255

Ala Thr Val Arg Phe Asp Gln Tyr Asp Ile His Asn Leu Arg Thr Ile
            260                 265                 270

Glu Lys Thr Trp Tyr Ala Arg His Ala Thr Leu His Asn Gly Lys Lys
            275                 280                 285

Ile Ser Ile Asn Asn Val Thr Glu Met Ala Pro Thr Ser Pro Ile Lys
            290                 295                 300

Thr Asn
305

<210> SEQ ID NO 114
<211> LENGTH: 306
<212> TYPE: PRT
<213> ORGANISM: Artificial Sequence
<220> FEATURE:
<223> OTHER INFORMATION: engineered

<400> SEQUENCE: 114

Met Ala Ile Leu Asp Leu Lys Ser Leu Val Leu Asn Ala Ile Asn Tyr
1               5                   10                  15

Trp Gly Pro Lys Asn Asn Asn Gly Ile Gln Gly Gly Asp Phe Gly Tyr
            20                  25                  30

Pro Ile Ser Glu Lys Gln Ile Asp Thr Ser Ile Ile Thr Ser Thr His
            35                  40                  45

Pro Arg Leu Ile Pro His Asp Leu Thr Ile Pro Gln Asn Leu Glu Thr
50                      55                  60

```
Ile Phe Thr Thr Thr Gln Val Leu Thr Asn Asn Thr Asp Leu Gln Gln
 65                  70                  75                  80

Ser Gln Thr Val Ser Phe Ala Lys Lys Thr Thr Thr Thr Ser Thr
                 85                  90                  95

Ser Thr Thr Asn Gly Trp Thr Glu Gly Gly Lys Ile Ser Asp Thr Leu
                100                 105                 110

Glu Glu Lys Val Ser Val Ser Ile Pro Phe Ile Gly Glu Gly Gly Gly
            115                 120                 125

Lys Asn Ser Thr Thr Ile Glu Ala Asn Phe Ala His Asn Ser Ser Thr
            130                 135                 140

Thr Thr Ala Gln Gln Ala Ser Thr Asp Ile Glu Trp Asn Ile Ser Gln
145                 150                 155                 160

Pro Val Leu Val Pro Arg Lys Gln Val Val Ala Thr Leu Val Ile
                165                 170                 175

Ala Gly Gly Asn Phe Thr Ile Pro Met Asp Leu Met Thr Thr Ile Asp
                180                 185                 190

Ser Thr Glu His Tyr Ser Gly Tyr Pro Ile Leu Thr Trp Ile Ser Ser
            195                 200                 205

Pro Asp Asn Ser Tyr Asn Gly Pro Phe Met Ser Trp Tyr Phe Ala Asn
210                 215                 220

Trp Pro Asn Leu Pro Ser Gly Phe Gly Pro Leu Asn Ser Asp Asn Thr
225                 230                 235                 240

Val Thr Tyr Thr Gly Ser Val Val Ser Gln Val Ser Ala Gly Val Tyr
                245                 250                 255

Ala Thr Val Arg Phe Asp Gln Tyr Asp Ile His Asn Leu Arg Thr Ile
                260                 265                 270

Glu Lys Thr Trp Tyr Ala Arg His Ala Thr Leu His Asn Gly Lys Lys
            275                 280                 285

Ile Ser Ile Asn Asn Val Thr Glu Met Ala Pro Thr Ser Pro Ile Lys
            290                 295                 300

Thr Asn
305

<210> SEQ ID NO 115
<211> LENGTH: 306
<212> TYPE: PRT
<213> ORGANISM: Artificial Sequence
<220> FEATURE:
<223> OTHER INFORMATION: engineered

<400> SEQUENCE: 115

Met Ala Ile Leu Asp Leu Lys Ser Leu Val Leu Asn Ala Ile Asn Tyr
  1               5                  10                  15

Trp Gly Pro Lys Asn Asn Gly Ile Gln Gly Gly Asp Phe Gly Tyr
             20                  25                  30

Pro Ile Ser Glu Lys Gln Ile Asp Thr Ser Ile Ile Thr Ser Thr His
             35                  40                  45

Pro Arg Leu Ile Pro His Asp Leu Thr Ile Pro Gln Asn Leu Glu Thr
         50                  55                  60

Ile Phe Thr Thr Thr Gln Val Leu Thr Asn Asn Thr Asp Leu Gln Gln
 65                  70                  75                  80

Ser Gln Thr Val Ser Phe Ala Lys Lys Thr Thr Thr Thr Ser Thr
                 85                  90                  95

Ser Thr Thr Asn Gly Trp Thr Glu Gly Gly Lys Ile Ser Asp Thr Leu
                100                 105                 110
```

```
Glu Glu Lys Val Ser Val Ser Ile Pro Phe Ile Gly Glu Gly Gly
            115                 120                 125

Lys Asn Ser Thr Thr Ile Glu Ala Asn Phe Ala His Asn Ser Ser Thr
130                 135                 140

Thr Thr Ala Gln Gln Ala Ser Thr Asp Ile Glu Trp Asn Ile Ser Gln
145                 150                 155                 160

Pro Val Leu Val Pro Pro Arg Lys Gln Val Val Ala Thr Leu Val Ile
                165                 170                 175

Met Gly Gly Asn Phe Thr Ile Pro Met Asp Leu Met Thr Thr Ile Asp
            180                 185                 190

Ser Thr Glu His Tyr Ser Gly Tyr Pro Ile Leu Thr Trp Ile Ser Ser
            195                 200                 205

Pro Asp Asn Ser Tyr Asn Gly Pro Phe Met Ser Trp Tyr Phe Ala Asn
        210                 215                 220

Trp Pro Asn Leu Pro Ser Gly Phe Gly Pro Leu Asn Ser Asp Asn Thr
225                 230                 235                 240

Val Thr Tyr Thr Gly Ser Val Val Ser Gln Val Ser Ala Gly Val Tyr
                245                 250                 255

Ala Thr Val Arg Phe Asp Gln Tyr Asp Ile His Asn Leu Arg Thr Ile
            260                 265                 270

Glu Lys Thr Trp Tyr Ala Arg His Ala Thr Leu His Asn Gly Lys Lys
            275                 280                 285

Ile Ser Ile Asn Asn Val Thr Glu Ala Ala Pro Thr Ser Pro Ile Lys
            290                 295                 300

Thr Asn
305

<210> SEQ ID NO 116
<211> LENGTH: 306
<212> TYPE: PRT
<213> ORGANISM: Artificial Sequence
<220> FEATURE:
<223> OTHER INFORMATION: engineered

<400> SEQUENCE: 116

Met Ala Ile Leu Asp Leu Lys Ser Leu Val Leu Asn Ala Ile Asn Tyr
1               5                   10                  15

Trp Gly Pro Lys Asn Asn Gly Ile Gln Gly Gly Asp Phe Gly Tyr
            20                  25                  30

Pro Ile Ser Glu Lys Gln Ile Asp Thr Ser Ile Thr Ser Thr His
        35                  40                  45

Pro Arg Leu Ile Pro His Asp Leu Thr Ile Pro Gln Asn Leu Glu Thr
50                  55                  60

Ile Phe Thr Thr Thr Gln Val Leu Thr Asn Asn Thr Asp Leu Gln Gln
65                  70                  75                  80

Ser Gln Thr Val Ser Phe Ala Lys Lys Thr Thr Thr Thr Ala Thr
                85                  90                  95

Ser Thr Thr Asn Gly Trp Thr Glu Gly Gly Lys Ile Ser Asp Thr Leu
            100                 105                 110

Glu Glu Lys Val Ser Val Ser Ile Pro Phe Ile Gly Glu Gly Gly
            115                 120                 125

Lys Asn Ser Thr Thr Ile Glu Ala Asn Phe Ala His Asn Ser Ser Thr
130                 135                 140

Thr Thr Phe Gln Gln Ala Ser Thr Asp Ile Glu Trp Asn Ile Ser Gln
145                 150                 155                 160
```

```
Pro Val Leu Val Pro Pro Arg Lys Gln Val Val Ala Thr Leu Val Ile
            165                 170                 175

Met Gly Gly Asn Phe Thr Ile Pro Met Asp Leu Met Thr Thr Ile Asp
        180                 185                 190

Ser Thr Glu His Tyr Ser Gly Tyr Pro Ile Leu Thr Trp Ile Ser Ser
        195                 200                 205

Pro Asp Asn Ser Tyr Asn Gly Pro Phe Met Ser Trp Tyr Phe Ala Asn
        210                 215                 220

Trp Pro Asn Leu Pro Ser Gly Phe Gly Pro Leu Asn Ser Asp Asn Thr
225                 230                 235                 240

Val Thr Tyr Thr Gly Ser Val Val Ser Gln Val Ser Ala Gly Val Tyr
        245                 250                 255

Ala Thr Val Arg Phe Asp Gln Tyr Asp Ile His Asn Leu Arg Thr Ile
        260                 265                 270

Glu Lys Thr Trp Tyr Ala Arg His Ala Thr Leu His Asn Gly Lys Lys
        275                 280                 285

Ile Ser Ile Asn Asn Val Thr Glu Met Ala Pro Thr Ser Ala Ile Lys
        290                 295                 300

Thr Asn
305

<210> SEQ ID NO 117
<211> LENGTH: 306
<212> TYPE: PRT
<213> ORGANISM: Artificial Sequence
<220> FEATURE:
<223> OTHER INFORMATION: engineered

<400> SEQUENCE: 117

Met Ala Ile Leu Asp Leu Lys Ser Leu Val Leu Asn Ala Ile Asn Tyr
1               5                   10                  15

Trp Gly Pro Lys Asn Asn Gly Ile Gln Gly Gly Asp Phe Gly Tyr
            20                  25                  30

Pro Ile Ser Glu Lys Gln Ile Asp Thr Ser Ile Ile Thr Ser Thr His
        35                  40                  45

Pro Arg Leu Ile Pro His Asp Leu Thr Ile Pro Gln Asn Leu Glu Thr
    50                  55                  60

Ile Phe Thr Thr Thr Gln Val Leu Thr Asn Asn Thr Asp Leu Gln Gln
65                  70                  75                  80

Ser Gln Thr Val Ser Phe Ala Lys Lys Thr Thr Thr Thr Ser Thr
            85                  90                  95

Ser Thr Thr Asn Gly Trp Thr Glu Gly Gly Lys Ile Ser Asp Thr Leu
        100                 105                 110

Glu Glu Lys Val Ser Val Ser Ile Pro Phe Ile Gly Glu Gly Gly Gly
        115                 120                 125

Lys Asn Ser Thr Thr Ile Glu Ala Asn Phe Ala His Asn Ser Ser Thr
    130                 135                 140

Thr Thr Ala Gln Gln Ala Ser Thr Asp Ile Glu Trp Asn Ile Ser Gln
145                 150                 155                 160

Pro Val Leu Val Pro Pro Arg Lys Gln Val Val Ala Thr Leu Val Ile
            165                 170                 175

Met Gly Gly Asn Phe Thr Ile Pro Met Asp Leu Met Thr Thr Ile Asp
        180                 185                 190

Ser Thr Glu Ala Tyr Ser Gly Tyr Pro Ile Leu Thr Trp Ile Ser Ser
        195                 200                 205
```

```
Pro Asp Asn Ser Tyr Asn Gly Pro Phe Met Ser Trp Tyr Phe Ala Asn
    210                 215                 220

Trp Pro Asn Leu Pro Ser Gly Phe Gly Pro Leu Asn Ser Asp Asn Thr
225                 230                 235                 240

Val Thr Tyr Thr Gly Ser Val Val Ser Gln Val Ser Ala Gly Val Tyr
                245                 250                 255

Ala Thr Val Arg Phe Asp Gln Tyr Asp Ile His Asn Leu Arg Thr Ile
            260                 265                 270

Glu Lys Thr Trp Tyr Ala Arg His Ala Thr Leu His Asn Gly Lys Lys
                275                 280                 285

Ile Ser Ile Asn Asn Val Thr Glu Met Ala Pro Thr Ser Pro Ile Lys
290                 295                 300

Thr Asn
305

<210> SEQ ID NO 118
<211> LENGTH: 306
<212> TYPE: PRT
<213> ORGANISM: Artificial Sequence
<220> FEATURE:
<223> OTHER INFORMATION: engineered

<400> SEQUENCE: 118

Met Ala Ile Leu Asp Leu Lys Ser Leu Val Leu Asn Ala Ile Asn Tyr
1               5                   10                  15

Trp Gly Pro Lys Asn Asn Gly Ile Gln Gly Gly Asp Phe Gly Tyr
                20                  25                  30

Pro Ile Ser Glu Lys Gln Ile Asp Thr Ser Ile Ile Thr Ser Thr His
            35                  40                  45

Pro Arg Leu Ile Pro His Asp Leu Thr Ile Pro Gln Asn Leu Glu Thr
50                  55                  60

Ile Phe Thr Thr Thr Gln Val Leu Thr Asn Asn Thr Asp Leu Gln Gln
65                  70                  75                  80

Ser Gln Thr Val Ser Phe Ala Lys Lys Thr Thr Thr Thr Ser Thr
                85                  90                  95

Ser Thr Thr Asn Gly Trp Thr Glu Gly Gly Lys Ile Ser Asp Thr Leu
                100                 105                 110

Glu Glu Lys Val Ser Val Ser Ile Pro Phe Ile Gly Glu Gly Gly Gly
            115                 120                 125

Lys Asn Ser Thr Thr Ile Glu Ala Asn Phe Ser His Asn Ser Ser Thr
130                 135                 140

Thr Thr Ala Gln Gln Ala Ser Thr Asp Ile Glu Trp Asn Ile Ser Gln
145                 150                 155                 160

Pro Val Leu Val Pro Arg Lys Gln Val Ala Thr Leu Val Ile
                165                 170                 175

Met Gly Gly Asn Phe Thr Ile Pro Met Asp Leu Met Thr Thr Ile Asp
                180                 185                 190

Ser Thr Glu His Tyr Ser Gly Tyr Pro Ile Leu Thr Trp Ile Ser Ser
            195                 200                 205

Pro Asp Asn Ser Tyr Asn Gly Pro Phe Met Ser Trp Tyr Phe Ala Asn
    210                 215                 220

Trp Pro Asn Leu Pro Ser Gly Phe Gly Pro Leu Asn Ser Asp Asn Thr
225                 230                 235                 240

Val Thr Tyr Thr Gly Ser Val Val Ser Gln Val Ser Ala Gly Val Tyr
                245                 250                 255
```

Ala Thr Val Arg Phe Asp Gln Tyr Asp Ile His Asn Leu Arg Thr Ile
            260                 265                 270

Glu Lys Thr Trp Tyr Ala Arg His Ala Thr Leu His Asn Gly Lys Lys
        275                 280                 285

Ile Ser Ile Asn Asn Val Thr Glu Met Ala Pro Thr Ser Pro Ile Lys
    290                 295                 300

Thr Asn
305

<210> SEQ ID NO 119
<211> LENGTH: 306
<212> TYPE: PRT
<213> ORGANISM: Artificial Sequence
<220> FEATURE:
<223> OTHER INFORMATION: engineered

<400> SEQUENCE: 119

Met Ala Ile Leu Asp Leu Lys Ser Leu Val Leu Asn Ala Ile Asn Tyr
1               5                   10                  15

Trp Gly Pro Lys Asn Asn Gly Ile Gln Gly Gly Asp Phe Gly Tyr
            20                  25                  30

Pro Ile Ser Glu Lys Gln Ile Asp Thr Ser Ile Thr Ser Thr His
        35                  40                  45

Pro Arg Leu Ile Pro His Asp Leu Thr Ile Pro Gln Asn Leu Glu Thr
    50                  55                  60

Ile Phe Thr Thr Thr Gln Val Leu Thr Asn Asn Thr Asp Leu Gln Gln
65                  70                  75                  80

Ser Gln Thr Val Ser Phe Ala Lys Lys Thr Thr Thr Ala Thr Ser Thr
                85                  90                  95

Ser Thr Thr Asn Gly Trp Thr Glu Gly Gly Lys Ile Ser Asp Thr Leu
            100                 105                 110

Glu Glu Lys Val Ser Val Ser Ile Pro Phe Ile Gly Glu Gly Gly Gly
        115                 120                 125

Lys Asn Ser Thr Thr Ile Glu Ala Asn Phe Ala His Asn Ser Ser Thr
130                 135                 140

Thr Thr Phe Gln Gln Ala Ser Thr Asp Ile Glu Trp Asn Ile Ser Gln
145                 150                 155                 160

Pro Val Leu Val Pro Pro Arg Lys Gln Val Ala Thr Leu Val Ile
                165                 170                 175

Met Gly Gly Asn Phe Thr Ile Pro Met Asp Leu Met Thr Thr Ile Asp
            180                 185                 190

Ser Thr Glu His Tyr Ser Gly Tyr Pro Ile Leu Thr Trp Ile Ser Ser
        195                 200                 205

Pro Asp Asn Ser Tyr Asn Gly Pro Phe Met Ser Trp Tyr Phe Ala Asn
    210                 215                 220

Trp Pro Asn Leu Pro Ser Gly Phe Gly Pro Leu Asn Ser Asp Asn Thr
225                 230                 235                 240

Val Thr Tyr Thr Gly Ser Val Val Ser Gln Val Ser Ala Gly Val Tyr
                245                 250                 255

Ala Thr Val Arg Phe Asp Gln Tyr Asp Ile His Asn Leu Arg Thr Ile
            260                 265                 270

Glu Lys Thr Trp Tyr Ala Arg His Ala Thr Leu His Asn Gly Lys Lys
        275                 280                 285

Ile Ser Ile Ala Asn Val Thr Glu Met Ala Pro Thr Ser Pro Ile Lys
    290                 295                 300

Thr Asn
305

<210> SEQ ID NO 120
<211> LENGTH: 306
<212> TYPE: PRT
<213> ORGANISM: Artificial Sequence
<220> FEATURE:
<223> OTHER INFORMATION: engineered

<400> SEQUENCE: 120

Met Ala Ile Leu Asp Leu Lys Ser Leu Val Leu Asn Ala Ile Asn Tyr
1               5                   10                  15

Trp Gly Pro Lys Asn Asn Asn Gly Ile Gln Gly Gly Asp Phe Gly Tyr
            20                  25                  30

Pro Ile Ser Glu Lys Gln Ile Asp Thr Ser Ile Ile Thr Ser Thr His
        35                  40                  45

Pro Arg Leu Ile Pro His Asp Leu Thr Ile Pro Gln Asn Leu Glu Thr
    50                  55                  60

Ile Phe Thr Thr Thr Gln Val Leu Thr Asn Asn Thr Asp Leu Gln Gln
65                  70                  75                  80

Ser Gln Thr Val Ser Phe Ala Lys Lys Thr Thr Thr Ala Thr Ser Thr
                85                  90                  95

Ser Thr Thr Asn Gly Trp Thr Glu Gly Gly Lys Ile Ser Asp Thr Leu
            100                 105                 110

Glu Glu Lys Val Ser Val Ser Ile Pro Phe Ile Gly Glu Gly Gly Gly
        115                 120                 125

Lys Asn Ser Thr Thr Ile Glu Ala Asn Phe Ala His Asn Ser Ser Thr
    130                 135                 140

Ala Thr Phe Gln Gln Ala Ser Thr Asp Ile Glu Trp Asn Ile Ser Gln
145                 150                 155                 160

Pro Val Leu Val Pro Arg Lys Gln Val Val Ala Thr Leu Val Ile
                165                 170                 175

Met Gly Gly Asn Phe Thr Ile Pro Met Asp Leu Met Thr Thr Ile Asp
            180                 185                 190

Ser Thr Glu His Tyr Ser Gly Tyr Pro Ile Leu Thr Trp Ile Ser Ser
        195                 200                 205

Pro Asp Asn Ser Tyr Asn Gly Pro Phe Met Ser Trp Tyr Phe Ala Asn
    210                 215                 220

Trp Pro Asn Leu Pro Ser Gly Phe Gly Pro Leu Asn Ser Asp Asn Thr
225                 230                 235                 240

Val Thr Tyr Thr Gly Ser Val Val Ser Gln Val Ser Ala Gly Val Tyr
                245                 250                 255

Ala Thr Val Arg Phe Asp Gln Tyr Asp Ile His Asn Leu Arg Thr Ile
            260                 265                 270

Glu Lys Thr Trp Tyr Ala Arg His Ala Thr Leu His Asn Gly Lys Lys
        275                 280                 285

Ile Ser Ile Asn Asn Val Thr Glu Met Ala Pro Thr Ser Pro Ile Lys
    290                 295                 300

Thr Asn
305

<210> SEQ ID NO 121
<211> LENGTH: 306
<212> TYPE: PRT
<213> ORGANISM: Artificial Sequence
<220> FEATURE:

<223> OTHER INFORMATION: engineered

<400> SEQUENCE: 121

Met Ala Ile Leu Asp Leu Lys Ser Leu Val Leu Asn Ala Ile Asn Tyr
1               5                   10                  15

Trp Gly Pro Lys Asn Asn Asn Gly Ile Gln Gly Gly Asp Phe Gly Tyr
            20                  25                  30

Pro Ile Ser Glu Lys Gln Ile Asp Thr Ser Ile Ile Thr Ser Thr His
        35                  40                  45

Pro Arg Leu Ile Pro His Asp Leu Thr Ile Pro Gln Asn Leu Glu Thr
    50                  55                  60

Ile Phe Thr Thr Thr Gln Val Leu Thr Asn Asn Thr Leu Gln Gln
65                  70                  75                  80

Ser Gln Thr Val Ser Phe Ala Lys Lys Thr Thr Thr Thr Ser Thr
                85                  90                  95

Ser Thr Thr Asn Gly Trp Thr Glu Gly Gly Lys Ile Ser Asp Thr Leu
                100                 105                 110

Glu Glu Lys Val Ala Val Ser Ile Pro Phe Ile Gly Glu Gly Gly Gly
            115                 120                 125

Lys Asn Ser Thr Thr Ile Glu Ala Asn Phe Ala His Asn Ser Ser Thr
130                 135                 140

Thr Thr Ala Gln Gln Ala Ser Thr Asp Ile Glu Trp Asn Ile Ser Gln
145                 150                 155                 160

Pro Val Leu Val Pro Pro Arg Lys Gln Val Val Ala Thr Leu Val Ile
                165                 170                 175

Met Gly Gly Asn Phe Thr Ile Pro Met Asp Leu Met Thr Thr Ile Asp
            180                 185                 190

Ser Thr Glu His Tyr Ser Gly Tyr Pro Ile Leu Thr Trp Ile Ser Ser
        195                 200                 205

Pro Asp Asn Ser Tyr Asn Gly Pro Phe Met Ser Trp Tyr Phe Ala Asn
    210                 215                 220

Trp Pro Asn Leu Pro Ser Gly Phe Gly Pro Leu Asn Ser Asp Asn Thr
225                 230                 235                 240

Val Thr Tyr Thr Gly Ser Val Val Ser Gln Val Ser Ala Gly Val Tyr
                245                 250                 255

Ala Thr Val Arg Phe Asp Gln Tyr Asp Ile His Asn Leu Arg Thr Ile
            260                 265                 270

Glu Lys Thr Trp Tyr Ala Arg His Ala Thr Leu His Asn Gly Lys Lys
        275                 280                 285

Ile Ser Ile Asn Asn Val Thr Glu Met Ala Pro Thr Ser Pro Ile Lys
    290                 295                 300

Thr Asn
305

<210> SEQ ID NO 122
<211> LENGTH: 306
<212> TYPE: PRT
<213> ORGANISM: Artificial Sequence
<220> FEATURE:
<223> OTHER INFORMATION: engineered

<400> SEQUENCE: 122

Met Ala Ile Leu Asp Leu Lys Ser Leu Val Leu Asn Ala Ile Asn Tyr
1               5                   10                  15

Trp Gly Pro Lys Asn Asn Asn Gly Ile Gln Gly Gly Asp Phe Gly Tyr
            20                  25                  30

```
Pro Ile Ser Glu Lys Gln Ile Asp Thr Ser Ile Ile Thr Ser Thr His
        35                  40                  45

Pro Arg Leu Ile Pro His Asp Leu Thr Ile Pro Gln Asn Leu Glu Thr
    50                  55                  60

Ile Phe Thr Thr Thr Gln Val Leu Thr Asn Asn Thr Asp Leu Gln Gln
 65                  70                  75                  80

Ser Gln Thr Val Ser Phe Ala Lys Lys Thr Thr Ala Thr Ser Thr
                 85                  90                  95

Ser Thr Thr Asn Gly Trp Thr Glu Gly Gly Lys Ile Ser Asp Thr Leu
            100                 105                 110

Glu Glu Lys Val Ser Val Ser Ile Pro Phe Ile Gly Glu Gly Gly Gly
            115                 120                 125

Lys Asn Ser Thr Thr Ile Glu Ala Asn Phe Ala His Asn Ser Ser Thr
            130                 135                 140

Thr Thr Phe Gln Gln Ala Ser Thr Asp Ile Glu Trp Asn Ile Ser Gln
145                 150                 155                 160

Pro Val Leu Val Pro Pro Arg Lys Gln Val Val Ala Thr Leu Val Ile
                165                 170                 175

Met Gly Gly Asn Phe Thr Ile Pro Met Asp Leu Met Thr Thr Ile Asp
            180                 185                 190

Ser Thr Glu His Tyr Ser Gly Tyr Pro Ile Leu Thr Trp Ile Ser Ser
            195                 200                 205

Pro Asp Asn Ser Tyr Asn Gly Pro Phe Met Ser Trp Tyr Phe Ala Asn
    210                 215                 220

Trp Pro Asn Leu Pro Ser Gly Phe Gly Pro Leu Asn Ser Asp Asn Thr
225                 230                 235                 240

Val Thr Tyr Thr Gly Ser Val Val Ser Gln Val Ser Ala Gly Val Tyr
                245                 250                 255

Ala Thr Val Arg Phe Asp Gln Tyr Asp Ile His Asn Leu Arg Thr Ala
            260                 265                 270

Glu Lys Thr Trp Tyr Ala Arg His Ala Thr Leu His Asn Gly Lys Lys
            275                 280                 285

Ile Ser Ile Asn Asn Val Thr Glu Met Ala Pro Thr Ser Pro Ile Lys
    290                 295                 300

Thr Asn
305

<210> SEQ ID NO 123
<211> LENGTH: 306
<212> TYPE: PRT
<213> ORGANISM: Artificial Sequence
<220> FEATURE:
<223> OTHER INFORMATION: engineered

<400> SEQUENCE: 123

Met Ala Ile Leu Asp Leu Lys Ser Leu Val Leu Asn Ala Ile Asn Tyr
  1               5                  10                  15

Trp Gly Pro Lys Asn Asn Asn Gly Ile Gln Gly Gly Asp Phe Gly Tyr
             20                  25                  30

Pro Ile Ser Glu Lys Gln Ile Asp Thr Ser Ile Ile Thr Ser Thr His
        35                  40                  45

Pro Arg Leu Ile Pro His Asp Leu Thr Ile Pro Gln Asn Leu Glu Thr
    50                  55                  60

Ile Phe Thr Thr Thr Gln Val Leu Thr Asn Asn Thr Asp Leu Gln Gln
 65                  70                  75                  80
```

```
Ser Gln Thr Val Ser Phe Ala Lys Lys Thr Thr Thr Thr Ala Thr
            85                  90                  95

Ser Thr Thr Asn Gly Trp Thr Glu Gly Gly Lys Ile Ser Asp Thr Leu
            100                 105                 110

Glu Glu Lys Val Ser Val Ser Ile Pro Phe Ile Gly Glu Gly Gly Gly
            115                 120                 125

Lys Asn Ser Thr Thr Ile Glu Ala Asn Phe Ala His Asn Ser Ser Thr
130                 135                 140

Thr Thr Phe Gln Gln Ala Ser Thr Asp Ile Glu Trp Asn Ile Ser Gln
145                 150                 155                 160

Pro Val Leu Val Pro Pro Arg Lys Gln Val Val Ala Thr Leu Val Ile
                165                 170                 175

Met Gly Gly Asn Phe Thr Ile Pro Met Asp Leu Met Thr Thr Ile Asp
            180                 185                 190

Ser Thr Glu His Tyr Ser Gly Tyr Pro Ile Leu Thr Trp Ile Ser Ser
            195                 200                 205

Pro Asp Asn Ser Tyr Asn Gly Pro Phe Met Ser Trp Tyr Phe Ala Asn
210                 215                 220

Trp Pro Asn Leu Pro Ser Gly Phe Gly Pro Leu Asn Ser Asp Asn Thr
225                 230                 235                 240

Val Thr Tyr Thr Gly Ser Val Val Ser Gln Val Ser Ala Gly Val Tyr
                245                 250                 255

Ala Thr Val Arg Phe Asp Gln Tyr Asp Ile His Asn Leu Arg Thr Ile
            260                 265                 270

Glu Lys Thr Trp Tyr Ala Arg His Ala Thr Leu Ala Asn Gly Lys Lys
            275                 280                 285

Ile Ser Ile Asn Asn Val Thr Glu Met Ala Pro Thr Ser Pro Ile Lys
            290                 295                 300

Thr Asn
305

<210> SEQ ID NO 124
<211> LENGTH: 306
<212> TYPE: PRT
<213> ORGANISM: Artificial Sequence
<220> FEATURE:
<223> OTHER INFORMATION: engineered

<400> SEQUENCE: 124

Met Ala Ile Leu Asp Leu Lys Ser Leu Val Leu Asn Ala Ile Asn Tyr
1               5                   10                  15

Trp Gly Pro Lys Asn Asn Gly Ile Gln Gly Gly Asp Phe Gly Tyr
            20                  25                  30

Pro Ile Ser Glu Lys Gln Ile Asp Thr Ser Ile Ile Thr Ser Thr His
            35                  40                  45

Pro Arg Leu Ile Pro His Asp Leu Thr Ile Pro Gln Asn Leu Glu Thr
            50                  55                  60

Ile Phe Thr Thr Thr Gln Val Leu Thr Asn Asn Thr Asp Leu Gln Gln
65                  70                  75                  80

Ser Gln Thr Val Ser Phe Ala Lys Lys Thr Thr Thr Thr Ala Thr
            85                  90                  95

Ser Thr Thr Asn Gly Trp Thr Glu Ala Gly Lys Ile Ser Asp Thr Leu
            100                 105                 110

Glu Glu Lys Val Ser Val Ser Ile Pro Phe Ile Gly Glu Gly Gly Gly
            115                 120                 125
```

Lys Asn Ser Thr Thr Ile Glu Ala Asn Phe Ala His Asn Ser Ser Thr
            130                 135                 140

Thr Thr Phe Gln Gln Ala Ser Thr Asp Ile Glu Trp Asn Ile Ser Gln
145                 150                 155                 160

Pro Val Leu Val Pro Pro Arg Lys Gln Val Val Ala Thr Leu Val Ile
                165                 170                 175

Met Gly Gly Asn Phe Thr Ile Pro Met Asp Leu Met Thr Thr Ile Asp
            180                 185                 190

Ser Thr Glu His Tyr Ser Gly Tyr Pro Ile Leu Thr Trp Ile Ser Ser
        195                 200                 205

Pro Asp Asn Ser Tyr Asn Gly Pro Phe Met Ser Trp Tyr Phe Ala Asn
            210                 215                 220

Trp Pro Asn Leu Pro Ser Gly Phe Gly Pro Leu Asn Ser Asp Asn Thr
225                 230                 235                 240

Val Thr Tyr Thr Gly Ser Val Val Ser Gln Val Ser Ala Gly Val Tyr
                245                 250                 255

Ala Thr Val Arg Phe Asp Gln Tyr Asp Ile His Asn Leu Arg Thr Ile
            260                 265                 270

Glu Lys Thr Trp Tyr Ala Arg His Ala Thr Leu His Asn Gly Lys Lys
        275                 280                 285

Ile Ser Ile Asn Asn Val Thr Glu Met Ala Pro Thr Ser Pro Ile Lys
            290                 295                 300

Thr Asn
305

<210> SEQ ID NO 125
<211> LENGTH: 306
<212> TYPE: PRT
<213> ORGANISM: Artificial Sequence
<220> FEATURE:
<223> OTHER INFORMATION: engineered

<400> SEQUENCE: 125

Met Ala Ile Leu Asp Leu Lys Ser Leu Val Leu Asn Ala Ile Asn Tyr
1               5                   10                  15

Trp Gly Pro Lys Asn Asn Gly Ile Gln Gly Gly Asp Phe Gly Tyr
            20                  25                  30

Pro Ile Ser Glu Lys Gln Ile Asp Thr Ser Ile Ile Thr Ser Thr His
        35                  40                  45

Pro Arg Leu Ile Pro His Asp Leu Thr Ile Pro Gln Asn Leu Glu Thr
50                  55                  60

Ile Phe Thr Thr Thr Gln Val Leu Thr Asn Asn Thr Asp Leu Gln Gln
65                  70                  75                  80

Ser Gln Thr Val Ser Phe Ala Lys Lys Thr Thr Thr Thr Ala Thr
            85                  90                  95

Ser Thr Thr Asn Gly Trp Thr Glu Gly Gly Lys Ile Ser Asp Thr Leu
            100                 105                 110

Glu Glu Lys Val Ser Val Ser Ile Pro Phe Ile Gly Glu Gly Gly Gly
        115                 120                 125

Lys Asn Ser Thr Thr Ile Glu Ala Asn Phe Ala His Asn Ser Ser Thr
            130                 135                 140

Thr Thr Phe Gln Gln Ala Ser Thr Asp Ile Glu Trp Asn Ile Ser Gln
145                 150                 155                 160

Pro Val Leu Val Pro Pro Arg Lys Gln Val Val Ala Thr Leu Val Ile
                165                 170                 175

Met Gly Gly Asn Phe Thr Ile Pro Met Asp Leu Met Thr Ile Asp
                180                 185                 190

Ser Thr Glu His Tyr Ser Gly Tyr Pro Ile Leu Thr Trp Ile Ser Ser
            195                 200                 205

Pro Asp Asn Ser Tyr Asn Gly Pro Phe Met Ser Trp Tyr Phe Ala Asn
210                 215                 220

Trp Pro Asn Leu Pro Ser Gly Phe Gly Pro Leu Asn Ser Asp Asn Thr
225                 230                 235                 240

Val Thr Tyr Thr Gly Ser Val Val Ser Gln Val Ser Ala Gly Val Tyr
                245                 250                 255

Ala Thr Val Arg Phe Asp Gln Tyr Asp Ile His Asn Leu Arg Thr Ile
            260                 265                 270

Glu Lys Thr Trp Tyr Ala Arg His Ala Thr Leu His Asn Gly Lys Lys
            275                 280                 285

Ile Ser Ile Asn Asn Val Thr Glu Met Ala Pro Thr Ser Pro Ile Lys
            290                 295                 300

Thr Asn
305

<210> SEQ ID NO 126
<211> LENGTH: 306
<212> TYPE: PRT
<213> ORGANISM: Artificial Sequence
<220> FEATURE:
<223> OTHER INFORMATION: engineered

<400> SEQUENCE: 126

Met Ala Ile Leu Asp Leu Lys Ser Leu Val Leu Asn Ala Ile Asn Tyr
1               5                   10                  15

Trp Gly Pro Lys Asn Asn Asn Gly Ile Gln Gly Gly Asp Phe Gly Tyr
                20                  25                  30

Pro Ile Ser Glu Lys Gln Ile Asp Thr Ser Ile Ile Thr Ser Thr His
            35                  40                  45

Pro Arg Leu Ile Pro His Asp Leu Thr Ile Pro Gln Asn Leu Glu Thr
50                  55                  60

Ile Phe Thr Thr Thr Gln Val Leu Thr Asn Asn Thr Asp Leu Gln Gln
65                  70                  75                  80

Ser Gln Thr Val Ser Phe Ala Lys Lys Thr Thr Thr Thr Ala Thr
                85                  90                  95

Ser Thr Thr Asn Gly Trp Thr Glu Gly Gly Lys Ile Ser Asp Thr Leu
            100                 105                 110

Glu Glu Lys Val Ser Val Ser Ile Pro Phe Ile Gly Glu Gly Gly Gly
            115                 120                 125

Lys Asn Ser Thr Thr Ala Glu Ala Asn Phe Ala His Asn Ser Ser Thr
            130                 135                 140

Thr Thr Phe Gln Gln Ala Ser Thr Asp Ile Glu Trp Asn Ile Ser Gln
145                 150                 155                 160

Pro Val Leu Val Pro Pro Arg Lys Gln Val Val Ala Thr Leu Val Ile
                165                 170                 175

Met Gly Gly Asn Phe Thr Ile Pro Met Asp Leu Met Thr Ile Asp
                180                 185                 190

Ser Thr Glu His Tyr Ser Gly Tyr Pro Ile Leu Thr Trp Ile Ser Ser
            195                 200                 205

Pro Asp Asn Ser Tyr Asn Gly Pro Phe Met Ser Trp Tyr Phe Ala Asn
210                 215                 220

```
Trp Pro Asn Leu Pro Ser Gly Phe Gly Pro Leu Asn Ser Asp Asn Thr
225                 230                 235                 240

Val Thr Tyr Thr Gly Ser Val Val Ser Gln Val Ser Ala Gly Val Tyr
            245                 250                 255

Ala Thr Val Arg Phe Asp Gln Tyr Asp Ile His Asn Leu Arg Thr Ile
        260                 265                 270

Glu Lys Thr Trp Tyr Ala Arg His Ala Thr Leu His Asn Gly Lys Lys
    275                 280                 285

Ile Ser Ile Asn Asn Val Thr Glu Met Ala Pro Thr Ser Pro Ile Lys
290                 295                 300

Thr Asn
305
```

<210> SEQ ID NO 127
<211> LENGTH: 306
<212> TYPE: PRT
<213> ORGANISM: Artificial Sequence
<220> FEATURE:
<223> OTHER INFORMATION: engineered

<400> SEQUENCE: 127

```
Met Ala Ile Leu Asp Leu Lys Ser Leu Val Leu Asn Ala Ile Asn Tyr
1               5                   10                  15

Trp Gly Pro Lys Asn Asn Asn Gly Ile Gln Gly Gly Asp Phe Gly Tyr
            20                  25                  30

Pro Ile Ser Glu Lys Gln Ile Asp Thr Ser Ile Ile Thr Ser Thr His
        35                  40                  45

Pro Arg Leu Ile Pro His Asp Leu Thr Ile Pro Gln Asn Leu Glu Thr
    50                  55                  60

Ile Phe Thr Thr Thr Gln Val Leu Thr Asn Asn Thr Asp Leu Gln Gln
65                  70                  75                  80

Ser Gln Thr Val Ser Phe Ala Lys Lys Thr Thr Thr Ala Thr Ser Thr
                85                  90                  95

Ser Thr Thr Asn Gly Trp Thr Glu Gly Gly Lys Ile Ser Asp Thr Leu
            100                 105                 110

Glu Glu Lys Val Ser Val Ser Ile Pro Phe Ile Gly Glu Gly Gly Gly
        115                 120                 125

Lys Asn Ser Thr Thr Ile Glu Ala Asn Phe Ala His Asn Ser Ser Thr
    130                 135                 140

Thr Thr Phe Gln Gln Ala Ser Thr Asp Ile Glu Trp Asn Ile Ser Gln
145                 150                 155                 160

Pro Val Leu Val Pro Pro Arg Lys Gln Val Val Ala Thr Leu Val Ile
                165                 170                 175

Met Gly Gly Asn Phe Thr Ile Pro Met Asp Leu Met Thr Thr Ile Asp
            180                 185                 190

Ser Thr Glu His Tyr Ser Gly Tyr Pro Ile Leu Thr Trp Ile Ser Ser
        195                 200                 205

Pro Asp Asn Ser Tyr Asn Gly Pro Phe Met Ser Trp Tyr Phe Ala Asn
    210                 215                 220

Trp Pro Asn Leu Pro Ser Gly Phe Gly Pro Leu Asn Ser Asp Asn Thr
225                 230                 235                 240

Val Thr Tyr Thr Gly Ser Val Val Ser Gln Val Ser Ala Gly Val Tyr
                245                 250                 255

Ala Thr Val Arg Phe Asp Gln Tyr Asp Ile His Asn Leu Arg Thr Ile
            260                 265                 270
```

```
Glu Lys Thr Trp Tyr Ala Arg His Ala Thr Leu His Asn Gly Lys Lys
        275                 280                 285

Ile Ser Ile Asn Asn Val Thr Glu Ala Ala Pro Thr Ser Pro Ile Lys
        290                 295                 300

Thr Asn
305

<210> SEQ ID NO 128
<211> LENGTH: 306
<212> TYPE: PRT
<213> ORGANISM: Artificial Sequence
<220> FEATURE:
<223> OTHER INFORMATION: engineered

<400> SEQUENCE: 128

Met Ala Ile Leu Asp Leu Lys Ser Leu Val Leu Asn Ala Ile Asn Tyr
1               5                   10                  15

Trp Gly Pro Lys Asn Asn Gly Ile Gln Gly Gly Asp Phe Gly Tyr
            20                  25                  30

Pro Ile Ser Glu Lys Gln Ile Asp Thr Ser Ile Ile Thr Ser Thr His
        35                  40                  45

Pro Arg Leu Ile Pro His Asp Leu Thr Ile Pro Gln Asn Leu Glu Thr
    50                  55                  60

Ile Phe Thr Thr Thr Gln Val Leu Thr Asn Asn Thr Asp Leu Gln Gln
65                  70                  75                  80

Ser Gln Thr Val Ser Phe Ala Lys Lys Thr Thr Thr Ala Thr Ser Thr
                85                  90                  95

Ser Thr Thr Asn Gly Trp Thr Glu Gly Gly Lys Ile Ser Asp Thr Leu
            100                 105                 110

Glu Glu Lys Val Ser Val Ser Ile Pro Phe Ile Gly Glu Gly Gly Gly
        115                 120                 125

Lys Asn Ser Thr Thr Ile Glu Ala Asn Phe Ala His Asn Ser Ser Thr
    130                 135                 140

Thr Thr Phe Gln Gln Ala Ser Thr Asp Ile Glu Trp Asn Ile Ser Gln
145                 150                 155                 160

Pro Val Leu Val Pro Pro Arg Lys Gln Val Val Ala Thr Leu Val Ile
                165                 170                 175

Met Gly Gly Asn Phe Thr Ile Pro Met Asp Leu Met Thr Thr Ile Asp
            180                 185                 190

Ser Thr Glu His Tyr Ser Gly Tyr Pro Ile Leu Thr Trp Ile Ser Ser
        195                 200                 205

Pro Asp Asn Ser Tyr Asn Gly Pro Phe Met Ser Trp Tyr Phe Ala Asn
    210                 215                 220

Trp Pro Asn Leu Pro Ser Gly Phe Gly Pro Leu Asn Ser Asp Asn Thr
225                 230                 235                 240

Val Thr Tyr Thr Gly Ser Val Val Ser Gln Val Ser Ala Gly Val Tyr
                245                 250                 255

Ala Thr Val Arg Phe Asp Gln Tyr Asp Ile His Asn Leu Arg Thr Ile
            260                 265                 270

Glu Lys Thr Trp Tyr Ala Arg His Ala Thr Leu His Asn Gly Lys Lys
        275                 280                 285

Ile Ser Ile Asn Asn Val Thr Glu Met Ala Pro Ala Ser Pro Ile Lys
    290                 295                 300

Thr Asn
305
```

<210> SEQ ID NO 129
<211> LENGTH: 306
<212> TYPE: PRT
<213> ORGANISM: Artificial Sequence
<220> FEATURE:
<223> OTHER INFORMATION: engineered

<400> SEQUENCE: 129

```
Met Ala Ile Leu Asp Leu Lys Ser Leu Val Leu Asn Ala Ile Asn Tyr
  1               5                  10                  15

Trp Gly Pro Lys Asn Asn Asn Gly Ile Gln Gly Gly Asp Phe Gly Tyr
             20                  25                  30

Pro Ile Ser Glu Lys Gln Ile Asp Thr Ser Ile Ile Thr Ser Thr His
         35                  40                  45

Pro Arg Leu Ile Pro His Asp Leu Thr Ile Pro Gln Asn Leu Glu Thr
     50                  55                  60

Ile Phe Thr Thr Thr Gln Val Leu Thr Asn Asn Thr Asp Leu Gln Gln
 65                  70                  75                  80

Ser Gln Thr Val Ser Phe Ala Lys Lys Thr Thr Thr Ala Thr Ser Thr
                 85                  90                  95

Ser Thr Thr Asn Gly Trp Thr Glu Gly Gly Lys Ile Ser Asp Thr Leu
            100                 105                 110

Glu Glu Lys Val Ser Val Ser Ile Pro Phe Ile Gly Glu Gly Gly Gly
        115                 120                 125

Lys Asn Ser Thr Thr Ile Glu Ala Asn Phe Ala His Asn Ser Ser Thr
    130                 135                 140

Thr Thr Phe Gln Gln Ser Ser Thr Asp Ile Glu Trp Asn Ile Ser Gln
145                 150                 155                 160

Pro Val Leu Val Pro Arg Lys Gln Val Val Ala Thr Leu Val Ile
                165                 170                 175

Met Gly Gly Asn Phe Thr Ile Pro Met Asp Leu Met Thr Thr Ile Asp
                180                 185                 190

Ser Thr Glu His Tyr Ser Gly Tyr Pro Ile Leu Thr Trp Ile Ser Ser
            195                 200                 205

Pro Asp Asn Ser Tyr Asn Gly Pro Phe Met Ser Trp Tyr Phe Ala Asn
    210                 215                 220

Trp Pro Asn Leu Pro Ser Gly Phe Gly Pro Leu Asn Ser Asp Asn Thr
225                 230                 235                 240

Val Thr Tyr Thr Gly Ser Val Val Ser Gln Val Ser Ala Gly Val Tyr
                245                 250                 255

Ala Thr Val Arg Phe Asp Gln Tyr Asp Ile His Asn Leu Arg Thr Ile
                260                 265                 270

Glu Lys Thr Trp Tyr Ala Arg His Ala Thr Leu His Asn Gly Lys Lys
            275                 280                 285

Ile Ser Ile Asn Asn Val Thr Glu Met Ala Pro Thr Ser Pro Ile Lys
        290                 295                 300

Thr Asn
305
```

<210> SEQ ID NO 130
<211> LENGTH: 306
<212> TYPE: PRT
<213> ORGANISM: Artificial Sequence
<220> FEATURE:
<223> OTHER INFORMATION: engineered -continued

<400> SEQUENCE: 130

Met Ala Ile Leu Asp Leu Lys Ser Leu Val Leu Asn Ala Ile Asn Tyr
1               5                   10                  15

Trp Gly Pro Lys Asn Asn Asn Gly Ile Gln Gly Gly Asp Phe Gly Tyr
            20                  25                  30

Pro Ile Ser Glu Lys Gln Ile Asp Thr Ser Ile Ile Thr Ser Thr His
        35                  40                  45

Pro Arg Leu Ile Pro His Asp Leu Thr Ile Pro Gln Asn Leu Glu Thr
    50                  55                  60

Ile Phe Thr Thr Thr Gln Val Leu Thr Asn Asn Thr Asp Leu Gln Gln
65                  70                  75                  80

Ser Gln Thr Val Ser Phe Ala Lys Lys Thr Thr Thr Thr Ala Thr
                85                  90                  95

Ser Thr Thr Asn Gly Trp Thr Glu Gly Gly Lys Ile Ser Asp Thr Leu
                100                 105                 110

Glu Glu Lys Val Ser Val Ser Ile Pro Phe Ile Gly Glu Gly Gly Gly
            115                 120                 125

Lys Asn Ser Thr Thr Ile Glu Ala Asn Phe Ala His Asn Ser Ser Thr
            130                 135                 140

Thr Thr Phe Gln Gln Ala Ser Thr Asp Ile Ala Trp Asn Ile Ser Gln
145                 150                 155                 160

Pro Val Leu Val Pro Arg Lys Gln Val Val Ala Thr Leu Val Ile
                165                 170                 175

Met Gly Gly Asn Phe Thr Ile Pro Met Asp Leu Met Thr Thr Ile Asp
                180                 185                 190

Ser Thr Glu His Tyr Ser Gly Tyr Pro Ile Leu Thr Trp Ile Ser Ser
            195                 200                 205

Pro Asp Asn Ser Tyr Asn Gly Pro Phe Met Ser Trp Tyr Phe Ala Asn
        210                 215                 220

Trp Pro Asn Leu Pro Ser Gly Phe Gly Pro Leu Asn Ser Asp Asn Thr
225                 230                 235                 240

Val Thr Tyr Thr Gly Ser Val Val Ser Gln Val Ser Ala Gly Val Tyr
                245                 250                 255

Ala Thr Val Arg Phe Asp Gln Tyr Asp Ile His Asn Leu Arg Thr Ile
                260                 265                 270

Glu Lys Thr Trp Tyr Ala Arg His Ala Thr Leu His Asn Gly Lys Lys
            275                 280                 285

Ile Ser Ile Asn Asn Val Thr Glu Met Ala Pro Thr Ser Pro Ile Lys
        290                 295                 300

Thr Asn
305

<210> SEQ ID NO 131
<211> LENGTH: 306
<212> TYPE: PRT
<213> ORGANISM: Artificial Sequence
<220> FEATURE:
<223> OTHER INFORMATION: engineered

<400> SEQUENCE: 131

Met Ala Ile Leu Asp Leu Lys Ser Leu Val Leu Asn Ala Ile Asn Tyr
1               5                   10                  15

Trp Gly Pro Lys Asn Asn Asn Gly Ile Gln Gly Gly Asp Phe Gly Tyr
            20                  25                  30

Pro Ile Ser Glu Lys Gln Ile Asp Thr Ser Ile Ile Thr Ser Thr His

```
                35                  40                  45
Pro Arg Leu Ile Pro His Asp Leu Thr Ile Pro Gln Asn Leu Glu Thr
 50                  55                  60
Ile Phe Thr Thr Thr Gln Val Leu Thr Asn Asn Thr Asp Leu Gln Gln
 65                  70                  75                  80
Ser Gln Thr Val Ser Phe Ala Lys Lys Thr Thr Thr Ala Thr Ser Thr
                 85                  90                  95
Ser Thr Thr Asn Gly Trp Thr Glu Gly Gly Lys Ile Ser Asp Thr Leu
                100                 105                 110
Glu Glu Lys Val Ser Val Ser Ile Pro Phe Ile Gly Glu Gly Gly Gly
                115                 120                 125
Lys Asn Ser Thr Thr Ile Glu Ala Asn Phe Ala His Asn Ser Ser Thr
                130                 135                 140
Ala Thr Phe Gln Gln Ala Ser Thr Asp Ile Glu Trp Asn Ile Ser Gln
145                 150                 155                 160
Pro Val Leu Val Pro Pro Arg Lys Gln Val Val Ala Thr Leu Val Ile
                165                 170                 175
Met Gly Gly Asn Phe Thr Ile Pro Met Asp Leu Met Thr Thr Ile Asp
                180                 185                 190
Ser Thr Glu His Tyr Ser Gly Tyr Pro Ile Leu Thr Trp Ile Ser Ser
                195                 200                 205
Pro Asp Asn Ser Tyr Asn Gly Pro Phe Met Ser Trp Tyr Phe Ala Asn
                210                 215                 220
Trp Pro Asn Leu Pro Ser Gly Phe Gly Pro Leu Asn Ser Asp Asn Thr
225                 230                 235                 240
Val Thr Tyr Thr Gly Ser Val Val Ser Gln Val Ser Ala Gly Val Tyr
                245                 250                 255
Ala Thr Val Arg Phe Asp Gln Tyr Asp Ile His Asn Leu Arg Thr Ile
                260                 265                 270
Glu Lys Thr Trp Tyr Ala Arg His Ala Thr Leu His Asn Gly Lys Lys
                275                 280                 285
Ile Ser Ile Asn Asn Val Thr Glu Met Ala Pro Thr Ser Pro Ile Lys
                290                 295                 300
Thr Asn
305

<210> SEQ ID NO 132
<211> LENGTH: 306
<212> TYPE: PRT
<213> ORGANISM: Artificial Sequence
<220> FEATURE:
<223> OTHER INFORMATION: engineered

<400> SEQUENCE: 132

Met Ala Ile Leu Asp Leu Lys Ser Leu Val Leu Asn Ala Ile Asn Tyr
 1               5                  10                  15
Trp Gly Pro Lys Asn Asn Asn Gly Ile Gln Gly Gly Asp Phe Gly Tyr
                 20                  25                  30
Pro Ile Ser Glu Lys Gln Ile Asp Thr Ser Ile Ile Thr Ser Thr His
                 35                  40                  45
Pro Arg Leu Ile Pro His Asp Leu Thr Ile Pro Gln Asn Leu Glu Thr
 50                  55                  60
Ile Phe Thr Thr Thr Gln Val Leu Thr Asn Asn Thr Asp Leu Gln Gln
 65                  70                  75                  80
Ser Gln Thr Val Ser Phe Ala Lys Lys Thr Thr Thr Thr Thr Ala Thr
```

```
                    85                  90                  95
Ser Thr Thr Asn Gly Trp Thr Glu Gly Gly Lys Ile Ser Asp Thr Leu
                100                 105                 110

Glu Glu Lys Val Ser Val Ser Ile Pro Phe Ile Gly Glu Gly Gly Gly
            115                 120                 125

Lys Asn Ser Thr Thr Ile Glu Ala Asn Phe Ala His Asn Ser Ser Thr
        130                 135                 140

Thr Thr Phe Gln Gln Ala Ser Thr Asp Ile Glu Trp Asn Ile Ser Gln
145                 150                 155                 160

Pro Val Leu Val Pro Pro Arg Lys Gln Val Val Ala Thr Leu Val Ile
                165                 170                 175

Met Gly Gly Asn Phe Thr Ile Pro Met Asp Leu Met Thr Thr Ile Asp
                180                 185                 190

Ser Thr Glu His Tyr Ser Gly Tyr Pro Ile Leu Thr Ala Ile Ser Ser
                195                 200                 205

Pro Asp Asn Ser Tyr Asn Gly Pro Phe Met Ser Trp Tyr Phe Ala Asn
            210                 215                 220

Trp Pro Asn Leu Pro Ser Gly Phe Gly Pro Leu Asn Ser Asp Asn Thr
225                 230                 235                 240

Val Thr Tyr Thr Gly Ser Val Val Ser Gln Val Ser Ala Gly Val Tyr
                245                 250                 255

Ala Thr Val Arg Phe Asp Gln Tyr Asp Ile His Asn Leu Arg Thr Ile
                260                 265                 270

Glu Lys Thr Trp Tyr Ala Arg His Ala Thr Leu His Asn Gly Lys Lys
            275                 280                 285

Ile Ser Ile Asn Asn Val Thr Glu Met Ala Pro Thr Ser Pro Ile Lys
        290                 295                 300

Thr Asn
305
```

<210> SEQ ID NO 133
<211> LENGTH: 306
<212> TYPE: PRT
<213> ORGANISM: Artificial Sequence
<220> FEATURE:
<223> OTHER INFORMATION: engineered

<400> SEQUENCE: 133

```
Met Ala Ile Leu Asp Leu Lys Ser Leu Val Leu Asn Ala Ile Asn Tyr
1               5                   10                  15

Trp Gly Pro Lys Asn Asn Asn Gly Ile Gln Gly Gly Asp Phe Gly Tyr
                20                  25                  30

Pro Ile Ser Glu Lys Gln Ile Asp Thr Ser Ile Ile Thr Ser Thr His
            35                  40                  45

Pro Arg Leu Ile Pro His Asp Leu Thr Ile Pro Gln Asn Leu Glu Thr
    50                  55                  60

Ile Phe Thr Thr Thr Gln Val Leu Thr Asn Asn Thr Asp Leu Gln Gln
65                  70                  75                  80

Ser Gln Thr Val Ser Phe Ala Lys Lys Thr Thr Thr Thr Ala Thr
                85                  90                  95

Ser Thr Thr Asn Gly Trp Thr Glu Gly Gly Lys Ile Ser Asp Thr Leu
                100                 105                 110

Glu Glu Lys Val Ser Val Ser Ile Pro Phe Ile Gly Glu Gly Gly Gly
            115                 120                 125

Lys Asn Ser Thr Thr Ile Glu Ala Asn Phe Ala His Asn Ser Ser Thr
```

```
                130               135               140
Thr Thr Phe Gln Gln Ala Ser Thr Asp Ile Glu Trp Asn Ile Ser Gln
145                 150                 155                 160

Pro Val Leu Val Pro Pro Arg Lys Gln Val Ala Thr Leu Val Ile
                165                 170                 175

Met Gly Gly Asn Phe Ala Ile Pro Met Asp Leu Met Thr Thr Ile Asp
                180                 185                 190

Ser Thr Glu His Tyr Ser Gly Tyr Pro Ile Leu Thr Trp Ile Ser Ser
                195                 200                 205

Pro Asp Asn Ser Tyr Asn Gly Pro Phe Met Ser Trp Tyr Phe Ala Asn
210                 215                 220

Trp Pro Asn Leu Pro Ser Gly Phe Gly Pro Leu Asn Ser Asp Asn Thr
225                 230                 235                 240

Val Thr Tyr Thr Gly Ser Val Val Ser Gln Val Ser Ala Gly Val Tyr
                245                 250                 255

Ala Thr Val Arg Phe Asp Gln Tyr Asp Ile His Asn Leu Arg Thr Ile
                260                 265                 270

Glu Lys Thr Trp Tyr Ala Arg His Ala Thr Leu His Asn Gly Lys Lys
                275                 280                 285

Ile Ser Ile Asn Asn Val Thr Glu Met Ala Pro Thr Ser Pro Ile Lys
                290                 295                 300

Thr Asn
305

<210> SEQ ID NO 134
<211> LENGTH: 306
<212> TYPE: PRT
<213> ORGANISM: Artificial Sequence
<220> FEATURE:
<223> OTHER INFORMATION: engineered

<400> SEQUENCE: 134

Met Ala Ile Leu Asp Leu Lys Ser Leu Val Leu Asn Ala Ile Asn Tyr
1               5                   10                  15

Trp Gly Pro Lys Asn Asn Asn Gly Ile Gln Gly Gly Asp Phe Gly Tyr
                20                  25                  30

Pro Ile Ser Glu Lys Gln Ile Asp Thr Ser Ile Ile Thr Ser Thr His
                35                  40                  45

Pro Arg Leu Ile Pro His Asp Leu Thr Ile Pro Gln Asn Leu Glu Thr
            50                  55                  60

Ile Phe Thr Thr Thr Gln Val Leu Thr Asn Asn Thr Asp Leu Gln Gln
65                  70                  75                  80

Ser Gln Thr Val Ser Phe Ala Lys Lys Thr Thr Thr Ala Thr Ser Thr
                85                  90                  95

Ser Thr Thr Asn Gly Trp Thr Glu Gly Gly Lys Ile Ser Asp Thr Leu
                100                 105                 110

Glu Glu Lys Val Ser Val Ser Ile Pro Phe Ile Gly Glu Gly Gly Gly
                115                 120                 125

Lys Asn Ser Thr Thr Ile Glu Ala Asn Phe Ala His Asn Ser Ser Thr
                130                 135                 140

Thr Thr Phe Gln Gln Ala Ser Thr Asp Ile Glu Trp Asn Ile Ser Gln
145                 150                 155                 160

Pro Val Leu Val Pro Pro Arg Lys Gln Val Ala Thr Leu Val Ile
                165                 170                 175

Met Gly Gly Asn Phe Thr Ile Pro Met Asp Leu Met Thr Thr Ile Asp
```

```
            180             185                 190
Ser Thr Glu His Tyr Ser Gly Tyr Pro Ile Leu Thr Trp Ile Ser Ser
            195                 200                 205
Pro Asp Asn Ser Tyr Asn Gly Pro Phe Met Ser Trp Tyr Phe Ala Asn
            210                 215                 220
Trp Pro Asn Leu Pro Ser Gly Phe Gly Pro Leu Asn Ser Asp Asn Ala
225                 230                 235                 240
Val Thr Tyr Thr Gly Ser Val Val Ser Gln Val Ser Ala Gly Val Tyr
                245                 250                 255
Ala Thr Val Arg Phe Asp Gln Tyr Asp Ile His Asn Leu Arg Thr Ile
            260                 265                 270
Glu Lys Thr Trp Tyr Ala Arg His Ala Thr Leu His Asn Gly Lys Lys
            275                 280                 285
Ile Ser Ile Asn Asn Val Thr Glu Met Ala Pro Thr Ser Pro Ile Lys
            290                 295                 300
Thr Asn
305

<210> SEQ ID NO 135
<211> LENGTH: 306
<212> TYPE: PRT
<213> ORGANISM: Artificial Sequence
<220> FEATURE:
<223> OTHER INFORMATION: engineered

<400> SEQUENCE: 135

Met Ala Ile Leu Asp Leu Lys Ser Leu Val Leu Asn Ala Ile Asn Tyr
1               5                   10                  15
Trp Gly Pro Lys Asn Asn Gly Ile Gln Gly Gly Asp Phe Gly Tyr
            20                  25                  30
Pro Ile Ser Glu Lys Gln Ile Asp Thr Ser Ile Ile Thr Ser Thr His
            35                  40                  45
Pro Arg Leu Ile Pro His Asp Leu Thr Ile Pro Gln Asn Leu Glu Thr
        50                  55                  60
Ile Phe Thr Thr Thr Gln Val Leu Thr Asn Asn Thr Asp Leu Gln Gln
65                  70                  75                  80
Ser Gln Thr Val Ser Phe Ala Lys Lys Thr Thr Thr Thr Ala Thr
                85                  90                  95
Ser Thr Thr Asn Gly Trp Thr Glu Gly Gly Lys Ile Ser Asp Thr Leu
            100                 105                 110
Glu Glu Lys Val Ser Val Ser Ile Pro Phe Ile Gly Glu Gly Gly Gly
            115                 120                 125
Lys Asn Ser Thr Thr Ile Glu Ala Asn Phe Ala His Asn Ser Ser Thr
        130                 135                 140
Thr Phe Gln Gln Ala Ser Thr Asp Ile Glu Trp Asn Ile Ser Gln
145                 150                 155                 160
Pro Val Leu Val Pro Arg Lys Gln Val Val Ala Thr Leu Val Ile
                165                 170                 175
Met Gly Gly Asn Phe Thr Ile Pro Met Asp Leu Met Thr Thr Ile Asp
            180                 185                 190
Ser Thr Glu His Tyr Ser Gly Tyr Pro Ile Leu Thr Trp Ile Ser Ser
            195                 200                 205
Pro Asp Asn Ser Tyr Asn Gly Pro Phe Met Ser Trp Tyr Phe Ala Asn
            210                 215                 220
Trp Pro Asn Leu Pro Ser Gly Phe Gly Pro Leu Asn Ser Asp Asn Thr
```

```
                225                 230                 235                 240
Val Thr Tyr Thr Gly Ser Val Val Ser Gln Val Ser Ala Gly Val Tyr
            245                 250                 255

Ala Thr Val Arg Phe Asp Gln Tyr Asp Ile His Asn Leu Arg Thr Ile
            260                 265                 270

Glu Lys Thr Trp Tyr Ala Arg His Ala Thr Leu His Asn Gly Lys Lys
            275                 280                 285

Ile Ser Ile Asn Asn Val Thr Glu Met Ala Pro Thr Ser Pro Ala Lys
            290                 295                 300

Thr Asn
305

<210> SEQ ID NO 136
<211> LENGTH: 306
<212> TYPE: PRT
<213> ORGANISM: Artificial Sequence
<220> FEATURE:
<223> OTHER INFORMATION: engineered

<400> SEQUENCE: 136

Met Ala Ile Leu Asp Leu Lys Ser Leu Val Leu Asn Ala Ile Asn Tyr
1               5                   10                  15

Trp Gly Pro Lys Asn Asn Gly Ile Gln Gly Gly Asp Phe Gly Tyr
            20                  25                  30

Pro Ile Ser Glu Lys Gln Ile Asp Thr Ser Ile Ile Thr Ser Thr His
            35                  40                  45

Pro Arg Leu Ile Pro His Asp Leu Thr Ile Pro Gln Asn Leu Glu Thr
50                  55                  60

Ile Phe Thr Thr Thr Gln Val Leu Thr Asn Asn Thr Asp Leu Gln Gln
65                  70                  75                  80

Ser Gln Thr Val Ser Phe Ala Lys Lys Thr Thr Thr Thr Ala Thr
            85                  90                  95

Ser Thr Thr Asn Gly Trp Thr Glu Gly Gly Lys Ile Ser Asp Thr Leu
            100                 105                 110

Glu Glu Lys Val Ala Val Ser Ile Pro Phe Ile Gly Glu Gly Gly Gly
            115                 120                 125

Lys Asn Ser Thr Thr Ile Glu Ala Asn Phe Ala His Asn Ser Ser Thr
            130                 135                 140

Thr Thr Phe Gln Gln Ala Ser Thr Asp Ile Glu Trp Asn Ile Ser Gln
145                 150                 155                 160

Pro Val Leu Val Pro Pro Arg Lys Gln Val Val Ala Thr Leu Val Ile
            165                 170                 175

Met Gly Gly Asn Phe Thr Ile Pro Met Asp Leu Met Thr Thr Ile Asp
            180                 185                 190

Ser Thr Glu His Tyr Ser Gly Tyr Pro Ile Leu Thr Trp Ile Ser Ser
            195                 200                 205

Pro Asp Asn Ser Tyr Asn Gly Pro Phe Met Ser Trp Tyr Phe Ala Asn
            210                 215                 220

Trp Pro Asn Leu Pro Ser Gly Phe Gly Pro Leu Asn Ser Asp Asn Thr
225                 230                 235                 240

Val Thr Tyr Thr Gly Ser Val Val Ser Gln Val Ser Ala Gly Val Tyr
            245                 250                 255

Ala Thr Val Arg Phe Asp Gln Tyr Asp Ile His Asn Leu Arg Thr Ile
            260                 265                 270

Glu Lys Thr Trp Tyr Ala Arg His Ala Thr Leu His Asn Gly Lys Lys
```

```
                275                 280                 285
Ile Ser Ile Asn Asn Val Thr Glu Met Ala Pro Thr Ser Pro Ile Lys
        290                 295                 300

Thr Asn
305

<210> SEQ ID NO 137
<211> LENGTH: 306
<212> TYPE: PRT
<213> ORGANISM: Artificial Sequence
<220> FEATURE:
<223> OTHER INFORMATION: engineered

<400> SEQUENCE: 137

Met Ala Ile Leu Asp Leu Lys Ser Leu Val Leu Asn Ala Ile Asn Tyr
1               5                   10                  15

Trp Gly Pro Lys Asn Asn Gly Ile Gln Gly Gly Asp Phe Gly Tyr
            20                  25                  30

Pro Ile Ser Glu Lys Gln Ile Asp Thr Ser Ile Ile Thr Ser Thr His
        35                  40                  45

Pro Arg Leu Ile Pro His Asp Leu Thr Ile Pro Gln Asn Leu Glu Thr
50                  55                  60

Ile Phe Thr Thr Thr Gln Val Leu Thr Asn Asn Thr Asp Leu Gln Gln
65                  70                  75                  80

Ser Gln Thr Val Ser Phe Ala Lys Lys Thr Thr Thr Ala Thr Ser Thr
                85                  90                  95

Ser Thr Thr Asn Gly Trp Thr Glu Gly Gly Lys Ile Ser Asp Thr Leu
            100                 105                 110

Glu Glu Lys Val Ser Val Ala Ile Pro Phe Ile Gly Glu Gly Gly Gly
        115                 120                 125

Lys Asn Ser Thr Thr Ile Glu Ala Asn Phe Ala His Asn Ser Ser Thr
130                 135                 140

Thr Thr Phe Gln Gln Ala Ser Thr Asp Ile Glu Trp Asn Ile Ser Gln
145                 150                 155                 160

Pro Val Leu Val Pro Pro Arg Lys Gln Val Val Ala Thr Leu Val Ile
                165                 170                 175

Met Gly Gly Asn Phe Thr Ile Pro Met Asp Leu Met Thr Thr Ile Asp
            180                 185                 190

Ser Thr Glu His Tyr Ser Gly Tyr Pro Ile Leu Thr Trp Ile Ser Ser
        195                 200                 205

Pro Asp Asn Ser Tyr Asn Gly Pro Phe Met Ser Trp Tyr Phe Ala Asn
210                 215                 220

Trp Pro Asn Leu Pro Ser Gly Phe Gly Pro Leu Asn Ser Asp Asn Thr
225                 230                 235                 240

Val Thr Tyr Thr Gly Ser Val Ser Gln Val Ser Ala Gly Val Tyr
                245                 250                 255

Ala Thr Val Arg Phe Asp Gln Tyr Asp Ile His Asn Leu Arg Thr Ile
            260                 265                 270

Glu Lys Thr Trp Tyr Ala Arg His Ala Thr Leu His Asn Gly Lys Lys
        275                 280                 285

Ile Ser Ile Asn Asn Val Thr Glu Met Ala Pro Thr Ser Pro Ile Lys
        290                 295                 300

Thr Asn
305
```

-continued

```
<210> SEQ ID NO 138
<211> LENGTH: 306
<212> TYPE: PRT
<213> ORGANISM: Artificial Sequence
<220> FEATURE:
<223> OTHER INFORMATION: engineered

<400> SEQUENCE: 138

Met Ala Ile Leu Asp Leu Lys Ser Leu Val Leu Asn Ala Ile Asn Tyr
1               5                   10                  15

Trp Gly Pro Lys Asn Asn Asn Gly Ile Gln Gly Gly Asp Phe Gly Tyr
            20                  25                  30

Pro Ile Ser Glu Lys Gln Ile Asp Thr Ser Ile Ile Thr Ser Thr His
        35                  40                  45

Pro Arg Leu Ile Pro His Asp Leu Thr Ile Pro Gln Asn Leu Glu Thr
    50                  55                  60

Ile Phe Thr Ala Thr Gln Val Leu Thr Asn Asn Thr Asp Leu Gln Gln
65                  70                  75                  80

Ser Gln Thr Val Ser Phe Ala Lys Lys Thr Thr Thr Thr Ser Thr
                85                  90                  95

Ser Thr Thr Asn Gly Trp Thr Glu Gly Gly Lys Ile Ser Asp Thr Leu
            100                 105                 110

Glu Glu Lys Val Ser Val Ser Ile Pro Phe Ile Gly Glu Gly Gly Gly
        115                 120                 125

Lys Asn Ser Thr Thr Ile Glu Ala Asn Phe Ala His Asn Ser Ser Thr
    130                 135                 140

Thr Thr Ala Gln Gln Ala Ser Thr Asp Ile Glu Trp Asn Ile Ser Gln
145                 150                 155                 160

Pro Val Leu Val Pro Pro Arg Lys Gln Val Val Ala Thr Leu Val Ile
                165                 170                 175

Met Gly Gly Asn Phe Thr Ile Pro Met Asp Leu Met Thr Thr Ile Asp
            180                 185                 190

Ser Thr Glu His Tyr Ser Gly Tyr Pro Ile Leu Thr Trp Ile Ser Ser
        195                 200                 205

Pro Asp Asn Ser Tyr Asn Gly Pro Phe Met Ser Trp Tyr Phe Ala Asn
    210                 215                 220

Trp Pro Asn Leu Pro Ser Gly Phe Gly Pro Leu Asn Ser Asp Asn Thr
225                 230                 235                 240

Val Thr Tyr Thr Gly Ser Val Val Ser Gln Val Ser Ala Gly Val Tyr
                245                 250                 255

Ala Thr Val Arg Phe Asp Gln Tyr Asp Ile His Asn Leu Arg Thr Ile
            260                 265                 270

Glu Lys Thr Trp Tyr Ala Arg His Ala Thr Leu His Asn Gly Lys Lys
        275                 280                 285

Ile Ser Ile Asn Asn Val Thr Glu Met Ala Pro Thr Ser Pro Ile Lys
    290                 295                 300

Thr Asn
305

<210> SEQ ID NO 139
<211> LENGTH: 306
<212> TYPE: PRT
<213> ORGANISM: Artificial Sequence
<220> FEATURE:
<223> OTHER INFORMATION: engineered

<400> SEQUENCE: 139
```

```
Met Ala Ile Leu Asp Leu Lys Ser Leu Val Leu Asn Ala Ile Asn Tyr
1               5                   10                  15

Trp Gly Pro Lys Asn Asn Gly Ile Gln Gly Gly Asp Phe Gly Tyr
            20                  25                  30

Pro Ile Ser Glu Lys Gln Ile Asp Thr Ser Ile Ile Thr Ser Thr His
            35                  40                  45

Pro Arg Leu Ile Pro His Asp Leu Thr Ile Pro Gln Asn Leu Glu Thr
50                  55                  60

Ile Phe Thr Thr Thr Gln Val Leu Thr Asn Asn Thr Asp Leu Gln Gln
65                  70                  75                  80

Ser Gln Thr Val Ser Phe Ala Lys Lys Thr Thr Thr Thr Ser Thr
                85                  90                  95

Ser Thr Thr Asn Gly Trp Thr Glu Ala Gly Lys Ile Ser Asp Thr Leu
            100                 105                 110

Glu Glu Lys Val Ser Val Ser Ile Pro Phe Ile Gly Glu Gly Gly Gly
            115                 120                 125

Lys Asn Ser Thr Thr Ile Glu Ala Asn Phe Ala His Asn Ser Ser Thr
            130                 135                 140

Thr Thr Ala Gln Gln Ala Ser Thr Asp Ile Glu Trp Asn Ile Ser Gln
145                 150                 155                 160

Pro Val Leu Val Pro Pro Arg Lys Gln Val Val Ala Thr Leu Val Ile
                165                 170                 175

Met Gly Gly Asn Phe Thr Ile Pro Met Asp Leu Met Thr Thr Ile Asp
            180                 185                 190

Ser Thr Glu His Tyr Ser Gly Tyr Pro Ile Leu Thr Trp Ile Ser Ser
            195                 200                 205

Pro Asp Asn Ser Tyr Asn Gly Pro Phe Met Ser Trp Tyr Phe Ala Asn
210                 215                 220

Trp Pro Asn Leu Pro Ser Gly Phe Gly Pro Leu Asn Ser Asp Asn Thr
225                 230                 235                 240

Val Thr Tyr Thr Gly Ser Val Val Ser Gln Val Ser Ala Gly Val Tyr
                245                 250                 255

Ala Thr Val Arg Phe Asp Gln Tyr Asp Ile His Asn Leu Arg Thr Ile
            260                 265                 270

Glu Lys Thr Trp Tyr Ala Arg His Ala Thr Leu His Asn Gly Lys Lys
            275                 280                 285

Ile Ser Ile Asn Asn Val Thr Glu Met Ala Pro Thr Ser Pro Ile Lys
            290                 295                 300

Thr Asn
305

<210> SEQ ID NO 140
<211> LENGTH: 306
<212> TYPE: PRT
<213> ORGANISM: Artificial Sequence
<220> FEATURE:
<223> OTHER INFORMATION: engineered

<400> SEQUENCE: 140

Met Ala Ile Leu Asp Leu Lys Ser Leu Val Leu Asn Ala Ile Asn Tyr
1               5                   10                  15

Trp Gly Pro Lys Asn Asn Gly Ile Gln Gly Gly Asp Phe Gly Tyr
            20                  25                  30

Pro Ile Ser Glu Lys Gln Ile Asp Thr Ser Ile Ile Thr Ser Thr His
            35                  40                  45
```

Pro Arg Leu Ile Pro His Asp Leu Thr Ile Pro Gln Asn Leu Glu Thr
    50                  55                  60

Ile Phe Thr Thr Thr Gln Val Leu Thr Asn Asn Thr Asp Leu Gln Gln
65                  70                  75                  80

Ser Gln Thr Val Ser Phe Ala Lys Lys Thr Thr Thr Thr Ala Thr
                85                  90                  95

Ser Thr Thr Asn Gly Trp Thr Glu Gly Gly Lys Ile Ser Asp Thr Leu
                100                 105                 110

Glu Glu Lys Val Ser Val Ser Ile Pro Phe Ile Gly Ala Gly Gly Gly
            115                 120                 125

Lys Asn Ser Thr Thr Ile Glu Ala Asn Phe Ala His Asn Ser Ser Thr
        130                 135                 140

Thr Thr Phe Gln Gln Ala Ser Thr Asp Ile Glu Trp Asn Ile Ser Gln
145                 150                 155                 160

Pro Val Leu Val Pro Pro Arg Lys Gln Val Val Ala Thr Leu Val Ile
                165                 170                 175

Met Gly Gly Asn Phe Thr Ile Pro Met Asp Leu Met Thr Thr Ile Asp
                180                 185                 190

Ser Thr Glu His Tyr Ser Gly Tyr Pro Ile Leu Thr Trp Ile Ser Ser
            195                 200                 205

Pro Asp Asn Ser Tyr Asn Gly Pro Phe Met Ser Trp Tyr Phe Ala Asn
210                 215                 220

Trp Pro Asn Leu Pro Ser Gly Phe Gly Pro Leu Asn Ser Asp Asn Thr
225                 230                 235                 240

Val Thr Tyr Thr Gly Ser Val Val Ser Gln Val Ser Ala Gly Val Tyr
                245                 250                 255

Ala Thr Val Arg Phe Asp Gln Tyr Asp Ile His Asn Leu Arg Thr Ile
                260                 265                 270

Glu Lys Thr Trp Tyr Ala Arg His Ala Thr Leu His Asn Gly Lys Lys
            275                 280                 285

Ile Ser Ile Asn Asn Val Thr Glu Met Ala Pro Thr Ser Pro Ile Lys
        290                 295                 300

Thr Asn
305

<210> SEQ ID NO 141
<211> LENGTH: 306
<212> TYPE: PRT
<213> ORGANISM: Artificial Sequence
<220> FEATURE:
<223> OTHER INFORMATION: engineered

<400> SEQUENCE: 141

Met Ala Ile Leu Asp Leu Lys Ser Leu Val Leu Asn Ala Ile Asn Tyr
1               5                   10                  15

Trp Gly Pro Lys Asn Asn Gly Ile Gln Gly Gly Asp Phe Gly Tyr
            20                  25                  30

Pro Ile Ser Glu Lys Gln Ile Asp Thr Ser Ile Ile Thr Ser Thr His
                35                  40                  45

Pro Arg Leu Ile Pro His Asp Leu Thr Ile Pro Gln Asn Leu Glu Thr
    50                  55                  60

Ile Phe Thr Thr Thr Gln Val Leu Thr Asn Asn Thr Asp Leu Gln Gln
65                  70                  75                  80

Ser Gln Thr Val Ser Phe Ala Lys Lys Thr Thr Thr Ala Thr Ser Thr
                85                  90                  95

Ser Thr Thr Asn Gly Trp Thr Glu Gly Gly Lys Ile Ser Asp Thr Leu
            100                 105                 110

Glu Glu Lys Val Ser Val Ser Ile Pro Phe Ile Gly Glu Gly Gly Gly
            115                 120                 125

Lys Asn Ser Thr Thr Ile Glu Ala Asn Phe Ala His Asn Ser Ser Thr
            130                 135                 140

Thr Thr Phe Gln Gln Ala Ser Thr Asp Ile Ala Trp Asn Ile Ser Gln
145                 150                 155                 160

Pro Val Leu Val Pro Pro Arg Lys Gln Val Val Ala Thr Leu Val Ile
                165                 170                 175

Met Gly Gly Asn Phe Thr Ile Pro Met Asp Leu Met Thr Thr Ile Asp
            180                 185                 190

Ser Thr Glu His Tyr Ser Gly Tyr Pro Ile Leu Thr Trp Ile Ser Ser
            195                 200                 205

Pro Asp Asn Ser Tyr Asn Gly Pro Phe Met Ser Trp Tyr Phe Ala Asn
210                 215                 220

Trp Pro Asn Leu Pro Ser Gly Phe Gly Pro Leu Asn Ser Asp Asn Thr
225                 230                 235                 240

Val Thr Tyr Thr Gly Ser Val Val Ser Gln Val Ser Ala Gly Val Tyr
                245                 250                 255

Ala Thr Val Arg Phe Asp Gln Tyr Asp Ile His Asn Leu Arg Thr Ile
            260                 265                 270

Glu Lys Thr Trp Tyr Ala Arg His Ala Thr Leu His Asn Gly Lys Lys
            275                 280                 285

Ile Ser Ile Asn Asn Val Thr Glu Met Ala Pro Thr Ser Pro Ile Lys
            290                 295                 300

Thr Asn
305

<210> SEQ ID NO 142
<211> LENGTH: 306
<212> TYPE: PRT
<213> ORGANISM: Artificial Sequence
<220> FEATURE:
<223> OTHER INFORMATION: engineered

<400> SEQUENCE: 142

Met Ala Ile Leu Asp Leu Lys Ser Leu Val Leu Asn Ala Ile Asn Tyr
1               5                   10                  15

Trp Gly Pro Lys Asn Asn Gly Ile Gln Gly Gly Asp Phe Gly Tyr
            20                  25                  30

Pro Ile Ser Glu Lys Gln Ile Asp Thr Ser Ile Ile Thr Ser Thr His
            35                  40                  45

Pro Arg Leu Ile Pro His Asp Leu Thr Ile Pro Gln Asn Leu Glu Thr
        50                  55                  60

Ile Phe Thr Thr Thr Gln Val Leu Thr Asn Asn Thr Asp Leu Gln Gln
65                  70                  75                  80

Ser Gln Thr Val Ser Phe Ala Lys Lys Thr Thr Thr Ala Thr Ser Thr
                85                  90                  95

Ser Thr Thr Asn Gly Trp Thr Glu Gly Gly Lys Ile Ser Asp Thr Leu
            100                 105                 110

Glu Glu Lys Val Ser Val Ser Ile Pro Phe Ile Gly Glu Gly Gly Gly
            115                 120                 125

Lys Asn Ser Thr Thr Ile Glu Ala Asn Phe Ala His Asn Ser Ser Thr
            130                 135                 140

```
Thr Thr Phe Gln Gln Ala Ser Thr Asp Ile Glu Trp Asn Ile Ser Gln
145                 150                 155                 160

Pro Val Leu Val Pro Arg Lys Gln Val Val Ala Thr Leu Val Ile
                165                 170                 175

Met Gly Gly Asn Phe Thr Ile Pro Met Asp Leu Met Thr Thr Ile Asp
                180                 185                 190

Ser Thr Glu His Tyr Ser Gly Tyr Pro Ile Leu Thr Trp Ile Ser Ser
            195                 200                 205

Pro Asp Asn Ser Tyr Asn Gly Pro Phe Met Ser Trp Tyr Phe Ala Asn
        210                 215                 220

Trp Pro Asn Leu Pro Ser Gly Phe Gly Pro Leu Asn Ser Asp Asn Thr
225                 230                 235                 240

Val Thr Tyr Thr Gly Ser Val Val Ser Gln Val Ser Ala Gly Val Tyr
                245                 250                 255

Ala Thr Val Arg Phe Asp Gln Tyr Asp Ile His Asn Leu Arg Thr Ile
                260                 265                 270

Glu Lys Thr Trp Tyr Ala Arg His Ala Thr Leu His Asn Gly Lys Lys
            275                 280                 285

Ile Ser Ile Asn Asn Val Thr Glu Met Ala Pro Thr Ser Ala Ile Lys
        290                 295                 300

Thr Asn
305

<210> SEQ ID NO 143
<211> LENGTH: 306
<212> TYPE: PRT
<213> ORGANISM: Artificial Sequence
<220> FEATURE:
<223> OTHER INFORMATION: engineered

<400> SEQUENCE: 143

Met Ala Ile Leu Asp Leu Lys Ser Leu Val Leu Asn Ala Ile Asn Tyr
1               5                   10                  15

Trp Gly Pro Lys Asn Asn Gly Ile Gln Gly Gly Asp Phe Gly Tyr
                20                  25                  30

Pro Ile Ser Glu Lys Gln Ile Asp Thr Ser Ile Ile Thr Ser Thr His
            35                  40                  45

Pro Arg Leu Ile Pro His Asp Leu Thr Ile Pro Gln Asn Leu Glu Thr
        50                  55                  60

Ile Phe Thr Thr Thr Gln Val Leu Thr Asn Asn Thr Asp Leu Gln Gln
65                  70                  75                  80

Ser Gln Thr Val Ser Phe Ala Lys Lys Thr Thr Thr Thr Ala Thr
                85                  90                  95

Ser Thr Thr Asn Gly Trp Thr Glu Gly Gly Lys Ile Ser Asp Thr Leu
                100                 105                 110

Glu Glu Lys Val Ser Val Ser Ile Pro Phe Ile Gly Glu Gly Gly Gly
            115                 120                 125

Lys Asn Ser Thr Thr Ile Glu Ala Asn Phe Ala His Asn Ser Ser Thr
        130                 135                 140

Thr Thr Phe Gln Gln Ala Ser Thr Asp Ile Glu Trp Asn Ile Ser Gln
145                 150                 155                 160

Pro Val Leu Val Pro Arg Lys Gln Val Val Ala Thr Leu Val Ile
                165                 170                 175

Ala Gly Gly Asn Phe Thr Ile Pro Met Asp Leu Met Thr Thr Ile Asp
                180                 185                 190
```

```
Ser Thr Glu His Tyr Ser Gly Tyr Pro Ile Leu Thr Trp Ile Ser Ser
            195                 200                 205

Pro Asp Asn Ser Tyr Asn Gly Pro Phe Met Ser Trp Tyr Phe Ala Asn
210                 215                 220

Trp Pro Asn Leu Pro Ser Gly Phe Gly Pro Leu Asn Ser Asp Asn Thr
225                 230                 235                 240

Val Thr Tyr Thr Gly Ser Val Val Ser Gln Val Ser Ala Gly Val Tyr
                245                 250                 255

Ala Thr Val Arg Phe Asp Gln Tyr Asp Ile His Asn Leu Arg Thr Ile
                260                 265                 270

Glu Lys Thr Trp Tyr Ala Arg His Ala Thr Leu His Asn Gly Lys Lys
            275                 280                 285

Ile Ser Ile Asn Asn Val Thr Glu Met Ala Pro Thr Ser Pro Ile Lys
            290                 295                 300

Thr Asn
305

<210> SEQ ID NO 144
<211> LENGTH: 306
<212> TYPE: PRT
<213> ORGANISM: Artificial Sequence
<220> FEATURE:
<223> OTHER INFORMATION: engineered

<400> SEQUENCE: 144

Met Ala Ile Leu Asp Leu Lys Ser Leu Val Leu Asn Ala Ile Asn Tyr
1               5                   10                  15

Trp Gly Pro Lys Asn Asn Asn Gly Ile Gln Gly Gly Asp Phe Gly Tyr
                20                  25                  30

Pro Ile Ser Glu Lys Gln Ile Asp Thr Ser Ile Ile Thr Ser Thr His
            35                  40                  45

Pro Arg Leu Ile Pro His Asp Leu Thr Ile Pro Gln Asn Leu Glu Thr
50                  55                  60

Ile Phe Thr Thr Thr Gln Val Leu Thr Asn Asn Thr Asp Leu Gln Gln
65                  70                  75                  80

Ser Gln Thr Val Ser Phe Ala Lys Lys Thr Thr Thr Ala Thr Ser Thr
                85                  90                  95

Ser Thr Thr Asn Gly Trp Thr Glu Gly Gly Lys Ile Ser Asp Thr Leu
            100                 105                 110

Glu Glu Lys Val Ser Val Ser Ile Pro Phe Ile Gly Glu Gly Gly Gly
        115                 120                 125

Lys Asn Ser Thr Thr Ile Glu Ala Asn Phe Ala His Asn Ser Ser Thr
    130                 135                 140

Thr Thr Phe Gln Gln Ala Ser Thr Asp Ile Glu Trp Asn Ile Ser Gln
145                 150                 155                 160

Pro Val Leu Val Pro Pro Arg Lys Gln Val Val Ala Thr Leu Val Ile
                165                 170                 175

Met Gly Gly Asn Phe Thr Ile Pro Met Asp Leu Met Thr Thr Ile Asp
            180                 185                 190

Ser Thr Glu Ala Tyr Ser Gly Tyr Pro Ile Leu Thr Trp Ile Ser Ser
        195                 200                 205

Pro Asp Asn Ser Tyr Asn Gly Pro Phe Met Ser Trp Tyr Phe Ala Asn
    210                 215                 220

Trp Pro Asn Leu Pro Ser Gly Phe Gly Pro Leu Asn Ser Asp Asn Thr
225                 230                 235                 240
```

```
Val Thr Tyr Thr Gly Ser Val Val Ser Gln Val Ser Ala Gly Val Tyr
                245                 250                 255

Ala Thr Val Arg Phe Asp Gln Tyr Asp Ile His Asn Leu Arg Thr Ile
            260                 265                 270

Glu Lys Thr Trp Tyr Ala Arg His Ala Thr Leu His Asn Gly Lys Lys
        275                 280                 285

Ile Ser Ile Asn Asn Val Thr Glu Met Ala Pro Thr Ser Pro Ile Lys
    290                 295                 300

Thr Asn
305

<210> SEQ ID NO 145
<211> LENGTH: 306
<212> TYPE: PRT
<213> ORGANISM: Artificial Sequence
<220> FEATURE:
<223> OTHER INFORMATION: engineered

<400> SEQUENCE: 145

Met Ala Ile Leu Asp Leu Lys Ser Leu Val Leu Asn Ala Ile Asn Tyr
1               5                   10                  15

Trp Gly Pro Lys Asn Asn Asn Gly Ile Gln Gly Gly Asp Phe Gly Tyr
            20                  25                  30

Pro Ile Ser Glu Lys Gln Ile Asp Thr Ser Ile Ile Thr Ser Thr His
        35                  40                  45

Pro Arg Leu Ile Pro His Asp Leu Thr Ile Pro Gln Asn Leu Glu Thr
    50                  55                  60

Ile Phe Thr Thr Thr Gln Val Leu Thr Asn Asn Thr Asp Leu Gln Gln
65                  70                  75                  80

Ser Gln Thr Val Ser Phe Ala Lys Lys Thr Thr Thr Ala Thr Ser Thr
                85                  90                  95

Ser Thr Thr Asn Gly Trp Thr Glu Gly Gly Lys Ile Ser Asp Thr Leu
            100                 105                 110

Glu Glu Lys Val Ser Val Ser Ile Pro Phe Ile Gly Glu Gly Gly Gly
        115                 120                 125

Lys Asn Ser Thr Thr Ile Glu Ala Asn Phe Ala His Asn Ser Ser Thr
    130                 135                 140

Thr Thr Phe Gln Gln Ala Ser Thr Ala Ile Glu Trp Asn Ile Ser Gln
145                 150                 155                 160

Pro Val Leu Val Pro Pro Arg Lys Gln Val Val Ala Thr Leu Val Ile
                165                 170                 175

Met Gly Gly Asn Phe Thr Ile Pro Met Asp Leu Met Thr Thr Ile Asp
            180                 185                 190

Ser Thr Glu His Tyr Ser Gly Tyr Pro Ile Leu Thr Trp Ile Ser Ser
        195                 200                 205

Pro Asp Asn Ser Tyr Asn Gly Pro Phe Met Ser Trp Tyr Phe Ala Asn
    210                 215                 220

Trp Pro Asn Leu Pro Ser Gly Phe Gly Pro Leu Asn Ser Asp Asn Thr
225                 230                 235                 240

Val Thr Tyr Thr Gly Ser Val Val Ser Gln Val Ser Ala Gly Val Tyr
                245                 250                 255

Ala Thr Val Arg Phe Asp Gln Tyr Asp Ile His Asn Leu Arg Thr Ile
            260                 265                 270

Glu Lys Thr Trp Tyr Ala Arg His Ala Thr Leu His Asn Gly Lys Lys
        275                 280                 285
```

Ile Ser Ile Asn Asn Val Thr Glu Met Ala Pro Thr Ser Pro Ile Lys
290                 295                 300

Thr Asn
305

<210> SEQ ID NO 146
<211> LENGTH: 306
<212> TYPE: PRT
<213> ORGANISM: Artificial Sequence
<220> FEATURE:
<223> OTHER INFORMATION: engineered

<400> SEQUENCE: 146

Met Ala Ile Leu Asp Leu Lys Ser Leu Val Leu Asn Ala Ile Asn Tyr
1               5                   10                  15

Trp Gly Pro Lys Asn Asn Gly Ile Gln Gly Gly Asp Phe Gly Tyr
            20                  25                  30

Pro Ile Ser Glu Lys Gln Ile Asp Thr Ser Ile Ile Thr Ser Thr His
        35                  40                  45

Pro Arg Leu Ile Pro His Asp Leu Thr Ile Pro Gln Asn Leu Glu Thr
    50                  55                  60

Ile Phe Thr Thr Thr Gln Val Leu Thr Asn Asn Thr Asp Leu Gln Gln
65                  70                  75                  80

Ser Gln Thr Val Ser Phe Ala Lys Lys Thr Thr Thr Thr Ser Thr
                85                  90                  95

Ser Thr Thr Asn Gly Trp Thr Glu Gly Gly Lys Ile Ser Asp Thr Leu
            100                 105                 110

Glu Glu Lys Val Ser Val Ser Ile Pro Phe Ile Gly Glu Gly Gly
        115                 120                 125

Lys Asn Ser Thr Thr Ile Glu Ala Asn Phe Ala His Asn Ser Ser Thr
130                 135                 140

Thr Thr Ala Gln Gln Ala Ser Thr Asp Ile Glu Trp Asn Ile Ser Gln
145                 150                 155                 160

Pro Val Leu Val Pro Pro Arg Lys Gln Val Val Ala Thr Leu Val Ile
                165                 170                 175

Met Gly Gly Asn Phe Thr Ile Pro Met Asp Leu Met Thr Thr Ile Asp
            180                 185                 190

Ser Thr Glu His Tyr Ser Gly Tyr Pro Ile Leu Thr Ala Ile Ser Ser
        195                 200                 205

Pro Asp Asn Ser Tyr Asn Gly Pro Phe Met Ser Trp Tyr Phe Ala Asn
    210                 215                 220

Trp Pro Asn Leu Pro Ser Gly Phe Gly Pro Leu Asn Ser Asp Asn Thr
225                 230                 235                 240

Val Thr Tyr Thr Gly Ser Val Val Ser Gln Val Ser Ala Gly Val Tyr
                245                 250                 255

Ala Thr Val Arg Phe Asp Gln Tyr Asp Ile His Asn Leu Arg Thr Ile
            260                 265                 270

Glu Lys Thr Trp Tyr Ala Arg His Ala Thr Leu His Asn Gly Lys Lys
        275                 280                 285

Ile Ser Ile Asn Asn Val Thr Glu Met Ala Pro Thr Ser Pro Ile Lys
    290                 295                 300

Thr Asn
305

<210> SEQ ID NO 147
<211> LENGTH: 306

```
<212> TYPE: PRT
<213> ORGANISM: Artificial Sequence
<220> FEATURE:
<223> OTHER INFORMATION: engineered

<400> SEQUENCE: 147
```

Met Ala Ile Leu Asp Leu Lys Ser Leu Val Leu Asn Ala Ile Asn Tyr
1               5                   10                  15

Trp Gly Pro Lys Asn Asn Asn Gly Ile Gln Gly Gly Asp Phe Gly Tyr
            20                  25                  30

Pro Ile Ser Glu Lys Gln Ile Asp Thr Ser Ile Ile Thr Ser Thr His
        35                  40                  45

Pro Arg Leu Ile Pro His Asp Leu Thr Ile Pro Gln Asn Leu Glu Thr
    50                  55                  60

Ile Phe Thr Thr Thr Gln Val Leu Thr Asn Asn Thr Asp Leu Gln Gln
65                  70                  75                  80

Ser Gln Thr Val Ser Phe Ala Lys Lys Thr Thr Thr Ala Thr Ser Thr
                85                  90                  95

Ser Thr Thr Asn Gly Trp Thr Glu Gly Gly Lys Ile Ser Asp Thr Leu
            100                 105                 110

Glu Glu Lys Val Ser Val Ser Ile Pro Phe Ile Gly Glu Gly Gly Gly
        115                 120                 125

Lys Asn Ser Thr Thr Ile Glu Ala Asn Phe Ala His Asn Ser Ser Thr
130                 135                 140

Thr Thr Phe Gln Gln Ala Ser Thr Asp Ile Glu Trp Asn Ile Ser Gln
145                 150                 155                 160

Pro Val Leu Val Pro Pro Arg Lys Gln Val Val Ala Thr Leu Val Ile
                165                 170                 175

Met Gly Gly Asn Phe Thr Ile Pro Met Asp Leu Met Thr Thr Ile Asp
            180                 185                 190

Ser Thr Glu His Tyr Ser Gly Tyr Pro Ile Leu Thr Trp Ile Ser Ser
        195                 200                 205

Pro Asp Asn Ser Tyr Asn Gly Pro Phe Met Ser Trp Tyr Phe Ala Asn
    210                 215                 220

Trp Pro Asn Leu Pro Ser Gly Phe Gly Pro Leu Asn Ser Asp Asn Thr
225                 230                 235                 240

Val Thr Tyr Thr Gly Ser Val Val Ser Gln Val Ser Ala Gly Val Tyr
                245                 250                 255

Ala Thr Val Arg Phe Asp Gln Tyr Asp Ile His Asn Leu Arg Thr Ile
            260                 265                 270

Glu Lys Thr Trp Tyr Ala Arg His Ala Thr Leu His Asn Gly Lys Lys
        275                 280                 285

Ile Ser Ile Asn Asn Val Thr Glu Met Ala Pro Thr Ser Pro Ala Lys
    290                 295                 300

Thr Asn
305

```
<210> SEQ ID NO 148
<211> LENGTH: 306
<212> TYPE: PRT
<213> ORGANISM: Artificial Sequence
<220> FEATURE:
<223> OTHER INFORMATION: engineered

<400> SEQUENCE: 148
```

Met Ala Ile Leu Asp Leu Lys Ser Leu Val Leu Asn Ala Ile Asn Tyr
1               5                   10                  15

Trp Gly Pro Lys Asn Asn Asn Gly Ile Gln Gly Gly Asp Phe Gly Tyr
            20                  25                  30

Pro Ile Ser Glu Lys Gln Ile Asp Thr Ser Ile Ile Thr Ser Thr His
            35                  40                  45

Pro Arg Leu Ile Pro His Asp Leu Thr Ile Pro Gln Asn Leu Glu Thr
        50                  55                  60

Ile Phe Thr Thr Thr Gln Val Leu Thr Asn Asn Thr Asp Leu Gln Gln
65                  70                  75                  80

Ser Gln Thr Val Ser Phe Ala Lys Lys Thr Thr Thr Thr Ala Thr
                85                  90                  95

Ser Thr Thr Asn Gly Trp Thr Glu Gly Gly Lys Ile Ser Asp Thr Leu
            100                 105                 110

Glu Glu Lys Val Ser Val Ser Ile Pro Phe Ile Gly Glu Gly Gly Gly
            115                 120                 125

Lys Asn Ser Thr Thr Ile Glu Ala Asn Phe Ala His Asn Ser Ser Thr
130                 135                 140

Thr Thr Phe Gln Gln Ala Ser Thr Asp Ile Glu Trp Asn Ile Ser Gln
145                 150                 155                 160

Pro Val Leu Val Pro Arg Lys Gln Val Val Ala Thr Leu Val Ile
                165                 170                 175

Met Gly Gly Asn Phe Thr Ile Pro Met Asp Leu Met Thr Thr Ile Asp
            180                 185                 190

Ser Thr Glu Ala Tyr Ser Gly Tyr Pro Ile Leu Thr Trp Ile Ser Ser
            195                 200                 205

Pro Asp Asn Ser Tyr Asn Gly Pro Phe Met Ser Trp Tyr Phe Ala Asn
        210                 215                 220

Trp Pro Asn Leu Pro Ser Gly Phe Gly Pro Leu Asn Ser Asp Asn Thr
225                 230                 235                 240

Val Thr Tyr Thr Gly Ser Val Val Ser Gln Val Ser Ala Gly Val Tyr
                245                 250                 255

Ala Thr Val Arg Phe Asp Gln Tyr Asp Ile His Asn Leu Arg Thr Ile
            260                 265                 270

Glu Lys Thr Trp Tyr Ala Arg His Ala Thr Leu His Asn Gly Lys Lys
        275                 280                 285

Ile Ser Ile Asn Asn Val Thr Glu Met Ala Pro Thr Ser Pro Ile Lys
290                 295                 300

Thr Asn
305

<210> SEQ ID NO 149
<211> LENGTH: 306
<212> TYPE: PRT
<213> ORGANISM: Artificial Sequence
<220> FEATURE:
<223> OTHER INFORMATION: engineered

<400> SEQUENCE: 149

Met Ala Ile Leu Asp Leu Lys Ser Leu Val Leu Asn Ala Ile Asn Tyr
1               5                   10                  15

Trp Gly Pro Lys Asn Asn Asn Gly Ile Gln Gly Gly Asp Phe Gly Tyr
            20                  25                  30

Pro Ile Ser Glu Lys Gln Ile Asp Thr Ser Ile Ile Thr Ser Thr His
            35                  40                  45

Pro Arg Leu Ile Pro His Asp Leu Thr Ile Pro Gln Asn Leu Glu Thr
        50                  55                  60

Ile Phe Thr Thr Thr Gln Val Leu Thr Asn Asn Thr Asp Leu Gln Gln
65                  70                  75                  80

Ser Gln Thr Val Ser Phe Ala Lys Lys Thr Thr Thr Thr Ala Thr
            85                  90                  95

Ser Thr Thr Asn Gly Trp Thr Glu Gly Gly Lys Ile Ser Asp Thr Leu
            100                 105                 110

Glu Glu Lys Val Ser Val Ser Ile Pro Phe Ile Gly Glu Gly Gly Gly
            115                 120                 125

Lys Asn Ser Thr Thr Ile Glu Ala Asn Phe Ala His Asn Ser Ser Thr
            130                 135                 140

Thr Thr Phe Gln Ala Ala Ser Thr Asp Ile Glu Trp Asn Ile Ser Gln
145                 150                 155                 160

Pro Val Leu Val Pro Pro Arg Lys Gln Val Val Ala Thr Leu Val Ile
                165                 170                 175

Met Gly Gly Asn Phe Thr Ile Pro Met Asp Leu Met Thr Thr Ile Asp
                180                 185                 190

Ser Thr Glu His Tyr Ser Gly Tyr Pro Ile Leu Thr Trp Ile Ser Ser
            195                 200                 205

Pro Asp Asn Ser Tyr Asn Gly Pro Phe Met Ser Trp Tyr Phe Ala Asn
            210                 215                 220

Trp Pro Asn Leu Pro Ser Gly Phe Gly Pro Leu Asn Ser Asp Asn Thr
225                 230                 235                 240

Val Thr Tyr Thr Gly Ser Val Val Ser Gln Val Ser Ala Gly Val Tyr
                245                 250                 255

Ala Thr Val Arg Phe Asp Gln Tyr Asp Ile His Asn Leu Arg Thr Ile
            260                 265                 270

Glu Lys Thr Trp Tyr Ala Arg His Ala Thr Leu His Asn Gly Lys Lys
            275                 280                 285

Ile Ser Ile Asn Asn Val Thr Glu Met Ala Pro Thr Ser Pro Ile Lys
            290                 295                 300

Thr Asn
305

<210> SEQ ID NO 150
<211> LENGTH: 306
<212> TYPE: PRT
<213> ORGANISM: Artificial Sequence
<220> FEATURE:
<223> OTHER INFORMATION: engineered

<400> SEQUENCE: 150

Met Ala Ile Leu Asp Leu Lys Ser Leu Val Leu Asn Ala Ile Asn Tyr
1               5                   10                  15

Trp Gly Pro Lys Asn Asn Asn Gly Ile Gln Gly Gly Asp Phe Gly Tyr
            20                  25                  30

Pro Ile Ser Glu Lys Gln Ile Asp Thr Ser Ile Thr Ser Thr His
            35                  40                  45

Pro Arg Leu Ile Pro His Asp Leu Thr Ile Pro Gln Asn Leu Glu Thr
    50                  55                  60

Ile Phe Thr Thr Thr Gln Val Leu Thr Asn Asn Thr Asp Leu Gln Gln
65                  70                  75                  80

Ser Gln Thr Val Ser Phe Ala Lys Lys Thr Thr Thr Thr Ala Thr
            85                  90                  95

Ser Thr Thr Asn Gly Trp Thr Glu Gly Gly Lys Ile Ser Asp Thr Leu
            100                 105                 110

```
Glu Glu Lys Val Ser Val Ser Ile Pro Phe Ile Gly Glu Gly Gly Gly
        115                 120                 125

Lys Asn Ser Thr Thr Ile Glu Ala Asn Phe Ala His Asn Ser Ser Thr
    130                 135                 140

Thr Thr Phe Gln Gln Ala Ser Thr Asp Ile Glu Trp Asn Ile Ser Gln
145                 150                 155                 160

Pro Val Leu Val Pro Arg Lys Gln Val Val Ala Thr Leu Val Ile
            165                 170                 175

Met Gly Gly Asn Phe Thr Ile Pro Met Asp Leu Met Thr Thr Ile Asp
                180                 185                 190

Ser Thr Glu His Tyr Ser Gly Tyr Pro Ile Leu Thr Trp Ile Ser Ser
        195                 200                 205

Pro Asp Asn Ser Tyr Asn Gly Pro Phe Met Ser Trp Tyr Phe Ala Asn
            210                 215                 220

Trp Pro Asn Leu Pro Ser Gly Phe Gly Pro Leu Asn Ser Asp Asn Thr
225                 230                 235                 240

Val Thr Tyr Thr Gly Ser Val Val Ser Gln Val Ser Ala Gly Val Tyr
                245                 250                 255

Ala Thr Val Arg Phe Asp Gln Tyr Asp Ile His Asn Leu Arg Thr Ile
            260                 265                 270

Glu Lys Thr Trp Tyr Ala Arg His Ala Thr Leu His Asn Gly Lys Lys
        275                 280                 285

Ile Ala Ile Asn Asn Val Thr Glu Met Ala Pro Thr Ser Pro Ile Lys
        290                 295                 300

Thr Asn
305

<210> SEQ ID NO 151
<211> LENGTH: 306
<212> TYPE: PRT
<213> ORGANISM: Artificial Sequence
<220> FEATURE:
<223> OTHER INFORMATION: engineered

<400> SEQUENCE: 151

Met Ala Ile Leu Asp Leu Lys Ser Leu Val Leu Asn Ala Ile Asn Tyr
1               5                   10                  15

Trp Gly Pro Lys Asn Asn Asn Gly Ile Gln Gly Gly Asp Phe Gly Tyr
            20                  25                  30

Pro Ile Ser Glu Lys Gln Ile Asp Thr Ser Ile Thr Ser Thr His
        35                  40                  45

Pro Arg Leu Ile Pro His Asp Leu Thr Ile Pro Gln Asn Leu Glu Thr
50                  55                  60

Ile Phe Thr Thr Thr Gln Val Leu Thr Asn Asn Thr Asp Leu Gln Gln
65                  70                  75                  80

Ser Gln Thr Val Ser Phe Ala Lys Lys Thr Thr Thr Thr Ala Thr
                85                  90                  95

Ser Thr Thr Asn Gly Trp Thr Glu Gly Gly Lys Ile Ser Asp Thr Leu
            100                 105                 110

Glu Glu Lys Val Ser Val Ser Ile Pro Phe Ile Gly Glu Gly Gly Gly
        115                 120                 125

Lys Asn Ser Thr Thr Ile Glu Ala Asn Phe Ala His Asn Ser Ser Thr
    130                 135                 140

Thr Thr Phe Gln Gln Ser Ser Thr Asp Ile Glu Trp Asn Ile Ser Gln
145                 150                 155                 160
```

```
Pro Val Leu Val Pro Arg Lys Gln Val Val Ala Thr Leu Val Ile
            165                 170                 175

Met Gly Gly Asn Phe Thr Ile Pro Met Asp Leu Met Thr Thr Ile Asp
            180                 185                 190

Ser Thr Glu His Tyr Ser Gly Tyr Pro Ile Leu Thr Trp Ile Ser Ser
            195                 200                 205

Pro Asp Asn Ser Tyr Asn Gly Pro Phe Met Ser Trp Tyr Phe Ala Asn
            210                 215                 220

Trp Pro Asn Leu Pro Ser Gly Phe Gly Pro Leu Asn Ser Asp Asn Thr
225                 230                 235                 240

Val Thr Tyr Thr Gly Ser Val Val Ser Gln Val Ser Ala Gly Val Tyr
            245                 250                 255

Ala Thr Val Arg Phe Asp Gln Tyr Asp Ile His Asn Leu Arg Thr Ile
            260                 265                 270

Glu Lys Thr Trp Tyr Ala Arg His Ala Thr Leu His Asn Gly Lys Lys
            275                 280                 285

Ile Ser Ile Asn Asn Val Thr Glu Met Ala Pro Thr Ser Pro Ile Lys
            290                 295                 300

Thr Asn
305

<210> SEQ ID NO 152
<211> LENGTH: 306
<212> TYPE: PRT
<213> ORGANISM: Artificial Sequence
<220> FEATURE:
<223> OTHER INFORMATION: engineered

<400> SEQUENCE: 152

Met Ala Ile Leu Asp Leu Lys Ser Leu Val Leu Asn Ala Ile Asn Tyr
1               5                   10                  15

Trp Gly Pro Lys Asn Asn Asn Gly Ile Gln Gly Gly Asp Phe Gly Tyr
            20                  25                  30

Pro Ile Ser Glu Lys Gln Ile Asp Thr Ser Ile Ile Thr Ser Thr His
            35                  40                  45

Pro Arg Leu Ile Pro His Asp Leu Thr Ile Pro Gln Asn Leu Glu Thr
        50                  55                  60

Ile Phe Thr Thr Thr Gln Val Leu Thr Asn Asn Thr Asp Leu Gln Gln
65                  70                  75                  80

Ser Gln Thr Val Ser Phe Ala Lys Lys Thr Thr Thr Thr Thr Ser Thr
                85                  90                  95

Ser Thr Thr Asn Gly Trp Thr Glu Gly Gly Lys Ile Ser Asp Thr Leu
            100                 105                 110

Glu Glu Lys Val Ser Val Ala Ile Pro Phe Ile Gly Glu Gly Gly Gly
            115                 120                 125

Lys Asn Ser Thr Thr Ile Glu Ala Asn Phe Ala His Asn Ser Ser Thr
130                 135                 140

Thr Thr Ala Gln Gln Ala Ser Thr Asp Ile Glu Trp Asn Ile Ser Gln
145                 150                 155                 160

Pro Val Leu Val Pro Arg Lys Gln Val Val Ala Thr Leu Val Ile
            165                 170                 175

Met Gly Gly Asn Phe Thr Ile Pro Met Asp Leu Met Thr Thr Ile Asp
            180                 185                 190

Ser Thr Glu His Tyr Ser Gly Tyr Pro Ile Leu Thr Trp Ile Ser Ser
            195                 200                 205
```

```
Pro Asp Asn Ser Tyr Asn Gly Pro Phe Met Ser Trp Tyr Phe Ala Asn
    210                 215                 220

Trp Pro Asn Leu Pro Ser Gly Phe Gly Pro Leu Asn Ser Asp Asn Thr
225                 230                 235                 240

Val Thr Tyr Thr Gly Ser Val Val Ser Gln Val Ser Ala Gly Val Tyr
                245                 250                 255

Ala Thr Val Arg Phe Asp Gln Tyr Asp Ile His Asn Leu Arg Thr Ile
            260                 265                 270

Glu Lys Thr Trp Tyr Ala Arg His Ala Thr Leu His Asn Gly Lys Lys
            275                 280                 285

Ile Ser Ile Asn Asn Val Thr Glu Met Ala Pro Thr Ser Pro Ile Lys
    290                 295                 300

Thr Asn
305

<210> SEQ ID NO 153
<211> LENGTH: 306
<212> TYPE: PRT
<213> ORGANISM: Artificial Sequence
<220> FEATURE:
<223> OTHER INFORMATION: engineered

<400> SEQUENCE: 153

Met Ala Ile Leu Asp Leu Lys Ser Leu Val Leu Asn Ala Ile Asn Tyr
1               5                   10                  15

Trp Gly Pro Lys Asn Asn Gly Ile Gln Gly Gly Asp Phe Gly Tyr
                20                  25                  30

Pro Ile Ser Glu Lys Gln Ile Asp Thr Ser Ile Ile Thr Ser Thr His
            35                  40                  45

Pro Arg Leu Ile Pro His Asp Leu Thr Ile Pro Gln Asn Leu Glu Thr
    50                  55                  60

Ile Phe Thr Thr Thr Gln Val Leu Thr Asn Asn Thr Asp Leu Gln Gln
65                  70                  75                  80

Ser Gln Thr Val Ser Phe Ala Lys Lys Thr Thr Thr Thr Ala Thr
                85                  90                  95

Ser Thr Thr Asn Gly Trp Thr Glu Gly Gly Lys Ile Ser Asp Thr Leu
                100                 105                 110

Glu Glu Lys Val Ser Val Ser Ile Pro Phe Ile Gly Glu Gly Gly Gly
            115                 120                 125

Lys Asn Ser Thr Thr Ile Glu Ala Asn Phe Ala His Asn Ser Ser Thr
    130                 135                 140

Thr Thr Phe Gln Gln Ala Ser Thr Asp Ile Glu Trp Asn Ile Ser Gln
145                 150                 155                 160

Pro Val Leu Val Pro Pro Ala Lys Gln Val Val Ala Thr Leu Val Ile
                165                 170                 175

Met Gly Gly Asn Phe Thr Ile Pro Met Asp Leu Met Thr Thr Ile Asp
                180                 185                 190

Ser Thr Glu His Tyr Ser Gly Tyr Pro Ile Leu Thr Trp Ile Ser Ser
            195                 200                 205

Pro Asp Asn Ser Tyr Asn Gly Pro Phe Met Ser Trp Tyr Phe Ala Asn
    210                 215                 220

Trp Pro Asn Leu Pro Ser Gly Phe Gly Pro Leu Asn Ser Asp Asn Thr
225                 230                 235                 240

Val Thr Tyr Thr Gly Ser Val Val Ser Gln Val Ser Ala Gly Val Tyr
                245                 250                 255
```

```
Ala Thr Val Arg Phe Asp Gln Tyr Asp Ile His Asn Leu Arg Thr Ile
            260                 265                 270

Glu Lys Thr Trp Tyr Ala Arg His Ala Thr Leu His Asn Gly Lys Lys
        275                 280                 285

Ile Ser Ile Asn Asn Val Thr Glu Met Ala Pro Thr Ser Pro Ile Lys
290                 295                 300

Thr Asn
305

<210> SEQ ID NO 154
<211> LENGTH: 306
<212> TYPE: PRT
<213> ORGANISM: Artificial Sequence
<220> FEATURE:
<223> OTHER INFORMATION: engineered

<400> SEQUENCE: 154

Met Ala Ile Leu Asp Leu Lys Ser Leu Val Leu Asn Ala Ile Asn Tyr
1               5                   10                  15

Trp Gly Pro Lys Asn Asn Asn Gly Ile Gln Gly Gly Asp Phe Gly Tyr
            20                  25                  30

Pro Ile Ser Glu Lys Gln Ile Asp Thr Ser Ile Ile Thr Ser Thr His
        35                  40                  45

Pro Arg Leu Ile Pro His Asp Leu Thr Ile Pro Gln Asn Leu Glu Thr
    50                  55                  60

Ile Phe Thr Thr Thr Gln Val Leu Thr Asn Asn Thr Asp Leu Gln Gln
65                  70                  75                  80

Ser Gln Thr Val Ser Phe Ala Lys Lys Thr Thr Thr Thr Thr Ser Thr
                85                  90                  95

Ser Thr Thr Asn Gly Trp Thr Glu Gly Gly Lys Ile Ser Asp Thr Leu
            100                 105                 110

Glu Glu Lys Val Ser Val Ser Ile Pro Phe Ile Gly Glu Gly Gly Gly
        115                 120                 125

Lys Asn Ser Thr Thr Ile Glu Ala Asn Phe Ala His Asn Ser Ser Thr
    130                 135                 140

Thr Thr Ala Gln Gln Ala Ser Thr Asp Ile Glu Trp Asn Ala Ser Gln
145                 150                 155                 160

Pro Val Leu Val Pro Arg Lys Gln Val Ala Thr Leu Val Ile
                165                 170                 175

Met Gly Gly Asn Phe Thr Ile Pro Met Asp Leu Met Thr Thr Ile Asp
            180                 185                 190

Ser Thr Glu His Tyr Ser Gly Tyr Pro Ile Leu Thr Trp Ile Ser Ser
        195                 200                 205

Pro Asp Asn Ser Tyr Asn Gly Pro Phe Met Ser Trp Tyr Phe Ala Asn
    210                 215                 220

Trp Pro Asn Leu Pro Ser Gly Phe Gly Pro Leu Asn Ser Asp Asn Thr
225                 230                 235                 240

Val Thr Tyr Thr Gly Ser Val Val Ser Gln Val Ser Ala Gly Val Tyr
                245                 250                 255

Ala Thr Val Arg Phe Asp Gln Tyr Asp Ile His Asn Leu Arg Thr Ile
            260                 265                 270

Glu Lys Thr Trp Tyr Ala Arg His Ala Thr Leu His Asn Gly Lys Lys
        275                 280                 285

Ile Ser Ile Asn Asn Val Thr Glu Met Ala Pro Thr Ser Pro Ile Lys
    290                 295                 300
```

Thr Asn
305

<210> SEQ ID NO 155
<211> LENGTH: 306
<212> TYPE: PRT
<213> ORGANISM: Artificial Sequence
<220> FEATURE:
<223> OTHER INFORMATION: engineered

<400> SEQUENCE: 155

Met Ala Ile Leu Asp Leu Lys Ser Leu Val Leu Asn Ala Ile Asn Tyr
1               5                   10                  15

Trp Gly Pro Lys Asn Asn Gly Ile Gln Gly Gly Asp Phe Gly Tyr
            20                  25                  30

Pro Ile Ser Glu Lys Gln Ile Asp Thr Ser Ile Ile Thr Ser Thr His
        35                  40                  45

Pro Arg Leu Ile Pro His Asp Leu Thr Ile Pro Gln Asn Leu Glu Thr
50                  55                  60

Ile Phe Thr Thr Thr Gln Val Leu Thr Asn Asn Thr Asp Leu Gln Gln
65                  70                  75                  80

Ser Gln Thr Val Ser Phe Ala Lys Lys Thr Thr Thr Thr Ala Thr
                85                  90                  95

Ser Thr Thr Asn Gly Trp Thr Glu Gly Gly Lys Ile Ser Asp Thr Leu
            100                 105                 110

Glu Glu Lys Val Ser Val Ser Ile Pro Phe Ile Gly Glu Gly Gly Gly
            115                 120                 125

Lys Asn Ser Thr Thr Ile Glu Ala Asn Phe Ala His Asn Ser Ser Thr
        130                 135                 140

Thr Thr Phe Gln Gln Ala Ser Thr Asp Ile Glu Trp Asn Ile Ser Gln
145                 150                 155                 160

Pro Val Leu Val Pro Pro Arg Lys Gln Val Val Ala Thr Leu Val Ile
                165                 170                 175

Met Gly Gly Asn Phe Thr Ile Pro Met Asp Leu Met Thr Thr Ile Asp
            180                 185                 190

Ser Thr Glu His Tyr Ser Gly Tyr Pro Ile Leu Thr Trp Ile Ser Ser
        195                 200                 205

Pro Asp Asn Ser Tyr Asn Gly Pro Phe Met Ser Trp Tyr Phe Ala Asn
    210                 215                 220

Trp Pro Asn Leu Pro Ser Gly Phe Gly Pro Leu Asn Ser Asp Asn Thr
225                 230                 235                 240

Val Thr Tyr Thr Gly Ser Val Val Ser Gln Val Ser Ala Gly Val Tyr
                245                 250                 255

Ala Thr Val Arg Phe Asp Gln Tyr Asp Ile His Asn Leu Arg Thr Ile
            260                 265                 270

Glu Lys Thr Trp Tyr Ala Arg His Ala Thr Leu His Asn Gly Lys Lys
        275                 280                 285

Ile Ser Ile Asn Asn Val Thr Glu Ala Ala Pro Thr Ser Pro Ile Lys
    290                 295                 300

Thr Asn
305

<210> SEQ ID NO 156
<211> LENGTH: 306
<212> TYPE: PRT
<213> ORGANISM: Artificial Sequence

```
<220> FEATURE:
<223> OTHER INFORMATION: engineered

<400> SEQUENCE: 156

Met Ala Ile Leu Asp Leu Lys Ser Leu Val Leu Asn Ala Ile Asn Tyr
1               5                   10                  15

Trp Gly Pro Lys Asn Asn Asn Gly Ile Gln Gly Gly Asp Phe Gly Tyr
            20                  25                  30

Pro Ile Ser Glu Lys Gln Ile Asp Thr Ser Ile Ile Thr Ser Thr His
        35                  40                  45

Pro Arg Leu Ile Pro His Asp Leu Thr Ile Pro Gln Asn Leu Glu Thr
    50                  55                  60

Ile Phe Thr Thr Thr Gln Val Leu Thr Asn Asn Thr Asp Leu Gln Gln
65                  70                  75                  80

Ser Gln Thr Val Ser Phe Ala Lys Lys Thr Thr Thr Thr Thr Ser Thr
                85                  90                  95

Ser Thr Thr Asn Gly Trp Thr Glu Gly Gly Lys Ile Ser Asp Thr Leu
            100                 105                 110

Glu Glu Lys Val Ser Val Ser Ile Pro Phe Ile Gly Glu Gly Gly Gly
        115                 120                 125

Lys Asn Ser Thr Thr Ile Glu Ala Asn Phe Ala His Asn Ser Ser Thr
130                 135                 140

Thr Thr Ala Gln Gln Ala Ser Thr Asp Ile Glu Trp Asn Ile Ser Gln
145                 150                 155                 160

Pro Val Leu Val Pro Pro Arg Lys Gln Val Val Ala Thr Leu Val Ile
                165                 170                 175

Met Gly Gly Asn Phe Ala Ile Pro Met Asp Leu Met Thr Thr Ile Asp
            180                 185                 190

Ser Thr Glu His Tyr Ser Gly Tyr Pro Ile Leu Thr Trp Ile Ser Ser
        195                 200                 205

Pro Asp Asn Ser Tyr Asn Gly Pro Phe Met Ser Trp Tyr Phe Ala Asn
    210                 215                 220

Trp Pro Asn Leu Pro Ser Gly Phe Gly Pro Leu Asn Ser Asp Asn Thr
225                 230                 235                 240

Val Thr Tyr Thr Gly Ser Val Val Ser Gln Val Ser Ala Gly Val Tyr
                245                 250                 255

Ala Thr Val Arg Phe Asp Gln Tyr Asp Ile His Asn Leu Arg Thr Ile
            260                 265                 270

Glu Lys Thr Trp Tyr Ala Arg His Ala Thr Leu His Asn Gly Lys Lys
        275                 280                 285

Ile Ser Ile Asn Asn Val Thr Glu Met Ala Pro Thr Ser Pro Ile Lys
    290                 295                 300

Thr Asn
305

<210> SEQ ID NO 157
<211> LENGTH: 306
<212> TYPE: PRT
<213> ORGANISM: Artificial Sequence
<220> FEATURE:
<223> OTHER INFORMATION: engineered

<400> SEQUENCE: 157

Met Ala Ile Leu Asp Leu Lys Ser Leu Val Leu Asn Ala Ile Asn Tyr
1               5                   10                  15

Trp Gly Pro Lys Asn Asn Asn Gly Ile Gln Gly Gly Asp Phe Gly Tyr
```

```
            20                  25                  30
Pro Ile Ser Glu Lys Gln Ile Asp Thr Ser Ile Ile Thr Ser Thr His
        35                  40                  45

Pro Arg Leu Ile Pro His Asp Leu Thr Ile Pro Gln Asn Leu Glu Thr
50                  55                  60

Ile Phe Thr Thr Thr Gln Val Leu Thr Asn Asn Thr Asp Leu Gln Gln
65                  70                  75                  80

Ser Gln Thr Val Ser Phe Ala Lys Lys Thr Thr Thr Thr Ser Thr Thr
                85                  90                  95

Ser Thr Thr Asn Gly Trp Thr Glu Gly Gly Lys Ile Ser Asp Thr Leu
            100                 105                 110

Glu Glu Lys Val Ser Val Ser Ile Pro Phe Ile Gly Glu Gly Gly Gly
        115                 120                 125

Lys Asn Ser Thr Thr Ile Glu Ala Asn Phe Ala His Asn Ser Ser Thr
    130                 135                 140

Thr Thr Ala Gln Gln Ala Ser Thr Asp Ile Glu Trp Asn Ile Ser Gln
145                 150                 155                 160

Pro Val Leu Val Pro Pro Arg Lys Gln Val Val Ala Thr Leu Val Ile
                165                 170                 175

Met Gly Gly Asn Phe Thr Ile Pro Met Asp Leu Met Thr Thr Ile Asp
            180                 185                 190

Ser Thr Glu His Tyr Ser Gly Tyr Pro Ile Leu Thr Trp Ile Ser Ser
        195                 200                 205

Pro Asp Asn Ser Tyr Asn Gly Pro Phe Met Ser Trp Tyr Phe Ala Asn
    210                 215                 220

Trp Pro Asn Leu Pro Ser Gly Ala Gly Pro Leu Asn Ser Asp Asn Thr
225                 230                 235                 240

Val Thr Tyr Thr Gly Ser Val Val Ser Gln Val Ser Ala Gly Val Tyr
                245                 250                 255

Ala Thr Val Arg Phe Asp Gln Tyr Asp Ile His Asn Leu Arg Thr Ile
            260                 265                 270

Glu Lys Thr Trp Tyr Ala Arg His Ala Thr Leu His Asn Gly Lys Lys
        275                 280                 285

Ile Ser Ile Asn Asn Val Thr Glu Met Ala Pro Thr Ser Pro Ile Lys
    290                 295                 300

Thr Asn
305

<210> SEQ ID NO 158
<211> LENGTH: 306
<212> TYPE: PRT
<213> ORGANISM: Artificial Sequence
<220> FEATURE:
<223> OTHER INFORMATION: engineered

<400> SEQUENCE: 158

Met Ala Ile Leu Asp Leu Lys Ser Leu Val Leu Asn Ala Ile Asn Tyr
1               5                   10                  15

Trp Gly Pro Lys Asn Asn Gly Ile Gln Gly Gly Asp Phe Gly Tyr
            20                  25                  30

Pro Ile Ser Glu Lys Gln Ile Asp Thr Ser Ile Ile Thr Ser Thr His
        35                  40                  45

Pro Arg Leu Ile Pro His Asp Leu Thr Ile Pro Gln Asn Leu Glu Thr
50                  55                  60

Ile Phe Thr Thr Thr Gln Val Leu Thr Asn Asn Thr Asp Leu Gln Gln
```

```
                65                  70                  75                  80
Ser Gln Thr Val Ser Phe Ala Lys Lys Thr Thr Thr Thr Ser Thr
                    85                  90                  95

Ser Thr Thr Asn Gly Trp Thr Glu Gly Gly Lys Ile Ser Asp Thr Leu
                100                 105                 110

Glu Glu Lys Val Ser Val Ser Ile Pro Phe Ile Gly Glu Gly Gly Gly
                115                 120                 125

Lys Asn Ser Thr Thr Ile Glu Ala Asn Phe Ala His Asn Ser Ser Thr
    130                 135                 140

Thr Thr Ala Gln Gln Ala Ser Thr Asp Ile Glu Trp Asn Ile Ser Gln
145                 150                 155                 160

Pro Val Leu Val Pro Ala Lys Gln Val Val Ala Thr Leu Val Ile
                165                 170                 175

Met Gly Gly Asn Phe Thr Ile Pro Met Asp Leu Met Thr Thr Ile Asp
                180                 185                 190

Ser Thr Glu His Tyr Ser Gly Tyr Pro Ile Leu Thr Trp Ile Ser Ser
                195                 200                 205

Pro Asp Asn Ser Tyr Asn Gly Pro Phe Met Ser Trp Tyr Phe Ala Asn
    210                 215                 220

Trp Pro Asn Leu Pro Ser Gly Phe Gly Pro Leu Asn Ser Asp Asn Thr
225                 230                 235                 240

Val Thr Tyr Thr Gly Ser Val Val Ser Gln Val Ser Ala Gly Val Tyr
                245                 250                 255

Ala Thr Val Arg Phe Asp Gln Tyr Asp Ile His Asn Leu Arg Thr Ile
                260                 265                 270

Glu Lys Thr Trp Tyr Ala Arg His Ala Thr Leu His Asn Gly Lys Lys
                275                 280                 285

Ile Ser Ile Asn Asn Val Thr Glu Met Ala Pro Thr Ser Pro Ile Lys
    290                 295                 300

Thr Asn
305

<210> SEQ ID NO 159
<211> LENGTH: 306
<212> TYPE: PRT
<213> ORGANISM: Artificial Sequence
<220> FEATURE:
<223> OTHER INFORMATION: engineered

<400> SEQUENCE: 159

Met Ala Ile Leu Asp Leu Lys Ser Leu Val Leu Asn Ala Ile Asn Tyr
1               5                   10                  15

Trp Gly Pro Lys Asn Asn Gly Ile Gln Gly Gly Asp Phe Gly Tyr
                20                  25                  30

Pro Ile Ser Glu Lys Gln Ile Asp Thr Ser Ile Ile Thr Ser Thr His
                35                  40                  45

Pro Arg Leu Ile Pro His Asp Leu Thr Ile Pro Gln Asn Leu Glu Thr
    50                  55                  60

Ile Phe Thr Thr Thr Gln Val Leu Thr Asn Asn Thr Asp Leu Gln Gln
65                  70                  75                  80

Ser Gln Thr Val Ser Phe Ala Lys Lys Thr Thr Thr Ala Thr Ser Thr
                    85                  90                  95

Ser Thr Thr Asn Gly Trp Thr Glu Gly Gly Lys Ile Ser Asp Thr Leu
                100                 105                 110

Glu Glu Lys Val Ser Val Ser Ile Pro Phe Ile Gly Glu Gly Gly Gly
```

```
            115                 120                 125
Lys Asn Ser Thr Thr Ile Glu Ala Asn Phe Ala His Asn Ser Ser Thr
    130                 135                 140

Thr Thr Phe Gln Gln Ala Ser Thr Asp Ile Glu Trp Asn Ile Ser Gln
145                 150                 155                 160

Pro Val Leu Val Pro Pro Arg Lys Gln Val Val Ala Thr Leu Val Ile
                165                 170                 175

Met Gly Gly Asn Phe Thr Ile Pro Met Asp Leu Met Thr Thr Ile Asp
            180                 185                 190

Ser Thr Glu His Tyr Ser Gly Tyr Pro Ile Leu Thr Trp Ile Ser Ser
        195                 200                 205

Pro Asp Asn Ser Tyr Asn Gly Pro Phe Met Ser Trp Tyr Phe Ala Asn
    210                 215                 220

Trp Pro Asn Leu Pro Ser Gly Phe Gly Pro Leu Asn Ser Ala Asn Thr
225                 230                 235                 240

Val Thr Tyr Thr Gly Ser Val Val Ser Gln Val Ser Ala Gly Val Tyr
                245                 250                 255

Ala Thr Val Arg Phe Asp Gln Tyr Asp Ile His Asn Leu Arg Thr Ile
            260                 265                 270

Glu Lys Thr Trp Tyr Ala Arg His Ala Thr Leu His Asn Gly Lys Lys
        275                 280                 285

Ile Ser Ile Asn Asn Val Thr Glu Met Ala Pro Thr Ser Pro Ile Lys
    290                 295                 300

Thr Asn
305

<210> SEQ ID NO 160
<211> LENGTH: 306
<212> TYPE: PRT
<213> ORGANISM: Artificial Sequence
<220> FEATURE:
<223> OTHER INFORMATION: engineered

<400> SEQUENCE: 160

Met Ala Ile Leu Asp Leu Lys Ser Leu Val Leu Asn Ala Ile Asn Tyr
1               5                   10                  15

Trp Gly Pro Lys Asn Asn Gly Ile Gln Gly Gly Asp Phe Gly Tyr
            20                  25                  30

Pro Ile Ser Glu Lys Gln Ile Asp Thr Ser Ile Ile Thr Ser Thr His
            35                  40                  45

Pro Arg Leu Ile Pro His Asp Leu Thr Ile Pro Gln Asn Leu Glu Thr
        50                  55                  60

Ile Phe Thr Thr Thr Gln Val Leu Thr Asn Asn Thr Asp Leu Gln Gln
65                  70                  75                  80

Ser Gln Thr Val Ser Phe Ala Lys Lys Thr Thr Thr Thr Ala Thr
                85                  90                  95

Ser Thr Thr Asn Gly Trp Thr Glu Gly Gly Lys Ile Ser Asp Thr Leu
            100                 105                 110

Glu Glu Lys Val Ser Val Ser Ile Pro Phe Ile Gly Glu Gly Gly Gly
        115                 120                 125

Lys Asn Ser Thr Thr Ile Glu Ala Asn Phe Ala His Asn Ser Ser Thr
    130                 135                 140

Thr Thr Phe Gln Gln Ala Ser Thr Asp Ile Glu Trp Asn Ile Ser Gln
145                 150                 155                 160

Pro Val Leu Val Pro Pro Arg Lys Gln Val Val Ala Thr Leu Val Ile
```

```
                    165                 170                 175
Met Gly Gly Asn Phe Thr Ile Pro Met Asp Leu Met Thr Thr Ile Asp
                180                 185                 190

Ser Thr Glu His Tyr Ser Gly Tyr Pro Ile Leu Thr Trp Ile Ser Ser
            195                 200                 205

Pro Asp Asn Ser Tyr Asn Gly Pro Phe Met Ser Trp Tyr Phe Ala Asn
        210                 215                 220

Trp Pro Asn Leu Pro Ser Gly Phe Gly Pro Leu Asn Ser Asp Asn Thr
225                 230                 235                 240

Val Thr Tyr Thr Gly Ser Val Val Ser Gln Val Ser Ala Gly Val Tyr
                245                 250                 255

Ala Thr Val Arg Phe Asp Gln Tyr Asp Ile His Asn Leu Arg Ala Ile
                260                 265                 270

Glu Lys Thr Trp Tyr Ala Arg His Ala Thr Leu His Asn Gly Lys Lys
            275                 280                 285

Ile Ser Ile Asn Asn Val Thr Glu Met Ala Pro Thr Ser Pro Ile Lys
        290                 295                 300

Thr Asn
305

<210> SEQ ID NO 161
<211> LENGTH: 306
<212> TYPE: PRT
<213> ORGANISM: Artificial Sequence
<220> FEATURE:
<223> OTHER INFORMATION: engineered

<400> SEQUENCE: 161

Met Ala Ile Leu Asp Leu Lys Ser Leu Val Leu Asn Ala Ile Asn Tyr
1               5                   10                  15

Trp Gly Pro Lys Asn Asn Gly Ile Gln Gly Gly Asp Phe Gly Tyr
                20                  25                  30

Pro Ile Ser Glu Lys Gln Ile Asp Thr Ser Ile Ile Thr Ser Thr His
            35                  40                  45

Pro Arg Leu Ile Pro His Asp Leu Thr Ile Pro Gln Asn Leu Glu Thr
        50                  55                  60

Ile Phe Thr Thr Thr Gln Val Leu Thr Asn Asn Thr Asp Leu Gln Gln
65                  70                  75                  80

Ser Gln Thr Val Ser Phe Ala Lys Lys Thr Thr Ala Thr Ser Thr
                85                  90                  95

Ser Thr Thr Asn Gly Trp Thr Glu Gly Gly Lys Ile Ser Asp Thr Leu
            100                 105                 110

Glu Glu Lys Val Ser Val Ser Ile Pro Phe Ile Gly Glu Gly Gly Gly
        115                 120                 125

Lys Asn Ser Thr Thr Ile Glu Ala Asn Phe Ala His Asn Ser Ser Thr
130                 135                 140

Thr Thr Phe Ala Gln Ala Ser Asp Ile Glu Trp Asn Ile Ser Gln
145                 150                 155                 160

Pro Val Leu Val Pro Pro Arg Lys Gln Val Val Ala Thr Leu Val Ile
                165                 170                 175

Met Gly Gly Asn Phe Thr Ile Pro Met Asp Leu Met Thr Thr Ile Asp
            180                 185                 190

Ser Thr Glu His Tyr Ser Gly Tyr Pro Ile Leu Thr Trp Ile Ser Ser
        195                 200                 205

Pro Asp Asn Ser Tyr Asn Gly Pro Phe Met Ser Trp Tyr Phe Ala Asn
```

```
            210                 215                 220
Trp Pro Asn Leu Pro Ser Gly Phe Gly Pro Leu Asn Ser Asp Asn Thr
225                 230                 235                 240

Val Thr Tyr Thr Gly Ser Val Val Ser Gln Val Ser Ala Gly Val Tyr
                245                 250                 255

Ala Thr Val Arg Phe Asp Gln Tyr Asp Ile His Asn Leu Arg Thr Ile
                260                 265                 270

Glu Lys Thr Trp Tyr Ala Arg His Ala Thr Leu His Asn Gly Lys Lys
            275                 280                 285

Ile Ser Ile Asn Asn Val Thr Glu Met Ala Pro Thr Ser Pro Ile Lys
            290                 295                 300

Thr Asn
305

<210> SEQ ID NO 162
<211> LENGTH: 306
<212> TYPE: PRT
<213> ORGANISM: Artificial Sequence
<220> FEATURE:
<223> OTHER INFORMATION: engineered

<400> SEQUENCE: 162

Met Ala Ile Leu Asp Leu Lys Ser Leu Val Leu Asn Ala Ile Asn Tyr
1               5                   10                  15

Trp Gly Pro Lys Asn Asn Gly Ile Gln Gly Gly Asp Phe Gly Tyr
            20                  25                  30

Pro Ile Ser Glu Lys Gln Ile Asp Thr Ser Ile Ile Thr Ser Thr His
            35                  40                  45

Pro Arg Leu Ile Pro His Asp Leu Thr Ile Pro Gln Asn Leu Glu Thr
        50                  55                  60

Ile Phe Thr Thr Thr Gln Val Leu Thr Asn Asn Thr Asp Leu Gln Gln
65                  70                  75                  80

Ser Gln Thr Val Ser Phe Ala Lys Lys Thr Thr Thr Thr Ala Thr
                85                  90                  95

Ser Thr Thr Asn Gly Trp Thr Glu Gly Gly Lys Ile Ser Asp Thr Leu
            100                 105                 110

Glu Glu Lys Val Ser Val Ser Ile Pro Phe Ile Gly Glu Gly Gly Gly
        115                 120                 125

Lys Asn Ser Thr Thr Ile Glu Ala Asn Phe Ala His Asn Ser Ser Thr
    130                 135                 140

Thr Thr Phe Gln Gln Ala Ser Thr Asp Ile Glu Trp Asn Ile Ser Gln
145                 150                 155                 160

Pro Val Leu Val Pro Pro Arg Lys Gln Val Val Ala Thr Leu Val Ile
                165                 170                 175

Met Gly Gly Asn Phe Thr Ile Pro Met Asp Leu Met Thr Thr Ile Asp
            180                 185                 190

Ser Thr Glu His Tyr Ser Gly Tyr Pro Ile Leu Thr Trp Ile Ser Ser
        195                 200                 205

Pro Asp Asn Ser Tyr Asn Gly Pro Phe Met Ser Trp Tyr Phe Ala Asn
    210                 215                 220

Trp Pro Asn Leu Pro Ser Gly Phe Gly Pro Leu Asn Ser Ala Asn Thr
225                 230                 235                 240

Val Thr Tyr Thr Gly Ser Val Val Ser Gln Val Ser Ala Gly Val Tyr
                245                 250                 255

Ala Thr Val Arg Phe Asp Gln Tyr Asp Ile His Asn Leu Arg Thr Ile
```

```
                260                 265                 270
Glu Lys Thr Trp Tyr Ala Arg His Ala Thr Leu His Asn Gly Lys Lys
            275                 280                 285

Ile Ser Ile Asn Asn Val Thr Glu Met Ala Pro Thr Ser Pro Ile Lys
        290                 295                 300

Thr Asn
305

<210> SEQ ID NO 163
<211> LENGTH: 306
<212> TYPE: PRT
<213> ORGANISM: Artificial Sequence
<220> FEATURE:
<223> OTHER INFORMATION: engineered

<400> SEQUENCE: 163

Met Ala Ile Leu Asp Leu Lys Ser Leu Val Leu Asn Ala Ile Asn Tyr
1               5                   10                  15

Trp Gly Pro Lys Asn Asn Asn Gly Ile Gln Gly Gly Asp Phe Gly Tyr
            20                  25                  30

Pro Ile Ser Glu Lys Gln Ile Asp Thr Ser Ile Ile Thr Ser Thr His
        35                  40                  45

Pro Arg Leu Ile Pro His Asp Leu Thr Ile Pro Gln Asn Leu Glu Thr
    50                  55                  60

Ile Phe Thr Thr Thr Gln Val Leu Thr Asn Asn Thr Asp Leu Gln Gln
65                  70                  75                  80

Ser Gln Thr Val Ser Phe Ala Lys Lys Thr Thr Thr Thr Thr Ala Thr
                85                  90                  95

Ser Thr Thr Asn Gly Trp Thr Glu Gly Gly Lys Ile Ser Asp Thr Leu
            100                 105                 110

Glu Glu Lys Val Ser Val Ser Ile Pro Phe Ile Gly Glu Gly Gly Gly
        115                 120                 125

Lys Asn Ser Thr Thr Ile Glu Ala Asn Phe Ala His Asn Ser Ser Thr
    130                 135                 140

Thr Thr Phe Gln Gln Ala Ser Thr Asp Ile Ala Trp Asn Ile Ser Gln
145                 150                 155                 160

Pro Val Leu Val Pro Pro Arg Lys Gln Val Val Ala Thr Leu Val Ile
                165                 170                 175

Met Gly Gly Asn Phe Thr Ile Pro Met Asp Leu Met Thr Thr Ile Asp
            180                 185                 190

Ser Thr Glu His Tyr Ser Gly Tyr Pro Ile Leu Thr Trp Ile Ser Ser
        195                 200                 205

Pro Asp Asn Ser Tyr Asn Gly Pro Phe Met Ser Trp Tyr Phe Ala Asn
    210                 215                 220

Trp Pro Asn Leu Pro Ser Gly Phe Gly Pro Leu Asn Ser Asp Asn Thr
225                 230                 235                 240

Val Thr Tyr Thr Gly Ser Val Val Ser Gln Val Ser Ala Gly Val Tyr
                245                 250                 255

Ala Thr Val Arg Phe Asp Gln Tyr Asp Ile His Asn Leu Arg Thr Ile
            260                 265                 270

Glu Lys Thr Trp Tyr Ala Arg His Ala Thr Leu His Asn Gly Lys Lys
        275                 280                 285

Ile Ser Ile Asn Asn Val Thr Glu Met Ala Pro Thr Ser Pro Ile Lys
    290                 295                 300

Thr Asn
```

<210> SEQ ID NO 164
<211> LENGTH: 306
<212> TYPE: PRT
<213> ORGANISM: Artificial Sequence
<220> FEATURE:
<223> OTHER INFORMATION: engineered

<400> SEQUENCE: 164

```
Met Ala Ile Leu Asp Leu Lys Ser Leu Val Leu Asn Ala Ile Asn Tyr
1               5                   10                  15

Trp Gly Pro Lys Asn Asn Asn Gly Ile Gln Gly Gly Asp Phe Gly Tyr
            20                  25                  30

Pro Ile Ser Glu Lys Gln Ile Asp Thr Ser Ile Ile Thr Ser Thr His
        35                  40                  45

Pro Arg Leu Ile Pro His Asp Leu Thr Ile Pro Gln Asn Leu Glu Thr
    50                  55                  60

Ile Phe Thr Thr Thr Gln Val Leu Thr Asn Asn Thr Asp Leu Gln Gln
65                  70                  75                  80

Ser Gln Thr Val Ser Phe Ala Lys Lys Thr Thr Thr Ala Thr Ser Thr
                85                  90                  95

Ser Thr Thr Asn Gly Trp Thr Glu Gly Gly Lys Ile Ser Asp Thr Leu
            100                 105                 110

Glu Glu Lys Val Ser Val Ser Ile Pro Phe Ile Gly Glu Gly Gly Gly
        115                 120                 125

Lys Asn Ser Thr Thr Ile Glu Ala Asn Phe Ala His Asn Ser Ser Thr
130                 135                 140

Thr Thr Phe Gln Gln Ala Ser Thr Asp Ile Glu Trp Asn Ile Ser Gln
145                 150                 155                 160

Pro Val Leu Val Pro Pro Arg Lys Gln Val Val Ala Thr Leu Val Ile
                165                 170                 175

Met Gly Gly Asn Phe Thr Ile Pro Met Asp Ala Met Thr Thr Ile Asp
            180                 185                 190

Ser Thr Glu His Tyr Ser Gly Tyr Pro Ile Leu Thr Trp Ile Ser Ser
        195                 200                 205

Pro Asp Asn Ser Tyr Asn Gly Pro Phe Met Ser Trp Tyr Phe Ala Asn
    210                 215                 220

Trp Pro Asn Leu Pro Ser Gly Phe Gly Pro Leu Asn Ser Asp Asn Thr
225                 230                 235                 240

Val Thr Tyr Thr Gly Ser Val Val Ser Gln Val Ser Ala Gly Val Tyr
                245                 250                 255

Ala Thr Val Arg Phe Asp Gln Tyr Asp Ile His Asn Leu Arg Thr Ile
            260                 265                 270

Glu Lys Thr Trp Tyr Ala Arg His Ala Thr Leu His Asn Gly Lys Lys
        275                 280                 285

Ile Ser Ile Asn Asn Val Thr Glu Met Ala Pro Thr Ser Pro Ile Lys
    290                 295                 300

Thr Asn
305
```

<210> SEQ ID NO 165
<211> LENGTH: 306
<212> TYPE: PRT
<213> ORGANISM: Artificial Sequence
<220> FEATURE:
<223> OTHER INFORMATION: engineered

<400> SEQUENCE: 165

```
Met Ala Ile Leu Asp Leu Lys Ser Leu Val Leu Asn Ala Ile Asn Tyr
1               5                   10                  15

Trp Gly Pro Lys Asn Asn Asn Gly Ile Gln Gly Gly Asp Phe Gly Tyr
            20                  25                  30

Pro Ile Ser Glu Lys Gln Ile Asp Thr Ser Ile Ile Thr Ser Thr His
        35                  40                  45

Pro Arg Leu Ile Pro His Asp Leu Thr Ile Pro Gln Asn Leu Glu Thr
    50                  55                  60

Ile Phe Thr Thr Thr Gln Val Leu Thr Asn Asn Thr Asp Leu Gln Gln
65                  70                  75                  80

Ser Gln Thr Val Ser Phe Ala Lys Lys Thr Thr Ala Thr Ser Thr
                85                  90                  95

Ser Thr Thr Asn Gly Trp Thr Glu Gly Gly Lys Ile Ser Asp Thr Leu
            100                 105                 110

Glu Glu Lys Val Ser Val Ser Ile Pro Phe Ile Gly Glu Gly Gly Gly
        115                 120                 125

Lys Asn Ser Thr Thr Ile Glu Ala Asn Phe Ala His Asn Ser Ser Thr
    130                 135                 140

Thr Thr Phe Gln Gln Ala Ser Thr Asp Ile Glu Trp Asn Ile Ser Gln
145                 150                 155                 160

Pro Val Leu Val Pro Pro Arg Lys Gln Val Val Ala Thr Leu Val Ile
                165                 170                 175

Met Gly Gly Asn Phe Thr Ile Pro Met Asp Leu Met Thr Thr Ile Asp
            180                 185                 190

Ser Thr Glu His Tyr Ser Gly Tyr Pro Ile Leu Thr Trp Ile Ser Ser
        195                 200                 205

Pro Asp Asn Ser Tyr Asn Gly Pro Phe Met Ser Trp Tyr Phe Ala Asn
    210                 215                 220

Trp Pro Asn Leu Pro Ser Gly Phe Gly Pro Leu Asn Ser Asp Asn Thr
225                 230                 235                 240

Val Thr Tyr Thr Gly Ser Val Val Ser Gln Val Ser Ala Gly Val Tyr
                245                 250                 255

Ala Thr Val Arg Phe Asp Gln Tyr Asp Ile His Asn Leu Arg Thr Ile
            260                 265                 270

Glu Lys Thr Trp Tyr Ala Arg His Ala Thr Leu His Asn Gly Lys Lys
        275                 280                 285

Ile Ser Ile Asn Asn Val Thr Glu Met Ala Pro Ala Ser Pro Ile Lys
    290                 295                 300

Thr Asn
305
```

<210> SEQ ID NO 166
<211> LENGTH: 306
<212> TYPE: PRT
<213> ORGANISM: Artificial Sequence
<220> FEATURE:
<223> OTHER INFORMATION: engineered

<400> SEQUENCE: 166

```
Met Ala Ile Leu Asp Leu Lys Ser Leu Val Leu Asn Ala Ile Asn Tyr
1               5                   10                  15

Trp Gly Pro Lys Asn Asn Asn Gly Ile Gln Gly Gly Asp Phe Gly Tyr
            20                  25                  30
```

Pro Ile Ser Glu Lys Gln Ile Asp Thr Ser Ile Ile Thr Ser Thr His
         35                  40                  45

Pro Arg Leu Ile Pro His Asp Leu Thr Ile Pro Gln Asn Leu Glu Thr
     50                  55                  60

Ile Phe Thr Thr Thr Gln Val Leu Thr Asn Asn Thr Asp Leu Gln Gln
 65                  70                  75                  80

Ser Gln Thr Val Ser Phe Ala Lys Lys Thr Thr Ala Thr Ser Thr
                 85                  90                  95

Ser Thr Thr Asn Gly Trp Thr Glu Gly Lys Ile Ser Asp Thr Leu
             100                 105                 110

Glu Glu Lys Val Ser Val Ser Ile Pro Phe Ile Gly Glu Gly Gly
         115                 120                 125

Lys Asn Ser Thr Thr Ile Glu Ala Asn Phe Ala His Asn Ser Ser Thr
130                 135                 140

Thr Thr Phe Gln Gln Ala Ser Thr Asp Ile Ala Trp Asn Ile Ser Gln
145                 150                 155                 160

Pro Val Leu Val Pro Pro Arg Lys Gln Val Val Ala Thr Leu Val Ile
                 165                 170                 175

Met Gly Gly Asn Phe Thr Ile Pro Met Asp Leu Met Thr Thr Ile Asp
             180                 185                 190

Ser Thr Glu His Tyr Ser Gly Tyr Pro Ile Leu Thr Trp Ile Ser Ser
         195                 200                 205

Pro Asp Asn Ser Tyr Asn Gly Pro Phe Met Ser Trp Tyr Phe Ala Asn
    210                 215                 220

Trp Pro Asn Leu Pro Ser Gly Phe Gly Pro Leu Asn Ser Asp Asn Thr
225                 230                 235                 240

Val Thr Tyr Thr Gly Ser Val Val Ser Gln Val Ser Ala Gly Val Tyr
                 245                 250                 255

Ala Thr Val Arg Phe Asp Gln Tyr Asp Ile His Asn Leu Arg Thr Ile
             260                 265                 270

Glu Lys Thr Trp Tyr Ala Arg His Ala Thr Leu His Asn Gly Lys Lys
         275                 280                 285

Ile Ser Ile Asn Asn Val Thr Glu Met Ala Pro Thr Ser Pro Ile Lys
    290                 295                 300

Thr Asn
305

<210> SEQ ID NO 167
<211> LENGTH: 306
<212> TYPE: PRT
<213> ORGANISM: Artificial Sequence
<220> FEATURE:
<223> OTHER INFORMATION: engineered

<400> SEQUENCE: 167

Met Ala Ile Leu Asp Leu Lys Ser Leu Val Leu Asn Ala Ile Asn Tyr
 1               5                  10                  15

Trp Gly Pro Lys Asn Asn Gly Ile Gln Gly Gly Asp Phe Gly Tyr
             20                  25                  30

Pro Ile Ser Glu Lys Gln Ile Asp Thr Ser Ile Ile Thr Ser Thr His
         35                  40                  45

Pro Arg Leu Ile Pro His Asp Leu Thr Ile Pro Gln Asn Leu Glu Thr
     50                  55                  60

Ile Phe Thr Thr Thr Gln Val Leu Thr Asn Asn Thr Asp Leu Gln Gln
 65                  70                  75                  80

```
Ser Gln Thr Val Ser Phe Ala Lys Lys Thr Thr Ala Thr Ser Thr
                85                  90                  95

Ser Thr Thr Asn Gly Trp Thr Glu Gly Gly Lys Ile Ser Asp Thr Leu
            100                 105                 110

Glu Glu Lys Val Ser Val Ser Ile Pro Phe Ile Gly Glu Gly Gly Gly
            115                 120                 125

Lys Asn Ser Thr Thr Ile Glu Ala Asn Phe Ala His Asn Ser Ser Thr
            130                 135                 140

Thr Thr Phe Gln Gln Ala Ser Thr Ala Ile Glu Trp Asn Ile Ser Gln
145                 150                 155                 160

Pro Val Leu Val Pro Arg Lys Gln Val Val Ala Thr Leu Val Ile
                165                 170                 175

Met Gly Gly Asn Phe Thr Ile Pro Met Asp Leu Met Thr Thr Ile Asp
                180                 185                 190

Ser Thr Glu His Tyr Ser Gly Tyr Pro Ile Leu Thr Trp Ile Ser Ser
            195                 200                 205

Pro Asp Asn Ser Tyr Asn Gly Pro Phe Met Ser Trp Tyr Phe Ala Asn
            210                 215                 220

Trp Pro Asn Leu Pro Ser Gly Phe Gly Pro Leu Asn Ser Asp Asn Thr
225                 230                 235                 240

Val Thr Tyr Thr Gly Ser Val Val Ser Gln Val Ser Ala Gly Val Tyr
                245                 250                 255

Ala Thr Val Arg Phe Asp Gln Tyr Asp Ile His Asn Leu Arg Thr Ile
                260                 265                 270

Glu Lys Thr Trp Tyr Ala Arg His Ala Thr Leu His Asn Gly Lys Lys
            275                 280                 285

Ile Ser Ile Asn Asn Val Thr Glu Met Ala Pro Thr Ser Pro Ile Lys
290                 295                 300

Thr Asn
305

<210> SEQ ID NO 168
<211> LENGTH: 306
<212> TYPE: PRT
<213> ORGANISM: Artificial Sequence
<220> FEATURE:
<223> OTHER INFORMATION: engineered

<400> SEQUENCE: 168

Met Ala Ile Leu Asp Leu Lys Ser Leu Val Leu Asn Ala Ile Asn Tyr
1               5                   10                  15

Trp Gly Pro Lys Asn Asn Asn Gly Ile Gln Gly Gly Asp Phe Gly Tyr
            20                  25                  30

Pro Ile Ser Glu Lys Gln Ile Asp Thr Ser Ile Thr Ser Thr His
            35                  40                  45

Pro Arg Leu Ile Pro His Asp Leu Thr Ile Pro Gln Asn Leu Glu Thr
50                  55                  60

Ile Phe Thr Thr Thr Gln Val Leu Thr Asn Asn Thr Asp Leu Gln Gln
65                  70                  75                  80

Ser Gln Thr Val Ser Phe Ala Lys Lys Thr Thr Ala Thr Ser Thr
                85                  90                  95

Ser Thr Thr Asn Gly Trp Thr Glu Gly Gly Lys Ile Ser Asp Thr Leu
            100                 105                 110

Glu Glu Lys Val Ser Val Ser Ile Pro Phe Ile Gly Glu Gly Gly Gly
            115                 120                 125
```

```
Lys Asn Ser Thr Thr Ala Glu Ala Asn Phe Ala His Asn Ser Ser Thr
130                 135                 140

Thr Thr Phe Gln Gln Ala Ser Thr Asp Ile Glu Trp Asn Ile Ser Gln
145                 150                 155                 160

Pro Val Leu Val Pro Pro Arg Lys Gln Val Val Ala Thr Leu Val Ile
                165                 170                 175

Met Gly Gly Asn Phe Thr Ile Pro Met Asp Leu Met Thr Thr Ile Asp
                180                 185                 190

Ser Thr Glu His Tyr Ser Gly Tyr Pro Ile Leu Thr Trp Ile Ser Ser
            195                 200                 205

Pro Asp Asn Ser Tyr Asn Gly Pro Phe Met Ser Trp Tyr Phe Ala Asn
210                 215                 220

Trp Pro Asn Leu Pro Ser Gly Phe Gly Pro Leu Asn Ser Asp Asn Thr
225                 230                 235                 240

Val Thr Tyr Thr Gly Ser Val Val Ser Gln Val Ser Ala Gly Val Tyr
                245                 250                 255

Ala Thr Val Arg Phe Asp Gln Tyr Asp Ile His Asn Leu Arg Thr Ile
                260                 265                 270

Glu Lys Thr Trp Tyr Ala Arg His Ala Thr Leu His Asn Gly Lys Lys
            275                 280                 285

Ile Ser Ile Asn Asn Val Thr Glu Met Ala Pro Thr Ser Pro Ile Lys
290                 295                 300

Thr Asn
305

<210> SEQ ID NO 169
<211> LENGTH: 306
<212> TYPE: PRT
<213> ORGANISM: Artificial Sequence
<220> FEATURE:
<223> OTHER INFORMATION: engineered
<220> FEATURE:
<221> NAME/KEY: VARIANT
<222> LOCATION: (133)..(133)
<223> OTHER INFORMATION: is not T
<220> FEATURE:
<221> NAME/KEY: VARIANT
<222> LOCATION: (135)..(135)
<223> OTHER INFORMATION: is not E
<220> FEATURE:
<221> NAME/KEY: VARIANT
<222> LOCATION: (137)..(137)
<223> OTHER INFORMATION: is not N

<400> SEQUENCE: 169

Met Ala Ile Leu Asp Leu Lys Ser Leu Val Leu Asn Ala Ile Asn Tyr
1               5                   10                  15

Trp Gly Pro Lys Asn Asn Asn Gly Ile Gln Gly Gly Asp Phe Gly Tyr
                20                  25                  30

Pro Ile Ser Glu Lys Gln Ile Asp Thr Ser Ile Ile Thr Ser Thr His
            35                  40                  45

Pro Arg Leu Ile Pro His Asp Leu Thr Ile Pro Gln Asn Leu Glu Thr
50                  55                  60

Ile Phe Thr Thr Thr Gln Val Leu Thr Asn Asn Thr Asp Leu Gln Gln
65                  70                  75                  80

Ser Gln Thr Val Ser Phe Ala Lys Lys Thr Thr Ala Thr Ser Thr
                85                  90                  95

Ser Thr Thr Asn Gly Trp Thr Glu Gly Gly Lys Ile Ser Asp Thr Leu
                100                 105                 110
```

```
Glu Glu Lys Val Ser Val Ser Ile Pro Phe Ile Gly Glu Gly Gly
            115                 120                 125

Lys Asn Ser Thr Xaa Ile Xaa Ala Xaa Phe Ala His Asn Ser Ser Thr
130                 135                 140

Thr Thr Phe Gln Gln Ala Ser Thr Asp Ile Glu Trp Asn Ile Ser Gln
145                 150                 155                 160

Pro Val Leu Val Pro Pro Arg Lys Gln Val Val Ala Thr Leu Val Ile
                165                 170                 175

Met Gly Gly Asn Phe Thr Ile Pro Met Asp Leu Met Thr Ile Asp
            180                 185                 190

Ser Thr Glu His Tyr Ser Gly Tyr Pro Ile Leu Thr Trp Ile Ser Ser
            195                 200                 205

Pro Asp Asn Ser Tyr Asn Gly Pro Phe Met Ser Trp Tyr Phe Ala Asn
            210                 215                 220

Trp Pro Asn Leu Pro Ser Gly Phe Gly Pro Leu Asn Ser Asp Asn Thr
225                 230                 235                 240

Val Thr Tyr Thr Gly Ser Val Val Ser Gln Val Ser Ala Gly Val Tyr
                245                 250                 255

Ala Thr Val Arg Phe Asp Gln Tyr Asp Ile His Asn Leu Arg Thr Ile
            260                 265                 270

Glu Lys Thr Trp Tyr Ala Arg His Ala Thr Leu His Asn Gly Lys Lys
            275                 280                 285

Ile Ser Ile Asn Asn Val Thr Glu Met Ala Pro Thr Ser Pro Ile Lys
            290                 295                 300

Thr Asn
305

<210> SEQ ID NO 170
<211> LENGTH: 309
<212> TYPE: PRT
<213> ORGANISM: Artificial Sequence
<220> FEATURE:
<223> OTHER INFORMATION: engineered
<220> FEATURE:
<221> NAME/KEY: VARIANT
<222> LOCATION: (125)..(125)
<223> OTHER INFORMATION: is not E

<400> SEQUENCE: 170

Met Ala Ile Leu Asp Leu Lys Ser Leu Val Leu Asn Ala Ile Asn Tyr
1               5                   10                  15

Trp Gly Pro Lys Asn Asn Gly Ile Gln Gly Gly Asp Phe Gly Tyr
            20                  25                  30

Pro Ile Ser Glu Lys Gln Ile Asp Thr Ser Ile Ile Thr Phe Thr His
            35                  40                  45

Pro Arg Leu Ile Pro Tyr Asp Leu Thr Ile Pro Gln Asn Leu Glu Thr
        50                  55                  60

Ile Phe Thr Thr Thr Gln Val Leu Thr Asn Asn Thr Asp Leu Gln Gln
65                  70                  75                  80

Ser Gln Thr Val Ser Phe Ala Lys Lys Thr Thr Thr Thr Ser Thr
                85                  90                  95

Ser Thr Thr Asn Gly Trp Thr Glu Gly Gly Lys Ile Ser Asp Thr Leu
            100                 105                 110

Glu Glu Lys Val Ser Val Ser Ile Pro Phe Ile Gly Xaa Gly Gly Gly
            115                 120                 125

Lys Asn Ser Thr Thr Ile Glu Ala Asn Phe Ala His Asn Ser Ser Thr
130                 135                 140
```

Thr Thr Phe Gln Gln Ala Ser Thr Asp Ile Glu Trp Asn Ile Ser Gln
145                 150                 155                 160

Pro Val Leu Val Pro Pro Ser Lys Gln Val Val Ala Thr Leu Val Ile
                165                 170                 175

Met Gly Gly Asn Phe Thr Ile Pro Met Asp Leu Met Thr Thr Ile Asp
            180                 185                 190

Ser Thr Glu His Tyr Ser His Tyr Ser Gly Tyr Pro Ile Leu Thr Trp
        195                 200                 205

Ile Ser Ser Pro Asp Asn Ser Tyr Ser Gly Pro Phe Met Ser Trp Tyr
    210                 215                 220

Phe Ala Asn Trp Pro Asn Leu Pro Ser Gly Phe Gly Pro Leu Asn Ser
225                 230                 235                 240

Asp Asn Thr Val Thr Tyr Thr Gly Ser Val Ser Gln Val Ser Ala
                245                 250                 255

Gly Val Tyr Ala Thr Val Arg Phe Asp Gln Tyr Asp Ile His Asn Leu
            260                 265                 270

Arg Thr Ile Glu Lys Thr Trp Tyr Ala Arg His Ala Thr Leu His Asn
        275                 280                 285

Gly Lys Lys Ile Ser Ile Asn Asn Val Thr Glu Met Ala Pro Thr Ser
    290                 295                 300

Pro Ile Lys Thr Asn
305

<210> SEQ ID NO 171
<211> LENGTH: 309
<212> TYPE: PRT
<213> ORGANISM: Artificial Sequence
<220> FEATURE:
<223> OTHER INFORMATION: engineered
<220> FEATURE:
<221> NAME/KEY: VARIANT
<222> LOCATION: (133)..(133)
<223> OTHER INFORMATION: is not T

<400> SEQUENCE: 171

Met Ala Ile Leu Asp Leu Lys Ser Leu Val Leu Asn Ala Ile Asn Tyr
1               5                   10                  15

Trp Gly Pro Lys Asn Asn Gly Ile Gln Gly Gly Asp Phe Gly Tyr
            20                  25                  30

Pro Ile Ser Glu Lys Gln Ile Asp Thr Ser Ile Ile Thr Phe Thr His
                35                  40                  45

Pro Arg Leu Ile Pro Tyr Asp Leu Thr Ile Pro Gln Asn Leu Glu Thr
        50                  55                  60

Ile Phe Thr Thr Thr Gln Val Leu Thr Asn Asn Thr Asp Leu Gln Gln
65                  70                  75                  80

Ser Gln Thr Val Ser Phe Ala Lys Lys Thr Thr Thr Thr Ser Thr
                85                  90                  95

Ser Thr Thr Asn Gly Trp Thr Glu Gly Gly Lys Ile Ser Asp Thr Leu
            100                 105                 110

Glu Glu Lys Val Ser Val Ser Ile Pro Phe Ile Gly Glu Gly Gly Gly
        115                 120                 125

Lys Asn Ser Thr Xaa Ile Glu Ala Asn Phe Ala His Asn Ser Ser Thr
    130                 135                 140

Thr Thr Phe Gln Gln Ala Ser Thr Asp Ile Glu Trp Asn Ile Ser Gln
145                 150                 155                 160

Pro Val Leu Val Pro Pro Ser Lys Gln Val Val Ala Thr Leu Val Ile

```
                        165                 170                 175
Met Gly Gly Asn Phe Thr Ile Pro Met Asp Leu Met Thr Thr Ile Asp
                180                 185                 190

Ser Thr Glu His Tyr Ser His Tyr Ser Gly Tyr Pro Ile Leu Thr Trp
            195                 200                 205

Ile Ser Ser Pro Asp Asn Ser Tyr Ser Gly Pro Phe Met Ser Trp Tyr
        210                 215                 220

Phe Ala Asn Trp Pro Asn Leu Pro Ser Gly Phe Gly Pro Leu Asn Ser
225                 230                 235                 240

Asp Asn Thr Val Thr Tyr Thr Gly Ser Val Val Ser Gln Val Ser Ala
                245                 250                 255

Gly Val Tyr Ala Thr Val Arg Phe Asp Gln Tyr Asp Ile His Asn Leu
            260                 265                 270

Arg Thr Ile Glu Lys Thr Trp Tyr Ala Arg His Ala Thr Leu His Asn
        275                 280                 285

Gly Lys Lys Ile Ser Ile Asn Asn Val Thr Glu Met Ala Pro Thr Ser
290                 295                 300

Pro Ile Lys Thr Asn
305

<210> SEQ ID NO 172
<211> LENGTH: 309
<212> TYPE: PRT
<213> ORGANISM: Artificial Sequence
<220> FEATURE:
<223> OTHER INFORMATION: engineered
<220> FEATURE:
<221> NAME/KEY: VARIANT
<222> LOCATION: (134)..(134)
<223> OTHER INFORMATION: is not I

<400> SEQUENCE: 172

Met Ala Ile Leu Asp Leu Lys Ser Leu Val Leu Asn Ala Ile Asn Tyr
1               5                   10                  15

Trp Gly Pro Lys Asn Asn Gly Ile Gln Gly Gly Asp Phe Gly Tyr
            20                  25                  30

Pro Ile Ser Glu Lys Gln Ile Asp Thr Ser Ile Ile Thr Phe Thr His
        35                  40                  45

Pro Arg Leu Ile Pro Tyr Asp Leu Thr Ile Pro Gln Asn Leu Glu Thr
    50                  55                  60

Ile Phe Thr Thr Thr Gln Val Leu Thr Asn Asn Thr Asp Leu Gln Gln
65                  70                  75                  80

Ser Gln Thr Val Ser Phe Ala Lys Lys Thr Thr Thr Thr Ser Thr
                85                  90                  95

Ser Thr Thr Asn Gly Trp Thr Glu Gly Gly Lys Ile Ser Asp Thr Leu
            100                 105                 110

Glu Glu Lys Val Ser Val Ser Ile Pro Phe Ile Gly Glu Gly Gly Gly
        115                 120                 125

Lys Asn Ser Thr Thr Xaa Glu Ala Asn Phe Ala His Asn Ser Ser Thr
    130                 135                 140

Thr Thr Phe Gln Gln Ala Ser Thr Asp Ile Glu Trp Asn Ile Ser Gln
145                 150                 155                 160

Pro Val Leu Val Pro Pro Ser Lys Gln Val Val Ala Thr Leu Val Ile
                165                 170                 175

Met Gly Gly Asn Phe Thr Ile Pro Met Asp Leu Met Thr Thr Ile Asp
            180                 185                 190
```

```
Ser Thr Glu His Tyr Ser His Tyr Ser Gly Tyr Pro Ile Leu Thr Trp
            195                 200                 205

Ile Ser Ser Pro Asp Asn Ser Tyr Ser Gly Pro Phe Met Ser Trp Tyr
        210                 215                 220

Phe Ala Asn Trp Pro Asn Leu Pro Ser Gly Phe Gly Pro Leu Asn Ser
225                 230                 235                 240

Asp Asn Thr Val Thr Tyr Thr Gly Ser Val Ser Gln Val Ser Ala
                245                 250                 255

Gly Val Tyr Ala Thr Val Arg Phe Asp Gln Tyr Asp Ile His Asn Leu
                260                 265                 270

Arg Thr Ile Glu Lys Thr Trp Tyr Ala Arg His Ala Thr Leu His Asn
            275                 280                 285

Gly Lys Lys Ile Ser Ile Asn Asn Val Thr Glu Met Ala Pro Thr Ser
        290                 295                 300

Pro Ile Lys Thr Asn
305

<210> SEQ ID NO 173
<211> LENGTH: 309
<212> TYPE: PRT
<213> ORGANISM: Artificial Sequence
<220> FEATURE:
<223> OTHER INFORMATION: engineered
<220> FEATURE:
<221> NAME/KEY: VARIANT
<222> LOCATION: (135)..(135)
<223> OTHER INFORMATION: is not E

<400> SEQUENCE: 173

Met Ala Ile Leu Asp Leu Lys Ser Leu Val Leu Asn Ala Ile Asn Tyr
1               5                   10                  15

Trp Gly Pro Lys Asn Asn Asn Gly Ile Gln Gly Gly Asp Phe Gly Tyr
            20                  25                  30

Pro Ile Ser Glu Lys Gln Ile Asp Thr Ser Ile Ile Thr Phe Thr His
        35                  40                  45

Pro Arg Leu Ile Pro Tyr Asp Leu Thr Ile Pro Gln Asn Leu Glu Thr
    50                  55                  60

Ile Phe Thr Thr Thr Gln Val Leu Thr Asn Asn Thr Asp Leu Gln Gln
65                  70                  75                  80

Ser Gln Thr Val Ser Phe Ala Lys Lys Thr Thr Thr Thr Thr Ser Thr
                85                  90                  95

Ser Thr Thr Asn Gly Trp Thr Glu Gly Gly Lys Ile Ser Asp Thr Leu
            100                 105                 110

Glu Glu Lys Val Ser Val Ser Ile Pro Phe Ile Gly Glu Gly Gly Gly
        115                 120                 125

Lys Asn Ser Thr Thr Ile Xaa Ala Asn Phe Ala His Asn Ser Ser Thr
    130                 135                 140

Thr Thr Phe Gln Gln Ala Ser Thr Asp Ile Glu Trp Asn Ile Ser Gln
145                 150                 155                 160

Pro Val Leu Val Pro Pro Ser Lys Gln Val Val Ala Thr Leu Val Ile
                165                 170                 175

Met Gly Gly Asn Phe Thr Ile Pro Met Asp Leu Met Thr Thr Ile Asp
            180                 185                 190

Ser Thr Glu His Tyr Ser His Tyr Ser Gly Tyr Pro Ile Leu Thr Trp
        195                 200                 205

Ile Ser Ser Pro Asp Asn Ser Tyr Ser Gly Pro Phe Met Ser Trp Tyr
    210                 215                 220
```

```
Phe Ala Asn Trp Pro Asn Leu Pro Ser Gly Phe Gly Pro Leu Asn Ser
225                 230                 235                 240

Asp Asn Thr Val Thr Tyr Thr Gly Ser Val Val Ser Gln Val Ser Ala
                245                 250                 255

Gly Val Tyr Ala Thr Val Arg Phe Asp Gln Tyr Asp Ile His Asn Leu
            260                 265                 270

Arg Thr Ile Glu Lys Thr Trp Tyr Ala Arg His Ala Thr Leu His Asn
        275                 280                 285

Gly Lys Lys Ile Ser Ile Asn Asn Val Thr Glu Met Ala Pro Thr Ser
    290                 295                 300

Pro Ile Lys Thr Asn
305

<210> SEQ ID NO 174
<211> LENGTH: 309
<212> TYPE: PRT
<213> ORGANISM: Artificial Sequence
<220> FEATURE:
<223> OTHER INFORMATION: engineered
<220> FEATURE:
<221> NAME/KEY: VARIANT
<222> LOCATION: (137)..(137)
<223> OTHER INFORMATION: is not N

<400> SEQUENCE: 174

Met Ala Ile Leu Asp Leu Lys Ser Leu Val Leu Asn Ala Ile Asn Tyr
1               5                   10                  15

Trp Gly Pro Lys Asn Asn Asn Gly Ile Gln Gly Gly Asp Phe Gly Tyr
            20                  25                  30

Pro Ile Ser Glu Lys Gln Ile Asp Thr Ser Ile Ile Thr Phe Thr His
        35                  40                  45

Pro Arg Leu Ile Pro Tyr Asp Leu Thr Ile Pro Gln Asn Leu Glu Thr
    50                  55                  60

Ile Phe Thr Thr Thr Gln Val Leu Thr Asn Asn Thr Asp Leu Gln Gln
65                  70                  75                  80

Ser Gln Thr Val Ser Phe Ala Lys Lys Thr Thr Thr Thr Ser Thr
                85                  90                  95

Ser Thr Thr Asn Gly Trp Thr Glu Gly Gly Lys Ile Ser Asp Thr Leu
            100                 105                 110

Glu Glu Lys Val Ser Val Ser Ile Pro Phe Ile Gly Glu Gly Gly Gly
        115                 120                 125

Lys Asn Ser Thr Thr Ile Glu Ala Xaa Phe Ala His Asn Ser Ser Thr
    130                 135                 140

Thr Thr Phe Gln Gln Ala Ser Thr Asp Ile Glu Trp Asn Ile Ser Gln
145                 150                 155                 160

Pro Val Leu Val Pro Pro Ser Lys Gln Val Val Ala Thr Leu Val Ile
                165                 170                 175

Met Gly Gly Asn Phe Thr Ile Pro Met Asp Leu Met Thr Thr Ile Asp
            180                 185                 190

Ser Thr Glu His Tyr Ser His Tyr Ser Gly Tyr Pro Ile Leu Thr Trp
        195                 200                 205

Ile Ser Ser Pro Asp Asn Ser Tyr Ser Gly Pro Phe Met Ser Trp Tyr
    210                 215                 220

Phe Ala Asn Trp Pro Asn Leu Pro Ser Gly Phe Gly Pro Leu Asn Ser
225                 230                 235                 240

Asp Asn Thr Val Thr Tyr Thr Gly Ser Val Val Ser Gln Val Ser Ala
```

```
                        245                 250                 255
Gly Val Tyr Ala Thr Val Arg Phe Asp Gln Tyr Asp Ile His Asn Leu
            260                 265                 270

Arg Thr Ile Glu Lys Thr Trp Tyr Ala Arg His Ala Thr Leu His Asn
            275                 280                 285

Gly Lys Lys Ile Ser Ile Asn Val Thr Glu Met Ala Pro Thr Ser
            290                 295                 300

Pro Ile Lys Thr Asn
305

<210> SEQ ID NO 175
<211> LENGTH: 309
<212> TYPE: PRT
<213> ORGANISM: Artificial Sequence
<220> FEATURE:
<223> OTHER INFORMATION: engineered
<220> FEATURE:
<221> NAME/KEY: VARIANT
<222> LOCATION: (147)..(147)
<223> OTHER INFORMATION: is not F

<400> SEQUENCE: 175

Met Ala Ile Leu Asp Leu Lys Ser Leu Val Leu Asn Ala Ile Asn Tyr
1               5                   10                  15

Trp Gly Pro Lys Asn Asn Gly Ile Gln Gly Gly Asp Phe Gly Tyr
            20                  25                  30

Pro Ile Ser Glu Lys Gln Ile Asp Thr Ser Ile Ile Thr Phe Thr His
            35                  40                  45

Pro Arg Leu Ile Pro Tyr Asp Leu Thr Ile Pro Gln Asn Leu Glu Thr
50                  55                  60

Ile Phe Thr Thr Thr Gln Val Leu Thr Asn Asn Thr Asp Leu Gln Gln
65                  70                  75                  80

Ser Gln Thr Val Ser Phe Ala Lys Lys Thr Thr Thr Thr Ser Thr
            85                  90                  95

Ser Thr Thr Asn Gly Trp Thr Glu Gly Lys Ile Ser Asp Thr Leu
            100                 105                 110

Glu Glu Lys Val Ser Val Ser Ile Pro Phe Ile Gly Glu Gly Gly Gly
            115                 120                 125

Lys Asn Ser Thr Thr Ile Glu Ala Asn Phe Ala His Asn Ser Ser Thr
130                 135                 140

Thr Thr Xaa Gln Gln Ala Ser Thr Asp Ile Glu Trp Asn Ile Ser Gln
145                 150                 155                 160

Pro Val Leu Val Pro Pro Ser Lys Gln Val Val Ala Thr Leu Val Ile
            165                 170                 175

Met Gly Gly Asn Phe Thr Ile Pro Met Asp Leu Met Thr Thr Ile Asp
            180                 185                 190

Ser Thr Glu His Tyr Ser His Tyr Ser Gly Tyr Pro Ile Leu Thr Trp
            195                 200                 205

Ile Ser Ser Pro Asp Asn Ser Tyr Ser Gly Pro Phe Met Ser Trp Tyr
            210                 215                 220

Phe Ala Asn Trp Pro Asn Leu Pro Ser Gly Phe Gly Pro Leu Asn Ser
225                 230                 235                 240

Asp Asn Thr Val Thr Tyr Thr Gly Ser Val Val Ser Gln Val Ser Ala
            245                 250                 255

Gly Val Tyr Ala Thr Val Arg Phe Asp Gln Tyr Asp Ile His Asn Leu
            260                 265                 270
```

Arg Thr Ile Glu Lys Thr Trp Tyr Ala Arg His Ala Thr Leu His Asn
            275                 280                 285

Gly Lys Lys Ile Ser Ile Asn Asn Val Thr Glu Met Ala Pro Thr Ser
    290                 295                 300

Pro Ile Lys Thr Asn
305

<210> SEQ ID NO 176
<211> LENGTH: 309
<212> TYPE: PRT
<213> ORGANISM: Artificial Sequence
<220> FEATURE:
<223> OTHER INFORMATION: engineered
<220> FEATURE:
<221> NAME/KEY: VARIANT
<222> LOCATION: (149)..(149)
<223> OTHER INFORMATION: is not Q

<400> SEQUENCE: 176

Met Ala Ile Leu Asp Leu Lys Ser Leu Val Leu Asn Ala Ile Asn Tyr
1               5                   10                  15

Trp Gly Pro Lys Asn Asn Gly Ile Gln Gly Gly Asp Phe Gly Tyr
            20                  25                  30

Pro Ile Ser Glu Lys Gln Ile Asp Thr Ser Ile Ile Thr Phe Thr His
        35                  40                  45

Pro Arg Leu Ile Pro Tyr Asp Leu Thr Ile Pro Gln Asn Leu Glu Thr
    50                  55                  60

Ile Phe Thr Thr Thr Gln Val Leu Thr Asn Asn Thr Asp Leu Gln Gln
65                  70                  75                  80

Ser Gln Thr Val Ser Phe Ala Lys Lys Thr Thr Thr Thr Ser Thr
                85                  90                  95

Ser Thr Thr Asn Gly Trp Thr Glu Gly Gly Lys Ile Ser Asp Thr Leu
            100                 105                 110

Glu Glu Lys Val Ser Val Ser Ile Pro Phe Ile Gly Glu Gly Gly Gly
        115                 120                 125

Lys Asn Ser Thr Thr Ile Glu Ala Asn Phe Ala His Asn Ser Ser Thr
130                 135                 140

Thr Thr Phe Gln Xaa Ala Ser Thr Asp Ile Glu Trp Asn Ile Ser Gln
145                 150                 155                 160

Pro Val Leu Val Pro Ser Lys Gln Val Val Ala Thr Leu Val Ile
                165                 170                 175

Met Gly Gly Asn Phe Thr Ile Pro Met Asp Leu Met Thr Thr Ile Asp
            180                 185                 190

Ser Thr Glu His Tyr Ser His Tyr Ser Gly Tyr Pro Ile Leu Thr Trp
        195                 200                 205

Ile Ser Ser Pro Asp Asn Ser Tyr Ser Gly Pro Phe Met Ser Trp Tyr
210                 215                 220

Phe Ala Asn Trp Pro Asn Leu Pro Ser Gly Phe Gly Pro Leu Asn Ser
225                 230                 235                 240

Asp Asn Thr Val Thr Tyr Thr Gly Ser Val Val Ser Gln Val Ser Ala
                245                 250                 255

Gly Val Tyr Ala Thr Val Arg Phe Asp Gln Tyr Asp Ile His Asn Leu
            260                 265                 270

Arg Thr Ile Glu Lys Thr Trp Tyr Ala Arg His Ala Thr Leu His Asn
        275                 280                 285

Gly Lys Lys Ile Ser Ile Asn Asn Val Thr Glu Met Ala Pro Thr Ser
    290                 295                 300

```
Pro Ile Lys Thr Asn
305

<210> SEQ ID NO 177
<211> LENGTH: 309
<212> TYPE: PRT
<213> ORGANISM: Artificial Sequence
<220> FEATURE:
<223> OTHER INFORMATION: engineered
<220> FEATURE:
<221> NAME/KEY: VARIANT
<222> LOCATION: (150)..(150)
<223> OTHER INFORMATION: is not A

<400> SEQUENCE: 177

Met Ala Ile Leu Asp Leu Lys Ser Leu Val Leu Asn Ala Ile Asn Tyr
1               5                   10                  15

Trp Gly Pro Lys Asn Asn Gly Ile Gln Gly Gly Asp Phe Gly Tyr
            20                  25                  30

Pro Ile Ser Glu Lys Gln Ile Asp Thr Ser Ile Ile Thr Phe Thr His
        35                  40                  45

Pro Arg Leu Ile Pro Tyr Asp Leu Thr Ile Pro Gln Asn Leu Glu Thr
50                  55                  60

Ile Phe Thr Thr Thr Gln Val Leu Thr Asn Asn Thr Asp Leu Gln Gln
65                  70                  75                  80

Ser Gln Thr Val Ser Phe Ala Lys Lys Thr Thr Thr Thr Ser Thr
                85                  90                  95

Ser Thr Thr Asn Gly Trp Thr Glu Gly Gly Lys Ile Ser Asp Thr Leu
            100                 105                 110

Glu Glu Lys Val Ser Val Ser Ile Pro Phe Ile Gly Glu Gly Gly Gly
        115                 120                 125

Lys Asn Ser Thr Thr Ile Glu Ala Asn Phe Ala His Asn Ser Ser Thr
130                 135                 140

Thr Thr Phe Gln Gln Xaa Ser Thr Asp Ile Glu Trp Asn Ile Ser Gln
145                 150                 155                 160

Pro Val Leu Val Pro Pro Ser Lys Gln Val Val Ala Thr Leu Val Ile
                165                 170                 175

Met Gly Gly Asn Phe Thr Ile Pro Met Asp Leu Met Thr Thr Ile Asp
            180                 185                 190

Ser Thr Glu His Tyr Ser His Tyr Ser Gly Tyr Pro Ile Leu Thr Trp
        195                 200                 205

Ile Ser Ser Pro Asp Asn Ser Tyr Ser Gly Pro Phe Met Ser Trp Tyr
210                 215                 220

Phe Ala Asn Trp Pro Asn Leu Pro Ser Gly Phe Gly Pro Leu Asn Ser
225                 230                 235                 240

Asp Asn Thr Val Thr Tyr Thr Gly Ser Val Val Ser Gln Val Ser Ala
                245                 250                 255

Gly Val Tyr Ala Thr Val Arg Phe Asp Gln Tyr Asp Ile His Asn Leu
            260                 265                 270

Arg Thr Ile Glu Lys Thr Trp Tyr Ala Arg His Ala Thr Leu His Asn
        275                 280                 285

Gly Lys Lys Ile Ser Ile Asn Asn Val Thr Glu Met Ala Pro Thr Ser
    290                 295                 300

Pro Ile Lys Thr Asn
305
```

<210> SEQ ID NO 178
<211> LENGTH: 309
<212> TYPE: PRT
<213> ORGANISM: Artificial Sequence
<220> FEATURE:
<223> OTHER INFORMATION: engineered
<220> FEATURE:
<221> NAME/KEY: VARIANT
<222> LOCATION: (155)..(155)
<223> OTHER INFORMATION: is not E

<400> SEQUENCE: 178

```
Met Ala Ile Leu Asp Leu Lys Ser Leu Val Leu Asn Ala Ile Asn Tyr
1               5                   10                  15

Trp Gly Pro Lys Asn Asn Asn Gly Ile Gln Gly Gly Asp Phe Gly Tyr
            20                  25                  30

Pro Ile Ser Glu Lys Gln Ile Asp Thr Ser Ile Ile Thr Phe Thr His
        35                  40                  45

Pro Arg Leu Ile Pro Tyr Asp Leu Thr Ile Pro Gln Asn Leu Glu Thr
    50                  55                  60

Ile Phe Thr Thr Thr Gln Val Leu Thr Asn Asn Thr Asp Leu Gln Gln
65                  70                  75                  80

Ser Gln Thr Val Ser Phe Ala Lys Lys Thr Thr Thr Thr Thr Ser Thr
                85                  90                  95

Ser Thr Thr Asn Gly Trp Thr Glu Gly Gly Lys Ile Ser Asp Thr Leu
            100                 105                 110

Glu Glu Lys Val Ser Val Ser Ile Pro Phe Ile Gly Glu Gly Gly Gly
        115                 120                 125

Lys Asn Ser Thr Thr Ile Glu Ala Asn Phe Ala His Asn Ser Ser Thr
130                 135                 140

Thr Thr Phe Gln Gln Ala Ser Thr Asp Ile Xaa Trp Asn Ile Ser Gln
145                 150                 155                 160

Pro Val Leu Val Pro Pro Ser Lys Gln Val Val Ala Thr Leu Val Ile
                165                 170                 175

Met Gly Gly Asn Phe Thr Ile Pro Met Asp Leu Met Thr Thr Ile Asp
            180                 185                 190

Ser Thr Glu His Tyr Ser His Tyr Ser Gly Tyr Pro Ile Leu Thr Trp
        195                 200                 205

Ile Ser Ser Pro Asp Asn Ser Tyr Ser Gly Pro Phe Met Ser Trp Tyr
    210                 215                 220

Phe Ala Asn Trp Pro Asn Leu Pro Ser Gly Phe Gly Pro Leu Asn Ser
225                 230                 235                 240

Asp Asn Thr Val Thr Tyr Thr Gly Ser Val Val Ser Gln Val Ser Ala
                245                 250                 255

Gly Val Tyr Ala Thr Val Arg Phe Asp Gln Tyr Asp Ile His Asn Leu
            260                 265                 270

Arg Thr Ile Glu Lys Thr Trp Tyr Ala Arg His Ala Thr Leu His Asn
        275                 280                 285

Gly Lys Lys Ile Ser Ile Asn Asn Val Thr Glu Met Ala Pro Thr Ser
    290                 295                 300

Pro Ile Lys Thr Asn
305
```

<210> SEQ ID NO 179
<211> LENGTH: 309
<212> TYPE: PRT
<213> ORGANISM: Artificial Sequence
<220> FEATURE:

<223> OTHER INFORMATION: engineered
<220> FEATURE:
<221> NAME/KEY: VARIANT
<222> LOCATION: (157)..(157)
<223> OTHER INFORMATION: is not N

<400> SEQUENCE: 179

```
Met Ala Ile Leu Asp Leu Lys Ser Leu Val Leu Asn Ala Ile Asn Tyr
1               5                   10                  15
Trp Gly Pro Lys Asn Asn Gly Ile Gln Gly Gly Asp Phe Gly Tyr
            20                  25                  30
Pro Ile Ser Glu Lys Gln Ile Asp Thr Ser Ile Ile Thr Phe Thr His
                35                  40                  45
Pro Arg Leu Ile Pro Tyr Asp Leu Thr Ile Pro Gln Asn Leu Glu Thr
        50                  55                  60
Ile Phe Thr Thr Thr Gln Val Leu Thr Asn Asn Thr Asp Leu Gln Gln
65                  70                  75                  80
Ser Gln Thr Val Ser Phe Ala Lys Lys Thr Thr Thr Thr Ser Thr
                85                  90                  95
Ser Thr Thr Asn Gly Trp Thr Glu Gly Gly Lys Ile Ser Asp Thr Leu
                100                 105                 110
Glu Glu Lys Val Ser Val Ser Ile Pro Phe Ile Gly Glu Gly Gly Gly
            115                 120                 125
Lys Asn Ser Thr Thr Ile Glu Ala Asn Phe Ala His Asn Ser Ser Thr
        130                 135                 140
Thr Thr Phe Gln Gln Ala Ser Thr Asp Ile Glu Trp Xaa Ile Ser Gln
145                 150                 155                 160
Pro Val Leu Val Pro Pro Ser Lys Gln Val Val Ala Thr Leu Val Ile
                165                 170                 175
Met Gly Gly Asn Phe Thr Ile Pro Met Asp Leu Met Thr Thr Ile Asp
                180                 185                 190
Ser Thr Glu His Tyr Ser His Tyr Ser Gly Tyr Pro Ile Leu Thr Trp
            195                 200                 205
Ile Ser Ser Pro Asp Asn Ser Tyr Ser Gly Pro Phe Met Ser Trp Tyr
210                 215                 220
Phe Ala Asn Trp Pro Asn Leu Pro Ser Gly Phe Gly Pro Leu Asn Ser
225                 230                 235                 240
Asp Asn Thr Val Thr Tyr Thr Gly Ser Val Ser Gln Val Ser Ala
                245                 250                 255
Gly Val Tyr Ala Thr Val Arg Phe Asp Gln Tyr Asp Ile His Asn Leu
            260                 265                 270
Arg Thr Ile Glu Lys Thr Trp Tyr Ala Arg His Ala Thr Leu His Asn
        275                 280                 285
Gly Lys Lys Ile Ser Ile Asn Asn Val Thr Glu Met Ala Pro Thr Ser
    290                 295                 300
Pro Ile Lys Thr Asn
305
```

<210> SEQ ID NO 180
<211> LENGTH: 309
<212> TYPE: PRT
<213> ORGANISM: Artificial Sequence
<220> FEATURE:
<223> OTHER INFORMATION: engineered
<220> FEATURE:
<221> NAME/KEY: misc_feature
<223> OTHER INFORMATION: is not TIC807 (SEQ ID NO: 2)
<220> FEATURE:

```
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (46)..(46)
<223> OTHER INFORMATION: Xaa can be any naturally occurring amino acid
<220> FEATURE:
<221> NAME/KEY: misc_feature
<222> LOCATION: (52)..(52)
<223> OTHER INFORMATION: Xaa can be any naturally occurring amino acid
<220> FEATURE:
<221> NAME/KEY: misc_feature
<222> LOCATION: (54)..(54)
<223> OTHER INFORMATION: Xaa can be any naturally occurring amino acid
<220> FEATURE:
<221> NAME/KEY: misc_feature
<222> LOCATION: (68)..(68)
<223> OTHER INFORMATION: Xaa can be any naturally occurring amino acid
<220> FEATURE:
<221> NAME/KEY: misc_feature
<222> LOCATION: (70)..(70)
<223> OTHER INFORMATION: Xaa can be any naturally occurring amino acid
<220> FEATURE:
<221> NAME/KEY: misc_feature
<222> LOCATION: (87)..(87)
<223> OTHER INFORMATION: Xaa can be any naturally occurring amino acid
<220> FEATURE:
<221> NAME/KEY: misc_feature
<222> LOCATION: (93)..(93)
<223> OTHER INFORMATION: Xaa can be any naturally occurring amino acid
<220> FEATURE:
<221> NAME/KEY: misc_feature
<222> LOCATION: (95)..(95)
<223> OTHER INFORMATION: Xaa can be any naturally occurring amino acid
<220> FEATURE:
<221> NAME/KEY: misc_feature
<222> LOCATION: (105)..(105)
<223> OTHER INFORMATION: Xaa can be any naturally occurring amino acid
<220> FEATURE:
<221> NAME/KEY: misc_feature
<222> LOCATION: (117)..(117)
<223> OTHER INFORMATION: Xaa can be any naturally occurring amino acid
<220> FEATURE:
<221> NAME/KEY: misc_feature
<222> LOCATION: (119)..(119)
<223> OTHER INFORMATION: Xaa can be any naturally occurring amino acid
<220> FEATURE:
<221> NAME/KEY: misc_feature
<222> LOCATION: (125)..(125)
<223> OTHER INFORMATION: Xaa can be any naturally occurring amino acid
<220> FEATURE:
<221> NAME/KEY: misc_feature
<222> LOCATION: (128)..(128)
<223> OTHER INFORMATION: Xaa can be any naturally occurring amino acid
<220> FEATURE:
<221> NAME/KEY: misc_feature
<222> LOCATION: (133)..(135)
<223> OTHER INFORMATION: Xaa can be any naturally occurring amino acid
<220> FEATURE:
<221> NAME/KEY: misc_feature
<222> LOCATION: (137)..(139)
<223> OTHER INFORMATION: Xaa can be any naturally occurring amino acid
<220> FEATURE:
<221> NAME/KEY: misc_feature
<222> LOCATION: (145)..(145)
<223> OTHER INFORMATION: Xaa can be any naturally occurring amino acid
<220> FEATURE:
<221> NAME/KEY: misc_feature
<222> LOCATION: (147)..(151)
<223> OTHER INFORMATION: Xaa can be any naturally occurring amino acid
<220> FEATURE:
<221> NAME/KEY: misc_feature
<222> LOCATION: (153)..(153)
<223> OTHER INFORMATION: Xaa can be any naturally occurring amino acid
<220> FEATURE:
<221> NAME/KEY: misc_feature
<222> LOCATION: (155)..(155)
<223> OTHER INFORMATION: Xaa can be any naturally occurring amino acid
```

```
<220> FEATURE:
<221> NAME/KEY: misc_feature
<222> LOCATION: (157)..(159)
<223> OTHER INFORMATION: Xaa can be any naturally occurring amino acid
<220> FEATURE:
<221> NAME/KEY: misc_feature
<222> LOCATION: (167)..(167)
<223> OTHER INFORMATION: Xaa can be any naturally occurring amino acid
<220> FEATURE:
<221> NAME/KEY: misc_feature
<222> LOCATION: (175)..(175)
<223> OTHER INFORMATION: Xaa can be any naturally occurring amino acid
<220> FEATURE:
<221> NAME/KEY: misc_feature
<222> LOCATION: (177)..(177)
<223> OTHER INFORMATION: Xaa can be any naturally occurring amino acid
<220> FEATURE:
<221> NAME/KEY: misc_feature
<222> LOCATION: (180)..(180)
<223> OTHER INFORMATION: Xaa can be any naturally occurring amino acid
<220> FEATURE:
<221> NAME/KEY: misc_feature
<222> LOCATION: (182)..(182)
<223> OTHER INFORMATION: Xaa can be any naturally occurring amino acid
<220> FEATURE:
<221> NAME/KEY: misc_feature
<222> LOCATION: (187)..(187)
<223> OTHER INFORMATION: Xaa can be any naturally occurring amino acid
<220> FEATURE:
<221> NAME/KEY: misc_feature
<222> LOCATION: (196)..(201)
<223> OTHER INFORMATION: Xaa can be any naturally occurring amino acid
<220> FEATURE:
<221> NAME/KEY: misc_feature
<222> LOCATION: (208)..(208)
<223> OTHER INFORMATION: Xaa can be any naturally occurring amino acid
<220> FEATURE:
<221> NAME/KEY: misc_feature
<222> LOCATION: (217)..(217)
<223> OTHER INFORMATION: Xaa can be any naturally occurring amino acid
<220> FEATURE:
<221> NAME/KEY: misc_feature
<222> LOCATION: (219)..(219)
<223> OTHER INFORMATION: Xaa can be any naturally occurring amino acid
<220> FEATURE:
<221> NAME/KEY: misc_feature
<222> LOCATION: (223)..(223)
<223> OTHER INFORMATION: Xaa can be any naturally occurring amino acid
<220> FEATURE:
<221> NAME/KEY: misc_feature
<222> LOCATION: (235)..(235)
<223> OTHER INFORMATION: Xaa can be any naturally occurring amino acid
<220> FEATURE:
<221> NAME/KEY: misc_feature
<222> LOCATION: (239)..(239)
<223> OTHER INFORMATION: Xaa can be any naturally occurring amino acid
<220> FEATURE:
<221> NAME/KEY: misc_feature
<222> LOCATION: (241)..(241)
<223> OTHER INFORMATION: Xaa can be any naturally occurring amino acid
<220> FEATURE:
<221> NAME/KEY: misc_feature
<222> LOCATION: (243)..(247)
<223> OTHER INFORMATION: Xaa can be any naturally occurring amino acid
<220> FEATURE:
<221> NAME/KEY: misc_feature
<222> LOCATION: (249)..(252)
<223> OTHER INFORMATION: Xaa can be any naturally occurring amino acid
<220> FEATURE:
<221> NAME/KEY: misc_feature
<222> LOCATION: (273)..(275)
<223> OTHER INFORMATION: Xaa can be any naturally occurring amino acid
<220> FEATURE:
<221> NAME/KEY: misc_feature
<222> LOCATION: (282)..(282)
<223> OTHER INFORMATION: Xaa can be any naturally occurring amino acid
<220> FEATURE:
<221> NAME/KEY: misc_feature
<222> LOCATION: (287)..(287)
```

<223> OTHER INFORMATION: Xaa can be any naturally occurring amino acid
<220> FEATURE:
<221> NAME/KEY: misc_feature
<222> LOCATION: (293)..(293)
<223> OTHER INFORMATION: Xaa can be any naturally occurring amino acid
<220> FEATURE:
<221> NAME/KEY: misc_feature
<222> LOCATION: (295)..(295)
<223> OTHER INFORMATION: Xaa can be any naturally occurring amino acid
<220> FEATURE:
<221> NAME/KEY: misc_feature
<222> LOCATION: (299)..(300)
<223> OTHER INFORMATION: Xaa can be any naturally occurring amino acid
<220> FEATURE:
<221> NAME/KEY: misc_feature
<222> LOCATION: (303)..(303)
<223> OTHER INFORMATION: Xaa can be any naturally occurring amino acid
<220> FEATURE:
<221> NAME/KEY: misc_feature
<222> LOCATION: (305)..(306)
<223> OTHER INFORMATION: Xaa can be any naturally occurring amino acid
<220> FEATURE:
<221> NAME/KEY: misc_feature
<222> LOCATION: (308)..(308)
<223> OTHER INFORMATION: Xaa can be any naturally occurring amino acid

<400> SEQUENCE: 180

```
Met Ala Ile Leu Asp Leu Lys Ser Leu Val Leu Xaa Ala Ile Asn Tyr
1               5                   10                  15

Trp Gly Pro Lys Asn Asn Asn Gly Ile Gln Gly Gly Asp Phe Gly Tyr
            20                  25                  30

Pro Ile Ser Glu Lys Gln Ile Asp Thr Ser Ile Ile Thr Xaa Thr His
        35                  40                  45

Pro Arg Leu Xaa Pro Xaa Asp Leu Thr Ile Pro Gln Asn Leu Glu Thr
50                  55                  60

Ile Phe Thr Xaa Thr Xaa Val Leu Thr Asn Asn Thr Asp Leu Gln Gln
65                  70                  75                  80

Ser Gln Thr Val Ser Phe Xaa Lys Lys Thr Thr Thr Xaa Thr Xaa Thr
                85                  90                  95

Ser Thr Thr Asn Gly Trp Thr Glu Xaa Gly Lys Ile Ser Asp Thr Leu
            100                 105                 110

Glu Glu Lys Val Xaa Val Xaa Ile Pro Phe Ile Gly Xaa Gly Gly Xaa
        115                 120                 125

Lys Asn Ser Thr Xaa Xaa Xaa Ala Xaa Xaa Xaa His Asn Ser Ser Thr
130                 135                 140

Xaa Thr Xaa Xaa Xaa Xaa Xaa Thr Xaa Ile Xaa Trp Xaa Xaa Xaa Gln
145                 150                 155                 160

Pro Val Leu Val Pro Xaa Lys Gln Val Ala Thr Leu Xaa Ile
                165                 170                 175

Xaa Gly Gly Xaa Phe Xaa Ile Pro Met Asp Xaa Met Thr Thr Ile Asp
            180                 185                 190

Ser Thr Glu Xaa Xaa Xaa Xaa Xaa Gly Tyr Pro Ile Leu Thr Xaa
                195                 200                 205

Ile Ser Ser Pro Asp Asn Ser Tyr Xaa Gly Xaa Phe Met Ser Xaa Tyr
        210                 215                 220

Phe Ala Asn Trp Pro Asn Leu Pro Ser Gly Xaa Gly Pro Leu Xaa Ser
225                 230                 235                 240

Xaa Asn Xaa Xaa Xaa Xaa Xaa Gly Xaa Xaa Xaa Gln Val Ser Ala
            245                 250                 255

Gly Val Tyr Ala Thr Val Arg Phe Asp Gln Tyr Asp Ile His Asn Leu
            260                 265                 270
```

Xaa Xaa Xaa Glu Lys Thr Trp Tyr Ala Xaa His Ala Thr Leu Xaa Asn
        275                 280                 285

Gly Lys Lys Ile Xaa Ile Xaa Asn Val Thr Xaa Xaa Ala Pro Xaa Ser
    290                 295                 300

Xaa Xaa Lys Xaa Asn
305

<210> SEQ ID NO 181
<211> LENGTH: 927
<212> TYPE: DNA
<213> ORGANISM: Bacillus thuringiensis
<220> FEATURE:
<221> NAME/KEY: misc_feature
<223> OTHER INFORMATION: is a sequence representing a recombinant
      polynucleotide derived from a native gene from a Bacillus
      thuringiensis (Bt) species encoding a Cry51Aa1 protein
<300> PUBLICATION INFORMATION:
<308> DATABASE ACCESSION NUMBER: DQ836184
<309> DATABASE ENTRY DATE: 2007-08-01
<313> RELEVANT RESIDUES IN SEQ ID NO: (1)..(927)

<400> SEQUENCE: 181 atgattttt tggcaatttt agatttaaaa tctttagtac tcaatgcaat aaattattgg      60
ggtcctaaaa ataataatgg catacagggt ggtgattttg ttaccctat atcagaaaaa     120 caaatagata cgtctattat aacttctact catcctcgtt taattccaca tgatttaaca     180
attcctcaaa atttagaaac tattttact acaactcaag tattaacaaa taatacagat     240
ttacaacaaa gtcaaactgt ttcttttgct aaaaaaacaa cgacaacaac ttcaacttca     300
actacaaatg gttggacaga aggtgggaaa atttcagata cattagaaga aaagtaagt     360 gtatctattc cttttattgg agagggagga ggaaaaaaca gtacaactat agaagctaat     420
tttgcacata actctagtac tactactttt caacaggctt caactgatat agagtggaat     480
atttcacaac cagtattggt tcccccacgt aaacaagttg tagcaacatt agttattatg     540
ggaggtaatt ttactattcc tatggatttg atgactacta gattctac agaacattat     600 agtggttatc caatattaac atggatatcg agccccgata atagttataa tggtccatttt    660 atgagttggt attttgcaaa ttggcccaat ttaccatcgg ggtttggtcc tttaaattca     720
gataatacgg tcacttatac aggttctgtt gtaagtcaag tatcagctgg tgtatatgcc     780
actgtacgat ttgatcaata tgatatacac aatttaagga caattgaaaa aacttggtat     840
gcacgacatg caactcttca taatggaaag aaaatatcta taaataatgt tactgaaatg     900
gcaccaacaa gtccaataaa aacaaat                                         927

<210> SEQ ID NO 182
<211> LENGTH: 309
<212> TYPE: PRT
<213> ORGANISM: Artificial Sequence
<220> FEATURE:
<223> OTHER INFORMATION: engineered
<220> FEATURE:
<221> NAME/KEY: misc_feature
<223> OTHER INFORMATION: is an amino acid sequence translation of
      nucleotide (NT) positions 1 through 927 of SEQ ID NO: 181
<300> PUBLICATION INFORMATION:
<308> DATABASE ACCESSION NUMBER: ABI14444
<309> DATABASE ENTRY DATE: 2007-08-01
<313> RELEVANT RESIDUES IN SEQ ID NO: (1)..(309)

<400> SEQUENCE: 182

Met Ile Phe Leu Ala Ile Leu Asp Leu Lys Ser Leu Val Leu Asn Ala
1               5                   10                  15

Ile Asn Tyr Trp Gly Pro Lys Asn Asn Gly Ile Gln Gly Gly Asp
            20                  25                  30

Phe Gly Tyr Pro Ile Ser Glu Lys Gln Ile Asp Thr Ser Ile Ile Thr
        35                  40                  45

Ser Thr His Pro Arg Leu Ile Pro His Asp Leu Thr Ile Pro Gln Asn
50                  55                  60

Leu Glu Thr Ile Phe Thr Thr Thr Gln Val Leu Thr Asn Asn Thr Asp
65                  70                  75                  80

Leu Gln Gln Ser Gln Thr Val Ser Phe Ala Lys Lys Thr Thr Thr Thr
                85                  90                  95

Thr Ser Thr Ser Thr Thr Asn Gly Trp Thr Glu Gly Gly Lys Ile Ser
            100                 105                 110

Asp Thr Leu Glu Glu Lys Val Ser Val Ser Ile Pro Phe Ile Gly Glu
        115                 120                 125

Gly Gly Gly Lys Asn Ser Thr Thr Ile Glu Ala Asn Phe Ala His Asn
    130                 135                 140

Ser Ser Thr Thr Thr Phe Gln Gln Ala Ser Thr Asp Ile Glu Trp Asn
145                 150                 155                 160

Ile Ser Gln Pro Val Leu Val Pro Pro Arg Lys Gln Val Val Ala Thr
                165                 170                 175

Leu Val Ile Met Gly Gly Asn Phe Thr Ile Pro Met Asp Leu Met Thr
            180                 185                 190

Thr Ile Asp Ser Thr Glu His Tyr Ser Gly Tyr Pro Ile Leu Thr Trp
        195                 200                 205

Ile Ser Ser Pro Asp Asn Ser Tyr Asn Gly Pro Phe Met Ser Trp Tyr
210                 215                 220

Phe Ala Asn Trp Pro Asn Leu Pro Ser Gly Phe Gly Pro Leu Asn Ser
225                 230                 235                 240

Asp Asn Thr Val Thr Tyr Thr Gly Ser Val Val Ser Gln Val Ser Ala
                245                 250                 255

Gly Val Tyr Ala Thr Val Arg Phe Asp Gln Tyr Asp Ile His Asn Leu
            260                 265                 270

Arg Thr Ile Glu Lys Thr Trp Tyr Ala Arg His Ala Thr Leu His Asn
        275                 280                 285

Gly Lys Lys Ile Ser Ile Asn Asn Val Thr Glu Met Ala Pro Thr Ser
    290                 295                 300

Pro Ile Lys Thr Asn
305

<210> SEQ ID NO 183
<211> LENGTH: 918
<212> TYPE: DNA
<213> ORGANISM: Bacillus thuringiensis
<220> FEATURE:
<221> NAME/KEY: misc_feature
<223> OTHER INFORMATION: is a sequence representing a recombinant
      polynucleotide derived from a native gene from a Bacillus
      thuringiensis (Bt) species encoding a TIC853 protein

<400> SEQUENCE: 183
ttggcaattt tagatttaaa atctttagta ctcgatgcaa taaactattg gggtcctaaa      60
aataataatg gtatacaggg ttataatttt aattacccta tatcagaaag acaaatagat     120
acgtcgatta aacttctac tcattctcgt ttaatgccac atgatttaac aattcctcaa     180
aatttagaaa ctatttttac tacaactcaa gtattaacaa ataatacaga tgtacaacaa     240
agtcaaactg tttctttttc taaaaaaaca acgacaacaa cttcaacttc aactacagat     300

```
ggttggacag  aaggtgggag  aatttcagat  acattagaag  aaaacgtaag  tgtatctatt    360 cctttattg   gagcgggagg  agcaaaaaac  agtacaacta  tagaagctaa  tgttgcacat    420
aactctagta  ctactacttc  tcaacaggct  tcaactgaga  tagagtggaa  tatttcacaa    480
ccagtattgg  ttcccccacg  taaacaagtt  gtagcaacat  tagttattat  gggaggtgat    540
tttactgttc  ctatggattt  gataactact  atagattcta  cacaacattt  tactggttat    600
ccaatattaa  catggataga  gaaccccgag  cataatgtta  gaggtcgatt  tctgagttgg    660 tttttgcaa   attggcccaa  tttaccatcg  gagtttggtt  ctttaaattc  agataatacg    720
atcacttata  aaggttctgt  tgtaagtcga  atatcagctg  gtgtatatgc  tactgtacga    780
tttgatcaat  atgctataaa  taatttaaga  acaattgaaa  aaacttggta  tgcacgacat    840
ggaactcttc  ataatggaaa  gaaaatatct  ataaataatg  ttactgaaat  ggcaccaaca    900
agtccaatag  aaagaaat                                                     918
```

<210> SEQ ID NO 184
<211> LENGTH: 306
<212> TYPE: PRT
<213> ORGANISM: Artificial Sequence
<220> FEATURE:
<223> OTHER INFORMATION: engineered
<220> FEATURE:
<221> NAME/KEY: misc_feature
<223> OTHER INFORMATION: is an amino acid sequence translation of
      nucleotide (NT) positions 1 through 918 of SEQ ID NO: 183

<400> SEQUENCE: 184

```
Met Ala Ile Leu Asp Leu Lys Ser Leu Val Leu Asp Ala Ile Asn Tyr
1               5                   10                  15

Trp Gly Pro Lys Asn Asn Asn Gly Ile Gln Gly Tyr Asn Phe Asn Tyr
            20                  25                  30

Pro Ile Ser Glu Arg Gln Ile Asp Thr Ser Ile Ile Thr Ser Thr His
        35                  40                  45

Ser Arg Leu Met Pro His Asp Leu Thr Ile Pro Gln Asn Leu Glu Thr
    50                  55                  60

Ile Phe Thr Thr Thr Gln Val Leu Thr Asn Asn Thr Asp Val Gln Gln
65                  70                  75                  80

Ser Gln Thr Val Ser Phe Ser Lys Lys Thr Thr Thr Thr Ser Thr
                85                  90                  95

Ser Thr Thr Asp Gly Trp Thr Glu Gly Gly Arg Ile Ser Asp Thr Leu
            100                 105                 110

Glu Glu Asn Val Ser Val Ser Ile Pro Phe Ile Gly Ala Gly Gly Ala
        115                 120                 125

Lys Asn Ser Thr Thr Ile Glu Ala Asn Val Ala His Asn Ser Ser Thr
    130                 135                 140

Thr Thr Ser Gln Gln Ala Ser Thr Glu Ile Glu Trp Asn Ile Ser Gln
145                 150                 155                 160

Pro Val Leu Val Pro Pro Arg Lys Gln Val Ala Thr Leu Val Ile
                165                 170                 175

Met Gly Gly Asp Phe Thr Val Pro Met Asp Leu Ile Thr Thr Ile Asp
            180                 185                 190

Ser Thr Gln His Phe Thr Gly Tyr Pro Ile Leu Thr Trp Ile Glu Asn
        195                 200                 205

Pro Glu His Asn Val Arg Gly Arg Phe Leu Ser Trp Phe Phe Ala Asn
    210                 215                 220
```

```
Trp Pro Asn Leu Pro Ser Glu Phe Gly Ser Leu Asn Ser Asp Asn Thr
225                 230                 235                 240

Ile Thr Tyr Lys Gly Ser Val Val Ser Arg Ile Ser Ala Gly Val Tyr
            245                 250                 255

Ala Thr Val Arg Phe Asp Gln Tyr Ala Ile Asn Asn Leu Arg Thr Ile
            260                 265                 270

Glu Lys Thr Trp Tyr Ala Arg His Gly Thr Leu His Asn Gly Lys Lys
            275                 280                 285

Ile Ser Ile Asn Asn Val Thr Glu Met Ala Pro Thr Ser Pro Ile Glu
            290                 295                 300

Arg Asn
305
```

<210> SEQ ID NO 185
<211> LENGTH: 309
<212> TYPE: PRT
<213> ORGANISM: Artificial Sequence
<220> FEATURE:
<223> OTHER INFORMATION: engineered
<220> FEATURE:
<221> NAME/KEY: misc_feature
<223> OTHER INFORMATION: is TIC807 (SEQ ID NO: 2) position 11 Leucine
      substituted by a Methionine

<400> SEQUENCE: 185

```
Met Ala Ile Leu Asp Leu Lys Ser Leu Val Met Asn Ala Ile Asn Tyr
1               5                   10                  15

Trp Gly Pro Lys Asn Asn Asn Gly Ile Gln Gly Gly Asp Phe Gly Tyr
            20                  25                  30

Pro Ile Ser Glu Lys Gln Ile Asp Thr Ser Ile Ile Thr Phe Thr His
            35                  40                  45

Pro Arg Leu Ile Pro Tyr Asp Leu Thr Ile Pro Gln Asn Leu Glu Thr
        50                  55                  60

Ile Phe Thr Thr Thr Gln Val Leu Thr Asn Asn Thr Asp Leu Gln Gln
65                  70                  75                  80

Ser Gln Thr Val Ser Phe Ala Lys Lys Thr Thr Thr Thr Ser Thr
            85                  90                  95

Ser Thr Thr Asn Gly Trp Thr Glu Gly Gly Lys Ile Ser Asp Thr Leu
            100                 105                 110

Glu Glu Lys Val Ser Val Ser Ile Pro Phe Ile Gly Glu Gly Gly Gly
            115                 120                 125

Lys Asn Ser Thr Thr Ile Glu Ala Asn Phe Ala His Asn Ser Ser Thr
            130                 135                 140

Thr Thr Phe Gln Gln Ala Ser Thr Asp Ile Glu Trp Asn Ile Ser Gln
145                 150                 155                 160

Pro Val Leu Val Pro Ser Lys Gln Val Val Ala Thr Leu Val Ile
            165                 170                 175

Met Gly Gly Asn Phe Thr Ile Pro Met Asp Leu Met Thr Thr Ile Asp
            180                 185                 190

Ser Thr Glu His Tyr Ser His Tyr Ser Gly Tyr Pro Ile Leu Thr Trp
            195                 200                 205

Ile Ser Ser Pro Asp Asn Ser Tyr Ser Gly Pro Phe Met Ser Trp Tyr
            210                 215                 220

Phe Ala Asn Trp Pro Asn Leu Pro Ser Gly Phe Gly Pro Leu Asn Ser
225                 230                 235                 240

Asp Asn Thr Val Thr Tyr Thr Gly Ser Val Val Ser Gln Val Ser Ala
            245                 250                 255
```

Gly Val Tyr Ala Thr Val Arg Phe Asp Gln Tyr Asp Ile His Asn Leu
                260                 265                 270

Arg Thr Ile Glu Lys Thr Trp Tyr Ala Arg His Ala Thr Leu His Asn
            275                 280                 285

Gly Lys Lys Ile Ser Ile Asn Asn Val Thr Glu Met Ala Pro Thr Ser
        290                 295                 300

Pro Ile Lys Thr Asn
305

<210> SEQ ID NO 186
<211> LENGTH: 930
<212> TYPE: DNA
<213> ORGANISM: Artificial Sequence
<220> FEATURE:
<223> OTHER INFORMATION: engineered
<220> FEATURE:
<221> NAME/KEY: misc_feature
<223> OTHER INFORMATION: A nucleotide sequence encoding SEQ ID NO: 4
      with an open reading frame from 1 to 927.

<400> SEQUENCE: 186
atggctatcc tagaccttaa gtccctcgtg ctgaacgcca ttaactactg gggccctaag      60
aacaacaacg gcatccaggg cggtgacttc ggctacccca tctctgagaa gcagatcgac     120
actagcatca ttaccttcac ccaccctcgc ttgatcccct acgatcttac tatcccgcag     180
aaccttgaga ccatcttcac cacaacgcag gtgctcacca ataacactga cctccagcaa     240
tcccagaccg tgagctttgc gaagaagacc actaccacga cctcaactag cacgaccaac     300
ggttggacag aaggaggcaa gatcagcgac acgctggagg agaaagtttc ggttagcatt     360
ccgttcatcg gtgcgggtgg cgggaagaac tcgactacca tagaggccaa cttcgcacac     420
aactctagca ccactaccct tccagcaagca agcactgaca ttgagtggaa cattagccaa     480
ccggtgctgg ttcctcccct caaacaagtt gtcgcgaccc ttgtgatcat gggaggcaac     540
tttaccatcc ctatggactt gatgaccacg attgatagta cagagcacta ctcccactac     600
tccggttacc ctatcctcac ctggatctcg tccccagata actcttactc cggtcccttt     660
atgtcatggt actttgcaaa ctggcctaac cttccgagtg gattcggccc actgaatagt     720
gataacacgg tcacatacac tggctctgtc gtgtcccaag tttcggccgg tgtctacgct     780
accgtccggt tcgatcagta tgacattcac aatctccgta ctatcgagaa gacttggtat     840
gctcgccatg cgacgctgca taatggcaag aagatttcta tcaacaatgt cacggaaatg     900
gctccaacat cccctatcaa gacaaattga                                       930

<210> SEQ ID NO 187
<211> LENGTH: 930
<212> TYPE: DNA
<213> ORGANISM: Artificial Sequence
<220> FEATURE:
<223> OTHER INFORMATION: engineered
<220> FEATURE:
<221> NAME/KEY: misc_feature
<223> OTHER INFORMATION: A nucleotide sequence encoding SEQ ID NO: 6
      with an open reading frame from 1 to 927.

<400> SEQUENCE: 187
atggctatcc tagaccttaa gtccctcgtg ctgaacgcca ttaactactg gggccctaag      60
aacaacaacg gcatccaggg cggtgacttc ggctacccca tctctgagaa gcagatcgac     120
actagcatca ttaccttcac ccaccctcgc ttgatcccct acgatcttac tatcccgcag     180

```
aaccttgaga ccatcttcac cacaacgcag gtgctcacca ataacactga cctccagcaa    240
tcccagaccg tgagctttgc gaagaagacc actaccacga cctcaactag cacgaccaac    300
ggttggacag aaggaggcaa gatcagcgac acgctggagg agaaagtttc ggttagcatt    360
ccgttcatcg gtgagggtgg cgggaagaac tcgactacca tagaggccaa cttcgcacac    420
aactctagca ccactaccgc ccagcaagca agcactgaca ttgagtggaa cattagccaa    480
ccggtgctgg ttcctccctc taaacaagtt gtcgcgaccc ttgtgatcat gggaggcaac    540
tttaccatcc ctatggactt gatgaccacg attgatagta cagagcacta ctcccactac    600
tccggttacc ctatcctcac ctggatctcg tccccagata actcttactc cggtccctt     660 atgtcatggt actttgcaaa ctggcctaac cttccgagtg gattcggccc actgaatagt    720
gataacacgg tcacatacac tggctctgtc gtgtcccaag tttcggccgg tgtctacgct    780
accgtccggt tcgatcagta tgacattcac aatctccgta ctatcgagaa gacttggtat    840
gctcgccatg cgacgctgca taatggcaag aagatttcta tcaacaatgt cacggaaatg    900
gctccaacat ccccctatcaa gacaaattga                                    930

<210> SEQ ID NO 188
<211> LENGTH: 921
<212> TYPE: DNA
<213> ORGANISM: Artificial Sequence
<220> FEATURE:
<223> OTHER INFORMATION: engineered
<220> FEATURE:
<221> NAME/KEY: misc_feature
<223> OTHER INFORMATION: A nucleotide sequence encoding SEQ ID NO: 8
      with an open reading frame from 1 to 918.

<400> SEQUENCE: 188
atggctatcc tagaccttaa gtccctcgtg ctgaacgcca ttaactactg gggccctaag     60
aacaacaacg gcatccaggg cggtgacttc ggctacccca tctctgagaa gcagatcgac    120
actagcatca ttacctccac ccaccctcgc ttgatccccc acgatcttac tatcccgcag    180
aaccttgaga ccatcttcac cacaacgcag gtgctcacca ataacactga cctccagcaa    240
tcccagaccg tgagctttgc gaagaagacc actaccacga cctcaactag cacgaccaac    300
ggttggacag aaggaggcaa gatcagcgac acgctggagg agaaagtttc ggttagcatt    360
ccgttcatcg gtgagggtgg cgggaagaac tcgactacca tagaggccaa cttcgcacac    420
aactctagca ccactacctt ccagcaagca agcactgaca ttgagtggaa cattagccaa    480
ccggtccttg tgcctccccg caaacaggtt gttgccactc tcgttatcat gggtggcaac    540
ttcactattc ctatggatct tatgactacc attgactcta ctgagcacta ctctggctac    600
cccattctca cttggatctc ttctcctgac aatagctaca acggtccatt catgtcatgg    660
tacttcgcta actggccgaa tctcccttct ggctttggtc ctcttaactc tgataacact    720
gtgacctaca ctggctctgt cgtcagtcag gtctctgccg gtgtgtacgc aactgttcgc    780
ttcgatcagt atgacatcca taatctcagg actattgaga agacctggta cgctcgtcat    840
gcgacgcttc acaacggcaa gaagatcagc atcaataacg tgacagaaat ggcccctacc    900
agcccgatca agactaactg a                                              921

<210> SEQ ID NO 189
<211> LENGTH: 921
<212> TYPE: DNA
<213> ORGANISM: Artificial Sequence
<220> FEATURE:
<223> OTHER INFORMATION: engineered
```

```
<220> FEATURE:
<221> NAME/KEY: misc_feature
<223> OTHER INFORMATION: A nucleotide sequence encoding SEQ ID NO: 10
      with an open reading frame from 1 to 918.

<400> SEQUENCE: 189
atggctatcc tagaccttaa gtccctcgtg ctgaacgcca ttaactactg gggccctaag      60
aacaacaacg gcatccaggg cggtgacttc ggctacccca tctctgagaa gcagatcgac     120
actagcatca ttacctccac ccaccctcgc ttgatccccc acgatcttac tatcccgcag     180
aaccttgaga ccatcttcac cacaacgcag gtgctcacca ataacactga cctccagcaa     240
tcccagaccg tgagctttgc gaagaagacc actaccgcga cctcaactag cacgaccaac     300
ggttggacag aaggaggcaa gatcagcgac acgctggagg agaaagtttc ggttagcatt     360
ccgttcatcg gtgagggtgg cgggaagaac tcgactacca tagaggccaa cttcgcacac     420
aactctagca ccactacctt ccagcaagca agcactgaca ttgagtggaa cattagccaa     480
ccggtccttg tgcctccccg caaacaggtt gttgccactc tcgttatcat gggtggcaac     540
ttcactattc ctatggatct tatgactacc attgactcta ctgagcacta ctctggctac     600
cccattctca cttggatctc ttctcctgac aatagctaca acggtccatt catgtcatgg     660
tacttcgcta actggccgaa tctcccttct ggctttggtc ctcttaactc tgataacact     720
gtgacctaca ctggctctgt cgtcagtcag gtctctgccg gtgtgtacgc aactgttcgc     780
ttcgatcagt atgacatcca taatctcagg actattgaga gacctggta cgctcgtcat     840 gcgacgcttc acaacggcaa gaagatcagc atcaataacg tgacagaaat ggcccctacc     900
agcccgatca agactaactg a                                              921

<210> SEQ ID NO 190
<211> LENGTH: 921
<212> TYPE: DNA
<213> ORGANISM: Artificial Sequence
<220> FEATURE:
<223> OTHER INFORMATION: engineered
<220> FEATURE:
<221> NAME/KEY: misc_feature
<223> OTHER INFORMATION: A nucleotide sequence encoding SEQ ID NO: 12
      with an open reading frame from 1 to 918.

<400> SEQUENCE: 190
atggctatcc tagaccttaa gtccctcgtg ctgaacgcca ttaactactg gggccctaag      60
aacaacaacg gcatccaggg cggtgacttc ggctacccca tctctgagaa gcagatcgac     120
actagcatca ttacctccac ccaccctcgc ttgatccccc acgatcttac tatcccgcag     180
aaccttgaga ccatcttcac cacaacgcag gtgctcacca ataacactga cctccagcaa     240
tcccagaccg tgagctttgc gaagaagacc actaccacga ccgcaactag cacgaccaac     300
ggttggacag aaggaggcaa gatcagcgac acgctggagg agaaagtttc ggttagcatt     360
ccgttcatcg gtgagggtgg cgggaagaac tcgactacca tagaggccaa cttcgcacac     420
aactctagca ccactacctt ccagcaagca agcactgaca ttgagtggaa cattagccaa     480
ccggtccttg tgcctccccg caaacaggtt gttgccactc tcgttatcat gggtggcaac     540
ttcactattc ctatggatct tatgactacc attgactcta ctgagcacta ctctggctac     600
cccattctca cttggatctc ttctcctgac aatagctaca acggtccatt catgtcatgg     660
tacttcgcta actggccgaa tctcccttct ggctttggtc ctcttaactc tgataacact     720
gtgacctaca ctggctctgt cgtcagtcag gtctctgccg gtgtgtacgc aactgttcgc     780
```

```
ttcgatcagt atgacatcca taatctcagg actattgaga agacctggta cgctcgtcat    840
gcgacgcttc acaacggcaa gaagatcagc atcaataacg tgacagaaat ggcccctacc    900
agcccgatca agactaactg a                                              921
```

<210> SEQ ID NO 191
<211> LENGTH: 921
<212> TYPE: DNA
<213> ORGANISM: Artificial Sequence
<220> FEATURE:
<223> OTHER INFORMATION: engineered
<220> FEATURE:
<221> NAME/KEY: misc_feature
<223> OTHER INFORMATION: A nucleotide sequence encoding SEQ ID NO: 14 with an open reading frame from 1 to 918.

<400> SEQUENCE: 191

```
atggctatcc tagaccttaa gtccctcgtg ctgaacgcca ttaactactg gggccctaag     60
aacaacaacg gcatccaggg cggtgacttc ggctacccca tctctgagaa gcagatcgac    120
actagcatca ttacctccac ccaccctcgc ttgatccccc acgatcttac tatcccgcag    180
aaccttgaga ccatcttcac cacaacgcag gtgctcacca ataacactga cctccagcaa    240
tcccagaccg tgagctttgc gaagaagacc actaccacga cctcaactag cacgaccaac    300
ggttggacag aaggaggcaa gatcagcgac acgctggagg agaaagtttc ggttagcatt    360
ccgttcatcg gtgagggtgg cgggaagaac tcgactacca tagaggccaa cttcgcacac    420
aactctagca ccactaccgc ccagcaagca agcactgaca ttgagtggaa cattagccaa    480
ccggtccttg tgcctccccg caaacaggtt gttgccactc tcgttatcat gggtggcaac    540
ttcactattc ctatggatct tatgactacc attgactcta ctgagcacta ctctggctac    600
cccattctca cttggatctc ttctcctgac aatagctaca acggtccatt catgtcatgg    660
tacttcgcta actggccgaa tctcccttct ggctttggtc ctcttaactc tgataacact    720
gtgacctaca ctggctctgt cgtcagtcag gtctctgccg gtgtgtacgc aactgttcgc    780
ttcgatcagt atgacatcca taatctcagg actattgaga agacctggta cgctcgtcat    840
gcgacgcttc acaacggcaa gaagatcagc atcaataacg tgacagaaat ggcccctacc    900
agcccgatca agactaactg a                                              921
```

<210> SEQ ID NO 192
<211> LENGTH: 921
<212> TYPE: DNA
<213> ORGANISM: Artificial Sequence
<220> FEATURE:
<223> OTHER INFORMATION: engineered
<220> FEATURE:
<221> NAME/KEY: misc_feature
<223> OTHER INFORMATION: A nucleotide sequence encoding SEQ ID NO: 16 with an open reading frame from 1 to 918.

<400> SEQUENCE: 192

```
atggctatcc tagaccttaa gtccctcgtg ctgaacgcca ttaactactg gggccctaag     60
aacaacaacg gcatccaggg cggtgacttc ggctacccca tctctgagaa gcagatcgac    120
actagcatca ttacctccac ccaccctcgc ttgatccccc acgatcttac tatcccgcag    180
aaccttgaga ccatcttcac cacaacgcag gtgctcacca ataacactga cctccagcaa    240
tcccagaccg tgagctttgc gaagaagacc actaccacga ccgcaactag cacgaccaac    300
ggttggacag aaggaggcaa gatcagcgac acgctggagg agaaagtttc ggttagcatt    360
ccgttcatcg gtgagggtgg cgggaagaac tcgactacca tagaggccaa cttcgcacac    420
```

```
aactctagca ccactaccgc ccagcaagca agcactgaca ttgagtggaa cattagccaa    480
ccggtccttg tgcctccccg caaacaggtt gttgccactc tcgttatcat gggtggcaac    540
ttcactattc ctatggatct tatgactacc attgactcta ctgagcacta ctctggctac    600
cccattctca cttggatctc ttctcctgac aatagctaca acggtccatt catgtcatgg    660
tacttcgcta actggccgaa tctcccttct ggctttggtc ctcttaactc tgataacact    720
gtgacctaca ctggctctgt cgtcagtcag gtctctgccg gtgtgtacgc aactgttcgc    780
ttcgatcagt atgacatcca taatctcagg actattgaga agacctggta cgctcgtcat    840
gcgacgcttc acaacggcaa gaagatcagc atcaataacg tgacagaaat ggcccctacc    900
agcccgatca agactaactg a                                              921

<210> SEQ ID NO 193
<211> LENGTH: 921
<212> TYPE: DNA
<213> ORGANISM: Artificial Sequence
<220> FEATURE:
<223> OTHER INFORMATION: engineered
<220> FEATURE:
<221> NAME/KEY: misc_feature
<223> OTHER INFORMATION: A nucleotide sequence encoding SEQ ID NO: 18
      with an open reading frame from 1 to 918.

<400> SEQUENCE: 193
atggctatcc tagaccttaa gtccctcgtg ctgaacgcca ttaactactg gggccctaag     60
aacaacaacg gcatccaggg cggtgacttc ggctaccca tctctgagaa gcagatcgac    120
actagcatca ttacctccac ccaccctcgc ttgatccccc acgatcttac tatcccgcag    180
aaccttgaga ccatcttcac cacaacgcag gtgctcacca ataacactga cctccagcaa    240
tcccagaccg tgagctttgc gaagaagacc actaccgcga cctcaactag cacgaccaac    300
ggttggacag aaggaggcaa gatcagcgac acgctggagg agaaagtttc ggttagcatt    360
ccgttcatcg gtgagggtgg cgggaagaac tcgactacca tagaggccaa cttcgcacac    420
aactctagca ccactaccgc ccagcaagca agcactgaca ttgagtggaa cattagccaa    480
ccggtccttg tgcctccccg caaacaggtt gttgccactc tcgttatcat gggtggcaac    540
ttcactattc ctatggatct tatgactacc attgactcta ctgagcacta ctctggctac    600
cccattctca cttggatctc ttctcctgac aatagctaca acggtccatt catgtcatgg    660
tacttcgcta actggccgaa tctcccttct ggctttggtc ctcttaactc tgataacact    720
gtgacctaca ctggctctgt cgtcagtcag gtctctgccg gtgtgtacgc aactgttcgc    780
ttcgatcagt atgacatcca taatctcagg actattgaga agacctggta cgctcgtcat    840
gcgacgcttc acaacggcaa gaagatcagc atcaataacg tgacagaaat ggcccctacc    900
agcccgatca agactaactg a                                              921

<210> SEQ ID NO 194
<211> LENGTH: 921
<212> TYPE: DNA
<213> ORGANISM: Artificial Sequence
<220> FEATURE:
<223> OTHER INFORMATION: engineered
<220> FEATURE:
<221> NAME/KEY: misc_feature
<223> OTHER INFORMATION: A nucleotide sequence encoding SEQ ID NO: 20
      with an open reading frame from 1 to 918.

<400> SEQUENCE: 194
```

```
atggctatcc tagaccttaa gtccctcgtg ctgaacgcca ttaactactg gggccctaag      60
aacaacaacg gcatccaggg cggtgacttc ggctaccccca tctctgagaa gcagatcgac    120
actagcatca ttacctccac ccaccctcgc ttgatccccc acgatcttac tatcccgcag    180
aaccttgaga ccatcttcac cacaacgcag gtgctcacca ataacactga cctccagcaa    240
tcccagaccg tgagctttgc gaagaagacc actaccacga cctcaactag cacgaccaac    300
ggttggacag aaggaggcaa gatcagcgac acgctggagg agaaagtttc ggttagcatt    360
ccgttcatcg gtgagggtgg cgggaagaac tcgactacca tagaggccaa cttcgcacac    420
aactctagca ccactacctt ccaggaggca agcactgaca ttgagtggaa cattagccaa    480
ccggtccttg tgcctccccg caaacaggtt gttgccactc tcgttatcat gggtggcaac    540
ttcactattc ctatggatct tatgactacc attgactcta ctgagcacta ctctggctac    600
cccattctca cttggatctc ttctcctgac aatagctaca acggtccatt catgtcatgg    660
tacttcgcta actggccgaa tctcccttct ggctttggtc ctcttaactc tgataacact    720
gtgacctaca ctggctctgt cgtcagtcag gtctctgccg gtgtgtacgc aactgttcgc    780
ttcgatcagt atgacatcca taatctcagg actattgaga agacctggta cgctcgtcat    840
gcgacgcttc acaacggcaa gaagatcagc atcaataacg tgacagaaat ggcccctacc    900
agcccgatca agactaacta g                                              921
```

<210> SEQ ID NO 195
<211> LENGTH: 921
<212> TYPE: DNA
<213> ORGANISM: Artificial Sequence
<220> FEATURE:
<223> OTHER INFORMATION: engineered
<220> FEATURE:
<221> NAME/KEY: misc_feature
<223> OTHER INFORMATION: A nucleotide sequence encoding SEQ ID NO: 22
      with an open reading frame from 1 to 918.

<400> SEQUENCE: 195

```
atggctatcc tagaccttaa gtccctcgtg ctgaacgcca ttaactactg gggccctaag      60
aacaacaacg gcatccaggg cggtgacttc ggctaccccca tctctgagaa gcagatcgac    120
actagcatca ttacctccac ccaccctcgc ttgatccccc acgatcttac tatcccgcag    180
aaccttgaga ccatcttcac cacaacgcag gtgctcacca ataacactga cctccagcaa    240
tcccagaccg tgagctttgc gaagaagacc actaccgcga cctcaactag cacgaccaac    300
ggttggacag aaggaggcaa gatcagcgac acgctggagg agaaagtttc ggttagcatt    360
ccgttcatcg gtgagggtgg cgggaagaac tcgactacca tagaggccaa cttcgcacac    420
aactctagca ccactacctt ccaggcagca agcactgaca ttgagtggaa cattagccaa    480
ccggtccttg tgcctccccg caaacaggtt gttgccactc tcgttatcat gggtggcaac    540
ttcactattc ctatggatct tatgactacc attgactcta ctgagcacta ctctggctac    600
cccattctca cttggatctc ttctcctgac aatagctaca acggtccatt catgtcatgg    660
tacttcgcta actggccgaa tctcccttct ggctttggtc ctcttaactc tgataacact    720
gtgacctaca ctggctctgt cgtcagtcag gtctctgccg gtgtgtacgc aactgttcgc    780
ttcgatcagt atgacatcca taatctcagg actattgaga agacctggta cgctcgtcat    840
gcgacgcttc acaacggcaa gaagatcagc atcaataacg tgacagaaat ggcccctacc    900
agcccgatca agactaactg a                                              921
```

| <210> | SEQ ID NO 196 |
|---|---|
| <211> | LENGTH: 921 |
| <212> | TYPE: DNA |
| <213> | ORGANISM: Artificial Sequence |
| <220> | FEATURE: |
| <223> | OTHER INFORMATION: engineered |
| <220> | FEATURE: |
| <221> | NAME/KEY: misc_feature |
| <223> | OTHER INFORMATION: A nucleotide sequence encoding SEQ ID NO: 24 with an open reading frame from 1 to 918. |

<400> SEQUENCE: 196

```
atggctatcc tagaccttaa gtccctcgtg ctgaacgcca ttaactactg gggccctaag      60
aacaacaacg gcatccaggg cggtgacttc ggctacccca tctctgagaa gcagatcgac     120
actagcatca ttacctccac ccaccctcgc ttgatccccc acgatcttac tatcccgcag     180
aaccttgaga ccatcttcac cacaacgcag gtgctcacca ataacactga cctccagcaa     240
tcccagaccg tgagctttgc gaagaagacc actaccgcga cctcaactag cacgaccaac     300
ggttggacaa aggaggcaa gatcagcgac acgctggagg agaaagtttc ggttagcatt     360
ccgttcatcg gtgagggtgg cgggaagaac tcgactacca tagaggccaa cttcgcacac     420
aactctagca ccactacctt ccaggaggca agcactgaca ttgagtggaa cattagccaa     480
ccggtccttg tgcctccccg caaacaggtt gttgccactc tcgttatcat gggtggcaac     540
ttcactattc ctatggatct tatgactacc attgactcta ctgagcacta ctctggctac     600
cccattctca cttggatctc ttctcctgac aatagctaca acggtccatt catgtcatgg     660
tacttcgcta actggccgaa tctccccttct ggctttggtc ctcttaactc tgataacact     720
gtgacctaca ctggctctgt cgtcagtcag gtctctgccg gtgtgtacgc aactgttcgc     780
ttcgatcagt atgacatcca taatctcagg actattgaga agacctggta cgctcgtcat     840
gcgacgcttc acaacggcaa gaagatcagc atcaataacg tgacagaaat ggcccctacc     900
agcccgatca agactaactg a                                               921
```

| <210> | SEQ ID NO 197 |
|---|---|
| <211> | LENGTH: 921 |
| <212> | TYPE: DNA |
| <213> | ORGANISM: Artificial Sequence |
| <220> | FEATURE: |
| <223> | OTHER INFORMATION: engineered |
| <220> | FEATURE: |
| <221> | NAME/KEY: misc_feature |
| <223> | OTHER INFORMATION: A nucleotide sequence encoding SEQ ID NO: 26 with an open reading frame from 1 to 918. |

<400> SEQUENCE: 197

```
atggctatcc tagaccttaa gtccctcgtg ctgaacgcca ttaactactg gggccctaag      60
aacaacaacg gcatccaggg cggtgacttc ggctacccca tctctgagaa gcagatcgac     120
actagcatca ttacctccac ccaccctcgc ttgatccccc acgatcttac tatcccgcag     180
aaccttgaga ccatcttcac cacaacgcag gtgctcacca ataacactga cctccagcaa     240
tcccagaccg tgagctttgc gaagaagacc actaccacga ccgcaactag cacgaccaac     300
ggttggacag aaggaggcaa gatcagcgac acgctggagg agaaagtttc ggttagcatt     360
ccgttcatcg gtgagggtgg cgggaagaac tcgactacca tagaggccaa cttcgcacac     420
aactctagca ccactaccgc ccagcaagca agcactgaca ttgagtggaa cattagccaa     480
ccggtccttg tgcctccccg caaacaggtt gttgccactc tcgttatcat gggtggcaac     540
ttcactattc ctatggatct tatgactacc attgactcta ctgagcacta ctctggctac     600
```

```
cccattctca cttggatctc ttctcctgac aatagctaca gcggtccatt catgtcatgg      660
tacttcgcta actggccgaa tctcccttct ggctttggtc ctcttaactc tgataacact      720
gtgacctaca ctggctctgt cgtcagtcag gtctctgccg gtgtgtacgc aactgttcgc      780
ttcgatcagt atgacatcca taatctcagg actattgaga agacctggta cgctcgtcat      840
gcgacgcttc acaacggcaa gaagatcagc atcaataacg tgacagaaat ggcccctacc      900
agcccgatca agactaactg a                                                921
```

<210> SEQ ID NO 198
<211> LENGTH: 921
<212> TYPE: DNA
<213> ORGANISM: Artificial Sequence
<220> FEATURE:
<223> OTHER INFORMATION: engineered
<220> FEATURE:
<221> NAME/KEY: misc_feature
<223> OTHER INFORMATION: A nucleotide sequence encoding SEQ ID NO: 28
      with an open reading frame from 1 to 918.

<400> SEQUENCE: 198

```
atggctatcc tagaccttaa gtccctcgtg ctgaacgcca ttaactactg gggccctaag       60
aacaacaacg gcatccaggg cggtgacttc ggctacccca tctctgagaa gcagatcgac      120
actagcatca ttacctccac ccaccctcgc ttgatccccc acgatcttac tatcccgcag      180
aaccttgaga ccatcttcac cacaacgcag gtgctcacca ataacactga cctccagcaa      240
tcccagaccg tgagctttgc gaagaagacc actaccacga ccgcaactag cacgaccaac      300
ggttggacag aaggaggcaa gatcagcgac acgctggagg agaaagtttc ggttagcatt      360
ccgttcatcg gtgagggtgg cgggaagaac tcgactacca tagaggccaa cttcgcacac      420
aactctagca ccactaccgc ccagcaagca agcactgaca ttgagtggaa cattagccaa      480
ccggtccttg tgcctccccg caaacaggtt gttgccactc tcgttatcat gggtggcaac      540
ttcactattc ctatggatct tatgactacc attgactcta ctgagcacta ctctggctac      600
cccattctca cttggatctc ttctcctgac aatagctaca gcggtcgatt catgtcatgg      660
tacttcgcta actggccgaa tctcccttct ggctttggtc ctcttaactc tgataacact      720
gtgacctaca ctggctctgt cgtcagtcag gtctctgccg gtgtgtacgc aactgttcgc      780
ttcgatcagt atgacatcca taatctcagg actattgaga agacctggta cgctcgtcat      840
gcgacgcttc acaacggcaa gaagatcagc atcaataacg tgacagaaat ggcccctacc      900
agcccgatca agactaactg a                                                921
```

<210> SEQ ID NO 199
<211> LENGTH: 921
<212> TYPE: DNA
<213> ORGANISM: Artificial Sequence
<220> FEATURE:
<223> OTHER INFORMATION: engineered
<220> FEATURE:
<221> NAME/KEY: misc_feature
<223> OTHER INFORMATION: A nucleotide sequence encoding SEQ ID NO: 30
      with an open reading frame from 1 to 918.

<400> SEQUENCE: 199

```
atggctatcc tagaccttaa gtccctcgtg ctgaacgcca ttaactactg gggccctaag       60
aacaacaacg gcatccaggg cggtgacttc ggctacccca tctctgagaa gcagatcgac      120
actagcatca ttacctccac ccaccctcgc ttgatccccc acgatcttac tatcccgcag      180
aaccttgaga ccatcttcac cacaacgcag gtgctcacca ataacactga cctccagcaa      240
```

```
tcccagaccg tgagctttgc gaagaagacc actaccacga ccgcaactag cacgaccaac    300
ggttggacag aaggaggcaa gatcagcgac acgctggagg agaaagtttc ggttagcatt    360
ccgttcatcg gtgagggtgg cgggaagaac tcgactacca tagaggccaa cttcgcacac    420
aactctagca ccactaccgc ccagcaagca agcactgaca ttgagtggaa cattagccaa    480
ccggtccttg tgcctccccg caaacaggtt gttgccactc tcgttatcat gggtggcaac    540
ttcactattc ctatggatct tatgactacc attgactcta ctgagcacta ctctggctac    600
cccattctca cttggatctc ttctcctgac aatagctaca gcggtcgatt catgtcatgg    660
tacttcgcta actggccgaa tctcccttct ggctttggtc ctcttaactc tgataacact    720
gtgacctaca ctggctctgt cgccagtcag gtctctgccg gtgtgtacgc aactgttcgc    780
ttcgatcagt atgacatcca taatctcagg actattgaga agacctggta cgctcgtcat    840
gcgacgcttc acaacggcaa gaagatcagc atcaataacg tgacagaaat ggcccctacc    900
agcccgatca agactaactg a                                              921

<210> SEQ ID NO 200
<211> LENGTH: 921
<212> TYPE: DNA
<213> ORGANISM: Artificial Sequence
<220> FEATURE:
<223> OTHER INFORMATION: engineered
<220> FEATURE:
<221> NAME/KEY: misc_feature
<223> OTHER INFORMATION: A nucleotide sequence encoding SEQ ID NO: 32
      with an open reading frame from 1 to 918.

<400> SEQUENCE: 200
atggctatcc tagaccttaa gtccctcgtg ctgaacgcca ttaactactg gggccctaag     60
aacaacaacg gcatccaggg cggtgacttc ggctacccca tctctgagaa gcagatcgac    120
actagcatca ttacctccac ccaccctcgc ttgatccccc acgatcttac tatcccgcag    180
aaccttgaga ccatcttcac cacaacgcag gtgctcacca ataacactga cctccagcaa    240
tcccagaccg tgagctttgc gaagaagacc actaccacga ccgcaactag cacgaccaac    300
ggttggacag aaggaggcaa gatcagcgac acgctggagg agaaagtttc ggttagcatt    360
ccgttcatcg gtgagggtgg cgggaagaac tcgactacca tagaggccaa cttcgcacac    420
aactctagca ccactaccgc ccagcaagca agcactgaca ttgagtggaa cattagccaa    480
ccggtccttg tgcctccccg caaacaggtt gttgccactc tcgttatcat gggtggcaac    540
ttcactattc ctatggatct tatgactacc attgactcta ctgagcacta ctctggctac    600
cccattctca cttggatctc ttctcctgac aatagctaca gcggtcgatt catgtcatgg    660
tacttcgcta actggccgaa tctcccttct ggctttggtc ctcttaactc tgataacact    720
gtgacctaca ctggctctgt cgtcagtcag gtctctgccg gtgtgtacgc aactgttcgc    780
ttcgatcagt atgacatcca taatctctgg actattgaga agacctggta cgctcgtcat    840
gcgacgcttc acaacggcaa gaagatcagc atcaataacg tgacagaaat ggcccctacc    900
agcccgatca agactaactg a                                              921

<210> SEQ ID NO 201
<211> LENGTH: 921
<212> TYPE: DNA
<213> ORGANISM: Artificial Sequence
<220> FEATURE:
<223> OTHER INFORMATION: engineered
<220> FEATURE:
```

<221> NAME/KEY: misc_feature
<223> OTHER INFORMATION: A nucleotide sequence encoding SEQ ID NO: 34
      with an open reading frame from 1 to 918.

<400> SEQUENCE: 201

```
atggctatcc tagaccttaa gtccctcgtg ctgaacgcca ttaactactg gggccctaag      60
aacaacaacg gcatccaggg cggtgacttc ggctacccca tctctgagaa gcagatcgac     120
actagcatca ttacctccac ccaccctcgc ttgatccccc acgatcttac tatcccgcag     180
aaccttgaga ccatcttcac cacaacgcag gtgctcacca ataacactga cctccagcaa     240
tcccagaccg tgagctttgc gaagaagacc actaccacga ccgcaactag cacgaccaac     300
ggttggacag aaggaggcaa gatcagcgac acgctggagg agaaagtttc ggttagcatt     360
ccgttcatcg gtgagggtgg cgggaagaac tcgactacca tagaggccaa cttcgcacac     420
aactctagca ccactacctc ccaggaagca agcactgaca ttgagtggaa cattagccaa     480
ccggtccttg tgcctccccg caaacaggtt gttgccactc tcgttatcat gggtggcaac     540
ttcactattc ctatggatct tatgactacc attgactcta ctgagcacta ctctggctac     600
cccattctca cttggatctc ttctcctgac aatagctaca gcggtcgatt catgtcatgg     660
tacttcgcta actggccgaa tctcccttct ggctttggtc ctcttaactc tgataacact     720
gtgacctaca ctggctctgt cgtcagtcag gtctctgccg gtgtgtacgc aactgttcgc     780
ttcgatcagt atgacatcca taatctctgg actattgaga gacctggta cgctcgtcat     840
gcgacgcttc acaacggcaa gaagatcagc atcaataacg tgacagaaat ggcccctacc     900
agcccgatca agactaactg a                                               921
```

<210> SEQ ID NO 202
<211> LENGTH: 306
<212> TYPE: PRT
<213> ORGANISM: Artificial Sequence
<220> FEATURE:
<223> OTHER INFORMATION: engineered
<220> FEATURE:
<221> NAME/KEY: misc_feature
<223> OTHER INFORMATION: The AA sequence translation of nucleotides 1
      through 903 of SEQ ID NO: 15.

<400> SEQUENCE: 202

```
Met Ala Ile Leu Asp Leu Lys Ser Leu Val Leu Asn Ala Ile Asn Tyr
1               5                   10                  15

Trp Gly Pro Lys Asn Asn Asn Gly Ile Gln Gly Gly Asp Phe Gly Tyr
            20                  25                  30

Pro Ile Ser Glu Lys Gln Ile Asp Thr Ser Ile Ile Thr Ser Thr His
        35                  40                  45

Pro Arg Leu Ile Pro His Asp Leu Thr Ile Pro Gln Asn Leu Glu Thr
    50                  55                  60

Ile Phe Thr Thr Thr Gln Val Leu Thr Asn Asn Thr Asp Leu Gln Gln
65                  70                  75                  80

Ser Gln Thr Val Ser Phe Ala Lys Lys Thr Thr Thr Thr Ala Thr
            85                  90                  95

Ser Thr Thr Asn Gly Trp Thr Glu Gly Gly Lys Ile Ser Asp Thr Leu
        100                 105                 110

Glu Glu Lys Val Ser Val Ser Ile Pro Phe Ile Gly Glu Gly Gly Gly
    115                 120                 125

Lys Asn Ser Thr Thr Ile Glu Ala Asn Phe Ala His Asn Ser Ser Thr
        130                 135                 140
```

```
Thr Thr Ala Gln Gln Ala Ser Thr Asp Ile Glu Trp Asn Ile Ser Gln
145                 150                 155                 160

Pro Val Leu Val Pro Pro Arg Lys Gln Val Val Ala Thr Leu Val Ile
                165                 170                 175

Met Gly Gly Asn Phe Thr Ile Pro Met Asp Leu Met Thr Thr Ile Asp
            180                 185                 190

Ser Thr Glu His Tyr Ser Gly Tyr Pro Ile Leu Thr Trp Ile Ser Ser
        195                 200                 205

Pro Asp Asn Ser Tyr Asn Gly Pro Phe Met Ser Trp Tyr Phe Ala Asn
    210                 215                 220

Trp Pro Asn Leu Pro Ser Gly Phe Gly Pro Leu Asn Ser Asp Asn Thr
225                 230                 235                 240

Val Thr Tyr Thr Gly Ser Val Val Ser Gln Val Ser Ala Gly Val Tyr
                245                 250                 255

Ala Thr Val Arg Phe Asp Gln Tyr Asp Ile His Asn Leu Arg Thr Ile
            260                 265                 270

Glu Lys Thr Trp Tyr Ala Arg His Ala Thr Leu His Asn Gly Lys Lys
        275                 280                 285

Ile Ser Ile Asn Asn Val Thr Glu Met Ala Pro Thr Ser Pro Ile Lys
    290                 295                 300

Thr Asn
305

<210> SEQ ID NO 203
<211> LENGTH: 921
<212> TYPE: DNA
<213> ORGANISM: Artificial Sequence
<220> FEATURE:
<223> OTHER INFORMATION: engineered
<220> FEATURE:
<221> NAME/KEY: misc_feature
<223> OTHER INFORMATION: A nucleotide sequence encoding SEQ ID NO: 204
      with an open reading frame from 1 to 918.

<400> SEQUENCE: 203
atggctatcc tagaccttaa gtccctcgtg ctgaacgcca ttaactactg gggccctaag      60
aacaacaacg gcatccaggg cggtgacttc ggctacccca tctctgagaa gcagatcgac     120
actagcatca ttacctccac ccaccctcgc ttgatccccc acgatcttac tatcccgcag     180
aaccttgaga ccatcttcac cacaacgcag gtgctcacca ataacactga cctccagcaa     240
tcccagaccg tgagctttgc gaagaagacc actaccacga ccgcaactag cacgaccaac     300
ggttggacag aaggaggcaa gatcagcgac acgctgaggg agaaagtttc ggttagcatt     360
ccgttcatcg gtgagggtgg cgggaagaac tcgactacca tagaggccaa cttcgcacac     420
aactctagca ccactaccctc caggaagca agcactgaca ttgagtggaa cattagccaa     480
ccggtccttg tgcctccccg caaacaggtt gttgccactc tcgttatcat gggtggcaac     540
ttcactattc ctatggatct tatgactacc attgactcta ctgagcacta ctctggctac     600
cccattctca cttggatctc ttctcctgac aatagctaca gcggtcgatt catgtcatgg     660
tacttcgcta actggccgaa tctcccttct ggctttggtc ctcttaactc tgataacact     720
gtgacctaca ctggccgggt cgaaagtcgg gtctctgccg gtgtgtacgc aactgttcgc     780
ttcgatcagt atgacatcca taatctctgg actattgaga gacctggta cgctcgtcat     840 gcgacgcttc acaacggcaa gaagatcagc atcaataacg tgacagaaat ggcccctacc     900
agcccgatca agactaactg a                                               921
```

<210> SEQ ID NO 204
<211> LENGTH: 306
<212> TYPE: PRT
<213> ORGANISM: Artificial sequence
<220> FEATURE:
<223> OTHER INFORMATION: engineered
<220> FEATURE:
<221> NAME/KEY: misc_feature
<223> OTHER INFORMATION: The amino acid sequence translation of the open reading frame set forth as SEQ ID NO: 203.

<400> SEQUENCE: 204

Met Ala Ile Leu Asp Leu Lys Ser Leu Val Leu Asn Ala Ile Asn Tyr
1               5                   10                  15

Trp Gly Pro Lys Asn Asn Gly Ile Gln Gly Asp Phe Gly Tyr
            20                  25                  30

Pro Ile Ser Glu Lys Gln Ile Asp Thr Ser Ile Ile Thr Ser Thr His
        35                  40                  45

Pro Arg Leu Ile Pro His Asp Leu Thr Ile Pro Gln Asn Leu Glu Thr
    50                  55                  60

Ile Phe Thr Thr Thr Gln Val Leu Thr Asn Asn Thr Asp Leu Gln Gln
65                  70                  75                  80

Ser Gln Thr Val Ser Phe Ala Lys Lys Thr Thr Thr Thr Ala Thr
                85                  90                  95

Ser Thr Thr Asn Gly Trp Thr Glu Gly Gly Lys Ile Ser Asp Thr Leu
            100                 105                 110

Glu Glu Lys Val Ser Val Ser Ile Pro Phe Ile Gly Glu Gly Gly Gly
        115                 120                 125

Lys Asn Ser Thr Thr Ile Glu Ala Asn Phe Ala His Asn Ser Ser Thr
130                 135                 140

Thr Thr Ser Gln Glu Ala Ser Thr Asp Ile Glu Trp Asn Ile Ser Gln
145                 150                 155                 160

Pro Val Leu Val Pro Arg Lys Gln Val Val Ala Thr Leu Val Ile
                165                 170                 175

Met Gly Gly Asn Phe Thr Ile Pro Met Asp Leu Met Thr Thr Ile Asp
            180                 185                 190

Ser Thr Glu His Tyr Ser Gly Tyr Pro Ile Leu Thr Trp Ile Ser Ser
        195                 200                 205

Pro Asp Asn Ser Tyr Ser Gly Arg Phe Met Ser Trp Tyr Phe Ala Asn
    210                 215                 220

Trp Pro Asn Leu Pro Ser Gly Phe Gly Pro Leu Asn Ser Asp Asn Thr
225                 230                 235                 240

Val Thr Tyr Thr Gly Arg Val Glu Ser Arg Val Ser Ala Gly Val Tyr
                245                 250                 255

Ala Thr Val Arg Phe Asp Gln Tyr Asp Ile His Asn Leu Trp Thr Ile
            260                 265                 270

Glu Lys Thr Trp Tyr Ala Arg His Ala Thr Leu His Asn Gly Lys Lys
        275                 280                 285

Ile Ser Ile Asn Asn Val Thr Glu Met Ala Pro Thr Ser Pro Ile Lys
    290                 295                 300

Thr Asn
305

<210> SEQ ID NO 205
<211> LENGTH: 2577
<212> TYPE: DNA
<213> ORGANISM: Bacillus thuringiensis

```
<220> FEATURE:
<221> NAME/KEY: misc_feature
<223> OTHER INFORMATION: AXMI-171 US2010/0298207 A1 SEQ ID NO:204

<400> SEQUENCE: 205
atgaaaaata aaagaaaata tatgaagcca ctcgcagtag gcttgctcgc aactaacatt      60
attggatttg gtactcagac agtagcgttt gctgcgacag ataaagcggg ttccaaagaa     120
cagatgcagc aacaaatgaa aacacagaat aagagcttta atccgacagt attagccagt     180
atgccatcgg atacatcgga gcttcaaaaa atgttggaag acgcgattaa aaataaggat     240
acccagatta ctccggaatt aataaaaaaa cttcaggaca aaggatttga ttaccttagt     300
attgtaaagg gtttaactgg cggattactg aagcaaattc cgtatgcagg ttcaatcctc     360
tcccctttgg tagttggcct ttttccaggt aagggttatg taacgaaggc gaatgtctgg     420
ggagagatac aggatcgcgt ttcaaattta atagatcaaa aattagaaga gtcacaagta     480
aataacttaa ttgggaaact aacgggtatt caggataatt taggaatata ccaaactcgg     540
gttggtttag ttaatgggat aaaaccacca attgctaatt ttatacaaaa ggatgcaaat     600
tctgataaaa ataaggagaa tttaagaagc acaatagact ccttggacaa ggatttaggc     660
cgagtgatac ctgagtttgc tgttaaaggt tacgaggcag cttctcttcc atattatgta     720
caagttgcca atgtgcatct tttcttattg aaagatgcac ttacacatgc agatgagtgg     780
gggcttactg atgatgaaaa gagaggatat tgtcaagac ttcaacaaaa aattcaagag     840
tatagcagcg tcgtatatga ttcctttaat aaaggagtcg aagccgctaa agtaagggt     900 ggaagtaccg ccgacagttg gaacagaacc aatgcctatg taagaacaat gacattgtat     960
ggtttagatt ttgtggcttt atggccggct tttgatacta acattataa tcagccagta    1020 aaattgcagc aaaacgtga attatattct aacatgatag gaagaccaat aaactggcaa    1080
gactatgata caactcttca acaaattcat aatagtgggt atgcgggtta ccaggcgag    1140 ctgaaacaag ttggtgtttc acagtgggat cgtattgatg gaatcaggga aatatttgat    1200
tggactggag acggctcacg agattatacg ctacaatggg gccacgcaaa caaaaatggg    1260
tattcggacc gtagccagac cgtcaataac ccagcaatag gaatttcagc atatgaatcc    1320
aataatgcta atttctataa tatgtctact atcacatata acaaaataa cgaagtatct    1380 tggttctatg gtccatttac tactcaaagc gatagtaaag atggaagtag aatagatagc    1440
aaagctccag cgggccataa attatctcgc gtcaaagtac aagaaaaaag atcagatcta    1500
aatacaatat catctttgt ggctgcatat gttcctgaag aagttcatcc acagaatata    1560
cttgaggcta aagctattac aggggtacca gctgaaaaat atctcgcaca tgcaggattt    1620
gaagataaga ttgaatacat gaatggttcg aatgcgatgg tatcttctaa aaatggtgac    1680
acgatagatt acaatgttca aagtccagga aaacaaaaat ataaaatacg cctccgtgtt    1740
gcgacaaata gtgacacatc tgtgggaatc tctataaatg gggattctca gcaagtgaat    1800
ataaaaaata cagaagccgc aacaaagtta gaagacggta ttacagttaa aggtgtaaat    1860
gggaagtaca tgttaattga cggaccaact gttgaactta gcgaaggtgt gaatacaatt    1920
cagcttaaaa atagtggtgg agctaagatt gcattagatc gaatagaatt tgagcctata    1980
ggcggtgagc tacgcaagtg gaaacaggaa ggtgataagt ggtactttta cgatgaaaat    2040
gataaaaagt taacaggttg gcaaaagatt aatgaaagaa atactaccct tggacattct    2100
ggtgatggtt ctggtatgac cactgaaggg gagatggcaa caggctggaa aacgattgat    2160
ggagtacaat attactttgg acattctggt gatggttctg gtatggtcac tgaaggggag    2220
```

```
atggcaacag gctggaaaac gataaatgga gtaaaatatt attttggaca gactggtgat    2280
ggctctggta tgcaacacga aggggaaaag gcaacaggct ggaaaacgat tgatggagta    2340
aaatattact tcaataaaac tggtgatggc tctggtatgc aacacgaagg ggaaaaggca    2400
ataggctgga aaacgattga tggagtaaaa tattacttca ataaaactgg tgatggctct    2460
ggtatgcaac acgaaggaga aatggcatta ggagatatga cgattgatgg agtaaaacat    2520
cactttaata aaactggtga tggaacgggt cgcgaccatg aaggagagct cgtatgg    2577
```

<210> SEQ ID NO 206
<211> LENGTH: 859
<212> TYPE: PRT
<213> ORGANISM: Bacillus thuringiensis
<220> FEATURE:
<221> NAME/KEY: misc_feature
<223> OTHER INFORMATION: AXMI-171 US2010/0298207 A1 SEQ ID NO:205

<400> SEQUENCE: 206

```
Met Lys Asn Lys Lys Tyr Met Lys Pro Leu Ala Val Gly Leu Leu
1               5                   10                  15

Ala Thr Asn Ile Ile Gly Phe Gly Thr Gln Thr Val Ala Phe Ala Ala
            20                  25                  30

Thr Asp Lys Ala Gly Ser Lys Glu Gln Met Gln Gln Met Lys Thr
        35                  40                  45

Gln Asn Lys Ser Phe Asn Pro Thr Val Leu Ala Ser Met Pro Ser Asp
    50                  55                  60

Thr Ser Glu Leu Gln Lys Met Leu Glu Asp Ala Ile Lys Asn Lys Asp
65                  70                  75                  80

Thr Gln Ile Thr Pro Glu Leu Ile Lys Lys Leu Gln Asp Lys Gly Phe
                85                  90                  95

Asp Tyr Leu Ser Ile Val Lys Gly Leu Thr Gly Gly Leu Leu Lys Gln
            100                 105                 110

Ile Pro Tyr Ala Gly Ser Ile Leu Ser Pro Leu Val Val Gly Leu Phe
        115                 120                 125

Pro Gly Lys Gly Tyr Val Thr Lys Ala Asn Val Trp Gly Glu Ile Gln
    130                 135                 140

Asp Arg Val Ser Asn Leu Ile Asp Gln Lys Leu Glu Glu Ser Gln Val
145                 150                 155                 160

Asn Asn Leu Ile Gly Lys Leu Thr Gly Ile Gln Asp Asn Leu Gly Ile
                165                 170                 175

Tyr Gln Thr Arg Val Gly Leu Val Asn Gly Ile Lys Pro Pro Ile Ala
            180                 185                 190

Asn Phe Ile Gln Lys Asp Ala Asn Ser Asp Lys Asn Lys Glu Asn Leu
        195                 200                 205

Arg Ser Thr Ile Asp Ser Leu Asp Lys Asp Leu Gly Arg Val Ile Pro
    210                 215                 220

Glu Phe Ala Val Lys Gly Tyr Glu Ala Ala Ser Leu Pro Tyr Tyr Val
225                 230                 235                 240

Gln Val Ala Asn Val His Leu Phe Leu Leu Lys Asp Ala Leu Thr His
                245                 250                 255

Ala Asp Glu Trp Gly Leu Thr Asp Asp Glu Lys Arg Gly Tyr Leu Ser
            260                 265                 270

Arg Leu Gln Gln Lys Ile Gln Glu Tyr Ser Ser Val Val Tyr Asp Ser
        275                 280                 285

Phe Asn Lys Gly Val Glu Ala Ala Lys Ser Lys Gly Gly Ser Thr Ala
```

```
                    290                 295                 300
Asp Ser Trp Asn Arg Thr Asn Ala Tyr Val Arg Thr Met Thr Leu Tyr
305                 310                 315                 320

Gly Leu Asp Phe Val Ala Leu Trp Pro Ala Phe Asp Thr Lys His Tyr
                325                 330                 335

Asn Gln Pro Val Lys Leu Gln Gln Thr Arg Glu Leu Tyr Ser Asn Met
                340                 345                 350

Ile Gly Arg Pro Ile Asn Trp Gln Asp Tyr Asp Thr Thr Leu Gln Gln
                355                 360                 365

Ile His Asn Ser Gly Tyr Ala Gly Tyr Pro Gly Glu Leu Lys Gln Val
                370                 375                 380

Gly Val Ser Gln Trp Asp Arg Ile Asp Gly Ile Arg Glu Ile Phe Asp
385                 390                 395                 400

Trp Thr Gly Asp Gly Ser Arg Asp Tyr Thr Leu Gln Trp Gly His Ala
                405                 410                 415

Asn Lys Asn Gly Tyr Ser Asp Arg Ser Gln Thr Val Asn Asn Pro Ala
                420                 425                 430

Ile Gly Ile Ser Ala Tyr Glu Ser Asn Asn Ala Asn Phe Tyr Asn Met
                435                 440                 445

Ser Thr Ile Thr Tyr Lys Gln Asn Asn Glu Val Ser Trp Phe Tyr Gly
                450                 455                 460

Pro Phe Thr Thr Gln Ser Asp Ser Lys Asp Gly Ser Arg Ile Asp Ser
465                 470                 475                 480

Lys Ala Pro Ala Gly His Lys Leu Ser Arg Val Lys Val Gln Glu Lys
                485                 490                 495

Arg Ser Asp Leu Asn Thr Ile Ser Ser Phe Val Ala Ala Tyr Val Pro
                500                 505                 510

Glu Glu Val His Pro Gln Asn Ile Leu Glu Ala Lys Ala Ile Thr Gly
                515                 520                 525

Val Pro Ala Glu Lys Tyr Leu Ala His Ala Gly Phe Glu Asp Lys Ile
                530                 535                 540

Glu Tyr Met Asn Gly Ser Asn Ala Met Val Ser Ser Lys Asn Gly Asp
545                 550                 555                 560

Thr Ile Asp Tyr Asn Val Gln Ser Pro Gly Lys Gln Lys Tyr Lys Ile
                565                 570                 575

Arg Leu Arg Val Ala Thr Asn Ser Asp Thr Ser Val Gly Ile Ser Ile
                580                 585                 590

Asn Gly Asp Ser Gln Gln Val Asn Ile Lys Asn Thr Glu Ala Ala Thr
                595                 600                 605

Lys Leu Glu Asp Gly Ile Thr Val Lys Gly Val Asn Gly Lys Tyr Met
610                 615                 620

Leu Ile Asp Gly Pro Thr Val Glu Leu Ser Gly Val Asn Thr Ile
                630                 635                 640
625

Gln Leu Lys Asn Ser Gly Gly Ala Lys Ile Ala Leu Asp Arg Ile Glu
                645                 650                 655

Phe Glu Pro Ile Gly Gly Glu Leu Arg Lys Trp Lys Gln Glu Gly Asp
                660                 665                 670

Lys Trp Tyr Phe Tyr Asp Glu Asn Asp Lys Lys Leu Thr Gly Trp Gln
                675                 680                 685

Lys Ile Asn Glu Arg Lys Tyr Tyr Leu Gly His Ser Gly Asp Gly Ser
                690                 695                 700

Gly Met Thr Thr Glu Gly Glu Met Ala Thr Gly Trp Lys Thr Ile Asp
705                 710                 715                 720
```

-continued

```
Gly Val Gln Tyr Tyr Phe Gly His Ser Gly Asp Gly Ser Gly Met Val
            725                 730                 735

Thr Glu Gly Glu Met Ala Thr Gly Trp Lys Thr Ile Asn Gly Val Lys
            740                 745                 750

Tyr Tyr Phe Gly Gln Thr Gly Asp Gly Ser Gly Met Gln His Glu Gly
            755                 760                 765

Glu Lys Ala Thr Gly Trp Lys Thr Ile Asp Gly Val Lys Tyr Tyr Phe
            770                 775                 780

Asn Lys Thr Gly Asp Gly Ser Gly Met Gln His Glu Gly Glu Lys Ala
785                 790                 795                 800

Ile Gly Trp Lys Thr Ile Asp Gly Val Lys Tyr Tyr Phe Asn Lys Thr
            805                 810                 815

Gly Asp Gly Ser Gly Met Gln His Glu Gly Glu Met Ala Leu Gly Asp
            820                 825                 830

Met Thr Ile Asp Gly Val Lys His His Phe Asn Lys Thr Gly Asp Gly
            835                 840                 845

Thr Gly Arg Asp His Glu Gly Glu Leu Val Trp
850                 855
```